United States Patent
Wei et al.

(10) Patent No.: US 10,428,081 B2
(45) Date of Patent: Oct. 1, 2019

(54) EGFR INHIBITOR, PREPARATION METHOD AND USE THEREOF

(71) Applicants: Shanghai Hansoh Biomedical Co., Ltd., Shanghai (CN); Jiangsu Hansoh Pharmaceutical Group Co., Ltd., Lianyungang, Jiangsu (CN)

(72) Inventors: Mingsong Wei, Shanghai (CN); Guangjun Sun, Shanghai (CN); Songliang Tan, Shanghai (CN); Peng Gao, Shanghai (CN); Shaobao Wang, Shanghai (CN); Wenhua Xiu, Shanghai (CN); Fujun Zhang, Shanghai (CN); Rudi Bao, Shanghai (CN)

(73) Assignees: SHANGHAI HANSOH BIOMEDICAL CO., LTD., Shanghai (CN); JIANGSU HANSOH PHARMACEUTICAL GROUP CO., LTD., Jiangsu (CN)

( * ) Notice: Subject to any disclaimer, the term of this patent is extended or adjusted under 35 U.S.C. 154(b) by 0 days.

(21) Appl. No.: 16/207,968

(22) Filed: Dec. 3, 2018

(65) Prior Publication Data

US 2019/0100528 A1    Apr. 4, 2019

Related U.S. Application Data

(62) Division of application No. 15/517,193, filed as application No. PCT/CN2015/091189 on Sep. 30, 2015, now Pat. No. 10,259,820.

(30) Foreign Application Priority Data

Oct. 11, 2014    (CN) .......................... 2014 1 0534203

(51) Int. Cl.
    *C07D 471/04*    (2006.01)
    *C07D 491/107*   (2006.01)
    *C07D 403/12*    (2006.01)
    *C07D 405/14*    (2006.01)
    *A61K 31/505*    (2006.01)
    *A61K 31/506*    (2006.01)
    *A61K 31/675*    (2006.01)
    *C07F 9/53*      (2006.01)
    (Continued)

(52) U.S. Cl.
    CPC ........ *C07D 491/107* (2013.01); *A61K 31/505* (2013.01); *A61K 31/506* (2013.01); *A61K 31/675* (2013.01); *C07D 239/48* (2013.01); *C07D 403/04* (2013.01); *C07D 403/12* (2013.01); *C07D 405/12* (2013.01); *C07D 405/14* (2013.01); *C07D 413/14* (2013.01); *C07D 471/06* (2013.01); *C07D 471/10* (2013.01); *C07D 491/10* (2013.01); *C07F 9/53* (2013.01)

(58) Field of Classification Search
    CPC .................................................. C07D 403/04
    See application file for complete search history.

(56) References Cited

U.S. PATENT DOCUMENTS 9,796,712 B2 * 10/2017 Huang ................. C07D 403/14
2017/0166598 A1    6/2017 Huang et al.
                   (Continued)

FOREIGN PATENT DOCUMENTS

CN        103501612 A    1/2014
CN        103702990 A    4/2014
                   (Continued)

OTHER PUBLICATIONS

Int'l Search Report dated Jan. 11, 2016 in Int'l Application No. PCT/CN2015/091189.

(Continued)

*Primary Examiner* — Alexander R Pagano
(74) *Attorney, Agent, or Firm* — Panitch Schwarze Belisario & Nadel LLP

(57) ABSTRACT

Epidermal growth factor receptor (EGFR) inhibitors are provided. In particular, 4-substituted-2-(N-(5-substituted ally amide)phenyl)amino)pyrimidine derivatives of formula (I), a preparation method and use thereof as an EGFR inhibitor are provided. The 4-substituted-2-(N-(5-substituted ally amide)phenyl)amino)pyrimidine derivatives of formula (I) have inhibitory activity against the L858R EGFR mutant, the T790M EGFR mutant and the exon 19 deletion activating mutant, and can be used to treat diseases mediated alone or in part by EGFR mutant activity. The derivatives of formula (I) can be used to treat and/or prevent cancers, particularly non-small cell lung cancer.

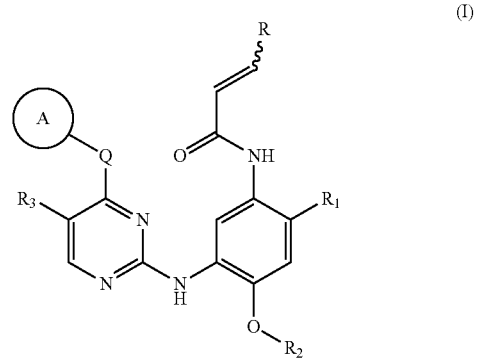

20 Claims, No Drawings

(51) Int. Cl.
C07D 403/04 (2006.01)
C07D 405/12 (2006.01)
C07D 239/48 (2006.01)
C07D 471/10 (2006.01)
C07D 413/14 (2006.01)
C07D 471/06 (2006.01)
C07D 491/10 (2006.01)

(56) References Cited

U.S. PATENT DOCUMENTS

2017/0355696 A1* 12/2017 Jiang ............... A61K 31/437
2017/0362204 A1* 12/2017 Gray ............... C07D 403/04
2018/0208581 A1* 7/2018 Zhu ............... A61K 31/506

FOREIGN PATENT DOCUMENTS

| CN | 2014/10421609 | * | 8/2014 | ........... C07D 403/14 |
| CN | 104140418 A | | 11/2014 | |
| CN | 104761544 A | | 7/2015 | |
| CN | 104860941 A | | 8/2015 | |
| CN | 201410421609 | | 9/2015 | |
| CN | 201510152615.0 | | 11/2015 | |
| CN | 201410619334.7 | | 1/2018 | |
| WO | 2011140338 A1 | | 11/2011 | |
| WO | 2013169401 A1 | | 11/2013 | |
| WO | 2015175632 A1 | | 11/2015 | |
| WO | WO-2015188777 A1 | * | 12/2015 | ........... A61K 31/506 |
| WO | WO-2015195228 A1 | * | 12/2015 | ........... C07D 403/14 |
| WO | 2016029839 A1 | | 3/2016 | |
| WO | WO-2016029839 A1 | * | 3/2016 | ........... A61K 31/506 |
| WO | 2016070816 A1 | | 5/2016 | |
| WO | WO-2017036263 A1 | * | 3/2017 | ........... C07D 401/14 |

OTHER PUBLICATIONS

Ciardiello et al., "EGFR Antagonist in Cancer Treatment," The New England Journal of Medicine, vol. 358, pp. 1160-1174 (2008).
Roskoski et al, "The ErbB/HER Receptor Protein-Tyrosine Kinases and Cancer," Biochemical and Biophysical Research Communications, vol. 319, pp. 1-11 (2004).
Paez et al, "EGFR Mutations in Lung Cancer: Correlation with Clinical Response to Gefitinib Therapy," Science, vol. 304, pp. 1497-1500 (2004).
Lynch et al, "Activating Mutations in the Epidermal Growth Factor Receptor Underlying Responsiveness of Non-Small-Cell Lung Cancer to Gefitinib," The New England Journal of Medicine, vol. 350, No. 21 pp. 2129-2139 (May 20, 2004).
Finlay et al, "Discovery of a Potent and Selective EGFR Inhibitor (AZD9291) of Both Sensitizing and T790M Resistance Mutations That Spares the Wild Type Form of the Receptor," Journal of Medicinal Chemistry, vol. 57, No. 20, pp. 8249-8267 (2014).

* cited by examiner

EGFR INHIBITOR, PREPARATION METHOD AND USE THEREOF

CROSS-REFERENCE TO RELATED APPLICATION

This application is a Divisional of U.S. patent application Ser. No. 15/517,193, filed Apr. 6, 2017, which is a Section 371 of International Application No. PCT/CN2015/091189, filed Sep. 30, 2015, which was published in the Chinese language on Apr. 14, 2016 under International Publication No. WO 2016/054987 A1, and which claims priority under 35 U.S.C. § 119(b) to Chinese Patent Application No. 201410534203.9, filed Oct. 11, 2014, and the disclosures of which are incorporated herein by reference.

FIELD OF THE INVENTION

The present invention relates to the field of pharmaceutical synthesis, and specifically relates to an EGFR inhibitor, preparation method and use thereof.

BACKGROUND OF THE INVENTION

EGFR (Epidermal Growth Factor Receptor) is a member of the erbB receptor family, which includes transmembrane protein tyrosine kinase receptors. By binding to its ligand, such as epidermal growth factor (EGF), EGFR can form a homodimer on the cell membrane or form a heterodimer with other receptors in the family, such as erbB2, erbB3, or erbB4. The formation of these dimers can cause the phosphorylation of key tyrosine residues in EGFR cells, thereby activating a number of downstream signaling pathways in cells. These intracellular signaling pathways play an important role in cell proliferation, survival and anti-apoptosis. Disorders of EGFR signal transduction pathways, including increased expression of ligands and receptors, EGFR gene amplification and mutation and the like, can promote malignant transformation of cells and play an important role in tumor cell proliferation, invasion, metastasis and angiogenesis. Therefore, EGFR is a reasonable target for the development of anticancer drugs.

The first generation of small molecule EGFR inhibitors, including gefitinib (Iressa™) and erlotinib (Tarceva™), have shown good efficacy in treatment of lung cancer and have been used as first-line drugs for treating non-small cell lung cancer (NSCLC) associated with EGFR-activated mutation (*New England Journal of Medicine* (2008) Vol. 358, 1160-74, *Biochemical and Biophysical Research Communications* (2004) Vol. 319, 1-11).

In contrast to the wild-type (WT) EGFR, the activated mutant-type EGFR (including L858R and delE746_A750 with exon 19 deletion), has lower affinity for adenosine triphosphate (ATP), but has higher affinity for small molecule inhibitors, which leads to increased susceptibility of tumor cells to the first generation of EGFR inhibitors such as gefitinib or erlotinib, thereby achieving a targeted therapy (*Science* (2004) No. 304, 1497-500; *New England Journal of medicine* (2004) No. 350, 2129-39).

However, after 10-12 months of treatment with the first generation of small-molecule EGFR inhibitors, resistance to these small molecule inhibitors has been observed in almost all NSCLC patients. The resistance mechanisms include secondary mutations of EGFR, bypass-activation and the like. Thereinto, half of the drug resistance is due to the secondary mutations of T790M, which is a gatekeeper gene residue of EGFR. The secondary mutations reduce the affinity of the drug with the target, thereby producing drug resistance, and resulting in tumor recurrence or disease progression.

In view of the importance and universality of this mutation for drug resistance produced in therapy targeting EGFR of lung cancer, a number of drug research and development companies (Pfizer, BI, AZ, etc.) have attempted to develop second generation small molecule EGFR inhibitors for treating these patients with drug-resistant lung cancer by inhibiting the EGFR-T790M mutant. However, all attempts failed due to poor selectivity. Even if afatinib has been approved by the FDA for the treatment of lung cancer, it was only used in the first-line treatment for patients associated with EGFR-activated mutation. However, afatinib did not show therapeutic efficacy in patients having the EGFR-T790M mutation because afatinib has a stronger inhibitory effect on wild-type EGFR, which causes serious skin and gastrointestinal toxicity, thereby limiting the administration dose.

Therefore, it is necessary to develop third generation small-molecule EGFR inhibitors which can inhibit the EGFR T790M mutant with high selectivity and have no or low activity to wild-type EGFR. Because of this high selectivity, the skin and gastrointestinal damage caused by the inhibition of wild-type EGFR can be greatly decreased and the drug-resistant tumor caused by the secondary mutation of EGFR-T790M can be treated. In addition, it makes sense to maintain the inhibitory activity to EGFR-activated mutant (including EGFR-L858R and delE746_A750 with exon 19 deletion). Due to the lower inhibition of wild-type EGFR, the third generation EGFR inhibitors have better safety than the first generation EGFR inhibitors, and are expected as the first-line therapy in treating NSCLC associated with EGFR-activated mutation, meanwhile, eliminating a small number of EGFR-T790T mutant that may exist in patients with the initial treatment to delay drug resistance.

Lung cancer is a major disease that threatens human health, and the mortality of lung cancer is the leading cause of all malignant tumors. In China, the incidence of lung cancer increases year by year, with nearly 700,000 new cases each year. In Europe and America, lung cancer associated with EGFR-activated mutation accounts for about 10% of all NSCLC; while in China, this ratio is up to 30%. Therefore, China has a larger market for the EGFR target.

SUMMARY OF THE INVENTION

During the course of research, the inventors identified a series of 4-substituted-2-(N-(5-allylamido)phenyl)amino) pyrimidine derivatives as represented by formula (I), which have inhibitory activity against the EGFR-L858R mutant, the EGFR-T790M mutant and the mutant activated by exon 19 deletion, and can be used alone or in combination to treat diseases mediated by the activity of EGFR mutants. For example, these derivatives are intended to have a wide use in preventing and treating cancer, particularly non-small cell lung cancer.

In one aspect, the present invention provides a compound of formula (I), a stereoisomer or a pharmaceutically acceptable salt thereof:

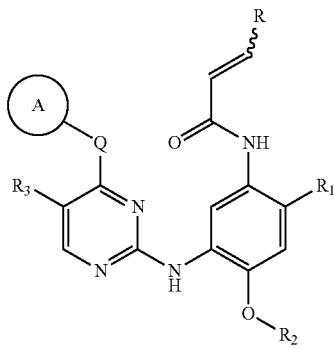

(I)

wherein:
ring A is selected from the group consisting of:

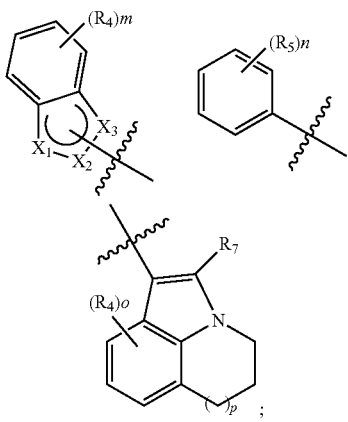

Q is selected from the group consisting of a bond, O, S, $NR_7$ and $CR_7R_8$; R is selected from the group consisting of hydrogen and bis $C_{1-8}$ alkylaminomethyl;

$X_1$, $X_2$ and $X_3$ are each independently selected from the group consisting of $NR_7$ and $CR_8$, provided that at least one of $X_1$, $X_2$ and $X_3$ is $NR_7$;

$R_1$ is selected from the group consisting of:

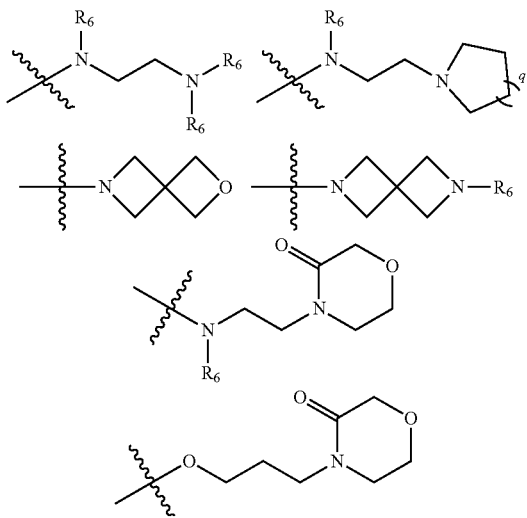

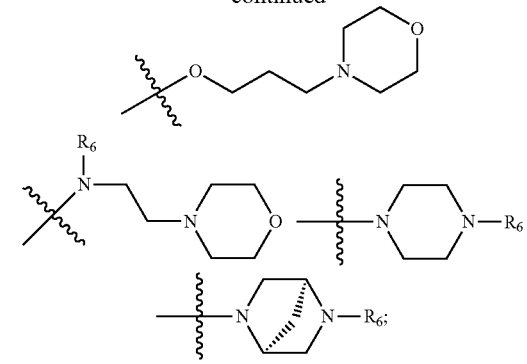

wherein the three $R_6$ in are optionally the same or different substituents;

$R_2$ is selected from the group consisting of $C_{1-8}$ alkyl and $C_{3-8}$ cycloalkyl, wherein the $C_{1-8}$ alkyl and $C_{3-8}$ cycloalkyl are each optionally substituted by one or more groups selected from the group consisting of halogen, hydroxy, $C_{1-8}$ alkyl, $C_{1-8}$ alkoxy, halo $C_{1-8}$ alkoxy, $C_{3-8}$ cycloalkyl and $C_{3-8}$ cycloalkoxy;

$R_3$ is selected from the group consisting of hydrogen, deuterium, halogen, cyano, nitro, $C_{1-8}$ alkyl, $C_{1-8}$ alkoxy, $C_{3-8}$ cycloalkyl, trifluoromethyl, trifluoromethoxy, $SO_2R_9$, $C(O)R_{10}$, $C(O)OR_{10}$ and $P(O)R_{11}R_{12}$;

$R_4$ and $R_5$ are each independently selected from the group consisting of hydrogen, deuterium, halogen, hydroxy, sulthydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, $—C_{0-8}—P(O)R_{11}R_{12}$, $—C_{0-8}—S(O)rR_9$, $—C_{0-8}—O—R_{10}$, $—C_{0-8}—C(O)R_{10}$, $—C_{0-8}—C(O)OR_{10}$, $—C_{0-8}—O—C(O)R_{10}$, $—C_{0-8}—NR_7R_8$, $—C_{0-8}—C(O)NR_7R_8$, $—N(R_7)—C(O)R_{10}$ and $—N(R_7)—C(O)OR_{10}$;

or, two $R_4$ or two $R_5$ are taken together with the carbon atoms of the attached benzene ring to form a 5- to 7-membered carbocycle, 5- to 7-membered heterocycle, $C_{5-7}$ aryl or 5- to 7-membered heteroaryl;

wherein the $C_{1-8}$ alkyl, $C_{3-8}$ cycloalkyl, 3- to 8-membered heterocyclyl, $C_{5-10}$ aryl, 5- to 10-membered heteroaryl, 5- to 7-membered carbocycle, 5- to 7-membered heterocycle, $C_{5-7}$ aryl and 5- to 7-membered heteroaryl are each optionally substituted by one or more groups selected from the group consisting of halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, $—C_{0-8}—S(O)rR_9$, $—C_{0-8}—O—R_{10}$, $—C_{0-8}—C(O)R_{10}$, $—C_{0-8}—C(O)OR_{10}$, $—C_{0-8}—O—C(O)R_{10}$, $—C_{0-8}—NR_7R_8$, $—C_{0-8}—C(O)NR_7R_8$, $—N(R_7)—C(O)R_{10}$ and $—N(R_7)—C(O)OR_{10}$;

$R_6$ is selected from the group consisting of hydrogen, deuterium, $C_{1-8}$ alkyl, halo$C_{1-8}$ alkyl and $C(O)R_{10}$;

$R_7$ is selected from the group consisting of hydrogen, deuterium, $C_{1-8}$ alkyl, $C_{2-8}$ alkenyl, $C_{2-8}$ alkynyl, $C_{3-8}$ cycloalkyl, 3- to 8-membered heterocyclyl, $C_{5-10}$ aryl, 5- to 10-membered heteroaryl, —$C_{0-8}$—S(O)r$R_9$, —$C_{0-8}$—O—$R_{10}$, —$C_{0-8}$—C(O)$R_{10}$, —$C_{0-8}$—C(O)O$R_{10}$, —$C_{0-8}$—O—C(O)$R_{10}$, —$C_{0-8}$—N$R_7R_8$ and —$C_{0-8}$—C(O)N$R_7R_8$;

wherein the $C_{1-8}$ alkyl, $C_{3-8}$ cycloalkyl, 3- to 8-membered heterocyclyl, $C_{5-10}$ aryl and 5- to 10-membered heteroaryl are each optionally substituted by one or more groups selected from the group consisting of halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, —$C_{0-8}$—S(O)r$R_9$, —$C_{0-8}$—O—$R_{10}$, —$C_{0-8}$—C(O)$R_{10}$, —$C_{0-8}$—C(O)O$R_{10}$, —$C_{0-8}$—O—C(O)$R_{10}$, —$C_{0-8}$—N$R_7R_8$, —$C_{0-8}$—C(O)N$R_7R_8$, —N($R_7$)—C(O)$R_{10}$ and —N($R_7$)—C(O)O$R_{10}$;

$R_8$ is selected from the group consisting of hydrogen, deuterium, halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, —$C_{0-8}$—S(O)r$R_9$, —$C_{0-8}$—O—$R_{10}$, —$C_{0-8}$—C(O)$R_{10}$, —$C_{0-8}$—C(O)O$R_{10}$, —$C_{0-8}$—O—C(O)$R_{10}$, —$C_{0-8}$—N$R_7R_8$, —$C_{0-8}$—C(O)N$R_7R_8$, —N($R_7$)—C(O)$R_{10}$ and —N($R_7$)—C(O)O$R_{10}$;

wherein the $C_{1-8}$ alkyl, $C_{3-8}$ cycloalkyl, 3- to 8-membered heterocyclyl, $C_{5-10}$ aryl and 5- to 10-membered heteroaryl are each optionally substituted by one or more groups selected from the group consisting of halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, —$C_{0-8}$—S(O)r$R_9$, —$C_{0-8}$—O—$R_{10}$, —$C_{0-8}$—C(O)$R_{10}$, —$C_{0-8}$—C(O)O$R_{10}$, —$C_{0-8}$—O—C(O)$R_{10}$, —$C_{0-8}$—N$R_7R_8$, —$C_{0-8}$—C(O)N$R_7R_8$, —N($R_7$)—C(O)$R_{10}$ and —N($R_7$)—C(O)O$R_{10}$;

$R_9$ is selected from the group consisting of hydrogen, deuterium, $C_{1-8}$ alkyl, $C_{3-8}$ cycloalkyl, halo$C_{1-8}$ alkyl, bis-$C_{1-8}$ alkylamino, phenyl and p-methylphenyl;

$R_{10}$, $R_{11}$ and $R_{12}$ are each independently selected from the group consisting of hydrogen, deuterium, $C_{1-8}$ alkyl, $C_{3-8}$ cycloalkyl, halo$C_{1-8}$ alkyl and hydroxy$C_{1-8}$ alkyl;

m is 0, 1, 2, 3 or 4;

n is 0, 1, 2, 3, 4 or 5;

r is 0, 1 or 2;

o is 0, 1, 2, 3 or 4;

p is 0, 1, 2 or 3;

q is 0, 1, 2, 3 or 4;

" $\rightsquigarrow$ " means that substituent R can have a Z or E configuration.

In a preferred embodiment, in the compound of formula (I), the stereoisomer or the pharmaceutically acceptable salt thereof, $R_2$ is selected from the group consisting of $C_{1-4}$ alkyl and $C_{3-6}$ cycloalkyl, wherein the $C_{1-4}$ alkyl and $C_{3-6}$ cycloalkyl are each optionally substituted by one or more groups selected from the group consisting of halogen, hydroxy, $C_{1-8}$ alkyl, $C_{1-8}$ alkoxy, halo$C_{1-8}$ alkoxy, $C_{3-8}$ cycloalkyl and $C_{3-8}$ cycloalkoxy; and ring A, Q, R, $X_1$, $X_2$, $X_3$, $R_1$, $R_3$, $R_4$, $R_5$, $R_6$, $R_7$, $R_8$, $R_9$, $R_{10}$, $R_{11}$, $R_{12}$, m, n, r, o, p and q are as defined in the compound of formula (I).

In a more preferred embodiment, in the compound of formula (I), the stereoisomer or the pharmaceutically acceptable salt thereof, $R_2$ is selected from the group consisting of $C_{1-4}$ alkyl and $C_{3-6}$ cycloalkyl, wherein the $C_{1-4}$ alkyl and $C_{3-6}$ cycloalkyl are each optionally substituted by one or more groups selected from the group consisting of halogen and hydroxy; and ring A, Q, R, $X_1$, $X_2$, $X_3$, $R_1$, $R_3$, $R_4$, $R_5$, $R_6$, $R_7$, $R_8$, $R_9$, $R_{10}$, $R_{11}$, $R_{12}$, m, n, r, o, p and q are as defined in the compound of formula (I).

In a more preferred embodiment, in the compound of formula (I), the stereoisomer or the pharmaceutically acceptable salt thereof, $R_2$ is $C_{1-4}$ alkyl optionally substituted by one or more groups selected from the group consisting of fluorine and hydroxy; and ring A, Q, R, $X_1$, $X_2$, $X_3$, $R_1$, $R_3$, $R_4$, $R_5$, $R_6$, $R_7$, $R_8$, $R_9$, $R_{10}$, $R_{11}$, $R_{12}$, m, n, r, o, p and q are as defined in the compound of formula (I).

In a more preferred embodiment, in the compound of formula (I), the stereoisomer or the pharmaceutically acceptable salt thereof, $R_2$ is selected from the group consisting of methyl, difluoromethyl and trifluoromethyl; and ring A, Q, R, $X_1$, $X_2$, $X_3$, $R_1$, $R_3$, $R_4$, $R_5$, $R_6$, $R_7$, $R_8$, $R_9$, $R_{10}$, $R_{11}$, $R_{12}$, m, n and r are as defined in the compound of formula (I).

In a more preferred embodiment, the compound of formula (I), the stereoisomer or the pharmaceutically acceptable salt thereof is a compound of formula (IA):

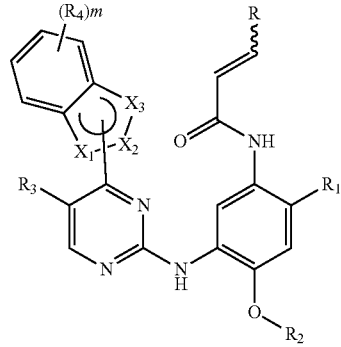

(IA)

wherein $R_2$ is selected from the group consisting of methyl, difluoromethyl and trifluoromethyl; and ring A, R, $X_1$, $X_2$, $X_3$, $R_1$, $R_3$, $R_4$, $R_6$, $R_7$, $R_8$, $R_9$, $R_{10}$, $R_{11}$, $R_{12}$, m, r and q are as defined in the compound of formula (I).

In a more preferred embodiment, the compound of formula (I), the stereoisomer or the pharmaceutically acceptable salt thereof is selected from the group consisting of a compound of formula (IIA1) and a compound of formula (IIA2):

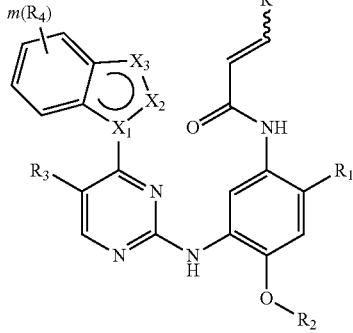

(IIA1)

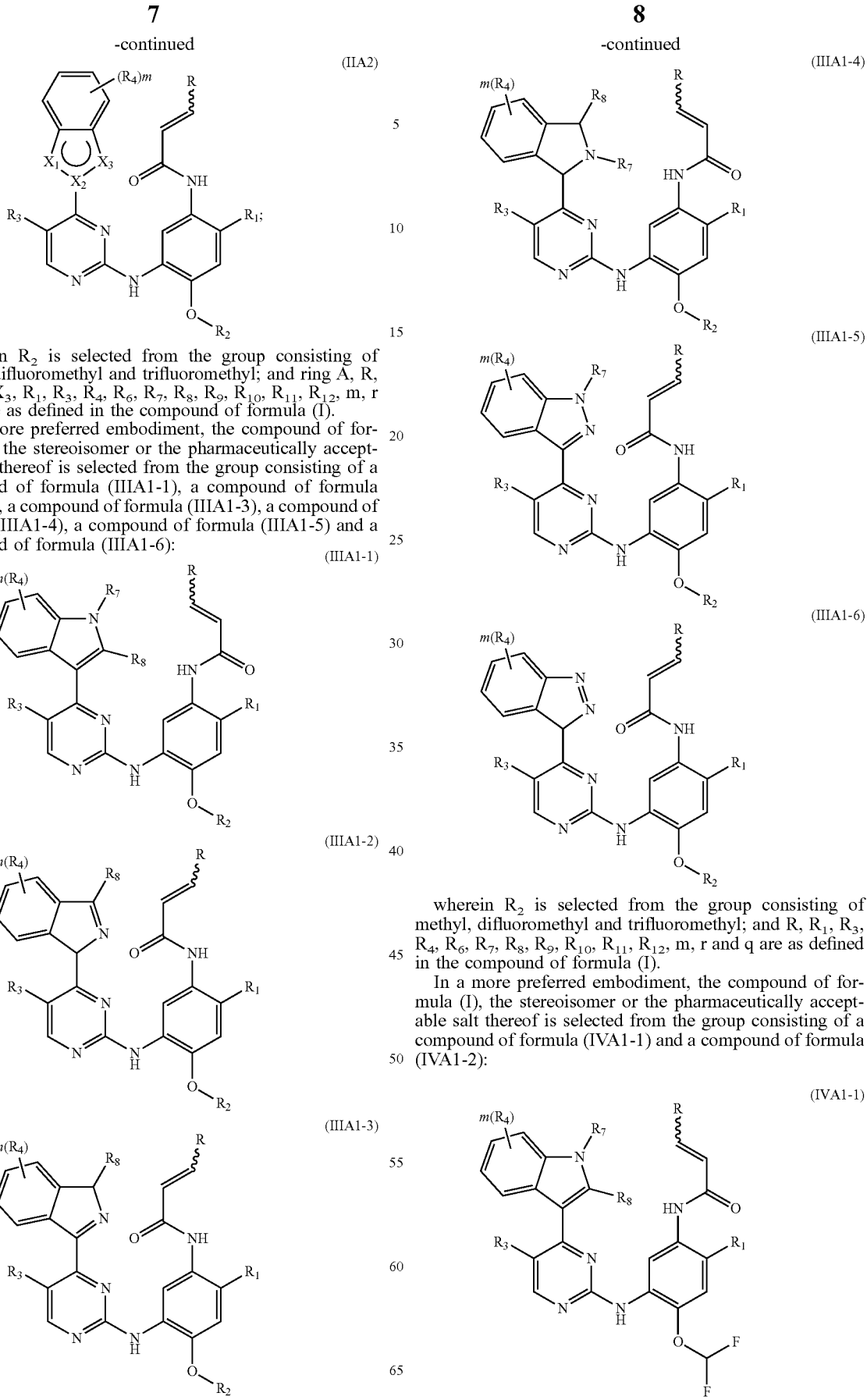

wherein $R_2$ is selected from the group consisting of methyl, difluoromethyl and trifluoromethyl; and ring A, R, $X_1$, $X_2$, $X_3$, $R_1$, $R_3$, $R_4$, $R_6$, $R_7$, $R_8$, $R_9$, $R_{10}$, $R_{11}$, $R_{12}$, m, r and q are as defined in the compound of formula (I).

In a more preferred embodiment, the compound of formula (I), the stereoisomer or the pharmaceutically acceptable salt thereof is selected from the group consisting of a compound of formula (IIIA1-1), a compound of formula (IIIA1-2), a compound of formula (IIIA1-3), a compound of formula (IIIA1-4), a compound of formula (IIIA1-5) and a compound of formula (IIIA1-6):

wherein $R_2$ is selected from the group consisting of methyl, difluoromethyl and trifluoromethyl; and R, $R_1$, $R_3$, $R_4$, $R_6$, $R_7$, $R_8$, $R_9$, $R_{10}$, $R_{11}$, $R_{12}$, m, r and q are as defined in the compound of formula (I).

In a more preferred embodiment, the compound of formula (I), the stereoisomer or the pharmaceutically acceptable salt thereof is selected from the group consisting of a compound of formula (IVA1-1) and a compound of formula (IVA1-2):

-continued

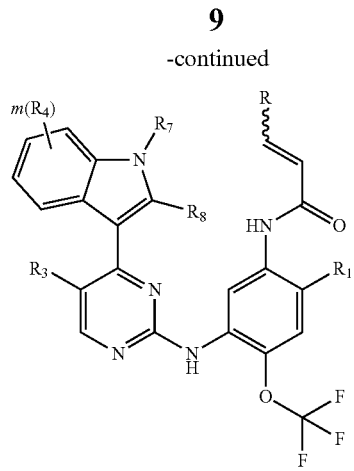

(IVA1-2)

wherein R, R₁, R₃, R₄, R₆, R₇, R₈, R₉, R₁₀, R₁₁, R₁₂, m, r and q are as defined in the compound of formula (I).

In a more preferred embodiment, in the compound of formula (I), the stereoisomer or the pharmaceutically acceptable salt thereof, R₃ is selected from the group consisting of hydrogen, deuterium, halogen, $C_{1-8}$ alkyl, $C_{1-8}$ alkoxy, $C_{3-8}$ cycloalkyl, trifluoromethyl and trifluoromethoxy; and R, R₁, R₄, R₆, R₇, R₈, R₉, R₁₀, R₁₁, R₁₂, m, r and q are as defined in the compound of formula (I).

In a more preferred embodiment, in the compound of formula (I), the stereoisomer or the pharmaceutically acceptable salt thereof, R₃ is selected from the group consisting of hydrogen, fluorine, chlorine, methyl, ethyl, isopropyl, methoxy, ethoxy, isopropoxy, cyclopropyl, cyclobutyl, trifluoromethyl and trifluoromethoxy; and R, R₁, R₄, R₆, R₇, R₈, R₉, R₁₀, R₁₁, R₁₂, m, r and q are as defined in the compound of formula (I).

In a more preferred embodiment, in the compound of formula (I), the stereoisomer or the pharmaceutically acceptable salt thereof, R₃ is selected from the group consisting of hydrogen, fluorine, chlorine, methyl, cyclopropyl and trifluoromethyl; and R, R₁, R₄, R₆, R₇, R₈, R₉, R₁₀, R₁₁, R₁₂, m, r and q are as defined in the compound of formula (I).

In the most preferred embodiment, the compound of formula (I), the stereoisomer or the pharmaceutically acceptable salt thereof is selected from the group consisting of:

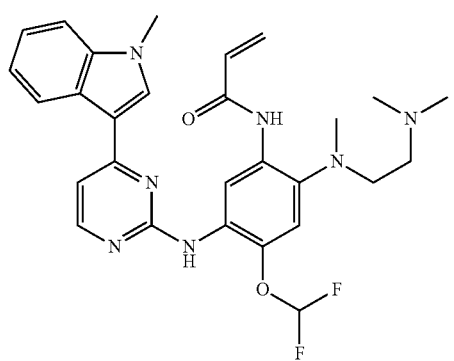

-continued

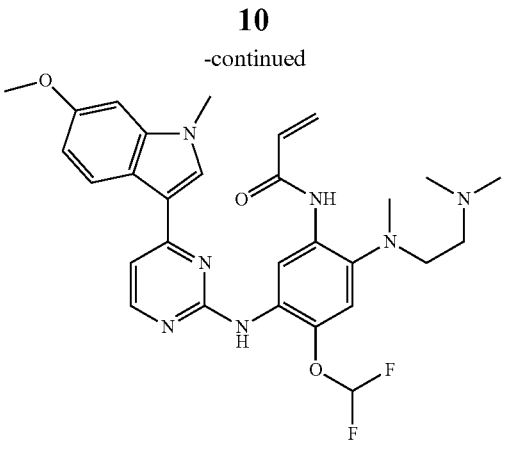

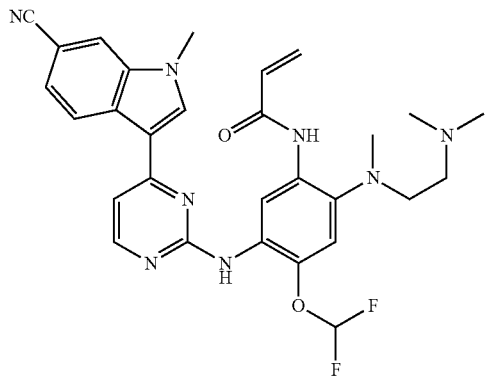

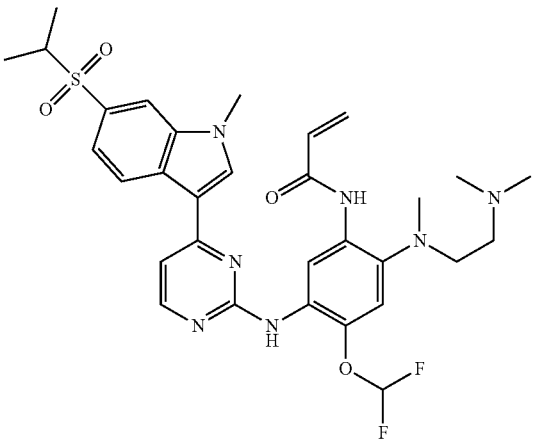

-continued

-continued
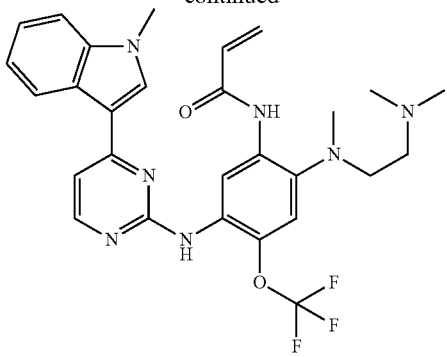
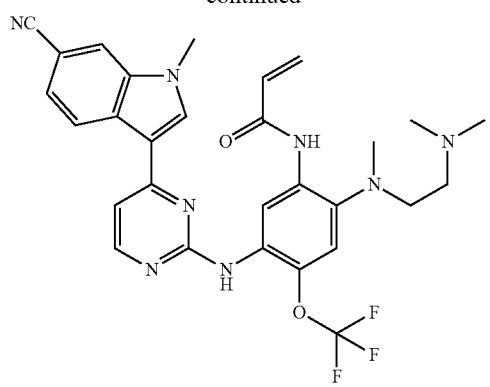
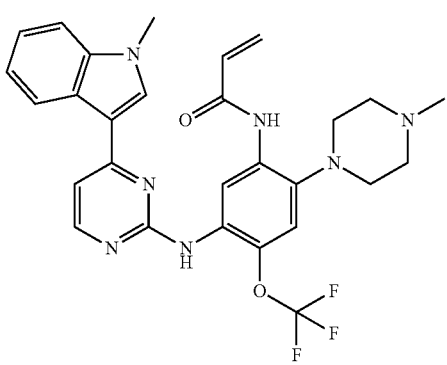
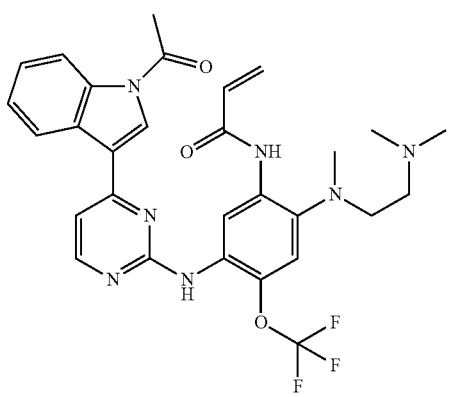
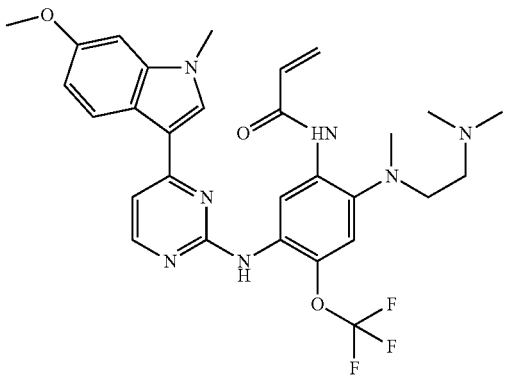
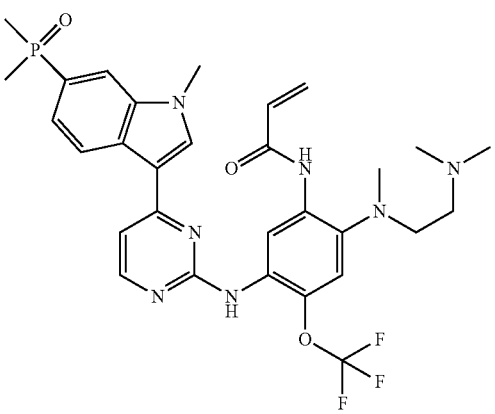
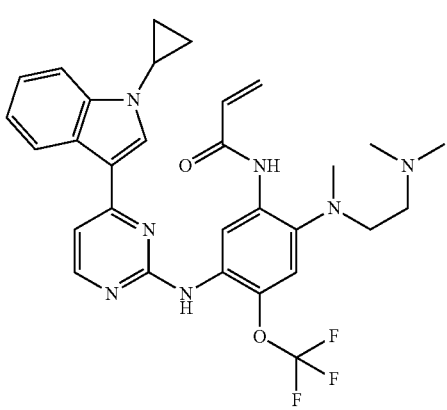
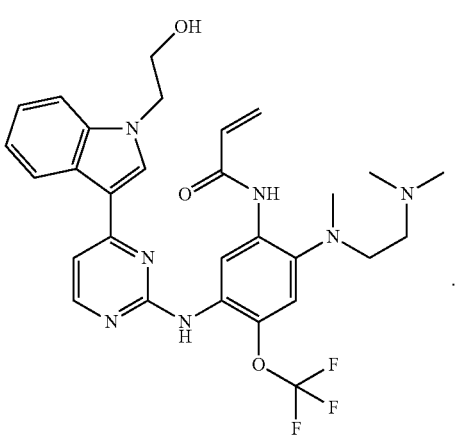 [SMILES: C=CC(=O)Nc1cc(Nc2nccc(-c3cn(CCO)c4ccccc34)n2)c(OC(F)(F)F)cc1N(C)CCN(C)C]
In a more preferred embodiment, the compound of formula (I), the stereoisomer or the pharmaceutically acceptable salt thereof is a compound of formula (IVA1-3):

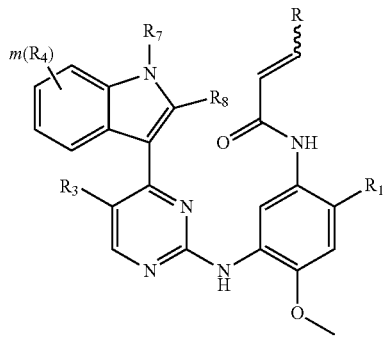

(IVA1-3)

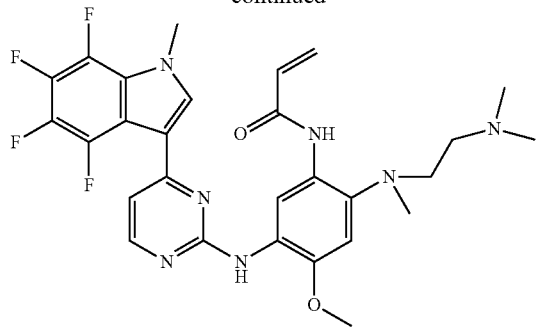

wherein R, $R_1$, $R_3$, $R_4$, $R_6$, $R_7$, $R_8$, $R_9$, $R_{10}$, $R_{11}$, $R_{12}$, m, r and q are as defined in the compound of formula (I).

In a more preferred embodiment, in the compound of formula (I), the stereoisomer or the pharmaceutically acceptable salt thereof, R, $R_1$, $R_3$, $R_4$, $R_6$, $R_7$, $R_8$, $R_9$, $R_{10}$, $R_{11}$, $R_{12}$, m, r and q are as defined in the compound of formula (I), provided that when both $R_7$ and $R_8$ are hydrogen, m is 3 or 4; or when one of $R_7$ and $R_8$ is hydrogen, m is 2, 3 or 4; or when both $R_7$ and $R_8$ are not hydrogen, m is 1, 2, 3 or 4.

In a more preferred embodiment, in the compound of formula (I), the stereoisomer or the pharmaceutically acceptable salt thereof, $R_3$ is selected from the group consisting of hydrogen, fluorine, chlorine, methyl, cyclopropyl and trifluoromethyl; and R, $R_1$, $R_4$, $R_6$, $R_7$, $R_8$, $R_9$, $R_{10}$, $R_{11}$, $R_{12}$, m, r and q are as defined in the compound of formula (I), provided that when both $R_7$ and $R_8$ are hydrogen, in is 3 or 4; or when one of $R_7$ and $R_8$ is hydrogen, in is 2, 3 or 4; or when both $R_7$ and $R_8$ are not hydrogen, m is 1, 2, 3 or 4.

In the most preferred embodiment, the compound of formula (I), the stereoisomer or the pharmaceutically acceptable salt thereof is selected from the group consisting of:

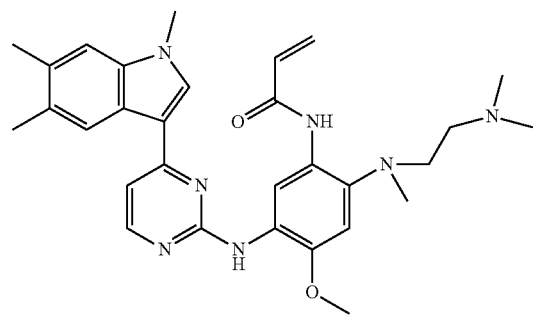

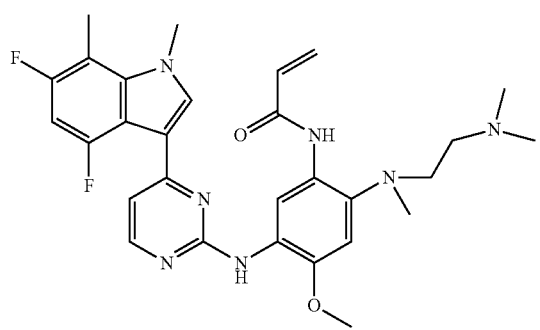

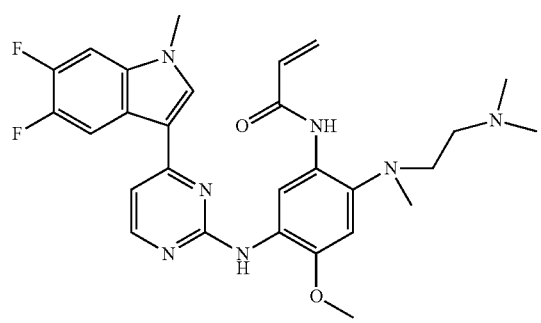

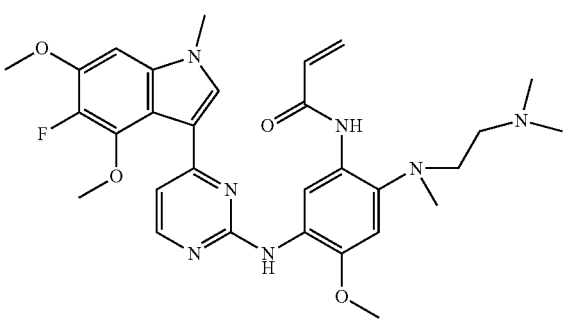

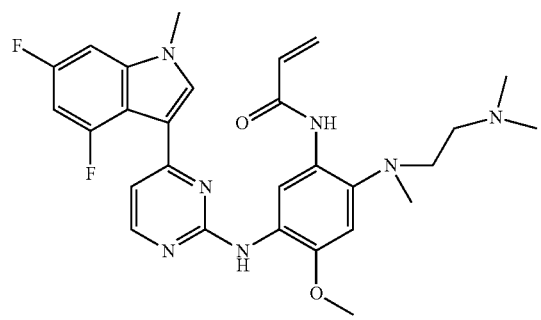

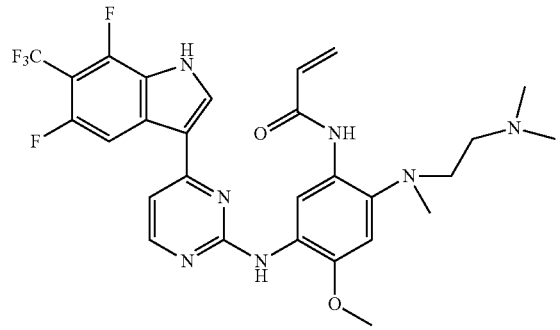

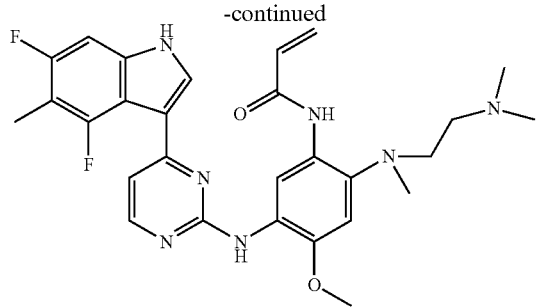
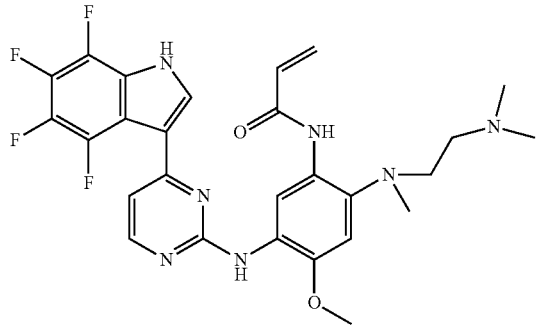
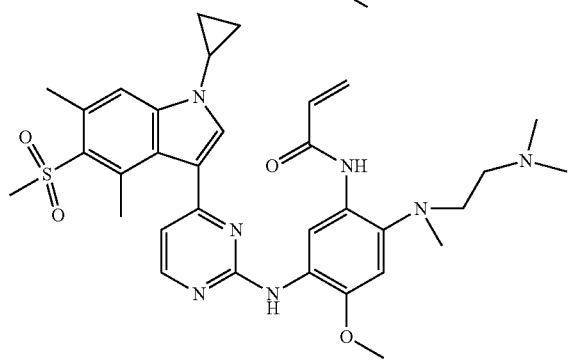
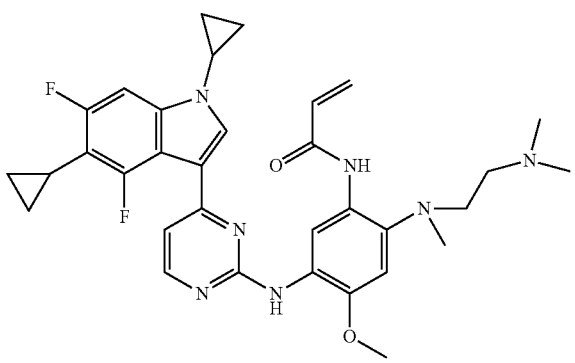
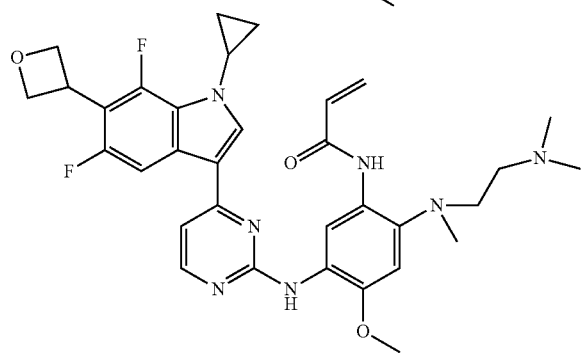

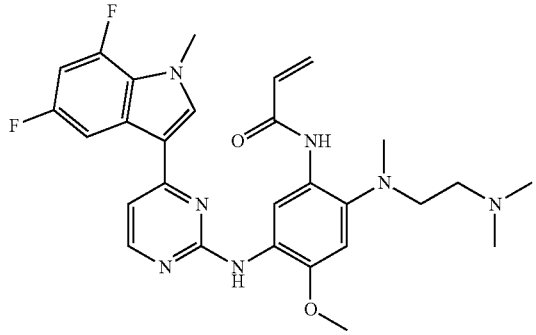
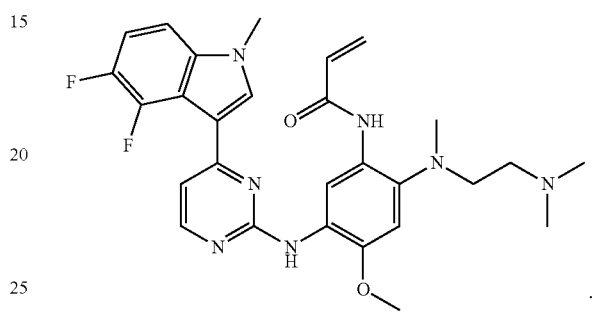

In a more preferred embodiment, in the compound of formula (I), the stereoisomer or the pharmaceutically acceptable salt thereof, wherein m is 2, 3 or 4, when $R_3$ is selected from the group consisting of hydrogen, fluorine, chlorine, methyl, cyclopropyl and trifluoromethyl; two $R_4$ are taken together with the carbon atoms of the attached benzene ring to form a 5- to 7-membered carbocycle, 5- to 7-membered heterocycle, $C_{5-7}$ aryl or 5- to 7-membered heteroaryl, wherein the 5- to 7-membered carbocycle, 5- to 7-membered heterocycle, $C_{5-7}$ aryl and 5- to 7-membered heteroaryl are selected from the group consisting of:

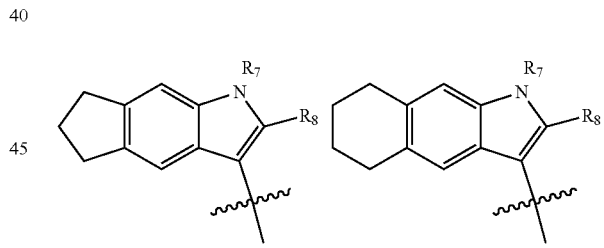
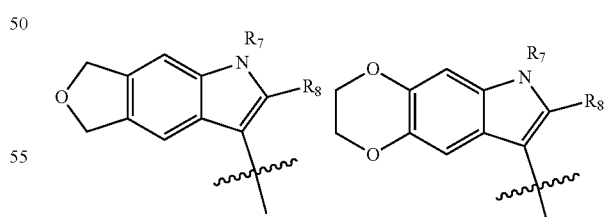
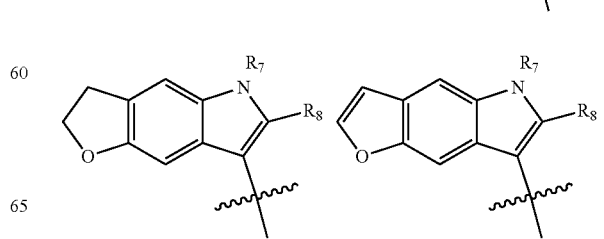

-continued

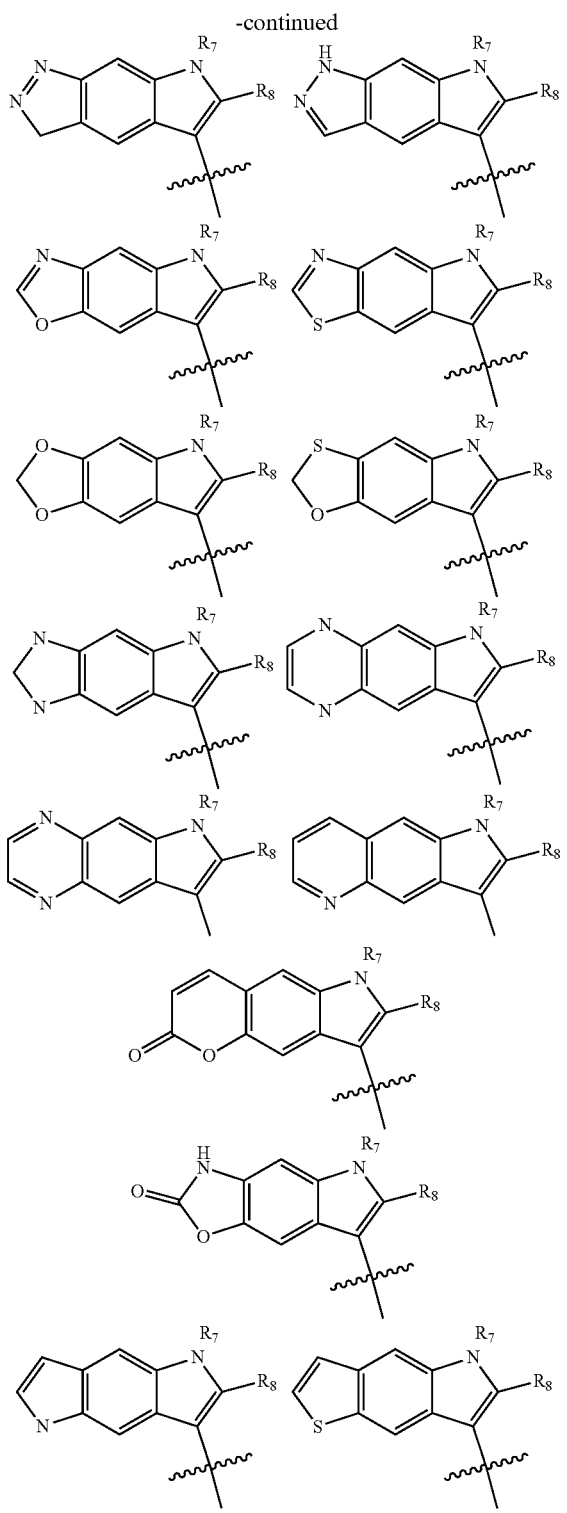

wherein the 5- to 7-membered carbocycle, 5- to 7-membered heterocycle, $C_{5-7}$ aryl and 5- to 7-membered heteroaryl are each optionally substituted by one or more groups selected from the group consisting of halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, —$C_{0-8}$—S(O)r$R_9$, —$C_{0-8}$—O—$R_{10}$, —$C_{0-8}$—C(O)$R_{10}$, —$C_{0-8}$—C(O)O$R_{10}$, —$C_{0-8}$—O—C(O)$R_{10}$, —$C_{0-8}$—N$R_7R_8$, —$C_{0-8}$—C(O)N$R_7R_8$, —N($R_7$)—C(O)$R_{10}$ and —N($R_7$)—C(O)O$R_{10}$; and R, $R_1$, $R_6$, $R_7$, $R_8$, $R_9$, $R_{10}$, $R_{11}$, $R_{12}$, m, r and q are as defined in the compound of formula (I).

In a more preferred embodiment, in the compound of formula (I), the stereoisomer or the pharmaceutically acceptable salt thereof, when both $R_7$ and $R_8$ are hydrogen, m is 1 or 2; or when one of $R_7$ and $R_8$ is hydrogen, m is 0 or 1; or when both $R_7$ and $R_8$ are not hydrogen, m is 0, 1 or 2; $R_3$ is selected from the group consisting of hydrogen, fluorine, chlorine, methyl, cyclopropyl and trifluoromethyl;

$R_4$ is selected from the group consisting of hydrogen, deuterium, halogen, hydroxy, sulthydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, —$C_{0-8}$—P(O)$R_{11}R_{12}$, —$C_{0-8}$—S(O)r$R_9$, —$C_{0-8}$—O—$R_{10}$, —$C_{0-8}$—C(O)$R_{10}$, —$C_{0-8}$—C(O)O$R_{10}$, —$C_{0-8}$—O—C(O)$R_{10}$, —$C_{0-8}$—N$R_7R_8$, —$C_{0-8}$—C(O)N$R_7R_8$, —N($R_7$)—C(O)$R_{10}$ and —N($R_7$)—C(O)O$R_{10}$;

wherein the $C_{1-8}$ alkyl, $C_{3-8}$ cycloalkyl, 3- to 8-membered heterocyclyl, $C_{5-10}$ aryl, 5- to 10-membered heteroaryl, 5- to 7-membered carbocycle, 5- to 7-membered heterocycle, $C_{5-7}$ aryl and 5- to 7-membered heteroaryl are each optionally substituted by one or more groups selected from the group consisting of halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, —$C_{0-8}$—S(O)r$R_9$, —$C_{0-8}$—O—$R_{10}$, —$C_{0-8}$—C(O)$R_{10}$, —$C_{0-8}$—C(O)O$R_{10}$, —$C_{0-8}$—O—C(O)$R_{10}$, —$C_{0-8}$—N$R_7R_8$, —$C_{0-8}$—C(O)N$R_7R_8$, —N($R_7$)—C(O)$R_{10}$ and —N($R_7$)—C(O)O$R_{10}$; and R, $R_1$, $R_6$, $R_7$, $R_8$, $R_9$, $R_{10}$, $R_{11}$, $R_{12}$, m, r and q are as defined in the compound of formula (I).

In a more preferred embodiment, in the compound of formula (I), the stereoisomer or the pharmaceutically acceptable salt thereof, $R_3$ is selected from the group consisting of hydrogen, fluorine, chlorine and trifluoromethyl: $R_4$ is selected from the group consisting of hydrogen, deuterium, halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, —$C_{0-8}$—S(O)r$R_9$, —$C_{0-8}$—O—$R_{10}$, —$C_{0-8}$—C(O)$R_{10}$, —$C_{0-8}$—C(O)O$R_{10}$, —$C_{0-8}$—O—C(O)$R_{10}$, —$C_{0-8}$—N$R_7R_8$, —$C_{0-8}$—C(O)N$R_7R_8$, —N($R_7$)—C(O)$R_{10}$ and —N($R_7$)—C(O)O$R_{10}$;

R, $R_1$, $R_6$, $R_7$, $R_8$, $R_9$, $R_{10}$, $R_{11}$, $R_{12}$, r and q are as defined in the compound of formula (I); and in is as defined above.

In a more preferred embodiment, in the compound of formula (I), the stereoisomer or the pharmaceutically acceptable salt thereof, $R_3$ is selected from the group consisting of hydrogen, fluorine, chlorine and trifluoromethyl; $R_4$ is selected from the group consisting of hydrogen, deuterium, hydroxy, cyano, $C_{2-8}$ alkenyl, $C_{2-8}$ alkynyl, $C_{3-8}$ cycloalkyl, 3- to 8-membered heterocyclyl, 3- to 8-membered heterocyclyloxy, $C_{5-10}$ aryl, $C_{5-10}$ aryloxy, 5- to 10-membered heteroaryl, 5- to 10-membered heteroaryloxy, —C$_{0-8}$—O—R$_{10}$, —C$_{0-8}$—C(O)OR$_{10}$, —C$_{0-8}$—O—C(O)R$_{10}$, —C$_{0-8}$—NR$_7$R$_8$, and —C$_{0-8}$—C(O)NR$_7$R$_8$;

R, R$_1$, R$_6$, R$_7$, R$_8$, R$_9$, R$_{10}$, R$_{11}$, R$_{12}$ and q are as defined in the compound of formula (I); and m is as defined above.

In a more preferred embodiment, in the compound of formula (I), the stereoisomer or the pharmaceutically acceptable salt thereof, R$_3$ is selected from the group consisting of hydrogen, fluorine, chlorine and trifluoromethyl; R$_4$ is selected from the group consisting of hydrogen, deuterium, hydroxy, cyano, ethenyl, ethynyl, cyclopropyl, cyclobutyl, oxetan-3-yl, N—R$_6$-azetidin-3-yl, cyclopropyloxy, cyclobutyloxy, phenyl, phenoxy, —C$_{0-8}$—O—R$_{10}$, —C$_{0-8}$—C(O)OR$_{10}$, —C$_{0-8}$—O—C(O)R$_{10}$, —C$_{0-8}$—NR$_7$R$_8$ and —C$_{0-8}$—C(O)NR$_7$R$_8$;

R, R$_1$, R$_6$, R$_7$, R$_8$, R$_9$, R$_{10}$, R$_{11}$, R$_{12}$ and q are as defined in the compound of formula (I); and m is as defined above.

In the most preferred embodiment, the compound of formula (I), the stereoisomer or the pharmaceutically acceptable salt thereof is selected from the group consisting of:

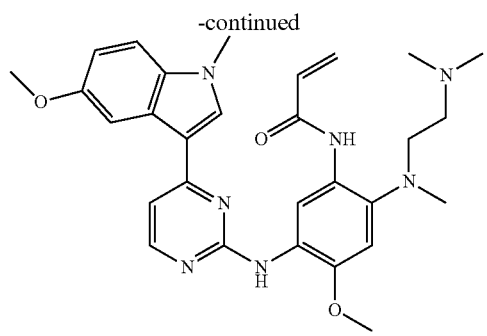

-continued

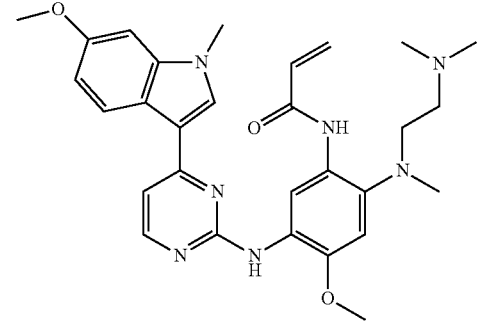

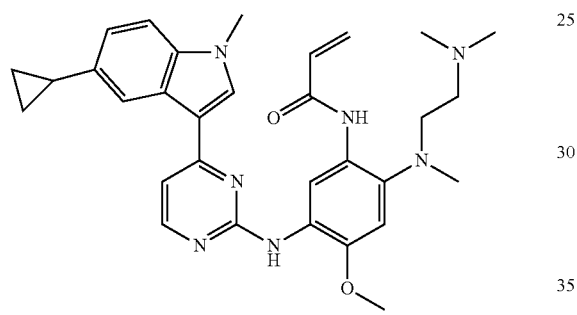

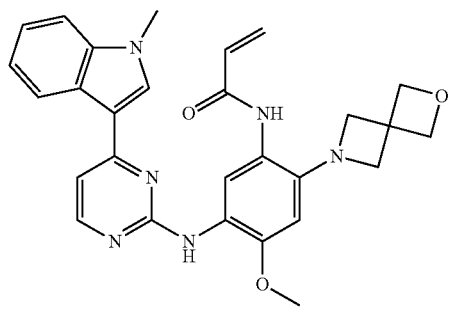

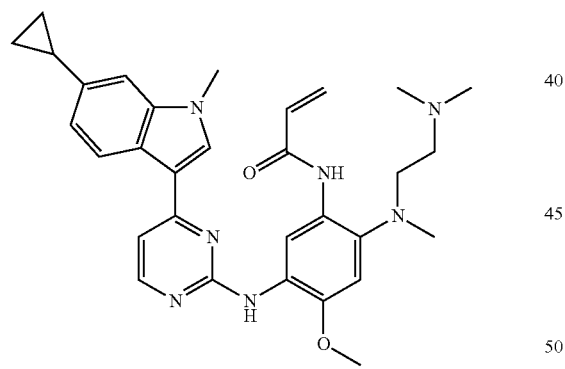

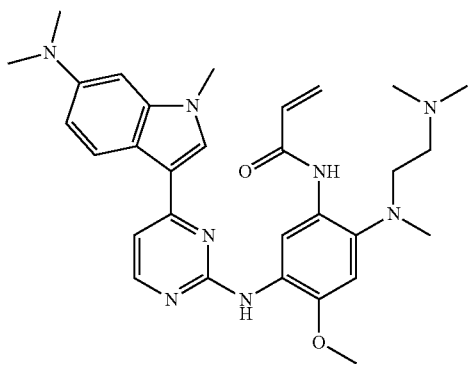

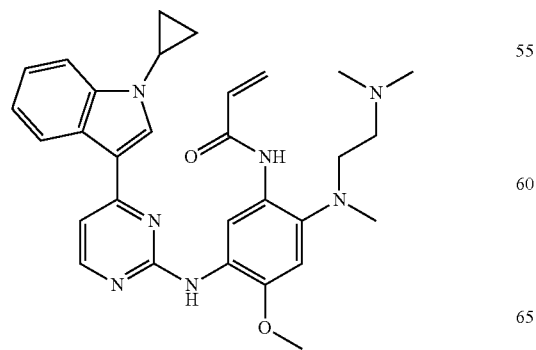

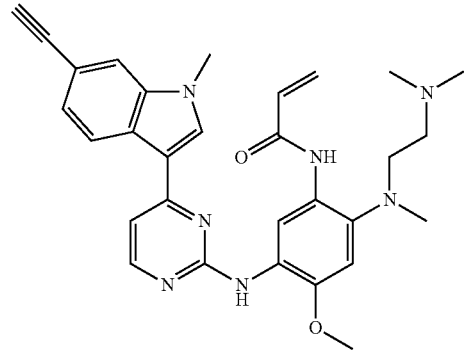

23
-continued
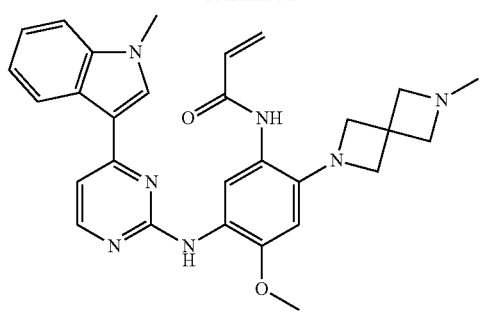
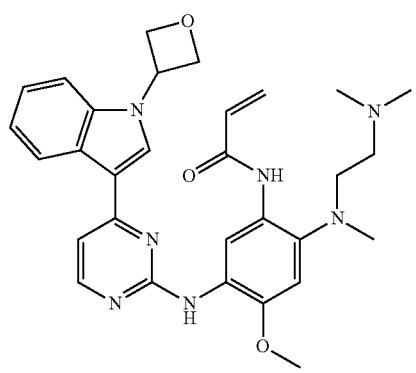
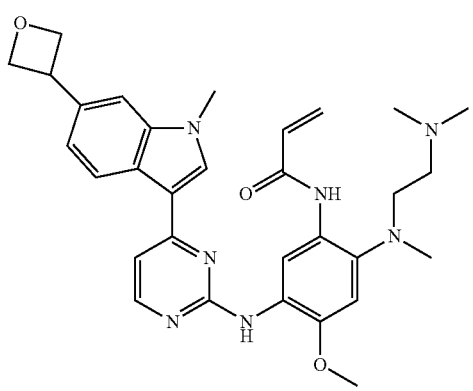
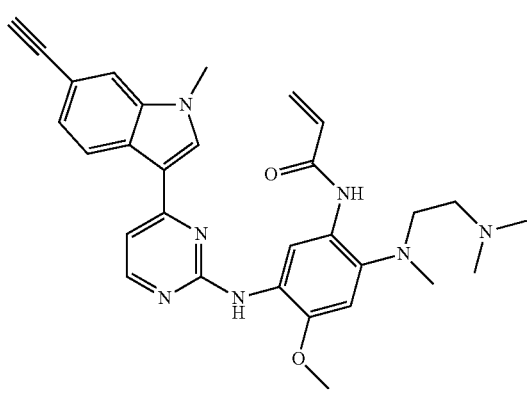
24
-continued
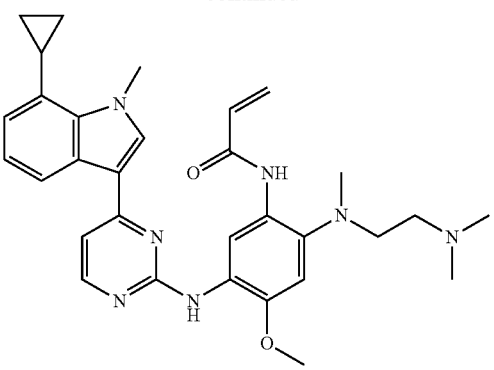
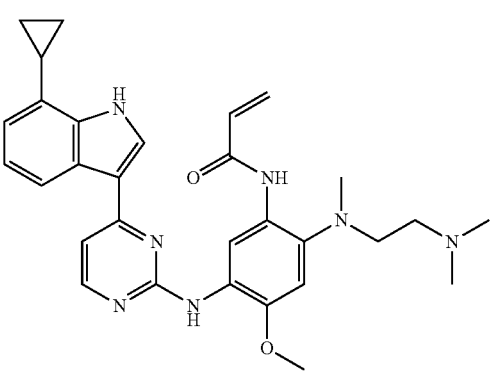
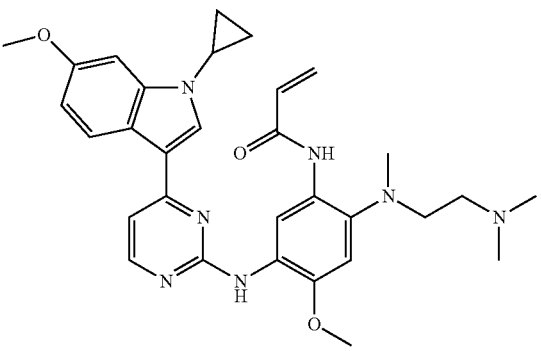
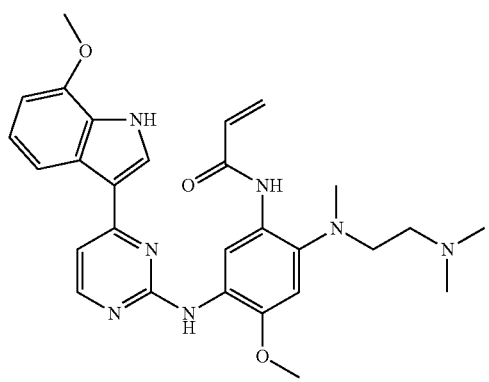

25
-continued
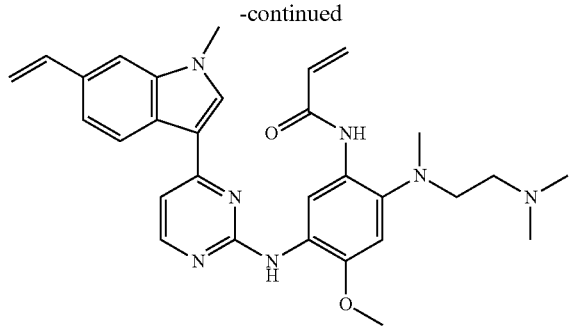
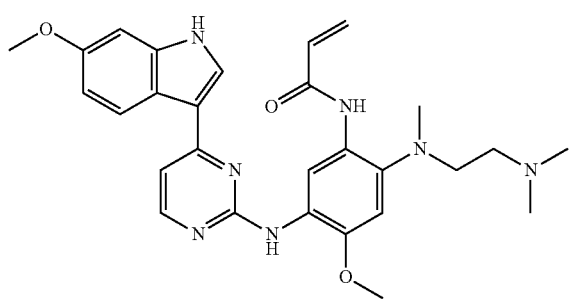
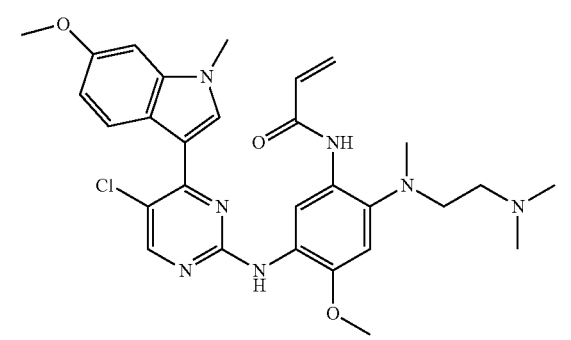
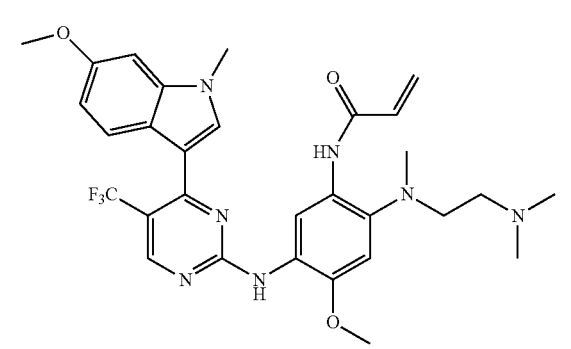
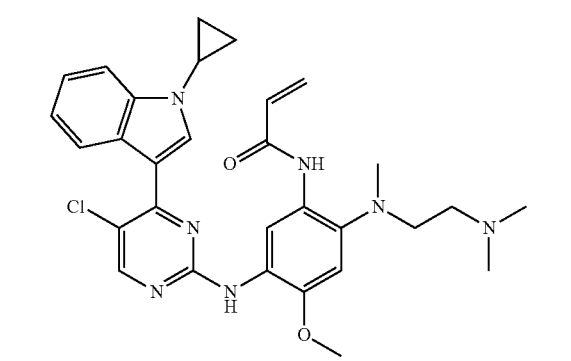
26
-continued
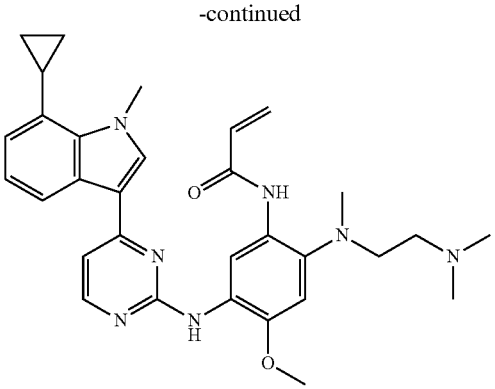
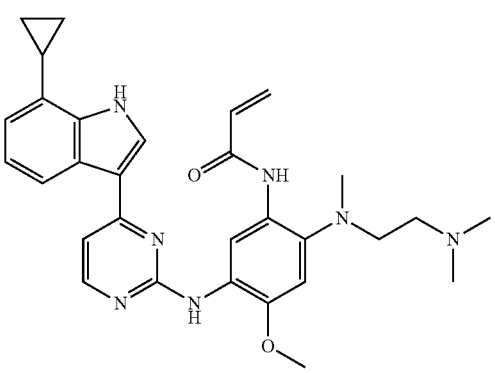
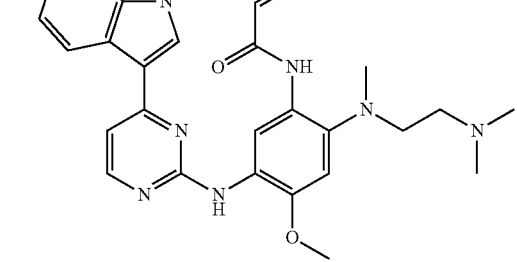
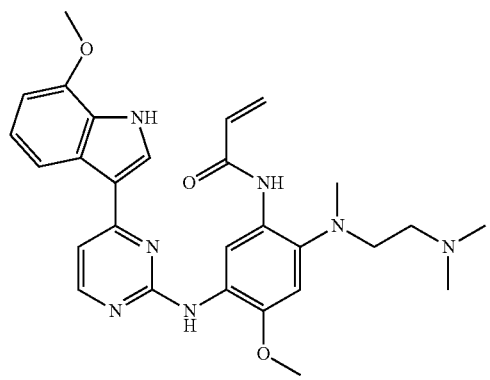

27
-continued
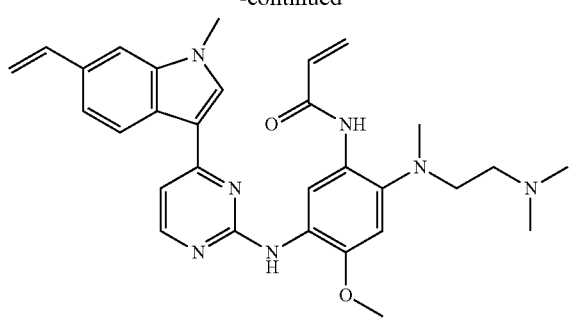
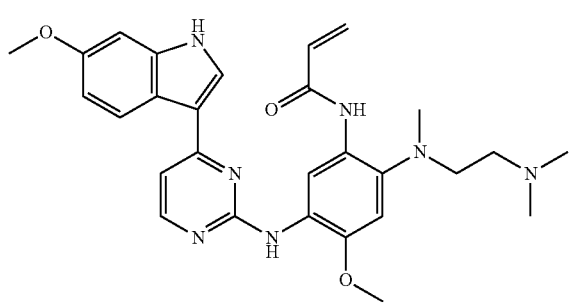
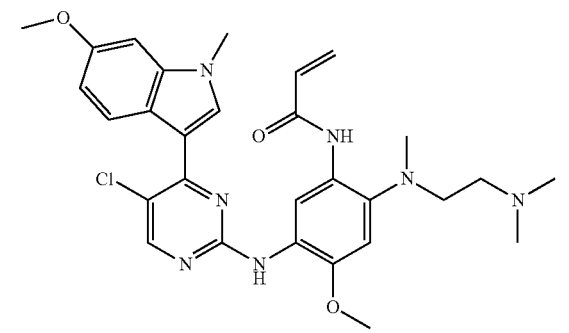
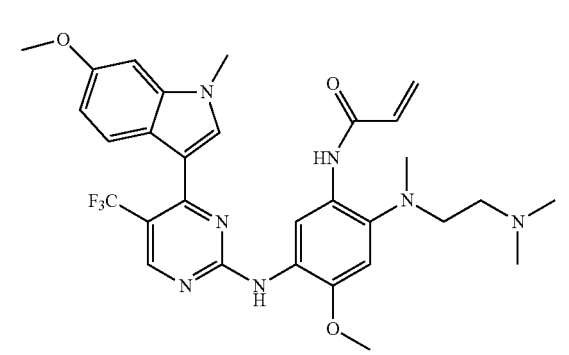
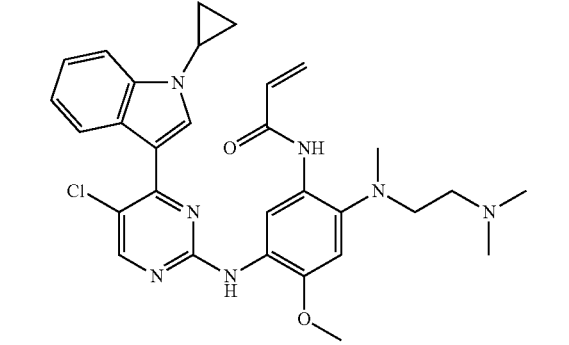
28
-continued
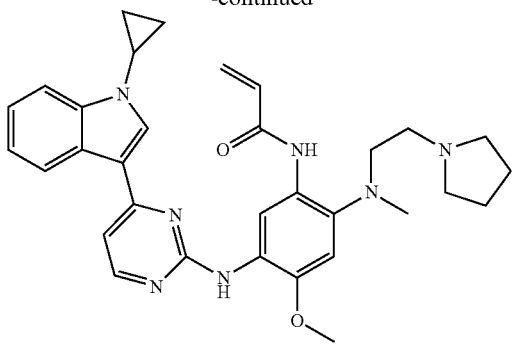
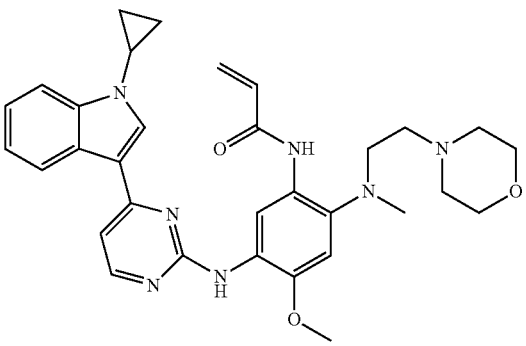
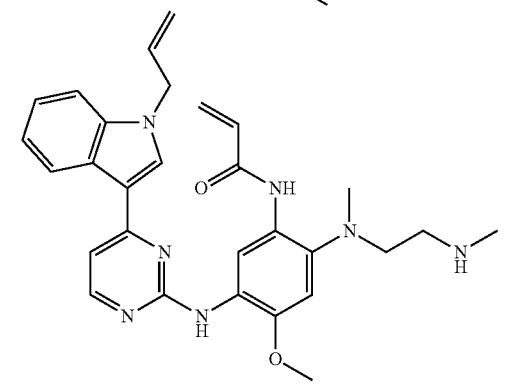
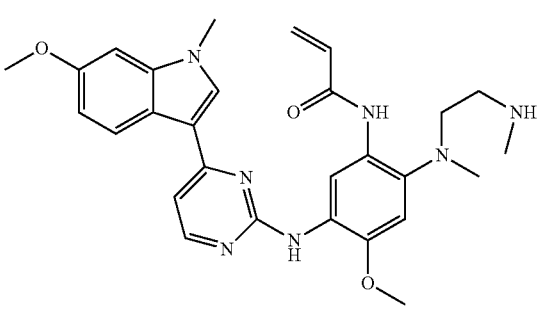
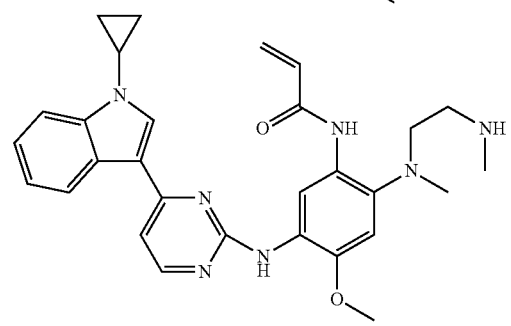

29
-continued
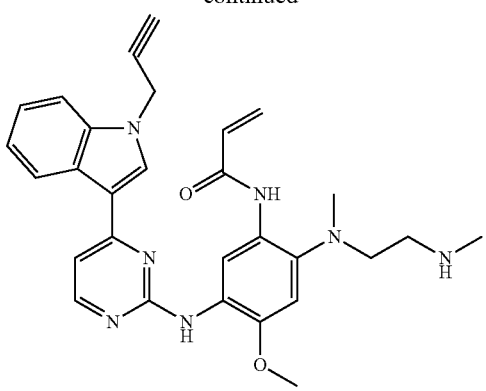
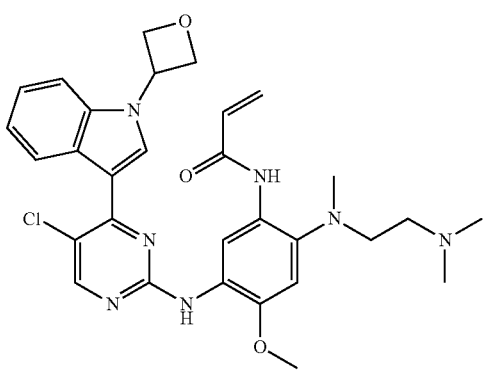
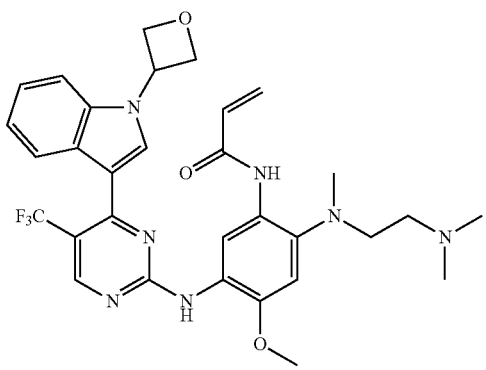
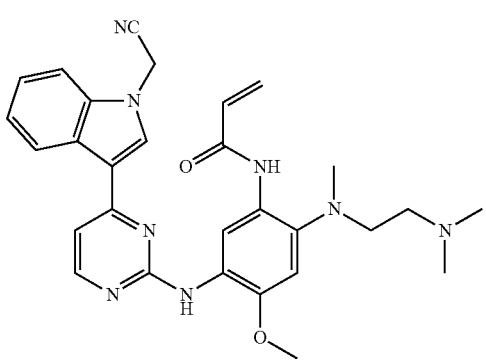
30
-continued
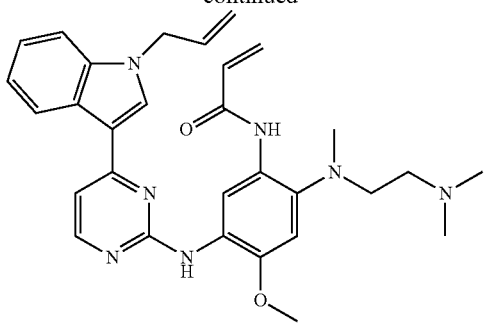
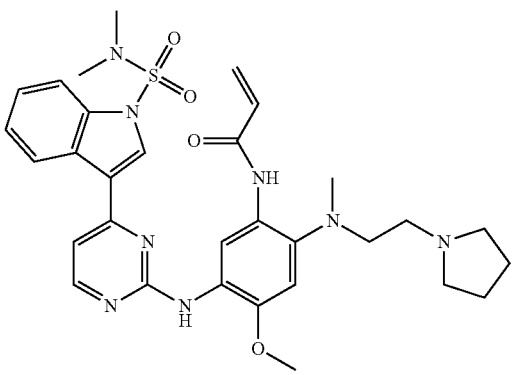
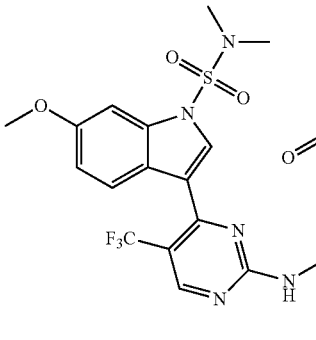
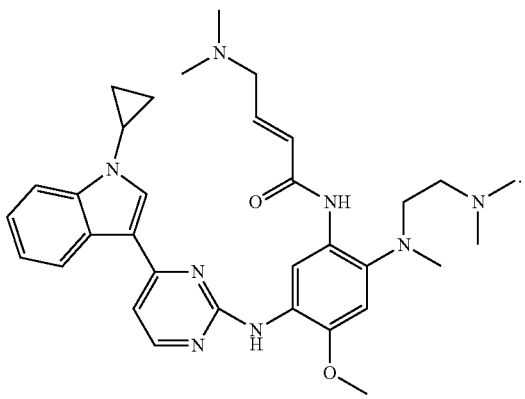
In a more preferred embodiment, the compound of formula (I), the stereoisomer or the pharmaceutically acceptable salt thereof is selected from the group consisting of a compound of formula (IIIA1-7), a compound of formula (IIIA1-8) and a compound of formula (IIIA1-9):

(IIIA1-7)

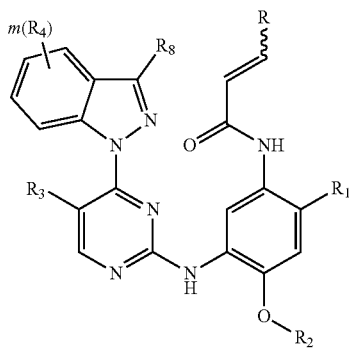

(IIIA1-8)

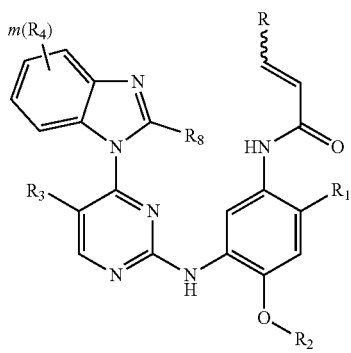

(IIIA1-9)

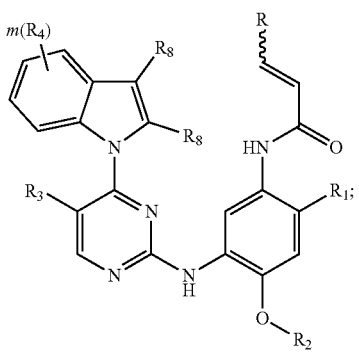

wherein $R_2$ is selected from the group consisting of methyl, difluoromethyl and trifluoromethyl; and R, $R_1$, $R_3$, $R_4$, $R_6$, $R_7$, $R_8$, $R_9$, $R_{10}$, $R_{11}$, $R_{12}$, m, r and q are as defined in the compound of formula (I).

In a more preferred embodiment, in the compound of formula (I), the stereoisomer or the pharmaceutically acceptable salt thereof, $R_2$ is selected from the group consisting of methyl, difluoromethyl and trifluoromethyl; $R_3$ is selected from the group consisting of hydrogen, fluorine, chlorine and trifluoromethyl; and R, $R_1$, $R_4$, $R_6$, $R_7$, $R_8$, $R_9$, $R_{10}$, $R_{11}$, $R_{12}$, m, r and q are as defined in the compound of formula (I).

In a more preferred embodiment, in the compound of formula (I), the stereoisomer or the pharmaceutically acceptable salt thereof, $R_1$ is selected from the group consisting of

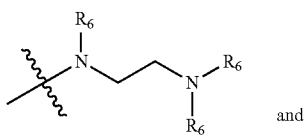

and

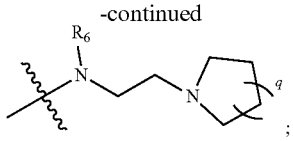

$R_2$ is selected from the group consisting of methyl, difluoromethyl and trifluoromethyl; $R_3$ is selected from the group consisting of hydrogen, fluorine, chlorine and trifluoromethyl; and R, $R_4$, $R_6$, $R_7$, $R_8$, $R_9$, $R_{10}$, $R_{11}$, $R_{12}$, m and r are as defined in the compound of formula (I).

In a more preferred embodiment, the compound of formula (I), the stereoisomer or the pharmaceutically acceptable salt thereof is selected from the group consisting of a compound of formula (IVA1-4) and a compound of formula (IVA1-5):

(IVA1-4)

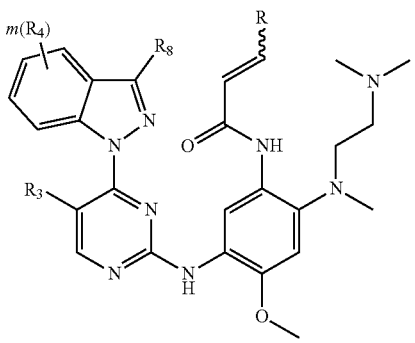

(IVA1-5)

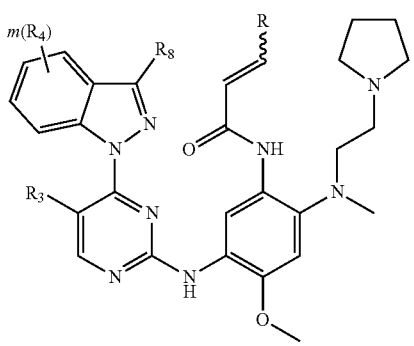

wherein $R_3$ is selected from the group consisting of hydrogen, fluorine, chlorine and trifluoromethyl; and R, $R_4$, $R_6$, $R_7$, $R_8$, $R_9$, $R_{10}$, $R_{11}$, $R_{12}$, m and r are as defined in the compound of formula (I).

In the most preferred embodiment, the compound of formula (I), the stereoisomer or the pharmaceutically acceptable salt thereof is selected from the group consisting of:

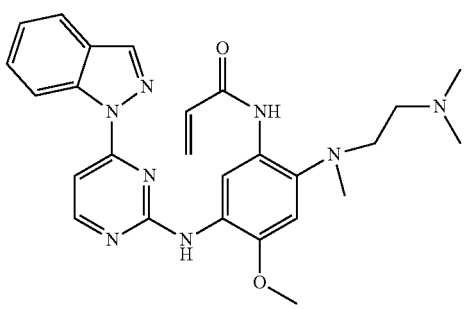

33
-continued
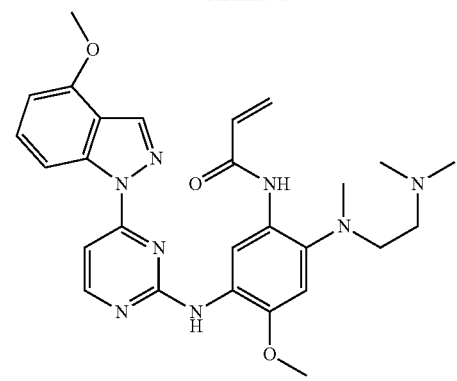
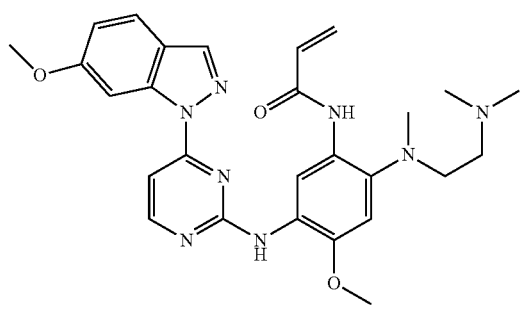
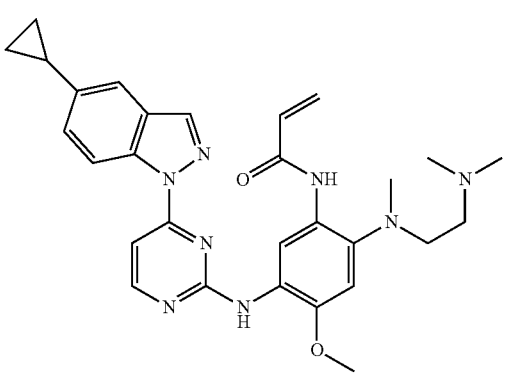
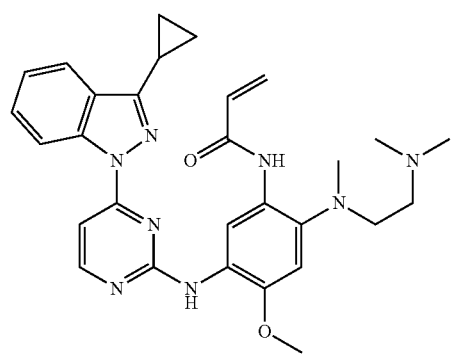
34
-continued
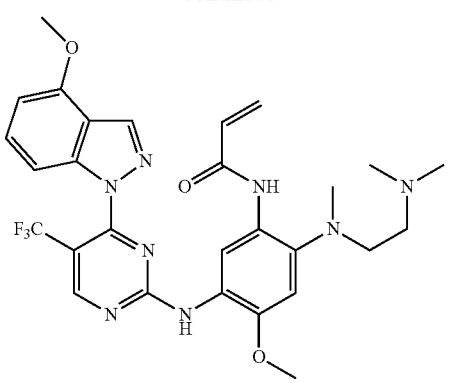
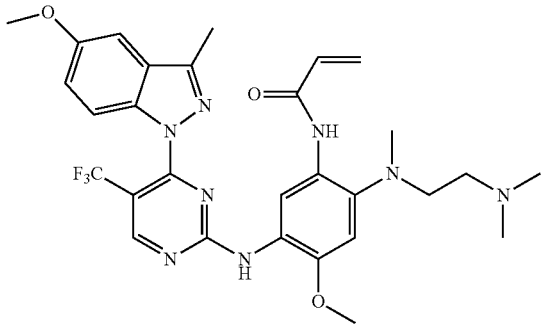
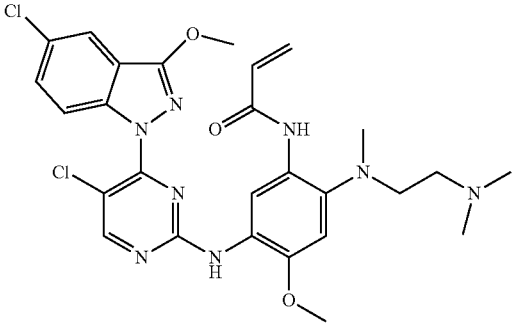
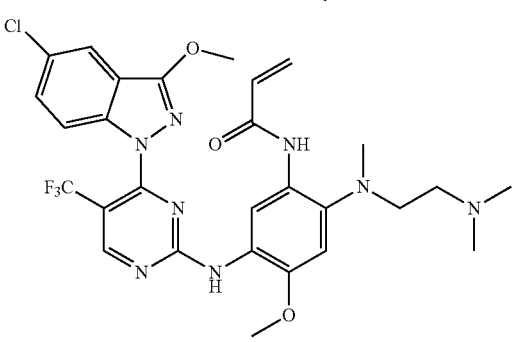
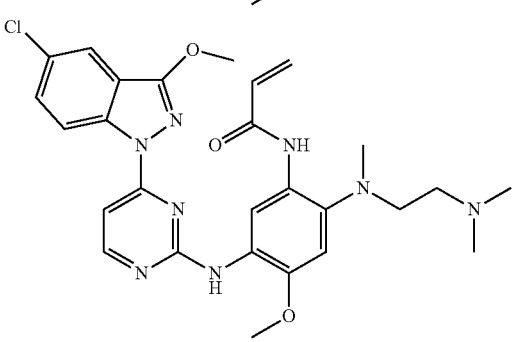

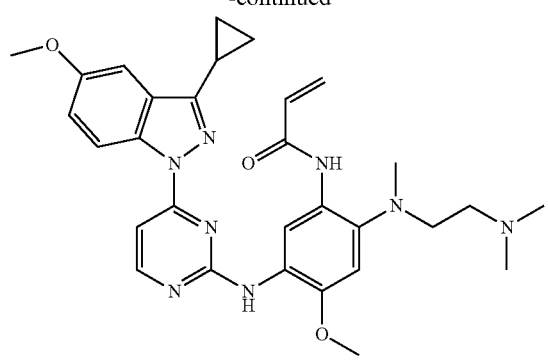
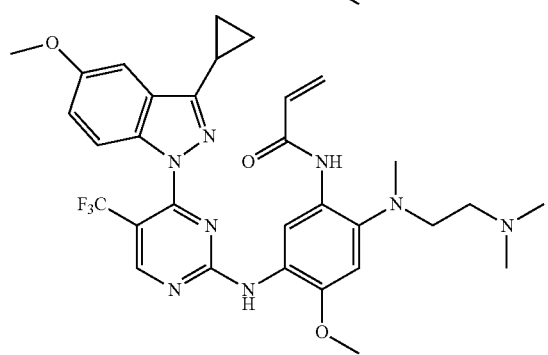
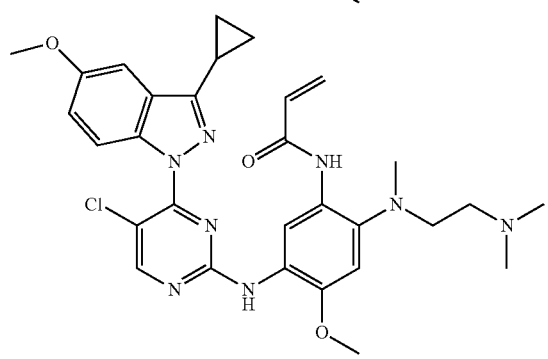
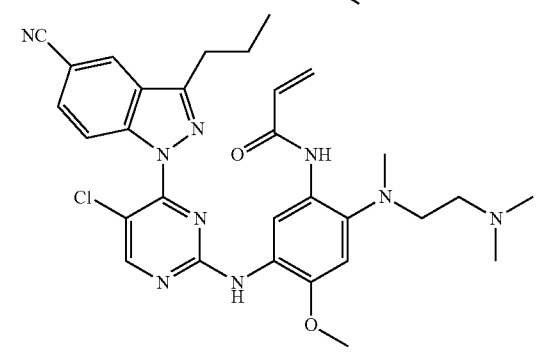
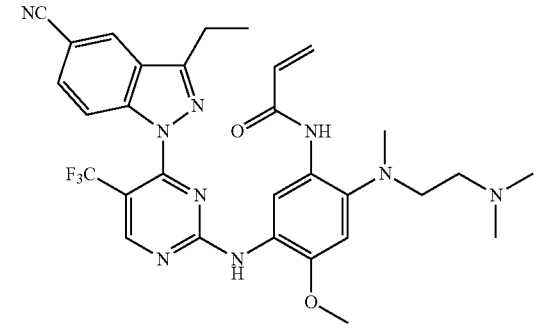
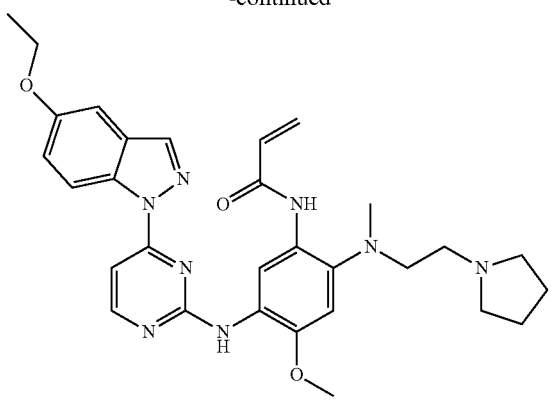
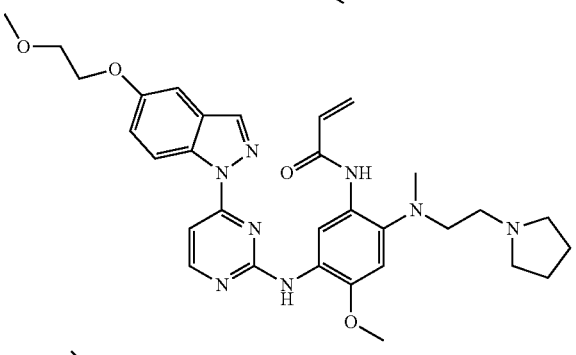
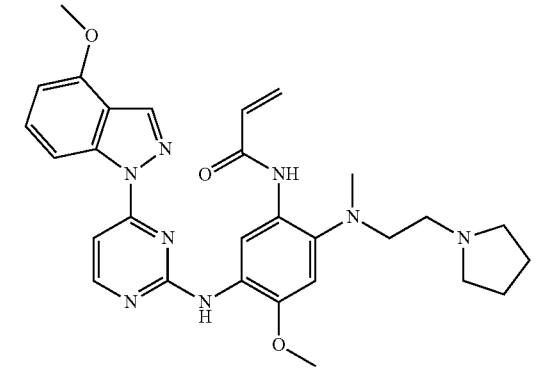
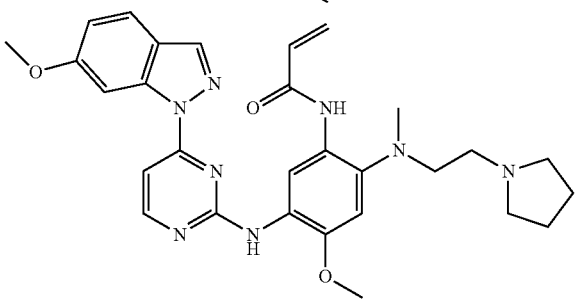
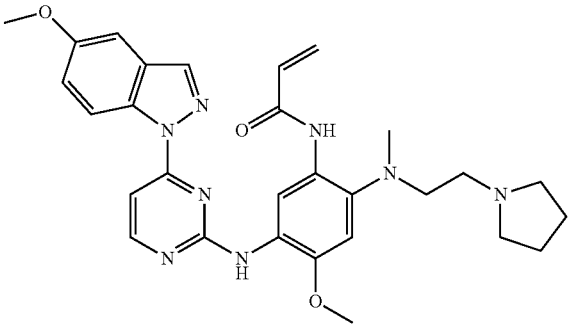

37
-continued
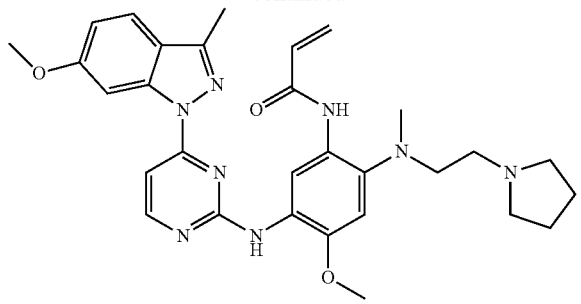
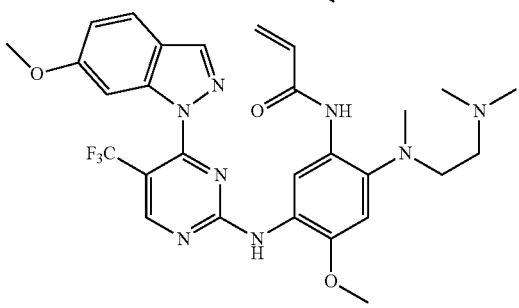
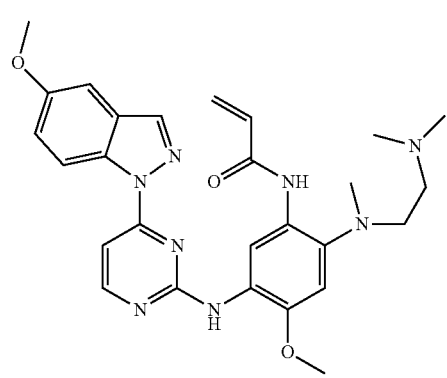
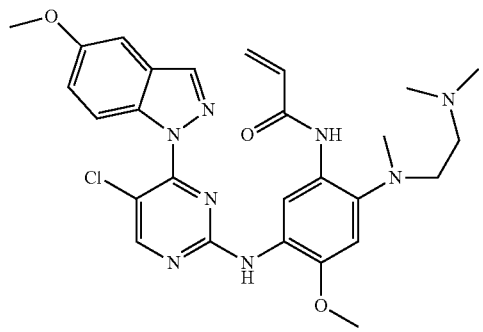
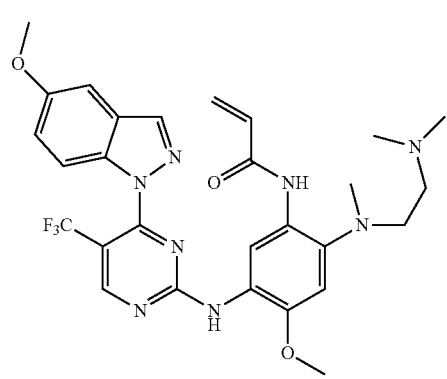
38
-continued
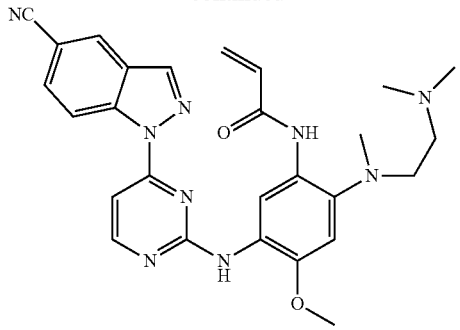
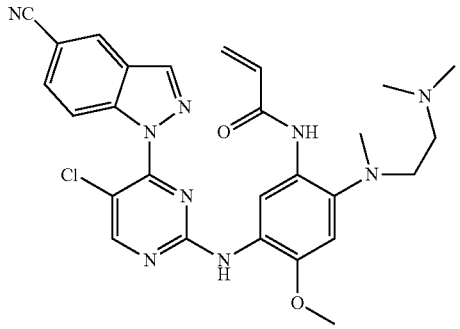
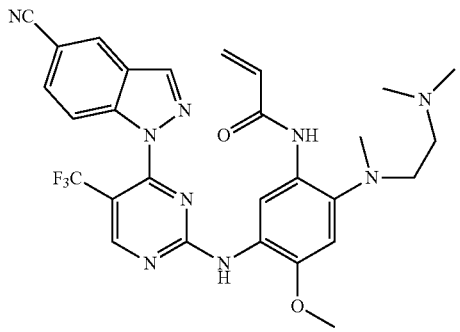
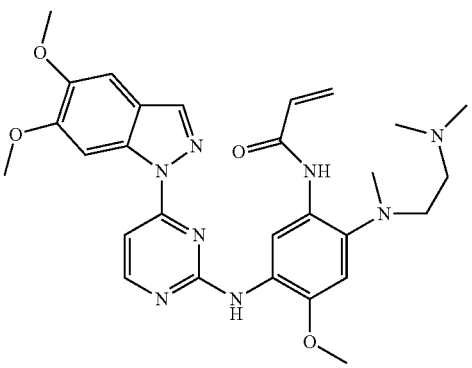
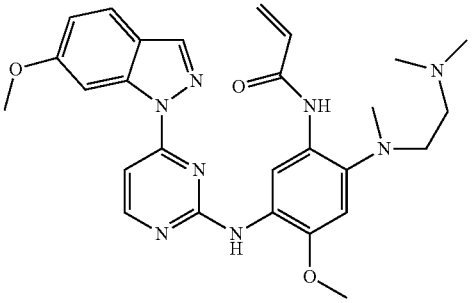

-continued

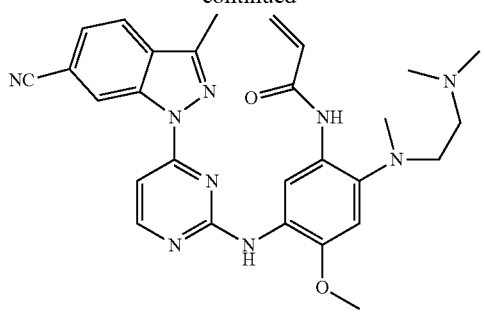

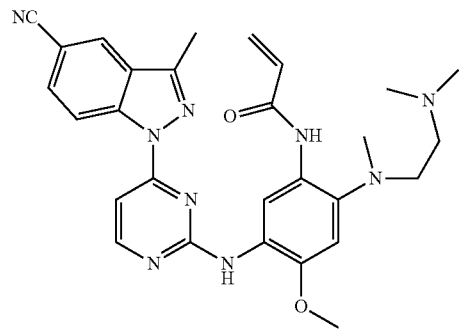

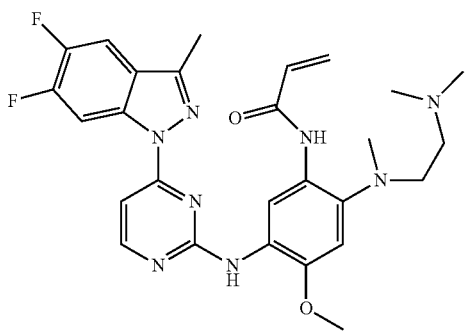

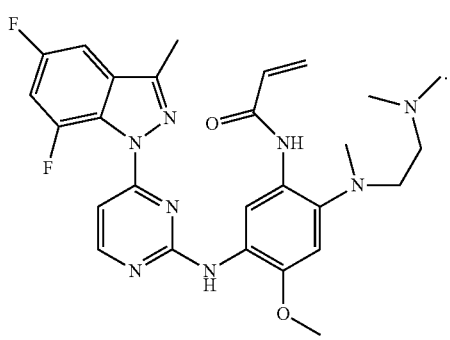

In a more preferred embodiment, the compound of formula (I), the stereoisomer or the pharmaceutically acceptable salt thereof is selected from the group consisting of a compound of formula (IVA1-6) and a compound of formula (IVA1-7):

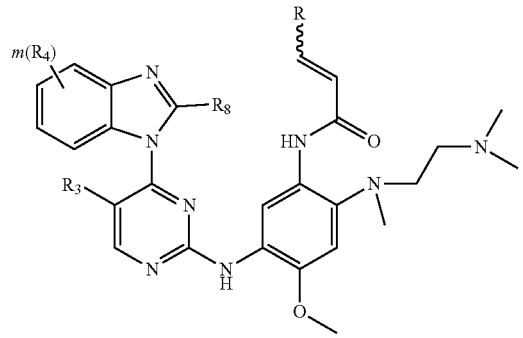
(IVA1-6)

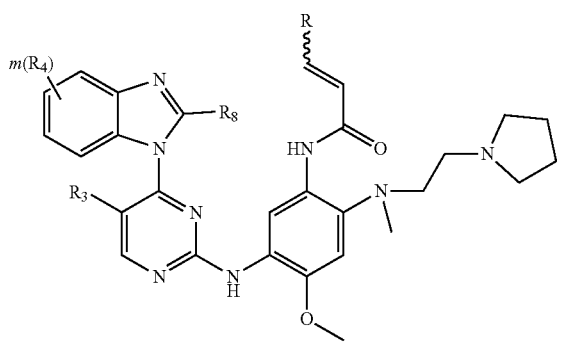
(IVA1-7)

wherein $R_3$ is selected from the group consisting of hydrogen, fluorine, chlorine and trifluoromethyl; and R, $R_4$, $R_6$, $R_7$, $R_8$, $R_9$, $R_{10}$, $R_{11}$, $R_{12}$, m and r are as defined in the compound of formula (I).

In the most preferred embodiment, the compound of formula (I), the stereoisomer or the pharmaceutically acceptable salt thereof is selected from the group consisting of:

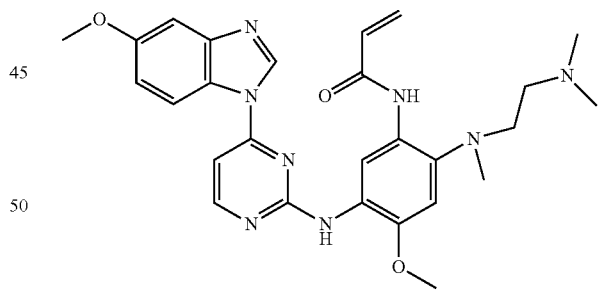

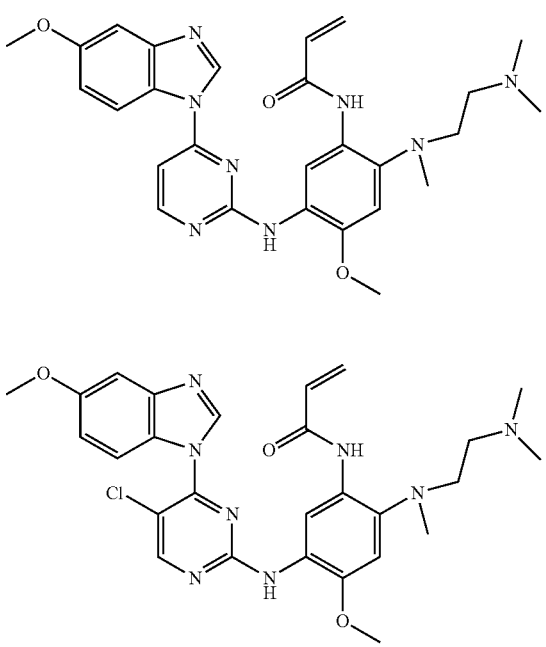

41
-continued
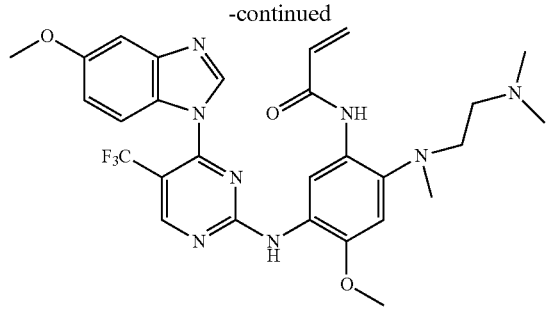
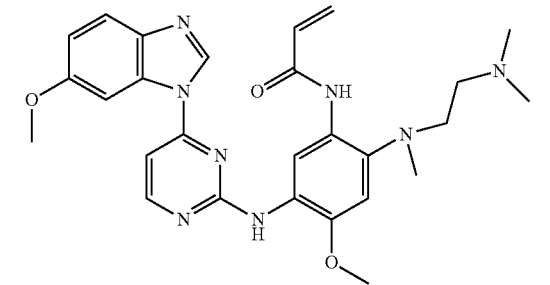
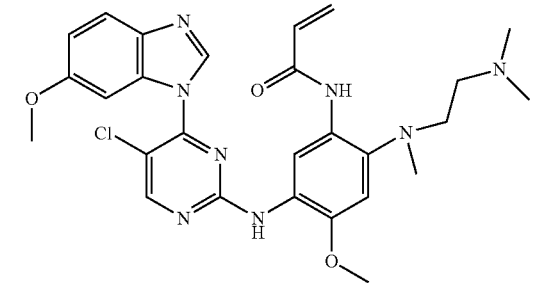
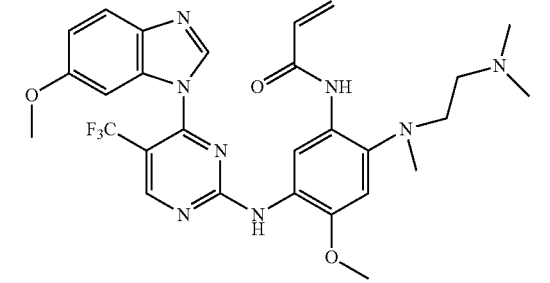
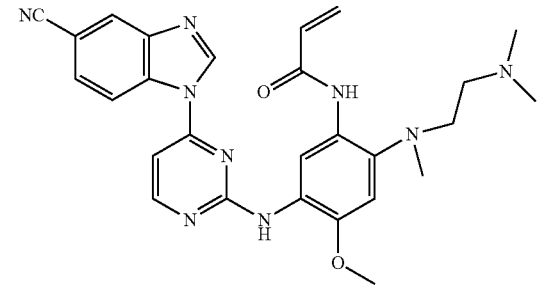
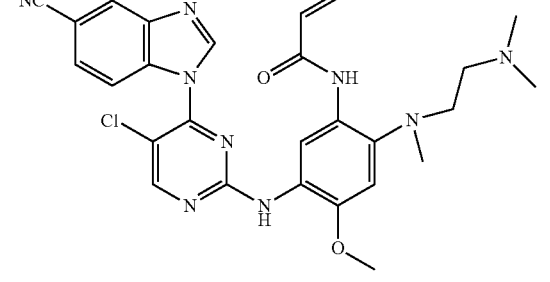
42
-continued
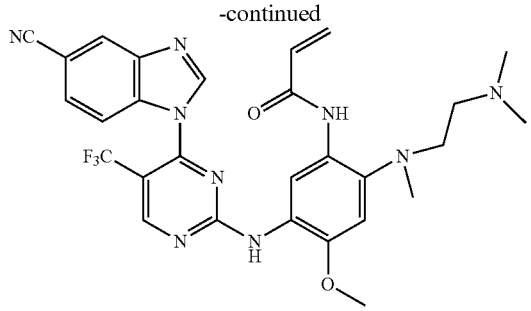
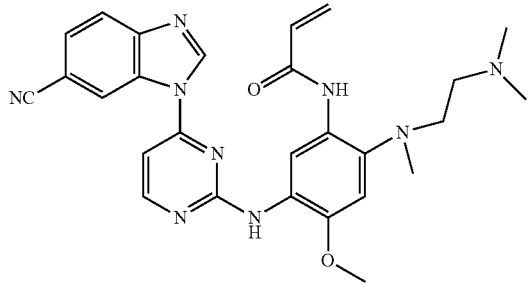
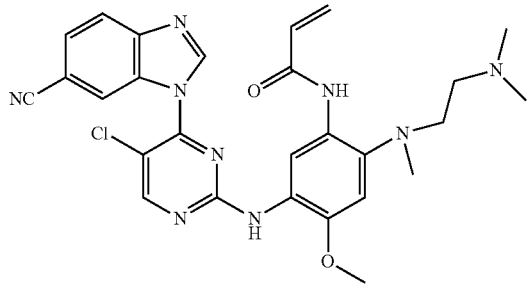
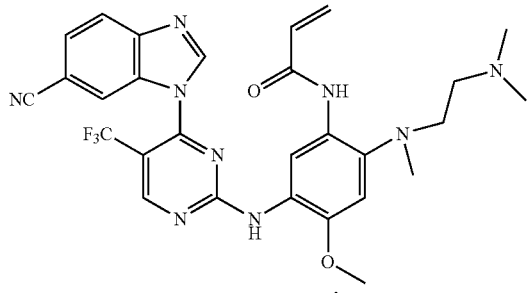
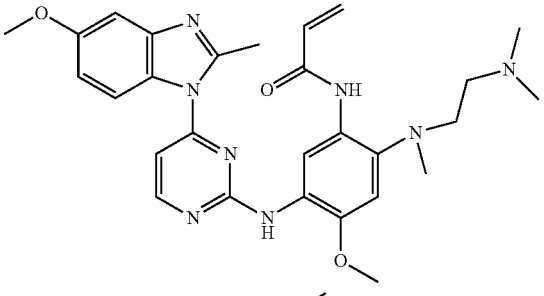
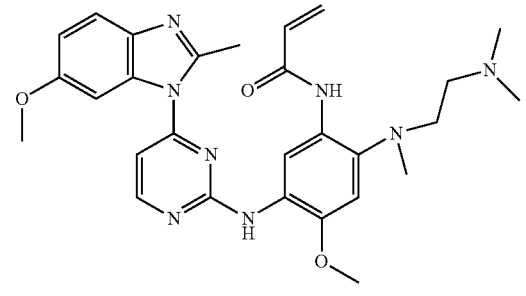

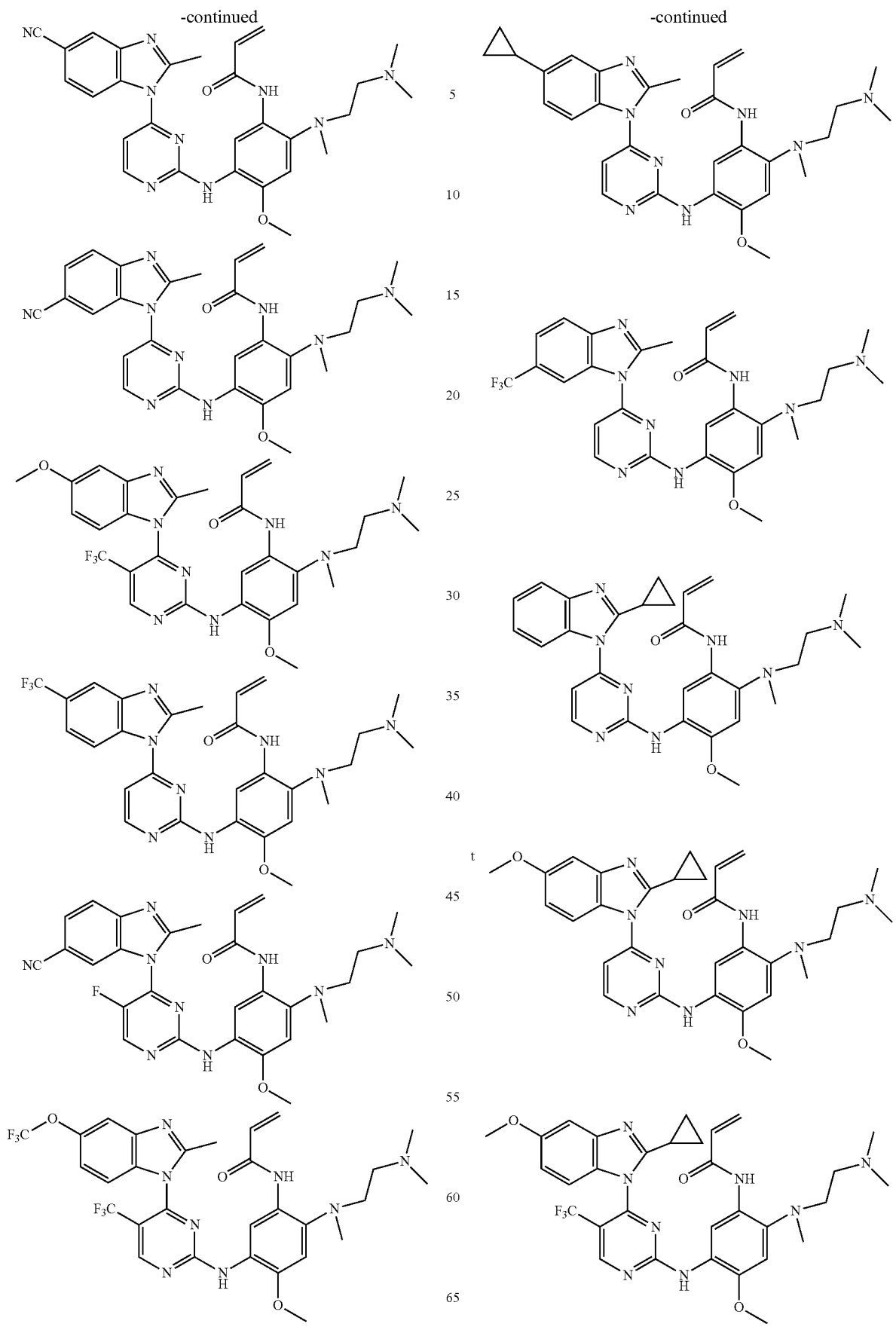

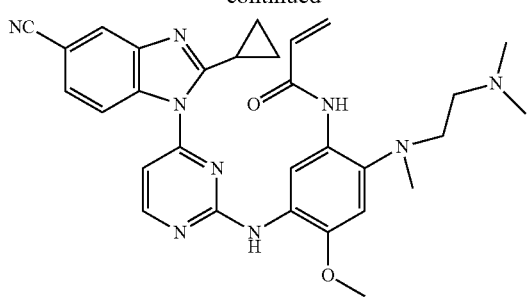
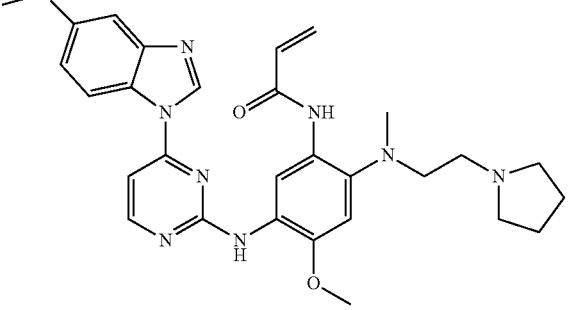
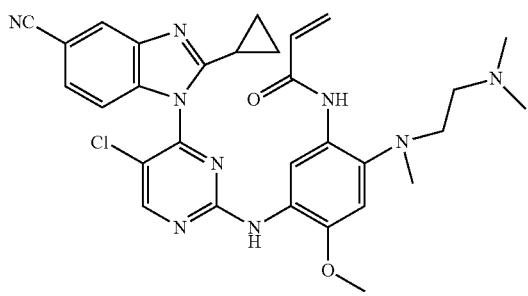
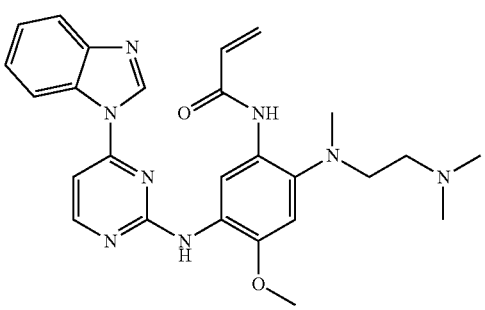
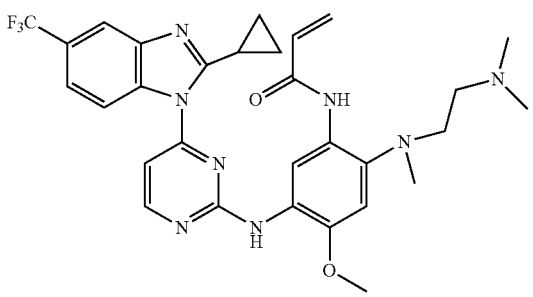
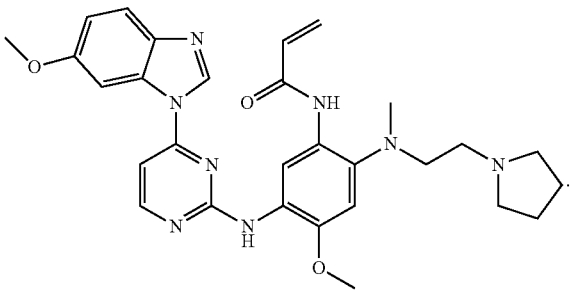
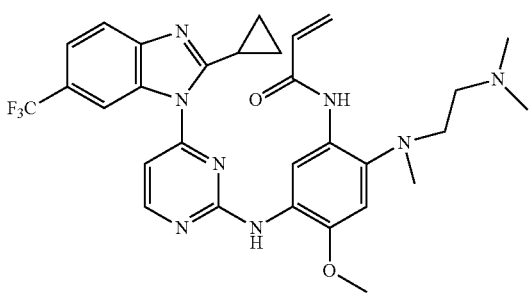
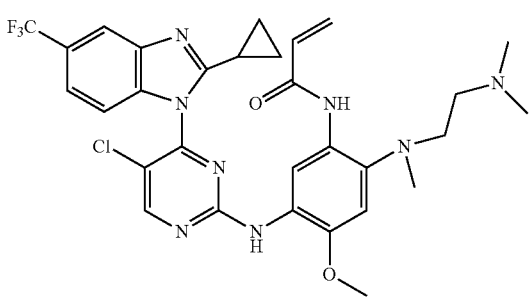
In a more preferred embodiment, the compound of formula (I), the stereoisomer or the pharmaceutically acceptable salt thereof is selected from the group consisting of a compound of formula (IIIA2-1), a compound of formula (IIIA2-2), a compound of formula (IIIA2-3), a compound of formula (IIIA2-4), a compound of formula (IIIA2-5) and a compound of formula (IIIA2-6):
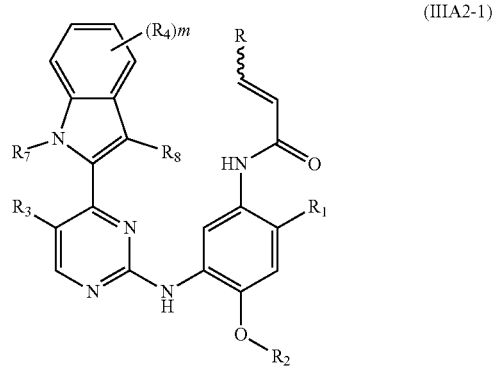
(IIIA2-1)

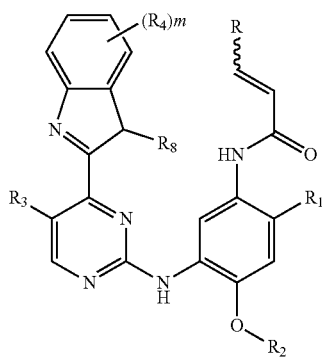

(IIIA2-2)

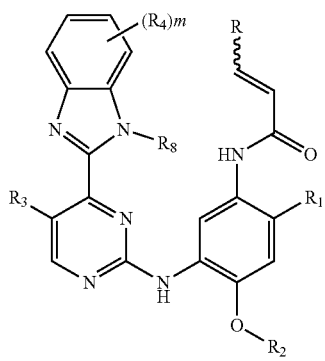

(IIIA2-3)

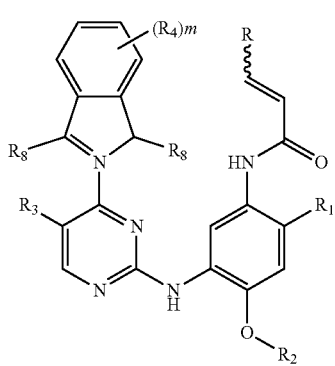

(IIIA2-4)

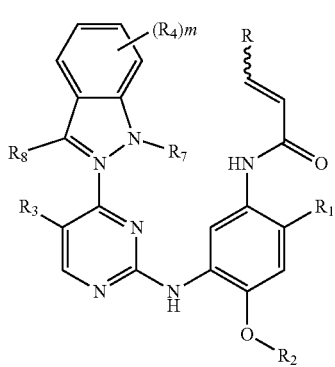

(IIIA2-5)

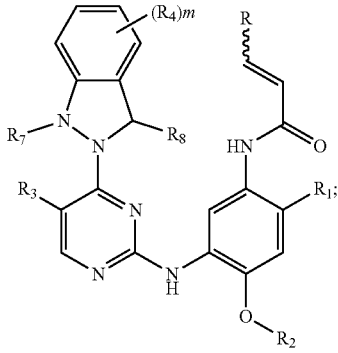

(IIIA2-6)

wherein $R_2$ is selected from the group consisting of methyl, difluoromethyl and trifluoromethyl; and R, $R_1$, $R_3$, $R_4$, $R_6$, $R_7$, $R_8$, $R_9$, $R_{10}$, $R_{11}$, $R_{12}$, m, r and q are as defined in the compound of formula (I).

In a more preferred embodiment, in the compound of formula (I), the stereoisomer or the pharmaceutically acceptable salt thereof, $R_2$ is selected from the group consisting of methyl, difluoromethyl and trifluoromethyl; $R_3$ is selected from the group consisting of hydrogen, fluorine, chlorine and trifluoromethyl; and R, $R_1$, $R_4$, $R_6$, $R_7$, $R_8$, $R_9$, $R_{10}$, $R_{11}$, $R_{12}$, m, r and q are as defined in the compound of formula (I).

In a more preferred embodiment, in the compound of formula (I), the stereoisomer or the pharmaceutically acceptable salt thereof, $R_1$ is

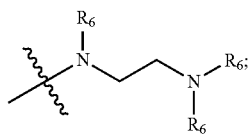

$R_2$ is selected from the group consisting of methyl, difluoromethyl and trifluoromethyl; $R_3$ is selected from the group consisting of hydrogen, fluorine, chlorine and trifluoromethyl; and $R_4$, $R_6$, $R_7$, $R_8$, $R_9$, $R_{10}$, $R_{11}$, $R_{12}$, m and r are as defined in the compound of formula (I).

In a more preferred embodiment, the compound of formula (I), the stereoisomer or the pharmaceutically acceptable salt thereof is a compound of formula (IB):

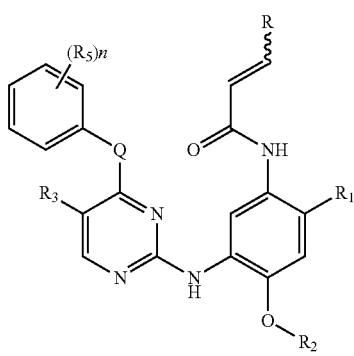

(IB)

wherein Q, R, $R_1$, $R_2$, $R_3$, $R_5$, $R_6$, $R_7$, $R_8$, $R_9$, $R_{10}$, $R_{11}$, $R_{12}$, r and q are as defined in the compound of formula (I).

In a more preferred embodiment, in the compound of formula (I), the stereoisomer or the pharmaceutically acceptable salt thereof, $R_2$ is selected from the group consisting of methyl, difluoromethyl and trifluoromethyl; $R_3$ is selected from the group consisting of hydrogen, fluorine, chlorine and trifluoromethyl; and Q, R, $R_1$, $R_5$, $R_6$, $R_7$, $R_8$, $R_9$, $R_{10}$, $R_{11}$, $R_{12}$, n, r and q are as defined in the compound of formula (I).

In a more preferred embodiment, in the compound of formula (I), the stereoisomer or the pharmaceutically acceptable salt thereof, $R_1$ is

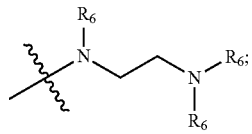

$R_2$ is selected from the group consisting of methyl, difluoromethyl and trifluoromethyl; $R_3$ is selected from the group consisting of hydrogen, fluorine, chlorine and trifluoromethyl; and Q, $R_5$, $R_6$, $R_7$, $R_8$, $R_9$, $R_{10}$, $R_{11}$, $R_{12}$, n and r are as defined in the compound of formula (I).

In a more preferred embodiment, the compound of formula (I), the stereoisomer or the pharmaceutically acceptable salt thereof is a compound of formula (IIB):

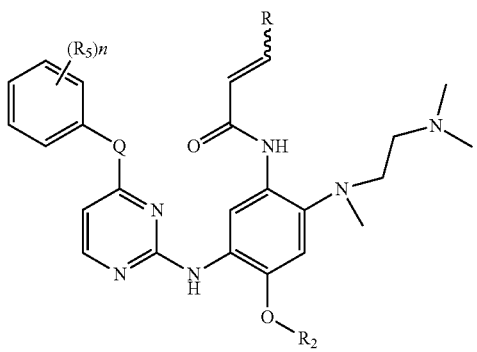

(IIB)

wherein $R_2$ is selected from the group consisting of methyl, difluoromethyl and trifluoromethyl; and Q, $R_5$, $R_6$, $R_7$, $R_8$, $R_9$, $R_{10}$, $R_{11}$, $R_{12}$, n and r is as defined in the compound of formula (I).

In a more preferred embodiment, the compound of formula (I), the stereoisomer or the pharmaceutically acceptable salt thereof is a compound of formula (IIIB):

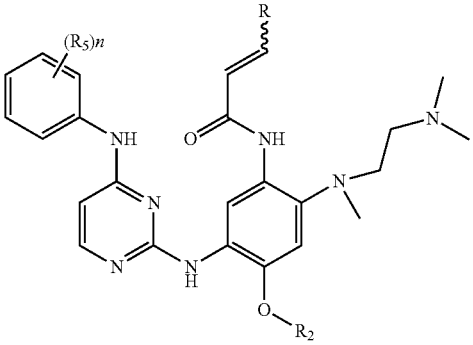

(IIIB)

wherein $R_2$ is selected from the group consisting of methyl, difluoromethyl and trifluoromethyl; and $R_5$, $R_6$, $R_7$, $R_8$, $R_9$, $R_{10}$, $R_{11}$, $R_{12}$, n and r are as defined in the compound of formula (I).

In the most preferred embodiment, the compound of formula (I), the stereoisomer or the pharmaceutically acceptable salt thereof is selected from the group consisting of:

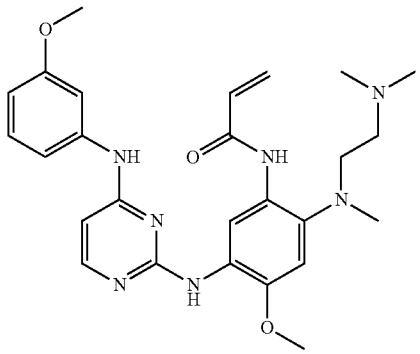

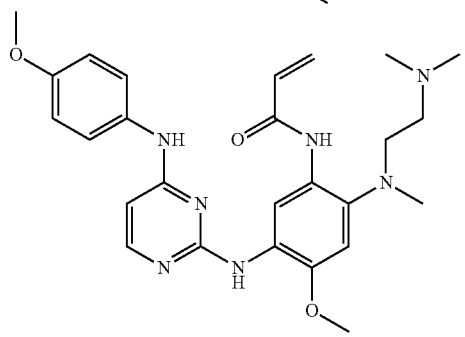

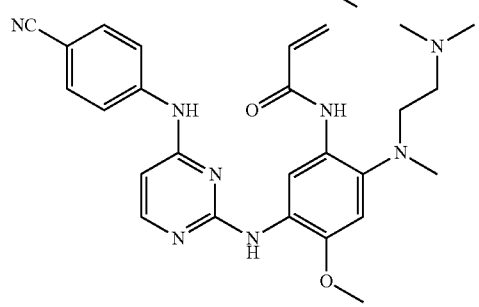

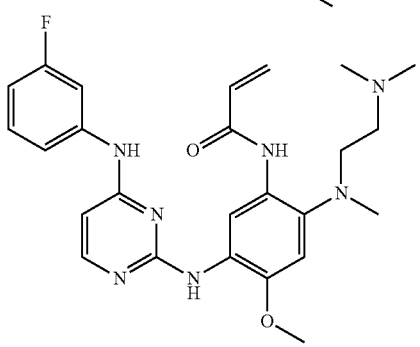

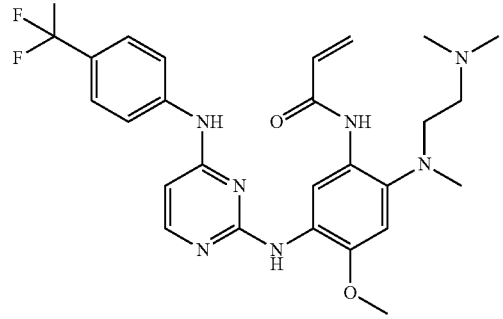

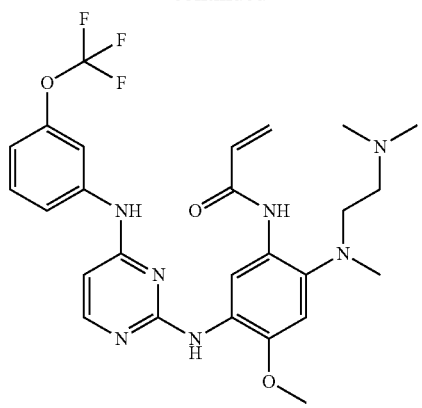
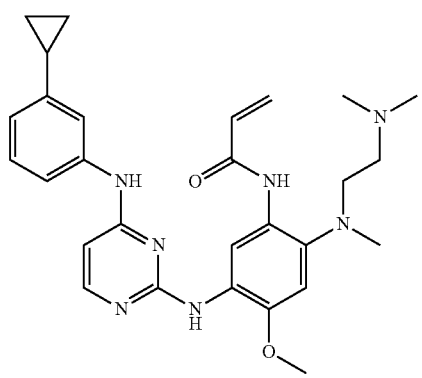
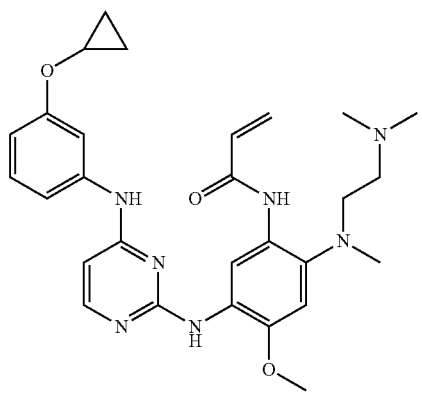
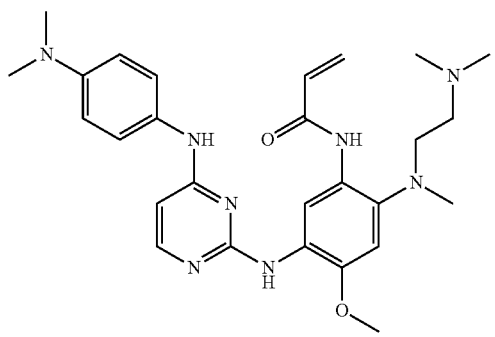
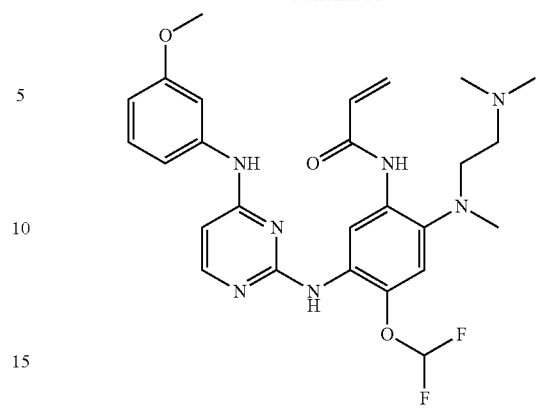
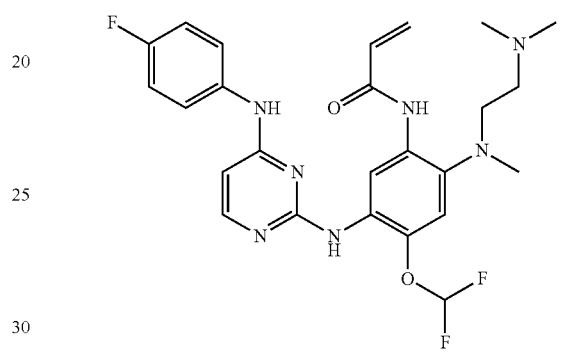
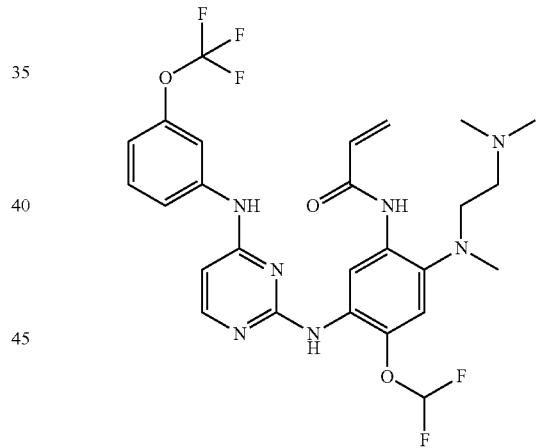
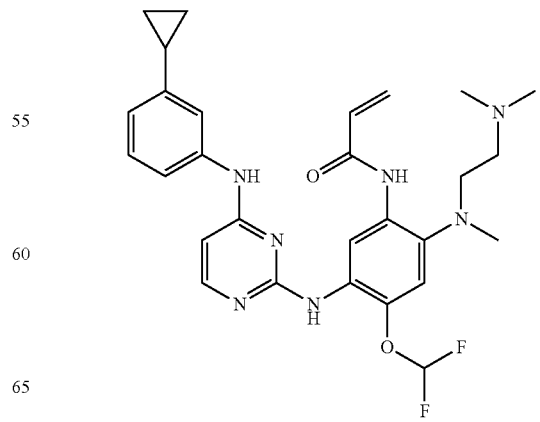

53
-continued
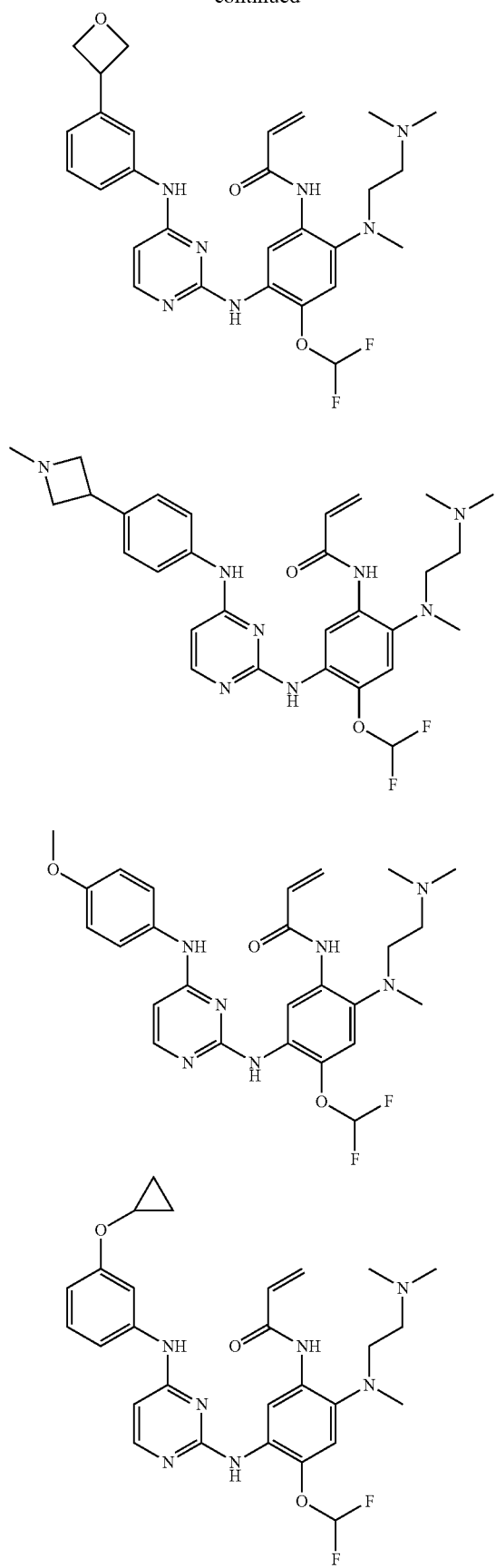
54
-continued
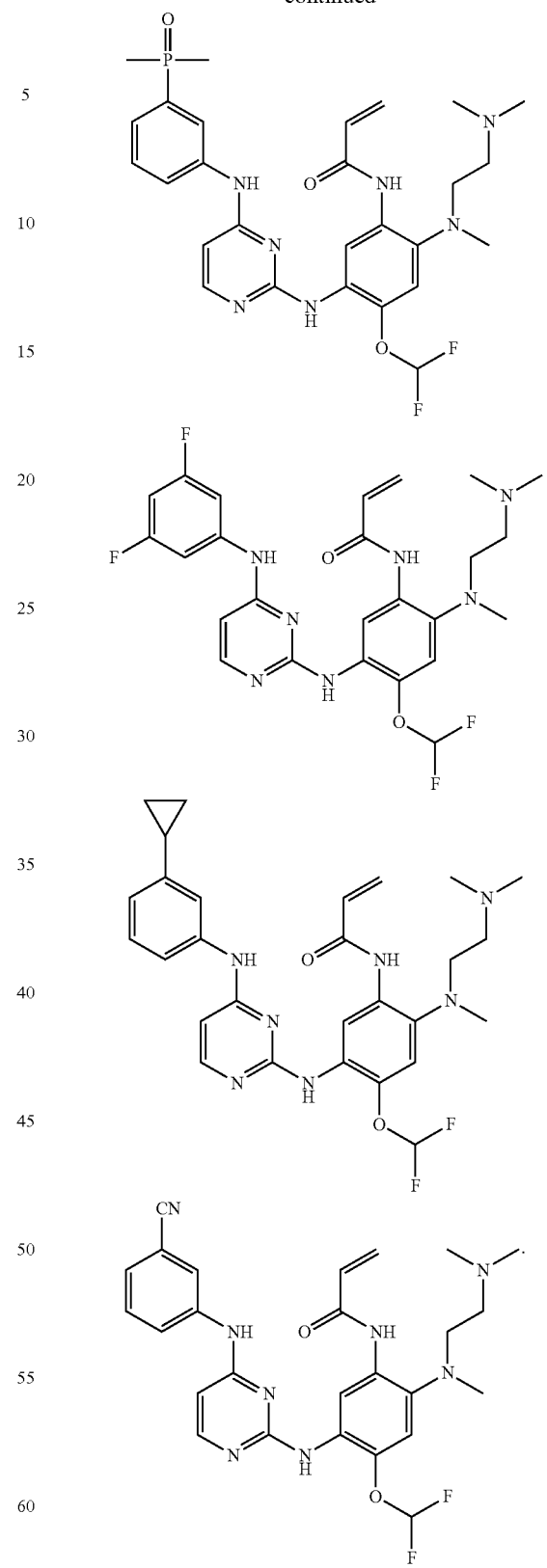
In a more preferred embodiment, the compound of formula (I), the stereoisomer or the pharmaceutically acceptable salt thereof is a compound of formula (IC):

(IC)

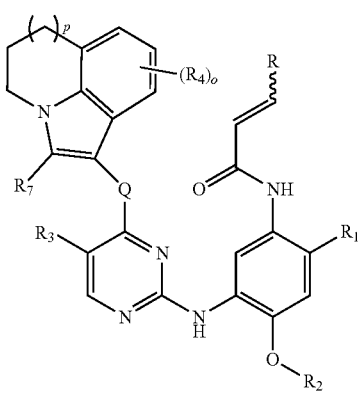

wherein Q, R, R₁, R₂, R₃, R₄, R₆, R₇, R₈, R₉, R₁₀, R₁₁, R₁₂, r, p, o and q are as defined in claim 1.

In a more preferred embodiment, in the compound of formula (I), the stereoisomer or the pharmaceutically acceptable salt thereof, R₂ is selected from the group consisting of difluoromethyl, trifluoromethyl and methyl; R₃ is selected from the group consisting of hydrogen, fluorine, chlorine, methyl, ethyl, trifluoromethyl, cyano and nitro; and Q, R, R₁, R₄, R₆, R₇, R₈, R₉, R₁₀, r, p and o are as defined in the compound of formula (I).

In a more preferred embodiment, the compound of formula (I), the stereoisomer or the pharmaceutically acceptable salt thereof is selected from the group consisting of a compound of formula (IIC1) and a compound of formula (IIC2):

(IIC1)

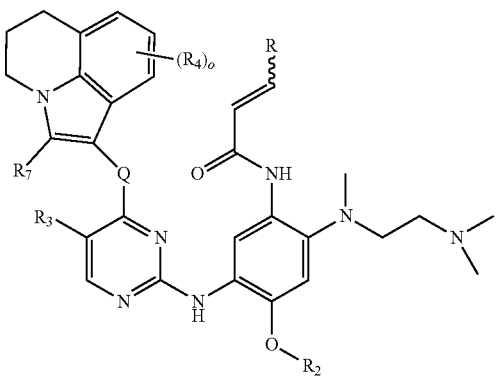

(IIC2)

wherein R₂ is selected from the group consisting of difluoromethyl, trifluoromethyl and methyl; R₃ is selected from the group consisting of hydrogen, fluorine, chlorine, methyl, ethyl, trifluoromethyl, cyano and nitro; and Q, R, R₄, R₆, R₇, R₈, R₉, R₁₀, R₁₁, R₁₂, o and r are as defined in the compound of formula (I).

In a more preferred embodiment, the compound of formula (I), the stereoisomer or the pharmaceutically acceptable salt thereof is selected from the group consisting of a compound of formula (IIIC 1) and a compound of formula (IIIC2):

(IIIC1)

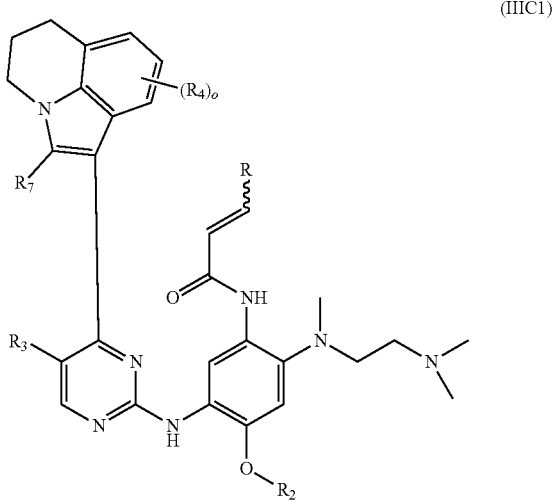

(IIIC2)

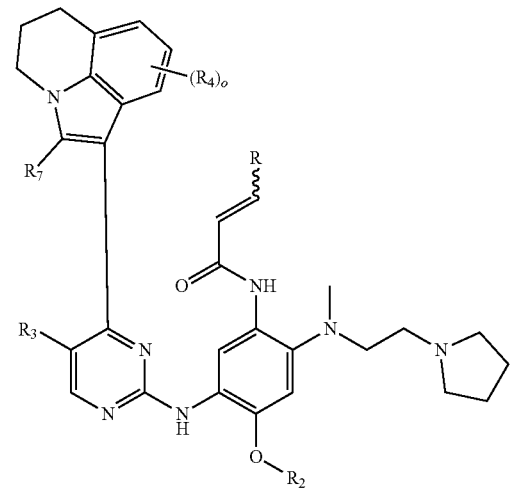

wherein R₂ is selected from the group consisting of difluoromethyl, trifluoromethyl and methyl; R₃ is selected from the group consisting of hydrogen, fluorine, chlorine, methyl, ethyl, trifluoromethyl, cyano and nitro; and Q, R, R₄, R₆, R₇, R₈, R₉, R₁₀, r and o are as defined in the compound of formula (I).

In a more preferred embodiment, the compound of formula (I), the stereoisomer or the pharmaceutically acceptable salt thereof is selected from the group consisting of:

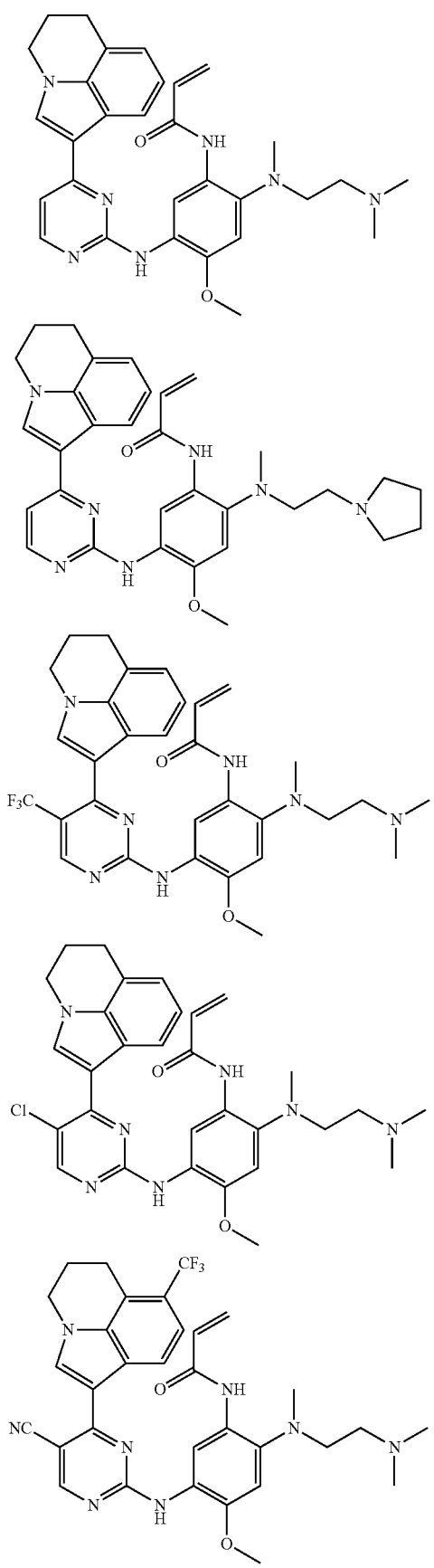
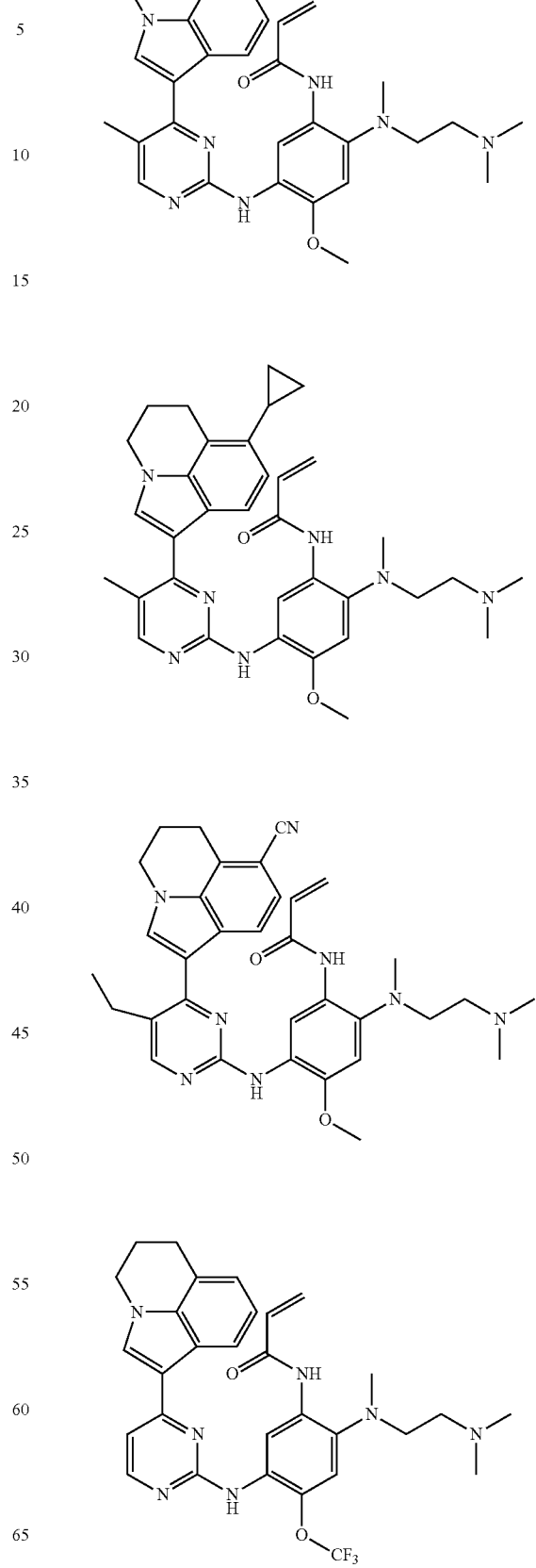

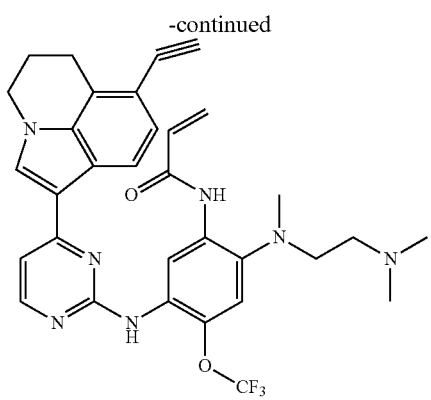
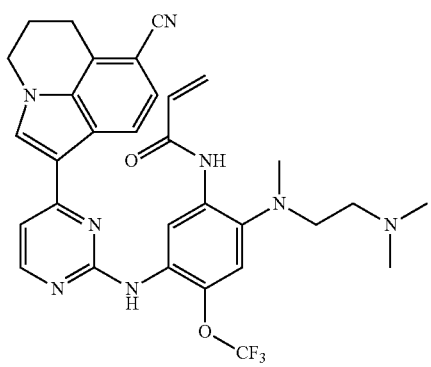
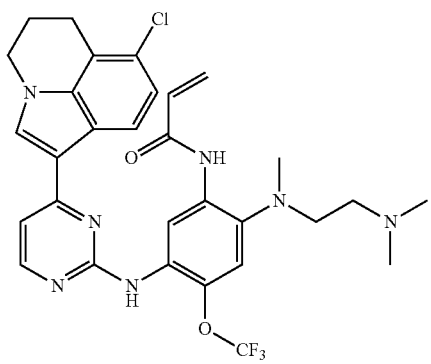
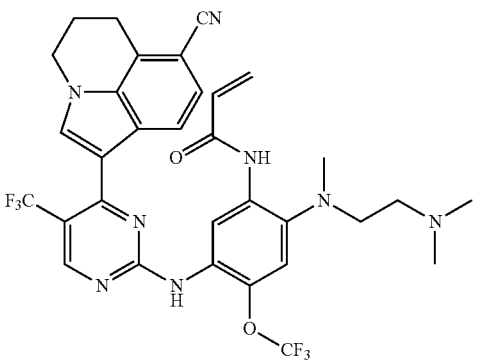
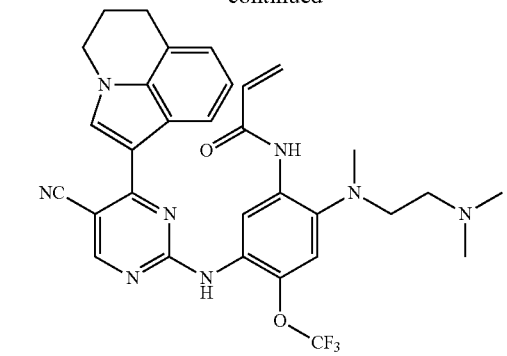
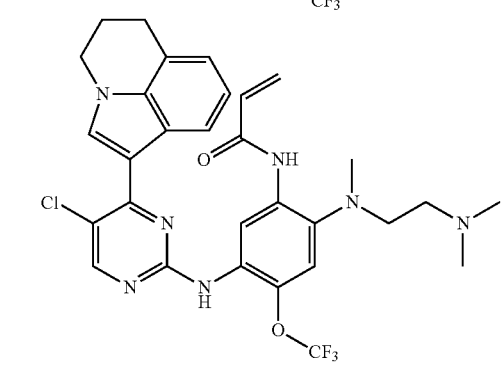
In another aspect, the present invention provides a process for preparing the compound of formula (I), the stereoisomer or the pharmaceutically acceptable salt thereof, comprising the steps of:
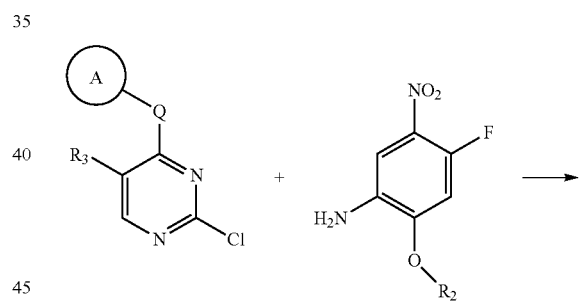
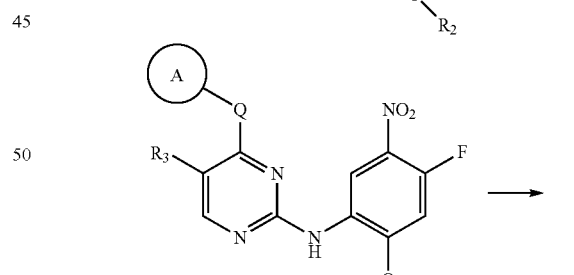
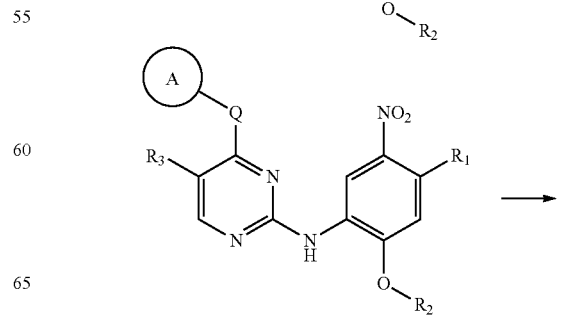

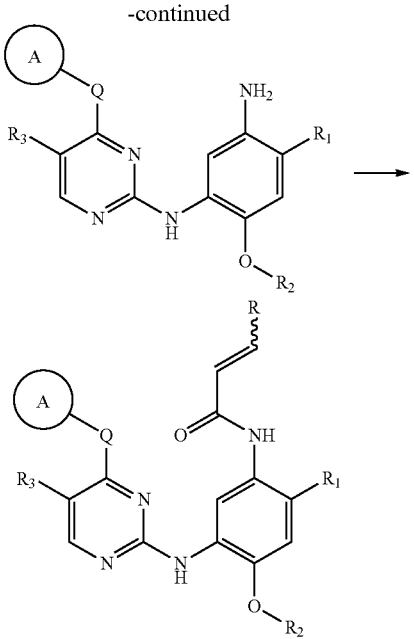

wherein ring A, Q, $X_1$, $X_2$, $X_3$, R, $R_1$, $R_2$, $R_3$, $R_4$, $R_5$, $R_6$, $R_7$, $R_8$, $R_9$, $R_{10}$, $R_{11}$, $R_{12}$, m, n, r, o, p and q are as defined in the compound of formula (I).

In another aspect, the present invention provides a pharmaceutical composition comprising a therapeutically effective amount of the aforementioned compound of formula (I), the stereoisomer or the pharmaceutically acceptable salt thereof and a pharmaceutical acceptable carrier.

In another aspect, the present invention relates to a use of the aforementioned compound of formula (I), the stereoisomer or the pharmaceutically acceptable salt thereof, or the aforementioned pharmaceutical composition in the preparation of a medicament for treating a disease mediated by the activity of an EGFR mutant, particularly EGFR-L858R mutant, EGFR-T790M mutant and the activity of a mutant activated by exon 19 deletion.

In another aspect, the present invention relates to a use of the aforementioned compound of formula (I), the stereoisomer or the pharmaceutically acceptable salt thereof, or the aforementioned pharmaceutical composition in the preparation of a medicament for treating a disease mediated alone or in part by the activity of an EGFR mutant.

In another aspect, the present invention relates to a use of the aforementioned compound of formula (I), the stereoisomer or the pharmaceutically acceptable salt thereof, or the aforementioned pharmaceutical composition in the preparation of a medicament for treating cancer.

In a more preferred embodiment, the cancer is selected from the group consisting of ovarian cancer, cervical cancer, colorectal cancer, breast cancer, pancreatic cancer, glioma, glioblastoma, melanoma, prostate cancer, leukemia, lymphoma, non-Hodgkin lymphoma, gastric cancer, lung cancer, hepatocellular carcinoma, gastric cancer, gastrointestinal stromal tumor (GIST), thyroid cancer, cholangiocarcinoma, endometrial cancer, renal cancer, anaplastic large cell lymphoma, acute myeloid leukemia (AML), multiple myeloma, melanoma or mesothelioma; preferably non-small cell lung cancer.

DETAILED DESCRIPTION OF THE INVENTION

Detailed description: unless otherwise stated, the following terms which are used in the description and the claims have the following meanings.

"$C_{1-8}$ alkyl" refers to a straight chain or branched chain alkyl group having 1 to 8 carbon atoms, "alkyl" refers to a saturated aliphatic hydrocarbon group, $C_{0-8}$ refers to carbon-free and $C_{1-8}$ alkyl group, such as methyl, ethyl, n-propyl, isopropyl, n-butyl, isobutyl, t-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl and various branched chain isomers thereof and the like.

The alkyl can be substituted or unsubstituted. When the alkyl is substituted, the substituent can be substituted at any available connection point, and is preferably one or more groups independently selected from the group consisting of halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, $-C_{0-8}-S(O)rR_9$, $-C_{0-8}-O-R_{10}$, $-C_{0-8}-C(O)R_{10}$, $-C_{0-8}-C(O)OR_{10}$, $-C_{0-8}-O-C(O)R_{10}$, $-C_{0-8}-NR_7R_8$, $-C_{0-8}-C(O)NR_7R_8$, $-N(R_7)-C(O)R_{10}$ and $-N(R_7)-C(O)OR_{10}$.

"Cycloalkyl" refers to a saturated or partially unsaturated monocyclic or polycyclic hydrocarbon substituent, "$C_{3-8}$ cycloalkyl" refers to a cycloalkyl group having 3 to 8 carbon atoms, and "5 to 10-membered cycloalkyl" refers to a cycloalkyl group having 5 to 10 carbon atoms, for example:

Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like.

Polycyclic cycloalkyl includes a cycloalkyl having a spiro ring, fused ring and bridged ring. "Spiro cycloalkyl" refers to a polycyclic group with rings connected through one common carbon atom (called a spiro atom), wherein these rings can contain one or more double bonds, but none of the rings has a completely conjugated π electronic system. Spirocycloalkyl can be divided into mono-spiro cycloalkyl, di-spiro cycloalkyl and poly-spiro cycloalkyl according to the number of the spiro atoms shared between the rings. Non-limiting examples of the spiro cycloalkyl include:

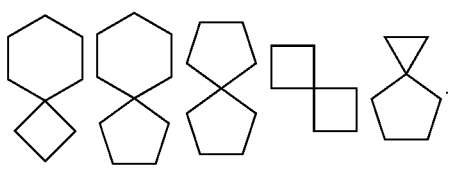

"Fused cycloalkyl" refers to an all-carbon polycyclic group in which each ring in the system shares an adjacent pair of carbon atoms with another ring, wherein one or more rings can contain one or more double bonds, but none of the rings has a completely conjugated π electronic system. According to the number of membered rings, fused-cycloalkyl can be divided into bicyclic, tricyclic, tetracyclic and polycyclic fused cycloalkyl. Non-limiting examples of the fused cycloalkyl include:

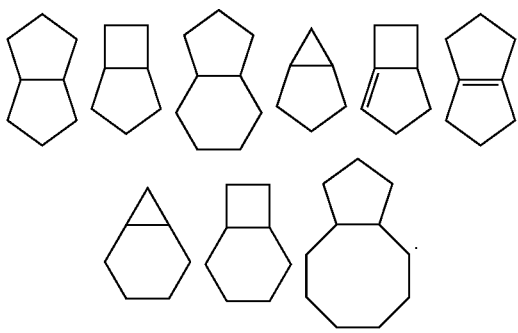

"Bridged cycloalkyl" refers to an all-carbon polycyclic group in which any two rings in the system share two disconnected carbon atoms, wherein these rings can contain one or more double bonds, but none of the rings has a completely conjugated π electronic system. According to the number of membered rings, bridged cycloalkyl can be divided into bicyclic, tricyclic, tetracyclic and polycyclic bridged cycloalkyl. Non-limiting examples of bridged cycloalkyl include:

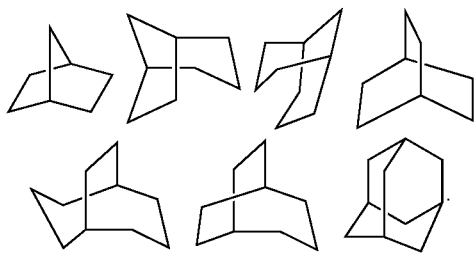

The cycloalkyl can be fused to the ring of aryl, heteroaryl or heterocyclyl, wherein the ring connected with the parent structure is the cycloalkyl, and non-limiting examples include indanyl, tetrahydronaphthyl, benzocycloheptylalkyl and the like.

Cycloalkyl can be optionally substituted or unsubstituted. When the cycloalkyl is substituted, the substituent is preferably one or more groups independently selected from the group consisting of halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, —$C_{0-8}$—S(O)r$R_9$, —$C_{0-8}$—O—$R_{10}$, —$C_{0-8}$—C(O)$R_{10}$, —$C_{0-8}$—C(O)O$R_{10}$, —$C_{0-8}$—O—C(O)$R_{10}$, —$C_{0-8}$—N$R_7R_8$, —$C_{0-8}$—C(O)N$R_7R_8$, —N($R_7$)—C(O)$R_{10}$ and —N($R_7$)—C(O)O$R_{10}$.

"Heterocyclyl" refers to a saturated or partially unsaturated monocyclic or polycyclic hydrocarbon substituent, wherein one or more ring atoms are heteroatoms selected from the group consisting of nitrogen, oxygen and S(O)r (wherein r is an integer from 0 to 2), but the cyclic part does not include —O—O—, —O—S— or —S—S—, and the remaining ring atoms are carbon. "5 to 10-membered heterocyclyl" refers to a heterocyclyl group having 5 to 10 ring atoms, and "3 to 8-membered heterocyclyl" refers to a heterocyclyl group having 3 to 8 ring atoms.

Non-limiting examples of the monocyclic heterocyclyl include pyrrolidinyl, piperidinyl, piperazinyl, morpholinyl, thiomorpholinyl, homopiperazinyl and the like.

Polycyclic heterocyclyl includes a heterocyclyl having a spiro ring, fused ring and bridged ring. "Spiro heterocyclyl" refers to a polycyclic heterocyclyl group with rings connected through one common atom (called a spiro atom), wherein one or more ring atoms are heteroatoms selected from nitrogen, oxygen or S(O)r (wherein r is an integer from 0 to 2), and the remaining ring atoms are carbon. These rings can contain one or more double bonds, but none of the rings has a completely conjugated π electronic system. The spirocycloalkyl can be divided into mono-spiro heterocyclyl, di-spiro heterocyclyl and poly-spiro heterocyclyl according to the number of the spiro atoms shared between the rings. The non-limiting examples of the spiro heterocyclyl include:

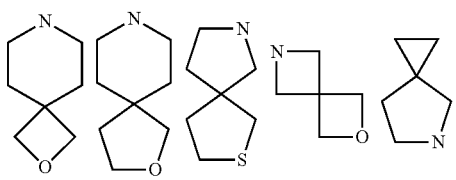

"Fused heterocyclyl" refers to a polycyclic heterocyclyl group in which each ring in the system shares an adjacent pair of atoms with another ring, wherein one or more rings can contain one or more double bonds, but none of the rings has a completely conjugated π electronic system, and wherein one or more ring atoms are heteroatoms selected from the group consisting of nitrogen, oxygen and S(O)r (wherein r is an integer from 0 to 2), and remaining ring atoms are carbon. According to the number of membered rings, the fused heterocyclyl can be divided into bicyclic, tricyclic, tetracyclic and polycyclic fused heterocyclyl. Non-limiting examples of the fused heterocyclyl include:

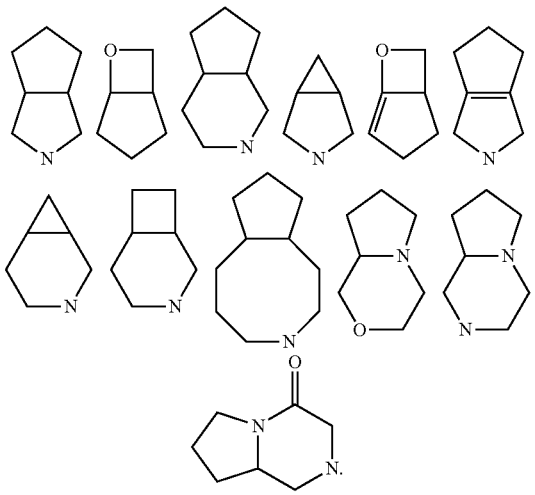

"Bridged heterocyclyl" refers to a polycyclic heterocyclic group in which any two rings in the system share two disconnected atoms, the rings can contain one or more double bonds, but none of the rings has a completely conjugated π electronic system, and one or more ring atoms are heteroatoms selected from the group consisting of nitrogen, oxygen and S(O)r (wherein r is an integer from 0 to 2), and the remaining ring atoms are carbon. According to the number of membered rings, the bridged heterocyclyl can be divided into bicyclic, tricyclic, tetracyclic and polycyclic bridged heterocyclyl. Non-limiting examples of the bridged heterocyclyl include:

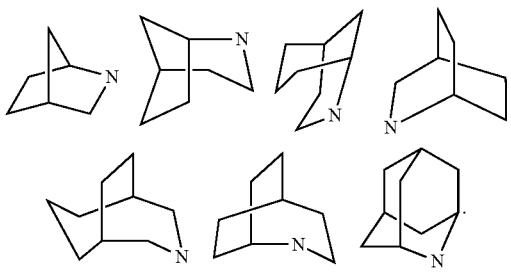

The heterocyclyl can be fused to the ring of aryl, heteroaryl or cycloalkyl, wherein the ring connected with the parent structure is the heterocyclyl, and the non-limiting examples include:

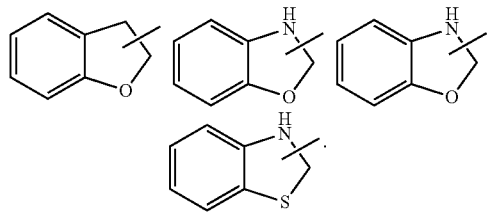

The heterocyclyl can be optionally substituted or unsubstituted. When the heterocyclyl is substituted, the substituent is preferably one or more groups independently selected from the group consisting of halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, $—C_{0-8}—S(O)rR_9$, $—C_{0-8}—O—R_{10}$, $—C_{0-8}—C(O)R_{10}$, $—C_{0-8}—O—C(O)R_{10}$, $—C_{0-8}—NR_7R_8$, $—C_{0-8}—C(O)NR_7R_8$, $—N(R_7)—C(O)R_{10}$ and $—N(R_7)—C(O)OR_{10}$.

"Aryl" refers to an all-carbon monocycle or fused polycycle (i.e., a ring in the system shares an adjacent pair of carbon atoms with another ring) with a conjugated π electron system. "$C_{5-10}$ aryl" refers to an all-carbon aryl group containing 5 to 10 carbon atoms, and "5 to 10-membered aryl" refers to an all-carbon aryl group containing 5 to 10 carbon atoms, such as phenyl and naphthyl. The aryl can be fused to the ring of heteroaryl, heterocyclyl or cycloalkyl, wherein the ring connected with the parent structure is aryl, and the non-limiting examples include:

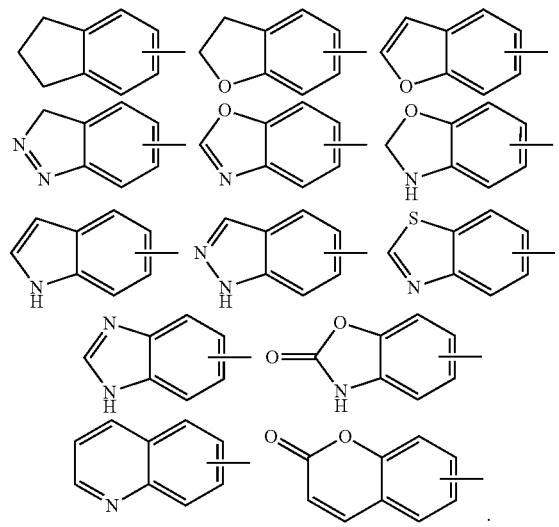

The aryl can be substituted or unsubstituted. When the alkyl is substituted, the substituent is preferably one or more groups independently selected from the group consisting of halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, $—C_{0-8}—S(O)rR_9$, $—C_{0-8}—O—R_{10}$, $—C_{0-8}—C(O)R_{10}$, $—C_{0-8}—C(O)OR_{10}$, $—C_{0-8}—O—C(O)R_{10}$, $—C_{0-8}—NR_7R_8$, $—C_{0-8}—C(O)NR_7R_8$, $—N(R_7)—C(O)R_{10}$ and $—N(R_7)—C(O)OR_{10}$.

"Heteroaryl" refers to a heteroaromatic system containing 1 to 4 heteroatoms, wherein the heteroatoms include nitrogen, oxygen or S(O)r (wherein r is an integer from 0 to 2). 5 to 7-membered heteroaryl refers to a heteroaromatic system having 5 to 7 ring atoms, and 5 to 10-membered heteroaryl refers to a heteroaromatic system having 5 to 10 ring atoms, such as furyl, thienyl, pyridyl, pyrrolyl, N-alkyl pyrrolyl, pyrimidinyl, pyrazinyl, imidazolyl tetrazolyl and the like. The heteroaryl can be fused to the ring of aryl, heterocyclyl or cycloalkyl, wherein the ring connected with the parent structure is heteroaryl, and the non-limiting examples include:

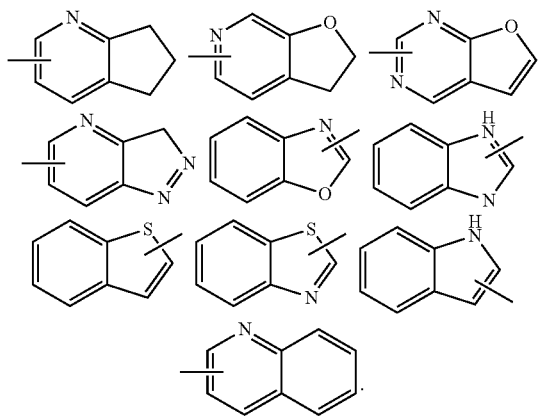

The heteroaryl can be optionally substituted or unsubstituted. When the heteroaryl is substituted, the substituent is preferably one or more groups independently selected from the group consisting of halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, —$C_{0-8}$—S(O)r$R_9$, —$C_{0-8}$—O—$R_{10}$, —$C_{0-8}$—C(O)$R_{10}$, —$C_{0-8}$—C(O)O$R_{10}$, —$C_{0-8}$—O—C(O)$R_{10}$, —$C_{0-8}$—N$R_7R_8$, —$C_{0-8}$—C(O)N$R_7R_8$, —N($R_7$)—C(O)$R_{10}$ and —N($R_7$)—C(O)O$R_{10}$.

"Alkenyl" refers to an alkyl group as defined above that has at least two carbon atoms and at least one carbon-carbon double bond, $C_{2-8}$ alkenyl refers to a straight chain or branched chain alkenyl group having 2 to 8 carbon atoms, for example, vinyl, 1-propenyl, 2-propenyl, 1-, 2- or 3-butenyl and the like.

Alkenyl can be substituted or unsubstituted. When the alkenyl is substituted, the substituent is preferably one or more groups independently selected from the group consisting of halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, —$C_{0-8}$—S(O)r$R_9$, —$C_{0-8}$—O—$R_{10}$, —$C_{0-8}$—C(O)$R_{10}$, —$C_{0-8}$—C(O)O$R_{10}$, —$C_{0-8}$—O—C(O)$R_{10}$, —$C_{0-8}$—N$R_7R_8$, —$C_{0-8}$—C(O)N$R_7R_8$, —N($R_7$)—C(O)$R_{10}$ and —N($R_7$)—C(O)O$R_{10}$.

"Alkynyl" refers to an alkyl group as defined above that has at least two carbon atoms and at least one carbon-carbon triple bond, $C_{2-8}$ alkynyl refers to a straight chain or branched chain alkynyl group having 2 to 8 carbons, for example, ethynyl, 1-propynyl, 2-propynyl, 1-, 2- or 3-butynyl and the like.

The alkynyl can be substituted or unsubstituted. When the alkynyl is substituted, the substituent is preferably one or more groups independently selected from the group consisting of halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, —$C_{0-8}$—S(O)r$R_9$, —$C_{0-8}$—O—$R_{10}$, —$C_{0-8}$—C(O)$R_{10}$, —$C_{0-8}$—C(O)O$R_{10}$, —$C_{0-8}$—O—C(O)$R_{10}$, —$C_{0-8}$—N$R_7R_8$, —$C_{0-8}$—C(O)N$R_7R_8$, —N($R_7$)—C(O)$R_{10}$ and —N($R_7$)—C(O)O$R_{10}$.

"Alkoxy" refers to an —O-(alkyl), wherein the alkyl is as defined above. $C_{1-8}$ alkoxy refers to an alkoxy having 1 to 8 carbons, and the non-limiting examples include methoxy, ethoxy, propoxy, butoxy and the like.

The alkoxy can be optionally substituted or unsubstituted. When the alkoxy is substituted, the substituent is preferably one or more groups independently selected from the group consisting of halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, —$C_{0-8}$—S(O)r$R_9$, —$C_{0-8}$—O—$R_{10}$, —$C_{0-8}$—C(O)$R_{10}$, —$C_{0-8}$—C(O)O$R_{10}$, —$C_{0-8}$—O—C(O)$R_{10}$, —$C_{0-8}$—N$R_7R_8$, —$C_{0-8}$—C(O)N$R_7R_8$, —N($R_7$)—C(O)$R_{10}$ and —N($R_7$)—C(O)O$R_{10}$.

"Cycloalkoxy" refers to an —O-(unsubstituted cycloalkyl), wherein the cycloalkyl is as defined above. $C_{3-8}$ cycloalkoxy refers to a cycloalkoxy group having 3 to 8 carbons, and the non-limiting examples include cyclopropoxy, cyclobutyloxy, cyclopentyloxy, cyclohexyloxy and the like.

The cycloalkoxy can be optionally substituted or unsubstituted. When the cycloalkoxy is substituted, the substituent is preferably one or more groups independently selected from the group consisting of halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, —$C_{0-8}$—S(O)r$R_9$, —$C_{0-8}$—O—$R_{10}$, —$C_{0-8}$—C(O)$R_{10}$, —$C_{0-8}$—C(O)O$R_{10}$, —$C_{0-8}$—O—C(O)$R_{10}$, —$C_{0-8}$—N$R_7R_8$, —$C_{0-8}$—C(O)N$R_7R_8$, —N($R_7$)—C(O)$R_{10}$ and —N($R_7$)—C(O)O$R_{10}$.

"halo$C_{1-8}$ alkyl" refers to a $C_{1-8}$ alkyl group wherein hydrogens in the alkyl are substituted by fluorine, chlorine, bromine and iodine atoms, for example, difluoromethyl, dichloromethyl, dibromomethyl, trifluoromethyl, trichloromethyl, tribromomethyl and the like.

"halo$C_{1-8}$ alkoxy" refers to a $C_{1-8}$ alkoxy group wherein hydrogens in the alkyl substituted by fluorine, chlorine, bromine and iodine, for example, difluoromethoxy, dichloromethoxy, dibromomethoxy, trifluoromethoxy, trichloromethoxy, tribromomethoxy and the like.

"Halogen" refers to fluorine, chlorine, bromine or iodine.

"C(O)$R_{10}$" refers to a carbonyl group substituted by $R_{10}$.

"—$C_{0-8}$—P(O)$R_{11}R_{12}$" refers to a phosphoryl $C_{0-8}$ alkyl group substituted by $R_{11}$ and $R_{12}$, wherein $R_{11}$ and $R_{12}$ are each optionally the same or different substituents.

"THF" refers to tetrahydrofuran.

"DCM" refers to dichloromethane.

"DMF" refers to N,N-dimethylformamide.

"DIPEA" refers to diisopropylethylamine.

"Optional" or "optionally" means that the subsequently described event or the circumstance can, but need not occur. Its meaning includes the instances in which the event or the circumstance does or does not occur. For example, "heterocyclyl optionally substituted by alkyl" means that the alkyl group can be, but need not be present. Its meaning includes the instances in which heterocyclyl is substituted or unsubstituted by alkyl.

"Substituted" means that one or more hydrogen atoms, preferably up to 5, and more preferably 1 to 3 hydrogen atoms in the group are each independently substituted by the corresponding number of the substituents. Obviously, the substituents are only positioned at their possible chemical positions, and the possible or impossible substitutions can be determined (through experiments or theory) by those skilled in the art without paying excessive efforts. For example, the combination of amino or hydroxy having free hydrogen and carbon atoms having unsaturated bonds (such as olefinic) may be unstable.

"Pharmaceutical composition" refers to a mixture comprising one or more of the compounds described herein or the physiological/pharmaceutical salts or prodrugs thereof and other chemical components, such as physiological/pharmaceutical carriers and excipients. The purpose of the pharmaceutical composition is to facilitate administration of a compound to an organism, which will help with absorption of the active ingredient, thereby realizing biological activity.

The following examples serve to illustrate the present invention in detail and more completely, but these examples should not be considered as limiting the scope of the present invention, and the present invention is not limited to the examples.

The structures of compounds in the present invention were identified by nuclear magnetic resonance (NMR) and/or liquid chromatography-mass spectrometry (LC-MS). The chemical shift of NMR is given in $10^{-6}$ (ppm). NMR was determined by a Bruker AVANCE-400 machine, the solvents for determination are deuterated dimethylsulfoxide (DMSO-d6), deuterated methanol ($CD_3OD$) and deuterated chloroform ($CDCl_3$), and the internal standard is tetramethylsilane (TMS).

Liquid chromatography-mass spectrometry (LC-MS) was determined by an Agilent 1200 Infinity Series mass spectrometer. HPLC was determined on an Agilent 1200DAD high pressure liquid chromatographic instrument (Sunfire C18 150×4.6 mm chromatographic column) and a Waters 2695-2996 high pressure liquid chromatographic instrument (Gimini C18 150×4.6 mm chromatographic column).

For thin-layer silica gel chromatography (TLC), Yantai Huanghai HSGF254 or Qingdao GF254 silica gel plate was used. The dimension of the plates used in TLC was 0.15 mm to 0.2 mm, and the dimension of the plates used in product purification was 0.4 mm to 0.5 mm. Column chromatography generally used Yantai Huanghai 200 to 300 mesh silica gel as carrier.

The starting materials used in the examples of the present invention are known and commercially available, or can be synthesized by adopting or according to known methods in the art.

Unless otherwise stated, all reactions of the present invention are carried out under continuous magnetic stirring in a dry nitrogen or argon atmosphere, the solvent is dry, and the reaction temperature is in degrees Celsius.

PREPARATION OF INTERMEDIATE

1. Intermediate 1: Preparation of 2-(difluoromethoxy)-4-fluoronitrobenzene

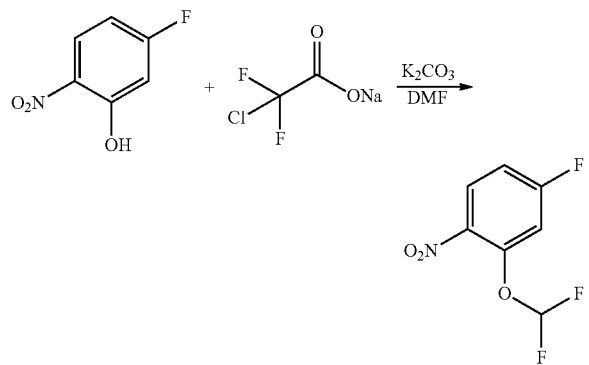

5-fluoro-2-nitrophenol (3.0 g, 19.1 mmol) and potassium carbonate (5.28 g, 38.2 mmol) were dissolved in DMF, followed by addition of sodium chlorodifluoroacetate (4.37 g, 28.6 mmol). The reaction solution was heated up to 100° C. in a nitrogen atmosphere and stirred for 16 hours, and then was concentrated. $H_2O$ (50 mL) and methyl tert-butyl ether (50 mL) were added to the resulting residue for extraction. The organic phase was washed three times with water, dried over anhydrous magnesium sulfate, filtered, and the filtrate was concentrated. The resulting residue was purified by flash silica gel column chromatography to obtain 2-(difluoromethoxy)-4-fluoronitrobenzene (3.0 g, 75%).

2. Intermediate 2: Preparation of 2-(difluoromethoxy)-4-fluoro-5-nitroaniline

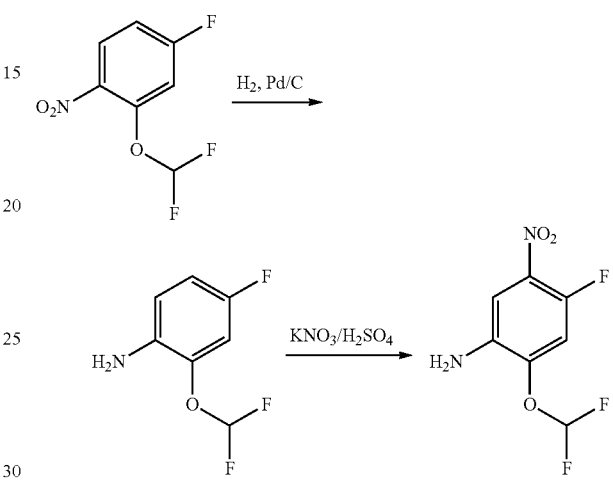

2-(difluoromethoxy)-4-fluoronitrobenzene (3.0 g, 14.5 mmol) was dissolved in methanol (30 mL), followed by addition of Pd/C (500 mg), and reacted in a hydrogen atmosphere at room temperature for 2 hours. After TLC showed completion of the reaction, the reaction solution was filtered through celite, and the filtrate was concentrated to obtain a crude product (1.7 g, 66%). The crude product was dissolved carefully in concentrated sulfuric acid (5 mL) in an ice bath. After the reaction mixture was stirred to get a clear solution in an ice bath, potassium nitrate (1.1 g, 9.5 mmol) was added slowly in batches, and then the reaction was stirred for 3 hours in an ice bath. After LC-MS showed completion of the reaction, the reaction solution was added slowly to saturated sodium carbonate aqueous solution (100 mL). After the reaction was quenched, the aqueous phase was extracted with methyl tert-butyl ether (3×20 mL), then the organic phase was dried over anhydrous magnesium sulfate and filtered. The filtrate was concentrated and the resulting residue was purified by flash silica gel column chromatography to obtain 2-(difluoromethoxy)-4-fluoro-5-nitroaniline (2.0 g, 90%).

3. Intermediate 3: Preparation of 4-fluoro-1-nitro-2-(trifluoromethoxy)benzene

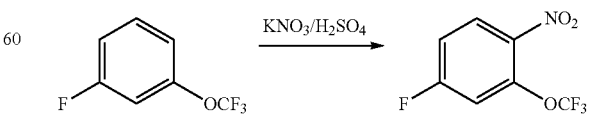

3-fluoro-trifluoromethoxy benzene (20 g) was dissolved in 40 ml of concentrated sulfuric acid under ice water cooling. Potassium nitrate (28 g) was added in batches under rapid stirring. The reaction mixture was stirred at 0° C. for 3 hours, and then stirred at room temperature overnight. The reaction solution was poured into 1 kg of crushed ice carefully, stirred for 30 minutes, extracted with ethyl acetate, dried over sodium sulfate, filtered and the filtrate was evaporated. The resulting residue was purified by column chromatography to obtain 12 g of crude product as a yellowish liquid.

4. Intermediate 4: Preparation of 4-fluoro-2-(trifluoromethoxy)aniline

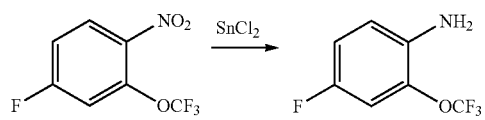

The crude product (12 g) of 4-fluoro-1-nitro-2-(trifluoromethoxy)benzene prepared in the previous step was dissolved in 100 mL of anhydrous ethanol, and then stannous chloride dihydrate (25 g) was added under ice water cooling. The reaction solution was stirred at room temperature overnight. 1 N sodium hydroxide aqueous solution was added to adjust the pH to about 12. The reaction solution was filtered and the filtrate was extracted with ethyl acetate. The extract was dried over anhydrous sodium sulfate, filtered and evaporated. The resulting residue was purified by column chromatography to obtain 4-fluoro-2-(trifluoromethoxy)aniline as a yellowish oily liquid (4.78 g, 46%).

$^1$H NMR (400 MHz, CDCl$_3$) δ 6.94 (d, J=8.8 Hz, 1H), 6.83 (m, 1H), 6.76 (dd, J=5.4, 8.8 Hz, 1H), 3.87-3.59 (br, 2H).

5. Intermediate 5: Preparation of 4-fluoro-5-nitro-2-(trifluoromethoxy)aniline

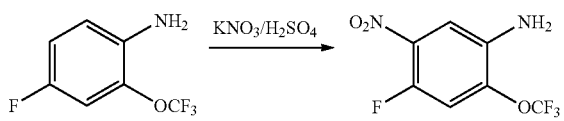

4-fluoro-2-(trifluoromethoxy)aniline (2.5 g) was dissolved in concentrated sulfuric acid (10 mL) under ice water cooling, followed by addition of potassium nitrate (3 g), and then the reaction mixture was stirred at room temperature for 3 hours. The reaction solution was poured into ice water, and 3 N sodium hydroxide aqueous solution was added to adjust the pH to about 10. The reaction mixture was extracted with ethyl acetate, and the extract was dried over anhydrous sodium sulfate, filtered, and concentrated. The resulting residue was purified by column chromatography to obtain 4-fluoro-5-nitro-2-(trifluoromethoxy)aniline (1.79 g, 58%).

6. Intermediate 6: Preparation of 6-methoxy-1-methyl-1H-indole

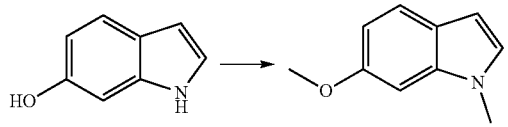

1H-indol-6-ol (1 g, 7.51 mmol) was dissolved in anhydrous DMF (20 mL), and NaH (900 mg, 22.53 mmol) was added in batches in an ice bath. The reaction was stirred in an ice bath for 20 minutes, then methyl iodide (2.67 g, 18.78 mmol) was added dropwise and slowly. The reaction was stirred for 2 hours in an ice bath. After LC-MS showed completion of the reaction, the reaction was quenched with saturated NH$_4$Cl (40 mL) in an ice bath, and extracted with methyl tert-butyl ether (3×30 mL). The organic phases were combined, washed with water (20 mL×2), dried over anhydrous magnesium sulfate, filtered and concentrated. The resulting residue was purified by flash silica gel column chromatography to obtain the product 6-methoxy-1-methyl-1H-indole (1.1 g, 90%).

7. Intermediate 7: Preparation of 3-(2-chloropyrimidin-4-yl)-1-methyl-1H-indole

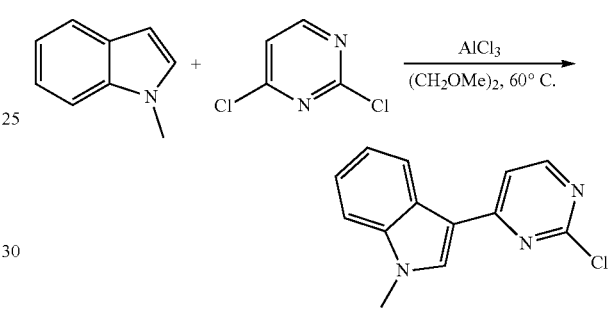

N-methylindole (300 mg, 2.29 mmol), 2,4-dichloropyrimidine (340 mg, 2.30 mmol) and anhydrous aluminum trichloride (460 mg, 3.43 mmol) were dissolved in ethylene glycol dimethyl ether (12 mL). The reaction was heated to 60° C. in a nitrogen atmosphere and stirred for 3 hours. After the reaction was completed, the reaction solution was poured into an ice-water mixture (about 50 mL) and extracted with methyl tert-butyl ether (20 mL×3). The organic phases were combined, dried over anhydrous magnesium sulfate, filtered and concentrated. The resulting residue was purified by column chromatography to obtain the product 3-(2-chloropyrimidin-4-yl)-1-methyl-1H-indole (400 mg, 72%).

8. Intermediate 8: Preparation of 3-(2-chloropyrimidin-4-yl)-6-methoxy-1-methyl-1H-indole

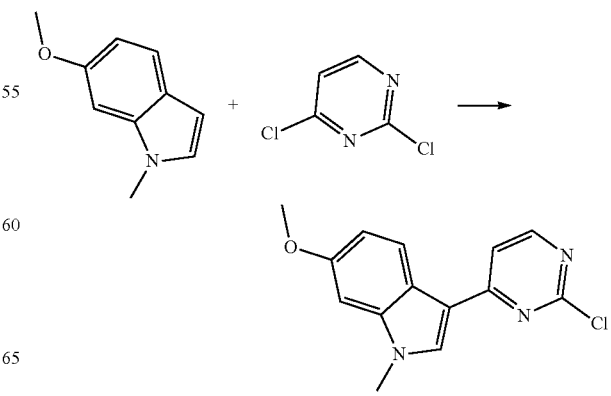

6-methoxy-1-methyl-1H-indole (300 mg, 1.86 mmol) and 2,4-dichloropyrimidine (330 mg, 2.23 mmol) were dissolved in ethyleneglycol dimethyl ether (10 mL), followed by addition of anhydrous aluminum trichloride (500 mg, 3.72 mmol). The reaction was heated to 60° C. in a nitrogen atmosphere and stirred for 3 hours. After LC-MS showed completion of the reaction, the reaction solution was poured into an ice-water mixture (about 50 mL) and extracted with methyl tert-butyl ether (50 mL×3). The organic phases were combined, washed successively with saturated sodium bicarbonate (30 mL×2) and $H_2O$ (30 mL), dried, filtered, and concentrated. The resulting residue was purified by flash silica gel column chromatography to obtain the product 3-(2-chloropyrimidin-4-yl)-6-methoxy-1-methyl-1H-indole (120 mg, 24%).

9. Intermediate 9: Preparation of 4-(2-(methylamino)ethyl)morpholin-3-one

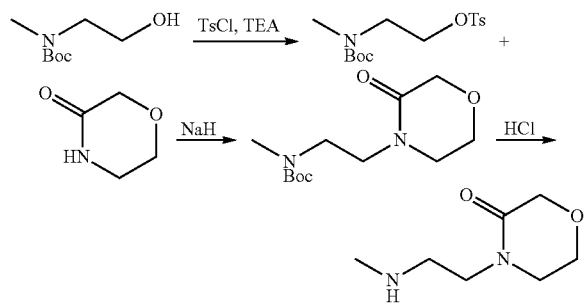

tert-butyl (2-hydroxyethyl)(methyl)carbamate (300 mg, 1.71 mmol) and triethylamine (350 mg, 3.42 mmol) were dissolved in anhydrous dichloromethane (10 mL). p-toluene sulfonyl chloride (490 mg, 2.57 mmol) was added in batches at room temperature. The reaction was stirred for 2 h at room temperature. After LC-MS showed completion of the reaction, the reaction solution was washed successively with saturated sodium bicarbonate aqueous solution (10 mL), 1N HCl (10 mL) and $H_2O$ (10 mL×2), dried over anhydrous magnesium sulfate and filtered. The filtrate was concentrated to obtain the crude product 2-((tert-butoxycarbonyl)(methyl)amino)ethyl 4-methylbenzenesulfonate (560 mg, 99%), which was used directly in the next step without further processing.

Morpholin-3-one (180.5 mg, 1.79 mmol) was dissolved in anhydrous DMF, NaH (136 mg, 3.4 mmol) was added at 0° C. and the reaction was stirred for 10 minutes in an ice bath. 2-((tert-butoxycarbonyl)(methyl)amino)ethyl-4-methylbenzenesulfonate (560 mg, 1.7 mmol) was added to the reaction solution, and the reaction was stirred at room temperature for 16 hours. After LC-MS showed completion of the reaction, the reaction solution was quenched with saturated $NH_4Cl$ aqueous solution (20 mL) and extracted with dichloromethane (10 mL×2). The organic phases were combined, dried over anhydrous magnesium sulfate, filtered and concentrated. The resulting residue was dissolved in a solution of 4 N hydrochloric acid in dioxane (10 mL) and stirred at room temperature for 1 hour. After LC-MS showed completion of the reaction, the reaction solution was concentrated to obtain the crude product 4-(2-(methylamino)ethyl)morpholin-3-one (150 mg, 98%) which was used directly in the next step without further purification.

10. Intermediate 10: Preparation of 1-(2-((tert-butyldimehylsilyl)oxy)ethyl)-1H-indole

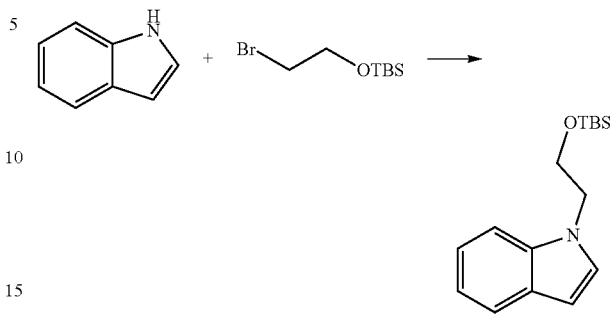

Indole (4.45 g, 38 mmol) was dissolved in 100 mL of DMF, and then 60% sodium hydride (4.6 g, 113.9 mmol) was added. After the reaction solution was stirred at room temperature for 15 minutes, ((tert-butyldimethylsilyl)oxy)-2-bromoethyl (10 g, 41.81 mmol) was added dropwise. The reaction was stirred at room temperature for 1 hour. Upon completion of the reaction, the reaction solution was poured into water and extracted three times with ethyl acetate. The organic phases were combined, washed with water and saturated brine, dried over anhydrous sodium sulfate, filtered, concentrated to obtain a crude product which was purified by flash silica gel column chromatography to obtain 1-(2-((tert-butyldimethylsilyl)oxy)ethyl)-1H-indole (9.54 g, 90%).

11. Intermediate 11: Preparation of 1-(2-((tert-butyldimethylsilyl)oxy)ethyl)-3-(2-chloropyrimidin-4-yl)-1H-indole

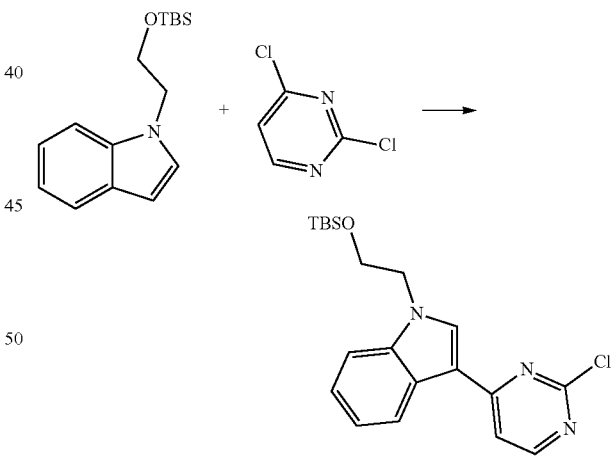

1-(2-((tert-butyldimethylsilyl)oxy)ethyl)-1H-indole (2 g, 7.26 mmol), 2,4-dichloropyrimidine (1.2 g, 8.00 mmol) and aluminum trichloride (1.45 g, 10.89 mmol) were dissolved in 30 mL of DME, and the reaction was stirred at 75° C. overnight. After the reaction was completed, the reaction solution was poured into ice water and extracted three times with methyl tert-butyl ether. The organic phases were combined, washed with water and saturated brine, dried over anhydrous sodium sulfate, filtered and concentrated to obtain a crude product which was further purified by flash silica gel column chromatography to obtain the product (1.1 g, 39%).

12. Intermediate 12: Preparation of 5-methoxy-1-methyl-1H-indole

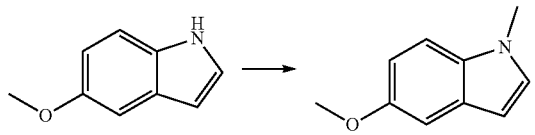

5-methoxy-1H-indole (2.2 g, 15 mmol) was dissolved in THF (30 mL), and the reaction solution was cooled to 0° C. before NaH (0.9 g, 32 mmol) was added under stirring. The reaction was stirred at 0° C. for 1 hour, and methyl iodide (4.2 g, 30 mmol) was added at the same temperature, and then the reaction was stirred at room temperature overnight. After disappearance of the starting material was detected by LC-MS, the solution was adjusted to pH 3 with HCl (1 N aq.). THF was removed under reduced pressure, then CH$_2$Cl$_2$ (60 mL) was added. The organic phase was washed with saturated brine, dried over anhydrous sodium sulfate, concentrated, and purified by column chromatography (Eluent: PE~PE:EtOAc=10:1) to obtain 5-methoxy-1-methyl-1H-indole (0.9 g, 35%).

$^1$H NMR (400 MHz, CD$_3$OD) δ 7.25 (d, J=8.4 Hz, 1H), 7.10 (d, J=2.8 Hz, 1H), 7.06 (d, J=2.0 Hz, 1H), 6.83 (d, J=2.4 Hz, 1H), 6.34 (m, 1H), 3.82 (s, 3H), 3.77 (s, 3H);

MS m/z (ESI): 162.2 [M+H]$^+$.

PREPARATION EXAMPLES

Example 1: Preparation of N-(4-(difluoromethoxy)-5-((4-(1-methyl-1H-indol-3-yl)pyrimidin-2-yl)amino)-2-(4-methylpiperazine-1-yl)phenyl)acrylamide

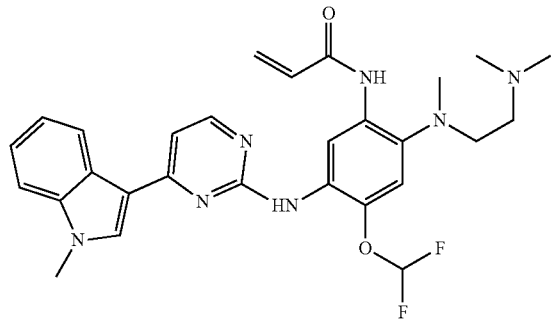 [SMILES: C=CC(=O)Nc1cc(Nc2nccc(-c3cn(C)c4ccccc34)n2)c(OC(F)F)cc1N(C)CCN(C)C]

Step 1: Preparation of 2-(difluoromethoxy)-N4-(2-(dimethylamino)ethyl)-N4-methyl-N1-(4-(1-methyl-1H-indol-3-yl)pyrimidin-2-yl)-5-nitrobenzene-1,4-diamine

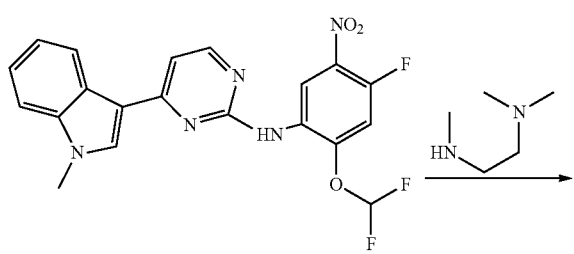

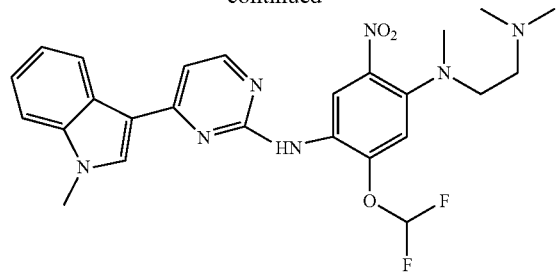

N-(2-(difluoromethoxy)-4-fluoro-5-nitrophenyl)-4-(1-methyl-1H-indol-3-yl)pyrimidin-2-amine (250 mg, 0.58 mmol) was dissolved in DMF, followed by addition of diisopropylethylamine (150 mg, 1.16 mmol) and trimethylethylenediamine (120 mg, 1.16 mmol). The reaction was heated up to 120° C. by microwave and reacted for 30 minutes. After LC-MS showed completion of the reaction, the reaction solution was concentrated to dryness. The resulting residue was extracted with dichloromethane (10 mL) and H$_2$O (10 mL). The organic phase was purified by preparative thin-layer chromatography to obtain the product 2-(difluoromethoxy)-N4-(2-(dimethylamino)ethyl)-N4-methyl-N1-(4-(1-methyl-1H-indol-3-yl)pyrimidin-2-yl)-5-nitrobenzene-1,4-diamine (150 mg, 50%).

Step 2: 5-(difluoromethoxy)-N1-(2-(dimethylamino)ethyl)-N1-methyl-N4-(4-(1-methyl-1H-indol-3-yl)pyrimidin-2-yl)benzene-1,2,4-triamine

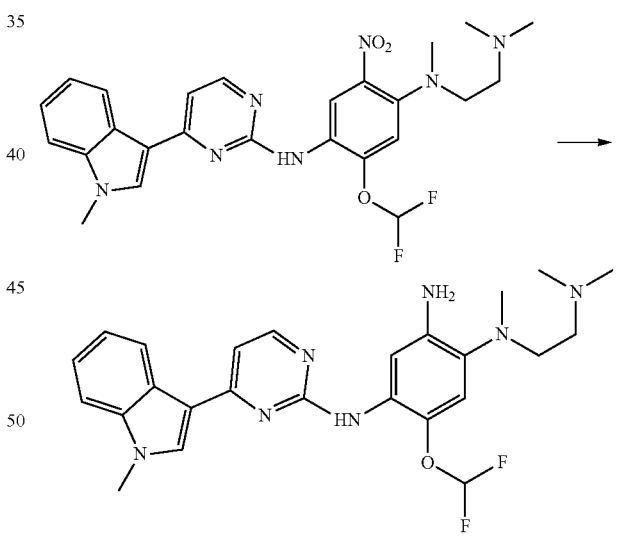

2-(difluoromethoxy)-N4-(2-(dimethylamino)ethyl)-N4-methyl-N1-(4-(1-methyl-1H-indol-3-yl)pyrimidin-2-yl)-5-nitrobenzene-1,4-diamine (60 mg, 0.12 mmol) was dissolved in methanol, followed by addition of Pd/C (10 mg), and then the reaction was stirred at room temperature in a hydrogen atmosphere for 2 hours. After LC-MS showed completion of the reaction, the solution was filtered and the filtrate was concentrated to obtain the product 5-(difluoromethoxy)-N1-(2-(dimethylamino)ethyl)-N1-methyl-N4-(4-(1-methyl-1H-indol-3-yl)pyrimidin-2-yl)benzene-1,2,4-triamine (55 mg, 95%) which was used directly in the next reaction.

Step 3: N-(4-(difluoromethoxy)-2-((2-(dimethyl-amino)ethyl)(methyl)amino)-5-((4-(1-methyl-1H-indol-3-yl)pyrimidin-2-yl)amino)phenyl)acrylamide

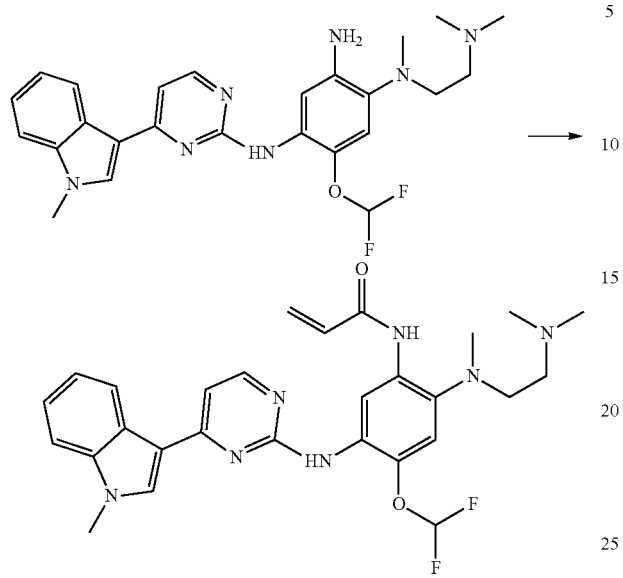

5-(difluoromethoxy)-N1-(2-(dimethylamino)ethyl)-N1-methyl-N4-(4-(1-methyl-1H-indol-3-yl)pyrimidin-2-yl)benzene-1,2,4-triamine (55 mg, 0.11 mmol) and triethylamine (58 mg, 0.57 mmol) were dissolved in anhydrous tetrahydrofuran (15 mL). After the reaction solution was stirred for 10 minutes in an ice-water bath, acryloyl chloride (0.17 mL, 1M in THF) was added dropwise and slowly. The reaction was stirred for 30 minutes in an ice bath. After LC-MS showed completion of the reaction, the reaction was quenched with saturated NH₄Cl aqueous solution (3 mL) and concentrated. The resulting residue was purified by preparative thin-layer chromatography to obtain the product N-(4-(difluoromethoxy)-2-((2-(dimethylamino)ethyl)(methyl)amino)-5-((4-(1-methyl-1H-indol-3-yl)pyrimidin-2-yl)amino)phenyl)acrylamide (12.3 mg, 20%).
$^1$H NMR (400 MHz, CDCl$_3$) δ 10.17 (s, 1H), 9.81 (s, 1H), 8.89 (s, 1H), 8.33 (d, J=5.3 Hz, 1H), 8.00 (dd, J=6.7, 2.0 Hz, 1H), 7.40 (s, 1H), 7.32 (dd, J=6.8, 1.9 Hz, 1H), 7.25-7.13 (m, 1H), 6.98 (s, 1H), 6.66-6.20 (m, 3H), 5.74-5.58 (m, 1H), 3.90 (s, 3H), 2.92-2.77 (m, 2H), 2.62 (s, 3H), 2.27 (s, 2H), 2.22 (s, 6H):
MS m/z (ESI): 536.2 [M+H]$^+$.

Example 2: Preparation of N-(4-(difluoromethoxy)-5-((4-(1-methyl-1H-indol-3-yl)pyrimidin-2-yl)amino)-2-(4-methylpiperazine-1-yl)phenyl)acrylamide

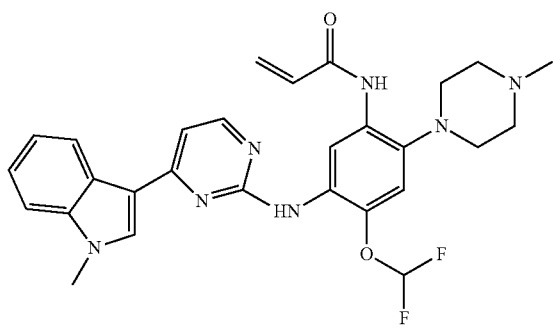 [SMILES: C=CC(=O)Nc1cc(Nc2nccc(-c3cn(C)c4ccccc34)n2)c(OC(F)F)cc1N1CCN(C)CC1]

Step 1: Preparation of N-(2-(difluoromethoxy)-4-fluoro-5-nitrophenyl)-4-(1-methyl-1H-indol-3-yl)pyrimidin-2-amine

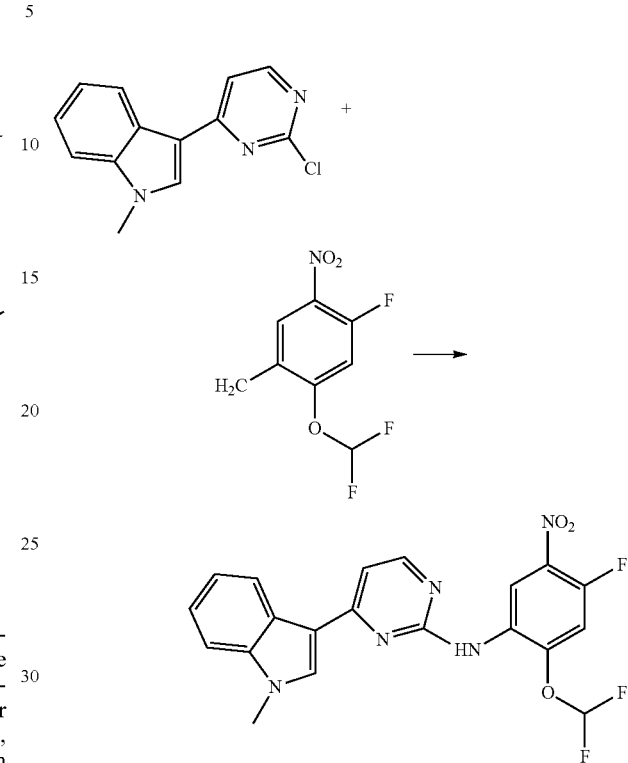

3-(2-chloropyrimidin-4-yl)-1-methyl-1H-indole (250 mg, 1.0 mmol), 2-(difluoromethoxy)-4-fluoro-5-nitroaniline (230 mg, 1.0 mmol) and p-toluenesulfonic acid monohydrate (200 mg, 1.1 mmol) were dissolved in 2-pentanol (2 mL). The reaction was heated up to 120° C. by microwave and reacted for 1 hour. After LC-MS showed completion of the reaction, the reaction solution was cooled to room temperature naturally, and a dark solid was precipitated. The solid was filtered, and the filter cake was washed with methanol (1 mL) and methyl tert-butyl ether (1 mL) to obtain the crude product N-(2-(difluoromethoxy)-4-fluoro-5-nitrophenyl)-4-(1-methyl-1H-indol-3-yl)pyrimidin-2-amine (250 mg).

Step 2: Preparation of N-(2-(difluoromethoxy)-4-(4-methylpiperazine-1-yl)-5-nitrophenyl)-4-(1-methyl-1H-indol-3-yl)pyrimidin-2-amine

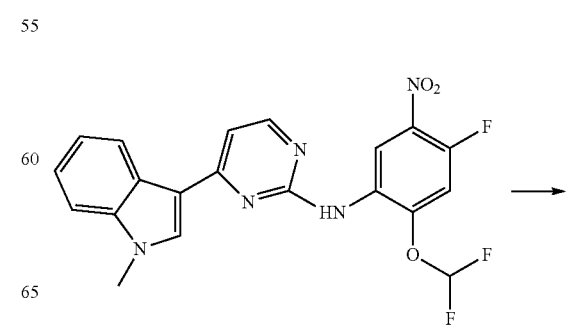

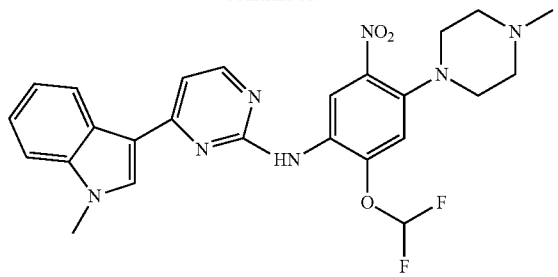

N-(2-(difluoromethoxy) 4-fluoro-5-nitrophenyl)-4-(1-methyl-1H-indol-3-yl)pyrimidin-2-amine (150 mg, 0.35 mmol) and methylpiperazine (105 mg, 1.05 mmol) were dissolved in DMF (2 mL). The reaction was heated up to 120° C. by microwave and reacted for 30 minutes. After LC-MS showed completion of the reaction, the reaction solution was concentrated. The resulting residue was purified by preparative thin-layer chromatography to obtain N-(2-(difluoromethoxy)-4-(4-methylpiperazine-1-yl)-5-nitrophenyl)-4-(1-methyl-1H-indol-3-yl)pyrimidin-2-amine (50 mg, 28%).

Step 3: Preparation of 6-(difluoromethoxy)-N1-(4-(1-methyl-1H-indol-3-yl)pyrimidin-2-yl)-4-(4-methylpiperazine-1-yl)benzene-1,3-diamine

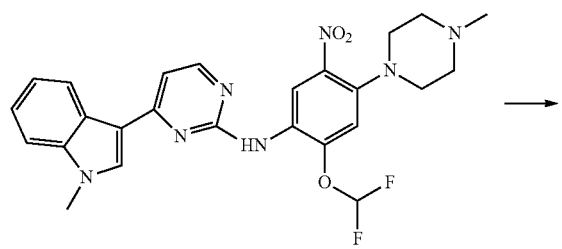

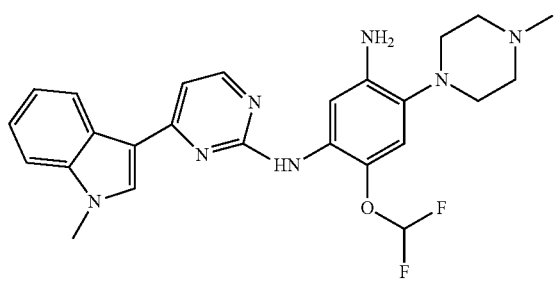

N-(2-(difluoromethoxy)-4-(4-methylpiperazine-1-yl)-5-nitrophenyl)-4-(1-methyl-1H-indol-3-yl)pyrimidin-2-amine (50 mg, 98.0 μmmol) was dissolved in methanol (10 mL), and then Pd/C (10 mg) was added. A hydrogenation reaction was carried out at room temperature for 2 hours. After LC-MS showed completion of the reaction, the reaction solution was filtered through celite, and the filtrate was concentrated to obtain the crude product 6-(difluoromethoxy)-N1-(4-(1-methyl-1H-indol-3-yl)pyrimidin-2-yl)-4-(4-methylpiperazine-1-yl)benzene 1,3-diamine (40 mg, 85%) which was used directly in the next reaction.

Step 4: Preparation of N-(4-(difluoromethoxy)-5-((4-(1-methyl-1H-indol-3-yl)pyrimidin-2-yl)amino)-2-(4-methylpiperazine-1-yl)phenyl)acrylamide

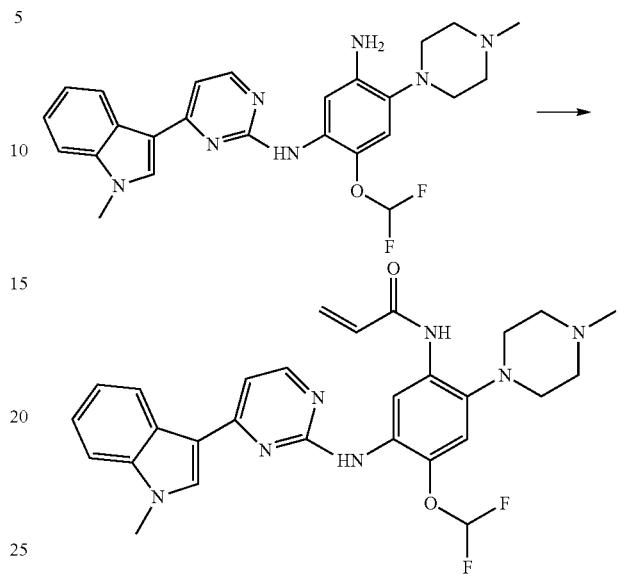

6-(difluoromethoxy)-N1-(4-(1-methyl-1H-indol-3-yl)pyrimidin-2-yl)-4-(4-methylpiperazine-1-yl)benzene 1,3-diamine (40 mg, 83.4 umol) and triethylamine (50 mg, 0.50 mmol) were dissolved in anhydrous tetrahydrofuran (15 mL). The reaction was stirred for 10 minutes in an ice bath, and acryloyl chloride (0.15 mL, 0.15 mmol, 1 M in THF) was added slowly. The reaction was stirred for 2 hours in an ice bath and quenched with saturated NH$_4$Cl (5 mL) after LC-MS showed completion of the reaction. The reaction solution was concentrated, and the remaining aqueous solution was extracted with dichloromethane (10 mL×3). The organic phases were combined, dried over anhydrous magnesium sulfate, filtered and concentrated. The resulting residue was purified by preparative thin-layer chromatography to obtain N-(4-(difluoromethoxy)-5-((4-(1-methyl-1H-indol-3-yl)pyrimidin-2-yl)amino)-2-(4-methylpiperazine-1-yl)phenyl)acrylamide (12 mg, 27%).

$^1$H NMR (400 MHz, CDCl$_3$) δ 9.76 (s, 1H), 8.82 (s, 1H), 8.66 (s, 1H), 8.33 (d, J=5.3 Hz, 1H), 8.05-7.97 (m, 1H), 7.44 (s, 1H), 7.33 (dd, J=6.9, 1.8 Hz, 1H), 7.23 (dd, J=7.1, 1.4 Hz, 2H), 7.18 (d, J=5.3 Hz, 1H), 7.00 (s, 1H), 6.64-6.20 (m, 3H), 5.75 (dd, J=10.0, 1.5 Hz, 1H), 3.90 (s, 3H), 2.90 (s, 4H), 2.68 (s, 4H), 2.41 (s, 3H);

MS m/z (ESI): 534.3 [M+H]$^+$.

Example 3: Preparation of N-(4-(difluoromethoxy)-2-(methyl(2-(3-carbonylmorpholino)ethyl)amino)-5-((4-(1-methyl-1H-indol-3-yl)pyrimidin-2-yl)amino)phenyl)acrylamide

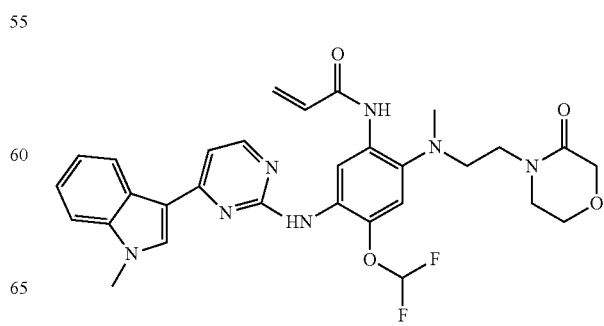

Step 1: Preparation of 4-(2-((5-(difluoromethoxy)-4-((4-(1-methyl-1H-indol-3-yl)pyrimidin-2-yl)amino)-2-nitrophenyl)(methyl)amino)ethyl)morpholin-3-one

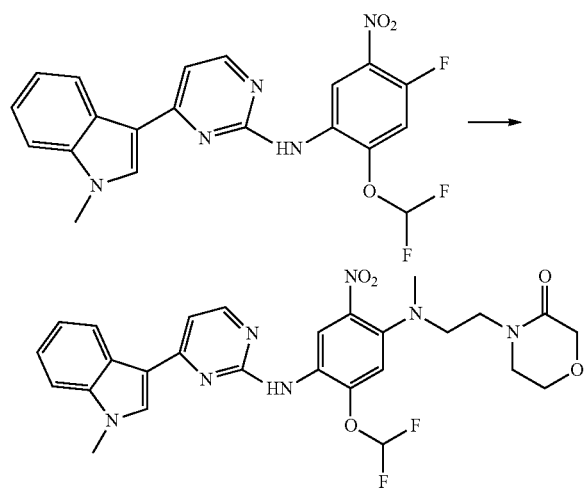

N-(2-(difluoromethoxy) 4-fluoro-5-nitrophenyl)-4-(1-methyl-1H-indol-3-yl)pyrimidin-2-amine (200 mg, 0.46 mmol), 4-(2-(methylamino)ethyl)morpholin-3-one (110 mg, 0.69 mmol) and diisopropylethylamine (180 mg, 1.4 mmol) were dissolved in DMF. The reaction was heated up to 120° C. by microwave for 30 min. After LC-MS showed completion of the reaction, the reaction solution was concentrated. The resulting residue was purified by preparative thin-layer chromatography to obtain the product 4-(2-((5-(difluoromethoxy)-4-((4-(1-methyl-1H-indol-3-yl)pyrimidin-2-yl)amino)-2-nitrophenyl)(methyl)amino)ethyl)morpholin-3-one (100 mg, 38%).

Step 2: Preparation of 4-(2-((2-amino-5-(difluoromethoxy)-4-((4-(1-methyl-1H-indol-3-yl)pyrimidin-2-yl)amino)phenyl)methyl)amino)ethyl)morpholin-3-one

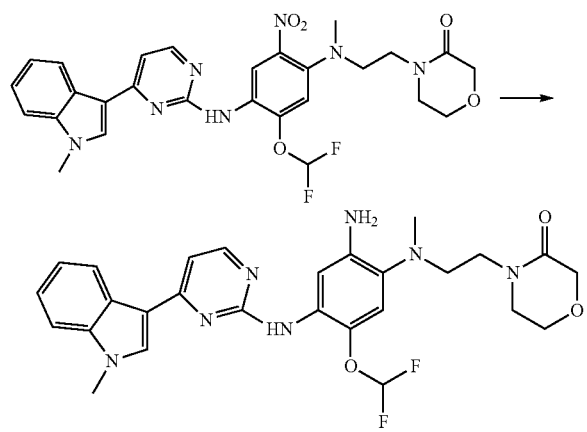

4-(2-((5-(difluoromethoxy)-4-((4-(1-methyl-1H-indol-3-yl)pyrimidin-2-yl)amino)-2-nitrophenyl)(methyl)amino)ethyl)morpholin-3-one (100 mg, 0.17 mmol) was dissolved in methanol (5 mL), followed by addition of Pd/C (10 mg). A hydrogenation reaction was carried out at room temperature for 2 hours. After LC-MS showed completion of the reaction, the reaction solution was filtered through celite, and the filtrate was concentrated to obtain the product 4-(2-((2-amino-5-(difluoromethoxy)-4-((4-(1-methyl-1H-indol-3-yl)pyrimidin-2-yl)amino)phenyl)(methyl)amino)ethyl)morpholin-3-one (40 mg, 40%).

Step 3: Preparation of N-(4-(difluoromethoxy)-2-(methyl(2-(3-carbonylmorpholino)ethyl)amino)-5-((4-(1-methyl-1H-indol-3-yl)pyrimidin-2-yl)amino)phenyl)acrylamide

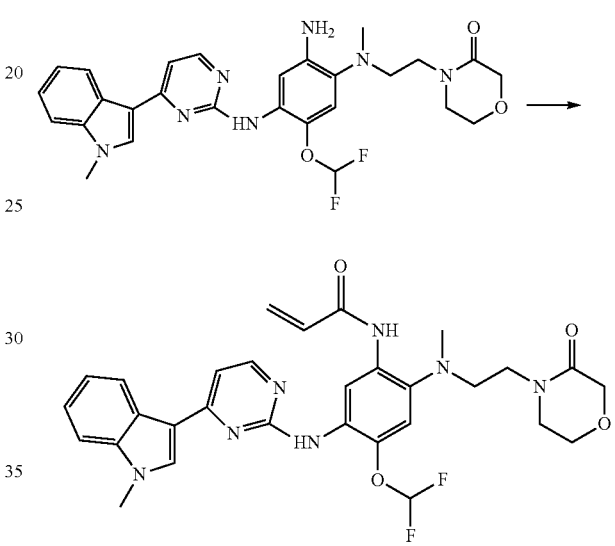

4-(2-((2-amino-5-(difluoromethoxy)-4-((4-(1-methyl-1H-indol-3-yl)pyrimidin-2-yl)amino)phenyl)(methyl)amino)ethyl)morpholin-3-one (40 mg, 74.4 μmmol) and triethylamine (40 mg, 0.37 mmol) were dissolved in anhydrous tetrahydrofuran (15 mL). The reaction was stirred for 10 minutes in an ice bath, and acryloyl chloride (0.1 mL, 100 μmol, 1 M in THF) was added slowly in an ice bath. The reaction was stirred for 30 minutes in an ice bath, after LC-MS showed completion of the reaction, the reaction was quenched with saturated $NH_4Cl$ (5 mL). The reaction solution was concentrated, then the remaining aqueous solution was extracted with dichloromethane (5 mL×3). The organic phases were combined, dried over anhydrous magnesium sulfate, filtered and concentrated. The resulting residue was purified by preparative thin-layer chromatography to obtain the product N-(4-(difluoromethoxy)-2-(methyl(2-(3-carbonylmorpholino)ethyl)amino)-5-((4-(1-methyl-1H-indol-3-yl)pyrimidin-2-yl)amino)phenyl)acrylamide (10 mg, 23%).

$^1$H NMR (400 MHz, $CDCl_3$) δ 9.79 (s, 1H), 8.83 (d, J=44.6 Hz, 2H), 8.30 (d, J=5.4 Hz, 1H), 7.99 (dd, J=6.7, 1.8 Hz, 1H), 7.33 (dd, J=6.9, 1.8 Hz, 1H), 7.25-7.20 (m, 2H), 7.18 (s, 1H), 6.96 (s, 1H), 6.71-6.30 (m, 3H), 5.74 (dd, J=9.5, 2.2 Hz, 1H), 4.08 (s, 2H), 3.90 (s, 3H), 3.73 (dd, J=5.7, 4.5 Hz, 2H), 3.49 (t, J=6.1 Hz, 2H), 3.24-3.19 (m, 2H), 3.05 (t, J=6.1 Hz, 2H), 2.61 (s, 3H);

MS m/z (ESI): 592.3 [M+H]$^+$.

Example 4: Preparation of N-(4-(difluoromethoxy)-2-((2-(dimethylamino)ethyl)(methyl)amino)-5-((4-(6-methoxy-1-methyl-1H-indol-3-yl)pyrimidin-2-yl)amino)phenyl)acrylamide

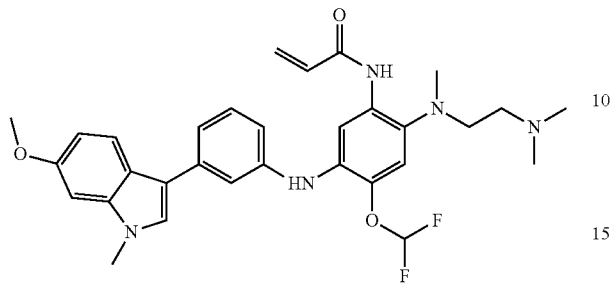

Step 1: Preparation of 3-(2-chloropyrimidin-4-yl)-6-methoxy-1-methyl-1H-indole

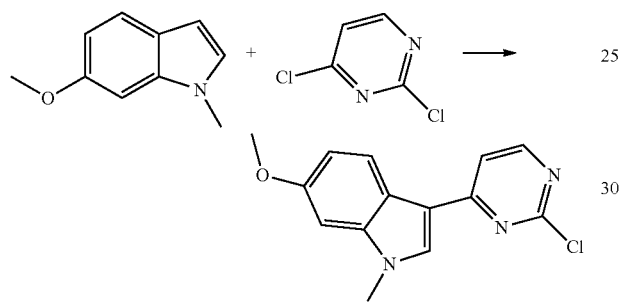

6-methoxy-1-methyl-1H-indole (300 mg, 1.86 mmol) and 2,4-dichloropyrimidine (330 mg, 2.23 mmol) were dissolved in ethylene glycol dimethyl ether (10 mL), then anhydrous aluminum trichloride (500 mg, 3.72 mmol) was added. The reaction was heated up to 60° C. in a nitrogen atmosphere and stirred for 3 h. After LC-MS showed completion of the reaction, the reaction solution was poured into about 50 mL of ice water and extracted with methyl tert-butyl ether (50 mL×3). The organic phases were combined, washed successively with saturated sodium bicarbonate (30 mL×2) and H$_2$O (30 mL), dried, filtered, and concentrated. The resulting residue was purified by flash silica gel column chromatography to obtain the product 3-(2-chloropyrimidin-4-yl)-6-methoxy-1-methyl-1H-indole (120 mg, 24%).

Step 2: Preparation of N-(2-(difluoromethoxy)-4-fluoro-5-nitrophenyl)-4-(6-methoxy-(1-methyl-1H-indol-3-yl)pyrimidin-2-amine

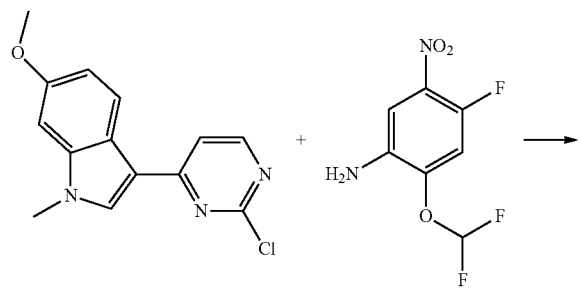

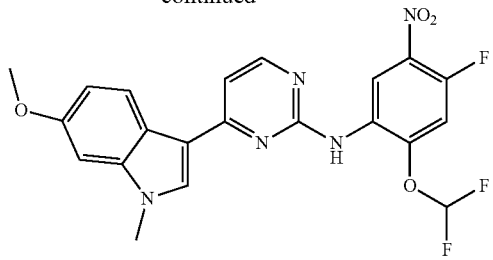

3-(2-chloropyrimidin-4-yl)-6-methoxy-1-methyl-1H-indole (120 mg, 0.44 mmol), 2-(difluoromethoxy)-4-fluoro-5-nitroaniline (120 mg, 0.53 mmol) and p-toluenesulfonyl chloride (110 mg, 0.57 mmol) were dissolved in 2-pentanol (5 mL). The reaction was heated up to 120° C. and stirred for 16 hours. After LC-MS showed completion of the reaction, the reaction solution was concentrated and extracted with DCM (10 mL) and saturated sodium bicarbonate aqueous solution (10 mL). The organic phase was dried and filtered. The filtrate was concentrated to obtain the crude product N-(2-(difluoromethoxy)-4-fluoro-5-nitrophenyl)-4-(6-methoxy-(1-methyl-1H-indol-3-yl)pyrimidin-2-amine (200 mg, 98%) which was used directly in the next step.

Step 3: Preparation of 2-(difluoromethoxy)-N4-(2-(dimethylamino)ethyl)-N1-(4-(6-methoxy-(1-methyl-1H-indol-3-yl)pyrimidin-2-yl)-N4-methyl-5-nitrobenzene-1,4-diamine

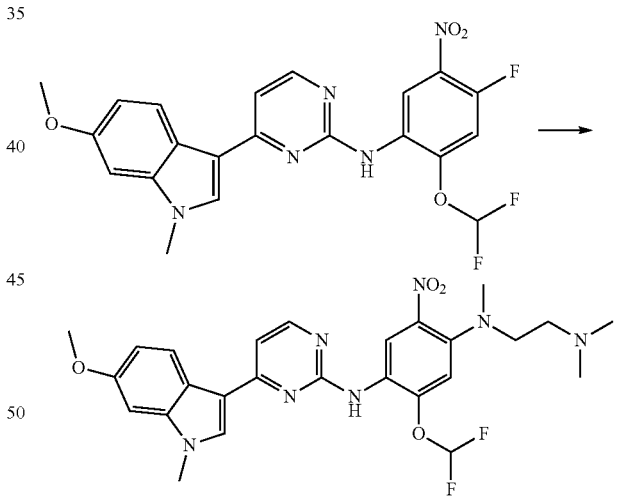

N-(2-(difluoromethoxy)-4-fluoro-5-nitrophenyl)-4-(6-methoxy-(1-methyl-1H-indol-3-yl)pyrimidin-2-amine (100 mg, 0.21 mmol), triethylamine (100 mg, 0.98 mmol) and trimethylethylenediamine (60 mg, 0.59 mmol) were dissolved in DMF (1 mL). The reaction was heated up to 120° C. by microwave and stirred for 30 minutes. After LC-MS showed completion of the reaction, the reaction solution was concentrated. The resulting residue was purified by preparative thin-layer chromatography to obtain the product 2-(difluoromethoxy)-N4-(2-(dimethylamino)ethyl)-N1-(4-(6-methoxy-1-methyl-1H-indol-3-yl)pyrimidin-2-yl)-N4-methyl-5-nitrobenzene-1,4-diamine (20 mg, 18%).

Step 4: Preparation of 5-(difluoromethoxy)-N1-(2-(dimethylamino)ethyl)-N4-(4-(6-methoxy-1-methyl-1H-indol-3-yl)pyrimidin-2-yl)-N1-methylbenzene-1,2,4-triamine

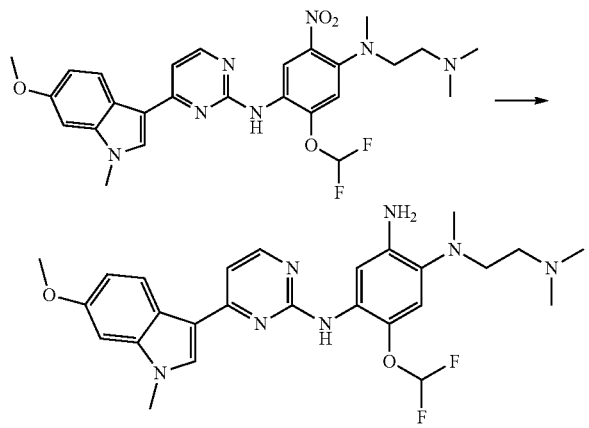

2-(difluoromethoxy)-N4-(2-(dimethylamino)ethyl)-N1-(4-(6-methoxy-1-methyl-1H-indol-3-yl)pyrimidin-2-yl)-N4-methyl-5-nitrobenzene-1,4-diamine (20 mg, 36.9 μmol) was dissolved in methanol (5 mL), then Pd/C (10 mg) was added. A hydrogenation reaction was carried out at room temperature for 2 hours. After LC-MS showed completion of the reaction, the reaction was filtered through celite, and the filtrate was concentrated to obtain the product 5-(difluoromethoxy)-N1-(2-(dimethylamino)ethyl)-N4-(4-(6-methoxy-1-methyl-1H-indol-3-yl)pyrimidin-2-yl)-N1-methylbenzene-1,2,4-triamine (15 mg, 80%) which was used directly in the next reaction.

Step 5: Preparation of N-(4-(difluoromethoxy)-2-((2-(dimethylamino)ethyl)(methyl)amino)-5-((4-(6-methoxy-1-methyl-1H-indol-3-yl)pyrimidin-2-yl)amino)phenyl)acrylamide

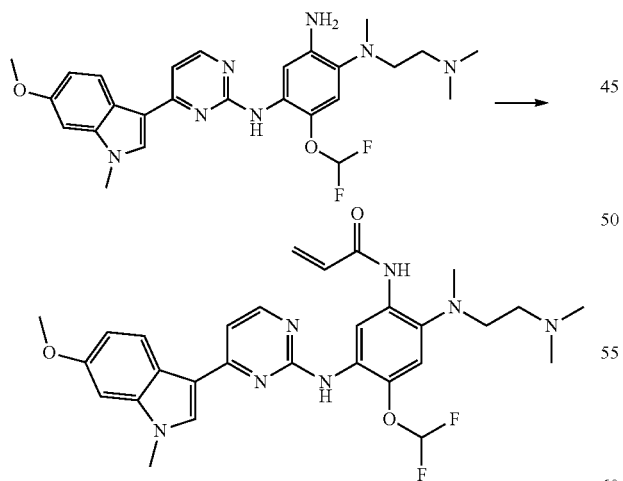

5-(difluoromethoxy)-N1-(2-(dimethylamino)ethyl)-N4-(4-(6-methoxy-1-methyl-1H-indol-3-yl)pyrimidin-2-yl)-N1-methylbenzene-1,2,4-triamine (15 mg, 29.4 μmmol) and triethylamine (50 mg) were dissolved in anhydrous tetrahydrofuran (15 mL). The reaction was stirred for 10 minutes in an ice bath, and then acryloyl chloride (0.1 mL, 100 umol, 1 M in THF) was added slowly in an ice bath. The reaction was stirred for 30 minutes in an ice bath and quenched with saturated NH4Cl (5 mL) after LC-MS showed completion of the reaction. The reaction solution was concentrated, and the remaining aqueous solution was extracted with dichloromethane (5 mL×3). The organic phases were combined, dried over anhydrous magnesium sulfate and filtered. The filtrate was concentrated, and the resulting residue was purified by preparative thin-layer chromatography to obtain the product N-(4-(difluoromethoxy)-2-((2-(dimethylamino)ethyl)(methyl)amino)-5-((4-(6-methoxy-1-methyl-1H-indol-3-yl)pyrimidin-2-yl)amino)phenyl)acrylamide (5.0 mg, 30%).

$^1$H NMR (400 MHz, CDCl$_3$) δ 10.01 (s, 1H), 9.70 (s, 1H), 8.63 (s, 1H), 8.25 (d, J=5.3 Hz, 1H), 7.83 (d, J=8.8 Hz, 1H), 7.33 (s, 1H), 7.06 (d, J=5.3 Hz, 1H), 6.91 (s, 1H), 6.79 (dd, J=8.8, 2.3 Hz, 1H), 6.72 (d, J=2.2 Hz, 1H), 6.37 (dd, J=83.2, 64.3 Hz, 3H), 5.63 (d, J=11.9 Hz, 1H), 3.78 (d, J=3.4 Hz, 3H), 3.36 (s, 3H), 2.82 (s, 2H), 2.57 (s, 3H), 2.24 (s, 6H), 1.89 (d, J=5.9 Hz, 2H);

MS m/z (ESI): 566.2 [M+H]$^+$.

Example 5: Preparation of N-(5-((5-chloro-4-(1-methyl-1H-indol-3-yl)pyrimidin-2-yl)amino)-4-(difluoromethoxy)-2-((2-(dimethylamino)ethyl)(methyl)amino)phenyl)acrylamide

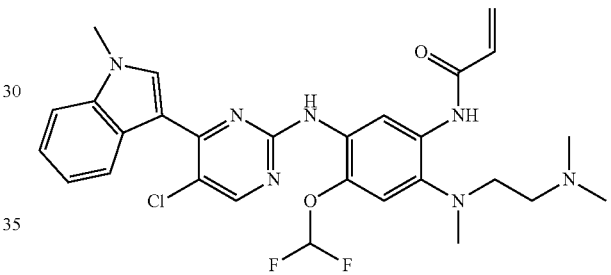

The preparation method of N-(5-((5-chloro-4-(1-methyl-1H-indol-3-yl)pyrimidin-2-yl)amino)-4-(difluoromethoxy)-2-((2-(dimethylamino)ethyl)(methyl)amino)phenyl)acrylamide was similar to Example 1.

$^1$H NMR (400 MHz, CDCl$_3$) δ 9.41 (s, 1H), 8.39 (s, 1H), 8.33 (d, J=5.3 Hz, 2H), 7.60-7.18 (m, 3H), 6.98 (s, 1H), 6.66-6.20 (m, 3H), 5.74-5.58 (m, 1H), 3.90 (s, 3H), 2.92-2.77 (m, 2H), 2.62 (s, 3H), 2.27 (s, 2H), 2.22 (s, 6H);

MS m/z (ESI): 571.0 [M+H]$^+$.

Example 6: Preparation of N-(4-(difluoromethoxy)-2-((2-(dimethylamino)ethyl)(methyl)amino)-5-((4-(1-(2-hydroxyethyl)-1H-indol-3-yl)pyrimidin-2-yl)amino)phenyl)acrylamide

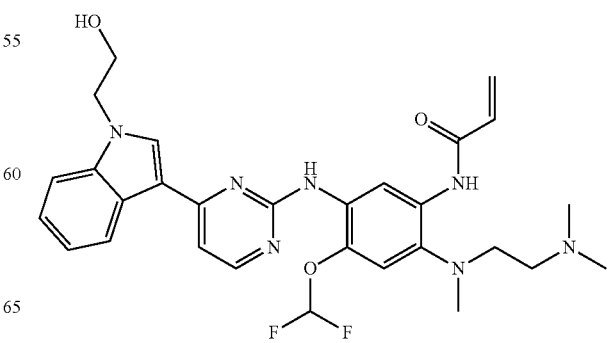

Step 1: Preparation of 2-(3-(2-((2-(difluoromethoxy)-4-fluoro-5-nitrophenyl)amino)pyrimidin-4-yl)-1H-indol-1-yl)ethan-1-ol

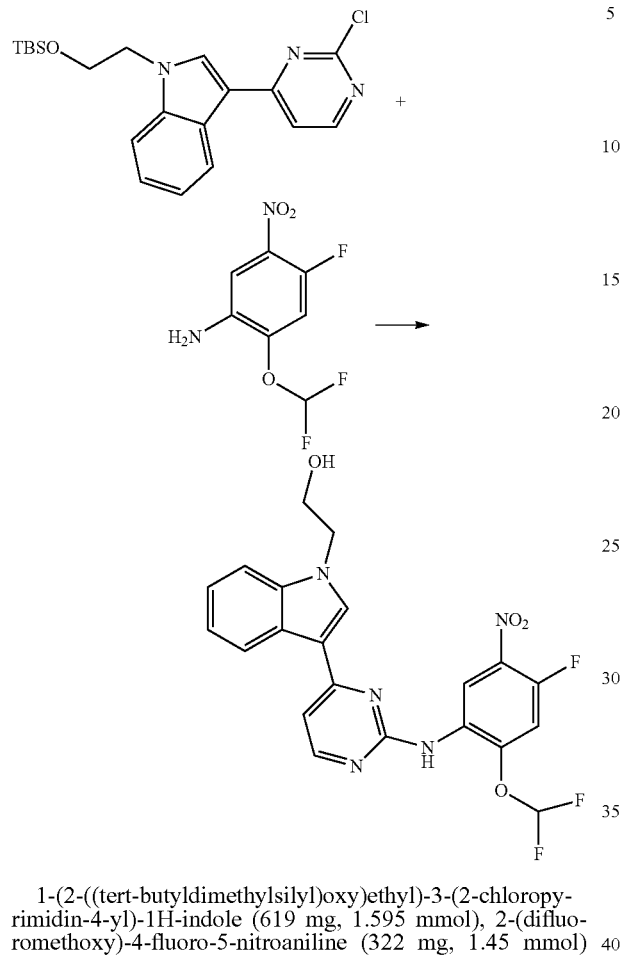

1-(2-((tert-butyldimethylsilyl)oxy)ethyl)-3-(2-chloropyrimidin-4-yl)-1H-indole (619 mg, 1.595 mmol), 2-(difluoromethoxy)-4-fluoro-5-nitroaniline (322 mg, 1.45 mmol) and p-toluenesulfonic acid monohydrate (276 mg, 1.45 mmol) were dissolved in 2-pentanol (5 mL). The reaction was heated up to 120° C. overnight. After LC-MS showed completion of the reaction, the reaction solution was cooled to room temperature naturally, and a dark solid was precipitated. The solid was filtered and the filter cake was washed with methanol (1 mL) and methyl tert-butyl ether (1 mL) to obtain the product 2-(3-(2-((2-(difluoromethoxy)-4-fluoro-5-nitrophenyl) amino)pyrimidin-4-yl)-1H-indol-1-yl)ethan-1-ol (135 mg, 20%).

Step 2: Preparation of 2-(3-(2-((2-(difluoromethoxy)-4-((2-(dimethylamino)ethyl)(methyl)amino)-5-nitrophenyl)amino)pyrimidin-4-yl)-1H-indol-ethan-1-ol

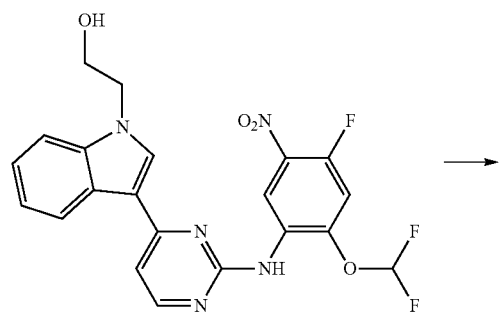

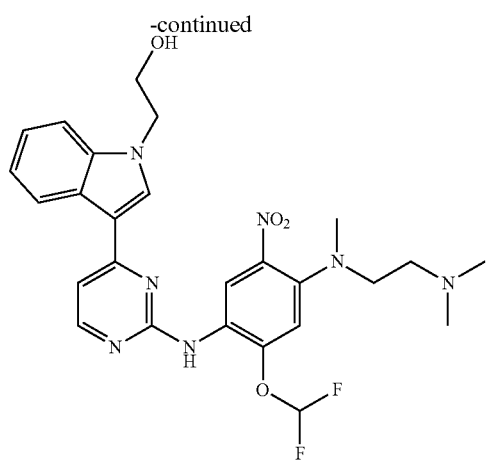

2-(3-(2-((2-(difluoromethoxy)-4-fluoro-5-nitrophenyl) amino)pyrimidin-4-yl)-1H-indol-1-yl)ethan-1-ol (130 mg, 0.283 mmol) was dissolved in 2 mL of DMF, then triethylamine (87 mg, 0.849 mmol) and trimethylethylenediamine (87 mg, 0.849 mmol) were added. The reaction was heated up to 120° C. by microwave and stirred for 30 minutes. After LC-MS showed completion of the reaction, the reaction solution was concentrated to dry. The crude product was purified by preparative thin-layer chromatography to obtain the product (131 mg, 90%).

Step 3: Preparation of 2-(3-(2-((5-amino-2-(difluoromethoxy)-4-((2-(dimethylamino)ethyl)(methyl)amino)phenyl)amino)pyrimidin-4-yl)-1H-indol-1-yl)ethan-1-ol

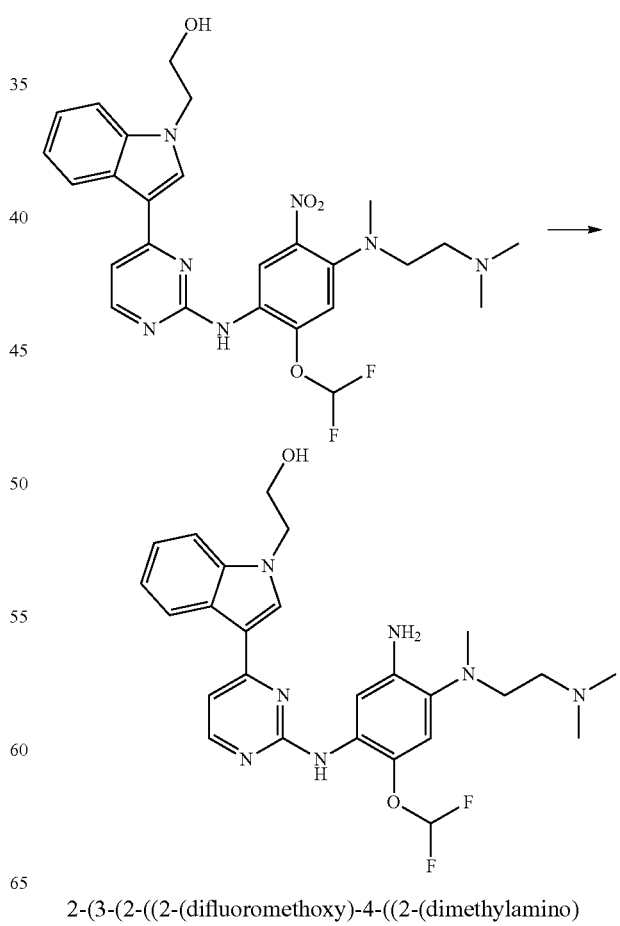

2-(3-(2-((2-(difluoromethoxy)-4-((2-(dimethylamino) ethyl)(methyl)amino)-5-nitrophenyl)amino)pyrimidin-4- yl)-1H-indol-ethan-1-ol (130 mg, 0.24 mmol) was dissolved in methanol (5 mL), and then Pd/C (10 mg) was added. The reaction was stirred for 1 hour in a hydrogen atmosphere at room temperature. After LC-MS showed completion of the reaction, the reaction solution was filtered, and the filtrate was concentrated to obtain the product (104 mg, 85%), which was used directly in the next step.

Step 4: Preparation of N-(4-(difluoromethoxy)-2-((2-(dimethylamino)ethyl)(methyl)amino)-5-((4-(1-(2-hydroxyethyl)-1H-indol-3-yl)pyrimidin-2-yl)amino)phenyl)acrylamide

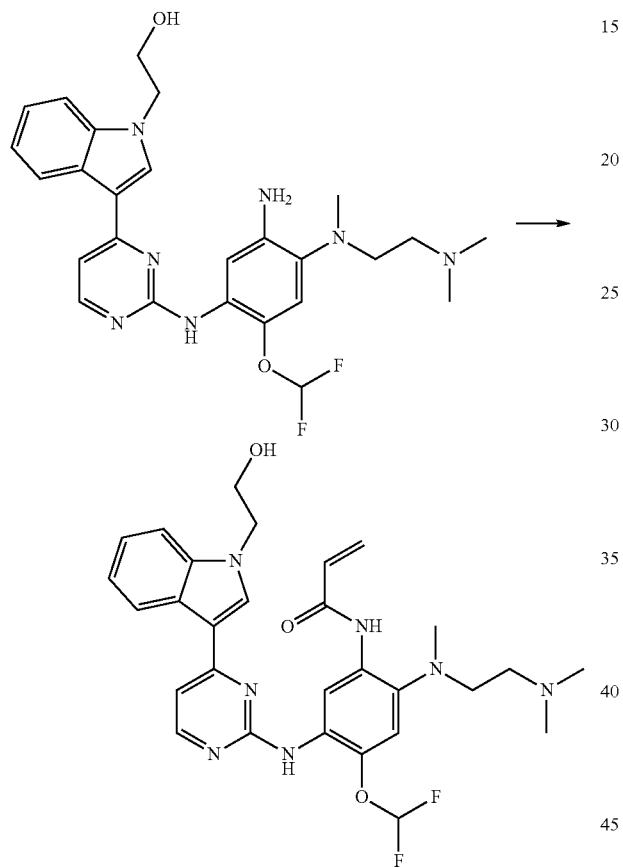

2-(3-(2-((5-amino-2-(difluoromethoxy)-4-((2-(dimethylamino)ethyl)(methyl)amino)phenyl)amino)pyrimidin-4-yl)-1H-indol-1-yl)ethan-1-ol (97 mg, 0.19 mmol) and triethylamine (19 mg, 0.19 mmol) were dissolved in anhydrous tetrahydrofuran (50 mL), and the reaction was stirred at −78° C. for 10 minutes. Acryloyl chloride (0.6 mL, 1 M in THF) was added slowly and dropwise. The reaction was stirred at this temperature for 30 minutes and quenched with methanol after LC-MS showed completion of the reaction. The reaction solution was concentrated, and the resulting residue was purified by preparative thin-layer chromatography to obtain the product N-(4-(difluoromethoxy)-2-((2-(dimethylamino)ethyl)(methyl)amino)-5-((4-(1-(2-hydroxyethyl)-1H-indol-3-yl)pyrimidin-2-yl)amino)phenyl)acrylamide (15 mg, 14%).

¹H NMR (400 MHz, CD₃OD) δ 8.59 (s, 1H), 8.45 (s, 1H), 8.25 (s, 1H), 8.07 (d, J=6.7 Hz, 1H), 7.58 (d, J=8.2 Hz, 1H), 7.53 (s, 1H), 7.44 (d, J=6.7 Hz, 1H), 7.41 (s, 1H), 7.35-7.16 (m, 5H), 7.01 (dd, J=17.2, 10.0 Hz, 2H), 6.42 (d, J=16.9 Hz, 1H), 5.83 (d, J=10.3 Hz, 1H), 4.41 (t, J=5.1 Hz, 2H), 3.95 (t, J=5.1 Hz, 2H), 3.50 (d, J=5.3 Hz, 2H), 3.44 (d, J=5.2 Hz, 2H), 3.37 (s, 1H), 2.93 (s, 6H), 2.81 (s, 3H);
MS m/z (ESI): 566 [M+H]⁺.

Example 7: Preparation of N-(5-((4-(1-acetyl-1H-indol-3-yl)pyrimidin-2-yl)amino)-4-(difluoromethoxy)-2-((2-(dimethylamino)ethyl)(methyl)amino)phenyl)acrylamide

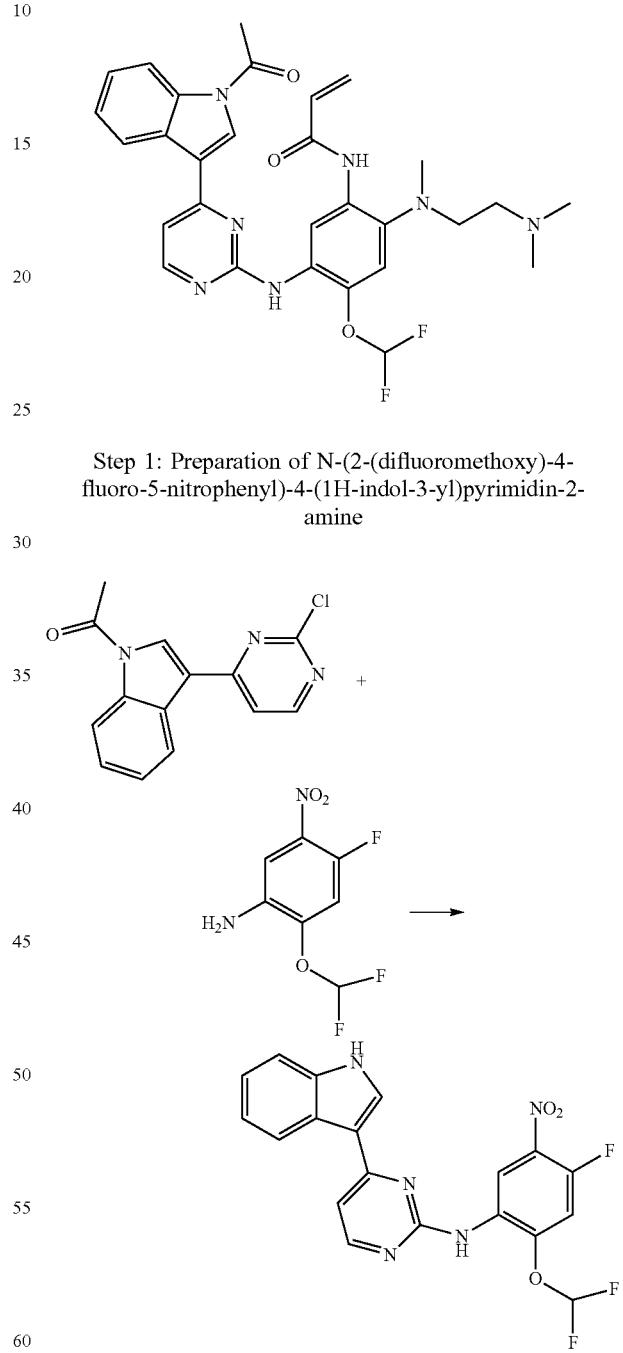

Step 1: Preparation of N-(2-(difluoromethoxy)-4-fluoro-5-nitrophenyl)-4-(1H-indol-3-yl)pyrimidin-2-amine 1-(3-(2-chloropyrimidin-4-yl)-1H-indol-1-yl)ethan-1-one (735 mg, 2.71 mmol), 2-(difluoromethoxy)-4-fluoro-5-nitroaniline (600 mg, 2.71 mmol) and p-toluenesulfonic acid monohydrate (514 mg, 2.71 mmol) were dissolved in 2-pentanol (20 mL), and the reaction was heated up to 120° C. overnight. After LC-MS showed completion of the reaction, the reaction solution was cooled to room temperature naturally, and a dark solid was precipitated. The solid was filtered, and the filter cake was washed with methanol (1 mL) and methyl tert-butyl ether (1 mL) to obtain N-(2-(difluoromethoxy)-4-fluoro-5-nitrophenyl)-4-(1H-indol-3-yl)pyrimidin-2-amine (250 mg, 20%).

Step 2: Preparation of N-(4-(1H-indol-3-yl)pyrimidin-2-yl)2-(difluoromethoxy)-(2-(dimethylamino)ethyl)-methyl-5-nitrobenzene-1,4-diamine

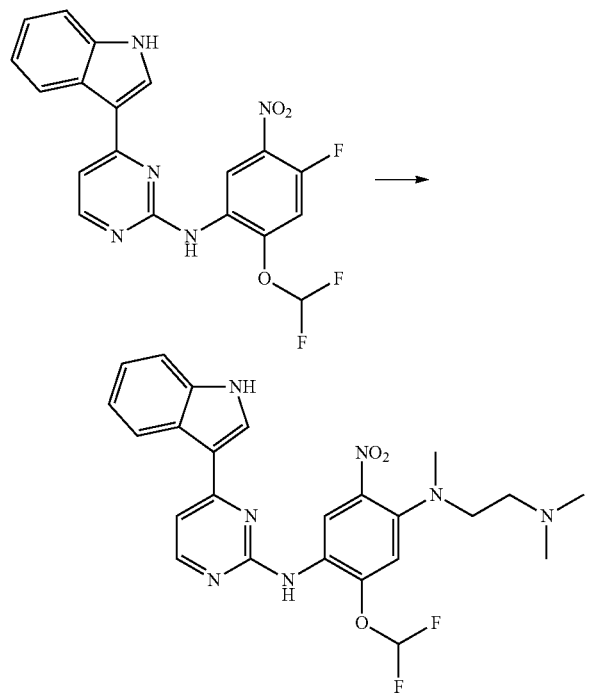

N-(2-(difluoromethoxy)-4-fluoro-5-nitrophenyl)-4-(1H-indol-3-yl)pyrimidin-2-amine (100 mg, 0.241 mmol) was dissolved in DMF (2 mL), and then triethylamine (73 mg, 0.72 mmol) and trimethylethylenediamine (74 mg, 0.72 mmol) were added. The reaction was heated up to 120° C. by microwave and stirred for 30 minutes. After LC-MS showed completion of the reaction, the reaction solution was concentrated. The crude product was purified by preparative thin-layer chromatography to obtain the product (100 mg, 83%).

Step 3: Preparation of N-(4-(1-acetyl-1H-indol-3-yl)pyrimidin-2-yl)-N-(2-(difluoromethoxy)-4-((2-(dimethylamino)ethyl)(methyl)amino)-5-nitrophenyl)acetamide

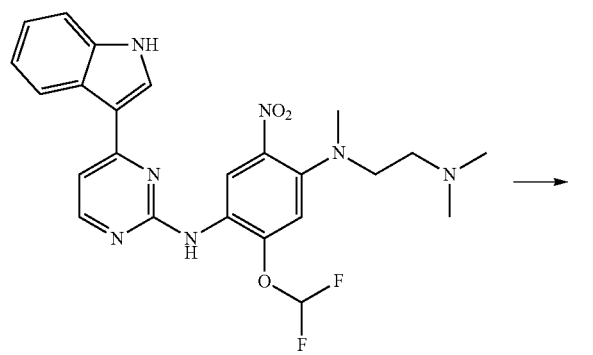

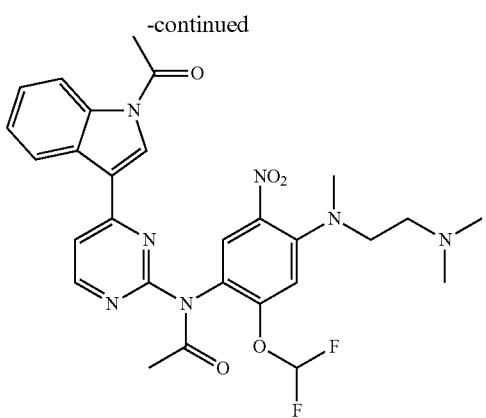

N-(4-(1H-indol-3-yl)pyrimidin-2-yl)-2-(difluoromethoxy)-(2-(dimethylamino)ethyl)-methyl-5-nitrobenzene-1,4-diamine (100 mg, 0.20 mmol) was dissolved in acetic anhydride (4 mL), and then triethylamine (0.5 mL) and DMAP (3 mg, 0.02 mmol) were added. The reaction was stirred at 120° C. for 30 minutes. Then the reaction solution was concentrated and extracted three times with ethyl acetate and water. The organic phases were combined, washed successively with saturated sodium bicarbonate aqueous solution, water and saturated brine, dried, filtered and concentrated to obtain the crude product, which was used directly in the next step.

Step 4: Preparation of 1-(3-(2-((5-amino-2-(difluoromethoxy)-4-((2-(dimethylamino)ethyl)(methyl)amino)phenyl)amino)pyrimidin-4-yl)-1H-indol-1-yl)ethan-1-one

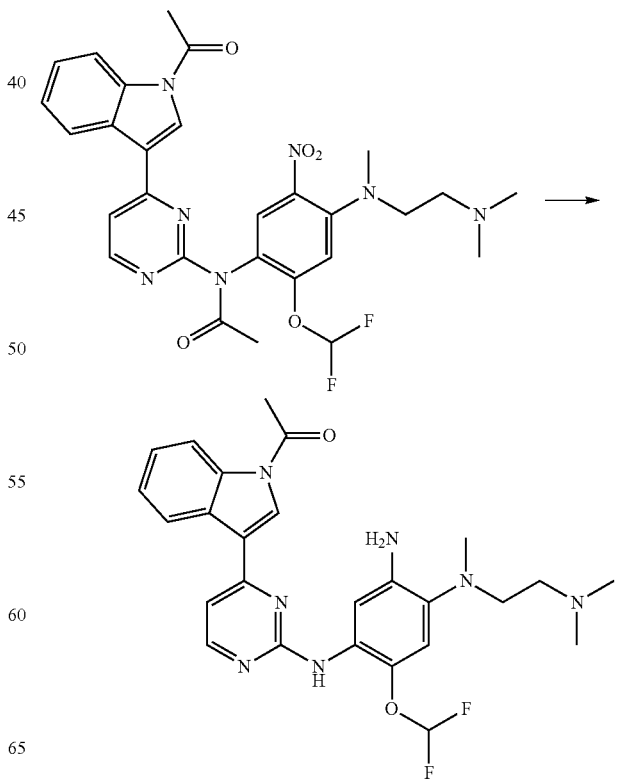

N-(4-(1-acetyl-1H-indol-3-yl)pyrimidin-2-yl)-N-(2-(difluoromethoxy)-4-((2-(dimethylamino)ethyl)(methyl)amino)-5-nitrophenyl)acetamide, which was obtained from the previous reaction, was dissolved in methanol (5 mL), Pd/C (15 mg) was added, and then the reaction was stirred at 24° C. in a hydrogen atmosphere for 1 hour. After LC-MS showed completion of the reaction, the reaction solution was filtered, and the filtrate was concentrated to obtain a crude product, which was further purified by flash column chromatography to obtain the product 1-(3-(2-((5-amino-2-(difluoromethoxy)-4-((2-(dimethylamino)ethyl)(methyl)amino)phenyl)amino)pyrimidin-4-yl)-1H-indol-1-yl)ethan-1-one (30 mg, 32%).

Step 5: Preparation of N-(5-(4-(1-acetyl-1H-indol-3-yl)pyrimidin-2-yl)amino)-4-(difluoromethoxy)-2-((2-(dimethylamino)ethyl)(methyl)amino)phenyl)acrylamide

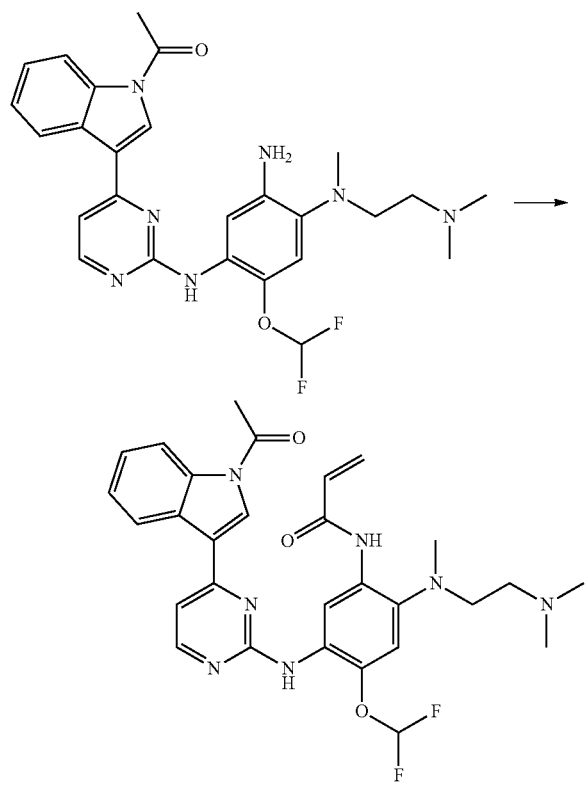

1-(3-(2-((5-amino-2-(difluoromethoxy)-4-((2-(dimethylamino)ethyl)(methyl)amino)phenyl)amino)pyrimidin-4-yl)-1H-indol-1-yl)ethan-1-one (30 mg, 0.059 mmol) and triethylamine (6 mg, 0.19 mmol) were dissolved in anhydrous tetrahydrofuran (30 mL). The reaction was stirred at –78° C. for 10 minutes, and acryloyl chloride (0.2 mL, 1 M in THF) was added slowly. The reaction was stirred at this temperature for 30 minutes, and quenched with methanol after LC-MS showed completion of the reaction. The reaction solution was concentrated, and the resulting residue was purified by preparative thin-layer chromatography to obtain the product N-(5-(4-(1-acetyl-1H-indol-3-yl)pyrimidin-2-yl)amino)-4-(difluoromethoxy)-2-((2-(dimethylamino)ethyl)(methyl)amino)phenyl)acrylamide (15 mg, 45%).

$^1$H NMR (400 MHz, CDCl$_3$) δ 9.81 (s, 1H), 9.34 (s, 1H), 8.61 (s, 1H), 8.40 (d, J=5.4 Hz, 1H), 7.90 (d, J=8.0 Hz, 1H), 7.78 (d, J=2.7 Hz, 1H), 7.35 (d, J=8.2 Hz, 1H), 7.20 (d, J=5.4 Hz, 1H), 7.08 (d, J=3.2 Hz, 1H), 6.54-6.33 (m, 3H), 6.22-6.04 (m, 2H), 5.82 (dd, J=4.0 Hz, 1H), 5.69 (dd, J=4.0 Hz, 1H), 3.07-3.02 (m, 2H), 2.84 (s, 2H), 2.92-2.76 (m, 3H), 2.59 (s, 3H), 2.53 (s, 6H);

MS m/z (ESI): 564 [M+H]$^+$.

Example 8: Preparation of N-(5-((4-(1H-indol-3-yl)pyrimidin-2-yl)amino)-4-(difluoromethoxy)-2-((2-(dimethylamino)ethyl)(methyl)amino) phenyl)acrylamide

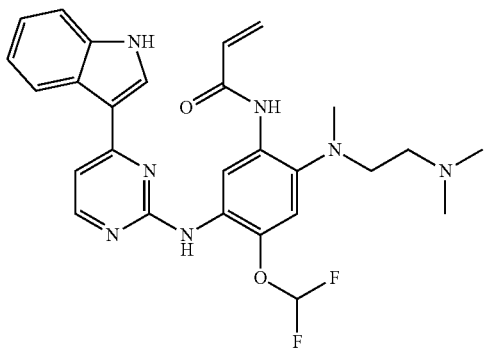 [SMILES: C=CC(=O)Nc1cc(Nc2nccc(-c3c[nH]c4ccccc34)n2)c(OC(F)F)cc1N(C)CCN(C)C]

N-(5-((4-(1-acetyl-1H-indol-3-yl)pyrimidin-2-yl)amino)-4-(difluoromethoxy)-2-((2-(dimethylamino)ethyl)(methyl)amino)phenyl)acrylamide (12 mg, 0.021 mmol) was dissolved in methanol (2 mL), and then an aqueous solution of 1 N sodium carbonate (1 mL) was added. The solution was reacted at room temperature for 3 hours and concentrated to obtain a crude product, which was further purified by flash silica gel column chromatography to obtain the product N-(5-((4-(1H-indol-3-yl)pyrimidin-2-yl)amino)-4-(difluoromethoxy)-2-((2-(dimethylamino)ethyl)(methyl)amino) phenyl)acrylamide (4 mg, 36.4%).

$^1$H NMR (400 MHz, CD$_3$OD) δ 8.54 (d, J=3.4 Hz, 1H), 8.38-8.04 (m, 3H), 7.51 (d, J=7.3 Hz, 2H), 7.39 (t, J=9.9 Hz, 1H), 7.31-7.15 (m, 3H), 6.87 (ddd, J=40.9, 27.6, 6.5 Hz, 2H), 6.45 (d, J=17.0 Hz, 1H), 5.85 (d, J=10.3 Hz, 1H), 5.36 (t, J=4.7 Hz, 1H), 3.56-3.47 (m, 2H), 3.45-3.38 (m, 2H), 2.93 (s, 6H), 2.82 (s, 3H);

MS m/z (ESI): 522 [M+H]$^+$.

Example 9: Preparation of N-(5-((4-(6-cyano-1-methyl-1H-indol-3-yl)pyrimidin-2-yl)amino)-4-(difluoromethoxy)-2-((2-(dimethylamino)ethyl)(methyl)amino)phenyl)acrylamide

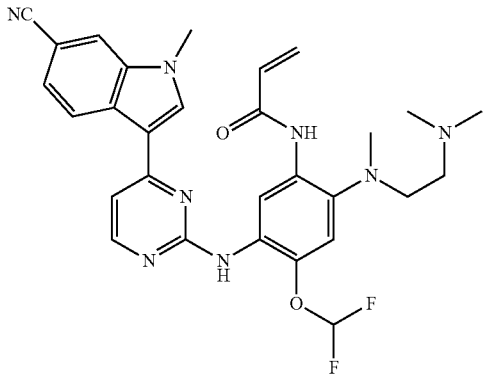 [SMILES: C=CC(=O)Nc1cc(Nc2nccc(-c3cn(C)c4cc(C#N)ccc34)n2)c(OC(F)F)cc1N(C)CCN(C)C]

The preparation method of N-(5-((4-(6-cyano-1-methyl-1H-indol-3-yl)pyrimidin-2-yl)amino)-4-(difluoromethoxy)-

2-((2-(dimethylamino)ethyl)(methyl)amino)phenyl)acrylamide was similar to Example 4.

Example 10: Preparation of N-(4-(difluoromethoxy)-2-((2-(dimethylamino)ethyl)(methyl)amino)-5-((4-(1-methyl-6-(isopropylsulfonyl)-1H-indol-3-yl)pyrimidin-2-yl)amino)phenyl)acrylamide

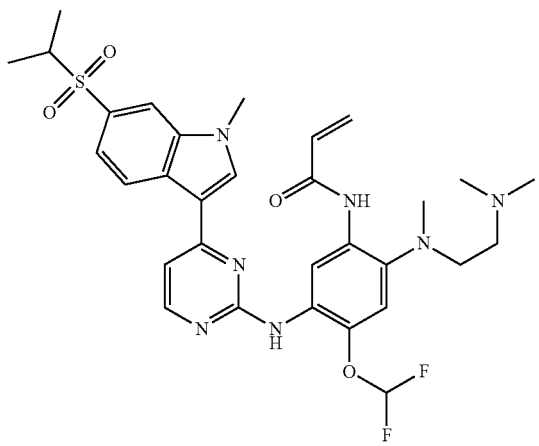 [SMILES: C=CC(=O)Nc1cc(Nc2nccc(-c3cn(C)c4cc(S(=O)(=O)C(C)C)ccc34)n2)c(OC(F)F)cc1N(C)CCN(C)C]

The preparation method of N-(4-(difluoromethoxy)-2-((2-(dimethylamino)ethyl)(methyl)amino)-5-((4-(1-methyl-6-(isopropylsulfonyl)-1H-indol-3-yl)pyrimidin-2-yl)amino)phenyl)acrylamide was similar to Example 4.

Example 11: Preparation of N-(4-(difluoromethoxy)-2-((2-(dimethylamino)ethyl)(methyl)amino)-5-((4-(6-(dimethylphosphoryl)-1-methyl-1H-indol-3-yl)pyrimidin-2-yl)amino)phenyl)acrylamide

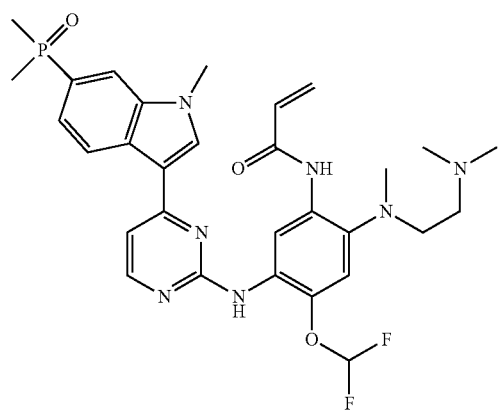

Step 1: Preparation of (3-(2-((2-(difluoromethoxy)-4-((2-(dimethylamino)ethyl)(methyl)amino)-5-nitrophenyl)amino)pyrimidin-4-yl)-1-methyl-1H-indol-6-yl)dimethylphosphine oxide

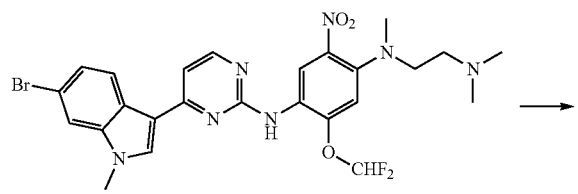

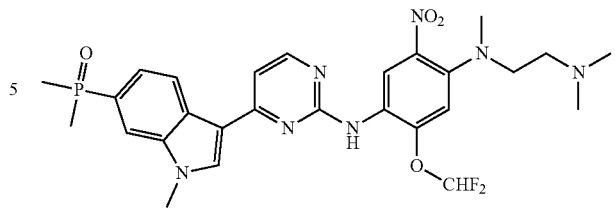

N1-(4-(6-bromo-1-methyl-1H-indol-3-yl)pyrimidin-2-yl)-2-(difluoromethoxy)-N4-(2-(dimethylamino)ethyl)-N4-methyl-5-nitrobenzene-1,4-diamine (50 mg, 84.6 µmol), dimethylphosphine oxide (66.1 mg, 0.85 mmol), palladium acetate (10 mg), triethylamine (0.25 mL) and X-Phos (20 mg) were dissolved in DMF (2 mL). The mixture was purged with nitrogen to remove oxygen for 10 minutes and heated up to 130° C. by microwave for 1 hour. After LC-MS showed completion of the reaction, the reaction solution was filtered, and the filtrate was evaporated to dry. The resulting residue was purified by preparative thin-layer chromatography to obtain (3-(2-((2-(difluoromethoxy)-4-((2-(dimethylamino)ethyl)(methyl)amino)-5-nitrophenyl) amino)pyrimidin-4-yl)-1-methyl-1H-indol-6-yl)dimethylphosphine oxide (40 mg, 80%).

Step 2: Preparation of (3-(4-((5-amino-2-(difluoromethoxy)-4-((2-(dimethylamino)ethyl)(methyl)amino)phenyl)amino)pyrimidin-4-yl)-1-methyl-1H-indol-6-yl)dimethylphosphine oxide

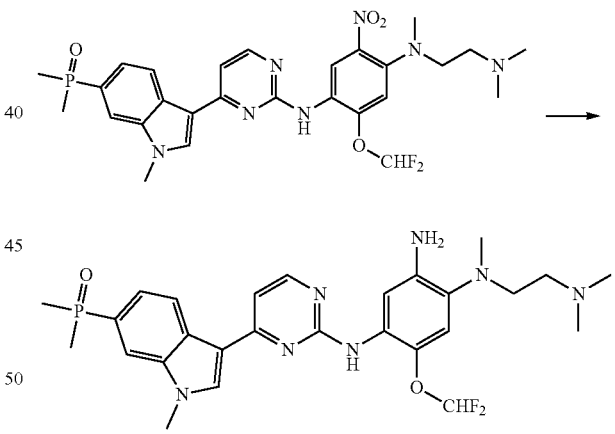

3-(2-((2-(difluoromethoxy)-4-((2-(dimethylamino)ethyl)(methyl)amino)-5-nitrophenyl)amino)pyrimidin-4-yl)-1-methyl-1H-indol-6-yl)dimethylphosphine oxide (40 mg, 68.1 µmol) was dissolved in methanol (5 mL), and then Pd/C (10 mg) was added. The reaction was stirred at room temperature in a hydrogen atmosphere for 10 minutes. After LC-MS showed completion of the reaction, the reaction solution was filtered, and the filtrate was concentrated. The resulting residue was purified by reversed phase column chromatography to obtain (3-(2-((5-amino-2-(difluoromethoxy)-4-((2-(dimethylamino)ethyl)(methyl)amino) phenyl)amino)pyrimidin-4-yl)-1-methyl-1H-indol-6-yl)dimethylphosphine oxide (15 mg, 27%).

Step 3: Preparation of N-(4-(difluoromethoxy)-2-((2-(dimethylamino)ethyl)(methyl)amino)-5-((4-(6-(dimethylphosphoryl)-1-methyl-1H-indol-3-yl)pyrimidin-2-yl)amino)phenyl)acrylamide

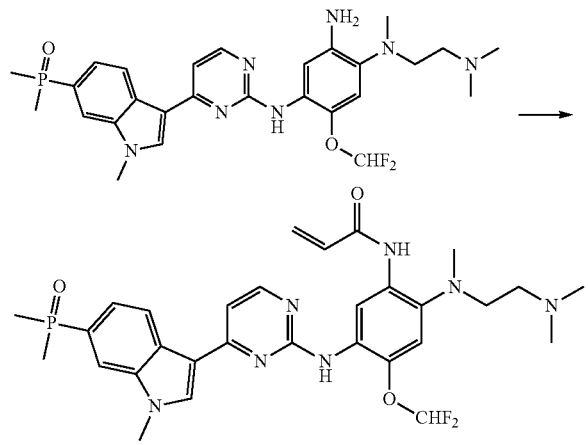

(3-(2-((5-amino-2-(difluoromethoxy)-4-((2-(dimethylamino)ethyl)(methyl)amino)phenyl)amino)pyrimidin-4-yl)-1-methyl-1H-indol-6-yl)dimethylphosphine oxide (15 mg, 26.9 μmol) and triethylamine (0.1 mL) were dissolved in tetrahydrofuran (10 mL), and the reaction solution was cooled to −10 to −5° C. Acryloyl chloride (0.1 mL, 1 M in THF) was added slowly in a nitrogen atmosphere. The reaction was stirred at −10 to −5° C. for 30 minutes. Upon completion of the reaction, methanol (3 mL) was added, and the reaction solution was further stirred for 10 minutes, then concentrated. The resulting residue was purified by preparative thin-layer chromatography followed by reverse phase column chromatography to obtain N-(4-(difluoromethoxy)-2-((2-(dimethylamino)ethyl)(methyl)amino)-5-((4-(6-(dimethyl phosphoryl)-1-methyl-1H-indol-3-yl)pyrimidin-2-yl)amino)phenyl)acrylamide (3.5 mg, 21%).

1H NMR (400 MHz, CD3OD) δ 8.67 (s, 1H), 8.39 (d, J=7.4 Hz, 1H), 8.25 (s, 1H), 8.20 (d, J=6.6 Hz, 1H), 8.00 (d, J=13.1 Hz, 1H), 7.58 (dd, J=10.6, 8.9 Hz, 1H), 7.48 (d, J=6.7 Hz, 1H), 7.32 (s, 1H), 6.97 (t, J=73.2 Hz, 2H), 6.62 (dd, J=16.9, 10.0 Hz, 1H), 6.50 (dd, J=16.9, 1.7 Hz, 1H), 5.89 (dd, J=10.0, 1.7 Hz, 1H), 4.05 (s, 3H), 3.53 (t, J=5.9 Hz, 2H), 3.38 (t, J=5.9 Hz, 2H), 2.96 (s, 6H), 2.82 (s, 3H), 1.86 (d, J=13.3 Hz, 6H);

MS m/z (ESI): 612.3 [M+H]+.

Example 12: Preparation of N-(5-((4-(1-cyclopropyl-1H-indol-3-yl)pyrimidin-2-yl)amino)-4-(difluoromethoxy)-2-((2-(dimethylamino)ethyl)(methyl)amino)phenyl)acrylamide

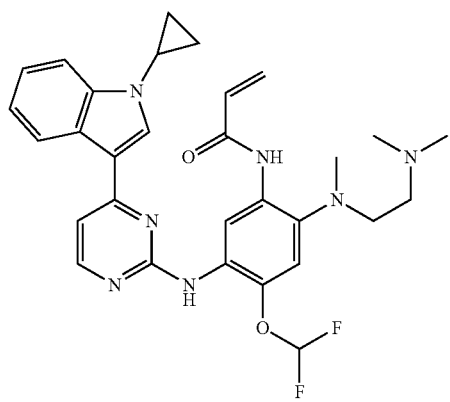 [SMILES: C=CC(=O)Nc1cc(Nc2nccc(-c3cn(C4CC4)c4ccccc34)n2)c(OC(F)F)cc1N(C)CCN(C)C]

Step 1: Preparation of 3-(2-chloropyrimidin-4-yl)-1-cyclopropyl-1H-indole

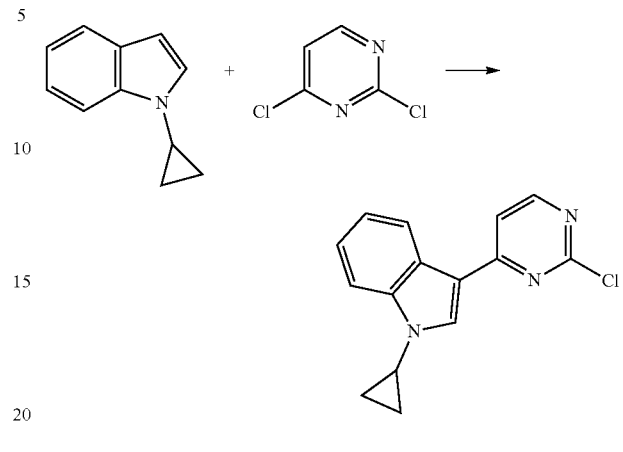

1-cyclopropyl-1H-indole (140 mg, 0.89 mmol) and 2,4-dichloropyrimidine (170 mg, 1.14 mmol) were dissolved in ethylene glycol dimethyl ether (10 mL), and then anhydrous aluminum chloride (180 mg, 1.35 mmol) was added. The reaction was heated up to 100° C. overnight. The reaction solution was cooled to room temperature and concentrated under reduced pressure. The resulting residue was dissolved in dichloromethane (30 mL), and the organic phase was washed twice with water, dried and concentrated. The resulting residue was purified by preparative thin-layer chromatography (petroleum ether: ethyl acetate=8:1) to obtain 3-(2-chloropyrimidin-4-yl)-1-cyclopropyl-1H-indole (80 mg, 80%).

MS m/z (ESI): 270.1 [M+H]+.

Step 2: Preparation of 4-(1-cyclopropyl-1H-indol-3-yl)-N-(2-(difluoromethoxy)-4-fluoro-5-nitrophenyl)pyrimidin-2-amine

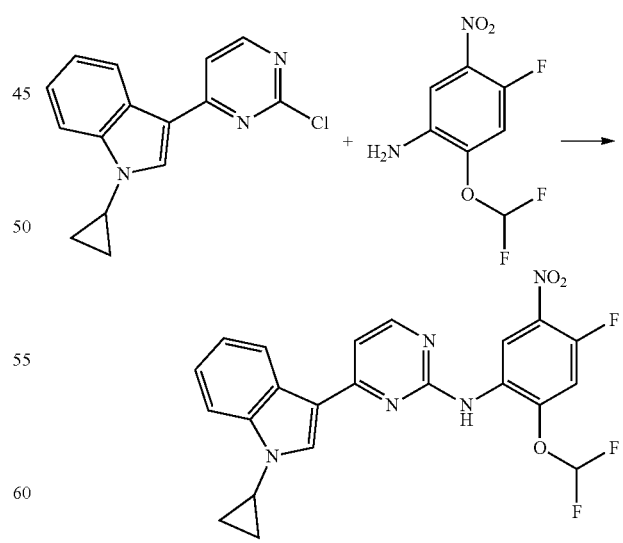

3-(2-chloropyrimidin-4-yl)-1-cyclopropyl-1H-indole (80 mg, 0.29 mmol) and 2-(difluoromethoxy)-4-fluoro-5-nitroaniline (64 mg, 0.29 mmol) were dissolved in 2-pentanol. The mixture was heated for 1 hour by microwave and cooled to room temperature. The solvent was evaporated, and the resulting residue was purified by preparative thin-layer chromatography to obtain 4-(1-cyclopropyl-1H-indol-3-yl)-N-(2-(difluoromethoxy)-4-fluoro-5-nitrophenyl)pyrimidin-2-amine (76 mg).

MS m/z (ESI): 456.1 [M+H]⁺.

Step 3: Preparation of N1-(4-(1-cyclopropyl-1H-indol-3-yl)pyrimidin-2-yl)-2-(difluoromethoxy)-N4-(2-(dimethylamino)ethyl)-N4-methyl-5-nitrobenzene-1,4-diamine

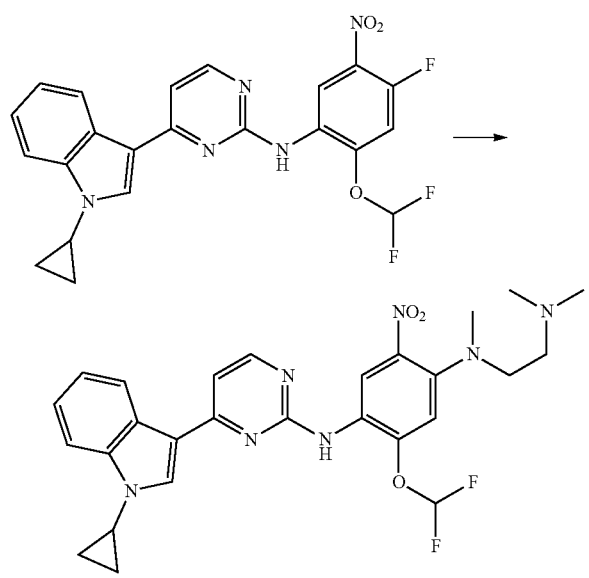

4-(1-cyclopropyl-1H-indol-3-yl)-N-(2-(difluoromethoxy)-4-fluoro-5-nitrophenyl)pyrimidin-2-amine (76 mg) was dissolved in N,N-dimethylacetamide, and then trimethylethylenediamine (0.1 g) was added. The mixture was heated up to reflux for 2 hours. The reaction solution was cooled to room temperature, and the solvent was evaporated to obtain N1-(4-(1-cyclopropyl-1H-indol-3-yl)pyrimidin-2-yl)-2-(difluoromethoxy)-N4-(2-(dimethylamino)ethyl)-N4-methyl-5-nitrobenzene-1,4-diamine (50 mg).

MS m/z (ESI): 538.3 [M+H]⁺.

Step 4: Preparation of N4-(4-(1-cyclopropyl-1H-indol-3-yl)pyrimidin-2-yl)-5-(difluoromethoxy)-N1-(2-(dimethylamino)ethyl)-N1-methylbenzene-1,2,4-triamine

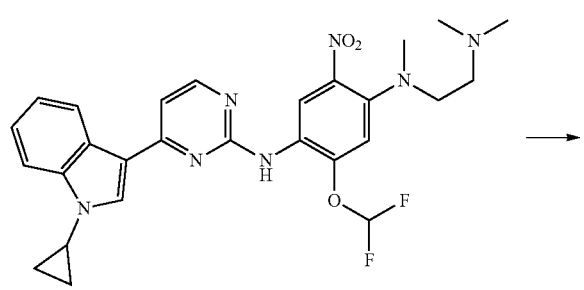

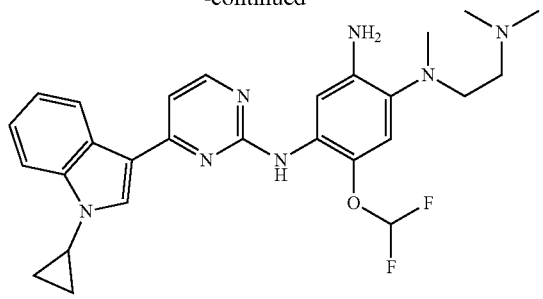

N1-(4-(1-cyclopropyl-1H-indol-3-yl)pyrimidin-2-yl)-2-(difluoromethoxy)-N4-(2-(dimethylamino)ethyl)-N4-methyl-5-nitrobenzene-1,4-diamine (50 mg) was dissolved in 6 mL of a mixed solvent of ethanol-water (5:1), then 65 mg of iron powder and 50 mg of ammonium chloride were added. The mixture was heated to reflux for 2 hours. The reaction solution was cooled to room temperature, filtered, and the filtrate was collected. The filtrate was concentrated under reduced pressure to remove ethanol, followed by addition of water and dichloromethane-methanol (20:1). The organic phase was separated and concentrated to obtain the crude product (20 mg).

MS m/z (ESI): 508.3 [M+H]⁺.

Step 5: Preparation of N-(5-((4-(1-cyclopropyl-1H-indol-3-yl)pyrimidin-2-yl)amino)-4-(difluoromethoxy)-2-((2-(dimethylamino)ethyl)(methyl)amino)phenyl)acrylamide

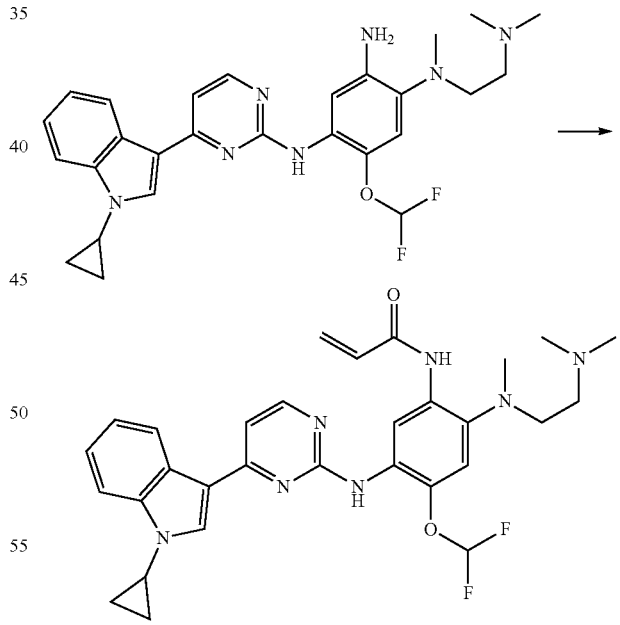

N4-(4-(1-cyclopropyl-1H-indol-3-yl)pyrimidin-2-yl)-5-(difluoromethoxy)-N1-(2-(dimethylamino)ethyl)-N1-methylbenzene-1,2,4-triamine (20 mg) was dissolved in anhydrous tetrahydrofuran. In a nitrogen atmosphere, DIPEA (0.1 mL) was added at 0° C., and a solution of 1 M acryloyl chloride in tetrahydrofuran (0.2 mL) was added dropwise. The reaction was carried out at 0° C. for 1 hour. Water and dichloromethane were added to the reaction solution, and the aqueous phase and the organic phase were separated. The aqueous phase was extracted three times with dichloromethane. Then the organic phases were combined, dried and concentrated. A crude product was obtained by thin-layer chromatography. The crude product was further purified by reverse-phase column chromatography (water:methanol=25:75) to obtain the final product (6.2 mg).

¹H NMR (400 MHz, CD₃OD) δ 8.56 (s, 1H), 8.26 (m, 2H), 8.08 (d, 1H), 7.71 (d, 1H), 7.50 (d, 1H), 7.32 (m, 3H), 6.96 (m, 1H), 6.79 (m, 1H), 6.44 (dd, 1H), 5.85 (d, 1H), 3.62 (m, 1H), 3.52 (m, 2H), 3.40 (m, 2H), 2.94 (s, 6H), 2.82 (s, 3H), 1.24 (m, 2H), 1.14 (m, 2H);

¹⁹F NMR (376 MHz, CD₃OD) δ −83.26;

MS m/z (ESI): 562.2 [M+H]⁺.

Example 13: Preparation of N-(2-((2-(dimethylamino)ethyl)(methyl)amino)-5-((4-(1-methyl-1H-indol-3-yl)pyrimidin-2-yl)amino)-4-(trifluoromethoxy)phenyl)acrylamide

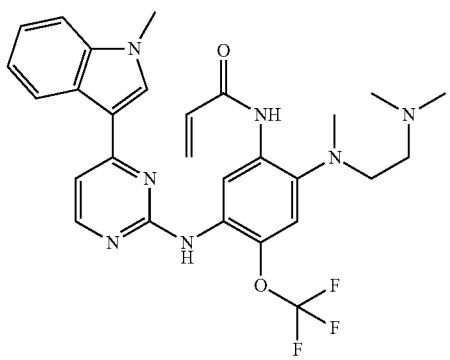 [SMILES: C=CC(=O)Nc1cc(Nc2nccc(-c3cn(C)c4ccccc34)n2)c(OC(F)(F)F)cc1N(C)CCN(C)C]

Step 1: Preparation of 4-fluoro-1-nitro-2-(trifluoromethoxy)benzene

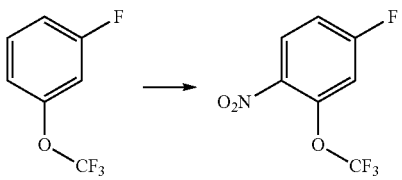 [SMILES: Fc1cccc(OC(F)(F)F)c1 ; O=[N+]([O-])c1ccc(F)cc1OC(F)(F)F]

1-fluoro-3-(trifluoromethoxy)benzene (7.5 g, 41.6 mmol) was dissolved in concentrated sulfuric acid (30 mL), and the mixture was cooled to 0° C. KNO₃ (1.04 g, 10.25 mmol) was added slowly in batches. The internal temperature is kept below 5° C. Upon completion of the addition, the mixture was stirred for 2 hours. An ice-water mixture (about 50 mL) was added. The reaction solution was extracted with methyl tert-butyl ether (20×3 mL), and the organic phases were combined, dried and filtered. The filtrate was concentrated and purified by flash silica gel column chromatography to obtain 4-fluoro-1-nitro-2-(trifluoromethoxy)benzene (4.0 g, 42%).

Step 2: Preparation of 4-fluoro-2-(trifluoromethoxy)aniline

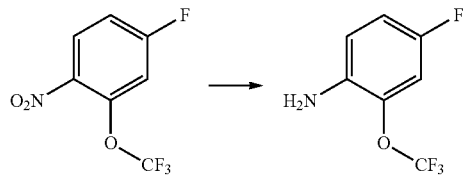 [SMILES: O=[N+]([O-])c1ccc(F)cc1OC(F)(F)F ; Nc1ccc(F)cc1OC(F)(F)F]

4-fluoro-1-nitro-2-(trifluoromethoxy)benzene (4.0 g, 17.8 mmol) was dissolved in methanol (50 mL), and then Pd/C (200 mg) was added. The reaction was stirred for 2 hours in a hydrogen atmosphere. After LC-MS showed completion of the reaction, the reaction solution was filtered and the filtrate was concentrated. The resulting residue was purified by reversed phase column chromatography to obtain 4-fluoro-2-(trifluoromethoxy)aniline (3.0 g, 86%).

Step 3: Preparation of 4-fluoro-5-nitro-2-(trifluoromethoxy)aniline

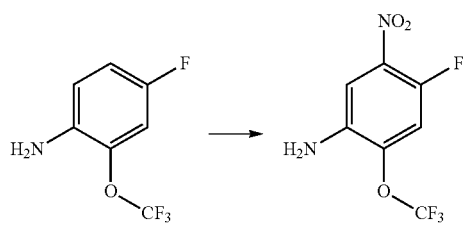 [SMILES: Nc1ccc(F)cc1OC(F)(F)F ; Nc1cc([N+](=O)[O-])c(F)cc1OC(F)(F)F]

4-fluoro-2-(trifluoromethoxy)aniline (2.0 g, 10.25 mmol) was dissolved in concentrated sulfuric acid (10 mL), and the mixture was cooled to −20° C. KNO₃ (1.04 g, 10.25 mmol) was added slowly in batches. The internal temperature was kept below −10° C. Upon completion of the addition, the mixture was stirred for 1 hour. An ice-water mixture (about 50 mL) was added. The reaction solution was extracted with methyl tert-butyl ether (20 mL×3), and the organic phases were combined, dried, and filtered. The filtrate was concentrated and purified by flash silica gel column chromatography to obtain 4-fluoro-5-nitro-2-(trifluoromethoxy)aniline (500 mg, 20%).

Step 4: preparation of N-(4-fluoro-5-nitro-2-(trifluoromethoxy)phenyl)-4-(1-methyl-1H-indol-3-yl)pyrimidin-2-amine

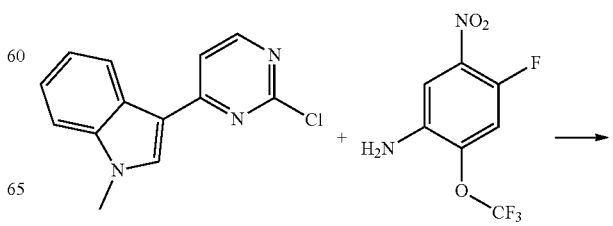

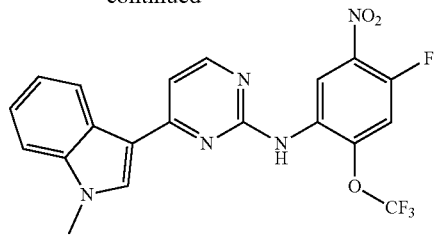

4-fluoro-5-nitro-2-(trifluoromethoxy)aniline (500 mg, 2.08 mmol), 3-(2-chloropyrimidin-4-yl)-1-methyl-1H-indole (508 mg, 2.08 mmol) and p-toluenesulfonic acid monohydrate (400 mg, 2.08 mmol) were dissolved in 1,4-dioxane (10 mL). The reaction was heated up to 110° C. and stirred for 16 hours. After LC-MS showed completion of the reaction, saturated NaHCO$_3$ aqueous solution (20 mL) was added, and the mixture was stirred for 20 minutes and filtered. The filter cake was washed with methyl t-butyl ether to obtain the crude product N-(4-fluoro-5-nitro-2-(trifluoromethoxy)phenyl)-4-(1-methyl-1H-indol-3-yl)pyrimidin-2-amine (400 mg, 43%).

Step 5: preparation of N1-(2-(dimethylamino)ethyl)-N1-methyl-N4-(4-(1-methyl-1H-indol-3-yl)pyrimidin-2-yl)-2-nitro-5-(trifluoromethoxy)benzene-1,4-diamine

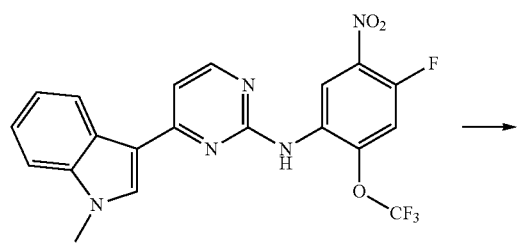

N-(4-fluoro-5-nitro-2-(trifluoromethoxy)phenyl)-4-(1-methyl-1H-indol-3-yl)pyrimidin-2-amine (400 mg, 0.89 mmol), N,N,N-trimethylethylenediamine (180 mg, 1.79 mmol) and triethylamine (1 mL) were dissolved in DMF (5 mL). The reaction was heated up to 110° C. for 2 hours. After LC-MS showed completion of the reaction, dichloromethane (10 mL) and water (10 mL) were added. The organic phase was washed three times with water, dried over anhydrous magnesium sulfate, filtered and concentrated. The resulting residue was purified by flash silica gel column chromatography to obtain N1-(2-(dimethylamino)ethyl)-N1-methyl-N4-(4-(1-methyl-1H-indol-3-yl)pyrimidin-2-yl) 2-nitro-5-(trifluoromethoxy)benzene-1,4-diamine (80 mg, 17%).

Step 6: Preparation of N1-(2-(dimethylamino)ethyl)-N1-methyl-N4-(4-(1-methyl-1H-indol-3-yl)pyrimidin-2-yl-5-(trifluoromethoxy)benzene-1,2,4-triamine

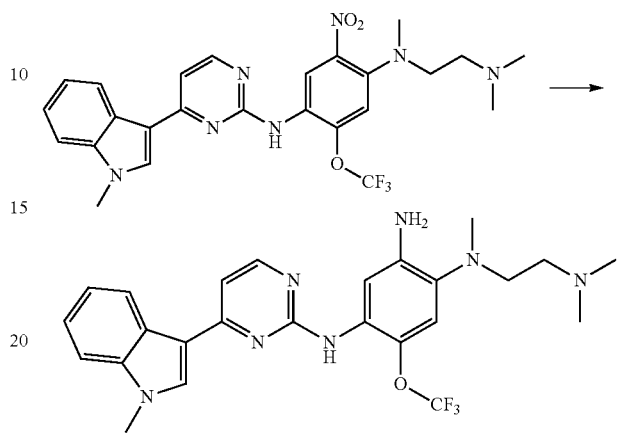

N1-(2-(dimethylamino)ethyl)-N1-methyl-N4-(4-(1-methyl-1H-indol-3-yl)pyrimidin-2-yl)-2-nitro-5-(trifluoromethoxy)benzene-1,4-diamine (80 mg, 0.15 mmol) was dissolved in methanol (5 mL), and then Pd/C (10 mg) was added. The reaction was stirred in a hydrogen atmosphere at room temperature for 10 minutes. After LC-MS showed completion of the reaction, the reaction solution was filtered, and the filtrate was concentrated to obtain N1-(2-(dimethylamino)ethyl)-N1-methyl-N4-(4-(1-methyl-1H-indol-3-yl)pyrimidin-2-yl-5-(trifluoromethoxy)benzene-1,2,4-triamine (50 mg, 70%), which was used directly in the next step without further purification.

Step 7: Preparation of N-(2-((2-(dimethylamino)ethyl)(methyl)amino)-5-((4-(1-methyl-1H-indol-3-yl)pyrimidin-2-yl)amino)-4-(trifluoromethoxy)phenyl)acrylamide

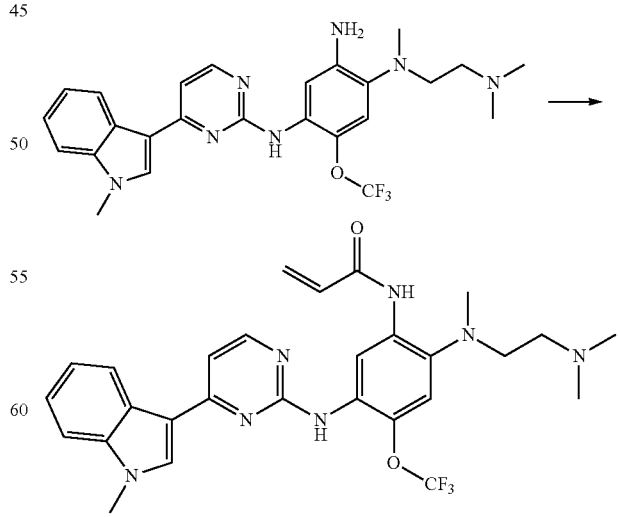

N1-(2-(dimethylamino)ethyl)-N1-methyl-N4-(4-(1-methyl-1H-indol-3-yl)pyrimidin-2-yl-5-(trifluoromethoxy)

benzene-1,2,4-triamine (50 mg, 0.24 mmol) and triethylamine (0.2 mL) were dissolved in tetrahydrofuran (10 mL). The reaction solution was cooled to −10 to −5° C. Acryloyl chloride (0.35 mL, 1 M in THF) was added slowly in a nitrogen atmosphere. The reaction was stirred at −10 to −5° C. for 30 minutes. Upon completion of the reaction, methanol (3 mL) was added, and the reaction solution was further stirred for 10 minutes, then concentrated under reduced pressure. The resulting residue was purified by preparative thin-layer chromatography followed by reverse phase column chromatography to obtain N-(2-((2-(dimethylamino)ethyl)(methyl)amino)-5-((4-(1-methyl-1H-indol-3-yl)pyrimidin-2-yl)amino)-4-(trifluoromethoxy)phenyl)acrylamide (19.0 mg, 14%).

¹H NMR (400 MHz, CD₃OD) δ 8.53 (s, 1H), 8.47 (s, 1H), 8.14 (d, J=7.8 Hz, 1H), 8.07 (d, J=6.8 Hz, 1H), 7.51 (d, J=8.2 Hz, 1H), 7.47 (d, J=0.9 Hz, 1H), 7.42 (d, J=6.9 Hz, 1H), 7.19 (t, J=7.5 Hz, 1H), 6.72 (dd, J=16.9, 10.2 Hz, 1H), 6.47 (dd, J=16.9, 1.5 Hz, 1H), 5.88 (dd, J=10.3, 1.5 Hz, 1H), 3.93 (s, 3H), 3.51 (t, J=5.9 Hz, 2H), 3.40 (t, J=5.8 Hz, 2H), 2.95 (s, 6H), 2.82 (s, 3H);

MS m/z (ESI): 554.2 [M+H]⁺.

Example 14: Preparation of N-(5-((4-(1-methyl-1H-indol-3-yl)pyrimidin-2-yl)amino)-2-(4-methylpiperazin-1-yl)-4-(trifluoromethoxy)phenyl)acrylamide

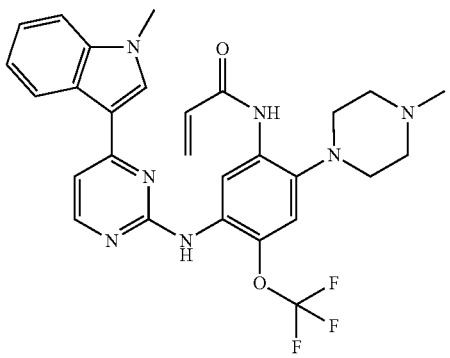 [SMILES: C=CC(=O)Nc1cc(Nc2nccc(-c3cn(C)c4ccccc34)n2)c(OC(F)(F)F)cc1N1CCN(C)CC1]

The preparation method of N-(5-((4-(1-methyl-1H-indol-3-yl)pyrimidin-2-yl)amino)-2-(4-methylpiperazin-1-yl)-4-(trifluoromethoxy)phenyl)acrylamide was similar to Example 2.

Example 15: Preparation of N-(2-((2-(dimethylamino)ethyl)(methyl)amino)-5-((4-(6-methoxy-1-methyl-1H-indol-3-yl)pyrimidin-2-yl)amino)-4-(trifluoromethoxy)phenyl)acrylamide

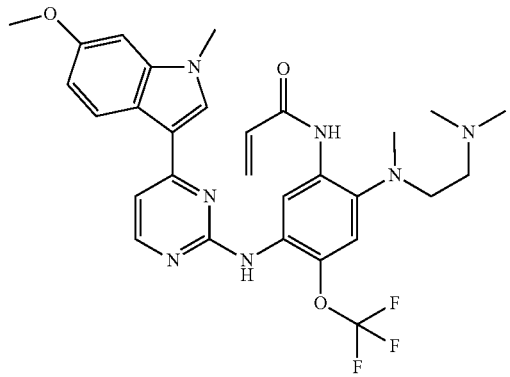

The preparation method of N-(2-((2-(dimethylamino)ethyl)(methyl)amino)-5-((4-(6-methoxy-1-methyl-1H-indol-3-yl)pyrimidin-2-yl)amino)-4-(trifluoromethoxy)phenyl)acrylamide was similar to Example 4.

Example 16: Preparation of N-(5-((4-(6-cyano-1-methyl-1H-indol-3-yl)pyrimidin-2-yl)amino)-2-((2-(dimethylamino)ethyl)(methyl)amino)-4-(trifluoromethoxy)phenyl)acrylamide

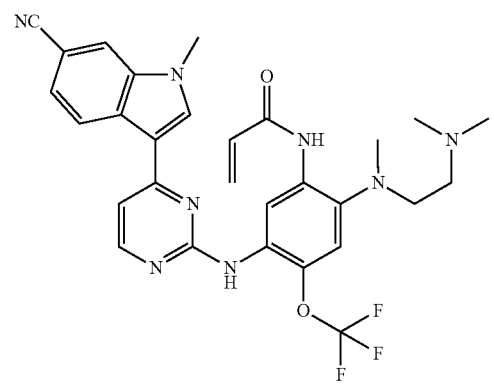 [SMILES: C=CC(=O)Nc1cc(Nc2nccc(-c3cn(C)c4cc(C#N)ccc34)n2)c(OC(F)(F)F)cc1N(C)CCN(C)C]

The preparation method of N-(5-((4-(6-cyano-1-methyl-1H-indol-3-yl)pyrimidin-2-yl)amino)-2-((2-(dimethylamino)ethyl)(methyl)amino)-4-(trifluoromethoxy)phenyl)acrylamide was similar to Example 4.

Example 17: Preparation of N-(5-((4-(1-cyclopropyl-1H-indol-3-yl)pyrimidin-2-yl)amino)-2-((2-(dimethylamino)etyl)methyl)amino)-4-(trifluoromethoxy)phenyl)acrylamide

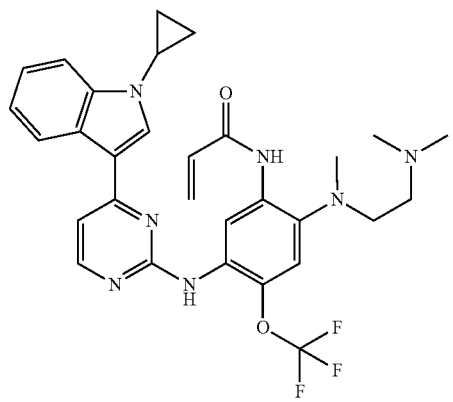 [SMILES: C=CC(=O)Nc1cc(Nc2nccc(-c3cn(C4CC4)c4ccccc34)n2)c(OC(F)(F)F)cc1N(C)CCN(C)C]

The preparation method of N-(5-((4-(1-cyclopropyl-1H-indol-3-yl)pyrimidin-2-yl)amino)-2-((2-(dimethylamino)ethyl)(methyl)amino)-4-(trifluoromethoxy)phenyl)acrylamide was similar to Example 1.

Example 18: Preparation of N-(2-((2-(dimethylamino)ethyl)(methyl)amino)-5-((4-(1-(2-hydroxyethyl)-1H-indol-3-yl)pyrimidin-2-yl)amino)-4-(trifluoromethoxy)phenyl)acrylamide

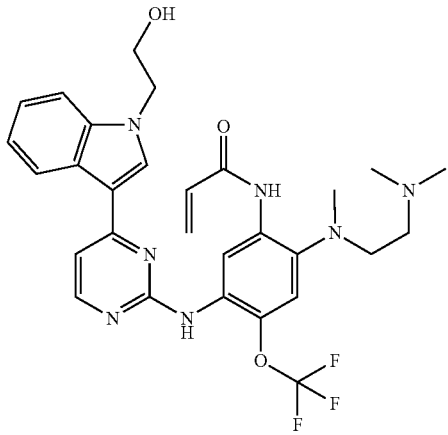 [SMILES: C=CC(=O)Nc1cc(Nc2nccc(-c3cn(CCO)c4ccccc34)n2)c(OC(F)(F)F)cc1N(C)CCN(C)C]

The preparation method of N-(2-((2-(dimethylamino)ethyl)(methyl)amino)-5-((4-(1-(2-hydroxyethyl)-1H-indol-3-yl)pyrimidin-2-yl)amino)-4-(trifluoromethoxy)phenyl)acrylamide was similar to Example 6.

Example 19: Preparation of N-(5-((4-(1-acetyl-1H-indol-3-yl)pyrimidin-2-yl)amino)-2-((2-(dimethylamino)ethyl)(methyl)amino)-4-(trifluoromethoxy)phenyl)acrylamide

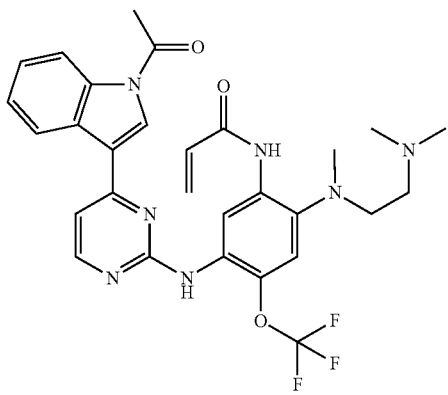 [SMILES: C=CC(=O)Nc1cc(Nc2nccc(-c3cn(C(C)=O)c4ccccc34)n2)c(OC(F)(F)F)cc1N(C)CCN(C)C]

The preparation method of N-(5-((4-(1-acetyl-1H-indol-3-yl)pyrimidin-2-yl)amino)-2-((2-(dimethylamino)ethyl)(methyl)amino)-4-(trifluoromethoxy)phenyl)acrylamide was similar to Example 4.

Example 20: Preparation of N-(2-((2-(dimethylamino)ethyl)(methyl)amino)-5-((4-(6-(dimethylphosphoryl)-1-methyl-1H-indol-3-yl)pyrimidin-2-yl)amino)-4-(trifluoromethoxy)phenyl)acrylamide

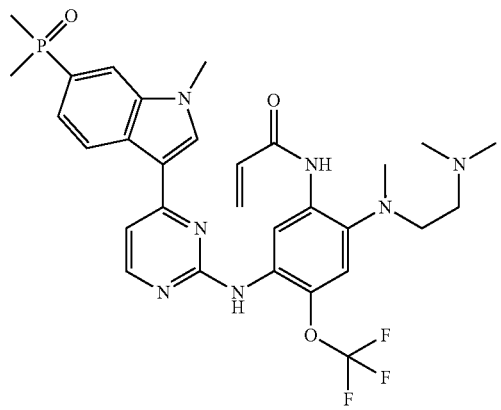

The preparation method of N-(2-((2-(dimethylamino)ethyl)(methyl)amino)-5-((4-(6-(dimethylphosphoryl)-1-methyl-1H-indol-3-yl)pyrimidin-2-yl)amino)-4-(trifluoromethoxy)phenyl)acrylamide was similar to Example 4.

Example 21: Preparation of N-(4-(difluoromethoxy)-2-((2-(dimethylamino)ethyl)(methyl)amino)-5-((4-(1-(N,N-dimethylsulfamoyl)-1H-indol-3-yl)pyrimidin-2-yl)amino)phenyl)acrylamide

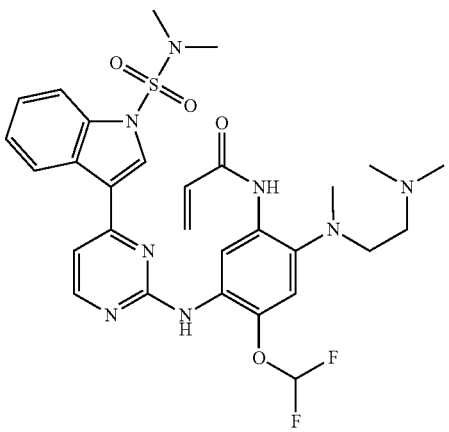 [SMILES: C=CC(=O)Nc1cc(Nc2nccc(-c3cn(S(=O)(=O)N(C)C)c4ccccc34)n2)c(OC(F)F)cc1N(C)CCN(C)C]

Step 1: Preparation of 3-(2-((2-(difluoromethoxy)-4-((2-(dimethylamino)ethyl)(methyl)amino)-5-nitrophenyl)amino)pyrimidin-4-yl)-N,N-dimethyl-1H-indole-1-sulfonamide

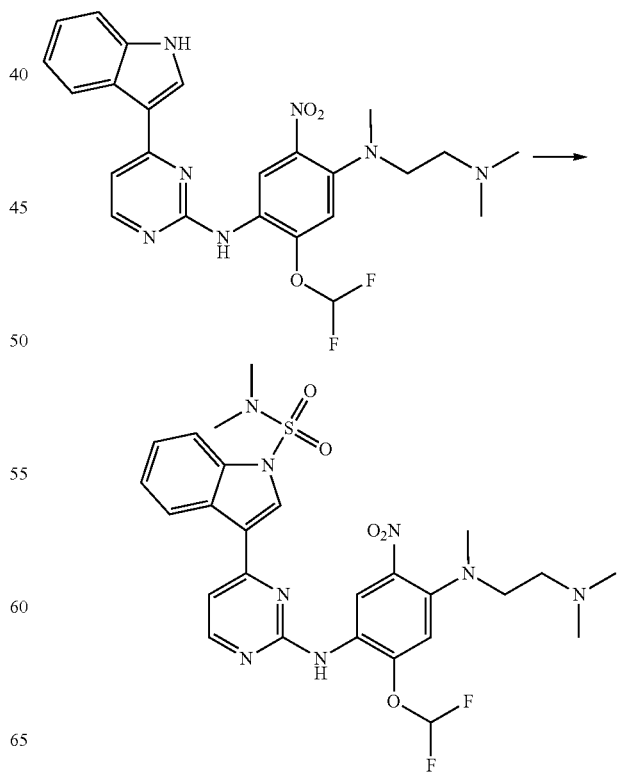

N-(4-(1H-indol-3-yl)pyrimidin-2-yl)-2-(difluoromethoxy)-(2-(dimethylamino)ethyl)-methyl-5-nitrophenyl-1,4-diamine (100 mg, 0.201 mmol) was dissolved in 10 mL of DMF, and the mixture was cooled to 0° C. in an ice bath, followed by addition of sodium hydride (24 mg, 0.603 mmol). After the reaction was carried out for 10 minutes at 0° C., dimethylsulfamoyl chloride (35 mg, 0.241 mmol) was added dropwise. The reaction was heated up to the room temperature and stirred for 30 minutes. After quenching, the reaction was added with dichloromethane and water, and extracted three times. The organic phases were combined, washed successively with saturated sodium bicarbonate aqueous solution, water and saturated brine, dried and concentrated to obtain a crude product, which was further purified by flash silica gel column chromatography to obtain the product (95 mg, 78%).

Step 2: Preparation of 3-(2-((5-amino-2-(difluoromethoxy)-4-((2-(dimethylamino)ethyl)(methyl)amino)phenyl)amino)pyrimidin-4-yl)-N,N-dimethyl-1H-indole-1-sulfonamide

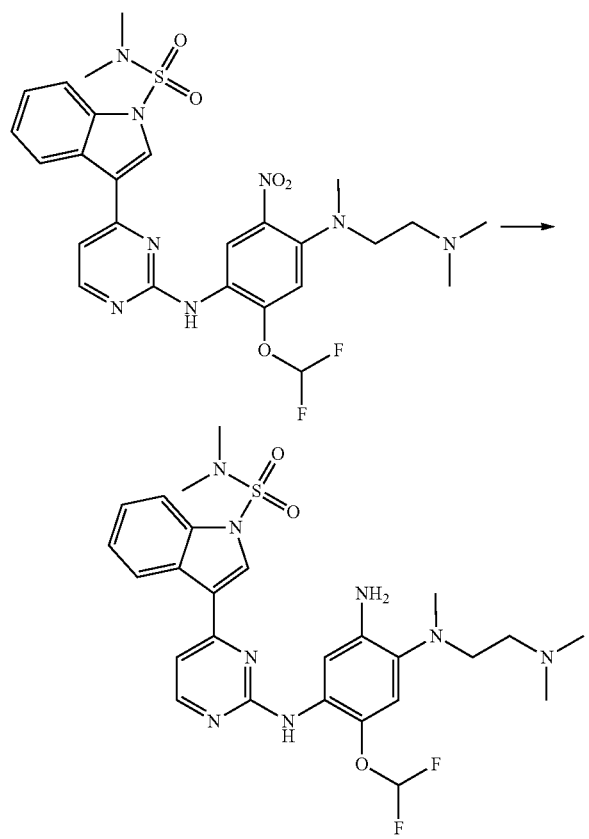

3-(2-((2-(difluoromethoxy)-4-((2-(dimethylamino)ethyl)(methyl)amino)-5-nitrophenyl)amino)pyrimidin-4-yl)-N,N-dimethyl-1H-indole-1-sulfonamide was dissolved in 5 mL of methanol, then Pd/C (15 mg) was added. The reaction was stirred at room temperature in a hydrogen atmosphere for 1 hour. After LC-MS showed completion of the reaction, the reaction was filtered, and the filtrate was concentrated to obtain a crude product, which was further purified by flash silica gel column chromatography to obtain the product (35 mg, 39%).

Step 3: Preparation of N-(4-(difluoromethoxy)-2-((2-(dimethylamino)ethyl)(methyl)amino)-5-((4-(1-(N,N-dimethylsulfamoyl)-1H-indol-3-yl)pyrimidin-2-yl)amino)phenyl)acrylamide

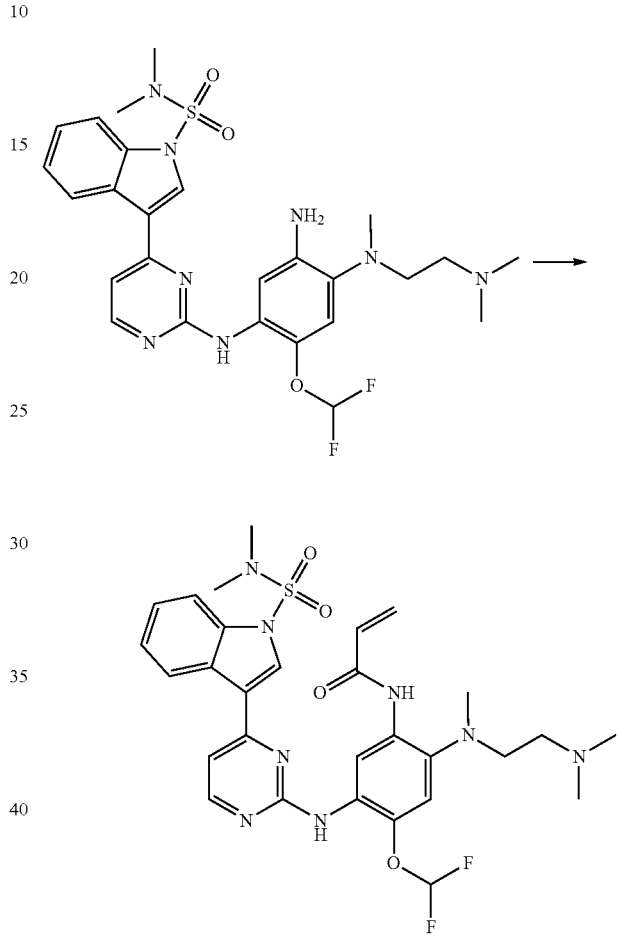

3-(2-((5-amino-2-(difluoromethoxy)-4-((2-(dimethylamino)ethyl)(methyl)amino)phenyl)amino)pyrimidin-4-yl)-N,N-dimethyl-1H-indole-1-sulfonamide (35 mg, 0.061 mmol) and triethylamine (18 mg, 0.183 mmol) were dissolved in anhydrous tetrahydrofuran (30 mL). The reaction solution was stirred at −78° C. for 10 minutes. Acryloyl chloride (0.2 mL, 1 M in THF) was added slowly and dropwise. The reaction was stirred at this temperature for 30 minutes. After LC-MS showed completion of the reaction, the reaction was quenched with methanol. The reaction solution was concentrated, and the resulting residue was purified by preparative thin-layer chromatography to obtain the product (25 mg, 65%).

$^1$H NMR (400 MHz, CD$_3$OD) δ 8.57 (s, 1H), 8.39 (s, 1H), 8.36-8.18 (m, 2H), 7.97 (d, J=8.4 Hz, 1H), 7.52 (d, J=6.2 Hz, 1H), 7.37 (t, J=7.7 Hz, 1H), 7.33-7.18 (m, 2H), 7.16-6.58 (m, 2H), 6.45 (d, J=16.0 Hz, 1H), 5.96-5.77 (m, 1H), 3.49 (t, J=5.6 Hz, 2H), 3.37 (t, J=5.6 Hz, 2H), 2.93 (s, 6H), 2.89 (s, 6H), 2.78 (s, 3H);

MS m/z (ESI): 629.2 [M+H]$^+$.

Example 22: Preparation of N-(5-((4-(6-cyclopropyl-1-methyl-1H-indol-3-yl)pyrimidin-2-yl)amino)-2-((2-(dimethylamino)ethyl)(methyl)amino)-4-methoxyphenyl)acrylamide

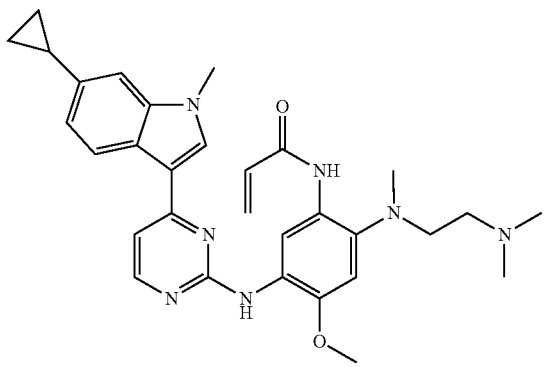 [SMILES: C=CC(=O)Nc1cc(Nc2nccc(-c3cn(C)c4cc(C5CC5)ccc34)n2)c(OC)cc1N(C)CCN(C)C]

Step 1: Preparation of 6-bromo-1-methyl-1H-indole

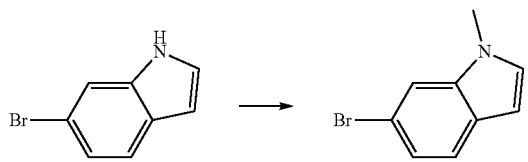

To a solution of 6-bromo-1H-indole (3.00 g, 15.3 mmol) in DMF (30 mL), NaH (60%, 734 mg, 18.4 mmol) was added in an ice-water bath, and the mixture was stirred at this temperature for 20 minutes. Then, a solution of MeI (1.14 mL, 18.4 mmol) in DMF (10 mL) was added dropwise, and the mixture was stirred at this temperature for 30 minutes. 100 mL of water were added, and the reaction solution was extracted with EtOAc. The EtOAc phase was washed several times with saturated brine, dried over anhydrous sodium sulfate, concentrated, and purified by column chromatography (eluent: pure PE) to obtain the title compound 6-bromo-1-methyl-1H-indole (2.70 g, 84%).

Step 2: Preparation of 6-cyclopropyl-1-methyl-1H-indole

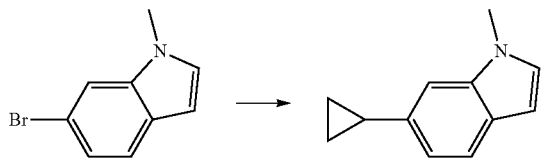

6-bromo-1-methyl-1H-indole (1.44 g, 6.85 mmol) and cyclopropylboronic acid (1.18 g, 13.7 mmol) were mixed in a mixed solvent of toluene (20 mL) and water (3 mL). The mixture was purged with nitrogen to remove oxygen in a nitrogen atmosphere for 5 minutes. Then Pd(OAc)$_2$ (231 mg, 1.03 mmol) and anhydrous potassium phosphate (4.37 g, 20.6 mmol) were added, and the mixture was purged with nitrogen for 10 minutes again. Finally, tricyclohexylphosphine (769 mg, 2.74 mmol) was added, and the mixture was purged with nitrogen for 5 minutes. In a nitrogen atmosphere, the reaction solution was stirred overnight at 100° C. in an oil bath. After cooling, the organic solvent was removed by evaporation. EtOAc and water were added, and two phases were separated. The EtOAc phase was washed with saturated brine, dried over anhydrous sodium sulfate, concentrated and purified by column chromatography (eluent: pure PE) to obtain the title compound 6-cyclopropyl-1-methyl-1H-indole (770 mg, 66%).

$^1$H NMR (400 MHz, CDCl$_3$): δ 7.55 (d, J=8.0 Hz, 1H), 7.09 (d, J=0.8 Hz, 1H), 7.01 (d, J=3.2 Hz, 1H), 6.93 (m, 1H), 6.46 (dd, J=3.2, 0.8 Hz, 1H), 3.79 (s, 3H), 2.09 (m, 1H), 1.01 (m, 2H), 0.80 (m, 2H).

Step 3: Preparation of 3-(2-chloropyrimidin-4-yl)-6-cyclopropyl-1-methyl-1H-indole

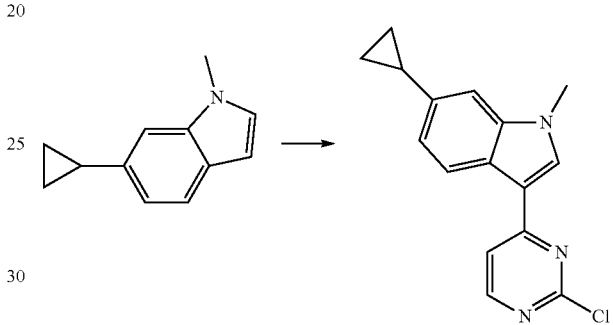

FeCl$_3$ (864 mg, 5.33 mmol) was added to a mixed solution of 6-cyclopropyl-1-methyl-1H-indole (760 mg, 4.44 mmol) and 2,4-dichloropyrimidine (674 mg, 4.44 mmol) in ethylene glycol dimethyl ether (10 mL), and the mixture was stirred overnight at 60° C. After cooling, a large amount of EtOAc and water were added, and two phases were separated. The undissolved substance was removed through celite, and then the aqueous phase was removed. The organic phase was washed successively with saturated sodium bicarbonate aqueous solution and saturated brine, dried over anhydrous sodium sulfate, and concentrated. The resulting residue was purified by column chromatography (eluent: PE:EtOAc=3:1) to obtain the title compound (533 mg, 42%).

MS m/z (ESI): 284.2 [M+H]$^+$.

Step 4: Preparation of 4-(6-cyclopropyl-1-methyl-1H-indol-3-yl)-N-(4-fluoro-2-methoxy-5-nitrophenyl)pyrimidin-2-amine

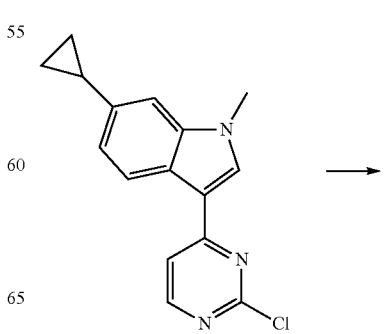

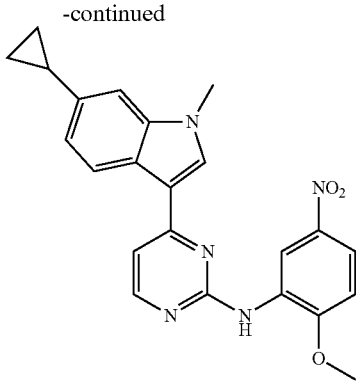

3-(2-chloropyrimidin-4-yl)-6-cyclopropyl-1-methyl-1H-indole (533 mg, 1.88 mmol), 4-fluoro-2-methoxy-5-nitroaniline (350 mg, 1.88 mmol) and TsOH.H₂O (429 mg, 2.25 mmol) were mixed in 2-pentanol (10 mL), and the reaction was carried out at 125° C. for 3 hours. After the mixture was cooled and filtered, the resulting solid was dissolved in CH₂Cl₂, washed with saturated sodium bicarbonate aqueous solution and saturated brine successively, dried over anhydrous sodium sulfate, and concentrated to obtain the title compound 4-(6-cyclopropyl-1-methyl-1H-indol-3-yl)-N-(4-fluoro-2-methoxy-5-nitrophenyl)pyrimidin-2-amine (750 mg, 92%).

MS m/z (ESI): 434.2 [M+H]⁺.

Step 5: Preparation of N1-(4-(6-cyclopropyl-1-methyl-1H-indol-3-yl)pyrimidin-2-yl)-N4-(2-(dimethylamino)ethyl)-2-methoxy-N4-methyl-5-nitrobenzene-1,4-diamine

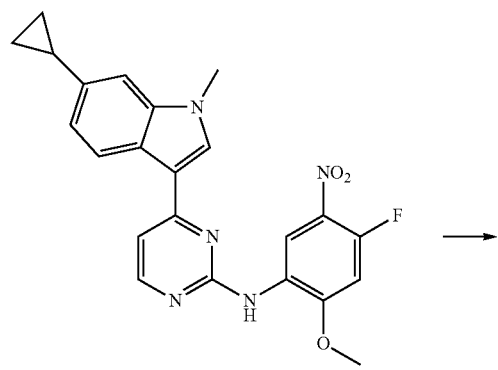

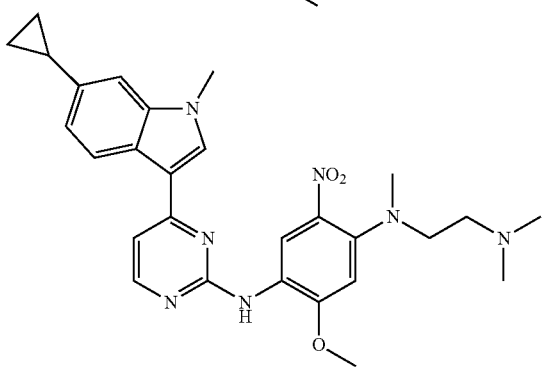

4-(6-cyclopropyl-1-methyl-1H-indol-3-yl)-N-(4-fluoro-2-methoxy-5-nitrophenyl)pyrimidin-2-amine (647 mg, 1.49 mmol), N1,N1,N2-trimethylethane-1,2-diamine (229 mg, 2.24 mmol) and DIPEA (0.740 mL, 4.48 mmol) were dissolved in DMA (10 mL), and the reaction was carried out at 85° C. for 3 hours. After cooling, water and EtOAc were added, and two phases were separated. The organic phase was washed several times with saturated brine, dried over anhydrous sodium sulfate, and concentrated to obtain the title compound N1-(4-(6-cyclopropyl-1-methyl-1H-indol-3-yl)pyrimidin-2-yl)-N4-(2-(dimethylamino)ethyl)-2-methoxy-N4-methyl-5-nitrobenzene-1,4-diamine as a crude product, which was used directly in the next step.

MS m/z (ESI): 516.3 [M+H]⁺.

Step 6: Preparation of N4-(4-(6-cyclopropyl-1-methyl-1H-indol-3-yl)pyrimidin-2-yl)-N1-(2-(dimethylamino)ethyl)-5-methoxy-N1-methylbenzene-1,2,4-triamine

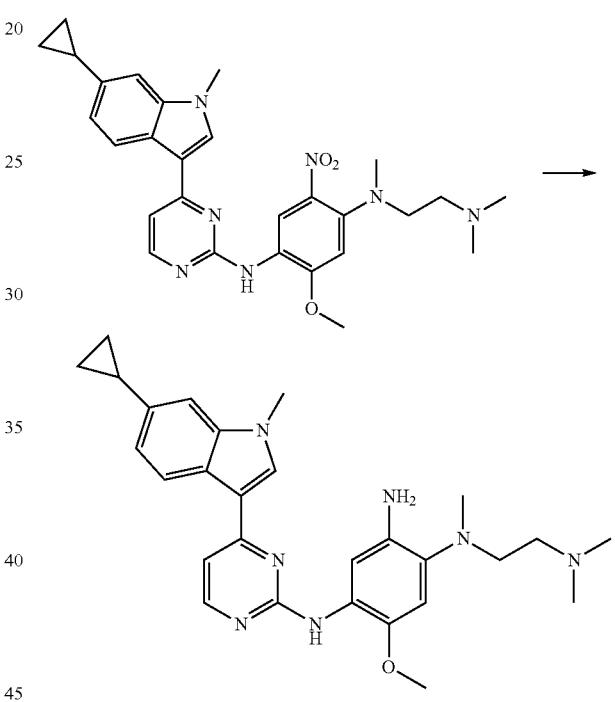

N1-(4-(6-cyclopropyl-1-methyl-1H-indol-3-yl)pyrimidin-2-yl)-N4-(2-(dimethylamino)ethyl)-2-methoxy-N4-methyl-5-nitrobenzene-1,4-diamine (1.4 g, a crude product), reduced iron powder (1.22 g, 21.7 mmol) and ammonium chloride (100 mg, 1.90 mmol) were mixed in a solution of EtOH (30 mL) and water (10 mL). The mixture was heated up to reflux for three hours. After cooling, a large amount of EtOH was added, and the undissolved substance was removed by filtration through celite. EtOH was removed under reduced pressure. Then, the aqueous phase was extracted with EtOAc, and the EtOAc phase was washed with saturated brine, dried over anhydrous sodium sulfate, concentrated, and purified by column chromatography [eluent: CH₂Cl₂→CH₂Cl₂:MeOH (containing 10% concentrated ammonia)=17:1] to obtain the title compound N4-(4-(6-cyclopropyl-1-methyl-1H-indol-3-yl)pyrimidin-2-yl)-N1-(2-(dimethylamino)ethyl)-5-methoxy-N1-methylbenzene-1,2,4-triamine (490 mg, yield of two steps: 68%).

MS m/z (ESI): 486.3 [M+H]⁺.

119

Step 7: preparation of N-(5-((4-(6-cyclopropyl-1-methyl-1H-indol-3-yl)pyrimidin-2-yl)amino)-2-((2-(dimethylamino)ethyl)(methyl)amino)-4-methoxyphenyl)acrylamide

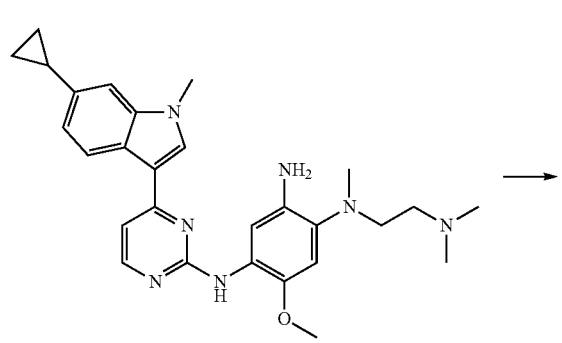

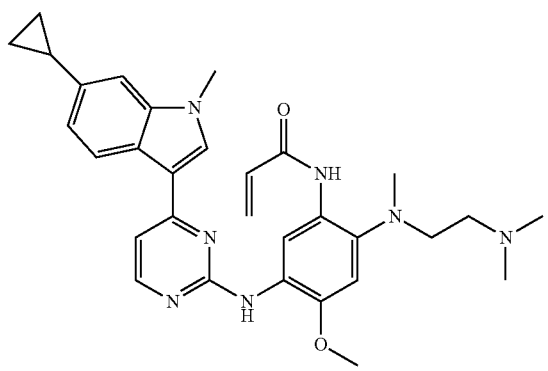

A solution of acryloyl chloride (22.0 mg, 0.247 mmol) in THF (1 mL) was added dropwise to a solution of N4-(4-(6-cyclopropyl-1-methyl-1H-indol-3-yl)pyrimidin-2-yl)-N1-(2-(dimethylamino)ethyl)-5-methoxy-N1-methylbenzene-1,2,4-triamine (80.0 mg, 0.164 mmol) and TEA (50.0 mg, 0.492 mmol) in THF (2 mL) in an ice-water bath. Upon completion of the addition, the mixture was stirred at the same temperature for 15 minutes. The reaction was quenched with methanol, concentrated under reduced pressure, and purified by preparative thin-layer chromatography (CH$_2$Cl$_2$:MeOH:concentrated ammonia=100:10:1) to obtain the title compound N-(5-((4-(6-cyclopropyl-1-methyl-1H-indol-3-yl)pyrimidin-2-yl)amino)-2-((2-(dimethylamino)ethyl)(methyl)amino)-4-methoxyphenyl)acrylamide (45 mg, 51%).

$^1$H NMR (400 MHz, CDCl3): δ 10.1 (br s, 1H), 9.83 (s, 1H), 9.00 (s, 1H), 8.36 (d, J=5.2 Hz, 1H), 7.93 (d, J=8.4 Hz, 1H), 7.71 (s, 1H), 7.16 (d, J=5.2 Hz, 1H), 7.10 (s, 1H), 7.00 (dd, J=8.4, 1.6 Hz, 1H), 6.79 (s, 1H), 6.39-6.44 (m, 2H), 5.70 (dd, J=9.6, 2.0 Hz, 1H), 3.95 (s, 3H), 3.87 (s, 3H), 2.89 (t, J=5.6 Hz, 2H), 2.69 (s, 3H), 2.27 (t, J=5.6 Hz, 2H), 2.25 (s, 6H), 2.06 (m, 1H), 1.00 (m, 2H), 0.78 (m, 2H);

MS m/z (ESI): 540.3 [M+H]$^+$.

120

Example 23: Preparation of N-(5-((4-(5-cyclopropyl-1-methyl-1H-indol-3-yl)pyrimidin-2-yl)amino)-2-((2-(dimethylamino)ethyl)(methyl)amino)-4-methoxyphenyl)acrylamide

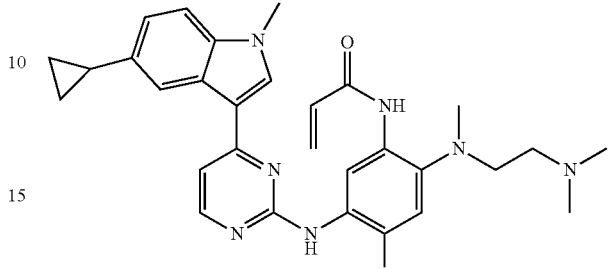

The preparation method of N-(5-((4-(5-cyclopropyl-1-methyl-1H-indol-3-yl)pyrimidin-2-yl)amino)-2-((2-(dimethylamino)ethyl)(methyl)amino)-4-methoxyphenyl)acrylamide was similar to Example 22.

$^1$H NMR (400 MHz, CDCl$_3$): δ 10.0 (brs, 1H), 9.76 (s, 1H), 8.99 (s, 1H), 8.31 (d, J=5.2 Hz, 1H), 7.72 (s, 1H), 7.65 (s, 1H), 7.21 (s, 1H), 7.13 (d, J=5.2 Hz, 1H), 6.94 (dd, J=8.4, 1.6 Hz, 1H), 6.72 (s, 1H), 6.36 (m, 2H), 5.63 (dd, J=8.8, 2.8 Hz, 1H), 3.89 (s, 3H), 3.82 (s, 3H), 2.84 (t, J=6.0 Hz, 2H), 2.62 (s, 3H), 2.25 (t, J=6.0 Hz, 2H), 2.20 (s, 6H), 2.00 (m, 1H), 0.93 (m, 2H), 0.75 (m, 2H);

MS m/z (ESI): 540.4 [M+H]$^+$.

Example 24: Preparation of N-(2-((2-(dimethylamino)ethyl)(methyl)amino)-4-methoxy-5-((4-(5-methoxy-1-methyl-1H-indol-3-yl)pyrimidin-2-yl)amino)phenyl)acrylamide

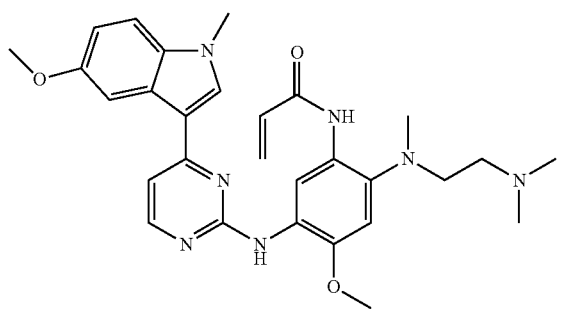

The preparation method of N-(2-((2-(dimethylamino)ethyl)(methyl)amino)-4-methoxy-5-((4-(5-methoxy-1-methyl-1H-indol-3-yl)pyrimidin-2-yl)amino)phenyl)acrylamide was similar to Example 22.

$^1$H NMR (400 MHz, CDCl$_3$): δ 10.09 (s, 1H), 9.76 (s, 1H), 8.97 (s, 1H), 8.30 (d, J=5.2 Hz, 1H), 7.64 (s, 1H), 7.44 (d, J=2.4 Hz, 1H), 7.20 (d, J=9.2 Hz, 1H), 7.05 (d, J=5.2 Hz, 1H), 6.85 (m, 1H), 6.72 (s, 1H), 6.36 (m, 2H), 5.63 (m, 1H), 3.89 (s, 3H), 3.85 (s, 3H), 3.81 (s, 3H), 2.81 (t, J=5.6 Hz, 2H), 2.63 (s, 3H), 2.20 (m, 8H);

MS m/z (ESI): 530.2 [M+H]$^+$.

Example 25: Preparation of N-(2-((2-(dimethylamino)ethyl)(methyl)amino)-4-methoxy-5-((4-(6-methoxy-1-methyl-1H-indol-3-yl)pyrimidin-2-yl)amino)phenyl)acrylamide

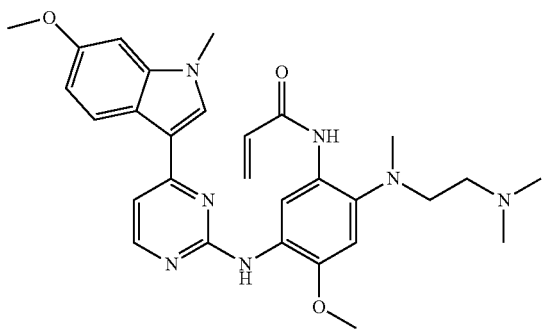

The preparation method of N-(2-((2-(dimethylamino)ethyl)(methyl)amino)-4-methoxy-5-(((4-(6-methoxy-1-methyl-1H-indol-3-yl)pyrimidin-2-yl)amino)phenyl)acrylamide was similar to Example 22.

$^1$H NMR (400 MHz, CDCl$_3$): δ 9.99 (d, J=29.8 Hz, 1H), 9.75 (s, 1H), 8.85 (s, 1H), 8.29 (d, J=5.3 Hz, 1H), 7.87 (d, J=8.8 Hz, 1H), 7.64 (s, 1H), 7.06 (d, J=5.3 Hz, 1H), 6.83 (dd, J=8.7, 2.3 Hz, 1H), 6.75 (t, J=8.0 Hz, 1H), 6.70 (s, 1H), 6.50-6.24 (m, 2H), 5.76-5.53 (m, 1H), 3.85 (s, 3H), 3.82 (d, J=4.9 Hz, 3H), 3.80 (s, 3H), 2.94-2.74 (m, 2H), 2.62 (s, 3H), 2.24 (d, J=4.8 Hz, 2H), 2.20 (s, 6H);

MS m/z (ESI): 530.3 [M+H]$^+$.

Example 26: Preparation of N-(5-((4-(1-cyclopropyl-1H-indol-3-yl)pyrimidin-2-yl)amino)-2-((2-(dimethylamino)ethyl)(methyl)amino)-4-methoxyphenyl)acrylamide

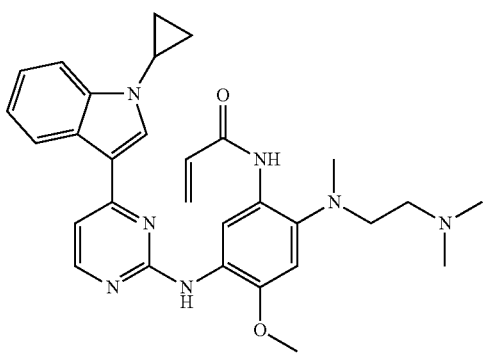 [SMILES: C=CC(=O)Nc1cc(Nc2nccc(-c3cn(C4CC4)c4ccccc34)n2)c(OC)cc1N(C)CCN(C)C]

The preparation method of N-(5-((4-(1-cyclopropyl-1H-indol-3-yl)pyrimidin-2-yl)amino)-2-((2-(dimethylamino)ethyl)(methyl)amino)-4-methoxyphenyl)acrylamide was similar to Example 22.

$^1$H NMR (400 MHz, CDCl$_3$): δ 9.78 (s, 1H), 9.74 (s, 1H), 8.55 (s, 1H), 8.39 (d, J=5.3 Hz, 1H), 8.11 (d, J=7.0 Hz, 1H), 7.74-7.55 (m, 2H), 7.18 (d, J=5.3 Hz, 1H), 6.76 (s, 1H), 6.62 (dd, J=16.8, 10.1 Hz, 1H), 6.46 (dd, J=16.9, 1.9 Hz, 1H), 6.24 (m, 1H), 5.80-5.59 (m, 1H), 3.88 (s, 3H), 3.55-3.34 (m, 1H), 3.02 (t, J=5.8 Hz, 2H), 2.68 (s, 3H), 2.57 (t, J=5.7 Hz, 2H), 2.42 (s, 6H), 1.24-1.17 (m, 2H), 1.14-1.04 (m, 2H);

MS m/z (ESI): 526.3 [M+H]$^+$.

Example 27: Preparation of N-(4-methoxy-5-((4-(1-methyl-1H-indol-3-yl)pyrimidin-2-yl)amino)-2-(2-oxa-6-azaspiro[3,3]heptan-6-yl)phenyl)acrylamide

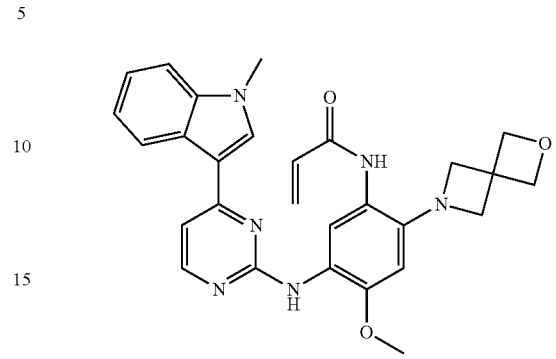

The preparation method of N-(4-methoxy-5-((4-(1-methyl-1H-indol-3-yl)pyrimidin-2-yl)amino)-2-(2-oxa-6-azaspiro[3.3]heptan-6-yl)phenyl)acrylamide was similar to Example 22.

$^1$H NMR (400 MHz, CDCl$_3$): δ 8.76 (s, 1H), 8.32 (d, J=26.6 Hz, 1H), 8.20 (dd, J=20.7, 6.3 Hz, 1H), 8.11-7.97 (m, 1H), 7.48-7.36 (m, 1H), 7.36-7.24 (m, 2H), 6.97 (dd, J=25.1, 11.6 Hz, 1H), 6.44-6.30 (m, 1H), 6.24 (dd, J=16.9, 10.0 Hz, 1H), 6.13-6.01 (m, 1H), 5.66 (dd, J=9.9, 1.5 Hz, 1H), 4.69 (s, 4H), 3.95-3.67 (m, 10H);

MS m/z (ESI): 497.2 [M+H]$^+$.

Example 28: Preparation of N-(5-((4-(5,6-difluoro-1-methyl-1H-indol-3-yl)pyrimidin-2-yl)amino)-2-((2-(dimethylamino)ethyl)(methyl)amino)-4-methoxyphenyl)acrylamide

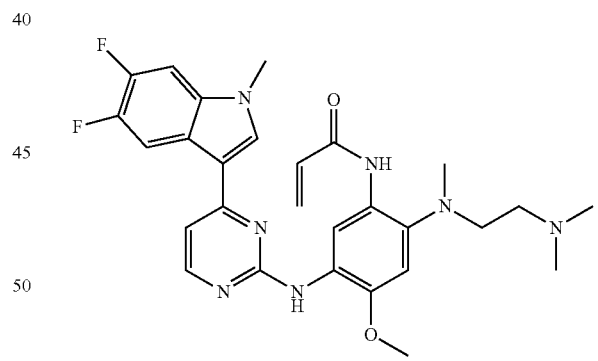

The preparation method of N-(5-((4-(5,6-difluoro-1-methyl-1H-indol-3-yl)pyrimidin-2-yl)amino)-2-((2-(dimethylamino)ethyl)(methyl)amino)-4-methoxyphenyl)acrylamide was similar to Example 22.

$^1$H NMR (400 MHz, CDCl$_3$): δ 10.06 (s, 1H), 9.83-9.46 (m, 1H), 8.86 (s, 1H), 8.30 (d, J=5.3 Hz, 1H), 7.78 (dd, J=11.4 Hz, 1H), 7.62 (s, 1H), 7.11-6.99 (m, 1H), 6.93 (t, J=6.2 Hz, 1H), 6.72 (s, 1H), 6.34 (d, J=5.6 Hz, 2H), 5.72-5.51 (m, 1H), 3.84 (d, J=6.4 Hz, 3H), 3.81 (d, J=4.4 Hz, 3H), 2.92-2.76 (m, 2H), 2.72-2.54 (m, 3H), 2.21 (s, 6H), 1.36-1.07 (m, 2H);

MS m/z (ESI): 536.2 [M+H]$^+$.

Example 29: Preparation of N-(5-((4-(4,6-difluoro-1-methyl-1H-indol-3-yl)pyrimidin-2-yl)amino)-2-((2-(dimethylamino)ethyl)(methyl)amino)-4-methoxyphenyl)acrylamide

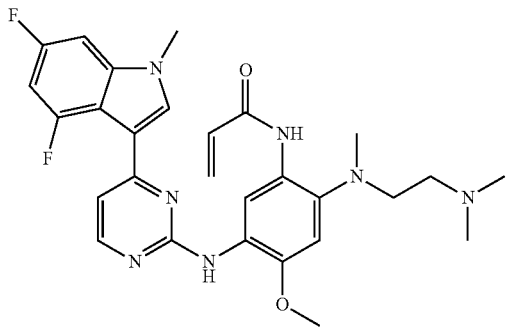 [SMILES: C=CC(=O)Nc1cc(Nc2nccc(-c3cn(C)c4cc(F)cc(F)c34)n2)c(OC)cc1N(C)CCN(C)C]

The preparation method of N-(5-((4-(4,6-difluoro-1-methyl-1H-indol-3-yl)pyrimidin-2-yl)amino)-2-((2-(dimethylamino)ethyl)(methyl)amino)-4-methoxyphenyl)acrylamide was similar to Example 22.

$^1$H NMR (400 MHz, CDCl$_3$): δ 9.97 (s, 1H), 9.71 (s, 1H), 9.00 (s, 1H), 8.53-8.19 (m, 1H), 7.71-7.56 (m, 1H), 7.33 (d, J=5.4 Hz, 1H), 6.79 (dd, J=8.8, 2.1 Hz, 1H), 6.71 (s, 1H), 6.65 (ddd, J=11.9, 9.7, 2.1 Hz, 1H), 6.42-6.22 (m, 2H), 5.68-5.53 (m, 1H), 3.87 (s, 3H), 3.81 (s, 3H), 2.94-2.77 (m, 2H), 2.62 (d, J=9.2 Hz, 3H), 2.28 (s, 2H), 2.23 (s, 6H);

MS m/z (ESI): 536.2 [M+H]$^+$.

Example 30: Preparation of N-(2-((2-(dimethylamino)ethyl)(methyl)amino)-4-methoxy-5-((4-(4,5,6,7-tetrafluoro-1-methyl-1H-indol-3-yl)pyrimidin-2-yl)amino)phenyl)acrylamide

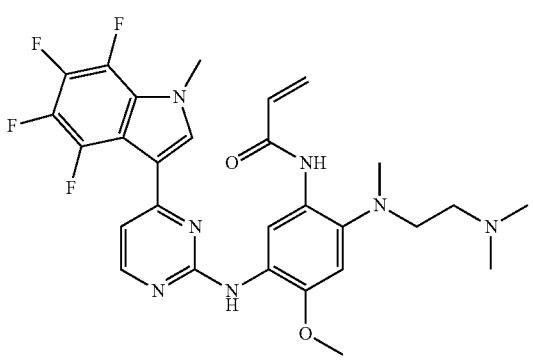 [SMILES: C=CC(=O)Nc1cc(Nc2nccc(-c3cn(C)c4c(F)c(F)c(F)c(F)c34)n2)c(OC)cc1N(C)CCN(C)C]

The preparation method of N-(2-((2-(dimethylamino)ethyl)(methyl)amino)-4-methoxy-5-((4-(4,5,6,7-tetrafluoro-1-methyl-1H-indol-3-yl)pyrimidin-2-yl)amino)phenyl)acrylamide was similar to Example 22.

Example 31: Preparation of N-(2-((2-(dimethylamino)ethyl)(methyl)amino)-4-methoxy-5-((4-(1,5,6-trimethyl-1H-indol-3-yl)pyrimidin-2-yl)amino)phenyl)acrylamide

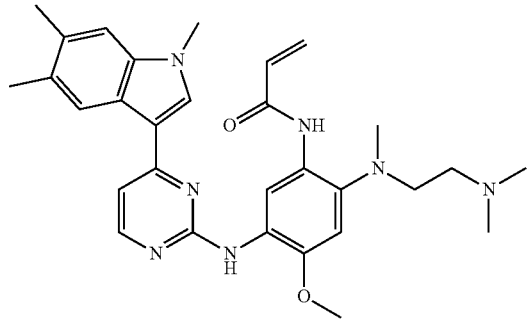

The preparation method of N-(2-((2-(dimethylamino)ethyl)(methyl)amino)-4-methoxy-5-((4-(1,5,6-trimethyl-1H-indol-3-yl)pyrimidin-2-yl)amino)phenyl)acrylamide was similar to Example 22.

Example 32: Preparation of N-(5-((4-(4,6-difluoro-1,7-dimethyl-1H-indol-3-yl)pyrimidin-2-yl)amino)-2-((2-(dimethylamino)ethyl)(methyl)amino)-4-methoxyphenyl)acrylamide

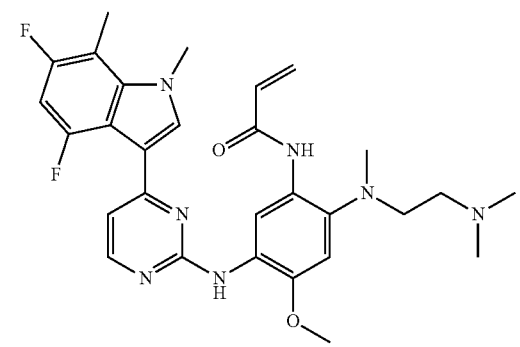 [SMILES: C=CC(=O)Nc1cc(Nc2nccc(-c3cn(C)c4c(C)c(F)cc(F)c34)n2)c(OC)cc1N(C)CCN(C)C]

The preparation method of N-(5-((4-(4,6-difluoro-1,7-dimethyl-1H-indol-3-yl)pyrimidin-2-yl)amino)-2-((2-(dimethylamino)ethyl)(methyl)amino)-4-methoxyphenyl)acrylamide was similar to Example 22.

Example 33: Preparation of N-(2-((2-(dimethylamino)ethyl)(methyl)amino)-5-((4-(5-fluoro-4,6-dimethoxy-1-methyl-1H-indol-3-yl)pyrimidin-2-yl)amino)-4-methoxyphenyl)acrylamide

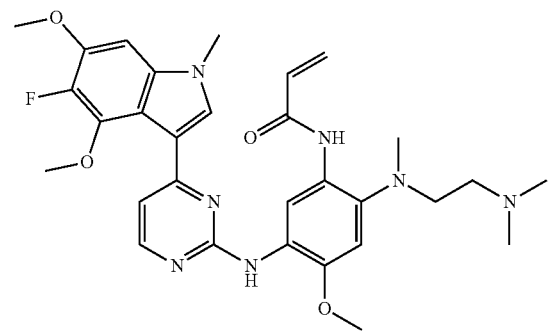

The preparation method of N-(2-((2-(dimethylamino)ethyl)(methyl)amino)-5-((4-(5-fluoro-4,6-dimethoxy-1-methyl-1H-indol-3-yl)pyrimidin-2-yl)amino)-4-methoxyphenyl)acrylamide was similar to Example 22.

Example 34: Preparation of N-(5-((4-(5,7-difluoro-6-(trifluoromethyl)-1H-indol-3-yl)pyrimidin-2-yl)amino)-2-((2-(dimethylamino)ethyl)(methyl)amino)-4-methoxyphenyl)acrylamide

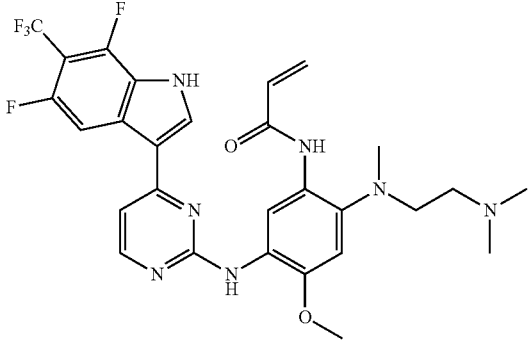 [SMILES: C=CC(=O)Nc1cc(Nc2nccc(-c3c[nH]c4c(F)c(C(F)(F)F)c(F)cc34)n2)c(OC)cc1N(C)CCN(C)C]

The preparation method of N-(5-((4-(5,7-difluoro-6-(trifluoromethyl)-1H-indol-3-yl)pyrimidin-2-yl)amino)-2-((2-(dimethylamino)ethyl)(methyl)amino)-4-methoxyphenyl)acrylamide was similar to Example 22.

Example 35: Preparation of N-(5-((4-(4,6-difluoro-5-methyl-1H-indol-3-yl)pyrimidin-2-yl)amino)-2-((2-(dimethylamino)ethyl)(methyl)amino)-4-methoxyphenyl)acrylamide

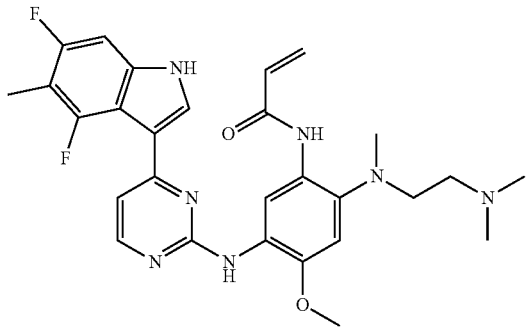

The preparation method of N-(5-((4-(4,6-difluoro-5-methyl-1H-indol-3-yl)pyrimidin-2-yl)amino)-2-((2-(dimethylamino)ethyl)(methyl)amino)-4-methoxyphenyl)acrylamide was similar to Example 22.

Example 36: Preparation of N-(2-((2-(dimethylamino)ethyl)(methyl)amino)-4-methoxy-5-((4-(4,5,6,7-tetrafluoro-1H-indol-3-yl)pyrimidin-2-yl)amino)phenyl)acrylamide

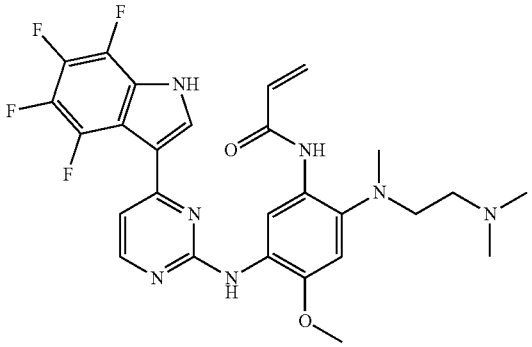 [SMILES: C=CC(=O)Nc1cc(Nc2nccc(-c3c[nH]c4c(F)c(F)c(F)c(F)c34)n2)c(OC)cc1N(C)CCN(C)C]

The preparation method of N-(2-((2-(dimethylamino)ethyl)(methyl)amino)-4-methoxy-5-((4-(4,5,6,7-tetrafluoro-1H-indol-3-yl)pyrimidin-2-yl)amino)phenyl)acrylamide was similar to Example 22.

Example 37: Preparation of N-(5-((4-(1-cyclopropyl-4,6-dimethyl-5-(methylsulfonyl)-1H-indol-3-yl)pyrimidin-2-yl)amino)-2-((2-(dimethylamino)ethyl)(methyl)amino)-4-methoxyphenyl)acrylamide

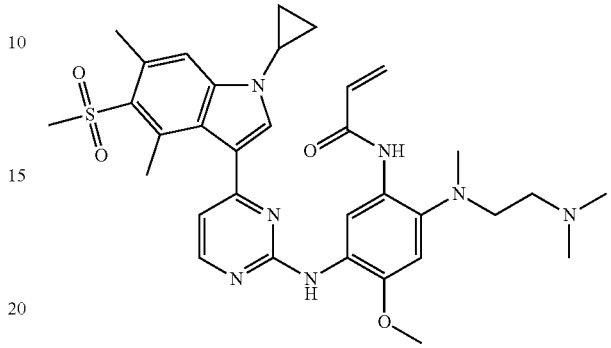

The preparation method of N-(5-((4-(1-cyclopropyl-4,6-dimethyl-5-(methylsulfonyl)-1H-indol-3-yl)pyrimidin-2-yl)amino)-2-((2-(dimethylamino)ethyl)(methyl)amino)-4-methoxyphenyl)acrylamide was similar to Example 22.

Example 38: Preparation of N-(5-((4-(1,5-dicyclopropyl-4,6-difluoro-1H-indol-3-yl)pyrimidin-2-yl)amino)-2-((2-(dimethylamino)ethyl)(methyl)amino)-4-methoxyphenyl)acrylamide

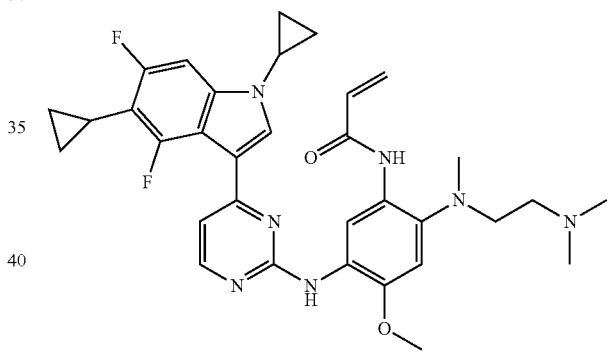

The preparation method of N-(5-((4-(1,5-dicyclopropyl-4,6-difluoro-1H-indol-3-yl)pyrimidin-2-yl)amino)-2-((2-(dimethylamino)ethyl)(methyl)amino)-4-methoxyphenyl)acrylamide was similar to Example 22.

Example 39: Preparation of N-(5-((4-(1-cyclopropyl-5,7-difluoro-6-(oxetan-3-yl)-1H-indol-3-yl)pyrimidin-2-yl)amino)-2-((2-(dimethylamino)ethyl)(methyl)amino)-4-methoxyphenyl)acrylamide

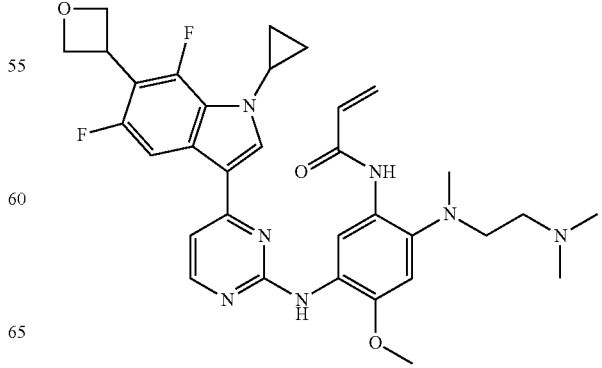

The preparation method of N-(5-((4-(1-cyclopropyl-5,7-difluoro-6-(oxetan-3-yl)-1H-indol-3-yl)pyrimidin-2-yl)amino)-2-((2-(dimethylamino)ethyl)(methyl)amino)-4-methoxyphenyl)acrylamide was similar to Example 22.

Example 40 Preparation of N-(5-((4-(1H-indazol-1-yl)pyrimidin-2-yl)amino)-2-((2-(dimethylamino)ethyl)(methyl)amino)-4-methoxyphenyl)acrylamide

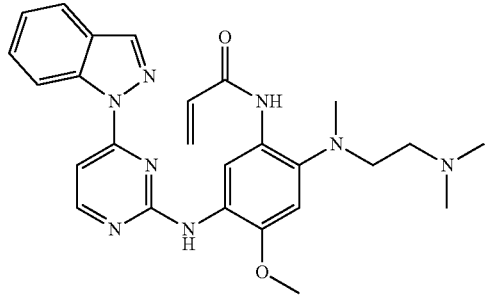 [SMILES: C=CC(=O)Nc1cc(Nc2nccc(-n3ncc4ccccc43)n2)c(OC)cc1N(C)CCN(C)C]

Step 1: Preparation of 1-(2-chloropyrimidin-4-yl)-1H-indazole

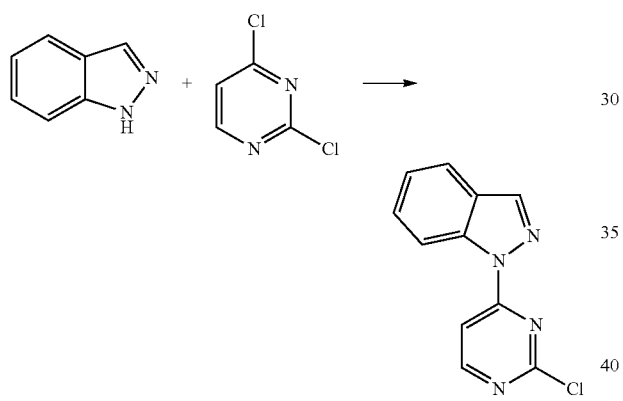

2,4-dichloropyrimidine (1.18 g, 8 mmol) and DMF (40 mL) were added in a 100 mL one-necked flask. NaH (0.4 g, 10 mmol) was added to the solution in batches, and the mixture was stirred at room temperature for a half hour. After cooling to 0° C., indazole (1.49 g, 12.6 mmol) was added. The reaction was heated up to room temperature under stirring slowly, and reacted for 4 hours. The reaction was quenched with water, extracted with ethyl acetate and purified by silica gel column chromatography (PE/EA=20/1) to obtain the title product 1-(2-chloropyrimidin-4-yl)-1H-indazole (450 mg, 26%).

Step 2: Preparation of N-(4-fluoro-2-methoxy-5-nitrophenyl)-4-(1H-indazol-1-yl)pyrimidin-2-amine

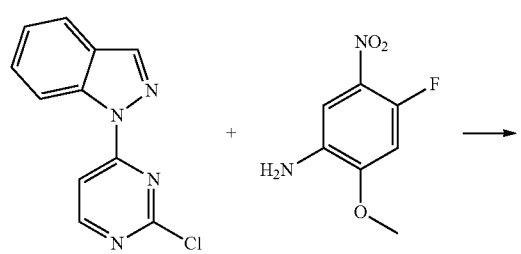

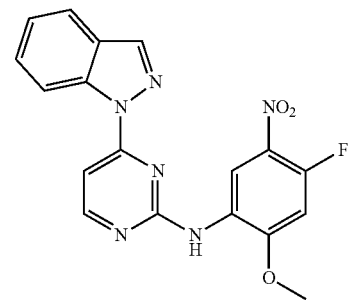

1-(2-chloropyrimidin-4-yl)-1H-indazole (450 mg, 1.96 mmol), 4-fluoro-2-methoxy-5-nitroaniline (363 mg, 1.96 mmol), p-toluenesulfonic acid (336 mg, 1.96 mmol) and 2-pentanol (20 mL) were added successively in a 50 mL one-necked flask. The mixture was stirred at 120° C. for 5 hours and concentrated to obtain a black mixture which was purified by silica gel column chromatography (1% MeOH/DCM) to obtain the title compound N-(4-fluoro-2-methoxy-5-nitrophenyl)-4-(1H-indazol-1-yl)pyrimidin-2-amine (200 mg, 27%).

Step 3: Preparation of N1-(4-(1H-indazol-1-yl)pyrimidin-2-yl)-N4-(2-(dimethylamino)ethyl)-2-methoxy-N4-methyl-5-nitrobenzene-1,4-diamine

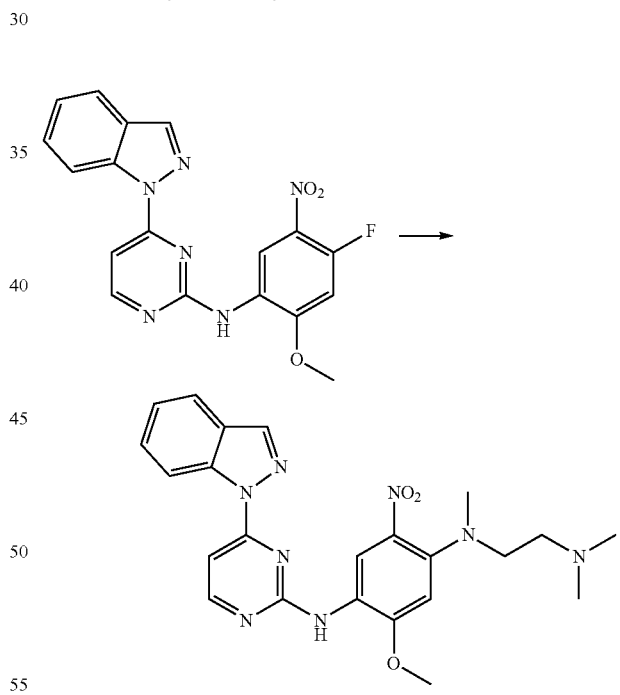

N-(4-fluoro-2-methoxy-5-nitrophenyl)-4-(1H-indazol-1-yl)pyrimidin-2-amine (200 mg, 0.53 mmol), trimethylethylenediamine (107 mg, 1.05 mmol), DIPEA (203 mg, 1.57 mmol) and DMF (8 mL) were added successively in a 50 mL one-necked flask. The reaction solution was stirred at 100° C. for 1 hour, concentrated and purified by preparative thin-layer chromatography (5% MeOH/DCM) to obtain the title compound N1-(4-(1H-indazol-1-yl)pyrimidin-2-yl)-N4-(2-(dimethylamino)ethyl)-2-methoxy-N4-methyl-5-nitrobenzene-1,4-diamine (300 mg, 60%).

Step 4: Preparation of N4-(4-(1H-indazol-1-yl)pyrimidin-2-yl)-N1-(2-(dimethylamino)ethyl)-5-methoxy-N1-methylbenzene-1,2,4-triamine

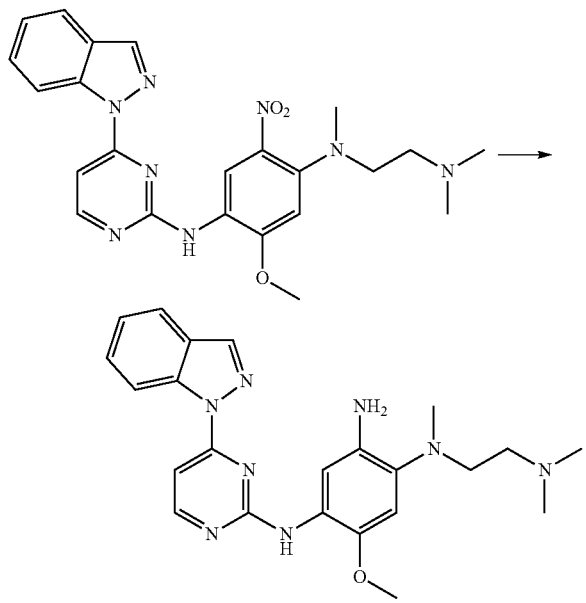

N1-(4-(1H-indazol-1-yl)pyrimidin-2-yl)-N4-(2-(dimethylamino)ethyl)-2-methoxy-N4-methyl-5-nitrobenzene-1,4-diamine (300 mg, 0.65 mmol), 5% Pd/C (100 mg) and methanol (50 mL) were added successively in a 50 mL one-necked flask. The mixture was stirred at room temperature for 2 hours. The reaction solution was concentrated and purified by thin-layer chromatography (5% MeOH/DCM) to obtain the title compound N4-(4-(1H-indazol-1-yl)pyrimidin-2-yl)-N1-(2-(dimethylamino)ethyl)-5-methoxy-N1-methylbenzene-1,2,4-triamine (110 mg, 30%).

Step 5: Preparation of N-(5-((4-(1H-indazol-1-yl)pyrimidin-2-yl)amino)-2-((2-(dimethylamino)ethyl)(methyl)amino)-4-methoxyphenyl)acrylamide

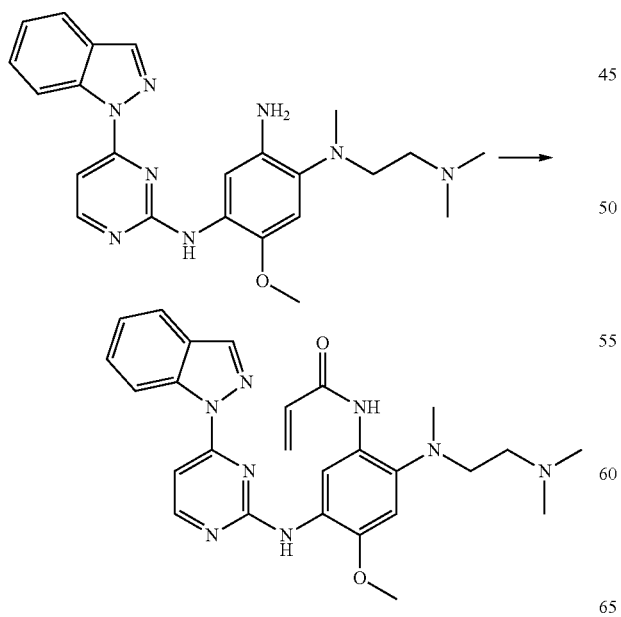

N4-(4-(1H-indazol-1-yl)pyrimidin-2-yl)-N1-(2-(dimethylamino)ethyl)-5-methoxy-N1-methylbenzene-1,2,4-triamine (110 mg, 0.25 mmol), DIPEA (109 mg, 0.84 mmol) and THF (30 mL) were added in a 100 mL one-necked flask. After cooling to 0° C., 0.5 mL of acryloyl chloride (1 M in THF) was added dropwise, and the reaction solution was stirred at 0° C. for 2 hours. The reaction was quenched with methanol, concentrated and purified by thin-layer chromatography (10% MeOH/DCM) to obtain the title compound N-(5-((4-(1H-indazol-1-yl)pyrimidin-2-yl)amino)-2-((2-(dimethylamino)ethyl)(methyl)amino)-4-methoxyphenyl)acrylamide (20 mg, 16%).

¹H NMR (400 MHz, CD₃OD) δ 8.52 (d, J=8.6 Hz, 1H), 8.43 (s, 1H), 8.29 (dd, J=5.6, 3.9 Hz, 1H), 8.19 (d, J=3.5 Hz, 1H), 7.70 (d, J=8.0 Hz, 1H), 7.45-7.23 (m, 2H), 7.17 (t, J=7.5 Hz, 1H), 6.90 (s, 1H), 6.42 (dd, J=17.0, 10.2 Hz, 1H), 6.24 (d, J=16.9 Hz, 1H), 5.68 (d, J=10.3 Hz, 1H), 3.83 (s, 3H), 3.16 (s, 2H), 2.79-2.61 (m, 5H), 2.66 (d, J=12.3 Hz, 3H), 2.44 (s, 5H);

MS m/z (ESI): 487 [M+H]⁺.

Example 41: Preparation of N-(2-((2-(dimethylamino)ethyl)(methyl)amino)-4-methoxy-5-((4-(4-methoxy-1H-indazol-1-yl)pyrimidin-2-yl)amino)phenyl)acrylamide

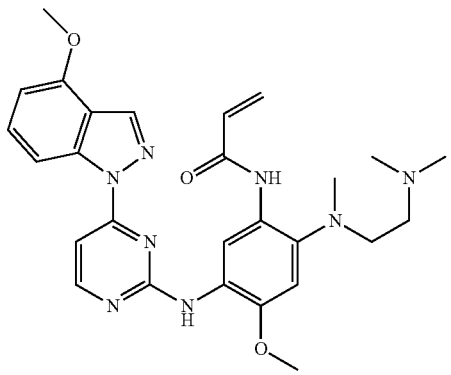 [SMILES: C=CC(=O)Nc1cc(Nc2nccc(-n3ncc4c(OC)cccc43)n2)c(OC)cc1N(C)CCN(C)C]

The preparation method of N-(2-((2-(dimethylamino)ethyl)(methyl)amino)-4-methoxy-5-((4-(4-methoxy-1H-indazol-1-yl)pyrimidin-2-yl)amino)phenyl)acrylamide was similar to Example 40.

¹H NMR (400 MHz, CD₃OD) δ 8.46 (s, 1H), 8.33 (d, J=7.3 Hz, 1H), 8.05 (s, 1H), 7.85 (s, 1H), 7.63 (d, J=6.4 Hz, 1H), 7.46 (t, J=8.0 Hz, 1H), 7.08 (s, 1H), 6.87 (d, J=7.9 Hz, 1H), 6.59 (dd, J=16.9, 10.0 Hz, 1H), 6.53-6.42 (m, 1H), 5.87 (d, J=9.9 Hz, 1H), 4.00 (s, 3H), 3.96 (s, 3H), 3.57 (t, J=5.4 Hz, 2H), 3.40-3.35 (m, 2H), 2.93 (s, 6H), 2.81 (s, 3H);

MS m/z (ESI): 517.3 [M+H]⁺.

Example 42: Preparation of N-(2-((2-(dimethylamino)ethyl)(methyl)amino)-4-methoxy-5-((4-(6-methoxy-1H-indazol-1-yl)pyrimidin-2-yl)amino)phenyl)acrylamide

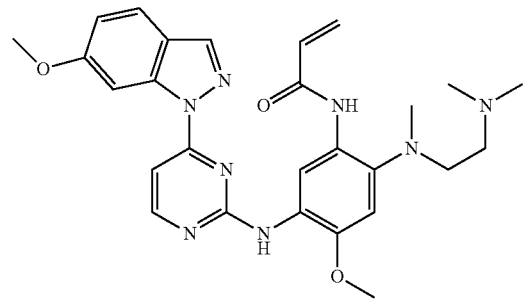

The preparation method of N-(2-((2-(dimethylamino)ethyl)(methyl)amino)-4-methoxy-5-((4-(6-methoxy-1H-indazol-1-yl)pyrimidin-2-yl)amino)phenyl)acrylamide was similar to Example 40.

¹H NMR (400 MHz, CD₃OD) δ 8.35 (s, 1H), 8.23 (d, J=6.3 Hz, 1H), 8.08 (s, 1H), 7.87 (s, 1H), 7.74 (d, J=8.7 Hz, 1H), 7.61 (d, J=6.8 Hz, 1H), 7.12-7.04 (m, 2H), 6.63 (dd, J=16.9, 10.2 Hz, 1H), 6.41 (dd, J=16.9, 1.2 Hz, 1H), 5.87-5.79 (m, 1H), 3.94 (s, 3H), 3.86 (s, 3H), 3.54 (t, J=5.6 Hz, 2H), 3.37 (t, J=5.6 Hz, 2H), 2.91 (s, 6H), 2.79 (s, 3H); MS m/z (ESI): 517.3 [M+H]⁺.

Example 43: Preparation of N-(2-((2-(dimethylamino)ethyl)(methyl)amino)-4-methoxy-5-((4-(5-methoxy-1H-indazol-1-yl)pyrimidin-2-yl)amino)phenyl)acrylamide

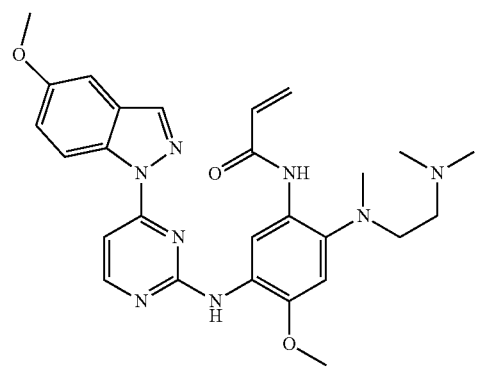 [SMILES: C=CC(=O)Nc1cc(Nc2nccc(-n3ncc4cc(OC)ccc43)n2)c(OC)cc1N(C)CCN(C)C]

Step 1: Preparation of 5-methoxy-1-(2-(methylthio)pyrimidin-4-yl)-1H-indazole

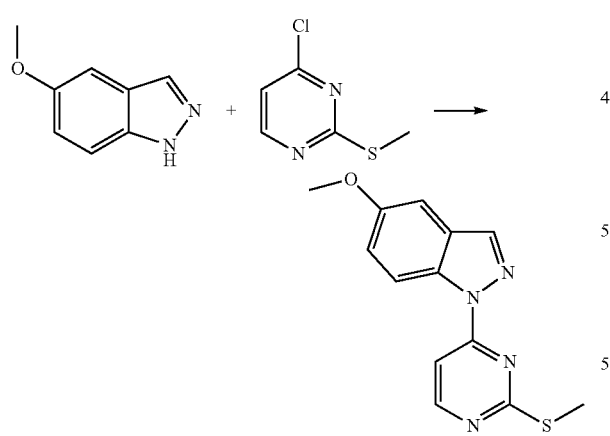

5-methoxy-1H-indazole (500 mg, 3.38 mmol) was dissolved in DMF (10 mL). NaH (148 mg, 3.72 mmol) was added at 0° C., and then 4-chloro-2-(methylthio)pyrimidine (542 mg, 3.38 mmol) was added. After stirring at this temperature for 2 hours, 30 mL of water was added. The reaction solution was filtered, extracted and dried to obtain 5-methoxy-1-(2-(methylthio)pyrimidin-4-yl)-1H-indazole (850 mg, 92%) as a white solid.

Step 2: Preparation of 5-methoxy-1-(2-(methylsulfonyl)pyrimidin-4-yl)-1H-indazole

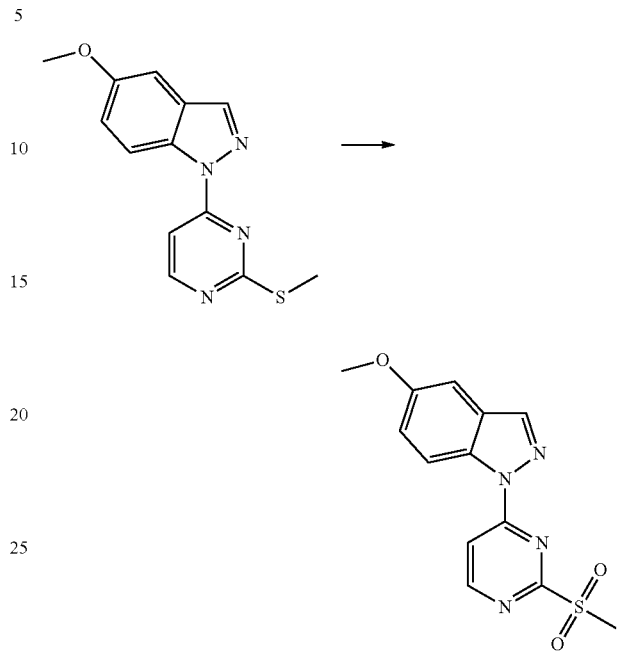

5-methoxy-1-(2-(methylthio)pyrimidin-4-yl)-1H-indazole (850 mg, 3.125 mmol) was dissolved in DCM (50 ml), then 3-chloroperoxybenzoic acid (1.68 g, 7.8125 mmol) was added. The mixture was stirred at 50° C. for 3 hours, extracted with DCM, and purified by column chromatography to obtain 5-methoxy-1-(2-(methylsulfonyl)pyrimidin-4-yl)-1H-indazole (400 mg, 42%).

Step 3: Preparation of N-(4-fluoro-2-methoxy-5-nitrophenyl)-4-(5-methoxy-1H-indazol-1-yl)pyrimidin-2-amine

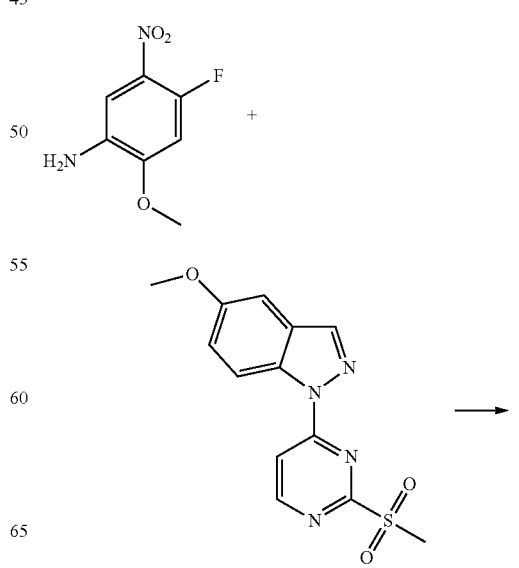

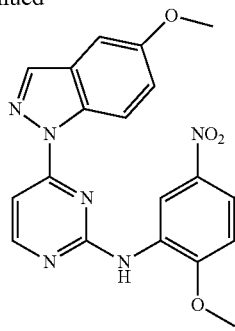

5-methoxy-1-(2-(methylsulfonyl)pyrimidin-4-yl)-1H-indazole (100 mg, 0.329 mmol), 4-fluoro-2-methoxy-5-nitroaniline (73 mg, 0.395 mmol) and p-toluenesulfonic acid (57 mg, 0.329 mmol) were dissolved in 1,4-dioxane (5 mL). The reaction solution was heated up to reflux overnight. After cooling, an appropriate amount of sodium bicarbonate aqueous solution was added. The reaction solution was filtered, extracted and dried to obtain a gray solid (200 mg), which was used directly in the next step.

Step 4: N1-(2-(dimethylamino)ethyl)-5-methoxy-N4-(4-(5-methoxy-1H-indazol-1-yl)pyrimidin-2-yl)-N1-methyl-2-nitrobenzene-1,4-diamine

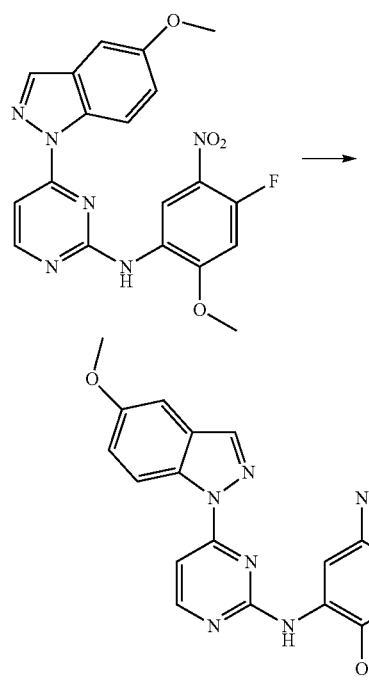

N-(4-fluoro-2-methoxy-5-nitrophenyl)-4-(5-methoxy-1H-indazol-1-yl)pyrimidin-2-amine (120 mg, 0.122 mmol), DIPEA (47 mg, 0.658 mol), and trimethylethylenediamine (37 mg, 0.366 mmol) were dissolved in DMF (5 mL). The reaction solution was heated at 100° C. for 1 hour, concentrated and purified by column chromatography to obtain 30 mg of a yellow solid, which was used directly in the next step.

Step 5: N1-(2-(dimethylamino)ethyl)-5-methoxy-N4-(4-(5-methoxy-1H-indazol-1-yl)pyrimidin-2-yl)-N1-methylbenzene-1,2,4-triamine

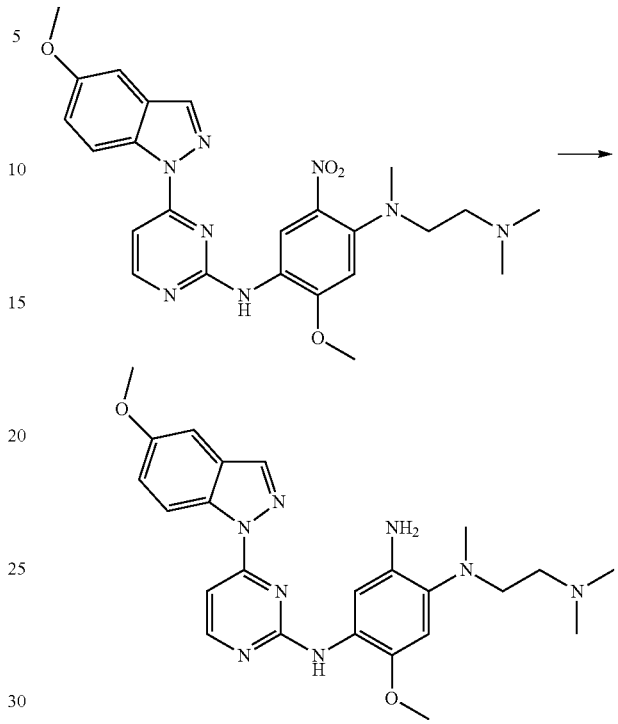

The preparation method of N1-(2-(dimethylamino)ethyl)-5-methoxy-N4-(4-(5-methoxy-1H-indazol-1-yl)pyrimidin-2-yl)-N1-methylbenzene-1,2,4-triamine was similar to Example 40.

Step 6: N-(2-((2-(dimethylamino)ethyl)(methyl)amino)-4-methoxy-5-((4-(5-methoxy-1H-indazol-1-yl)pyrimidin-2-yl)amino)phenyl)acrylamide

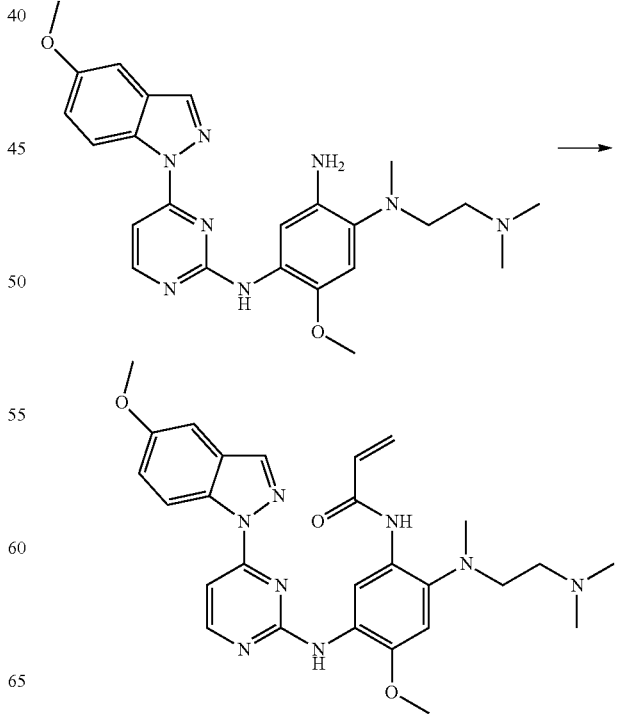

The preparation method of N-(2-((2-(dimethylamino)ethyl)(methyl)amino)-4-methoxy-5-((4-(5-methoxy-1H-indazol-1-yl)pyrimidin-2-yl)amino)phenyl)acrylamide was similar to Example 40.

$^1$H NMR (400 MHz, CD$_3$OD) δ 8.38 (s, 2H), 8.31 (d, J=6.6 Hz, 1H), 7.86 (s, 1H), 7.60 (d, J=6.7 Hz, 1H), 7.33 (d, J=2.4 Hz, 1H), 7.15 (dd, J=9.1, 2.2 Hz, 1H), 7.08 (s, 1H), 6.53 (dd, J=8.9, 5.9 Hz, 2H), 5.88 (dd, J=9.2, 2.6 Hz, 1H), 3.98 (s, 3H), 3.89 (s, 3H), 3.58 (t, J=5.7 Hz, 2H), 3.38-3.34 (m, 2H), 2.93 (s, 6H), 2.81 (s, 3H);

MS m/z (ESI): 517 [M+H]$^+$.

Example 44: Preparation of N-(5-((4-(3-cyclopropyl-1H-indazol-1-yl)pyrimidin-2-yl)amino)-2-((2-(dimethylamino)ethyl)(methyl)amino)-4-methoxyphenyl)acrylamide

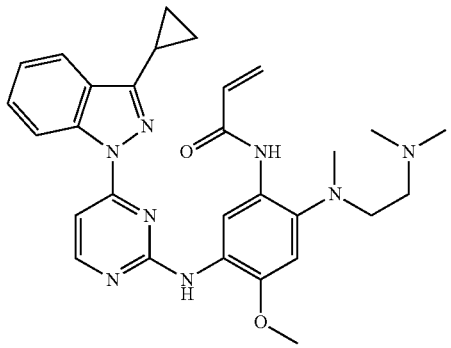 [SMILES: C=CC(=O)Nc1cc(Nc2nccc(-n3nc(C4CC4)c4ccccc43)n2)c(OC)cc1N(C)CCN(C)C]

The preparation method of N-(5-((4-(3-cyclopropyl-1H-indazol-1-yl)pyrimidin-2-yl)amino)-2-((2-(dimethylamino)ethyl)(methyl)amino)-4-methoxyphenyl)acrylamide was similar to Example 40.

$^1$H NMR (400 MHz, CD$_3$OD) δ 8.39 (s, 1H), 8.18 (d, J=5.2 Hz, 1H), 7.87 (d, J=7.3 Hz, 2H), 7.48 (dd, J=17.0, 7.1 Hz, 2H), 7.40 (t, J=7.4 Hz, 1H), 7.09 (s, 1H), 6.64 (dd, J=16.9, 10.2 Hz, 1H), 6.45 (d, J=16.8 Hz, 1H), 5.84 (d, J=10.2 Hz, 1H), 3.94 (s, 3H), 3.55 (d, J=5.2 Hz, 2H), 3.38 (t, J=5.3 Hz, 2H), 2.93 (s, 6H), 2.81 (s, 3H), 2.39-2.29 (m, 1H), 1.19 (d, J=6.5 Hz, 4H);

MS m/z (ESI): 527.3 [M+H]$^+$.

Example 45: Preparation of N-(2-((2-(dimethylamino)ethyl)(methyl)amino)-4-methoxy-5-((4-(4-methoxy-1H-indazol-1-yl)-5-(trifluoromethyl)pyrimidin-2-yl)amino)phenyl)acrylamide

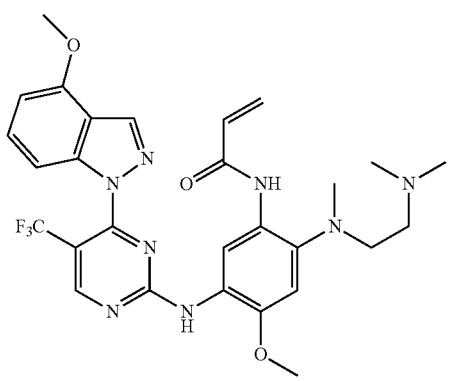 [SMILES: C=CC(=O)Nc1cc(Nc2ncc(C(F)(F)F)c(-n3ncc4c(OC)cccc43)n2)c(OC)cc1N(C)CCN(C)C]

The preparation method of N-(2-((2-(dimethylamino)ethyl)(methyl)amino)-4-methoxy-5-((4-(4-methoxy-1H-indazol-1-yl)-5-(trifluoromethyl)pyrimidin-2-yl)amino)phenyl)acrylamide was similar to Example 40.

Example 46: Preparation of N-(2-((2-(dimethylamino)ethyl)(methyl)amino)-4-methoxy-5-((4-(6-methoxy-1H-indazol-1-yl)-5-(trifluoromethyl)pyrimidin-2-yl)amino)phenyl)acrylamide

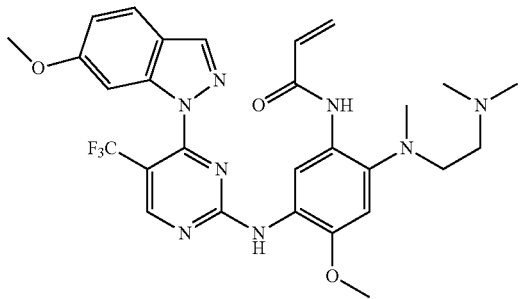

The preparation method of N-(2-((2-(dimethylamino)ethyl)(methyl)amino)-4-methoxy-5-((4-(6-methoxy-1H-indazol-1-yl)-5-(trifluoromethyl)pyrimidin-2-yl)amino)phenyl)acrylamide was similar to Example 40.

Example 47: Preparation of N-(5-((4-(5-cyclopropyl-1H-indazol-1-yl)pyrimidin-2-yl)amino)-2-((2-(dimethylamino)ethyl)(methyl)amino)-4-methoxyphenyl)acrylamide

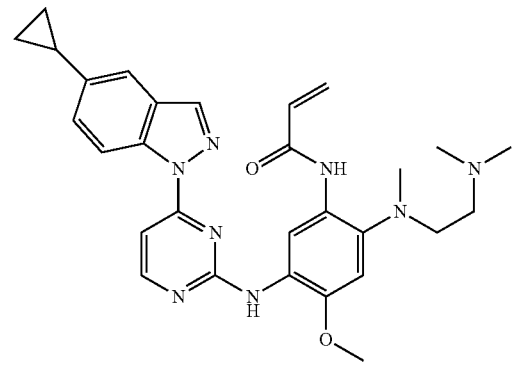 [SMILES: C=CC(=O)Nc1cc(Nc2nccc(-n3ncc4cc(C5CC5)ccc43)n2)c(OC)cc1N(C)CCN(C)C]

Step 1: Preparation of 5-bromo-1-((2-(trimethylsilyl)ethoxy)methyl)-1H-indazole

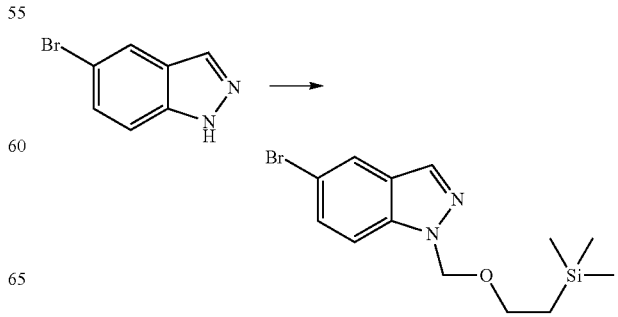

5-bromo-1H-indazole (2.0 g, 10 mmol) was dissolved in DMF (15 mL), and NaH (480 mg, 12 mmol) was added at 0° C. The reaction solution was warmed up to room temperature and stirred for 30 minutes, and then cooled to 0° C. After 2-(trimethylsilyl)ethyl hypochlorite (2.0 g, 12 mmol) was added, the reaction solution was stirred for 2 hours, quenched with 30 mL of water and extracted with methyl tert-butyl ether (30 mL×3). The organic phase was dried over anhydrous sodium sulfate and concentrated to obtain a crude product which was further purified by column chromatography to obtain 5-bromo-1-((2-(trimethylsilyl)ethoxy)methyl)-1H-indazole (2.0 g, 63%).

Step 2: Preparation of 5-cyclopropyl-1-((2-(trimethylsilyl)ethoxy)methyl)-1H-indazole

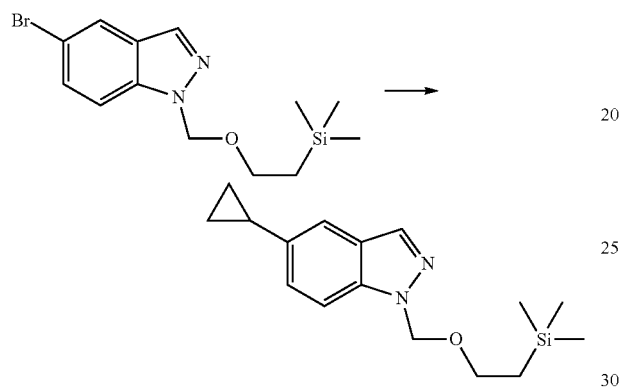

5-bromo-1-((2-(trimethylsilyl)ethoxy)methyl)-1H-indazole (1.5 g, 4.6 mmol), cyclopropylboronic acid (790 mg, 9.2 mmol) and potassium phosphate (3.0 g, 13.8 mmol) were dissolved in a mixture of toluene and water (30/10 ml). After the mixture was purged three times with nitrogen, palladium acetate (103 mg, 0.46 mmol) and tricyclohexylphosphine (258 mg, 0.92 mmol) were added. The reaction was stirred at 100° C. for 16 hours, quenched with 30 mL of water and extracted with ethyl acetate (50 mL×3). The organic phase was dried over anhydrous sodium sulfate and concentrated to obtain a crude product which was further purified by column chromatography to obtain 5-cyclopropyl-1-((2-(trimethylsilyl)ethoxy)methyl)-1H-indazole (1.2 g, 89%).

Step 3: Preparation of 5-cyclopropyl-1H-indazole

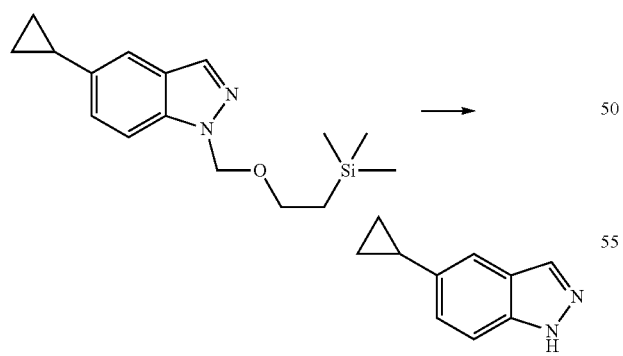

5-cyclopropyl-1-((2-(trimethylsilyl)ethoxy)-)methyl)-1H-indazole (1.2 g, 4.2 mmol) was dissolved in dichloromethane (30 mL). Trifluoroacetic acid (12 mL) was added, and the solution was reacted at room temperature for 2.5 h, and concentrated to dry. The crude product was dissolved in a mixture of dichloromethane (50 mL) and ethylenediamine (18 mL), and the mixture was stirred for 1 h. After 30 mL of water were added, the reaction solution was extracted with dichloromethane (50 mL×3). The organic phase was dried over anhydrous sodium sulfate and concentrated to obtain a crude product which was further purified by column chromatography to obtain 5-cyclopropyl-1H-indazole (280 mg, 42%).

Steps 4 to 9: Preparation of N-(5-((4-(5-cyclopropyl-1H-indazol-1-yl)pyrimidin-2-yl)amino)-2-((2-(dimethylamino)ethyl)(methyl)amino)-4-methoxyphenyl)acrylamide

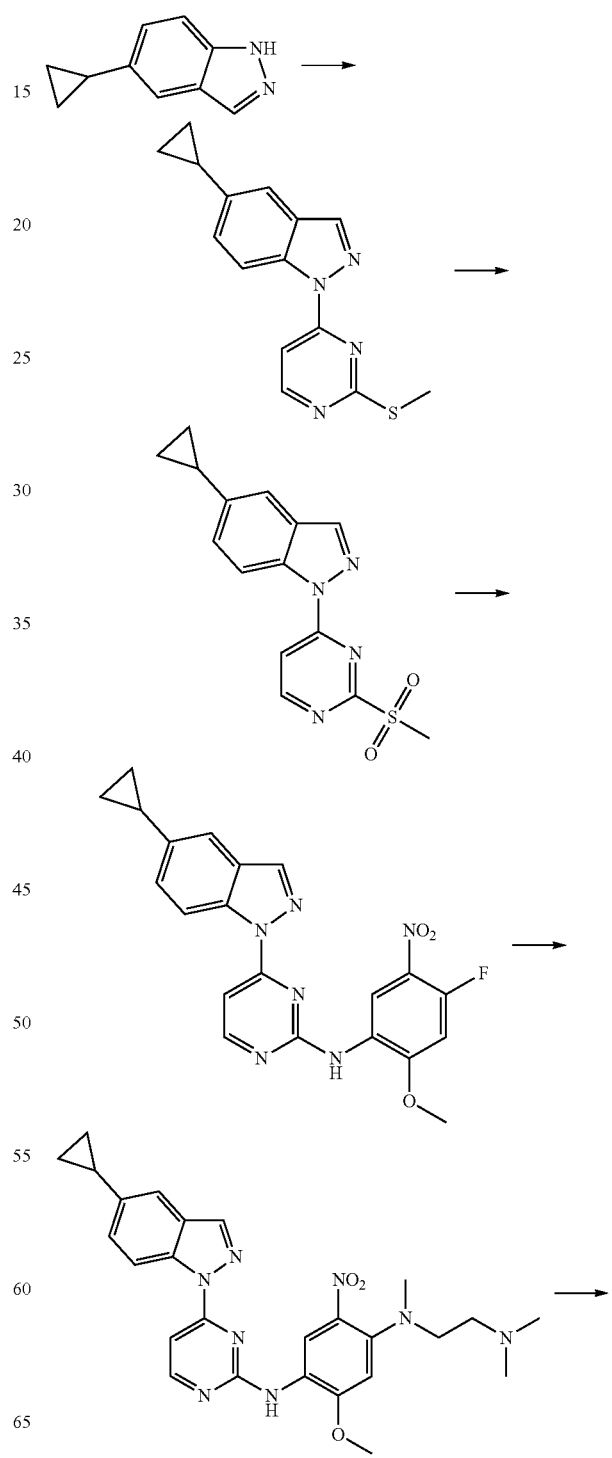

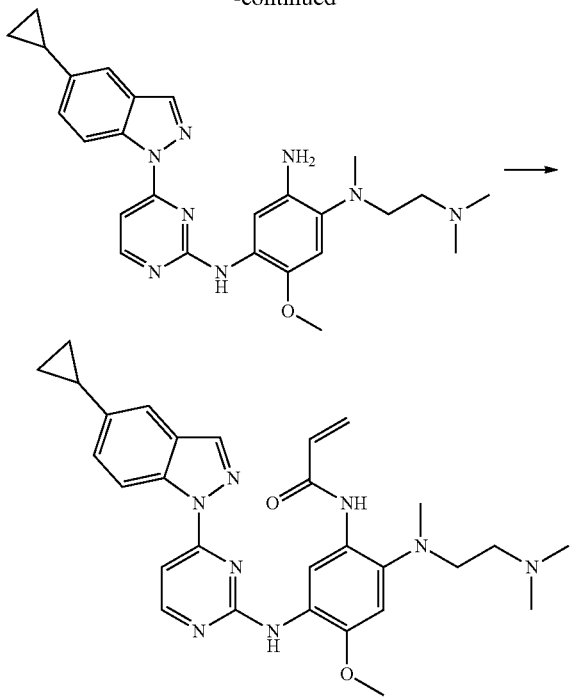

The preparation method of N-(5-((4-(5-cyclopropyl-1H-indazol-1-yl)pyrimidin-2-yl)amino)-2-((2-(dimethylamino)ethyl)(methyl)amino)-4-methoxyphenyl)acrylamide was similar to Example 43.

$^1$H NMR (400 MHz, CD$_3$OD) δ 8.26 (s, 2H), 8.19 (s, 1H), 7.78 (s, 1H), 7.49 (d, J=6.7 Hz, 1H), 7.44 (s, 1H), 7.15 (d, J=8.6 Hz, 1H), 6.98 (s, 1H), 6.49 (dd, J=16.9, 9.9 Hz, 1H), 6.38 (dd, J=16.9, 1.9 Hz, 1H), 5.77 (dd, J=9.9, 1.9 Hz, 1H), 3.86 (s, 3H), 3.46 (t, J=5.6 Hz, 2H), 3.26 (t, J=5.6 Hz, 2H), 2.82 (s, 6H), 2.69 (s, 3H), 2.00-1.88 (m, 1H), 0.97-0.89 (m, 2H), 0.67-0.59 (m, 2H);

MS m/z (ESI): 527.3 [M+H]$^+$.

Example 48: Preparation of N-(5-((5-chloro-4-(5-methoxy-1H-indazol-1-yl)pyrimidin-2-yl)amino)-2-((2-(dimethylamino)ethyl)(methyl)amino)-4-methoxyphenyl)acrylamide

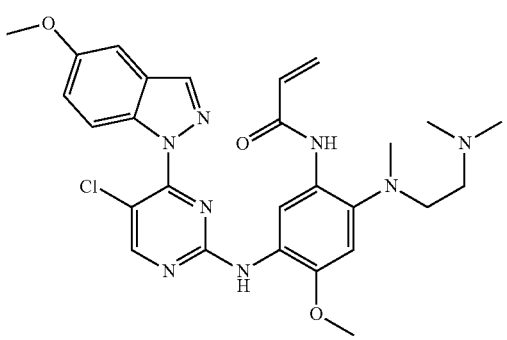

The preparation method of N-(5-((5-chloro-4-(5-methoxy-1H-indazol-1-yl)pyrimidin-2-yl)amino)-2-((2-(dimethylamino)ethyl)(methyl)amino)-4-methoxyphenyl)acrylamide was similar to Example 40.

$^1$H NMR (400 MHz, CD$_3$OD) δ 8.49 (s, 1H), 8.20 (d, J=10.0 Hz, 2H), 8.00 (d, J=9.0 Hz, 1H), 7.21 (s, 1H), 7.03 (d, J=9.0 Hz, 1H), 6.94 (s, 1H), 6.42 (s, 2H), 5.83 (s, 1H), 3.95 (s, 3H), 3.84 (s, 3H), 3.47 (s, 2H), 3.28 (s, 2H), 2.86 (s, 6H), 2.69 (s, 3H);

MS m/z (ESI): 551 [M+H]$^+$.

Example 49: Preparation of N-(2-((2-(dimethylamino)ethyl)(methyl)amino)-4-methoxy-5-((4-(5-methoxy-1H-indazol-1-yl)-5-(trifluoromethyl)pyrimidin-2-yl)amino)phenyl)acrylamide

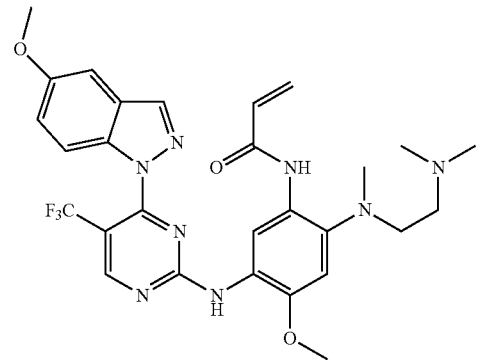 [SMILES: C=CC(=O)Nc1cc(Nc2ncc(C(F)(F)F)c(-n3ncc4cc(OC)ccc43)n2)c(OC)cc1N(C)CCN(C)C]

The preparation method of N-(2-((2-(dimethylamino)ethyl)(methyl)amino)-4-methoxy-5-((4-(5-methoxy-1H-indazol-1-yl)-5-(trifluoromethyl)pyrimidin-2-yl)amino)phenyl)acrylamide was similar to Example 40.

$^1$H NMR (400 MHz, CD3OD) δ 8.79 (s, 1H), 8.23 (s, 1H), 8.11-8.03 (m, 1H), 7.27 (s, 1H), 7.12-7.04 (m, 1H), 7.01 (s, 1H), 6.47 (s, 2H), 5.92-5.80 (m, 1H), 3.99 (s, 3H), 3.88 (s, 3H), 3.54 (s, 2H), 3.32-3.29 (m, 2H), 2.90 (s, 6H), 2.76 (s, 3H);

MS m/z (ESI): 585 [M+H]$^+$.

Example 50: Preparation of N-(5-((4-(5-cyano-1H-indazol-1-yl)pyrimidin-2-yl)amino)-2-((2-(dimethylamino)ethyl)(methyl)amino)-4-methoxyphenyl)acrylamide

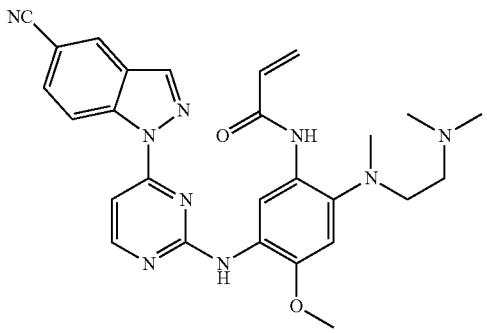 [SMILES: C=CC(=O)Nc1cc(Nc2nccc(-n3ncc4cc(C#N)ccc43)n2)c(OC)cc1N(C)CCN(C)C]

Step 1: Preparation of 1H-indazole-5-carbonitrile

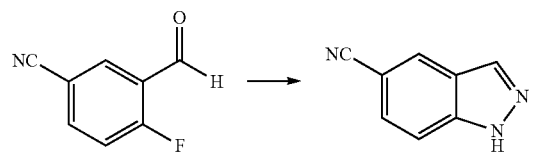 [SMILES: N#Cc1ccc(F)c(C=O)c1 ; N#Cc1ccc2[nH]ncc2c1]

4-fluoro-3-formylbenzonitrile (25 g, 16.78 mmol) was dissolved in 100 mL of hydrazine hydrate (85%). The mixture was stirred at room temperature for 24 hours and purified by column chromatography to obtain 1H-indazole-5-carbonitrile (2.1 g, 87%).

$^1$H NMR (400 MHz, DMSO) δ 13.60 (s, 1H), 8.42 (s, 1H), 8.27 (s, 1H), 7.73 (d, J=8.6 Hz, 1H), 7.67 (d, J=8.6 Hz, 1H); MS m/z (ESI): 144 [M+H]$^+$.

Steps 2 to 6: Preparation of N-(5-((4-(5-cyano-1H-indazol-1-yl)pyrimidin-2-yl)amino)-2-((2-(dimethylamino)ethyl)(methyl)amino)-4-methoxyphenyl)acrylamide

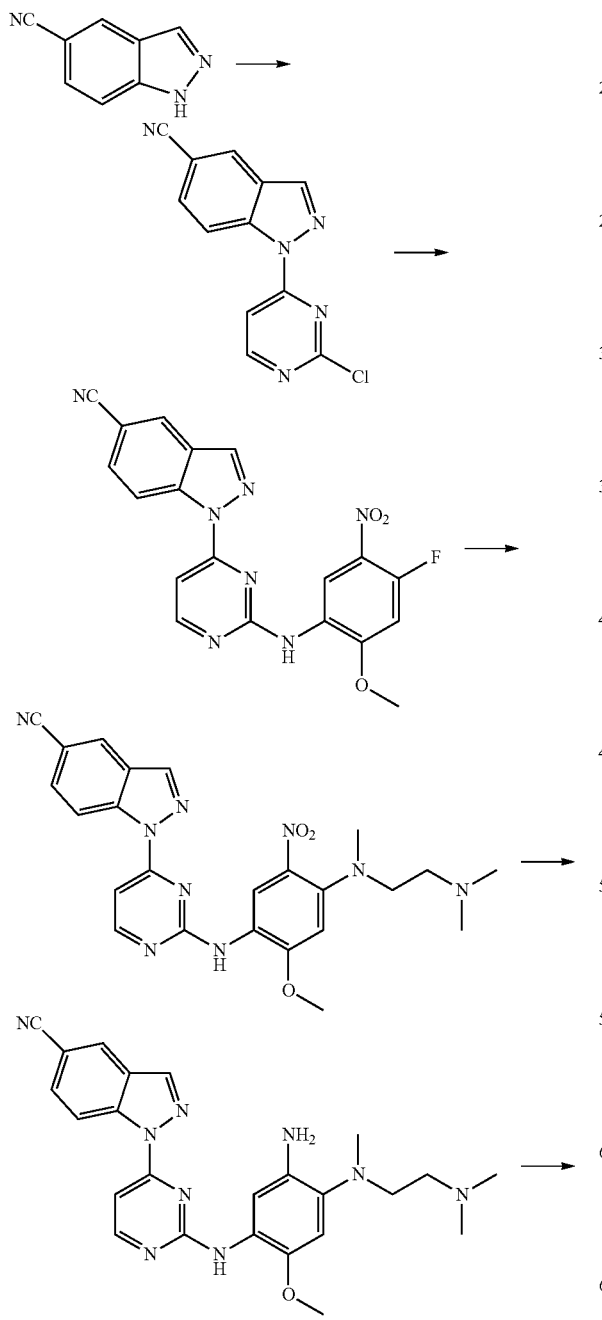

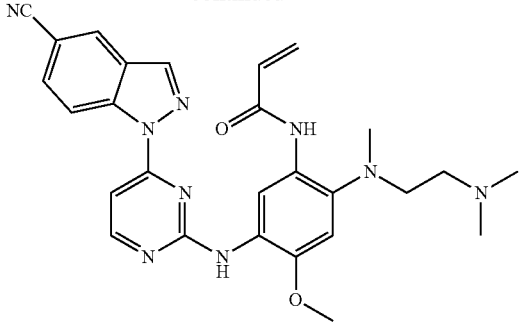

The preparation method of N-(5-((4-(5-cyano-1H-indazol-1-yl)pyrimidin-2-yl)amino)-2-((2-(dimethylamino)ethyl)(methyl)amino)-4-methoxyphenyl)acrylamide was similar to Example 40.

$^1$H NMR (400 MHz, CD$_3$OD) δ 8.77-8.68 (m, 1H), 8.53 (s, 1H), 8.47-8.41 (m, 1H), 8.33 (s, 1H), 7.99 (s, 1H), 7.75 (s, 1H), 7.56 (d, J=6.2 Hz, 1H), 7.06 (s, 1H), 6.55 (s, 1H), 6.53 (s, 1H), 5.92 (s, 1H), 4.00 (s, 3H), 3.56 (s, 2H), 3.36 (s, 2H), 2.94 (s, 6H), 2.80 (s, 3H);

MS m/z (ESI): 512 [M+H]$^+$.

Example 51: Preparation of N-(5-((5-chloro-4-(5-cyano-1H-indazol-1-yl)pyrimidin-2-yl)amino)-2-((2-(dimethylamino)ethyl)(methyl)amino)-4-methoxyphenyl)acrylamide

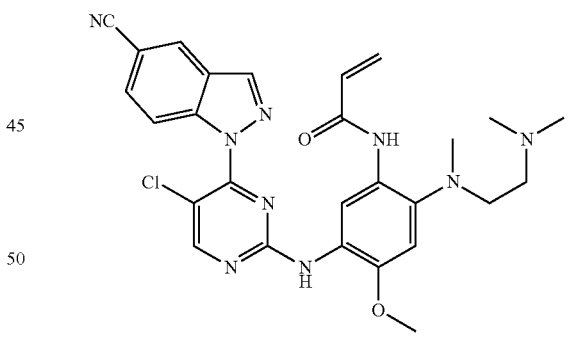

The preparation method of N-(5-((5-chloro-4-(5-cyano-1H-indazol-1-yl)pyrimidin-2-yl)amino)-2-((2-(dimethylamino)ethyl)(methyl)amino)-4-methoxyphenyl)acrylamide was similar to Example 50.

$^1$H NMR (400 MHz, CD$_3$OD) δ 8.60 (s, 1H), 8.46 (s, 1H), 8.33 (s, 1H), 8.25 (d, J=8.8 Hz, 1H), 8.20 (s, 1H), 7.63 (d, J=8.8 Hz, 1H), 6.98 (s, 1H), 6.59-6.37 (m, 2H), 5.96-5.86 (m, 1H), 4.00 (s, 3H), 3.50 (t, J=5.7 Hz, 2H), 3.32-3.28 (m, 2H), 2.90 (s, 6H), 2.72 (s, 3H);

MS m/z (ESI): 546 [M+H]$^+$.

Example 52: Preparation of N-(5-((4-(5-cyano-1H-indazol-1-yl)-5-(trifluoromethyl)pyrimidin-2-yl)amino)-2-((2-(dimethylamino)ethyl)(methyl)amino)-4-methoxyphenyl)acrylamide

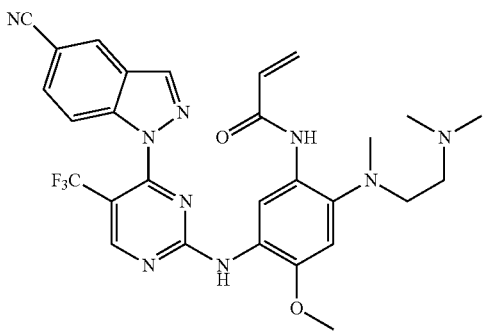 [SMILES: C=CC(=O)Nc1cc(Nc2ncc(Cl)c(-n3ncc4cc(C#N)ccc43)n2)c(OC)cc1N(C)CCN(C)C]

The preparation method of N-(5-((4-(5-cyano-1H-indazol-1-yl)-5-(trifluoromethyl)pyrimidin-2-yl)amino)-2-((2-(dimethylamino)ethyl)(methyl)amino)-4-methoxyphenyl)acrylamide was similar to Example 50.

$^1$H NMR (400 MHz, CD$_3$OD) δ 8.88 (s, 1H), 8.48 (s, 1H), 8.35 (s, 1H), 8.10 (s, 1H), 7.75-7.60 (m, 1H), 7.02 (s, 1H), 6.51 (s, 2H), 5.91 (d, J=11.7 Hz, 1H), 4.00 (s, 3H), 3.54 (s, 2H), 3.32 (s, 2H), 2.91 (s, 6H), 2.75 (s, 3H);

MS m/z (ESI): 580 [M+H]$^+$.

Example 53: Preparation of N-(5-((4-(5,6-dimethoxy-3-methyl-1H-indazol-1-yl)pyrimidin-2-yl)amino)-2-((2-(dimethylamino)ethyl)(methyl)amino)-4-methoxyphenyl)acrylamide

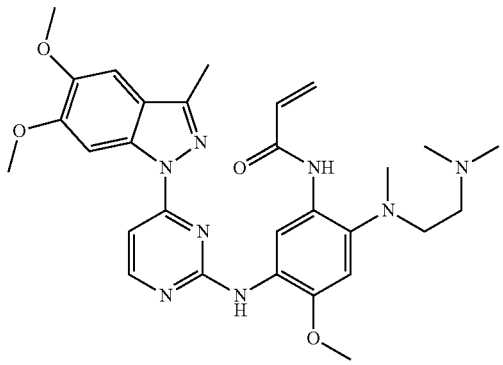

Step 1: Preparation of 1-(4,5-dimethoxy-2-nitrophenyl)ethan-1-one

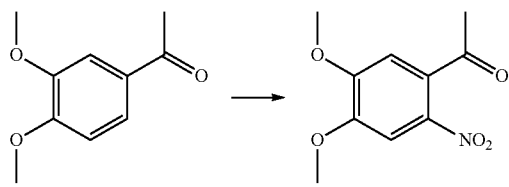 [SMILES: COc1ccc(C(C)=O)cc1OC ; COc1cc(C(C)=O)c([N+](=O)[O-])cc1OC]

1-(3,4-dimethoxyphenyl)ethan-1-one (10 g) was added to acetic anhydride (30 mL). After the solution was cooled to 0° C., a mixture of nitric acid (200 mL) and acetic anhydride (10 mL) were added dropwise. Upon completion of the addition, the reaction solution was stirred for 4 hours, poured into 1 L of ice water, filtered, washed with water and dried to obtain 1-(4,5-dimethoxy-2-nitrophenyl)ethan-1-one (8 g, 67%).

Step 2: Preparation of 1-(4,5-dimethoxy-2-aminophenyl)ethan-1-one

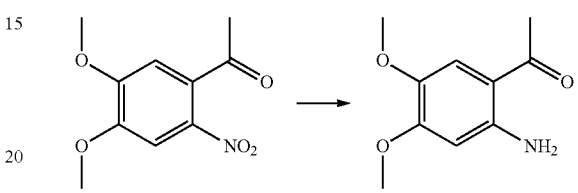

1-(4,5-dimethoxy-2-nitrophenyl)ethan-1-one (8 g) and iron powder (20 g) were added to a mixture of HOAc (70 mL), water (100 mL) and EtOAc (20 mL). The reaction was carried out at 100° C. for 2 hours, and the pH was adjusted to 7 with sodium bicarbonate aqueous solution. The reaction solution was added with 400 mL of ethyl acetate, filtered, and concentrated. The resulting residue was recrystallized from ethyl acetate-petroleum ether to obtain 1-(4,5-dimethoxy-2-aminophenyl)ethan-1-one (1.37 g, 30%).

Step 3: Preparation of 1-(2-amino-dimethoxyphenyl)ethan-1-one oxime

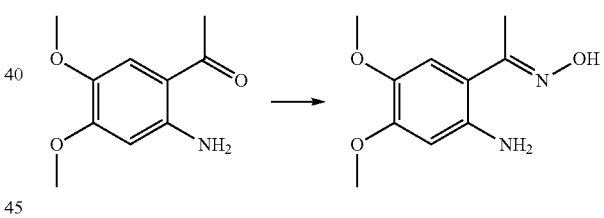

1-(4,5-dimethoxy-2-aminophenyl)ethan-1-one (800 mg, 4.1 mmol), hydroxylamine hydrochloride (880 mg, 12.3 mmol) and NaOH (1.31 g, 32.8 mmol) were added to 6 mL of ethanol aqueous solution (85%). The reaction solution was heated at 60° C. for 1 hour, concentrated, extracted with ethyl acetate and recrystallized from ethyl acetate-petroleum ether to obtain 1-(2-amino-dimethoxyphenyl)ethan-1-one oxime (500 mg, 58%).

Step 4: Preparation of 5,6-dimethoxy-3-methyl-1H-indazole

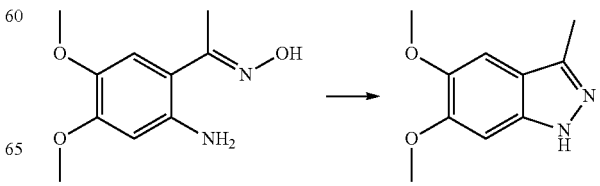

1-(2-amino-dimethoxyphenyl)ethan-1-one oxime (450 mg, 2.14 mmol) and triethylamine (432 mg, 4.28 mmol) were added in DCM (15 mL), and 0.2 mL of methanesulfonyl chloride were added dropwise at 0° C. The mixture was stirred at room temperature for one hour, concentrated, and purified by column chromatography to obtain 5,6-dimethoxy-3-methyl-1H-indazole (200 mg, 37%).

Steps 5 to 10: Preparation of N-(5-((4-(5,6-dimethoxy-3-methyl-1H-indazol-1-yl)pyrimidin-2-yl)amino)-2-((2-(dimethylamino)ethyl)(methyl)amino)-4-methoxyphenyl)acrylamide

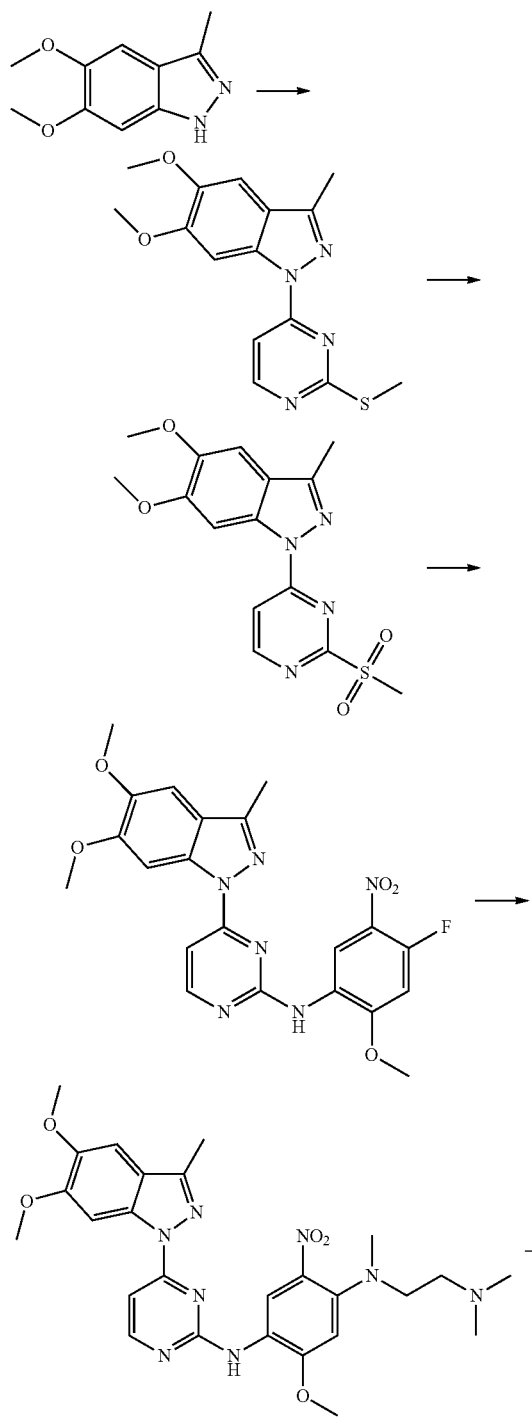

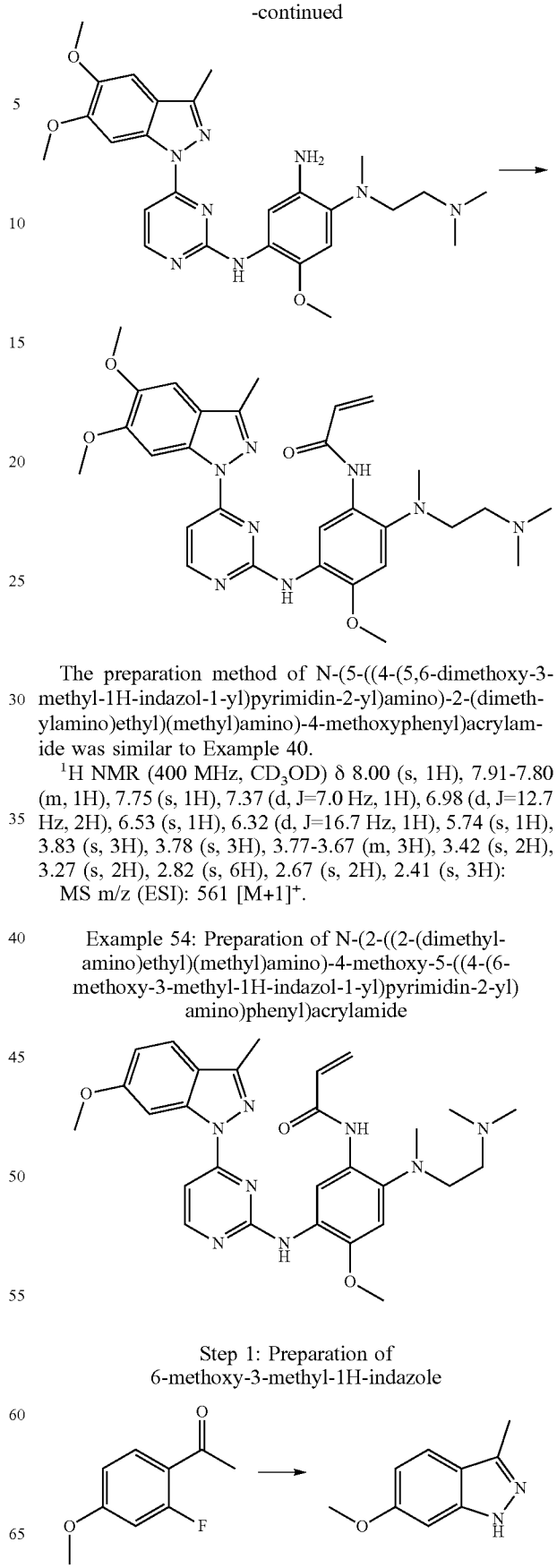

The preparation method of N-(5-((4-(5,6-dimethoxy-3-methyl-1H-indazol-1-yl)pyrimidin-2-yl)amino)-2-(dimethylamino)ethyl)(methyl)amino)-4-methoxyphenyl)acrylamide was similar to Example 40.

$^1$H NMR (400 MHz, CD$_3$OD) δ 8.00 (s, 1H), 7.91-7.80 (m, 1H), 7.75 (s, 1H), 7.37 (d, J=7.0 Hz, 1H), 6.98 (d, J=12.7 Hz, 2H), 6.53 (s, 1H), 6.32 (d, J=16.7 Hz, 1H), 5.74 (s, 1H), 3.83 (s, 3H), 3.78 (s, 3H), 3.77-3.67 (m, 3H), 3.42 (s, 2H), 3.27 (s, 2H), 2.82 (s, 6H), 2.67 (s, 2H), 2.41 (s, 3H):
MS m/z (ESI): 561 [M+1]$^+$.

Example 54: Preparation of N-(2-((2-(dimethylamino)ethyl)(methyl)amino)-4-methoxy-5-((4-(6-methoxy-3-methyl-1H-indazol-1-yl)pyrimidin-2-yl)amino)phenyl)acrylamide Step 1: Preparation of 6-methoxy-3-methyl-1H-indazole 1-(2-fluoro-4-methoxyphenyl)ethan-1-one (2 g, 11.9 mmol) was dissolved in 5 mL of a mixture of hydrazine hydrate (85%) and NMP (15 mL). The mixture was stirred at 120° C. for 24 hours and purified by column chromatography to obtain 6-methoxy-3-methyl-1H-indazole (1.5 g, 78%).

Steps 2 to 7: Preparation of N-(2-((2-(dimethylamino)ethyl)(methyl)amino)-4-methoxy-5-((4-(6-methoxy-3-methyl-1H-indazol-1-yl)pyrimidin-2-yl)amino)phenyl)acrylamide

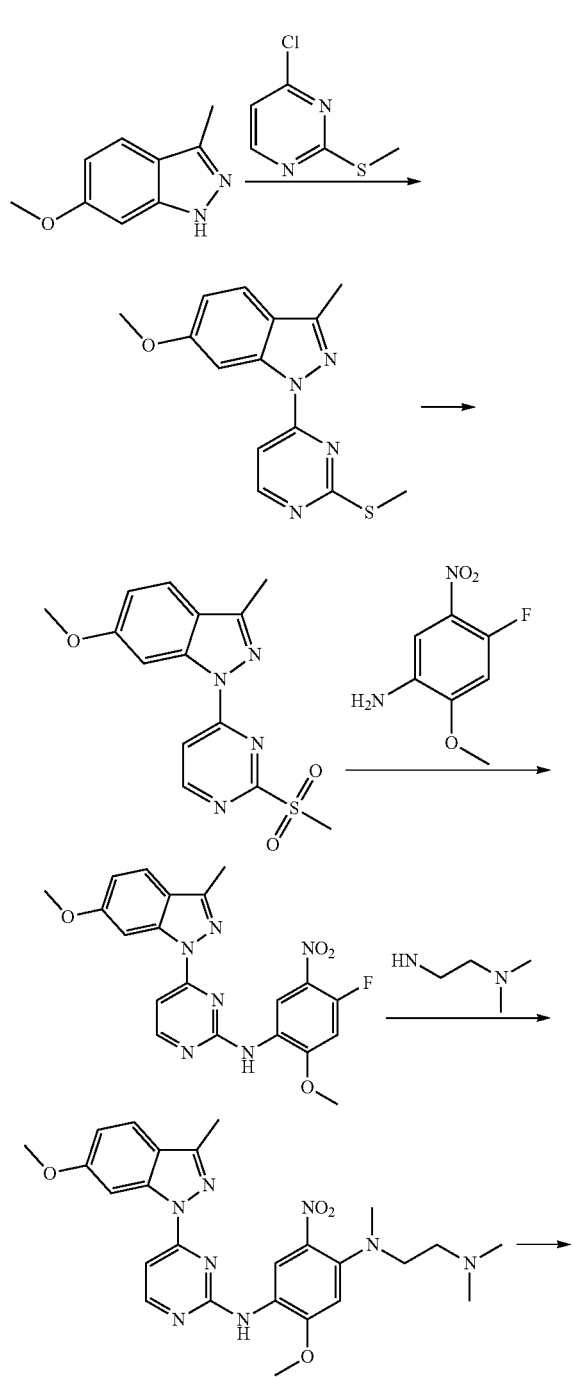

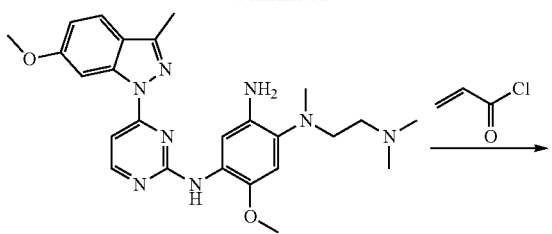

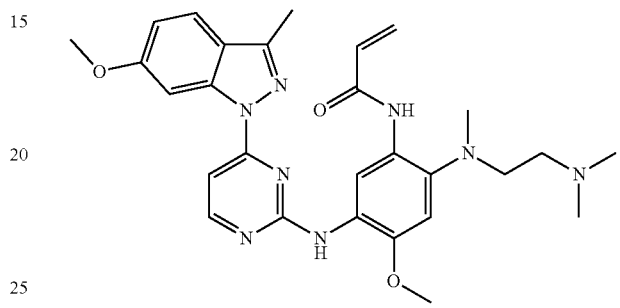

The preparation method of N-(2-((2-(dimethylamino)ethyl)(methyl)amino)-4-methoxy-5-((4-(6-methoxy-3-methyl-1H-indazol-1-yl)pyrimidin-2-yl)amino)phenyl)acrylamide was similar to Example 47.

$^1$H NMR (400 MHz, CD3OD) δ 8.25-8.13 (m, 1H), 8.11-8.00 (m, 1H), 7.81 (s, 1H), 7.70 (d, J=8.7 Hz, 1H), 7.59 (d, J=7.0 Hz, 1H), 7.09 (s, 2H), 6.69-6.56 (m, 1H), 6.45 (s, 1H), 5.86 (s, 1H), 3.95 (s, 3H), 3.87 (s, 3H), 3.56 (s, 2H), 3.38 (s, 2H), 2.92 (s, 6H), 2.81 (s, 3H), 2.58 (s, 3H);

MS m/z (ESI): 531 [M+1]$^+$.

Example 55: Preparation of N-(5-((4-(6-cyano-3-methyl-1H-indazol-1-yl)pyrimidin-2-yl)amino)-2-((2-(dimethylamino)ethyl)(methyl)amino)-4-methoxyphenyl)acrylamide

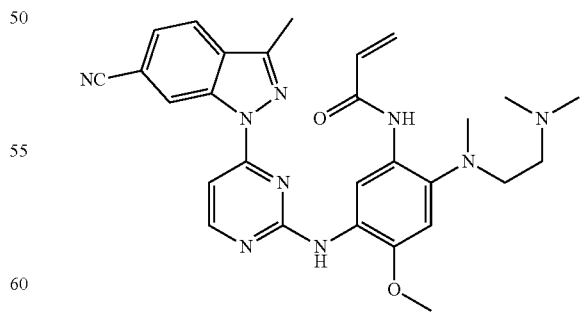

The preparation method of N-(5-((4-(6-cyano-3-methyl-1H-indazol-1-yl)pyrimidin-2-yl)amino)-2-((2-(dimethylamino)ethyl)(methyl)amino)-4-methoxyphenyl)acrylamide was similar to Example 40.

Example 56: Preparation of N-(5-((4-(5-cyano-3-methyl-1H-indazol-1-yl)pyrimidin-2-yl)amino)-2-((2-(dimethylamino)ethyl)(methyl)amino)-4-methoxyphenyl)acrylamide

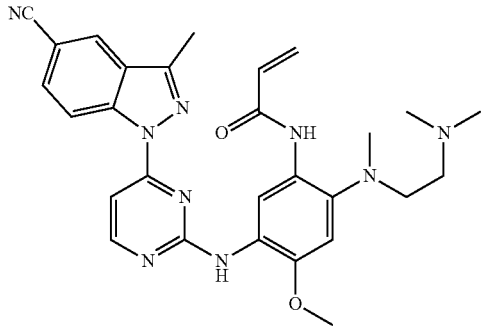 [SMILES: C=CC(=O)Nc1cc(Nc2nccc(-n3nc(C)c4cc(C#N)ccc43)n2)c(OC)cc1N(C)CCN(C)C]

The preparation method of N-(5-((4-(5-cyano-3-methyl-1H-indazol-1-yl)pyrimidin-2-yl)amino)-2-((2-(dimethylamino)ethyl)(methyl)amino)-4-methoxyphenyl)acrylamide was similar to Example 40.
$^1$H NMR (400 MHz, CD$_3$OD) δ 8.67-8.55 (m, 1H), 8.36 (d, J=6.4 Hz, 1H), 8.28 (s, 1H), 7.94 (s, 1H), 7.73 (d, J=8.7 Hz, 1H), 7.51 (d, J=6.5 Hz, 1H), 7.08 (s, 1H), 6.55 (dd, J=7.9, 5.9 Hz, 2H), 5.91 (d, J=11.8 Hz, 1H), 4.00 (s, 3H), 3.57 (s, 2H), 3.38 (d, J=5.9 Hz, 2H), 2.95 (s, 6H), 2.80 (s, 3H), 2.64 (s, 3H);
MS m/z (ESI): 526 [M+H]$^+$.

Example 57: Preparation of N-(5-((4-(5,6-difluoro-3-methyl-1H-indazol-1-yl)pyrimidin-2-yl)amino)-2-((2-(dimethylamino)ethyl)(methyl)amino)-4-methoxyphenyl)acrylamide

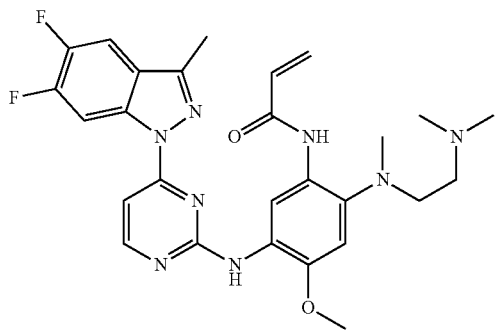 [SMILES: C=CC(=O)Nc1cc(Nc2nccc(-n3nc(C)c4cc(F)c(F)cc43)n2)c(OC)cc1N(C)CCN(C)C]

The preparation method of N-(5-((4-(5,6-difluoro-3-methyl-1H-indazol-1-yl)pyrimidin-2-yl)amino)-2-((2-(dimethylamino)ethyl)(methyl)amino)-4-methoxyphenyl)acrylamide was similar to Example 40.

Example 58: Preparation of N-(5-((4-(5,7-difluoro-3-methyl-1H-indazol-1-yl)pyrimidin-2-yl)amino)-2-((2-(dimethylamino)ethyl)(methyl)amino)-4-methoxyphenyl)acrylamide

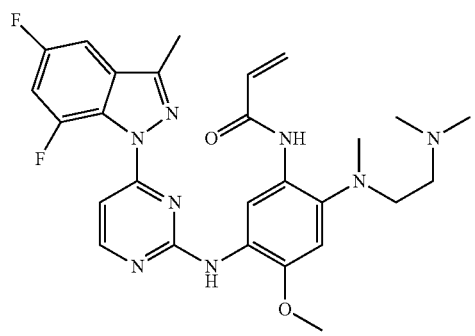 [SMILES: C=CC(=O)Nc1cc(Nc2nccc(-n3nc(C)c4cc(F)cc(F)c43)n2)c(OC)cc1N(C)CCN(C)C]

The preparation method of N-(5-((4-(5,7-difluoro-3-methyl-1H-indazol-1-yl)pyrimidin-2-yl)amino)-2-((2-(dimethylamino)ethyl)(methyl)amino)-4-methoxyphenyl)acrylamide was similar to Example 40.

Example 59: Preparation of N-(2-((2-(dimethylamino)ethyl)(methyl)amino)-4-methoxy-5-((4-(5-methoxy-1H-benzo[d]imidazol-1-yl)pyrimidin-2-yl)amino)phenyl)acrylamide

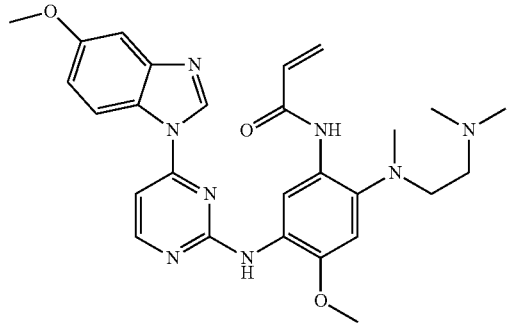

Step 1: Preparation of 2-chloro-N-(4-methoxy-2-nitrophenyl)pyrimidin-4-amine

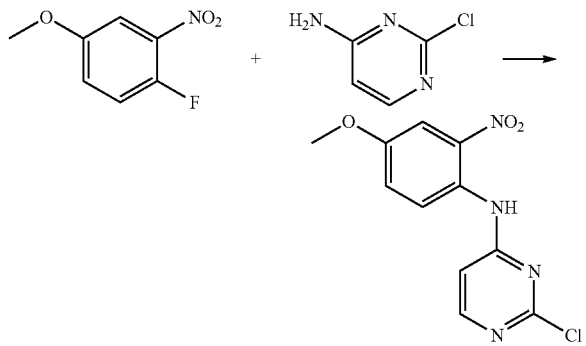

2-chloropyrimidin-4-amine (518.2 mg, 4 mmol) and DMF (10 mL) was added in a 100 mL round-bottom flask. Under the protection of N$_2$, the mixture was cooled to 0° C. with an ice-salt bath, and then NaH (295 mg, 8 mmol) was added. After stirring for 30 minutes, 1-fluoro-4-methoxy-2-nitrobenzene (684.5 mg, 4 mmol) was added, and the reaction solution was warmed up slowly to room temperature and stirred for 1 h. In an ice-salt bath, 30 mL of water were added, and a solid was precipitated. The solid was filtered, and the filter cake was dissolved in dichloromethane. The solution was dried over anhydrous sodium sulfate and concentrated to obtain 2-chloro-N-(4-methoxy-2-nitrophenyl)pyrimidin-4-amine (1 g, 89%).
MS m/z (ESI): 281.0 [M+H]$^+$.

Step 2: Preparation of N1-(2-chloropyrimidin-4-yl)-4-methoxybenzene-1,2-diamine

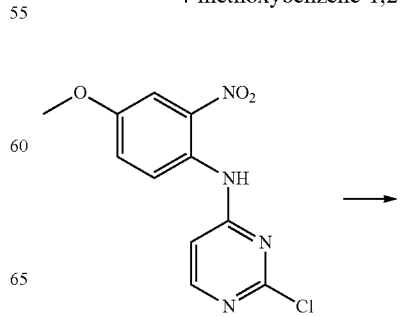

-continued

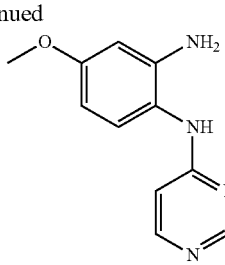

2-chloro-N-(4-methoxy-2-nitrophenyl)pyrimidin-4-amine, ethanol (15 mL) and water (5 mL) were added in a 100 mL round-bottom flask, followed by addition of iron powder (1.37 g, 24.5 mmol) and ammonium chloride (131.5 mg, 2.5 mmol). The reaction was carried out at 80° C. for 3 h before the mixture was filtered and concentrated. The resulting residue was dissolved in ethyl acetate (50 mL), and 30 mL of water was added, then two phases were separated. The organic phase was dried over anhydrous sodium sulphate, filtered and concentrated to obtain N1-(2-chloropyrimidin-4-yl)-4-methoxybenzene-1,2-diamine (676.9 mg, 77%).

MS m/z (ESI): 251.1 [M+H]$^+$.

Step 3: Preparation of 1-(2-chloropyrimidin-4-yl)-5-methoxy-1H-benzo[d]imidazole

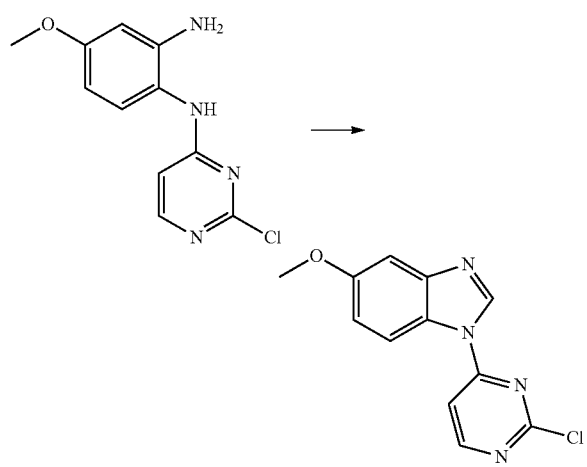

N1-(2-chloropyrimidin-4-yl)-4-methoxybenzene-1,2-diamine (300 mg, 1.2 mmol), ethanol (10 mL), trimethyl orthoformate (1.0 g, 9.6 mmol) and p-toluenesulfonic acid (20 mg, 0.12 mmol) were added in a 100 mL round-bottom flask, and the reaction was carried out at 80° C. for 1 h. After cooling to room temperature, the reaction solution was concentrated, and the resulting residue was subjected to column chromatography to obtain 1-(2-chloropyrimidin-4-yl)-5-methoxy-1H-benzo[d]imidazole (195 mg, 62%).

MS m/z (ESI): 261.1 [M+H]$^+$.

Step 4: Preparation of N-(4-fluoro-2-methoxy-5-nitrophenyl)-4-(5-methoxy-1H-benzo[d]imidazol-1-yl)pyrimidin-2-amine

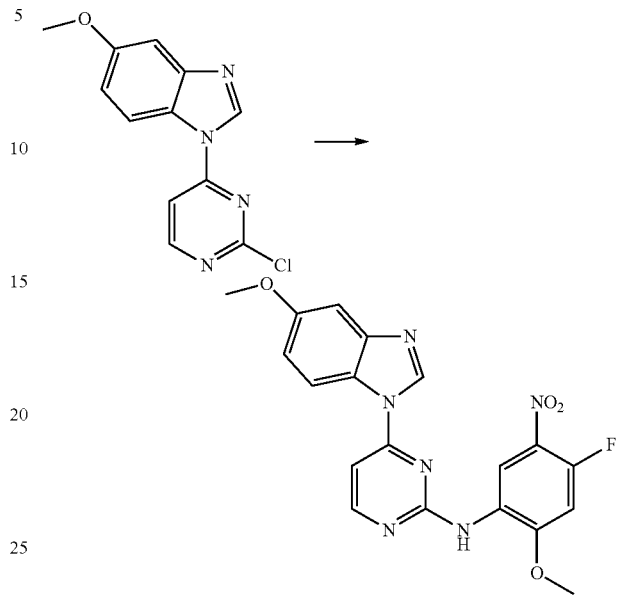

1-(2-chloropyrimidin-4-yl)-5-methoxy-1H-benzo[d]imidazole (195 mg, 0.75 mmol), 4-fluoro-2-methoxy-5-nitroaniline (140 mg, 0.75 mmol), p-toluenesulfonic (129 mg, 0.75 mmol) and 2-pentanol (5 mL) were added in a 100 mL round-bottomed flask, and the reaction was carried out at 100° C. for 4 h. After cooling to room temperature, the reaction solution was concentrated, and the residue was subjected to column chromatography to obtain N-(4-fluoro-2-methoxy-5-nitrophenyl)-4-(5-methoxy-1H-benzo[d]imidazol-1-yl)pyrimidin-2-amine (62 mg, 20%).

MS m/z (ESI): 411.1 [M+H]$^+$.

Step 5: Preparation of N1-(2-(dimethylamino)ethyl)-5-methoxy-N4-(4-(5-methoxy-1H-benzo[d]imidazol-1-yl)pyrimidin-2-yl)-N1-methyl-2-nitrobenzene-1,4-diamine

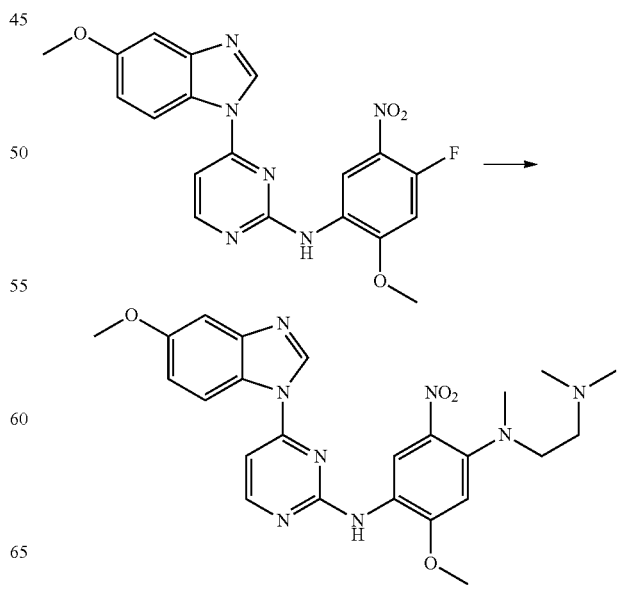

N-(4-fluoro-2-methoxy-5-nitrophenyl)-4-(5-methoxy-1H-benzo[d]imidazol-1-yl)pyrimidin-2-amine (62 mg, 0.15 mmol), N1,N1,N2,N2-tetramethylethane-1,2-diamine (30.6 mg, 0.3 mmol), DIPEA (58 mg, 0.45 mmol) and DMF (5 mL) were added in a 100 mL round-bottom flask, and the reaction was carried out at 80° C. for 1 h. After cooling to room temperature, the reaction solution was concentrated. The resulting residue was subjected to column chromatography to obtain N1-(2-(dimethylamino)ethyl)-5-methoxy-N4-(4-(5-methoxy-1H-benzo[d]imidazol-1-yl)pyrimidin-2-yl)-N1-methyl-2-nitrobenzene-1,4-diamine (40 mg, 54%).

MS m/z (ESI): 493.3 [M+H]$^+$.

Step 6: Preparation of N1-(2-(dimethylamino)ethyl)-5-methoxy-N4-(4-(5-methoxy-1H-benzo[d]imidazol-1-yl)pyrimidin-2-yl)-N1-methylbenzene-1,2,4-triamine

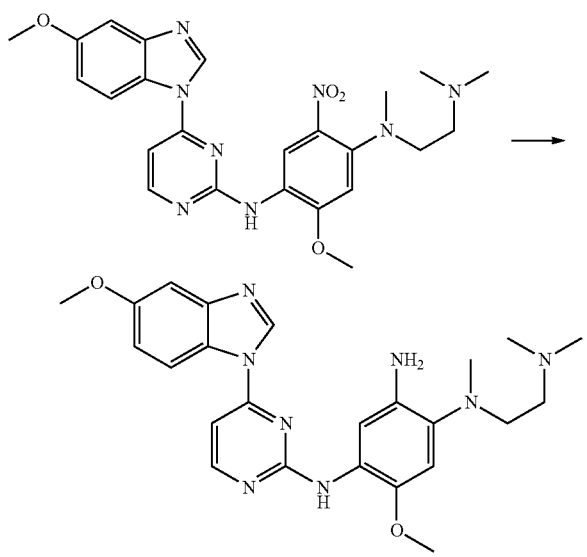

N1-(2-(dimethylamino)ethyl)-5-methoxy-N4-(4-(5-methoxy-1H-benzo[d]imidazol-1-yl)pyrimidin-2-yl)-N1-methyl-2-nitrobenzene-1,4-diamine (39.4 mg, 0.08 mmol) and methanol (20 mL) were added in a 100 mL round-bottom flask. In a hydrogen atmosphere, the reaction solution was reacted at room temperature for 30 minutes. Then, the reaction solution was filtered and concentrated to obtain N1-(2-(dimethylamino)ethyl)-5-methoxy-N4-(4-(5-methoxy-1H-benzo[d]imidazol-1-yl)pyrimidin-2-yl)-N1-methylbenzene-1,2,4-triamine (32 mg, 85%).

MS m/z (ESI): 463.1 [M+H]$^+$.

Step 7: Preparation of N-(2-((2-(dimethylamino)ethyl)(methyl)amino)-4-methoxy-5-((4-(5-methoxy-1H-benzo[d]imidazol-1-yl)pyrimidin-2-yl-amino)phenyl)acrylamide

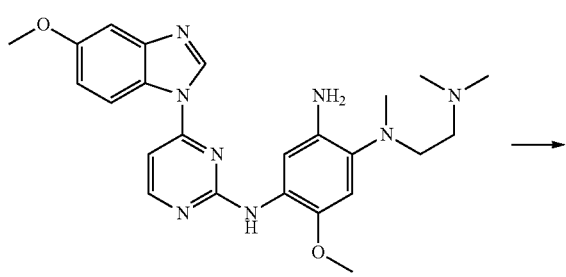

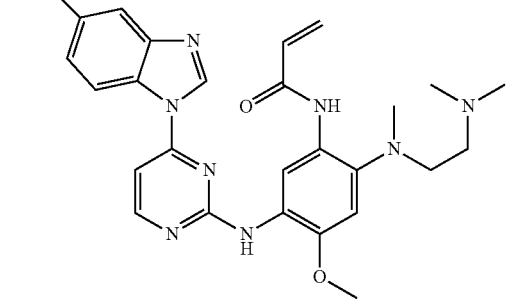

N1-(2-(dimethylamino)ethyl)-5-methoxy-N4-(4-(5-methoxy-1H-benzo[d]imidazol-1-yl)pyrimidin-2-yl)-N1-methylbenzene-1,2,4-triamine (32 mg, 0.07 mmol) and anhydrous tetrahydrofuran (20 mL) were added in a 100 mL round-bottom flask. Under the protection of N$_2$, the reaction solution was cooled to 0° C. in an ice salt bath, followed by addition of DIPEA (18 mg, 0.14 mmol) and acryloyl chloride (0.2 mL, 0.1 mmol). The reaction was carried out at 0° C. for 30 minutes and terminated by the addition of 0.5 mL of water, and then the reaction solution was concentrated. The resulting residue was subjected to column chromatography to obtain N-(2-((2-(dimethylamino)ethyl)(methyl)amino)-4-methoxy-5-((4-(5-methoxy-1H-benzo[d]imidazol-1-yl)pyrimidin-2-yl)amino)phenyl)acrylamide (10 mg, 28%).

$^1$H NMR (400 MHz, CD$_3$OD) δ 9.36 (s, 1H), 8.57 (d, J=5.4 Hz, 1H), 8.26 (s, 2H), 7.39-7.24 (m, 2H), 7.12-6.97 (m, 2H), 6.52 (qd, J=17.0, 5.8 Hz, 2H), 5.86 (dd, J=9.7, 1.8 Hz, 1H), 3.99 (s, 3H), 3.89 (s, 3H), 3.51 (d, J=5.5 Hz, 2H), 3.33 (s, 2H), 2.90 (d, J=5.1 Hz, 6H), 2.75 (s, 3H);

MS m/z (ESI): 517.2 [M+H]$^+$.

Example 60: Preparation of N-(2-((2-(dimethylamino)ethyl)(methyl)amino)-4-methoxy-5-((4-(6-methoxy-1H-benzo[d]imidazol-1-yl)pyrimidin-2-yl)amino)phenyl)acrylamide

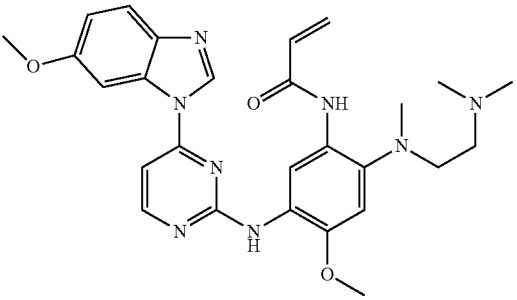

The preparation method of N-(2-((2-(dimethylamino)ethyl)(methyl)amino)-4-methoxy-5-((4-(6-methoxy-1H-benzo[d]imidazol-1-yl)pyrimidin-2-yl)amino)phenyl)acrylamide was similar to Example 59.

$^1$H NMR (400 MHz, CD$_3$OD) δ 9.21 (s, 1H), 8.58 (d, J=5.6 Hz, 1H), 8.34 (s, 1H), 7.86 (s, 1H), 7.69 (d, J=8.9 Hz, 1H), 7.30 (d, J=5.6 Hz, 1H), 7.11 (dd, J=8.7, 2.1 Hz, 1H), 7.00 (s, 1H), 6.57 (dd, J=16.9, 10.0 Hz, 1H), 6.44 (dd, J=16.9, 1.6 Hz, 1H), 5.84 (dd, J=10.1, 1.6 Hz, 1H), 3.98 (s, 3H), 3.86 (s, 3H), 3.50 (t, J=5.7 Hz, 2H), 3.32 (s, 2H), 2.89 (s, 6H), 2.74 (s, 3H);

MS m/z (ESI): 517.3 [M+H]$^+$.

Example 61: Preparation of N-(5-((4-(5-cyano-1H-benzo[d]imidazol-1-yl)pyrimidin-2-yl)amino)-2-((2-(dimethylamino)ethyl)(methyl)amino-4-methoxy-phenyl)acrylamide

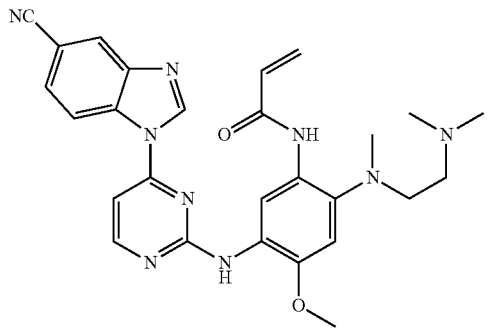 [SMILES: C=CC(=O)Nc1cc(Nc2nccc(-n3cnc4cc(C#N)ccc43)n2)c(OC)cc1N(C)CCN(C)C]

The preparation method of N-(5-((4-(5-cyano-1H-benzo[d]imidazol-1-yl)pyrimidin-2-yl)amino)-2-((2-(dimethylamino)ethyl)(methyl)amino)-4-methoxyphenyl)acrylamide was similar to Example 59.

Example 62: Preparation of N-(5-((4-(6-cyano-1H-benzo[d]imidazol-1-yl)pyrimidin-2-yl)amino)-2-((2-(dimethylamino)ethyl)(methyl)amino)-4-methoxy-phenyl)acrylamide

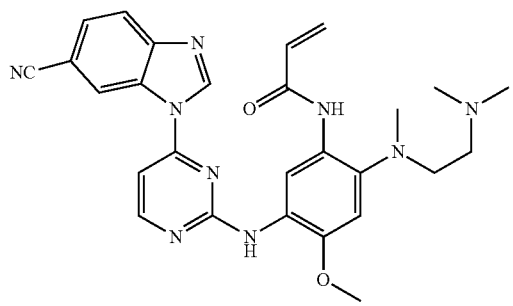 [SMILES: C=CC(=O)Nc1cc(Nc2nccc(-n3cnc4ccc(C#N)cc43)n2)c(OC)cc1N(C)CCN(C)C]

The preparation method of N-(5-((4-(6-cyano-1H-benzo[d]imidazol-1-yl)pyrimidin-2-yl)amino)-2-((2-(dimethylamino)ethyl)(methyl)amino)-4-methoxyphenyl)acrylamide was similar to Example 59.

$^1$H NMR (400 MHz, CD$_3$OD) δ 9.19 (s, 1H), 8.78 (s, 1H), 8.52 (d, J=5.7 Hz, 1H), 8.24 (s, 1H), 7.86 (d, J=8.3 Hz, 1H), 7.66 (dd, J=8.3, 1.2 Hz, 1H), 7.31 (d, J=5.8 Hz, 1H), 7.07 (s, 1H), 6.59 (dd, J=16.9, 10.2 Hz, 1H), 6.35 (d, J=16.8 Hz, 1H), 5.81 (dd, J=10.3, 1.2 Hz, 1H), 3.97 (s, 3H), 3.53 (t, J=5.8 Hz, 2H), 3.36 (t, J=5.8 Hz, 2H), 2.92 (s, 6H), 2.77 (s, 3H):

MS m/z (ESI): 512.2 [M+H]$^+$.

Example 63: Preparation of N-(5-((5-chloro-4-(5-methoxy-1H-benzo[d]imidazol-1-yl)pyrimidin-2-yl)amino)-2-((2-(dimethylamino)ethyl)(methyl)amino)-4-methoxyphenyl)acrylamide

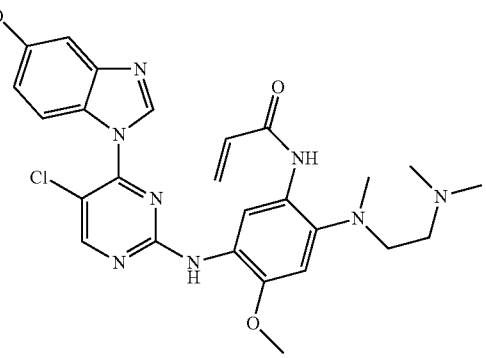

The preparation method of N-(5-((5-chloro-4-(5-methoxy-1H-benzo[d]imidazol-1-yl)pyrimidin-2-yl)amino)-2-((2-(dimethylamino)ethyl)(methyl)amino)-4-methoxyphenyl)acrylamide was similar to Example 59.

$^1$H NMR (400 MHz, CD$_3$OD) δ 9.25 (s, 1H), 8.74 (s, 1H), 8.25 (s, 1H), 7.85 (d, J=8.2 Hz, 1H), 7.33 (s, 1H), 7.08 (d, J=9.0 Hz, 1H), 6.98 (s, 1H), 6.47-6.41 (m, 2H), 5.85 (dd, J=7.8, 3.9 Hz, 1H), 4.00 (s, 3H), 3.91 (s, 3H), 3.49 (t, J=5.7 Hz, 2H), 3.28 (t, J=5.6 Hz, 2H), 2.86 (s, 6H), 2.71 (s, 3H); MS m/z (ESI): 551.2 [M+H]$^+$.

Example 64: Preparation of N-(5-((5-chloro-4-(6-methoxy-1H-benzo[d]imidazol-1-yl)pyrimidin-2-yl)amino)-2-((2-(dimethylamino)ethyl)(methyl)amino)-4-methoxyphenyl)acrylamide

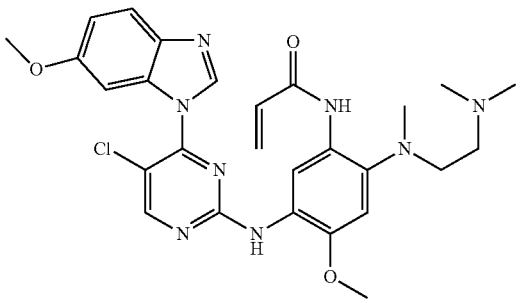

The preparation method of N-(5-((5-chloro-4-(6-methoxy-1H-benzo[d]imidazol-1-yl)pyrimidin-2-yl)amino)-2-((2-(dimethylamino)ethyl)(methyl)amino)-4-methoxyphenyl)acrylamide was similar to Example 59.

Example 65: Preparation of N-(5-((5-chloro-4-(5-cyano-1H-benzo[d]imidazol-1-yl)pyrimidin-2-yl)amino)-2-((2-(dimethylamino)ethyl)(methyl)amino)-4-methoxyphenyl)acrylamide

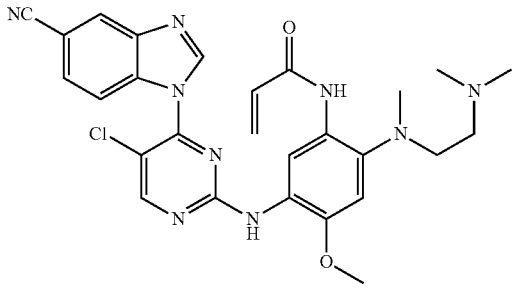

The preparation method of N-(5-((5-chloro-4-(5-cyano-1H-benzo[d]imidazol-1-yl)pyrimidin-2-yl)amino)-2-((2-(dimethylamino)ethyl)(methyl)amino)-4-methoxyphenyl)acrylamide was similar to Example 59.

Example 66: Preparation of N-(5-((5-chloro-4-(6-cyano-1H-benzo[d]imidazol-1-yl)pyrimidin-2-yl)amino)-2-((2-(dimethylamino)ethyl)(methyl)amino)-4-methoxyphenyl)acrylamide

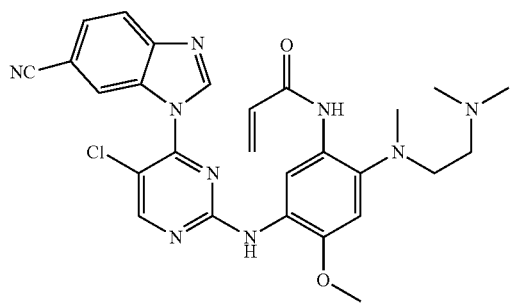 [SMILES: C=CC(=O)Nc1cc(Nc2ncc(Cl)c(-n3cnc4ccc(C#N)cc43)n2)c(OC)cc1N(C)CCN(C)C]

The preparation method of N-(5-((5-chloro-4-(6-cyano-1H-benzo[d]imidazol-1-yl)pyrimidin-2-yl)amino)-2-((2-(dimethylamino)ethyl)(methyl)amino)-4-methoxyphenyl)acrylamide was similar to Example 59.

Example 67: Preparation of N-(2-((2-(dimethylamino)ethyl)(methyl)amino)-4-methoxy-5-((4-(5-methoxy-1H-benzo[d]imidazol-1-yl)-5-(trifluoromethyl)pyrimidin-2-yl)amino)phenyl)acrylamide

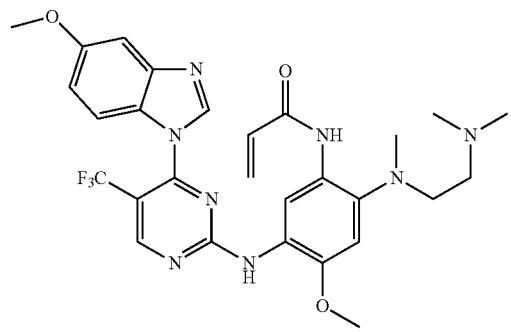

The preparation method of N-(2-((2-(dimethylamino)ethyl)(methyl)amino)-4-methoxy-5-((4-(5-methoxy-1H-benzo[d]imidazol-1-yl)-5-(trifluoromethyl)pyrimidin-2-yl)amino)phenyl)acrylamide was similar to Example 59.

$^1$H NMR (400 MHz, CD$_3$OD) δ 8.98 (s, 1H), 8.87 (s, 1H), 8.15 (s, 1H), 7.73 (d, J=8.7 Hz, 1H), 7.32 (s, 1H), 7.10 (s, 1H), 6.98 (s, 1H), 6.43 (s, 2H), 5.84 (d, J=11.1 Hz, 1H), 3.98 (s, 3H), 3.91 (s, 3H), 3.49 (t, J=5.3 Hz, 2H), 3.29 (d, J=5.4 Hz, 2H), 2.85 (s, 6H), 2.71 (s, 3H);

MS m/z (ESI): 585.3 [M+H]$^+$.

Example 68: Preparation of N-(2-((2-(dimethylamino)ethyl)(methyl)amino)-4-methoxy-5-((4-(6-methoxy-1H-benzo[d]imidazol-1-yl)-5-(trifluoromethyl)pyrimidin-2-yl)amino)phenyl)acrylamide

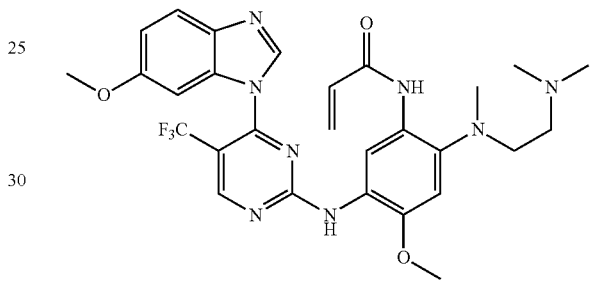

The preparation method of N-(2-((2-(dimethylamino)ethyl)(methyl)amino)-4-methoxy-5-((4-(6-methoxy-1H-benzo[d]imidazol-1-yl)-5-(trifluoromethyl)pyrimidin-2-yl)amino)phenyl)acrylamide was similar to Example 59.

Example 69: Preparation of N-(5-((4-(5-cyano-1H-benzo[d]imidazol-1-yl)-5-(trifluoromethyl)pyrimidin-2-yl)amino)-2-((2-(dimethylamino)ethyl)(methyl)amino)-4-methoxyphenyl)acrylamide

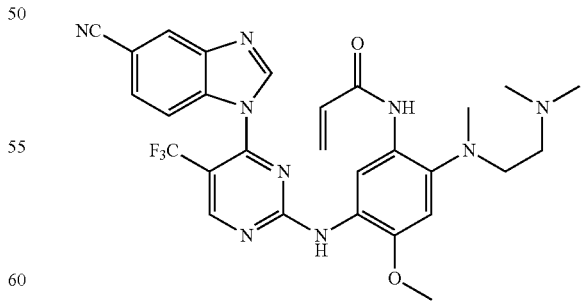

The preparation method of N-(5-((4-(5-cyano-1H-benzo[d]imidazol-1-yl)-5-(trifluoromethyl)pyrimidin-2-yl)amino)-2-((2-(dimethylamino)ethyl)(methyl)amino)-4-methoxyphenyl)acrylamide was similar to Example 59.

Example 70: Preparation of N-(5-((4-(6-cyano-1H-benzo[d]imidazol-1-yl)-5-(trifluoromethyl)pyrimidin-2-yl)amino)-2-((2-(dimethylamino)ethyl)(methyl)amino)-4-methoxyphenyl)acrylamide

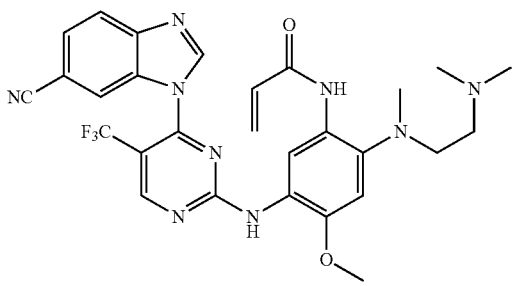 [SMILES: C=CC(=O)Nc1cc(Nc2ncc(C(F)(F)F)c(-n3cnc4ccc(C#N)cc43)n2)c(OC)cc1N(C)CCN(C)C]

The preparation method of N-(5-((4-(6-cyano-1H-benzo[d]imidazol-1-yl)-5-(trifluoromethyl)pyrimidin-2-yl)amino)-2-((2-(dimethylamino)ethyl)(methyl)amino)-4-methoxyphenyl)acrylamide was similar to Example 59.

Example 71: Preparation of N-(2-((2-(dimethylamino)ethyl)(methyl)amino)-4-methoxy-5-((4-(5-methoxy-2-methyl-1H-benzo[d]imidazol-1-yl)pyrimidin-2-yl)amino)phenyl)acrylamide

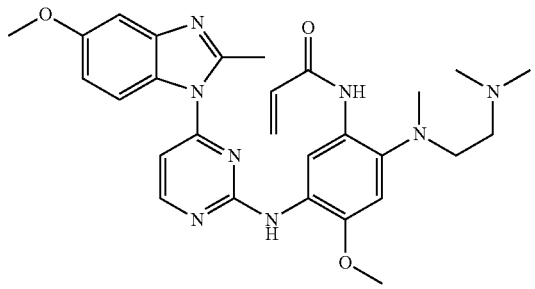

The preparation method of N-(2-((2-(dimethylamino)ethyl)(methyl)amino)-4-methoxy-5-((4-(5-methoxy-2-methyl-1H-benzo[d]imidazol-1-yl)pyrimidin-2-yl)amino)phenyl)acrylamide was similar to Example 59.

Example 72: Preparation of N-(2-((2-(dimethylamino)ethyl)(methyl)amino)-4-methoxy-5-((4-(6-methoxy-2-methyl-1H-benzo[d]imidazol-1-yl)pyrimidin-2-yl)amino)phenyl)acrylamide

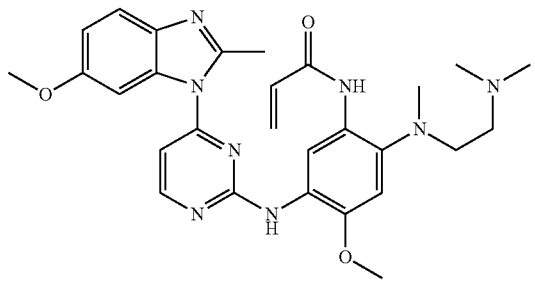

The preparation method of N-(2-((2-(dimethylamino)ethyl)(methyl)amino)-4-methoxy-5-((4-(6-methoxy-2-methyl-1H-benzo[d]imidazol-1-yl)pyrimidin-2-yl)amino)phenyl)acrylamide was similar to Example 59.

Example 73: Preparation of N-(5-((4-(5-cyano-2-methyl-1H-benzo[d]imidazol-1-yl)pyrimidin-2-yl)amino)-2-((2-(dimethylamino)ethyl)(methyl)amino)-4-methoxyphenyl)acrylamide

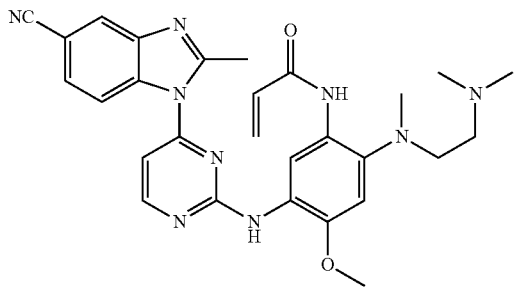 [SMILES: C=CC(=O)Nc1cc(Nc2nccc(-n3c(C)nc4cc(C#N)ccc43)n2)c(OC)cc1N(C)CCN(C)C]

The preparation method of N-(5-((4-(5-cyano-2-methyl-1H-benzo[d]imidazol-1-yl)pyrimidin-2-yl)amino)-2-((2-(dimethylamino)ethyl)(methyl)amino)-4-methoxyphenyl)acrylamide was similar to Example 59.

Example 74: Preparation of N-(5-((4-(6-cyano-2-methyl-1H-benzo[d]imidazol-1-yl)pyrimidin-2-yl)amino)-2-((2-(dimethylamino)ethyl)(methyl)amino)-4-methoxyphenyl)acrylamide

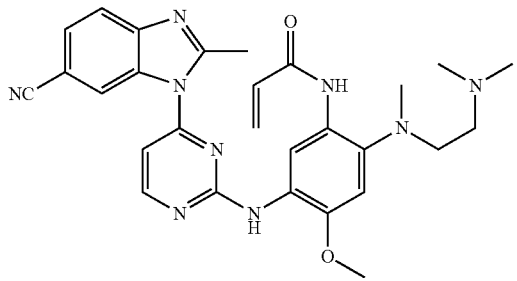 [SMILES: C=CC(=O)Nc1cc(Nc2nccc(-n3c(C)nc4ccc(C#N)cc43)n2)c(OC)cc1N(C)CCN(C)C]

The preparation method of N-(5-((4-(6-cyano-2-methyl-1H-benzo[d]imidazol-1-yl)pyrimidin-2-yl)amino)-2-((2-(dimethylamino)ethyl)(methyl)amino)-4-methoxyphenyl)acrylamide was similar to Example 59.

Example 75: Preparation of N-(2-((2-(dimethylamino)ethyl)(methyl)amino)-4-methoxy-5-((4-(5-methoxy-2-methyl-1H-benzo[d]imidazol-1-yl)-5-(trifluoromethyl)pyrimidin-2-yl)amino)phenyl)acrylamide

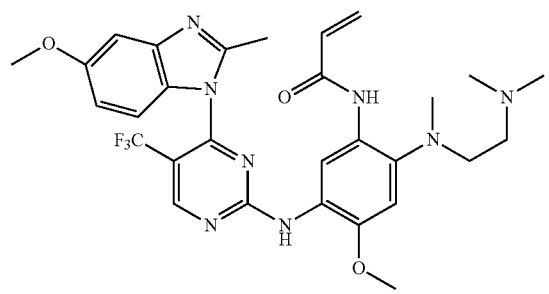

The preparation method of N-(2-((2-(dimethylamino)ethyl)(methyl)amino)-4-methoxy-5-((4-(5-methoxy-2-methyl-1H-benzo[d]imidazol-1-yl)-5-(trifluoromethyl)pyrimidin-2-yl)amino)phenyl)acrylamide was similar to Example 59.

Example 76: Preparation of N-(2-((2-(dimethylamino)ethyl)(methyl)amino)-4-methoxy-5-((4-(2-methyl-5-(trifluoromethyl)-1H-benzo[d]imidazol-1-yl)pyrimidin-2-yl)amino)phenyl)acrylamide

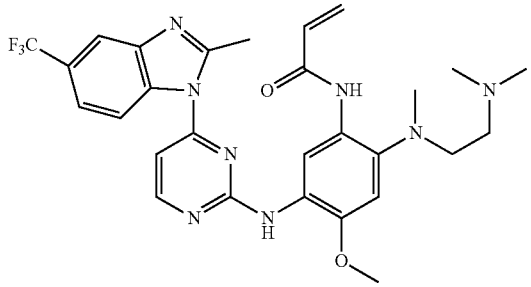 [SMILES: C=CC(=O)Nc1cc(Nc2nccc(-n3c(C)nc4cc(C(F)(F)F)ccc43)n2)c(OC)cc1N(C)CCN(C)C]

The preparation method of N-(2-((2-(dimethylamino)ethyl)(methyl)amino)-4-methoxy-5-((4-(2-methyl-5-(trifluoromethyl)-1H-benzo[d]imidazol-1-yl)pyrimidin-2-yl)amino)phenyl)acrylamide was similar to Example 59.

Example 77: Preparation of N-(5-((4-(6-cyano-2-methyl-1H-benzo[d]imidazol-1-yl)-5-fluoropyrimidin-2-yl)amino)-2-((2-(dimethylamino)ethyl)(methyl)amino)-4-methoxyphenyl)acrylamide

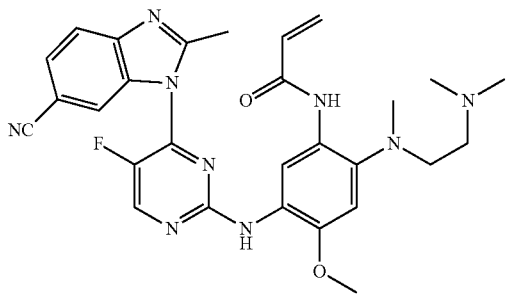 [SMILES: C=CC(=O)Nc1cc(Nc2ncc(F)c(-n3c(C)nc4ccc(C#N)cc43)n2)c(OC)cc1N(C)CCN(C)C]

The preparation method of N-(5-((4-(6-cyano-2-methyl-1H-benzo[d]imidazol-1-yl)-5-fluoropyrimidin-2-yl)amino)-2-((2-(dimethylamino)ethyl)(methyl)amino)-4-methoxyphenyl)acrylamide was similar to Example 59.

Example 78: Preparation of N-(2-((2-(dimethylamino)ethyl)(methyl)amino)-4-methoxy-5-((4-(2-methyl-5-(trifluoromethoxy)-1H-benzo[d]imidazol-1-yl)-5-(trifluoromethyl)pyrimidin-2-yl)amino)phenyl)acrylamide

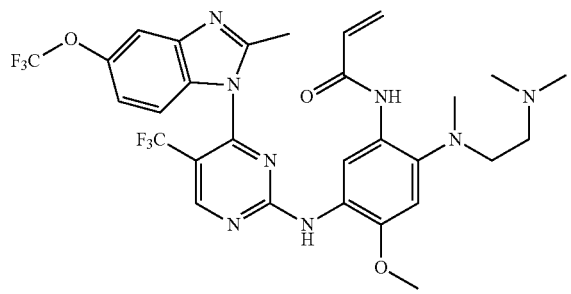 [SMILES: C=CC(=O)Nc1cc(Nc2ncc(C(F)(F)F)c(-n3c(C)nc4cc(OC(F)(F)F)ccc43)n2)c(OC)cc1N(C)CCN(C)C]

The preparation method of N-(2-((2-(dimethylamino)ethyl)(methyl)amino)-4-methoxy-5-((4-(2-methyl-5-(trifluoromethoxy)-1H-benzo[d]imidazol-1-yl)-5-(trifluoromethyl)pyrimidin-2-yl)amino)phenyl) acrylamide was similar to Example 59.

Example 79: Preparation of N-(5-((4-(5-cyclopropyl-2-methyl-1H-benzo[d]imidazol-1-yl)pyrimidin-2-yl)amino)-2-((2-(dimethylamino)ethyl)(methyl)amino)-4-methoxyphenyl)acrylamide

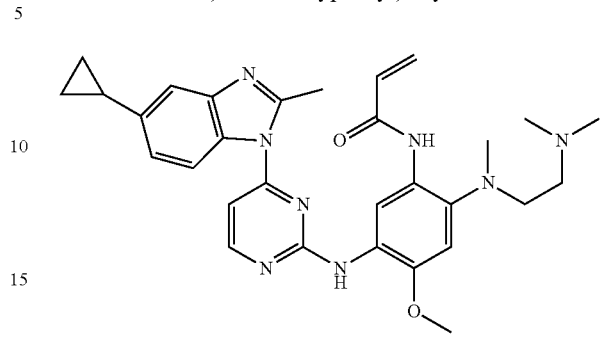

The preparation method of N-(5-((4-(5-cyclopropyl-2-methyl-1H-benzo[d]imidazol-1-yl)pyrimidin-2-yl)amino)-2-((2-(dimethylamino)ethyl)(methyl)amino)-4-methoxyphenyl)acrylamide was similar to Example 59.

Example 80: Preparation of N-(2-((2-(dimethylamino)ethyl)(methyl)amino)-4-methoxy-5-((4-(2-methyl-6-(trifluoromethyl)-1H-benzo[d]imidazol-1-yl)pyrimidin-2-yl)amino)phenyl)acrylamide

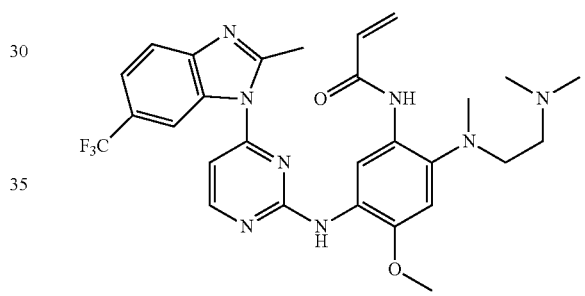

The preparation method of N-(2-((2-(dimethylamino)ethyl)(methyl)amino)-4-methoxy-5-((4-(2-methyl-6-(trifluoromethyl)-1H-benzo[d]imidazol-1-yl)pyrimidin-2-yl)amino)phenyl)acrylamide was similar to Example 59.

Example 81: Preparation of N-(5-((4-(2-cyclopropyl-5-methoxy-1H-benzo[d]imidazol-1-yl)pyrimidin-2-yl)amino)-2-((2-(dimethylamino)ethyl)(methyl)amino)-4-methoxyphenyl)acrylamide

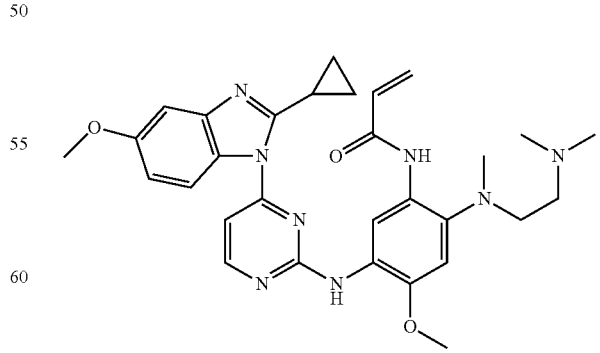

The preparation method of N-(5-((4-(2-cyclopropyl-5-methoxy-1H-benzo[d]imidazol-1-yl)pyrimidin-2-yl)amino)-2-((2-(dimethylamino)ethyl)(methyl)amino)-4-methoxyphenyl)acrylamide was similar to Example 59.

Example 82: Preparation of N-(5-((4-(2-cyclopropyl-5-methoxy-1H-benzo[d]imidazol-1-yl)-5-(trifluoromethyl)pyrimidin-2-yl)amino)-2-((2-(dimethylamino)ethyl)(methyl)amino)-4-methoxyphenyl)acrylamide

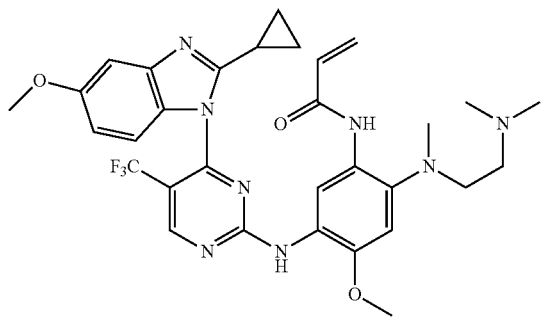

The preparation method of N-(5-((4-(2-cyclopropyl-5-methoxy-1H-benzo[d]imidazol-1-yl)-5-(trifluoromethyl)pyrimidin-2-yl)amino)-2-((2-(dimethylamino)ethyl)(methyl)amino)-4-methoxyphenyl)acrylamide was similar to Example 59.

Example 83: Preparation of N-(5-((4-(5-cyano-2-cyclopropyl-1H-benzo[d]imidazol-1-yl)pyrimidin-2-yl)amino)-2-((2-(dimethylamino)ethyl)(methyl)amino)-4-methoxyphenyl)acrylamide

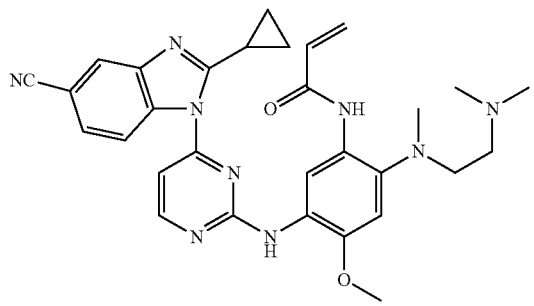 [SMILES: C=CC(=O)Nc1cc(Nc2nccc(-n3c(C4CC4)nc4cc(C#N)ccc43)n2)c(OC)cc1N(C)CCN(C)C]

The preparation method of N-(5-((4-(5-cyano-2-cyclopropyl-1H-benzo[d]imidazol-1-yl)pyrimidin-2-yl)amino)-2-((2-(dimethylamino)ethyl)(methyl)amino)-4-methoxyphenyl)acrylamide was similar to Example 59.

Example 84: Preparation of N-(5-((5-chloro-4-(5-cyano-2-cyclopropyl-1H-benzo[d]imidazol-1-yl)pyrimidin-2-yl)amino)-2-((2-(dimethylamino)ethyl)(methyl)amino)-4-methoxyphenyl)acrylamide

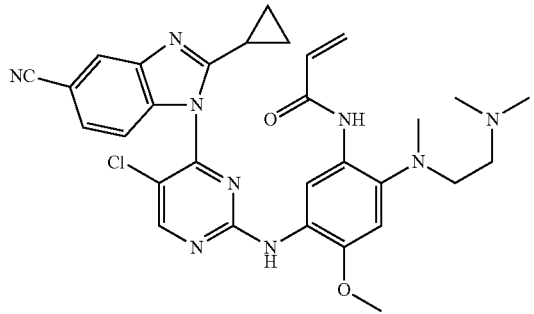 [SMILES: C=CC(=O)Nc1cc(Nc2ncc(Cl)c(-n3c(C4CC4)nc4cc(C#N)ccc43)n2)c(OC)cc1N(C)CCN(C)C]

The preparation method of N-(5-((5-chloro-4-(5-cyano-2-cyclopropyl-1H-benzo[d]imidazol-1-yl)pyrimidin-2-yl)amino)-2-((2-(dimethylamino)ethyl)(methyl)amino)-4-methoxyphenyl)acrylamide was similar to Example 59.

Example 85: Preparation of N-(5-((4-(2-cyclopropyl-5-(trifluoromethyl)-1H-benzo[d]imidazol-1-yl)pyrimidin-2-yl)amino)-2-((2-(dimethylamino)ethyl)(methyl)amino)-4-methoxyphenyl)acrylamide

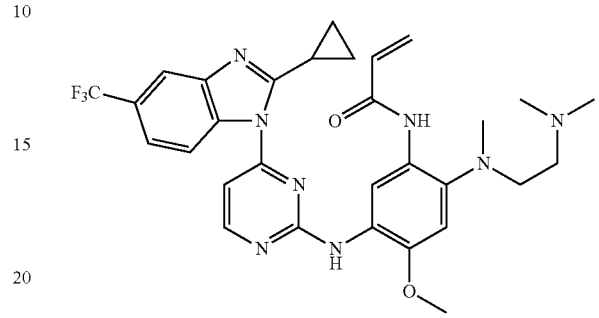

The preparation method of N-(5-((4-(2-cyclopropyl-5-(trifluoromethyl)-1H-benzo[d]imidazol-1-yl)pyrimidin-2-yl)amino)-2-((2-(dimethylamino)ethyl)(methyl)amino)-4-methoxyphenyl)acrylamide was similar to Example 59.

Example 86: Preparation of N-(5-((4-(2-cyclopropyl-6-(trifluoromethyl)-1H-benzo[d]imidazol-1-yl)pyrimidin-2-yl)amino)-2-((2-(dimethylamino)ethyl)(methyl)amino)-4-methoxyphenyl)acrylamide

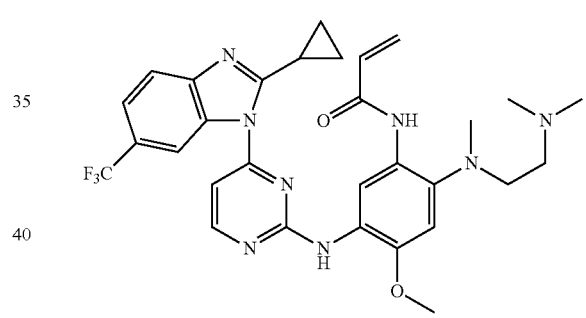

The preparation method of N-(5-((4-(2-cyclopropyl-6-(trifluoromethyl)-1H-benzo[d]imidazol-1-yl)pyrimidin-2-yl)amino)-2-((2-(dimethylamino)ethyl)(methyl)amino)-4-methoxyphenyl)acrylamide was similar to Example 59.

Example 87: Preparation of N-(5-((5-chloro-4-(2-cyclopropyl-5-(trifluoromethyl)-1H-benzo[d]imidazol-1-yl)pyrimidin-2-yl)amino)-2-((2-(dimethylamino)ethyl)(methyl)amino)-4-methoxyphenyl)acrylamide

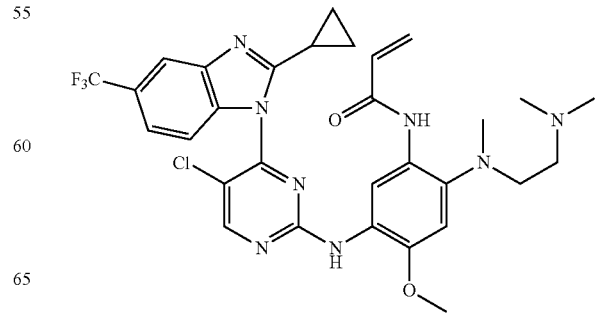

The preparation method of N-(5-((5-chloro-4-(2-cyclopropyl)-5-(trifluoromethyl)-1H-benzo[d]imidazol-1-yl)pyrimidin-2-yl)amino)-2-((2-(dimethylamino)ethyl)(methyl)amino)-4-methoxyphenyl)acrylamide was similar to Example 59.

Example 88: Preparation of N-(5-((4-(2-cyclopropyl-1H-benzo[d]imidazol-1-yl)pyrimidin-2-yl)amino)-2-((2-(dimethylamino)ethyl)(methyl)amino)-4-methoxyphenyl)acrylamide

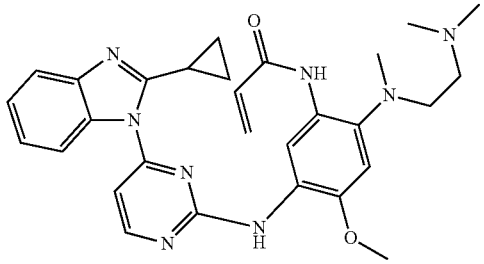 [SMILES: C=CC(=O)Nc1cc(Nc2nccc(-n3c(C4CC4)nc4ccccc43)n2)c(OC)cc1N(C)CCN(C)C]

The preparation method of N-(5-((4-(2-cyclopropyl-1H-benzo[d]imidazol-1-yl)pyrimidin-2-yl)amino)-2-((2-(dimethylamino)ethyl)(methyl)amino)-4-methoxyphenyl)acrylamide was similar to Example 59.

$^1$H NMR (400 MHz, CDCl$_3$): δ 10.3 (br s, 1H), 8.75 (s, 1H), 8.46 (d, J=6.0 Hz, 1H), 8.00 (dd, J=4.8, 1.6 Hz, 1H), 7.64 (dd, J=6.0, 1.6 Hz, 1H), 7.21 (m, 3H), 6.96 (d, J=6.4 Hz, 1H), 6.82 (s, 1H), 6.45 (m, 2H), 5.73 (d, J=9.2 Hz, 1H), 3.84 (s, 3H), 2.99 (m, 1H), 2.89 (m, 2H), 2.73 (s, 3H), 2.36 (m, 2H), 2.31 (s, 6H), 1.04 (m, 2H), 0.87 (m, 2H);
MS m/z (ESI): 527.2 [M+H]$^+$.

Example 89: Preparation of N-(5-((4-(5,7-difluoro-1-methyl-1H-indol-3-yl)pyrimidin-2-yl)amino)-2-((2-(dimethylamino)ethyl)(methyl)amino)-4-methoxyphenyl)acrylamide

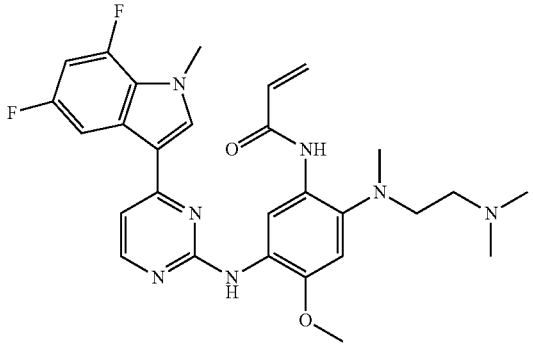 [SMILES: C=CC(=O)Nc1cc(Nc2nccc(-c3cn(C)c4c(F)cc(F)cc34)n2)c(OC)cc1N(C)CCN(C)C]

The preparation method of N-(5-((4-(5,7-difluoro-1-methyl-1H-indol-3-yl)pyrimidin-2-yl)amino)-2-((2-(dimethylamino)ethyl)(methyl)amino)-4-methoxyphenyl)acrylamide was similar to Example 22.

$^1$H NMR (400 MHz, CDCl$_3$): δ 10.2 (br s, 1H), 9.79 (s, 1H), 9.14 (s, 1H), 8.37 (d, J=5.2 Hz, 1H), 7.72 (s, 1H), 7.40 (d, J=5.2 Hz, 1H), 6.87 (dd, J=8.8, 1.6 Hz, 1H), 6.79 (s, 1H), 6.74 (m, 1H), 6.41 (m, 2H), 5.70 (m, 1H), 3.95 (s, 3H), 3.88 (s, 3H), 2.91 (m, 2H), 2.57 (s, 3H), 2.22 (m, 8H);
MS m/z (ESI): 527.3 [M+H]$^+$.

Example 90: Preparation of N-(5-((4-(4,5-difluoro-1-methyl-1H-indol-3-yl)pyrimidin-2-yl)amino)-2-((2-(dimethylamino)ethyl)(methyl)amino)-4-methoxyphenyl)acrylamide

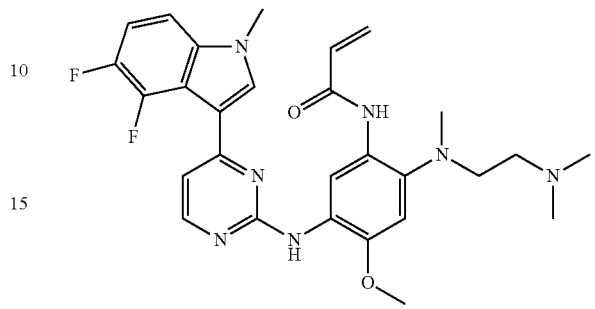

The preparation method of N-(5-((4-(4,5-difluoro-1-methyl-1H-indol-3-yl)pyrimidin-2-yl)amino)-2-((2-(dimethylamino)ethyl)(methyl)amino)-4-methoxyphenyl)acrylamide was similar to Example 22.

$^1$H NMR (400 MHz, CD$_3$OD): δ 9.20 (s, 1H), 8.36 (s, 1H), 8.18 (d, J=5.6 Hz, 1H), 7.99 (m, 1H), 7.26 (m, 1H), 7.04 (d, J=5.6 Hz, 1H), 6.97 (s, 1H), 6.56 (m, 1H), 6.29 (dd, J=17.2 Hz, 2.0 Hz, 1H), 5.74 (dd, J=10.4 Hz, 1.6 Hz, 1H), 3.91 (s, 3H), 3.80 (s, 3H), 3.06 (t, J=6.4 Hz, 2H), 2.70 (s, 3H), 2.46 (t, J=6.0 Hz, 1H), 2.31 (m, 6H);
MS m/z (ESI): 536.2 [M+H]$^+$.

Example 91: Preparation of N-(5-((4-(7-cyclopropyl-1-methyl-1H-indol-3-yl)pyrimidin-2-yl)amino)-2-((2-(dimethylamino)ethyl)(methyl)amino)-4-methoxyphenyl)acrylamide

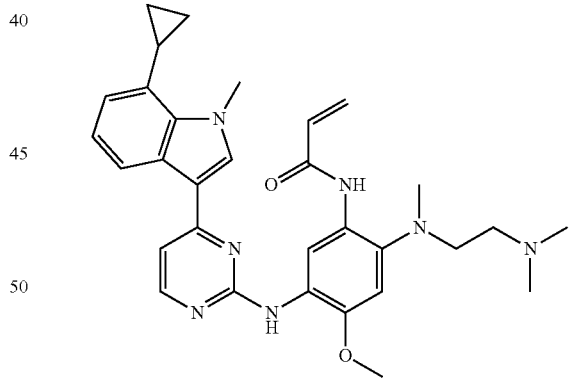

The preparation method of N-(5-((4-(7-cyclopropyl-1-methyl-1H-indol-3-yl)pyrimidin-2-yl)amino)-2-((2-(dimethylamino)ethyl)(methyl)amino)-4-methoxyphenyl)acrylamide was similar to Example 22.

$^1$H NMR (400 MHz, CDCl$_3$): δ 10.08 (s, 1H), 9.83 (s, 1H), 8.96 (s, 1H), 8.36 (d, J=5.2 Hz, 1H), 7.91 (d, J=8.0 Hz, 1H), 7.73 (s, 1H), 7.17 (d, J=5.2 Hz, 1H), 7.10 (t, J=7.6 Hz, 1H), 6.99 (d, J=7.2 Hz, 1H), 6.79 (s, 1H), 6.44 (m, 2H), 5.71 (m, 1H), 4.45 (s, 3H), 3.88 (s, 3H), 2.91 (t, J=5.6 Hz, 2H), 2.71 (s, 3H), 2.46 (m, 1H), 2.28 (m, 8H), 1.01 (m, 2H), 0.90 (m, 2H);
MS m/z (ESI): 540.2 [M+H]$^+$.

Example 92: N-(5-((4-(7-cyclopropyl-1H-indol-3-yl)pyrimidin-2-yl)amino)-2-((2-(dimethylamino)ethyl)(methyl)amino)-4-methoxyphenyl)acrylamide

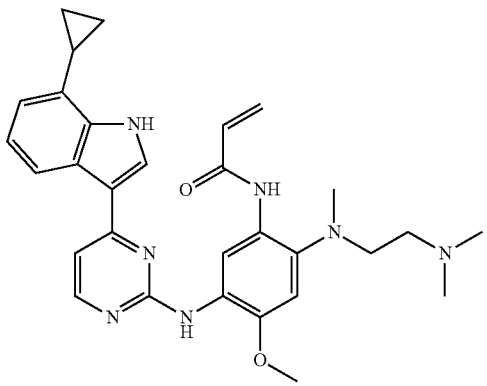 [SMILES: C=CC(=O)Nc1cc(Nc2nccc(-c3c[nH]c4c(C5CC5)cccc34)n2)c(OC)cc1N(C)CCN(C)C]

The preparation method of N-(5-((4-(7-cyclopropyl-1H-indol-3-yl)pyrimidin-2-yl)amino)-2-((2-(dimethylamino)ethyl)(methyl)amino)-4-methoxyphenyl)acrylamide was similar to Example 22.

$^1$H NMR (400 MHz, CDCl$_3$) δ 10.27 (s, 1H), 10.13 (s, 1H), 9.83 (s, 1H), 9.04 (s, 1H), 8.36 (d, J=5.3 Hz, 1H), 7.89 (d, J=8.0 Hz, 1H), 7.72 (s, 1H), 7.16 (d, J=5.3 Hz, 1H), 7.09 (t, J=7.7 Hz, 1H), 6.79 (d, J=5.6 Hz, 2H), 6.71-6.50 (m, 1H), 6.39 (s, 1H), 5.82-5.58 (m, 1H), 3.88 (s, 3H), 3.08-2.83 (m, 2H), 2.70 (s, 3H), 2.39-2.20 (m, 8H), 2.16 (t, J=5.1 Hz, 1H), 0.96-0.73 (m, 2H), 0.73-0.55 (m, 2H);

MS m/z (ESI): 526.7 [M+H]$^+$.

Example 93: Preparation of N-(5-((4-(1-cyclopropyl-6-methoxy-1H-indol-3-yl)pyrimidin-2-yl)amino)-2-((2-(dimethylamino)ethyl)(methyl)amino)-4-methoxyphenyl)acrylamide

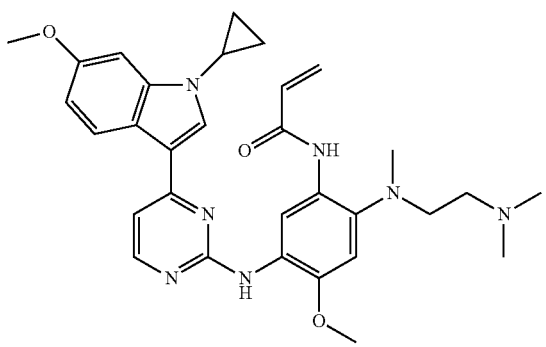

The preparation method of N-(5-((4-(1-cyclopropyl-6-methoxy-1H-indol-3-yl)pyrimidin-2-yl)amino)-2-((2-(dimethylamino)ethyl)(methyl)amino)-4-methoxyphenyl)acrylamide was similar to that in Example 22.

The TFA salt of N-(5-((4-(1-cyclopropyl-6-methoxy-1H-indol-3-yl)pyrimidin-2-yl)amino)-2-((2-(dimethylamino)ethyl)(methyl)amino)-4-methoxyphenyl)acrylamide $^1$H NMR (400 MHz, CD$_3$OD): δ 8.41 (s, 1H), 8.15 (br, 1H), 7.98 (d, J=6.8 Hz, 1H), 7.89 (s, 1H), 7.40 (d, J=6.8 Hz, 1H), 7.17 (d, J=2.4 Hz, 1H), 7.06 (m, 1H), 6.87 (m, 1H), 6.50 (m, 2H), 5.87 (m, 1H), 3.95 (s, 3H), 3.88 (s, 3H), 3.55 (m, 3H), 3.35 (m, 2H), 2.92 (s, 6H), 2.80 (s, 3H), 1.22 (m, 2H), 0.90 (m, 2H);

MS m/z (ESI): 556.2 [M+H]$^+$.

Example 94: Preparation of N-(2-((2-(dimethylamino)ethyl)(methyl)amino)-4-methoxy-5-((4-(7-methoxy-1H-indol-3-yl)pyrimidin-2-yl)amino)phenyl)acrylamide

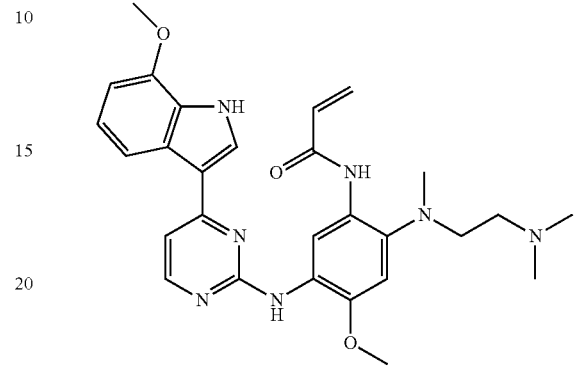

The preparation method of N-(2-((2-(dimethylamino)ethyl)(methyl)amino)-4-methoxy-5-((4-(7-methoxy-1H-indol-3-yl)pyrimidin-2-yl)amino)phenyl)acrylamide was similar to Example 22.

$^1$H NMR (400 MHz, CD$_3$OD): δ 8.40 (s, 1H), 8.03 (d, J=6.8 Hz, 1H), 7.46 (d, J=6.8 Hz, 1H), 7.12 (m, 1H), 7.09 (s, 1H), 6.77 (d, J=8.0 Hz, 1H), 6.51 (m, 2H), 5.87 (m, 1H), 3.98 (s, 3H), 3.87 (s, 3H), 3.57 (m, 2H), 3.36 (m, 2H), 2.92 (m, 6H), 2.80 (s, 3H);

MS m/z (ESI): 516.2 [M+H]$^+$.

Example 95: Preparation of N-(2-((2-(dimethylamino)ethyl)(methyl)amino)-5-((4-(6-ethynyl-1-methyl-1H-indol-3-yl)pyrimidin-2-yl)amino)-4-methoxyphenyl)acrylamide

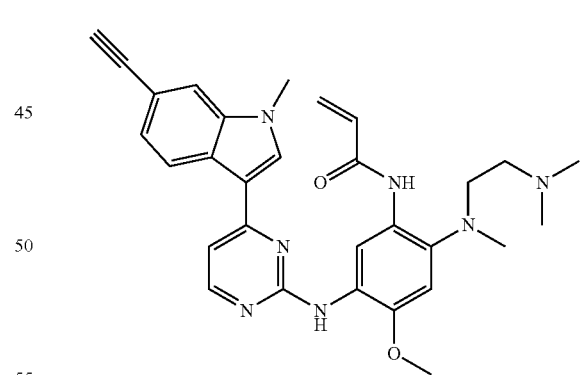

Step 1: Preparation of 6-iodo-1H-indole

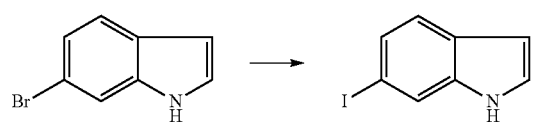 [SMILES: Brc1ccc2cc[nH]c2c1 ; Ic1ccc2cc[nH]c2c1]

NaI (4.59, 30.6 mmol), CuI (290 mg, 1.53 mmol) and N,N'-dimethylethylenediamine (0.35 mL) were added to a solution of 6-bromo-1H-indole (3.00 g, 15.3 mmol) in dioxane (30 mL) at the room temperature. The mixture was purged with nitrogen to remove oxygen for 5 minutes. The mixture was stirred at 110° C. in an oil bath overnight in a nitrogen atmosphere. After cooling, the organic solvent was removed by concentration under reduced pressure. EtOAc and water were added, and two phases were separated. The EtOAc phase was washed with saturated brine, dried over anhydrous sodium sulfate, concentrated, and purified by column chromatography (eluent: pure PE) to obtain the title compound 6-Iodo-1H-indole (2.1 g, 57%).

MS m/z (ESI): 244.0 [M+H]$^+$.

Step 2: Preparation of 6-iodo-1-methyl-1H-indole

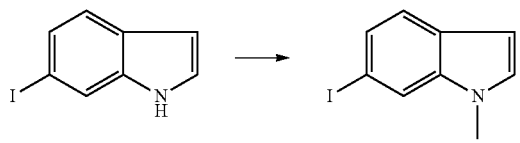

In an ice water bath, NaH (60%, 734 mg, 18.4 mmol) was added to a solution of 6-iodo-1H-indole (2.00 g, 8.23 mmol) in DMF (30 mL). The mixture was stirred for 20 minutes at this temperature, followed by addition of a solution of MeI (1.14 mL, 18.4 mmol) in DMF (10 mL), and further stirred at this temperature for 30 minutes. About 100 mL of water were added, and the reaction solution was extracted with EtOAc. The EtOAc phase was washed several times with saturated brine, dried over anhydrous sodium sulfate, concentrated, and purified by column chromatography (eluent: pure PE) to obtain the title compound 6-iodo-1-methyl-1H-indole (1.98 g, 94%).

MS m/z (ESI): 258.1 [M+H]$^+$.

Step 3: Preparation of 3-(2-chloropyrimidin-4-yl)-6-iodo-1-methyl-1H-indole

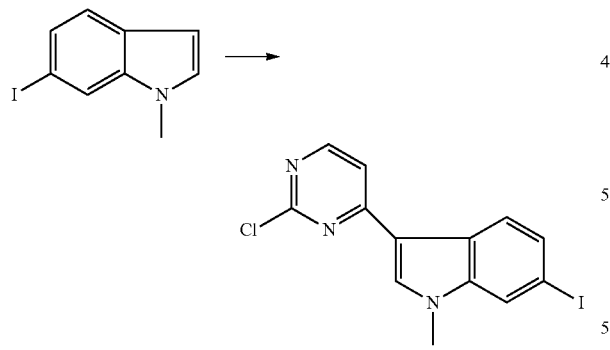

FeCl$_3$ (441 mg, 2.72 mmol) was add to a solution of 6-iodo-1-methyl-1H-indole (700 mg, 2.72 mmol) and 2,4-dichloropyrimidine (405 mg, 2.72 mmol) in ethylene glycol dimethyl ether (10 mL). The mixture was stirred at 60° C. overnight. After cooling, a large amount of EtOAc and water were added, and two phases were separated. The undissolved substance was removed through celite, and the aqueous phase was removed. The organic phase was washed successively with saturated sodium bicarbonate aqueous solution and saturated brine, dried over anhydrous sodium sulfate, concentrated and purified by column chromatography (eluent:EtOAc=3:1) to obtain the title compound 3-(2-chloropyrimidin-4-yl)-6-iodo-1-methyl-1H-indole (533 mg, 53%).

MS m/z (ESI): 370.59 [M+H]$^+$.

Step 4: Preparation of N-(4-fluoro-2-methoxy-5-nitrophenyl)-4-(6-iodo-1-methyl-1H-indol-3-yl)pyrimidin-2-amine

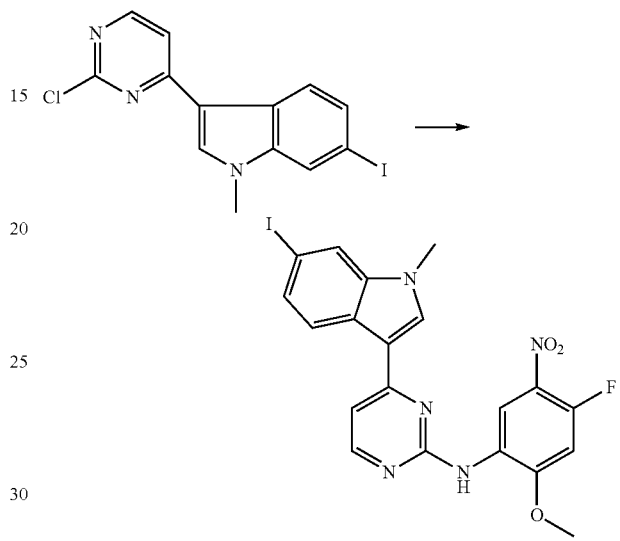

3-(2-chloropyrimidin-4-yl)-6-iodo-1-methyl-1H-indole (283 mg, 0.765 mmol), 4-fluoro-2-methoxy-5-nitroaniline (142 mg, 0.765 mmol) and TsOH.H$_2$O (175 mg, 0.918 mmol) were mixed in 2-pentanol (10 mL), and the reaction was carried out at 125° C. for 3 hours. After the mixture was cooled and filtered, the resulting solid was dissolved in CH$_2$Cl$_2$. Then, the solution was washed successively with saturated sodium bicarbonate aqueous solution and saturated brine, dried over anhydrous sodium sulfate, and concentrated to obtain the title compound N-(4-fluoro-2-methoxy-5-nitrophenyl)-4-(6-iodo-1-methyl-1H-indol-3-yl)pyrimidin-2-amine (350 mg, 88%).

MS m/z (ESI): 520.2 [M+H]$^+$.

Step 5: Preparation of N1-(2-(dimethylamino)ethyl)-N4-(4-(6-iodo-1-methyl-1H-indol-3-yl)pyrimidin-2-yl)-5-methoxy-N1-methyl-2-nitrobenzene-1,4-diamine

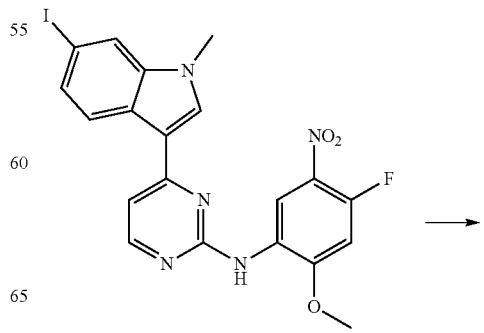

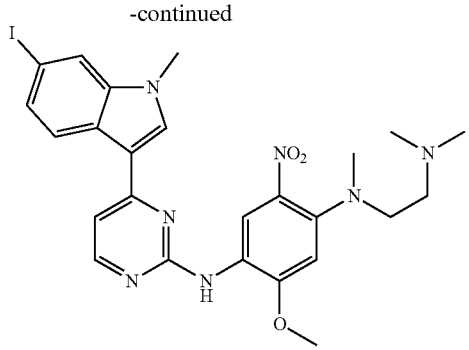

N-(4-fluoro-2-methoxy-5-nitrophenyl)-4-(6-iodo-1-methyl-1H-indol-3-yl)pyrimidin-2-amine (100 mg, 0.192 mmol), N1,N1,N2-trimethylethane-1,2-diamine (39 mg, 0.385 mmol) and DIPEA (42 mg, 0.385 mmol) were dissolved in DMA (10 mL), and the reaction was carried out at 85° C. for 3 hours. After cooling, EtOAc and water were added, and two phases were separated. The organic phase was washed several times with saturated brine, dried over anhydrous sodium sulfate, and concentrated to obtain 105 mg of the crude title compound N1-(2-(dimethylamino)ethyl)-N4-(4-(6-iodo-1-methyl-1H-indol-3-yl)pyrimidin-2-yl)-5-methoxy-N1-methyl-2-nitrobenzene-1,4-diamine, which was used directly for the next step.

MS m/z (ESI): 602.4 [M+H]$^+$.

Step 6: Preparation of N1-(2-(dimethylamino)ethyl)-5-methoxy-N1-methyl-N4-(4-(1-methyl-6-((trimethylsilyl)ethynyl)-1H-indol-3-yl)pyrimidin-2-yl)-2-nitrobenzene-1,4-diamine

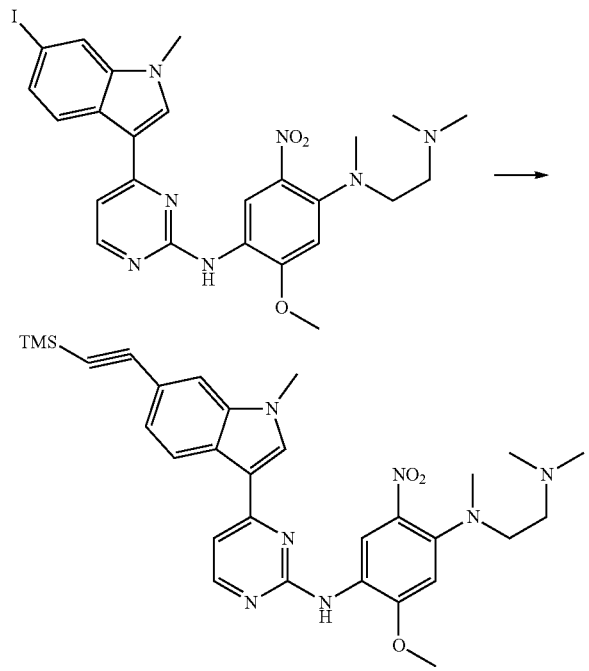

N1-(2-(dimethylamino)ethyl)-N4-(4-(6-iodo-1-indol-3-yl)pyrimidin-2-yl)-5-methoxy-N1-methyl-2-nitrobenzene-1,4-diamine (100 mg, 0.166 mmol), (trimethylsilyl)acetylene (48 mg, 0.498 mmol) and triethylamine (51 mg, 0.498 mmol) were mixed in a mixture of THF (10 mL) and DMF (5 mL), followed by addition of CuI (16 mg, 0.083 mmol) and tetrakis(triphenylphosphine)palladium (40 mg, 0.041 mmol). After purging three times with nitrogen, the reaction solution was heated up to 70° C. overnight in an oil bath. The solvent was removed under reduced pressure, and the aqueous phase was extracted with EtOAc. The EtOAc phase was washed with saturated brine, dried over anhydrous sodium sulfate, concentrated, and purified by column chromatography [eluent: CH$_2$Cl$_2$→CH$_2$Cl$_2$:MeOH=20:1] to obtain the title compound N1-(2-(dimethylamino)ethyl)-5-methoxy-N1-methyl-N4-(4-(1-methyl-6-((trimethylsilyl)ethynyl)-1H-indol-3-yl)pyrimidin-2-yl)-2-nitrobenzene-1,4-diamine (65 mg, 68%).

MS m/z (ESI): 572.7 [M+H]$^+$.

Step 7: Preparation of N1-(2-(dimethylamino)ethyl)-5-methoxy-N1-methyl-N4-(4-(1-methyl-6-((trimethylsilyl)ethynyl)-1H-indol-3-yl)pyrimidin-2-yl)benzene-1,2,4-triamine

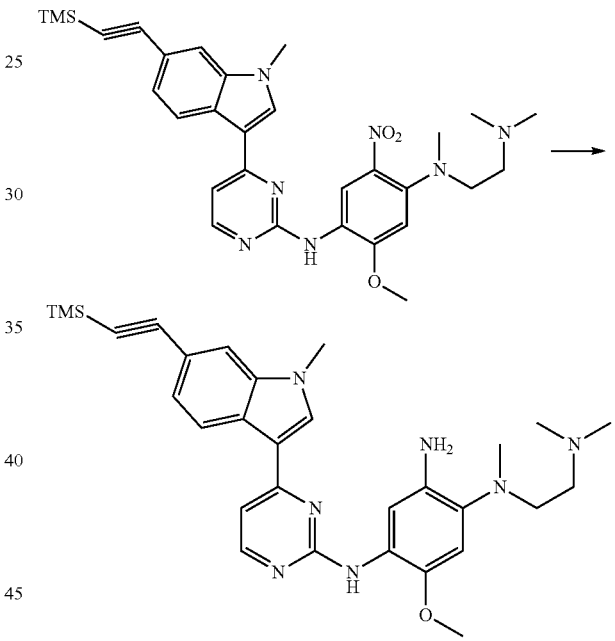

N1-(2-(dimethylamino)ethyl)-5-methoxy-N1-methyl-N4-(4-(1-methyl-6-((trimethylsilyl)ethynyl)-1H-indol-3-yl)pyrimidin-2-yl)-2-nitrobenzene-1,4-diamine (200 mg, 0.35 mmol), reduced iron powder (136 mg, 2.45 mmol) and ammonium chloride (20.6 mg, 0.386 mmol) were mixed in a mixture of EtOH (30 mL) and water (10 mL), and the mixture was heated up to reflux for three hours. After cooling, a large amount of EtOH was added, and the undissolved substance was removed by filtration through celite. EtOH was removed under reduced pressure, and the aqueous phase was extracted with EtOAc. The EtOAc phase was washed with saturated brine, dried over anhydrous sodium sulfate, concentrated, and purified by column chromatography (eluent: CH$_2$Cl$_2$→CH$_2$Cl$_2$:MeOH (containing 10% concentrated ammonia)=17:1] to obtain the title compound N1-(2-(dimethylamino)ethyl)-5-methoxy-N1-methyl-N4-(4-(1-methyl-6-((trimethylsilyl)ethynyl)-1H-indol-3-yl)pyrimidin-2-yl)benzene-1,2,4-triamine (166 mg, 88%).

MS m/z (ESI): 542.3 [M+H]$^+$.

Step 8: Preparation of N1-(2-(dimethylamino)ethyl)-N4-(4-(6-ethynyl-1-methyl-1H-indol-3-yl)pyrimidin-2-yl)-5-methoxy-N1-methylbenzene-1,2,4-triamine

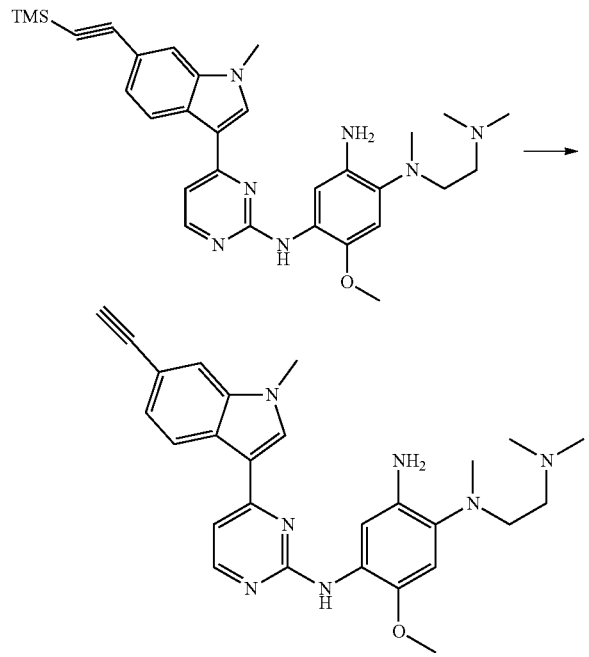

N1-(2-(dimethylamino)ethyl)-5-methoxy-N1-methyl-N4-(4-(1-methyl-6-((trimethylsilyl)ethynyl)-1H-indol-3-yl)pyrimidin-2-yl)benzene-1,2,4-triamine (90 mg, 0.166 mmol) was dissolved in a mixture of THF (10 mL) and MeOH (10 mL), then potassium carbonate (69 mg, 0.50 mmol) was added. The reaction solution was stirred at room temperature for 3 hours. The solvent was removed under reduced pressure, water and EtOAc were added, and the two phases were separated. The organic phase was washed several times with saturated brine, dried over anhydrous sodium sulfate and concentrated to obtain the title compound N1-(2-(dimethylamino)ethyl)-N4-(4-(6-ethynyl-1-methyl-1H-indol-3-yl)pyrimidin-2-yl)-5-methoxy-N1-methylbenzene-1,2,4-triamine (71 mg, 91%).

MS m/z (ESI): 470.26 [M+H]$^+$.

Step 9: Preparation of N-(2-((2-(dimethylamino)ethyl)(methyl)amino)-5-((4-(6-ethynyl-1-methyl-1H-indol-3-yl)pyrimidin-2-yl)amino)-4-methoxyphenyl)acrylamide

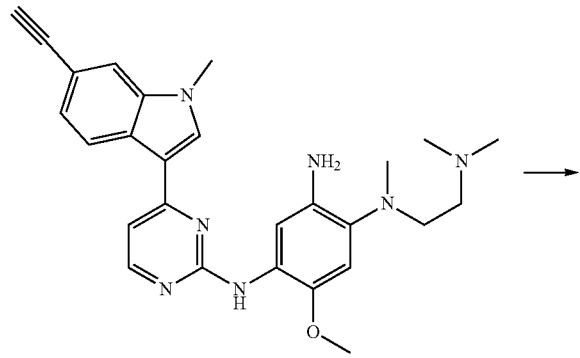

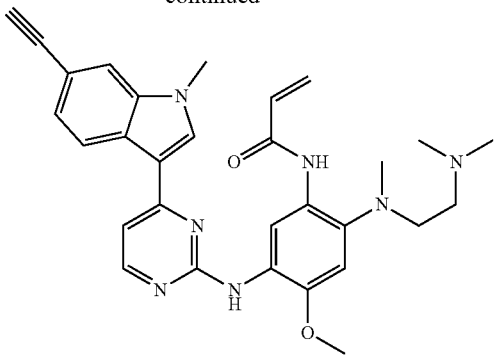

A solution of acryloyl chloride (22.0 mg, 0.247 mmol) in THF (1 mL) was added dropwise to a solution of N1-(2-(dimethylamino)ethyl)-N4-(4-(6-ethynyl-1-methyl-1H-indol-3-yl)pyrimidin-2-yl)-5-methoxy-N1-methylbenzene-1,2,4-triamine (80 mg, 0.169 mmol) and TEA (50 mg, 0.492 mmol) in THF (2 mL) in an ice-water bath. Upon completion of the addition, the mixture was stirred for 15 minutes at this temperature. The reaction was quenched with methanol. The reaction solution was concentrated under reduced pressure, and purified by preparative thin-layer chromatography (CH$_2$Cl$_2$:MeOH:concentrated ammonia=100:10:1) to obtain the title compound N-(2-((2-(dimethylamino)ethyl)(methyl)amino)-5-((4-(6-ethynyl-1-methyl-1H-indol-3-yl)pyrimidin-2-yl)amino)-4-methoxyphenyl)acrylamide (45 mg, 51%).

$^1$H NMR (400 MHz, CDCl3) δ 10.03 (s, 1H), 9.74 (d, J=6.2 Hz, 1H), 9.07 (s, 1H), 8.31 (d, J=5.3 Hz, 1H), 7.91 (d, J=8.3 Hz, 1H), 7.65 (s, 1H), 7.48 (s, 1H), 7.29 (dd, J=8.3, 1.2 Hz, 1H), 7.08 (d, J=5.3 Hz, 1H), 6.70 (s, 1H), 6.37 (d, J=16.3 Hz, 2H), 5.81-5.57 (m, 1H), 3.89 (d, J=13.0 Hz, 3H), 3.81 (s, 3H), 3.02 (s, 1H), 2.85 (s, 2H), 2.62 (s, 3H), 2.24 (m, 8H);

MS m/z (ESI): 524.6 [M+H]$^+$.

Example 96: Preparation of N-(2-((2-(dimethylamino)ethyl)(methyl)amino)-4-methoxy-5-((4-(1-methyl-6-vinyl-1H-indol-3-yl)pyrimidin-2-yl)amino)phenyl)acrylamide

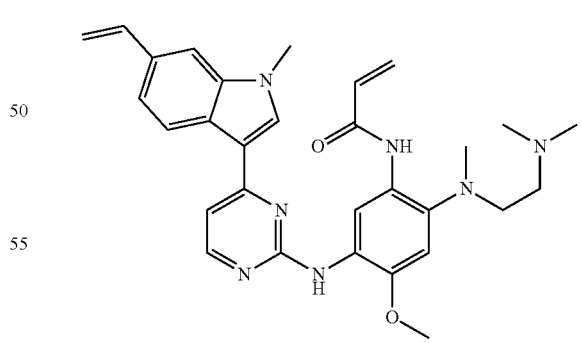

The preparation method of N-(2-((2-(dimethylamino)ethyl)(methyl)amino)-4-methoxy-5-((4-(1-methyl-6-vinyl-1H-indol-3-yl)pyrimidin-2-yl)amino)phenyl)acrylamide was similar to Example 95.

$^1$H NMR (400 MHz, CDCl$_3$) δ 9.96 (s, 1H), 9.76 (d, J=4.7 Hz, 1H), 8.99 (s, 1H), 8.30 (d, J=5.3 Hz, 1H), 7.92 (d, J=8.7 Hz, 1H), 7.64 (s, 1H), 7.30 (dd, J=4.3, 2.8 Hz, 2H), 7.11 (t, J=5.1 Hz, 1H), 6.80 (dd, J=17.5, 10.9 Hz, 1H), 6.69 (s, 1H), 6.38 (d, J=16.7 Hz, 2H), 5.90-5.52 (m, 2H), 5.19-5.06 (m, 1H), 3.91 (s, 3H), 3.80 (s, 3H), 2.88 (s, 2H), 2.63 (s, 3H), 2.28 (m, 8H);
MS m/z (ESI): 526.6 [M+H]$^+$.

Example 97: Preparation of N-(2-((2-(dimethylamino)ethyl)(methyl)amino)-4-methoxy-5-((4-(6-methoxy-1H-indol-3-yl)pyrimidin-2-yl)amino)phenyl)acrylamide

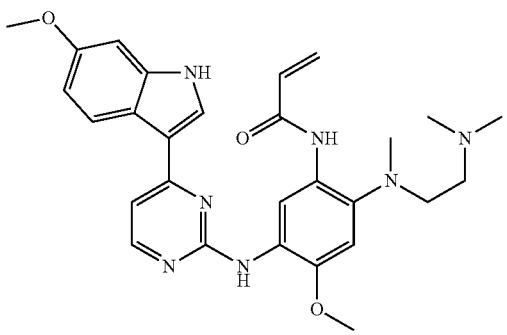

The preparation method of N-(2-((2-(dimethylamino)ethyl)(methyl)amino)-4-methoxy-5-((4-(6-methoxy-1H-indol-3-yl)pyrimidin-2-yl)amino)phenyl)acrylamide was similar to Example 22.

$^1$H NMR (400 MHz, CDCl$_3$) δ 10.29 (s, 1H), 9.85 (s, 1H), 9.70 (d, J=14.2 Hz, 1H), 8.29 (s, 1H), 8.16 (s, 1H), 7.88 (d, J=9.4 Hz, 1H), 7.56 (s, 1H), 6.88 (s, 1H), 6.79-6.60 (m, 3H), 6.43 (d, J=15.5 Hz, 2H), 5.62 (d, J=10.3 Hz, 1H), 3.81 (s, 3H), 3.62 (s, 3H), 2.84 (s, 2H), 2.64 (s, 3H), 2.21 (m, 8H);
MS m/z (ESI): 516.6 [M+H]$^+$.

Example 98: Preparation of N-(5-((5-chloro-4-(6-methoxy-1-methyl-1H-indol-3-yl)pyrimidin-2-yl)amino)-2-((2-(dimethylamino)ethyl)(methyl)amino)-4-methoxyphenyl)acrylamide

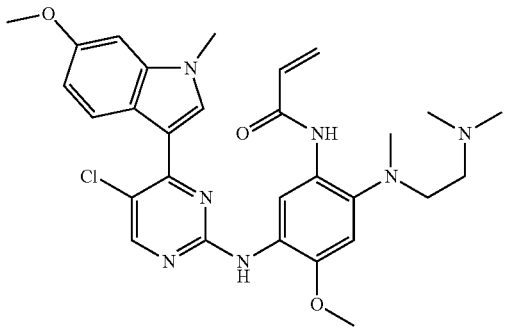

Step 1: Preparation of 6-methoxy-1-methyl-1H-indole

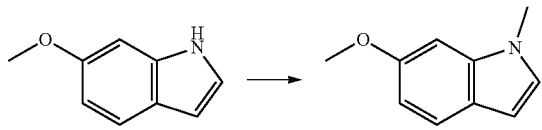

6-methoxy-1H-indole (500 mg, 3.4 mmol) was dissolved in N,N-dimethylformamide (16 mL). The solution was cooled in an ice bath, and sodium hydride (320 mg, 6.8 mmol) was added. After the reaction solution was stirred for 15 minutes, methyl iodide (0.25 mL, 3.7 mmol) was added dropwise. The reaction solution was warmed up to room temperature naturally and stirred for 2 h, and then quenched with saturated ammonium chloride aqueous solution (20 mL) and extracted with ethyl acetate (30 mL×3). The organic phase was dried over anhydrous sodium sulfate and concentrated to obtain a crude product, which was further purified by column chromatography to obtain 6-methoxy-1-methyl-1H-indole (480 mg, 88%).

Step 2: Preparation of 3-(2,5-dichloropyrimidin-4-yl)-6-methoxy-1-methyl-1H-indole

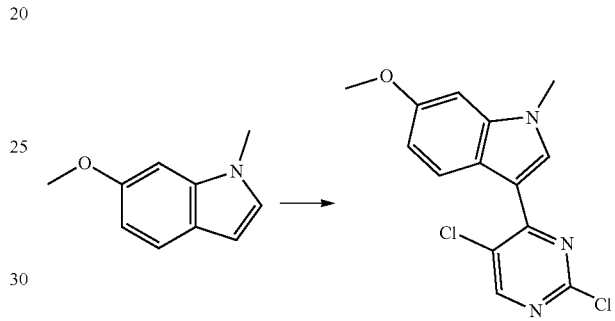

6-methoxy-1-methyl-1H-indole (480 mg, 3.0 mmol) and 2,4,5-trichloropyrimidine (660 mg, 3.6 mmol) were dissolved in ethylene glycol dimethyl ether (20 mL). The reaction was heated up to 80° C. for 20 min, and anhydrous aluminum chloride (720 mg, 5.4 mmol) was added. The reaction was stirred for 1 hour in a nitrogen atmosphere. The reaction was quenched with an ice-water mixture (about 50 mL), and the mixture was extracted with methyl tert-butyl ether (20 mL×3). The organic phases were combined, dried over magnesium sulfate, filtered and concentrated to obtain the crude product 3-(2,5-dichloropyrimidin-4-yl)-6-methoxy-1-methyl-1H-indole (320 mg, 30%), which was used directly in the next step.

Steps 3 to 6: Preparation of N-(5-((5-chloro-4-(6-methoxy-1-methyl-1H-indol-3-yl)pyrimidin-2-yl)amino)-2-((2-(dimethylamino)ethyl)(methyl)amino)-4-methoxyphenyl)acrylamide

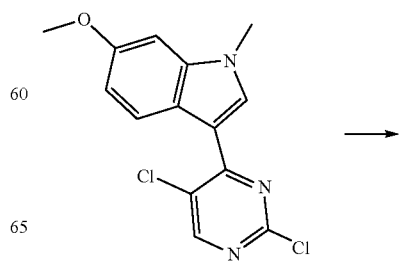

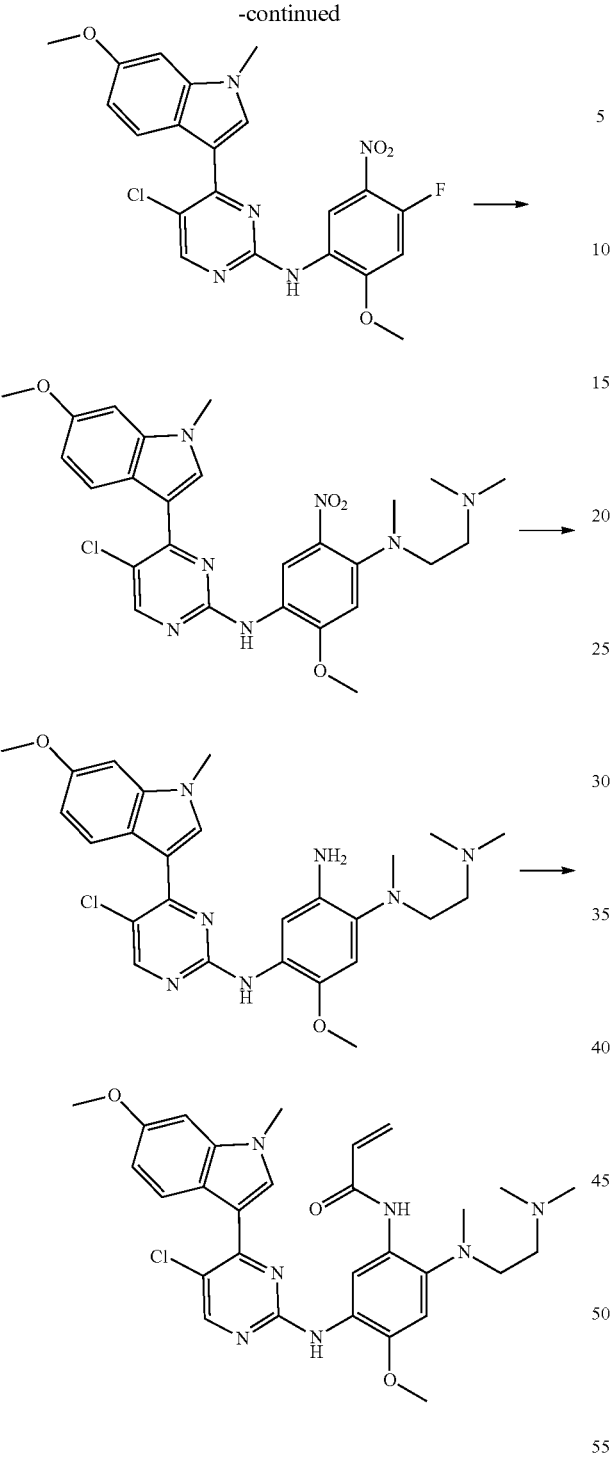

The preparation method of N-(5-((5-chloro-4-(6-methoxy-1-methyl-1H-indol-3-yl)pyrimidin-2-yl)amino)-2-((2-(dimethylamino)ethyl)(methyl)amino)-4-methoxyphenyl)acrylamide was similar to Example 22.

$^1$H NMR (400 MHz, CD3OD) δ 8.48 (s, 1H), 8.29-8.21 (m, 2H), 8.19 (s, 1H), 7.01 (s, 1H), 6.96 (d, J=2.2 Hz, 1H), 6.78 (dd, J=8.9, 2.2 Hz, 1H), 6.49-6.44 (m, 2H), 5.84 (dd, J=7.7, 4.1 Hz, 1H), 3.97 (s, 3H), 3.86 (d, J=10.8 Hz, 6H), 3.53 (t, J=5.7 Hz, 2H), 3.33-3.31 (m, 2H), 2.91 (s, 6H), 2.76 (s, 3H);

MS m/z (ESI): 564.3 [M+1]$^+$.

Example 99: Preparation of N-(2-((2-(dimethylamino)ethyl)(methyl)amino)-4-methoxy-5-((4-(6-methoxy-1-methyl-1H-indol-3-yl)-5-(trifluoromethyl)pyrimidin-2-yl)amino)phenyl)acrylamide

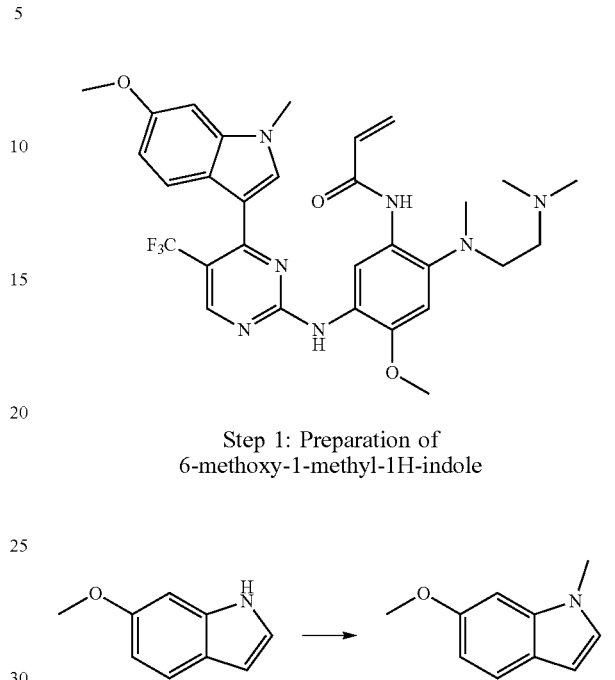

Step 1: Preparation of 6-methoxy-1-methyl-1H-indole

The starting material 6-methoxy-1H-indole (1 g, 6.793 mmol) was dissolved in DMF (20 mL), the mixture was cooled to 0° C., and then NaH (815 mg, 20.38 mmol) was added. The reaction solution was stirred at 0° C. for ten minutes. Iodomethane (1.447 g, 10.19 mmol) was then added to the reaction system. The reaction was warmed up to room temperature and stirred for 1 hour. The reaction solution was poured into ice water, and extracted with ethyl acetate. The organic phases were combined, washed with water and saturated brine, dried over anhydrous sodium sulfate, filtered, and concentrated to obtain a crude product, which was further purified by flash silica gel column chromatography to obtain the product 6-methoxy-1-methyl-1H-indole (850 mg, 77.3%).

Step 2: Preparation of 3-(2-chloro-5-(trifluoromethyl)pyrimidin-4-yl)-6-methoxy-1-methyl-1H-indole

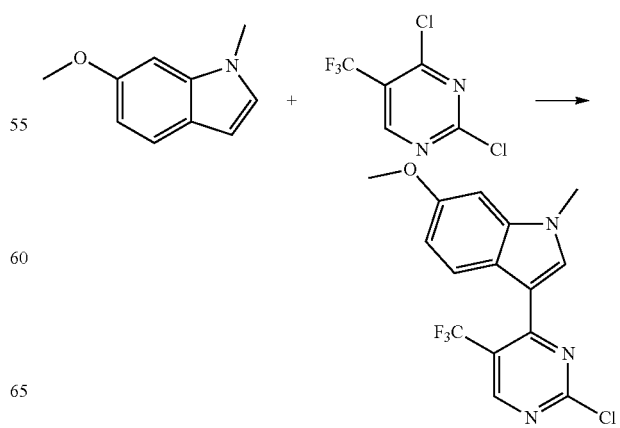

The starting material 6-methoxy-1-methyl-1H-indole (850 mg, 5.27 mmol), 2,4-dichloro-5-(trifluoromethyl)pyrimidine (1.26 g, 5.8 mmol) and aluminum trichloride (1.05 g, 7.91 mmol) were dissolved in DME (30 mL), and the reaction was stirred overnight at 70° C. After the reaction was completed, the reaction solution was poured into ice water and extracted three times with methyl tert-butyl ether. The organic phases were combined, washed with water and saturated brine, dried over anhydrous sodium sulfate, filtered, and evaporated to dryness to obtain a crude product, which was further purified by flash silica gel column chromatography to obtain the product 3-(2-chloro-5-(trifluoromethyl)pyrimidin-4-yl)-6-methoxy-1-methyl-1H-indole (700 mg, 39%).

Step 3: Preparation of N-(4-fluoro-2-methoxy-5-nitrophenyl)-4-(6-methoxy-1-methyl-1H-indol-3-yl)-5-(trifluoromethyl)pyrimidin-2-amine

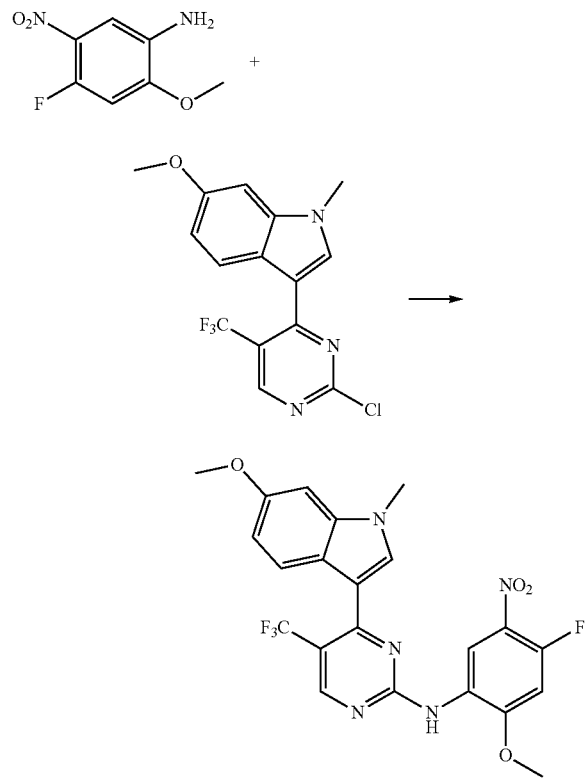

3-(2-chloro-5-(trifluoromethyl)pyrimidin-4-yl)-6-methoxy-1-methyl-1H-indole (700 mg, 2.05 mmol), the starting material 4-fluoro-2-methoxy-5-nitroaniline (419 mg, 2.25 mmol) and p-toluenesulfonic acid monohydrate (390 mg, 2.05 mmol) were dissolved in 2-pentanol (10 mL). The reaction was heated up to 120° C. and reacted overnight. After LC-MS showed completion of the reaction, the reaction solution was cooled to room temperature naturally, and a dark solid was precipitated. The solid was filtered and the filter cake was washed with methanol (1 mL) and methyl tert-butyl ether (1 mL) to obtain the product N-(4-fluoro-2-methoxy-5-nitrophenyl)-4-(6-methoxy-1-methyl-1H-indol-3-yl)-5-(trifluoromethyl)pyrimidin-2-amine (600 mg, 60%).

Step 4: Preparation of N1-(2-(dimethylamino)ethyl)-5-methoxy-N4-(4-(6-methoxy-1-methyl-1H-indol-3-yl)-5-(trifluoromethyl)pyrimidin-2-yl)-N1-methyl-2-nitrobenzene-1,4-diamine

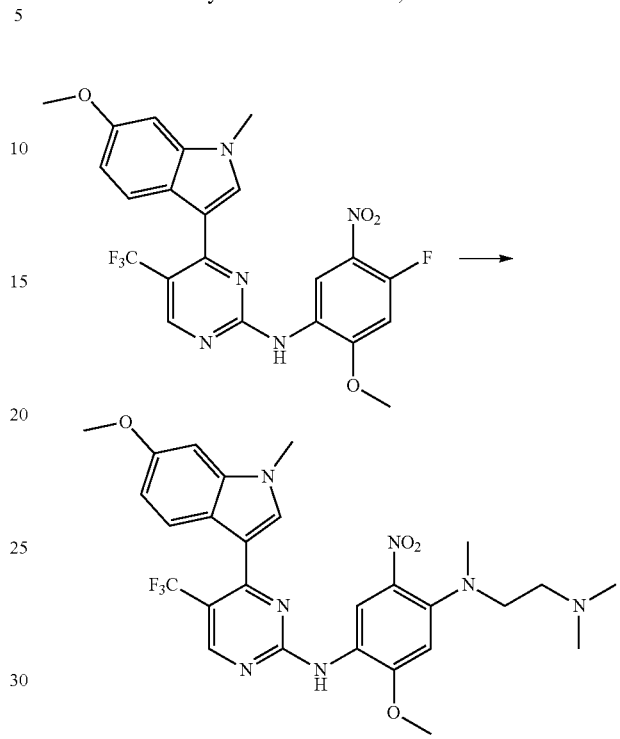

N-(4-fluoro-2-methoxy-5-nitrophenyl)-4-(6-methoxy-1-methyl-1H-indol-3-yl)-5-(trifluoromethyl)pyrimidin-2-amine (100 mg, 0.204 mmol) was dissolved in DMF (5 mL). Then, triethylamine (31 mg, 0.305 mmol) and N1,N1,N2-trimethylethane-1,2-diamine (42 mg, 0.407 mmol) were added. The reaction was heated up to 120° C. by microwave for 30 minutes. After LC-MS showed completion of the reaction, the reaction solution was concentrated to dryness to obtain a crude product, which was further purified by preparative thin-layer chromatography to obtain the product N1-(2-(dimethylamino)ethyl)-5-methoxy-N4-(4-(6-methoxy-1-methyl-1H-indol-3-yl)-5-(trifluoromethyl)pyrimidin-2-yl)-N1-methyl-2-nitrobenzene-1,4-diamine (90 mg, 77%).

Step 5: Preparation of N1-(2-(dimethylamino)ethyl)-5-methoxy-N4-(4-(6-methoxy-1-methyl-1H-indol-3-yl)-5-(trifluoromethyl)pyrimidin-2-yl)-N1-methylbenzene-1,2,4-triamine

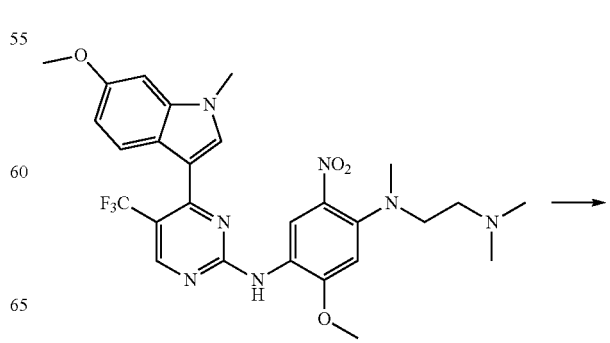

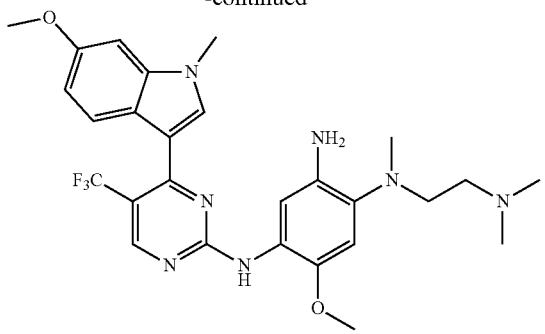

N1-(2-(dimethylamino)ethyl)-5-methoxy-N4-(4-(6-methoxy-1-methyl-1H-indol-3-yl)-5-(trifluoromethyl)pyrimidin-2-yl)-N1-methyl-2-nitrobenzene-1,4-diamine (90 mg, 0.157 mmol) was dissolved in 10 mL of methanol, and Pd/C (15 mg) was added. The reaction was stirred in a hydrogen atmosphere at 24° C. for 1 hour. After LC-MS showed completion of the reaction, the reaction solution was filtered, and the filtrate was concentrated. The resulting residue was purified by flash silica gel column chromatography to obtain 80 mg of the crude product N1-(2-(dimethylamino)ethyl)-5-methoxy-N4-(4-(6-methoxy-1-methyl-1H-indol-3-yl)-5-(trifluoromethyl)pyrimidin-2-yl)-N1-methylbenzene-1,2,4-triamine.

Step 6: Preparation of N-(2-((2-(dimethylamino)ethyl)(methyl)amino)-4-methoxy-5-((4-(6-methoxy-1-methyl-1H-indol-3-yl)-5-(trifluoromethyl)pyrimidin-2-yl)amino)phenyl)acrylamide

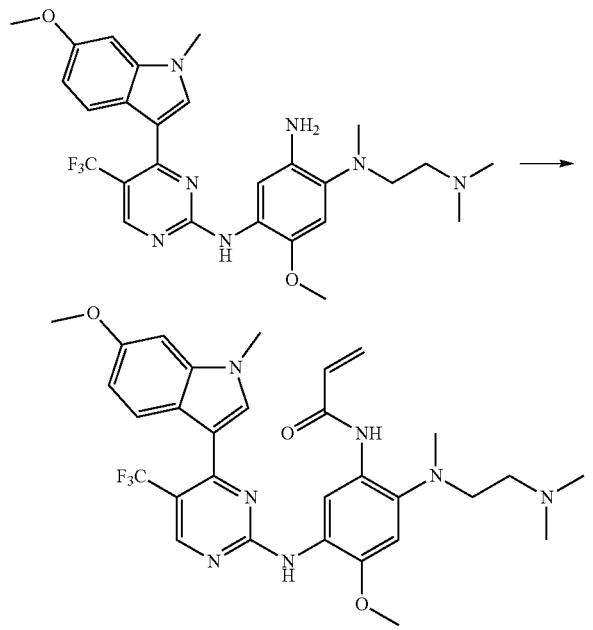

N1-(2-(dimethylamino)ethyl)-5-methoxy-N4-(4-(6-methoxy-1-methyl-1H-indol-3-yl)-5-(trifluoromethyl)pyrimidin-2-yl)-N1-methylbenzene-1,2,4-triamine (80 mg, 0.147 mmol) and triethylamine (45 mg, 0.442 mmol) were dissolved in anhydrous tetrahydrofuran (20 mL). The reaction solution was stirred at −78° C. for 10 minutes, and then acryloyl chloride (0.4 mL, 1 M in THF) was added slowly and dropwise. The reaction was stirred for 30 minutes in a dry ice bath. After LC-MS showed completion of the reaction, the reaction was quenched with methanol. The reaction solution was concentrated, and the resulting residue was purified by preparative thin-layer chromatography to obtain the product N-(2-((2-(dimethylamino)ethyl)(methyl)amino)-4-methoxy-5-((4-(6-methoxy-1-methyl-1H-indol-3-yl)-5-(trifluoromethyl)pyrimidin-2-yl)amino)phenyl)acrylamide (20 mg, 25%).

$^1$H NMR (400 MHz, CD$_3$OD) δ 8.64 (s, 1H), 8.37 (s, 1H), 8.09 (d, J=8.6 Hz, 1H), 7.75 (s, 1H), 7.02-6.95 (m, 2H), 6.78 (dd, J=8.8, 1.8 Hz, 1H), 6.46-6.34 (m, 2H), 5.83 (dd, J=8.3, 3.5 Hz, 1H), 4.00 (s, 3H), 3.87 (d, J=8.4 Hz, 6H), 3.51 (t J=5.7 Hz, 2H), 3.30 (t, J=5.7 Hz, 2H), 2.88 (s, 6H), 2.72 (s, 3H);

MS m/z (ESI): 598.4 [M+H]$^+$.

Example 100: Preparation of N-(5-((5-chloro-4-(1-cyclopropyl-1H-indol-3-yl)pyrimidin-2-yl)amino)-2-((2-(dimethylamino)ethyl)(methyl)amino)-4-methoxyphenyl)acrylamide

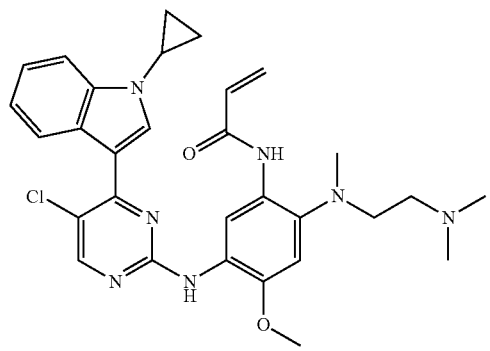 [SMILES: C=CC(=O)Nc1cc(Nc2ncc(Cl)c(-c3cn(C4CC4)c4ccccc34)n2)c(OC)cc1N(C)CCN(C)C]

The preparation method of N-(5-((5-chloro-4-(1-cyclopropyl-1H-indol-3-yl)pyrimidin-2-yl)amino)-2-((2-(dimethylamino)ethyl)(methyl)amino)-4-methoxyphenyl)acrylamide was similar to Example 98.

$^1$H NMR (400 MHz, CD$_3$OD) δ 8.44 (s, 1H), 8.37 (d, J=8.0 Hz, 1H), 8.31 (d, J=10.3 Hz, 2H), 7.66 (d, J=8.2 Hz, 1H), 7.31-7.23 (m, 1H), 7.16 (dd, J=11.2, 4.0 Hz, 1H), 6.99 (s, 1H), 6.45 (d, J=6.2 Hz, 2H), 5.88-5.80 (m, 1H), 3.99 (d, J=2.8 Hz, 3H), 3.52 (dt, J=7.1, 3.7 Hz, 3H), 3.32-3.29 (m, 2H), 2.89 (s, 6H), 2.73 (s, 3H), 1.20 (dt, J=7.2, 3.6 Hz, 2H), 1.08-1.00 (m, 2H);

MS m/z (ESI): 560.3 [M+H]$^+$.

Example 101: Preparation of N-(5-(4-(1-cyclopropyl-1H-indol-3-yl)-5-(trifluoromethyl)pyrimidin-2-yl)amino)-2-((2-(dimethylamino)ethyl)(methyl)amino)-4-methoxyphenyl)acrylamide

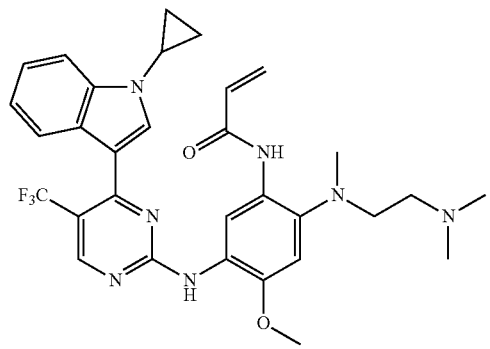 [SMILES: C=CC(=O)Nc1cc(Nc2ncc(C(F)(F)F)c(-c3cn(C4CC4)c4ccccc34)n2)c(OC)cc1N(C)CCN(C)C]

The preparation method of N-(5-((4-(1-cyclopropyl-1H-indol-3-yl)-5-(trifluoromethyl)pyrimidin-2-yl)amino)-2-((2-(dimethylamino)ethyl)(methyl)amino)-4-methoxyphenyl)acrylamide was similar to Example 98.

¹H NMR (400 MHz, CD₃OD) δ 8.68 (s, 1H), 8.41 (s, 1H), 8.19 (d, J=7.8 Hz, 1H), 7.82 (s, 1H), 7.67 (d, J=8.2 Hz, 1H), 7.26 (t, J=7.6 Hz, 1H), 7.14 (t, J=7.5 Hz, 1H), 6.99 (s, 1H), 6.44 (dt, J=14.3, 7.1 Hz, 2H), 5.85 (dd, J=9.2, 2.6 Hz, 1H), 4.01 (s, 3H), 3.60-3.44 (m, 3H), 3.29 (t, J=5.6 Hz, 2H), 2.87 (s, 6H), 2.71 (s, 3H), 1.25-1.18 (m, 2H), 1.06-0.98 (m, 2H): MS m/z (ESI): 594.3 [M+H]⁺.

Example 102: Preparation of N-(2-((2-(dimethylamino)ethyl)(methyl)amino)-5-((4-(1-(N,N-dimethylsulfamoyl)-1H-indol-3-yl)pyrimidin-2-yl)amino)-4-methoxyphenyl)acrylamide

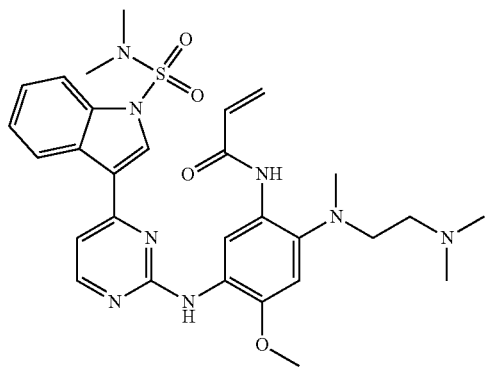 [SMILES: C=CC(=O)Nc1cc(Nc2nccc(-c3cn(S(=O)(=O)N(C)C)c4ccccc34)n2)c(OC)cc1N(C)CCN(C)C]

Step 1: Preparation of 3-(2-chloropyrimidin-4-yl)-1H-indole

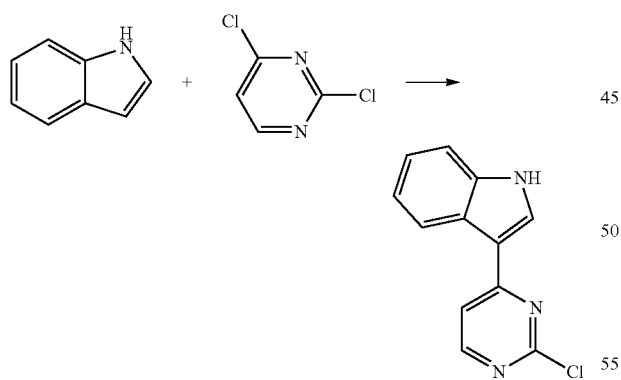

3-(2-chloropyrimidin-4-yl)-1H-indole (1 g, 4.37 mmol), 2-(difluoromethoxy)-4-fluoro-5-nitroaniline (810 mg, 4.37 mmol) and p-toluenesulfonic acid (750 mg, 4.37 mmol) were dissolved in 2-pentanol (40 mL), and then the reaction solution was heated at 110° C. for 3 hours. After LC-MS showed completion of the reaction, the reaction solution was cooled to room temperature naturally, and a dark solid was precipitated. The solid was filtered, and the filter cake was washed with methanol and methyl tert-butyl ether to obtain 3-(2-chloropyrimidin-4-yl)-1H-indole (1.3 g, 79%).

Step 2: Preparation of N-(4-fluoro-2-methoxy-5-nitrophenyl)-4-(1H-indol-3-yl)pyrimidin-2-amine

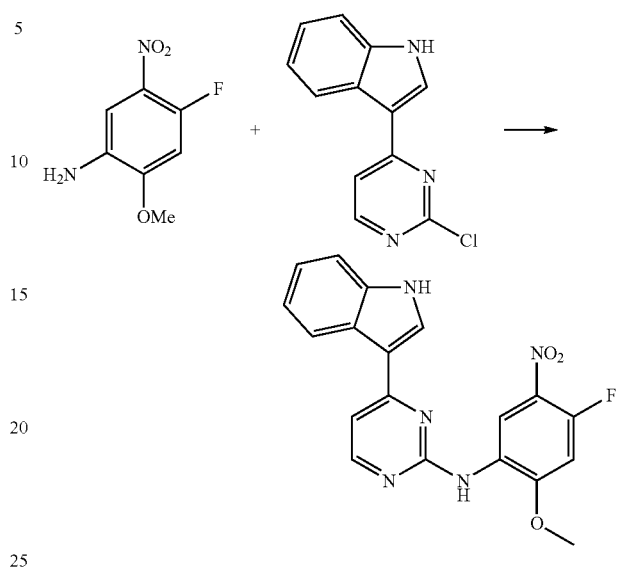

3-(2-chloropyrimidin-4-yl)-1H-indole (500 mg, 2.177 mmol), the starting material 4-fluoro-2-methoxy-5-nitroaniline (445 mg, 2.394 mmol) and p-toluenesulfonic acid monohydrate (414 mg, 2.177 mmol) were dissolved in 2-pentanol (20 mL). The reaction was heated up to 120° C. overnight. After LC-MS showed completion of the reaction, the reaction solution was cooled to room temperature naturally, and a dark solid was precipitated. The solid was filtered, and the filter cake was washed with methanol (1 mL) and methyl tert-butyl ether (1 mL) to obtain the product N-(4-fluoro-2-methoxy-5-nitrophenyl)-4-(1H-indol-3-yl)pyrimidin-2-amine (180 mg, 22%).

Step 3: Preparation of N1-(4-(1H-indol-3-yl)pyrimidin-2-yl)-N4-(2-(dimethylamino)ethyl)-2-methoxy-N4-methyl-5-nitrobenzene-1,4-diamine

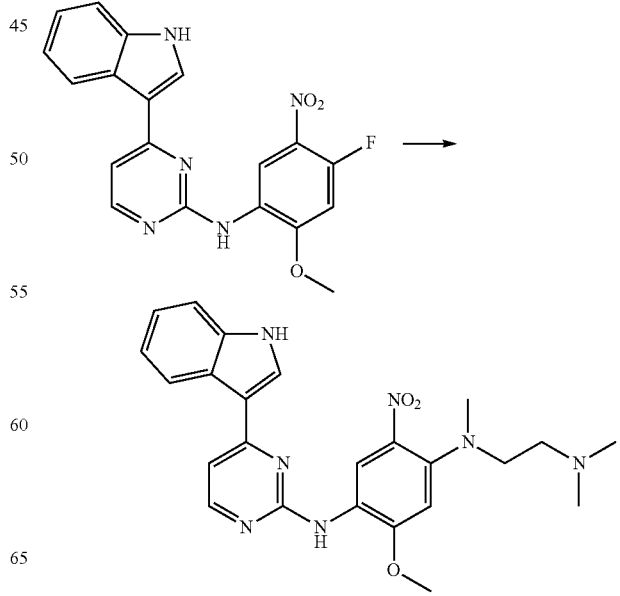

N-(4-fluoro-2-methoxy-5-nitrophenyl)-4-(1H-indol-3-yl) pyrimidin-2-amine (178 mg, 0.469 mmol) was dissolved in DMF (2 mL), followed by addition of triethylamine (142 mg, 1.41 mmol) and trimethylethylenediamine (144 mg, 1.41 mmol). The reaction was heated up to 120° C. by microwave, and then reacted for 30 minutes. After LC-MS showed completion of the reaction, the reaction solution was concentrated to dryness to obtain a crude product which was further purified by preparative thin-layer chromatography to obtain the product N1-(4-(1H-indol-3-yl)pyrimidin-2-yl)-N4-(2-(dimethylamino)ethyl)-2-methoxy-N4-methyl-5-nitrobenzene-1,4-diamine (217 mg, 100%).

Step 4: Preparation of 3-(2-((4-((2-(dimethylamino) ethyl)(methyl)amino) 2-methoxy-5-nitrophenyl) amino)pyrimidin-4-yl)-N,N-dimethyl-1H-indole-1-sulfonamide

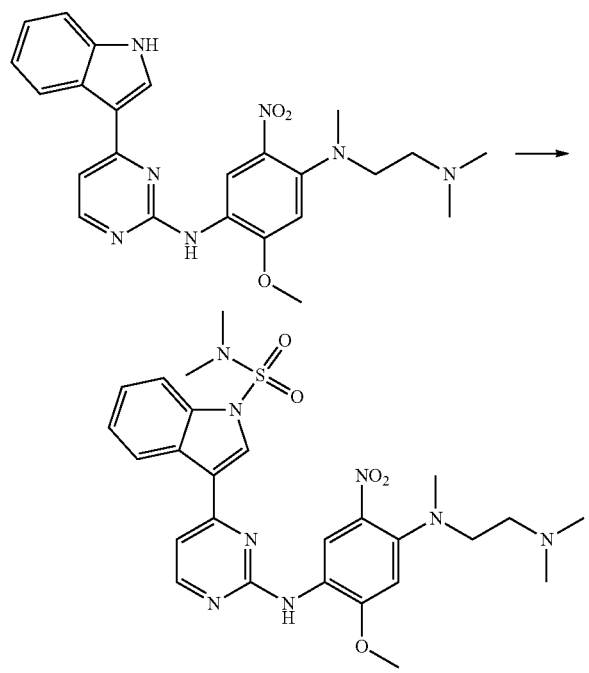

N1-(4-(1H-indol-3-yl)pyrimidin-2-yl)-N4-(2-(dimethylamino)ethyl)-2-methoxy-N4-methyl-5-nitrobenzene-1,4-diamine (217 mg, 0.47 mmol) was dissolved in DMF (10 mL), and the mixture was cooled to 0° C. in an ice bath, then NaH (56 mg, 1.41 mmol) was added. After the reaction was carried out at 0° C. for 10 minutes, dimethylsulfamoyl chloride (74 mg, 0.52 mmol) was added dropwise. The reaction solution was warmed up to room temperature and stirred for 30 minutes. After the reaction was quenched, dichloromethane and water were added. The reaction solution was extracted three times. The organic phases were combined, washed with saturated sodium bicarbonate, water and saturated brine, filtered, and concentrated to obtain a crude product, which was further purified by flash silica gel column chromatography to obtain the product 3-(2-((4-((2-(dimethylamino)ethyl)(methyl)amino)-2-methoxy-5-nitrophenyl)amino)pyrimidin-4-yl)-N,N-dimethyl-1H-indole-1-sulfonamide (160 mg, 60%).

Step 5: Preparation of 3-(2-((15-amino-4-((2-(dimethylamino)ethyl)(methyl)amino)-2-methoxyphenyl) amino)pyrimidin-4-yl)-N,N-dimethyl-1H-indole-1-sulfonamide

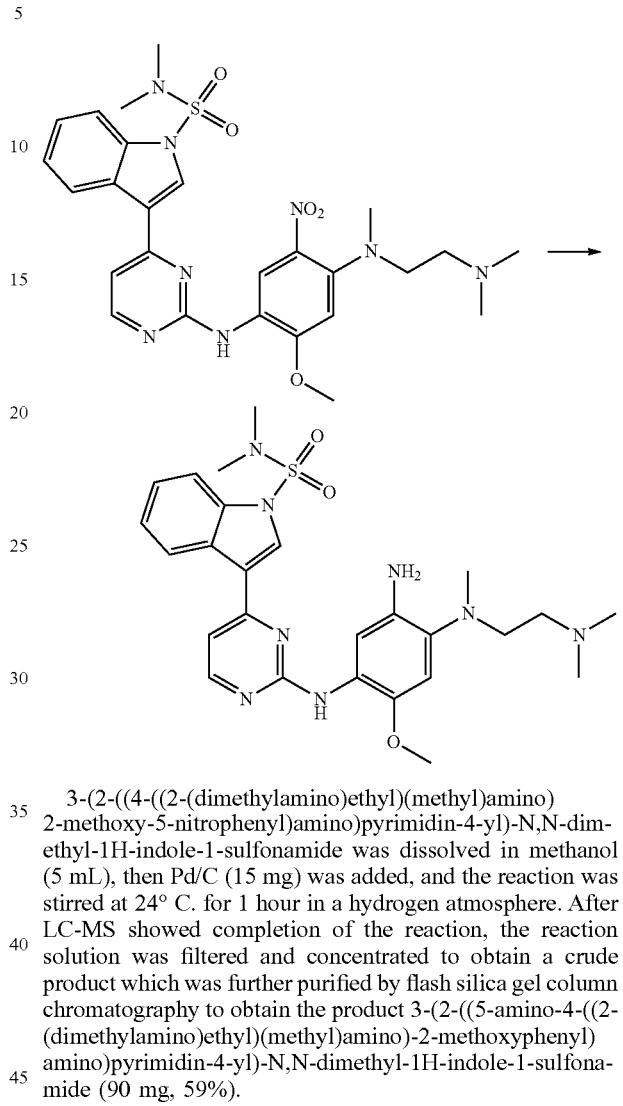

3-(2-((4-((2-(dimethylamino)ethyl)(methyl)amino) 2-methoxy-5-nitrophenyl)amino)pyrimidin-4-yl)-N,N-dimethyl-1H-indole-1-sulfonamide was dissolved in methanol (5 mL), then Pd/C (15 mg) was added, and the reaction was stirred at 24° C. for 1 hour in a hydrogen atmosphere. After LC-MS showed completion of the reaction, the reaction solution was filtered and concentrated to obtain a crude product which was further purified by flash silica gel column chromatography to obtain the product 3-(2-((5-amino-4-((2-(dimethylamino)ethyl)(methyl)amino)-2-methoxyphenyl) amino)pyrimidin-4-yl)-N,N-dimethyl-1H-indole-1-sulfonamide (90 mg, 59%).

Step 6: Preparation of N-(2-((2-(dimethylamino) ethyl)(methyl)amino)-5-((4-(1-(N,N-dimethylsulfamoyl)-1H-indol-3-yl)pyrimidin-2-yl)amino)-4-methoxyphenyl)acrylamide

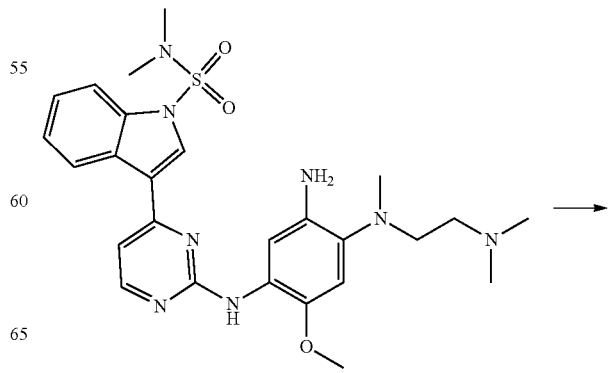

-continued

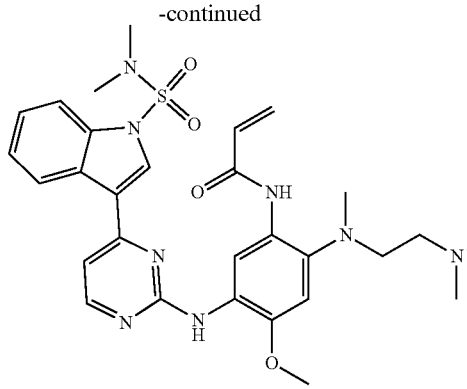

3-(2-((5-amino-4-((2-(dimethylamino)ethyl)(methyl)amino)-2-methoxyphenyl)amino)pyrimidin-4-yl)-N,N-dimethyl-1H-indole-1-sulfonamide (90 mg, 0.167 mmol) and triethylamine (51 mg, 0.501 mmol) were dissolved in anhydrous tetrahydrofuran (30 mL), and the reaction solution was stirred at −78° C. for 10 minutes. Acryloyl chloride (0.5 mL, 1M in THF) was added slowly and dropwise. The reaction was stirred in a dry ice bath for 30 minutes. After LC-MS showed completion of the reaction, the reaction was quenched with methanol. The reaction solution was concentrated, and the resulting residue was purified by preparative thin-layer chromatography to obtain the product N-(2-((2-(dimethylamino)ethyl)(methyl)amino)-5-((4-(1-(N,N-dimethylsulfamoyl)-1H-indol-3-yl)pyrimidin-2-yl)amino)-4-methoxyphenyl)acrylamide (10 mg, 10%).

$^1$H NMR (400 MHz, CD$_3$OD) δ 8.62 (s, 1H), 8.44 (d, J=7.9 Hz, 1H), 8.27 (d, J=6.2 Hz, 1H), 8.10 (s, 1H), 8.00 (d, J=8.3 Hz, 1H), 7.54 (d, J=6.3 Hz, 1H), 7.37 (dt, J=15.0, 7.3 Hz, 2H), 7.06 (s, 1H), 6.58 (dd, J=16.9, 10.0 Hz, 1H), 6.46 (dd, J=16.9, 1.8 Hz, 1H), 5.86 (dd, J=10.0, 1.7 Hz, 1H), 3.98 (s, 3H), 3.55 (t, J=5.7 Hz, 2H), 3.36 (d, J=5.9 Hz, 2H), 2.92 (d, J=3.7 Hz, 12H), 2.79 (s, 3H):

MS m/z (ESI): 593.5 [M+H]$^+$.

Example 103: Preparation of N-(2-((2-(diethylamino)ethyl)(methyl)amino)-5-(((4-(1-(N,N-dimethylsulfamoyl)-1H-indol-3-yl)pyrimidin-2-yl)amino)-4-methoxyphenyl)acrylamide

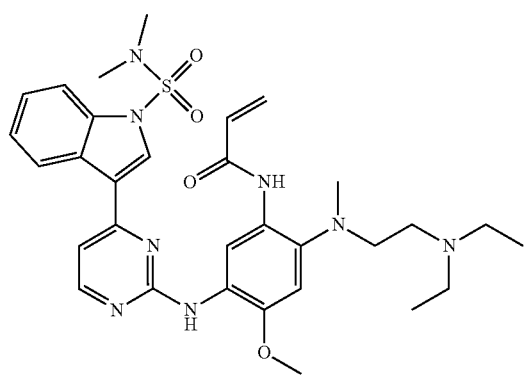 [SMILES: C=CC(=O)Nc1cc(Nc2nccc(-c3cn(S(=O)(=O)N(C)C)c4ccccc34)n2)c(OC)cc1N(C)CCN(CC)CC]

Step 1: Preparation of N1-(4-(1H-indol-3-yl)pyrimidin-2-yl)-N4-(2-(diethylamino)ethyl)-2-methoxy-N4-methyl-5-nitrobenzene-1,4-diamine

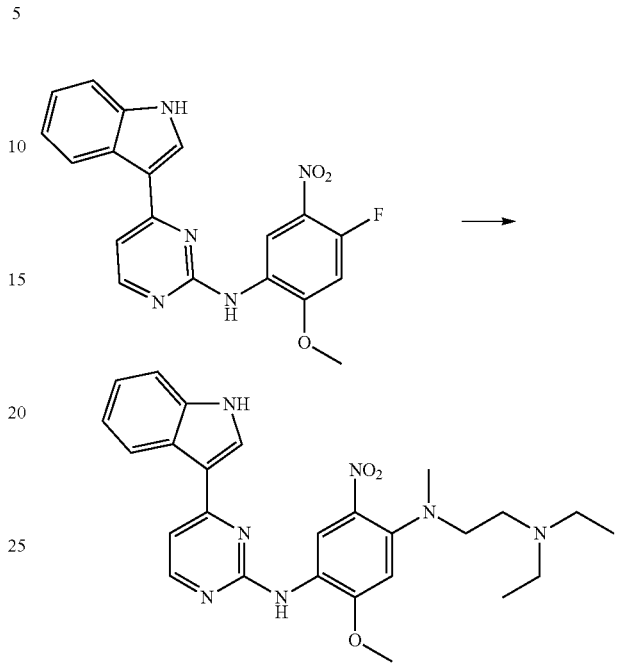

N-(4-fluoro-2-methoxy-5-nitrophenyl)-4-(1H-indol-3-yl)pyrimidin-2-amine (120 mg, 0.316 mmol) was dissolved in DMF (2 mL). Triethylamine (96 mg, 0.949 mmol) and N,N-diethyl-N-methylethane-1,2-diamine (124 mg, 0.949 mmol) were added. The reaction was heated up to 120° C. by microwave and reacted for 30 minutes. After LC-MS showed completion of the reaction, the reaction solution was concentrated to dryness to obtain a crude product, which was further purified by preparative thin-layer chromatography to obtain the product N1-(4-(1H-indol-3-yl)pyrimidin-2-yl)-N4-(2-(diethylamino)ethyl)-2-methoxy-N4-methyl-5-nitrobenzene-1,4-diamine (155 mg, 100%).

Step 2: Preparation of 3-(2-((4-(2-(diethylamino)ethyl)(methyl)amino)-2-methoxy-5-nitrophenyl)amino)pyrimidin-4-yl)-N,N-dimethyl-1H-indole-1-sulfonamide

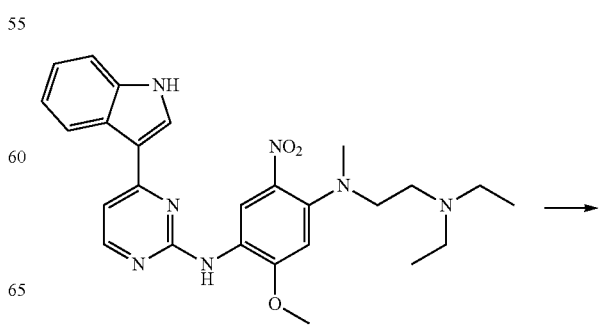

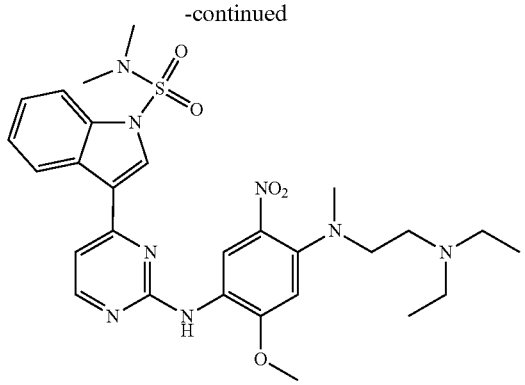

N1-(4-(1H-indol-3-yl)pyrimidin-2-yl)-N4-(2-(diethylamino)ethyl)-2-methoxy-N4-methyl-5-nitrobenzene-1,4-diamine (155 mg, 0.316 mmol) was dissolved in DMF (10 mL). The reaction was cooled to 0° C. in an ice bath, and then NaH (38 mg, 0.945 mmol) was added. After the reaction was carried out for 10 minutes at 0° C., dimethylsulfamoyl chloride (55 mg, 0.38 mmol) was added dropwise. The reaction solution was warmed up to room temperature and stirred for 30 minutes. After the reaction was quenched, dichloromethane and water were added. The reaction solution was extracted three times. The organic phases were combined, washed with saturated sodium bicarbonate aqueous solution, water and saturated brine, filtered, and evaporated to dryness to obtain a crude product, which was further purified by flash silica gel column chromatography to obtain the product 3-(2-((4-((2-(diethylamino)ethyl)(methyl)amino)-2-methoxy-5-nitrophenyl)amino)pyrimidin-4-yl)-N,N-dimethyl-1H-indole-1-sulfonamide (130 mg, 19%).

Step 3: Preparation of 3-(2-((5-amino-4-((2-(diethylamino)ethyl)(methyl)amino)-2-methoxyphenyl)amino) pyrimidin-4-yl)-N,N-dimethyl-1H-indole-1-sulfonamide

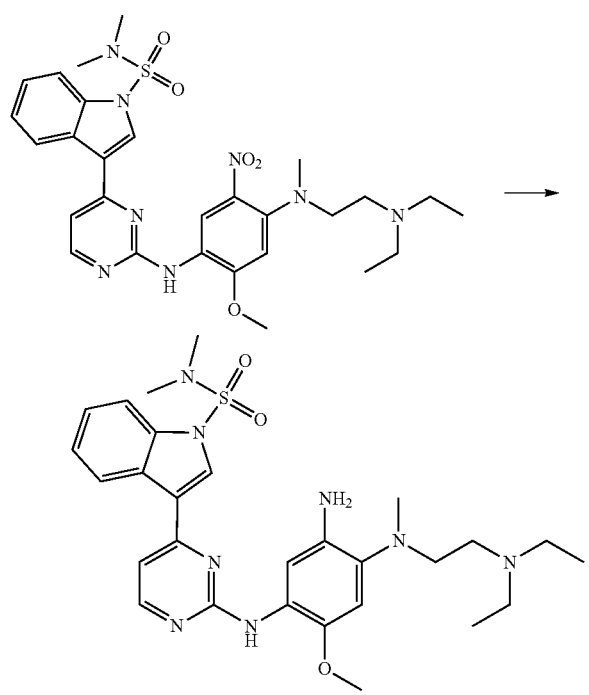

3-(2-((4-((2-(diethylamino)ethyl)(methyl)amino)-2-methoxy-5-nitrophenyl)amino)pyrimidin-4-yl)-N,N-dimethyl-1H-indole-1-sulfonamide was dissolved in methanol (5 mL), and Pd/C (15 mg) was added. The reaction was stirred in a hydrogen atmosphere at 24° C. for 1 hour. After LC-MS showed completion of the reaction, the reaction solution was filtered, and the filtrate was concentrated. The resulting residue was purified by flash silica gel column chromatography to obtain 118 mg of the crude product 3-(2-((5-amino-4-((2-(diethylamino)ethyl)(methyl)amino)-2-methoxyphenyl)amino)pyrimidin-4-yl)-N,N-dimethyl-1H-indole-1-sulfonamide.

Step 4: Preparation of N-(2-((2-(diethylamino)ethyl)(methyl)amino)-5-((4-(1-(N,N-dimethylsulfamoyl)-1H-indol-3-yl)pyrimidin-2-yl)amino)-4-methoxyphenyl)acrylamide

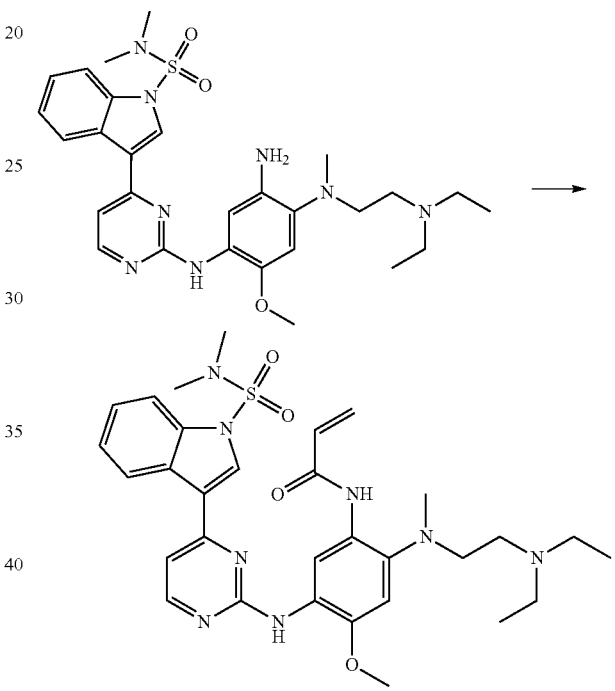

3-(2-((5-amino-4-((2-(diethylamino)ethyl)(methyl)amino)-2-methoxyphenyl)amino)pyrimidin-4-yl)-N,N-dimethyl-1H-indole-1-sulfonamide (118 mg, 0.208 mmol) and triethylamine (63 mg, 0.624 mmol) were dissolved in anhydrous tetrahydrofuran (30 mL). The reaction solution was stirred at −78° C. for 10 minutes, then acryloyl chloride (0.62 mL, 1 M in THF) was added slowly and dropwise. The reaction was stirred for 30 minutes in a dry ice bath. After LC-MS showed completion of the reaction, the reaction was quenched with methanol. The reaction solution was concentrated, and the resulting residue was purified by preparative thin-layer chromatography to obtain the product N-(2-((2-(diethylamino)ethyl)(methyl)amino)-5-((4-(1-(N,N-dimethylsulfamoyl)-1H-indol-3-yl)pyrimidin-2-yl)amino)-4-methoxyphenyl)acrylamide (4.8 mg, 3.7%).

$^1$H NMR (400 MHz, CD3OD) δ 8.61 (s, 1H), 8.46 (d, J=8.0 Hz, 1H), 8.33 (d, J=6.1 Hz, 1H), 8.08 (s, 1H), 8.02 (d, J=8.3 Hz, 1H), 7.55 (d, J=6.1 Hz, 1H), 7.45-7.26 (m, 2H), 7.04 (s, 1H), 6.48 (qd, J=17.0, 5.9 Hz, 2H), 5.87 (dd, J=9.4, 2.5 Hz, 1H), 4.01 (s, 3H), 3.57 (t, J=5.7 Hz, 2H), 3.25 (dt, J=19.4, 7.2 Hz, 4H), 2.93 (s, 6H), 2.79 (s, 3H), 1.29 (t, J=7.3 Hz, 6H):

MS m/z (ESI): 621.5 [M+H]$^+$.

Example 104: Preparation of N-(2-((2-(dimethyl-amino)ethyl)(methyl)amino)-4-methoxy-5-((4-(1-(oxetan-3-yl)-1H-indol-3-yl)pyrimidin-2-yl)amino)phenyl)acrylamide

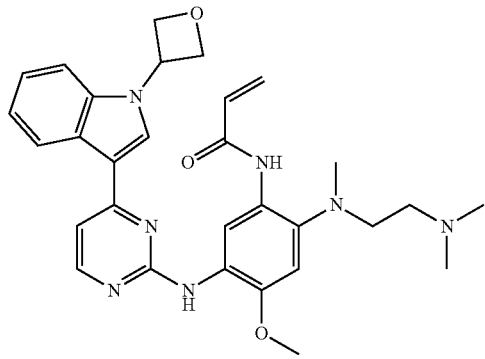 [SMILES: C=CC(=O)Nc1cc(Nc2nccc(-c3cn(C4COC4)c4ccccc34)n2)c(OC)cc1N(C)CCN(C)C]

Step 1: Preparation of 3-(2-chloropyrimidin-4-yl)-1-(oxetan-3-yl)-1H-indole

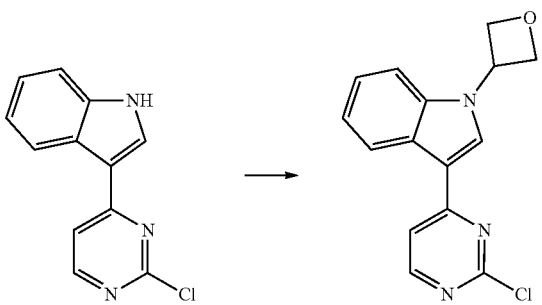 [SMILES: Clc1nccc(-c2c[nH]c3ccccc23)n1 ; Clc1nccc(-c2cn(C3COC3)c3ccccc23)n1]

3-(2-chloropyrimidin-4-yl)-1H-indole (500 mg, 2.18 mmol), 3-iodo-oxetane (480 mg, 2.61 mmol), and cesium carbonate (1.42 g, 4.36 mmol) were mixed in DMF (5 mL). The reaction was carried out at 110° C. for 1 hour in a microwave. After cooling, the reaction solution was diluted with CH₂Cl₂. The organic phase was washed three times with saturated brine, dried over anhydrous sodium sulfate, concentrated and purified by column chromatography to obtain the title compound 3-(2-chloropyrimidin-4-yl)-1-(oxetan-3-yl)-1H-indole (110 mg, 18%).

¹H NMR (400 MHz, CDCl₃): δ 8.54 (d, J=5.2 Hz, 1H), 8.38 (m, 1H), 8.33 (s, 1H), 7.60 (d, J=5.2 Hz, 1H), 7.54 (m, 1H), 7.38 (m, 2H), 5.66 (m, 1H), 5.26 (t, J=7.6 Hz, 2H), 5.14 (t, J=7.6 Hz, 2H);

MS m/z (ESI): 286.1 [M+H]⁺.

Step 2: Preparation of N-(4-fluoro-2-methoxy-5-nitrophenyl)-4-(1-(oxetan-3-yl)-1H-indol-3-yl)pyrimidin-2-amine

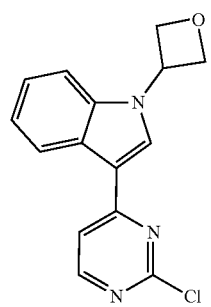

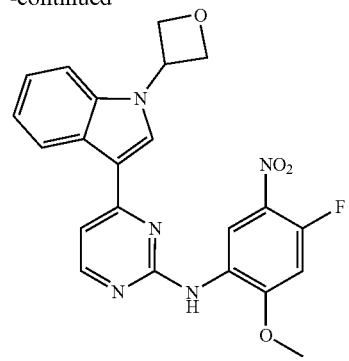

3-(2-chloropyrimidin-4-yl)-1-(oxetan-3-yl)-1H-indole (110 mg, 0.385 mmol), 4-fluoro-2-methoxy-5-nitroaniline (86 mg, 0.462 mmol), palladium acetate (9 mg, 0.0385 mmol) and cesium carbonate (376 mg, 1.16 mmol) were mixed in a mixture of DMA (1 mL) and 1,4-dioxane (2 mL). The reaction mixture was purged with nitrogen to remove oxygen for 15 minutes. Xantphos (45 mg, 0.0770 mmol) was added, and the reaction mixture was further purged with nitrogen for 5 minutes. The reaction was carried out at 160° C. for 30 minutes in a microwave reactor. After cooling, the reaction mixture was diluted with CH₂Cl₂, washed with saturated brine, dried over anhydrous sodium sulfate, concentrated and purified by preparative thin-layer chromatography to obtain the title compound N-(4-fluoro-2-methoxy-5-nitrophenyl)-4-(1-(oxetan-3-yl)-1H-indol-3-yl)pyrimidin-2-amine (80 mg, 46%).

MS m/z (ESI): 436.1 [M+H]⁺.

Step 3: Preparation of N1-(2-(dimethylamino)ethyl)-5-methoxy-N1-methyl-2-nitro-N4-(4-(1-(oxetan-3-yl)-1H-indol-3-yl)pyrimidin-2-yl)benzene-1,4-diamine

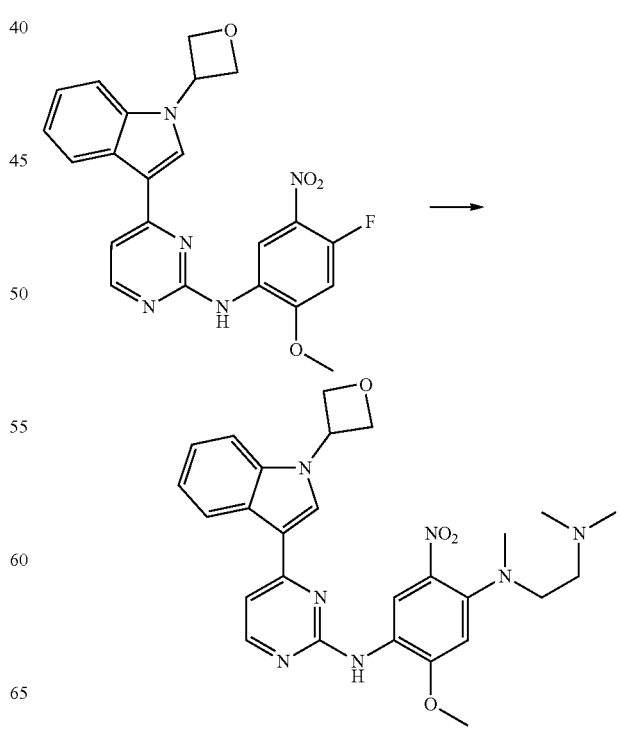

Trimethylethylenediamine (0.1 mL) and DIPEA (0.1 mL) were added to a solution of N-(4-fluoro-2-methoxy-5-nitrophenyl)-4-(1-(oxetan-3-yl)-1H-indol-3-yl)pyrimidin-2-amine (80 mg, 0.18 mmol) in DMA (1 mL). The reaction mixture was stirred at 85° C. for 3 hours. After cooling, water was added, and then a solid was precipitated. The solid was purified by preparative thin-layer chromatography to obtain the compound N1-(2-(dimethylamino)ethyl)-5-methoxy-N1-methyl-2-nitro-N4-(4-(1-(oxetan-3-yl)-1H-indol-3-yl)pyrimidin-2-yl)benzene-1,4-diamine (35 mg, 38%).

MS m/z (ESI): 518.2 [M+H]⁺.

Step 4: Preparation of N1-(2-(dimethylamino)ethyl)-5-methoxy-N1-methyl-N4-(4-(1-(oxetan-3-yl)-1H-indol-3-yl)pyrimidin-2-yl)benzene-1,2,4-triamine

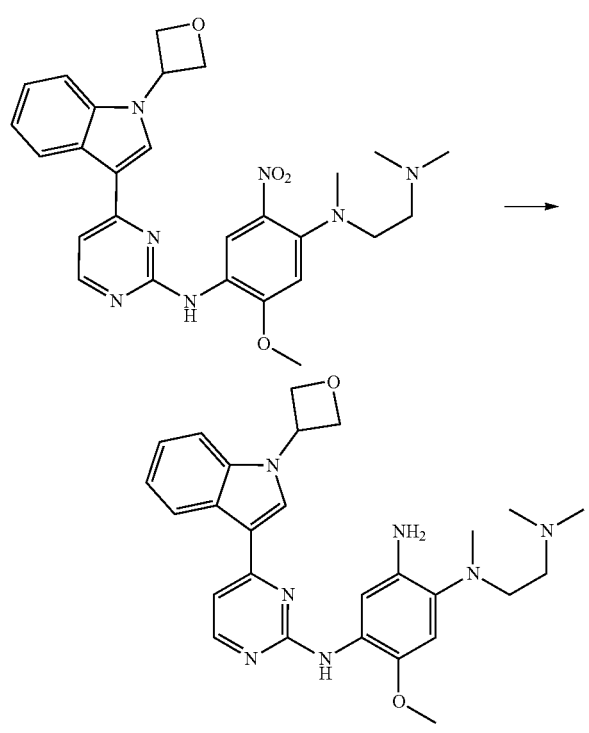

N1-(2-(dimethylamino)ethyl)-5-methoxy-N1-methyl-2-nitro-N4-(4-(1-(oxetan-3-yl)-1H-indol-3-yl)pyrimidin-2-yl)benzene-1,4-diamine (28 mg, 0.054 mmol), reduced iron powder (30 mg, 0.54 mmol) and ammonium chloride (2.0 mg, 0.032 mmol) were mixed in a mixture of ethanol (3 mL) and water (1 mL), and then the reaction mixture was heated up to reflux for one hour, then cooled, and filtered through celite. The resulting filtrate was concentrated and purified by preparative thin-layer chromatography to obtain the title compound N1-(2-(dimethylamino)ethyl)-5-methoxy-N1-methyl-N4-(4-(1-(oxetan-3-yl)-1H-indol-3-yl)pyrimidin-2-yl)benzene-1,2,4-triamine (25 mg, 95%).

MS m/z (ESI): 488.3 [M+H]⁺.

Step 5: Preparation of N-(2-((2-(dimethylamino)ethyl)(methyl)amino)-4-methoxy-5-((4-(1-(oxetan-3-yl)-1H-indol-3-yl)pyrimidin-2-yl)amino)phenyl)acrylamide

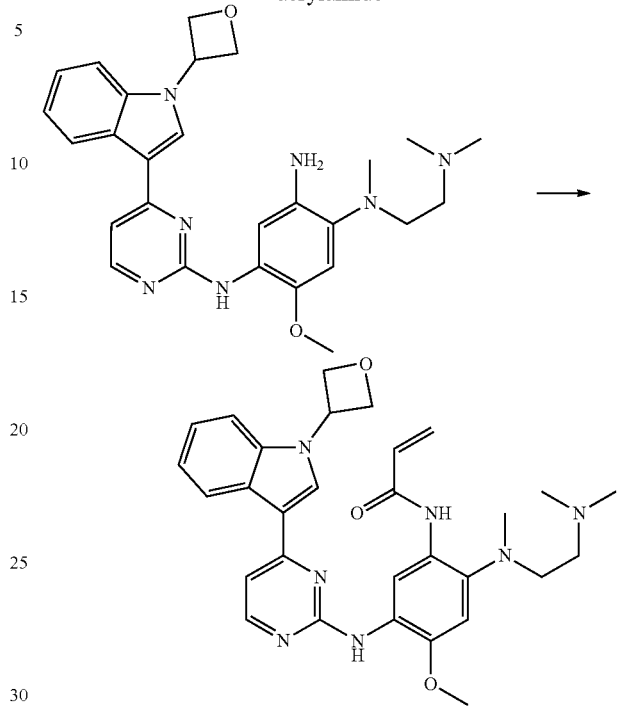

A solution of acryloyl chloride (0.025 mL, 0.31 mmol) in THF (0.5 mL) was added dropwise to a solution of N1-(2-(dimethylamino)ethyl)-5-methoxy-N1-methyl-N4-(4-(1-(oxetan-3-yl)-1H-indol-3-yl)pyrimidin-2-yl)benzene-1,2,4-triamine (25 mg, 0.051 mmol) and triethylamine (0.050 mL, 0.36 mmol) in THF (2 mL) at −15° C. Upon completion of the addition, the mixture was stirred at this temperature for 5 minutes, quenched with methanol, and purified by preparative thin-layer chromatography to obtain the title compound N-(2-((2-(dimethylamino)ethyl)(methyl)amino)-4-methoxy-5-((4-(1-(oxetan-3-yl)-1H-indol-3-yl)pyrimidin-2-yl)amino)phenyl)acrylamide (7 mg, 25%).

¹H NMR (400 MHz, CDCl₃): δ 10.2 (br s, 1H), 9.80 (s, 1H), 9.06 (s, 1H), 8.42 (d, J=5.2 Hz, 1H), 8.10 (m, 1H), 7.73 (m, 2H), 7.30 (m, 2H), 7.23 (d, J=5.2 Hz, 1H), 6.79 (s, 1H), 6.44 (m, 2H), 5.89 (m, 1H), 5.74 (m, 1H), 5.38 (t, J=6.8 Hz, 2H), 5.15 (t, J=7.6 Hz, 2H), 3.89 (s, 3H), 2.92 (m, 2H), 2.71 (s, 3H), 2.29 (m, 8H);

MS m/z (ESI): 542.3 [M+H]⁺.

Example 105: Preparation of N-(2-((2-(dimethylamino)ethyl)(methyl)amino)-5-((4-(5-ethoxy-1H-indazol-1-yl)pyrimidin-2-yl)amino)-4-methoxyphenyl)acrylamide

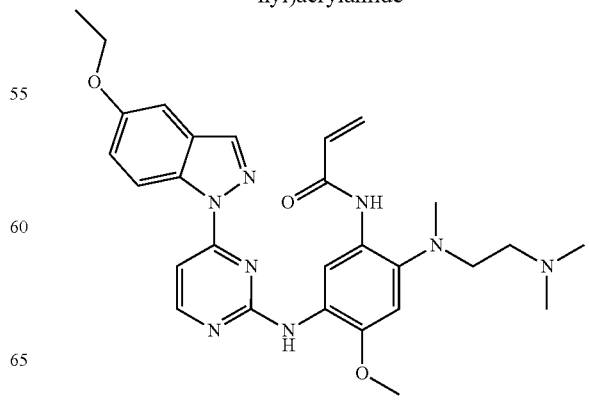

Step 1: Preparation of 5-ethoxy-1H-indazole

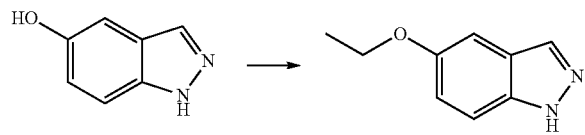

5-hydroxy-1H-indazole (2.68 g, 20 mmol) was dissolved in DMF (50 mL), and then ethyl iodide (3.28 g, 21 mmol) and potassium carbonate (4.16 g, 30 mmol) were added. The mixture was stirred at room temperature for 24 hours, extracted with ethyl acetate and purified by column chromatography to obtain 5-ethoxy-1H-indazole (1.5 g, 46%).

$^1$H NMR (400 MHz, CDCl$_3$) δ 8.73-8.18 (m, 1H), 8.03 (d, J=0.9 Hz, 1H), 7.42 (d, J=8.6 Hz, 1H), 7.15-7.06 (m, 2H), 4.10 (q, J=7.0 Hz, 2H), 1.48 (t, J=7.0 Hz, 3H);

MS m/z (ESI): 163 [M+H]$^+$.

Steps 2 and 3: Preparation of 5-ethoxy-1-(2-(methylsulfonyl)pyrimidin-4-yl)-1H-indazole

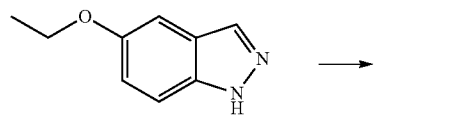

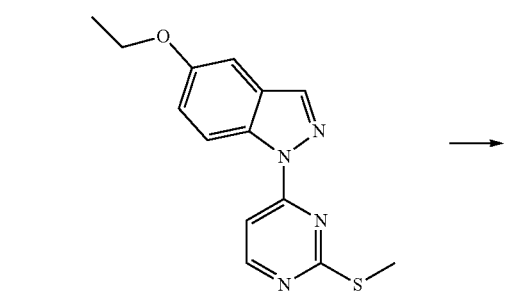

The preparation method of 5-ethoxy-1-(2-(methylsulfonyl)pyrimidin-4-yl)-1H-indazole was similar to Example 43.

Step 4: Preparation of 4-(5-ethoxy-1H-indazol-1-yl)-N-(4-fluoro-2-methoxy-5-nitrophenyl)pyrimidin-2-amine

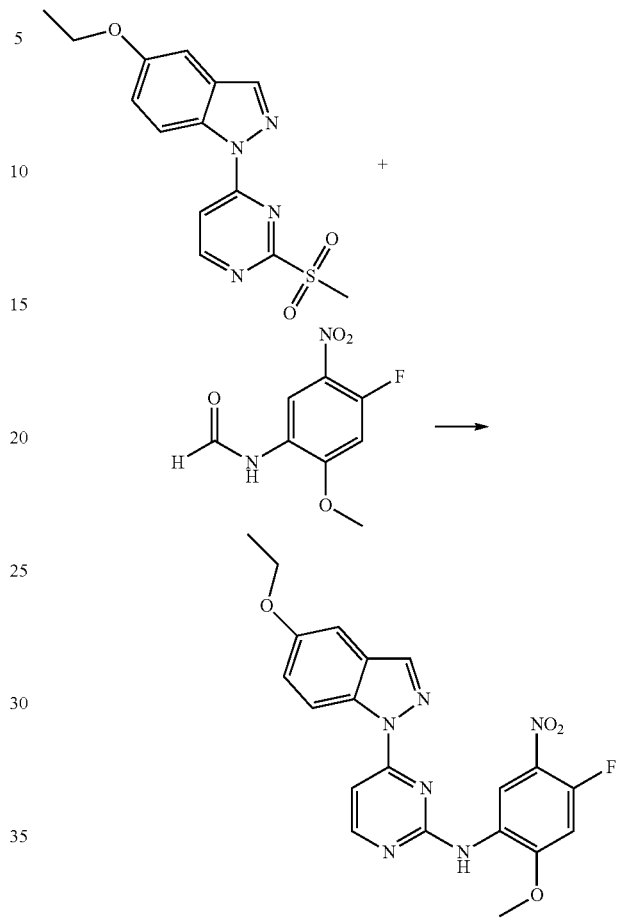

N-(4-fluoro-2-methoxy-5-nitrophenyl)formamide (134 mg, 0.63 mmol) was dissolved in THF (20 mL), and sodium hydride (50 mg, 1.26 mmol) was added at 0° C. After the mixture was stirred for 10 minutes, 5-ethoxy-1-(2-(methylsulfonyl)pyrimidin-4-yl)-1H-indazole (200 mg, 0.63 mmol) was added, and then the mixture was stirred overnight. After an appropriate amount of 1N sodium hydroxide aqueous solution was added, the mixture was stirred for 30 minutes, extracted with DCM, and purified by column chromatography to obtain 4-(5-ethoxy-1H-indazol-1-yl)-N-(4-fluoro-2-methoxy-5-nitrophenyl)pyrimidin-2-amine (210 mg, 78%).

Steps 5 to 7: Preparation of N-(2-((2-(dimethylamino)ethyl)(methyl)amino)-5-((4-(5-ethoxy-1H-indazol-1-yl)pyrimidin-2-yl)amino)-4-methoxyphenyl)acrylamide

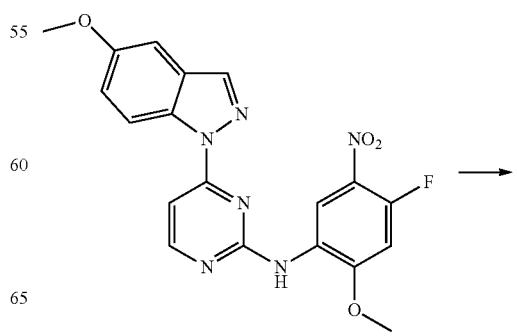

-continued

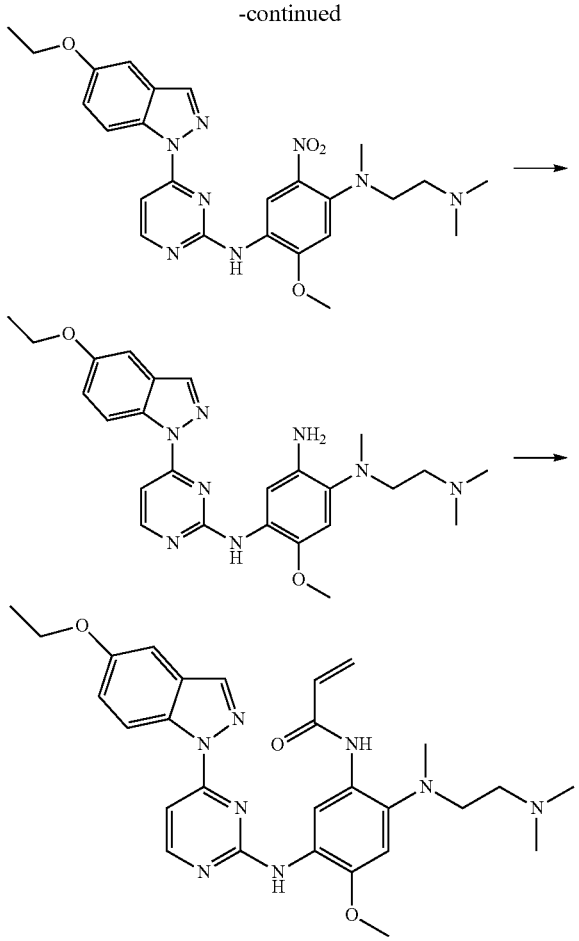

The preparation method of N-(2-((2-(dimethylamino)ethyl)(methyl)amino)-5-((4-(5-ethoxy-1H-indazol-1-yl)pyrimidin-2-yl)amino)-4-methoxyphenyl)acrylamide was similar to Example 43.

$^1$H NMR (400 MHz, CD$_3$OD) δ 8.39 (s, 2H), 8.33-8.22 (m, 1H), 7.84 (s, 1H), 7.62 (d, J=6.8 Hz, 1H), 7.31 (s, 1H), 7.19-7.11 (m, 1H), 7.09 (s, 1H), 6.52 (d, J=9.4 Hz, 2H), 5.95-5.84 (m, 1H), 4.12 (d, J=7.0 Hz, 2H), 3.97 (s, 3H), 3.58 (s, 2H), 3.37 (s, 2H), 2.94 (s, 6H), 2.82 (s, 3H), 1.45 (t, J=7.0 Hz, 3H);

MS m/z (ESI): 531 [M+H]$^+$.

Example 106: Preparation of N-(5-((4-(5-cyano-3-methyl-1H-indazol-1-yl)-5-(trifluoromethyl)pyrimidin-2-yl)amino)-2-((2-(dimethylamino)ethyl)(methyl)amino)-4-methoxyphenyl)acrylamide

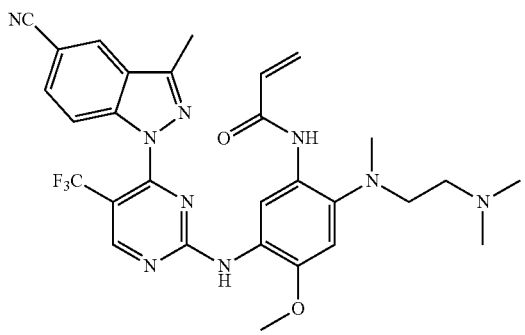 [SMILES: C=CC(=O)Nc1cc(Nc2ncc(C(F)(F)F)c(-n3nc(C)c4cc(C#N)ccc43)n2)c(OC)cc1N(C)CCN(C)C]

Step 1: Preparation of 5-bromo-3-methyl-1H-indazole

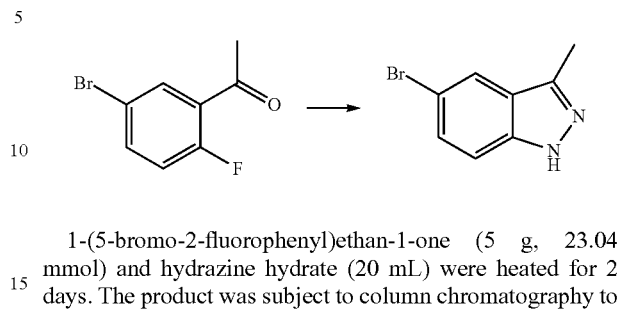

1-(5-bromo-2-fluorophenyl)ethan-1-one (5 g, 23.04 mmol) and hydrazine hydrate (20 mL) were heated for 2 days. The product was subject to column chromatography to obtain 5-bromo-3-methyl-1H-indazole (2.8 g, 58%).

Step 2: Preparation of 5-cyano-3-methyl-1H-indazole

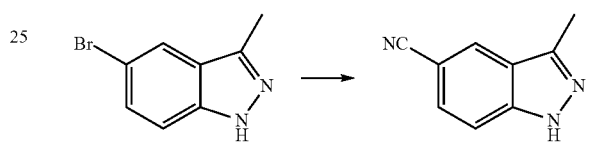

5-bromo-3-methyl-1H-indazole (500 mg, 2.38 mol), zinc cyanide (418 mg, 3.57 mmol), Pd$_2$(dba)$_3$ (194 mg, 0.238 mmol) and X-Phos (227 mg, 0.476 mol) were added to a microwave tube. After purging with nitrogen to remove oxygen, the mixture was heated for 1 hour, and then was subjected to column chromatography to obtain 5-cyano-3-methyl-1H-indazole (430 mg, 98%).

$^1$H NMR (400 MHz, CDCl$_3$) δ 8.12 (s, 1H), 7.61 (s, 1H), 7.56 (d, J=8.7 Hz, 1H), 2.66 (s, 3H);

MS m/z (ESI): 158 [M+H]$^+$.

Steps 3 to 7: Preparation of N-(5-((4-(5-cyano-3-methyl-1H-indazol-1-yl)-5-(trifluoromethyl)pyrimidin-2-yl)amino)-2-((2-(dimethylamino)ethyl)(methyl)amino)-4-methoxyphenyl)acrylamide

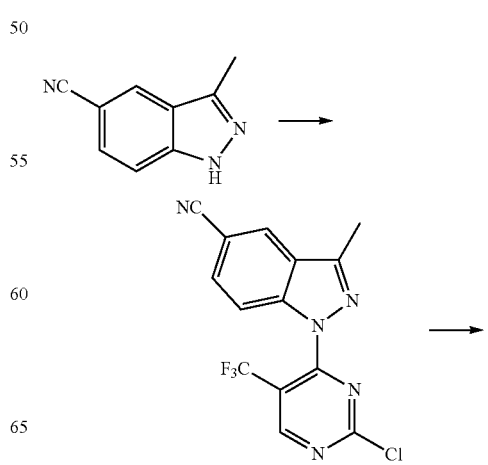

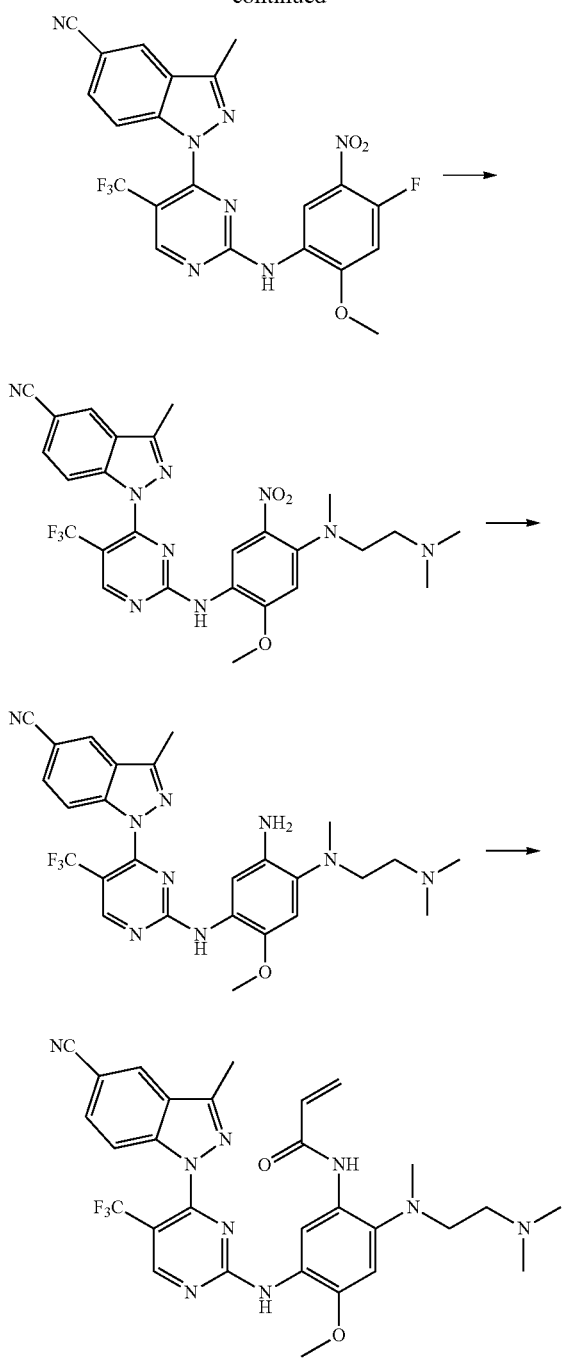

Steps 3 to 7: The preparation method of N-(5-((4-(5-cyano-3-methyl-1H-indazol-1-yl)-5-(trifluoromethyl)pyrimidin-2-yl)amino)-2-((2-(dimethylamino)ethyl)(methyl)amino)-4-methoxyphenyl)acrylamide was similar to Example 40.

$^1$H NMR (400 MHz, CD$_3$OD) δ 8.85 (s, 1H), 8.48-8.35 (m, 1H), 8.35-8.30 (m, 1H), 8.06 (s, 1H), 7.77-7.62 (m, 1H), 7.01 (s, 1H), 6.59-6.49 (m, 1H), 6.47-6.37 (m, 1H), 5.94-5.86 (m, 1H), 4.01 (s, 3H), 3.61-3.50 (m, 2H), 3.32 (s, 2H), 2.91 (s, 6H), 2.75 (s, 3H), 2.65 (s, 3H);

MS m/z (ESI): 594 [M+H]$^+$.

Example 107: Preparation of N-(2-((2-(dimethylamino)ethyl)(methyl)amino)-4-methoxy-5-((4-(5-methoxy-3-methyl-1H-indazol-5-(trifluoromethyl)pyrimidin-2-yl)amino)phenyl)acrylamide

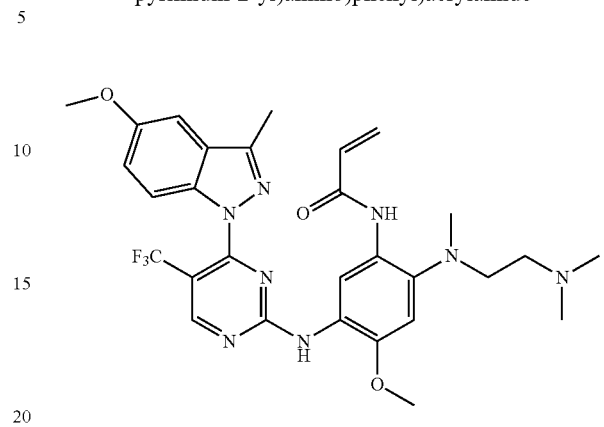

The preparation method of N-(2-((2-(dimethylamino)ethyl)(methyl)amino)-4-methoxy-5-((4-(5-methoxy-3-methyl-1H-indazol-5-(trifluoromethyl)pyrimidin-2-yl)amino)phenyl)acrylamide was similar to Example 40.

$^1$H NMR (400 MHz, CD$_3$OD) δ 8.74 (s, 1H), 8.25-8.10 (m, 1H), 8.04 (s, 1H), 7.18 (s, 1H), 7.10-7.03 (m, 1H), 7.00 (s, 1H), 6.47 (s, 2H), 5.89-5.83 (m, 1H), 3.98 (s, 3H), 3.89 (s, 3H), 3.54 (s, 2H), 3.01 (s, 1H), 2.90 (s, 6H), 2.88 (s, 1H), 2.76 (s, 3H), 2.57 (s, 3H);

MS m/z (ESI): 599 [M+H]$^+$.

Example 108: Preparation of N-(5-((5-chloro-4-(5-chloro-3-methoxy-1H-indazol-1-yl)pyrimidin-2-yl)amino)-2-((2-(dimethylamino)ethyl)(methyl)amino)-4-methoxyphenyl)acrylamide

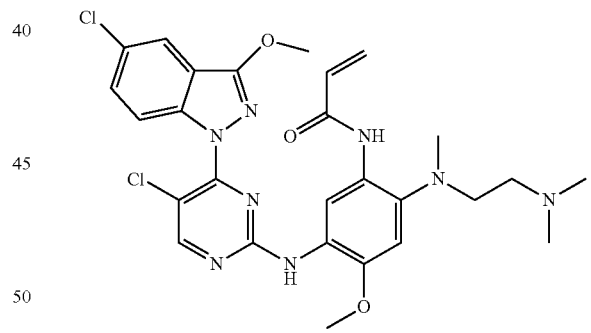

Step 1: Preparation of 5-chloro-2-hydrazinylbenzoic acid

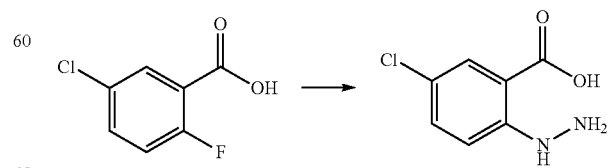

5-chloro-2-fluorobenzoic acid (5 g, 0.0287 mmol) and hydrazine hydrate (10 ml, 85%) were heated at 100° C.

overnight. The reaction solution was concentrated, acidified, filtered and dried to obtain 5-chloro-2-hydrazinylbenzoic acid (2.5 g, 50%).

Step 2: Preparation of 5-chloro-1H-indazol-3-ol

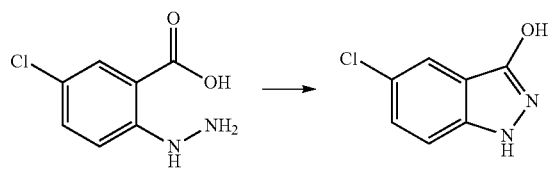 [SMILES: NNc1ccc(Cl)cc1C(=O)O ; Oc1n[nH]c2ccc(Cl)cc12]

5-chloro-2-hydrazinylbenzoic acid (2.5 g), concentrated hydrochloric acid (10 ml) and water (200 ml) were heated at 100° C. for 3 hours. Then, the mixture was concentrated to 100 mL, adjusted to pH 7.0 with sodium carbonate, filtered and dried to obtain 5-chloro-1H-indazol-3-ol (1.7 g, 60%).
$^1$H NMR (400 MHz, DMSO) δ 11.73 (s, 1H), 10.67 (s, 1H), 7.65 (d, J=1.3 Hz, 1H), 7.30 (dt, J=8.9, 5.1 Hz, 2H); MS m/z (ESI): 169 [M+H]$^+$.

Step 3: Preparation of ethyl 5-chloro-3-hydroxy-1H-indazole-1-carboxylate

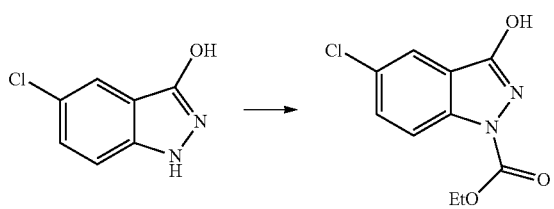 [SMILES: Oc1n[nH]c2ccc(Cl)cc12 ; CCOC(=O)n1nc(O)c2cc(Cl)ccc21]

5-chloro-1H-indazol-3-ol (1.7 g, 10.12 mmol) was dissolved in pyridine (10 mL), and then methyl chloroformate (1.31 g, 12.14 mmol) was added. The mixture was heated up to 100° C. for 2 hours. After the reaction was completed, the mixture was cooled, and 150 mL of water were added. The reaction solution was filtered and dried to obtain ethyl 5-chloro-3-hydroxy-1H-indazole-1-carboxylate (2.2 g, 90%).

Step 4: Preparation of ethyl 5-chloro-3-methoxy-1H-indazole-1-carboxylate

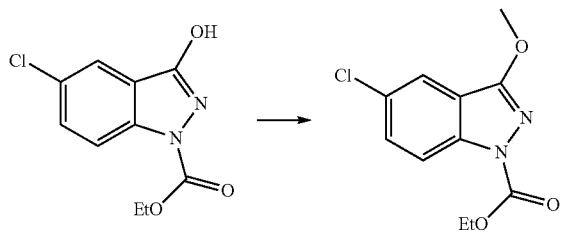 [SMILES: CCOC(=O)n1nc(O)c2cc(Cl)ccc21 ; CCOC(=O)n1nc(OC)c2cc(Cl)ccc21]

Ethyl 5-chloro-3-hydroxy-1H-indazole-1-carboxylate (2.2 g, 9.17 mmol) and cesium carbonate (3.6 g, 11.0 mmol) were added to acetone (20 mL). Then, iodomethane (1.56 g, 11.0 mmol) was added, and the mixture was heated at 70° C. for 2 hours, and was subjected to column chromatography to obtain ethyl 5-chloro-3-methoxy-1H-indazole-1-carboxylate (0.8 g, 30%).

Step 5: Preparation of 5-chloro-3-methoxy-1H-indazole

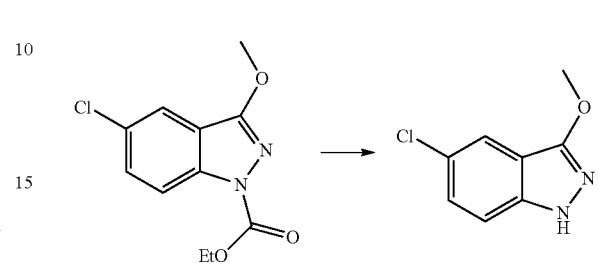

Ethyl 5-chloro-3-methoxy-1H-indazole-1-carboxylate (610 mg, 2.40 mmol), sodium hydroxide (3.6 mL, 1 N) and ethanol (20 mL) were stirred at room temperature for 2 hours. The pH was adjusted with concentrated hydrochloric acid, and then the product was subjected to column chromatography to obtain 5-chloro-3-methoxy-1H-indazole (360 mg, 60%).
$^1$H NMR (400 MHz, DMSO) δ 12.14 (s, 1H), 7.62 (s, 1H), 7.37 (dd, J=27.3, 8.9 Hz, 2H), 3.99 (s, 3H); MS m/z (ESI): 183 [M+H]$^+$.

Steps 6 to 10: Preparation of N-(5-((5-chloro-4-(5-chloro-3-methoxy-1H-indazol-1-yl)pyrimidin-2-yl)amino)-2-((2-(dimethylamino)ethyl)(methyl)amino)-4-methoxyphenyl)acrylamide

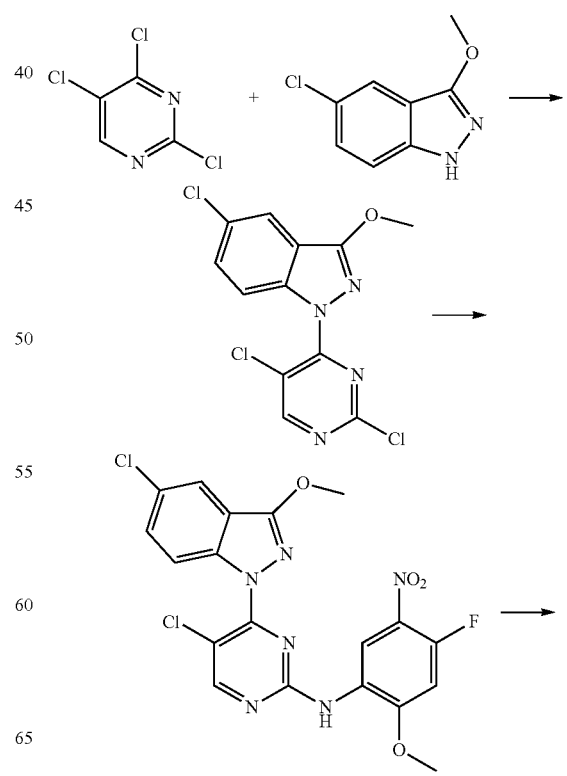

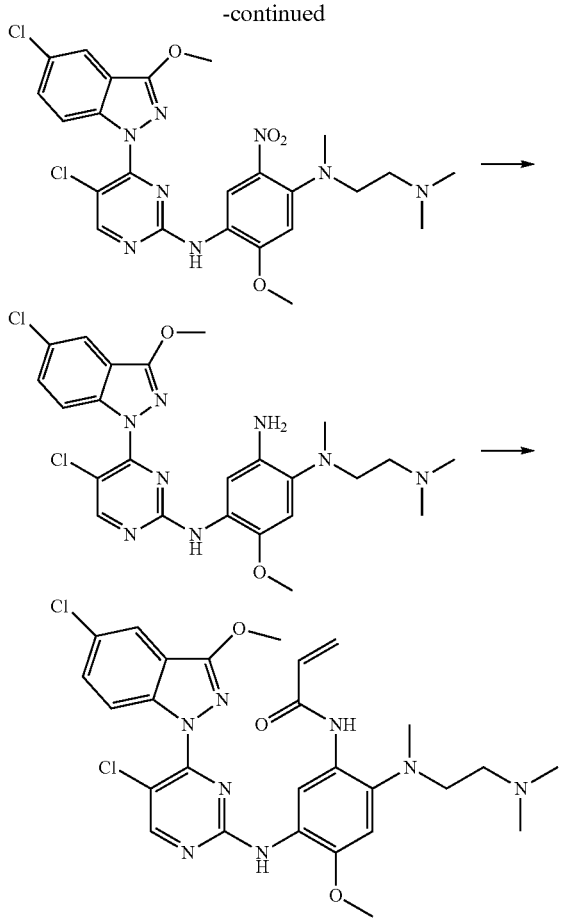

Steps 6 to 10: The preparation method of N-(5-(((5-chloro-4-(5-chloro-3-methoxy-1H-indazol-1-yl)pyrimidin-2-yl)amino)-2-((2-(dimethylamino)ethyl)(methyl)amino)-4-methoxyphenyl)acrylamide was similar to Example 40.

¹H NMR (400 MHz, CD₃OD) δ 8.41 (s, 1H), 8.13 (d, J=7.7 Hz, 2H), 7.61 (d, J=1.8 Hz, 1H), 7.35 (d, J=9.0 Hz, 1H), 6.98 (s, 1H), 6.57-6.37 (m, 2H), 5.87 (dd, J=8.2, 3.5 Hz, 1H), 4.13 (s, 3H), 3.99 (s, 3H), 3.51 (s, 2H), 3.30 (s, 2H), 2.90 (s, 6H), 2.73 (s, 3H);

MS m/z (ESI): 585 [M+H]⁺.

Example 109: Preparation of N-(5-((4-(5-chloro-3-methoxy-1H-indazol-1-yl)-5-(trifluoromethyl)pyrimidin-2-yl)amino)-2-((2-(dimethylamino)ethyl)(methyl)amino)-4-methoxyphenyl)acrylamide

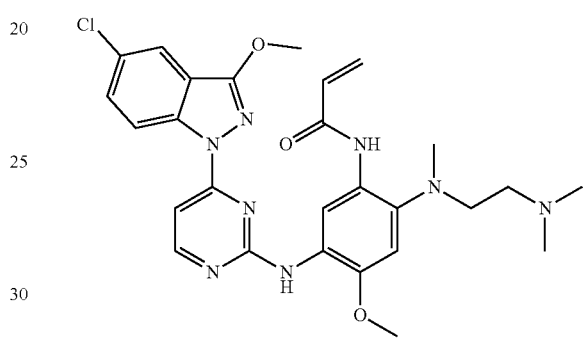

The preparation method of N-(5-((4-(5-chloro-3-methoxy-1H-indazol-1-yl)-5-(trifluoromethyl)pyrimidin-2-yl)amino)-2-((2-(dimethylamino)ethyl)(methyl)amino)-4-methoxyphenyl)acrylamide was similar to Example 108

¹H NMR (400 MHz, CD₃OD) δ 8.62 (s, 1H), 8.38-8.16 (m, 1H), 8.09 (s, 1H), 7.50 (s, 1H), 7.30 (s, 1H), 6.99 (s, 1H), 6.48 (t, J=15.4 Hz, 2H), 5.85 (d, J=11.5 Hz, 1H), 4.05 (s, 3H), 3.96 (s, 3H), 3.52 (s, 2H), 2.91 (s, 6H), 2.75 (s, 3H);

MS m/z (ESI): 619 [M+H]⁺.

Example 110: Preparation of N-(5-((4-(5-chloro-3-methoxy-1H-indazol-1-yl)pyrimidin-2-yl)amino)-2-((2-(dimethylamino)ethyl)(methyl)amino)-4-methoxyphenyl)acrylamide

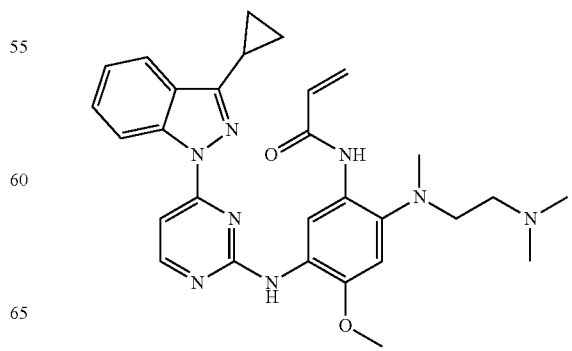

The preparation method of N-(5-((4-(5-chloro-3-methoxy-1H-indazol-1-yl)pyrimidin-2-yl)amino)-2-((2-(dimethylamino)ethyl)(methyl)amino)-4-methoxyphenyl)acrylamide was similar to Example 108.

¹H NMR (400 MHz, CD₃OD) δ 8.20 (s, 2H), 7.88 (s, 1H), 7.58 (s, 1H), 7.41 (d, J=8.8 Hz, 1H), 7.30 (d, J=6.9 Hz, 1H), 7.10 (s, 1H), 6.66 (dd, J=16.9, 10.1 Hz, 1H), 6.49 (d, J=16.9 Hz, 1H), 5.87 (d, J=11.7 Hz, 1H), 4.15 (s, 3H), 3.96 (s, 3H), 3.56 (d, J=5.7 Hz, 2H), 3.40 (d, J=5.6 Hz, 2H), 2.95 (s, 6H), 2.81 (s, 3H);

MS m/z (ESI): 551 [M+H]⁺.

Example 111: Preparation of N-(5-((4-(3-cyclopropyl-1H-indazol-1-yl)pyrimidin-2-yl)amino)-2-((2-(dimethylamino)ethyl)(methyl)amino)-4-methoxyphenyl)acrylamide

Step 1: Preparation of cyclopropyl(2-fluorophenyl)methanol

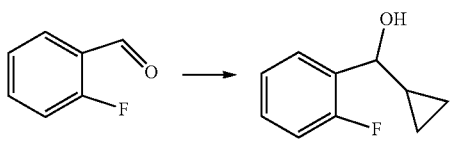 [SMILES: O=Cc1ccccc1F ; OC(c1ccccc1F)C1CC1]

2-fluorobenzaldehyde (1.0 g, 8 mmol) was dissolved in THF (20 mL), and the reaction solution was cooled in an ice bath. With purging three times with nitrogen, cyclopropylmagnesium bromide (32 mL, 16 mmol) was added dropwise. Upon completion of the addition, the reaction was warmed up to room temperature gradually, carried out for 16 h, quenched with 20 mL of saturated ammonium chloride aqueous solution and extracted with ethyl acetate (50 mL×3). The organic phase was dried over anhydrous sodium sulfate and concentrated to obtain a crude product, which was further purified by column chromatography to obtain cyclopropyl(2-fluorophenyl)methanol (800 mg, 62%).

Step 2: Preparation of cyclopropyl(2-fluorophenyl)methanone

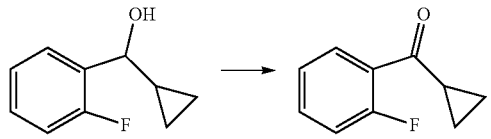 [SMILES: OC(c1ccccc1F)C1CC1 ; O=C(c1ccccc1F)C1CC1]

Cyclopropyl(2-fluorophenyl)methanol (800 mg, 4.8 mmol) was dissolved in dichloromethane (20 mL), and then Dess-Martin oxidant was added. The reaction was carried out at room temperature for 5.5 h, and quenched with 20 mL of saturated sodium bicarbonate aqueous solution and 20 mL of 10% sodium sulfite aqueous solution. After stirring for 15 minutes, the solution was extracted with dichloromethane (30 mL×4). The organic phase was dried over anhydrous sodium sulfate and concentrated to obtain a crude product which was further purified by column chromatography to obtain cyclopropyl(2-fluorophenyl)methanone (430 mg, 54%).

Step 3: Preparation of 3-cyclopropyl-1H-indazole

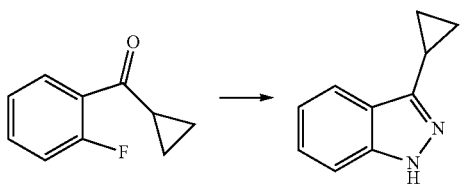 [SMILES: O=C(c1ccccc1F)C1CC1 ; c1ccc2c(C3CC3)n[nH]c2c1]

Cyclopropyl(2-fluorophenyl)methanone (430 mg, 2.6 mmol) was dissolved in 10 mL of hydrazine hydrate. The reaction was carried out at 120° C. for 1 h in microwave. The reaction solution was concentrated to obtain a crude product, which was further purified by column chromatography to obtain 3-cyclopropyl-1H-indazole (250 mg, 61%).

Steps 4 to 9: Preparation of N-(5-((4-(3-cyclopropyl-2H-indazol-2-yl)pyrimidin-2-yl)amino)-2-((2-(dimethylamino)ethyl)(methyl)amino)-4-methoxyphenyl)acrylamide

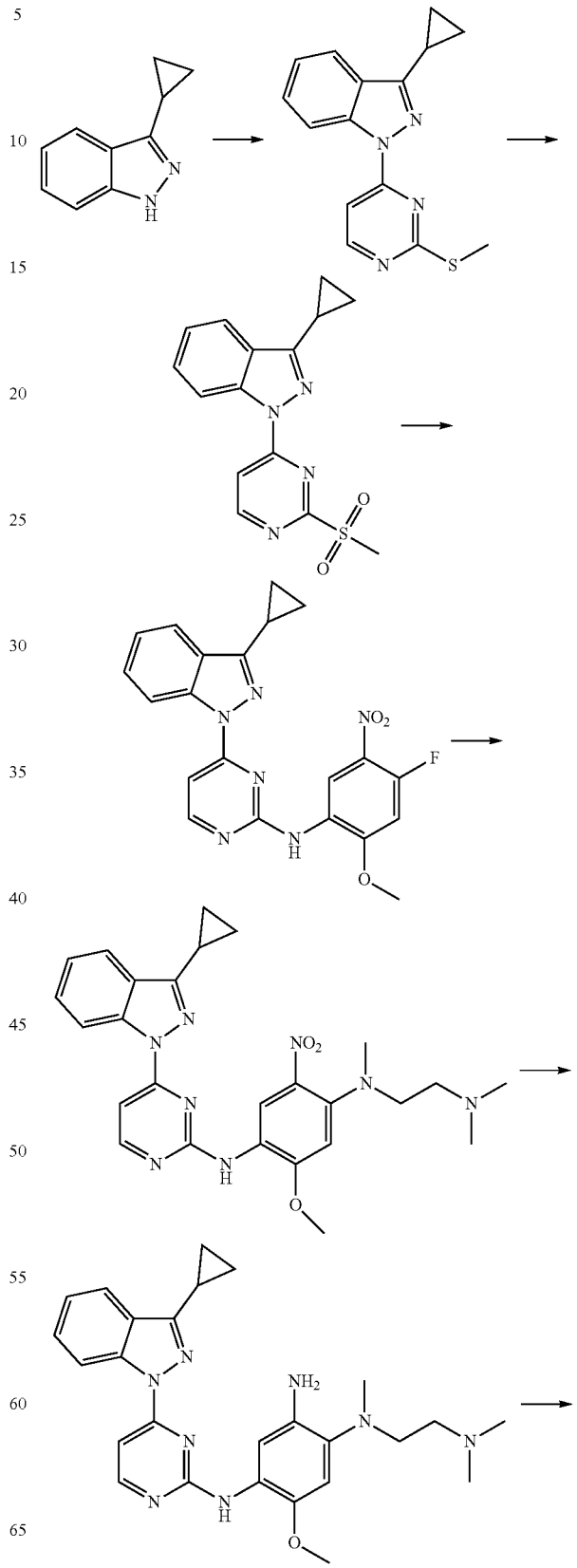

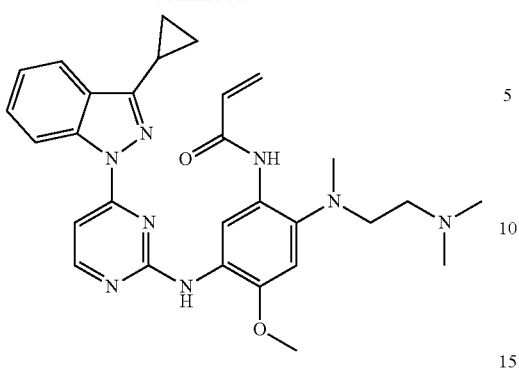

The preparation method of N-(5-((4-(3-cyclopropyl-2H-indazol-2-yl)pyrimidin-2-yl)amino)-((2-(dimethylamino)ethyl)(methyl)amino)-4-methoxyphenyl)acrylamide was similar to Example 43.

¹H NMR (400 MHz, CD₃OD) δ 8.43 (s, 1H), 8.19 (d, J=6.3 Hz, 1H), 7.91 (d, J=7.9 Hz, 1H), 7.83 (s, 1H), 7.52 (d, J=7.0 Hz, 2H), 7.43 (t, J=7.4 Hz, 1H), 7.10 (s, 1H), 6.63 (dd, J=169, 10.2 Hz, 1H), 6.46 (dd, J=16.9, 1.5 Hz, 1H), 5.85 (dd, J=10.2, 1.4 Hz, 1H), 3.94 (s, 3H), 3.57 (t, J=5.5 Hz, 2H), 3.39 (t, J=5.5 Hz, 2H), 2.93 (s, 6H), 2.82 (s, 3H), 2.42-2.33 (m, 1H), 1.24-1.18 (m, 4H);

MS m/z (ESI): 527.2 [M+H]⁺.

Example 112: Preparation of N-(5-((4-(6-cyano-1H-indazol-1-yl)pyrimidin-2-yl)amino)-2-((2-(dimethylamino)ethyl)(methyl)amino)-4-methoxyphenyl)acrylamide

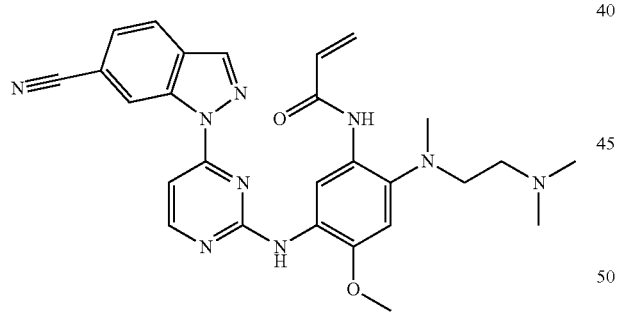

The preparation method of N-(5-((4-(6-cyano-1H-indazol-1-yl)pyrimidin-2-yl)amino)-2-((2-(dimethylamino)ethyl) (methyl)amino)-4-methoxyphenyl)acrylamide was similar to Example 43.

¹H NMR (400 MHz, CD₃OD) δ 9.01 (s, 1H), 8.59 (d, J=0.7 Hz, 1H), 8.40 (d, J=6.5 Hz, 1H), 8.10-8.02 (m, 2H), 7.67 (dd, J=8.2, 1.2 Hz, 1H), 7.62 (d, J=6.5 Hz, 1H), 7.14 (s, 1H), 6.60 (dd, J=16.9, 10.2 Hz, 1H), 6.36 (dd, J=16.9, 1.3 Hz, 1H), 5.82 (dd, J=10.3, 1.5 Hz, 1H), 3.98 (s, 3H), 3.57 (t, J=6.0 Hz, 2H), 3.39 (dd, J=11.1, 5.2 Hz, 2H), 2.94 (s, 6H), 2.81 (s, 3H);

MS m/z (ESI): 512.2 [M+H]⁺.

Example 113: Preparation of N-(5-((4-(3-cyclopropyl-5-methoxy-1H-indazol-1-yl)pyrimidin-2-yl)amino)-2-((2-(dimethylamino)ethyl)(methyl)amino)-4-methoxyphenyl)acrylamide

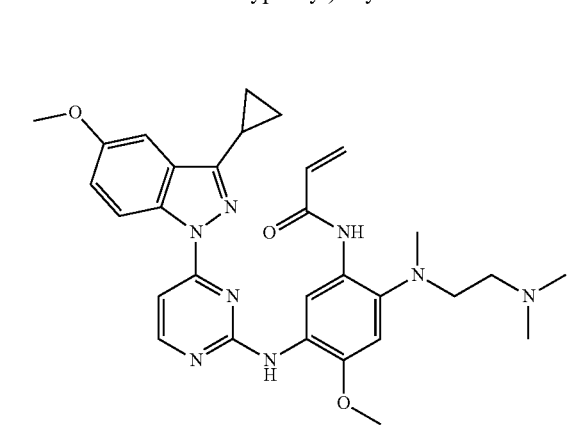

The preparation method of N-(5-((4-(3-cyclopropyl-5-methoxy-1H-indazol-1-yl)pyrimidin-2-yl)amino)-2-((2-(dimethylamino)ethyl)(methyl)amino)-4-methoxyphenyl)acrylamide was similar to Example 111.

¹H NMR (400 MHz, CD₃OD) δ 8.18 (dd, J=40.0, 6.7 Hz, 2H), 7.85 (s, 1H), 7.40 (d, J=7.1 Hz, 1H), 7.29 (d, J=2.3 Hz, 1H), 7.08 (d, J=10.5 Hz, 2H), 6.64 (dd, J=16.9, 10.1 Hz, 1H), 6.47 (dd, J=16.9, 1.6 Hz, 1H), 5.86 (dd, J=10.2, 1.6 Hz, 1H), 3.95 (s, 3H), 3.89 (s, 3H), 3.57 (t, J=5.7 Hz, 2H), 3.39 (t, J=5.6 Hz, 2H), 2.94 (s, 6H), 2.81 (s, 3H), 2.35-2.26 (m, 1H), 1.21-1.15 (m, 4H);

MS m/z (ESI): 557.3 [M+H]⁺.

Example 114: Preparation of N-(5-((4-(3-cyclopropyl-5-methoxy-1H-indazol-5-(trifluoromethyl)pyrimidin-2-yl)amino)-2-((2-(dimethylamino)ethyl)(methyl)amino)-4-methoxyphenyl)acrylamide

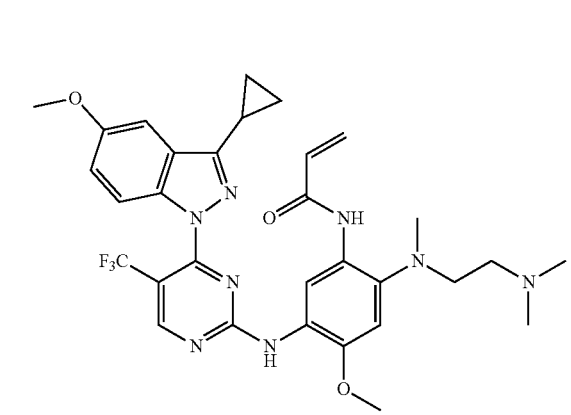

Steps 1 to 3: Preparation of 3-cyclopropyl-5-methoxy-1H-indazole

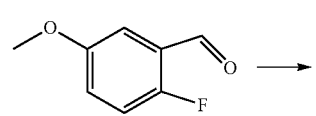

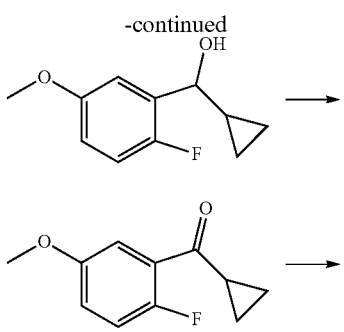

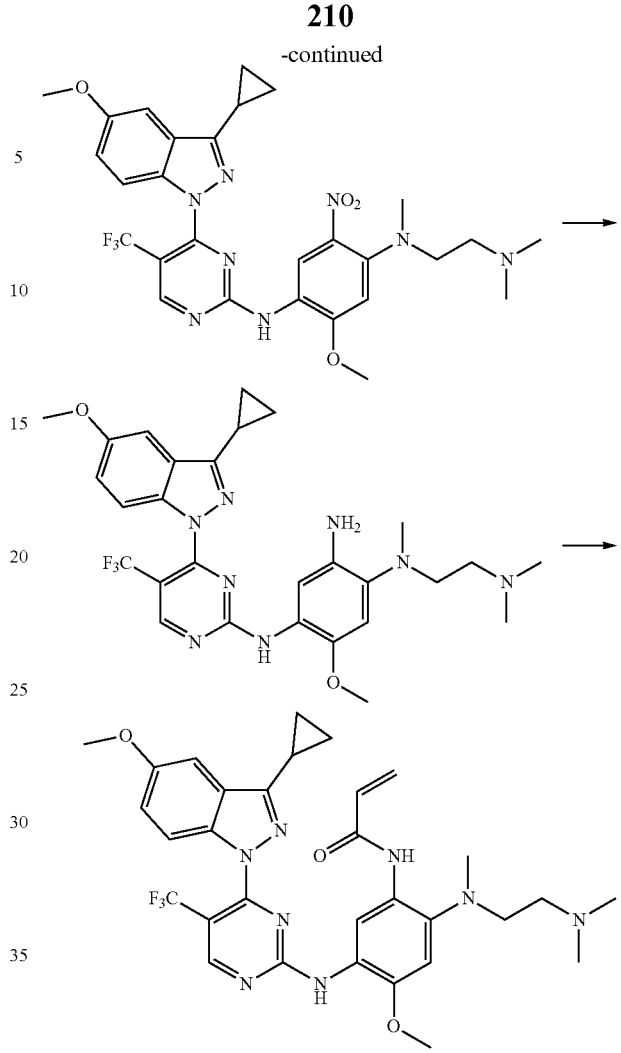

The preparation method of 3-cyclopropyl-5-methoxy-1H-indazole was similar to Example 111.

Steps 4 to 8: Preparation of N-(5-((4-(3-cyclopropyl-5-methoxy-1H-indazol-1-yl)-5-(trifluoromethyl)pyrimidin-2-yl)amino)-2-((2-(dimethylamino)ethyl)(methyl)amino)-4-methoxyphenyl)acrylamide

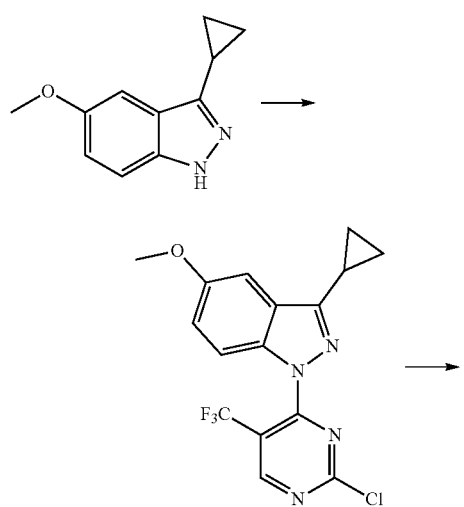

The preparation method of N-(5-((4-(3-cyclopropyl-5-methoxy-1H-indazol-1-yl)-5-(trifluoromethyl)pyrimidin-2-yl)amino)-2-((2-(dimethylamino)ethyl)(methyl)amino)-4-methoxyphenyl)acrylamide was similar to Example 40.

$^1$H NMR (400 MHz, CD$_3$OD) δ 8.70 (s, 1H), 8.19 (s, 1H), 8.03 (s, 1H), 7.30 (d, J=2.3 Hz, 1H), 7.09-6.97 (m, 2H), 6.47 (d, J=5.6 Hz, 2H), 5.91-5.81 (m, 1H), 3.97 (s, 3H), 3.90 (s, 3H), 3.54 (t, J=5.6 Hz, 2H), 3.31 (d, J=6.0 Hz, 2H), 2.90 (s, 6H), 2.76 (s, 3H), 2.28 (ddd, J=13.2, 6.2, 3.8 Hz, 1H), 1.11 (dt, J=4.0, 2.8 Hz, 4H):

MS m/z (ESI): 625.3 [M+H]$^+$.

Example 115: Preparation of N-(5-((5-chloro-4-(3-cyclopropyl-5-methoxy-1H-indazol-1-yl)pyrimidin-2-yl)amino)-2-((2-(dimethylamino)ethyl)(methyl)amino)-4-methoxyphenyl)acrylamide

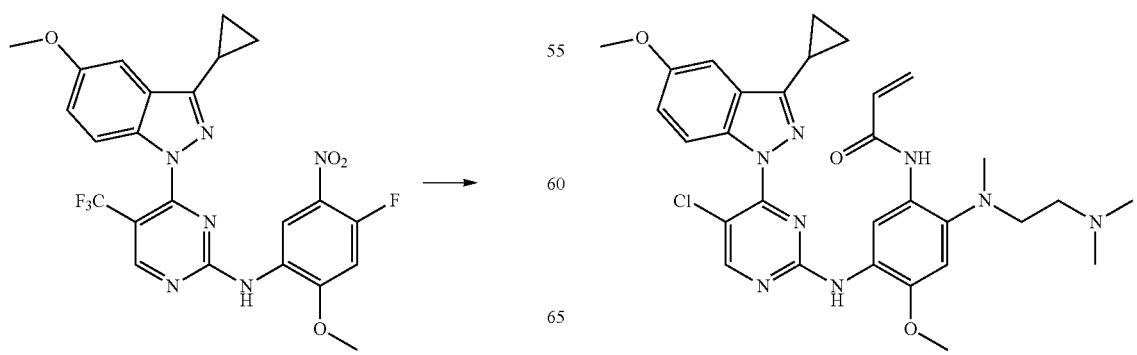

Steps 1 to 3: Preparation of 3-cyclopropyl-5-methoxy-1H-indazole

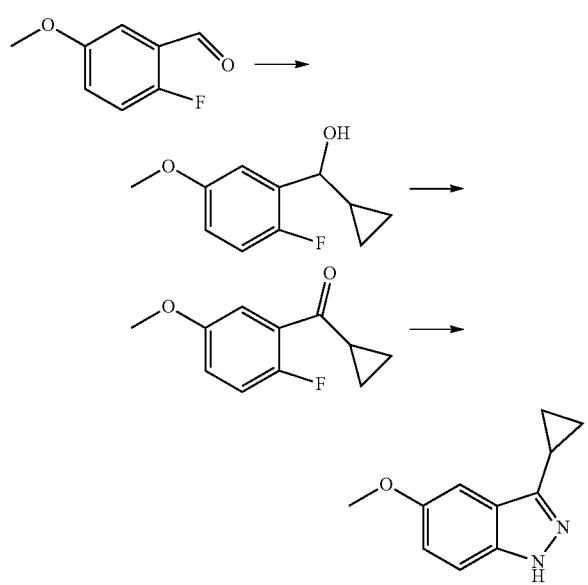

The preparation method of 3-cyclopropyl-5-methoxy-1H-indazole was similar to Example 111.

Steps 4 to 8: Preparation of N-(5-((5-chloro-4-(3-cyclopropyl-5-methoxy-1H-indazol-1-yl)pyrimidin-2-yl)amino)-2-((2-(dimethylamino)ethyl)(methyl)amino)-4-methoxyphenyl)acrylamide

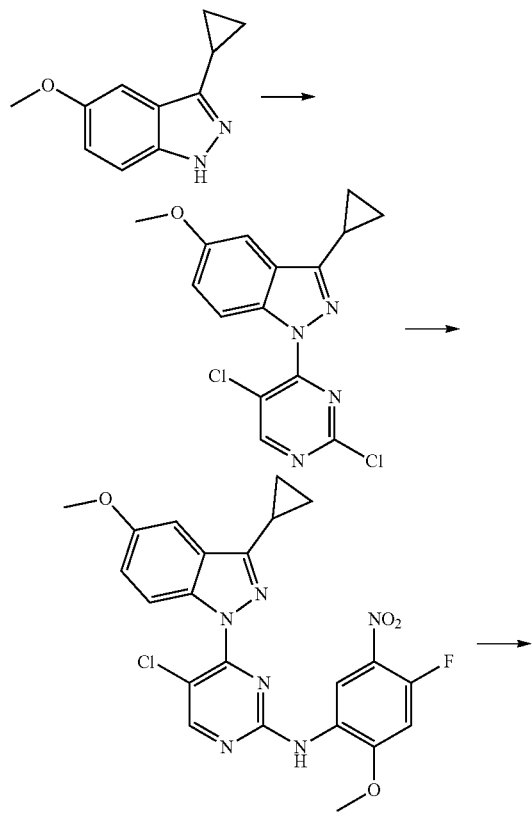

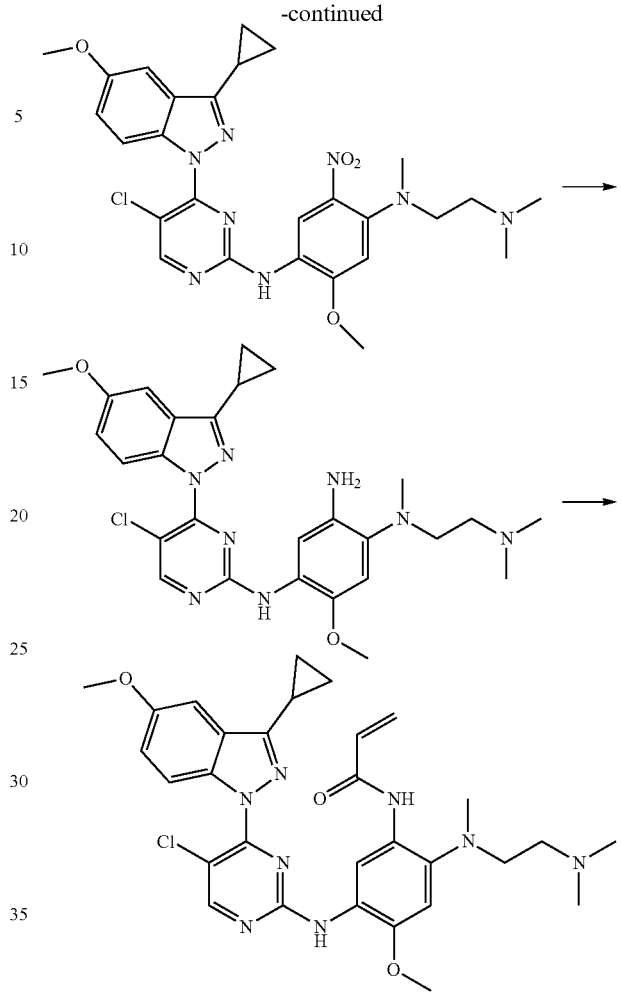

The preparation method of N-(5-((5-chloro-4-(3-cyclopropyl-5-methoxy-1H-indazol-1-yl)pyrimidin-2-yl)amino)-2-((2-(dimethylamino)ethyl)(methyl)amino)-4-methoxyphenyl)acrylamide was similar to Example 40.

$^1$H NMR (400 MHz, CD$_3$OD) δ 8.47 (s, 1H), 8.18 (s, 1H), 8.05 (d, J=9.1 Hz, 1H), 7.28 (d, J=2.3 Hz, 1H), 7.05 (dd, J=9.1, 2.4 Hz, 1H), 6.97 (s, 1H), 6.44 (dd, J=5.8, 4.1 Hz, 2H), 5.85 (dd, J=8.4, 3.4 Hz, 1H), 3.99 (s, 3H), 3.90 (s, 3H), 3.51 (t, J=5.6 Hz, 2H), 3.32-3.26 (m, 2H), 2.88 (s, 6H), 2.72 (s, 3H), 2.35-2.26 (m, 1H), 1.13 (dq, J=4.4, 2.4 Hz, 4H); MS m/z (ESI): 591.3 [M+H]$^+$.

Example 116: Preparation of N-(5-((5-chloro-4-(5-cyano-3-propyl-1H-indazol-1-yl)pyrimidin-2-yl)amino)-2-((2-(dimethylamino)ethyl)(methyl)amino)-4-methoxyphenyl)acrylamide

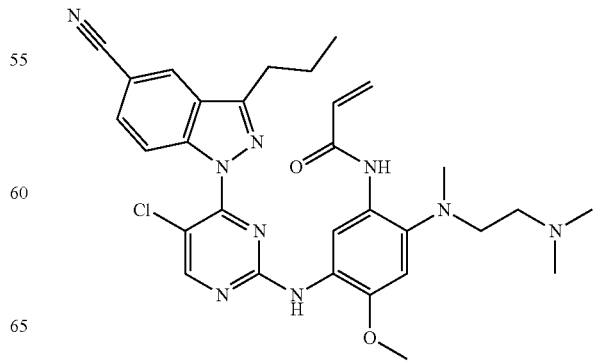

213

Step 1: Preparation of
1-(5-bromo-2-fluorophenyl)butan-1-ol

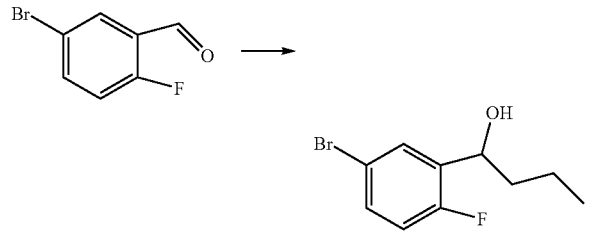

5-bromo-2-fluorobenzaldehyde (5.0 g, 24.6 mmol) was dissolved in THF (30 mL) and the reaction solution was cooled in an ice bath. With purging three times with nitrogen, propylmagnesium bromide (25 mL, 49.3 mmol) was added dropwise. Upon completion of the addition, the reaction was warmed up to room temperature gradually and carried out for 16 h, then quenched with 30 mL of saturated ammonium chloride aqueous solution and extracted with ethyl acetate (50 mL×4). The organic phase was dried over anhydrous sodium sulfate and concentrated to obtain a crude product, which was further purified by column chromatography to obtain 1-(5-bromo-2-fluorophenyl)butan-1-ol (2.2 g, 36%).

Step 2: Preparation of
1-(5-bromo-2-fluorophenyl)butan-1-one

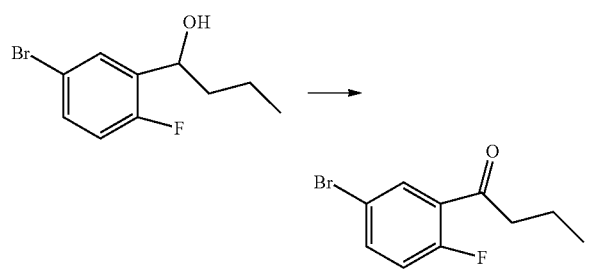

1-(5-bromo-2-fluorophenyl)butan-1-ol (2.2 g, 8.9 mmol) was dissolved in 50 ml of dichloromethane, and PCC oxidant (3.8 g, 17.8 mmol) was added. After the reaction was carried out for 16 h at room temperature, the reaction mixture was filtered through celite. The organic phase was dried over anhydrous sodium sulfate and concentrated to obtain a crude product, which was further purified by column chromatography to obtain 1-(5-bromo-2-fluorophenyl)butan-1-one (1.5 g, 71%).

Step 3: Preparation of
(1-(5-bromo-2-fluorophenyl)butylidene)hydrazine

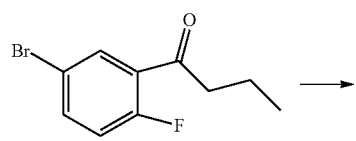

214

-continued

1-(5-bromo-2-fluorophenyl)butan-1-one (1.0 g, 4.1 mmol) was dissolved in 20 mL of hydrazine hydrate, and the reaction was carried out at 130° C. in microwave for 5 h. The reaction solution was concentrated, and the crude product was purified by column chromatography to obtain (1-(5-bromo-2-fluorophenyl)butylidene)hydrazine (800 mg, 80%).

Step 4: Preparation of
5-bromo-3-propyl-1H-indazole

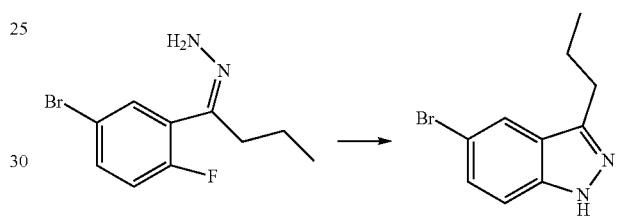

(1-(5-bromo-2-fluorophenyl)butylidene)hydrazine (600 mg, 2.3 mmol) was dissolved in 10 mL of N-methylpyrrolidone, and the reaction was carried out at 150° C. in a microwave for 1 h. Then, 20 mL of water were added, and the reaction solution was extracted with ethyl acetate (30 mL×3). The organic phase was dried over anhydrous sodium sulfate and concentrated to obtain a crude product, which was further purified by column chromatography to obtain 5-bromo-3-propyl-1H-indazole (380 mg, 69%).

Step 5: Preparation of
3-propyl-1H-indazole-5-carbonitrile

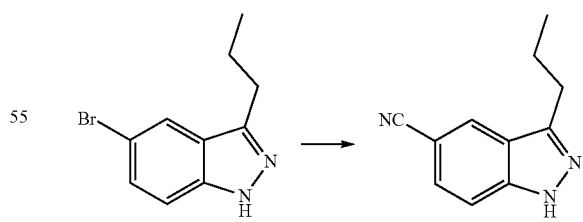

5-bromo-3-propyl-1H-indazole (380 mg, 1.6 mmol), zinc cyanide (223 mg, 1.9 mmol), tris(dibenzylideneacetone)dipalladium (140 mg, 0.16 mmol) and 2-dicyclohexylphosphino-2',4',6'-triisopropylbiphenyl (150 mg, 0.32 mmol) were dissolved in N,N-dimethylformamide (10 mL). The reaction was carried out at 150° C. in a microwave for 1 h, and then 20 mL of saturated sodium chloride aqueous solution was added. The reaction solution was extracted with ethyl acetate (30 mL×3). The organic phase was dried over anhydrous sodium sulfate and concentrated to obtain a crude product, which was further purified by column chromatography to obtain 3-propyl-1H-indazole-5-carbonitrile (110 mg, 38%).

Steps 6 to 10: Preparation of N-(5-((5-chloro-4-(5-cyano-3-propyl-1H-indazol-1-yl)pyrimidin-2-yl) amino)-2-((2-(dimethylamino)ethyl)(methyl)amino)-4-methoxyphenyl)acrylamide

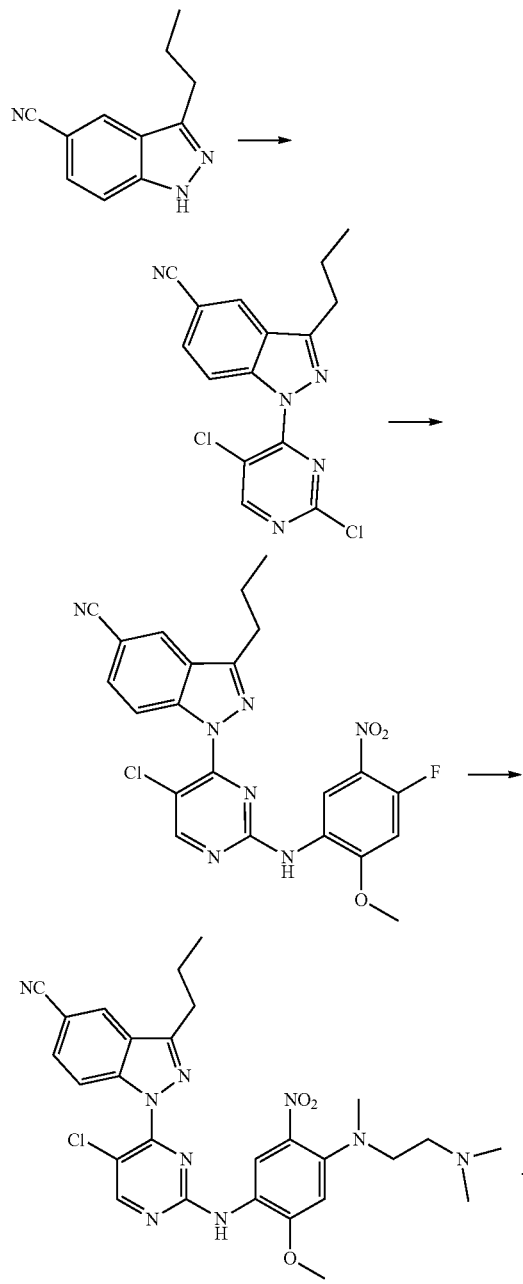

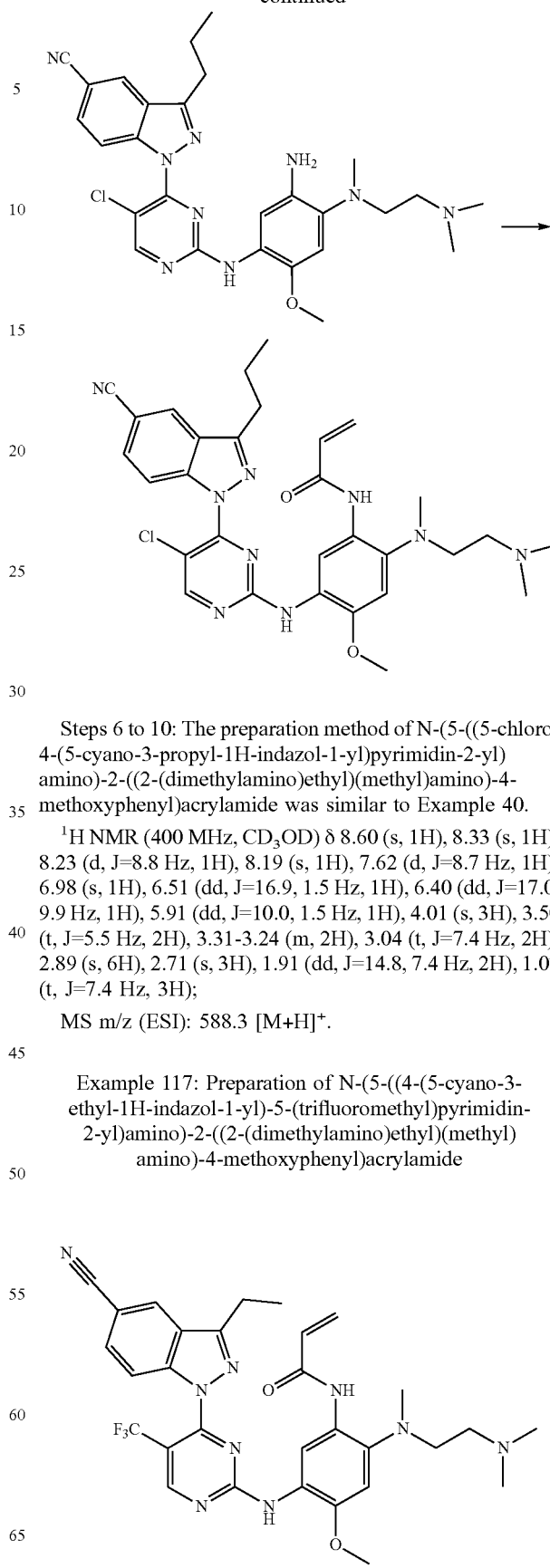

Steps 6 to 10: The preparation method of N-(5-((5-chloro-4-(5-cyano-3-propyl-1H-indazol-1-yl)pyrimidin-2-yl) amino)-2-((2-(dimethylamino)ethyl)(methyl)amino)-4-methoxyphenyl)acrylamide was similar to Example 40.

$^1$H NMR (400 MHz, CD$_3$OD) δ 8.60 (s, 1H), 8.33 (s, 1H), 8.23 (d, J=8.8 Hz, 1H), 8.19 (s, 1H), 7.62 (d, J=8.7 Hz, 1H), 6.98 (s, 1H), 6.51 (dd, J=16.9, 1.5 Hz, 1H), 6.40 (dd, J=17.0, 9.9 Hz, 1H), 5.91 (dd, J=10.0, 1.5 Hz, 1H), 4.01 (s, 3H), 3.50 (t, J=5.5 Hz, 2H), 3.31-3.24 (m, 2H), 3.04 (t, J=7.4 Hz, 2H), 2.89 (s, 6H), 2.71 (s, 3H), 1.91 (dd, J=14.8, 7.4 Hz, 2H), 1.07 (t, J=7.4 Hz, 3H);

MS m/z (ESI): 588.3 [M+H]$^+$.

Example 117: Preparation of N-(5-((4-(5-cyano-3-ethyl-1H-indazol-1-yl)-5-(trifluoromethyl)pyrimidin-2-yl)amino)-2-((2-(dimethylamino)ethyl)(methyl) amino)-4-methoxyphenyl)acrylamide

Step 1: Preparation of 3-bromo-1H-indazole-5-carbonitrile

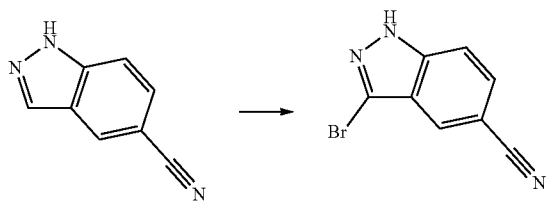 [SMILES: N#Cc1ccc2[nH]ncc2c1 ; N#Cc1ccc2[nH]nc(Br)c2c1]

1H-indazole-5-carbonitrile (544 mg, 3.8 mmol), NBS (812 mg, 4.6 mmol) and DMF (10 mL) were added in a 100 mL round-bottom flask. Under the protection of $N_2$, the mixture was stirred at room temperature for 2 h. The reaction solution was concentrated to obtain a crude product which was dissolved in 100 mL of DCM, washed with 50 mL of saturated sodium bicarbonate aqueous solution, water and saturated brine, respectively. The organic phase was dried over anhydrous sodium sulfate, and filtered. The resulting filtrate was concentrated to obtain 3-bromo-1H-indazole-5-carbonitrile (750 mg, 89%).

Step 2: Preparation of 3-bromo-1-((2-(trimethylsilyl)ethoxy)methyl)-1H-indazole-5-carbonitrile

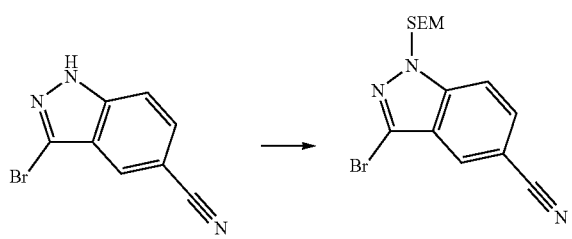 [SMILES: N#Cc1ccc2[nH]nc(Br)c2c1 ; C[Si](C)(C)CCOCn1nc(Br)c2cc(C#N)ccc21]

3-bromo-1H-indazole-5-carbonitrile (710 mg, 3.2 mmol) and THF (15 mL) were added in a 100 mL round-bottom flask, and SEM-Cl (640 mg, 3.8 mmol) was added dropwise in an ice-water bath. The reaction was carried out at 0° C. for 2 h, and then quenched with saturated ammonium chloride aqueous solution (1 mL). The reaction solution was concentrated to obtain a crude product, which was further purified by column chromatography (60% DCM/PE) to obtain 3-bromo-1-((2-(trimethylsilyl)ethoxy)methyl)-1H-indazole-5-carbonitrile (680 mg, 61%).

Step 3: Preparation of 3-ethyl-1-((2-(trimethylsilyl)ethoxy)methyl)-1H-indazole-5-carbonitrile

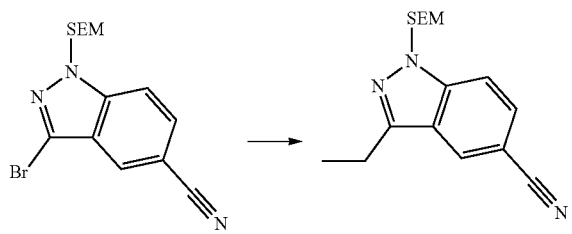 [SMILES: C[Si](C)(C)CCOCn1nc(Br)c2cc(C#N)ccc21 ; CCc1nn(COCC[Si](C)(C)C)c2ccc(C#N)cc12]

3-bromo-1-((2-(trimethylsilyl)ethoxy)methyl)-1H-indazole-5-carbonitrile (669 mg, 1.9 mmol), ethylboronic acid (281 mg, 3.8 mmol), $K_3PO_4$ (1.2 g, 5.7 mmol) and $PCy_3$ (213 mg, 0.4 mmol) were added in a 100 mL round bottom flask. After purging three times with nitrogen, $Pd(OAc)_2$ (85 mg, 0.2 mmol) was added, and the reaction was carried out at 100° C. for 2 h. After cooling to room temperature, the reaction mixture was diluted with 100 mL of ethyl acetate and washed with water (50 mL×2). The organic phase was concentrated under reduced pressure, and the resulting residue was purified by column chromatography to obtain 3-ethyl-1-((2-(trimethylsilyl)ethoxy)methyl)-1H-indazole-5-carbonitrile (605 mg, 100%).

MS m/z (ESI): 302.2 $[M+H]^+$.

Step 4: Preparation of 3-ethyl-1H-indazole-5-carbonitrile

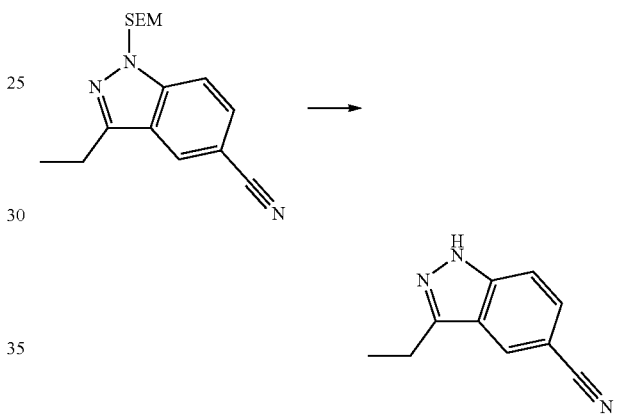

3-ethyl-1-((2-(trimethylsilyl)ethoxy)methyl)-1H-indazole-5-carbonitrile (603 mg, 1.9 mmol), 1M of TBAF/THF (30 mL), and ethylenediamine (240 mg) were added in a 100 mL round-bottom flask, and the reaction was carried out at 70° C. for 2 h. The reaction solution was concentrated to obtain a crude product. Then, 100 mL of ethyl acetate were added, and the reaction solution was washed with water (50 mL×2). The organic phase was concentrated, and the resulting residue was purified by reversed phase column chromatography (25% acetonitrile/water) to obtain 3-ethyl-1H-indazole-5-carbonitrile (170 mg, 50%).

Steps 5 to 8: Preparation of N-(5-((4-(5-cyano-3-ethyl-1H-indazol-1-yl)-5-(trifluoromethyl)pyrimidin-2-yl)amino)-2-((2-(dimethylamino)ethyl)(methyl)amino)-4-methoxyphenyl)acrylamide

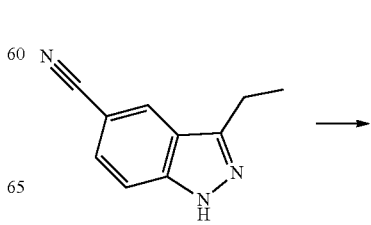

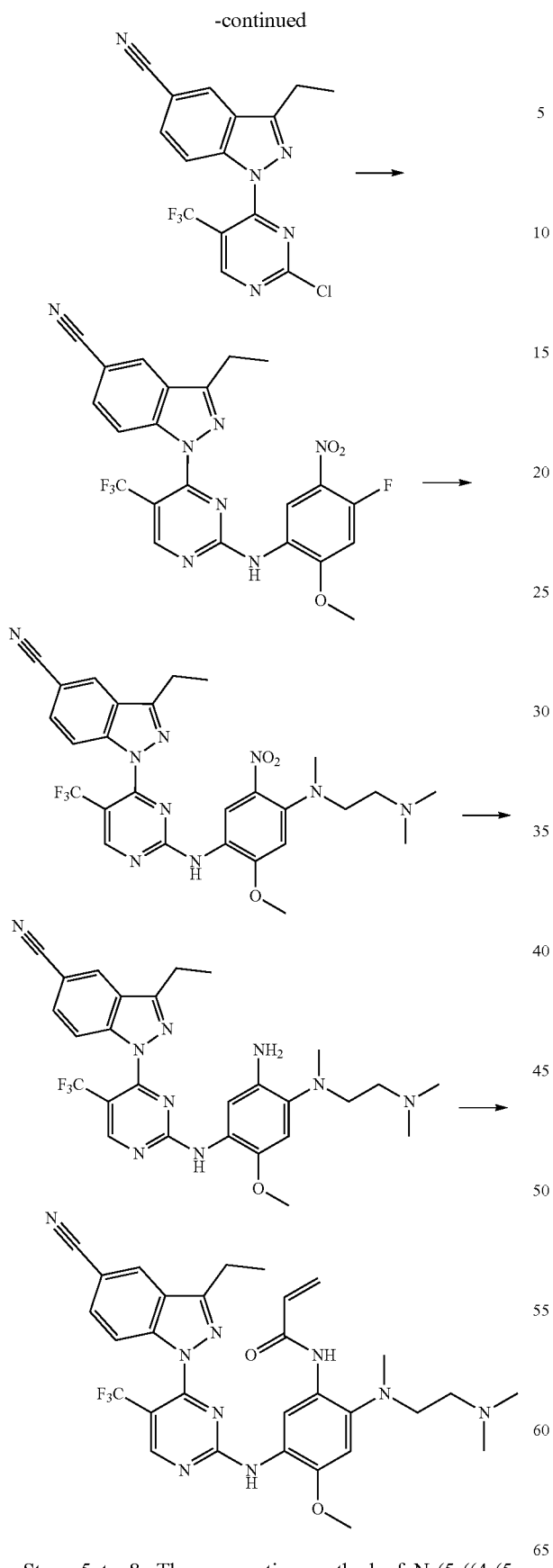

Steps 5 to 8: The preparation method of N-(5-((4-(5-cyano-3-ethyl-1H-indazol-1-yl)-5-(trifluoromethyl)pyrimi-din-2-yl)amino)-2-((2-(dimethylamino)ethyl)(methyl)amino)-4-methoxyphenyl)acrylamide was similar to Example 106.

¹H NMR (400 MHz, CD₃OD) δ 8.80 (s, 1H), 8.39 (s, 1H), 8.27 (d, J=0.7 Hz, 1H), 8.12 (s, 1H), 7.63 (s, 1H), 7.02 (s, 1H), 6.56-6.44 (m, 2H), 5.93-5.87 (m, 1H), 4.00 (s, 3H), 3.53 (t, J=5.7 Hz, 2H), 3.36-3.33 (m, 2H), 3.03 (q, J=7.5 Hz, 2H), 2.92 (s, 6H), 2.75 (s, 3H), 1.44 (t, J=7.5 Hz, 3H);

MS m/z (ESI): 608.3 [M+H]⁺.

Example 118: Preparation of N-(5-((5-chloro-4-(5-cyano-3-ethyl-1H-indazol-1-yl)pyrimidin-2-yl)amino)-2-((2-(dimethylamino)ethyl)(methyl)amino)-4-methoxyphenyl)acrylamide The preparation method of N-(5-((5-chloro-4-(5-cyano-3-ethyl-1H-indazol-1-yl)pyrimidin-2-yl)amino)-2-((2-(dimethylamino)ethyl)(methyl)amino)-4-methoxyphenyl)acrylamide was similar to Example 117.

¹H NMR (400 MHz, CD₃OD) δ 8.44 (s, 1H), 8.18 (s, 1H), 8.09 (d, J=11.2 Hz, 2H), 7.49 (d, J=8.7 Hz, 1H), 6.86 (s, 1H), 6.34 (qd, J=16.9, 5.7 Hz, 2H), 5.79 (dd, J=9.9, 1.6 Hz, 1H), 3.89 (s, 3H), 3.39 (t, J=5.4 Hz, 2H), 3.18 (d, J=5.3 Hz, 2H), 2.95 (q, J=7.5 Hz, 2H), 2.78 (s, 6H), 2.60 (s, 3H), 1.33 (t, J=7.5 Hz, 3H);

MS m/z (ESI): 574.3 [M+H]⁺.

Example 119: Preparation of N-(5-((4-(1-cyclopropyl-1H-indazol-3-yl)pyrimidin-2-yl)amino)-2-((2-(dimethylamino)ethyl)(methyl)amino)-4-methoxyphenyl)acrylamide

Step 1: Preparation of (2-fluorophenyl)(2-(methylthio)pyrimidin-4-yl)methanone

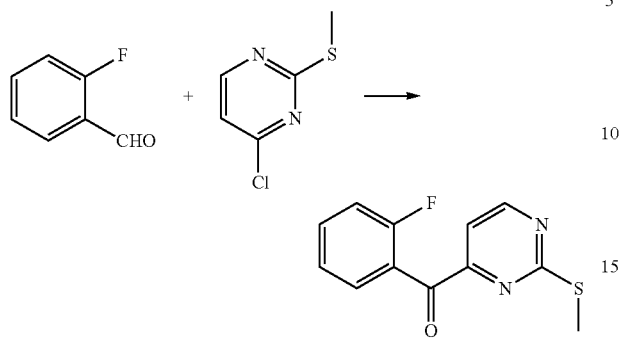

4-chloro-2-(methylthio)pyrimidine (5.00 g, 31.1 mmol), and 2-fluorobenzaldehyde (4.64 g, 37.4 mmol) were dissolved in 1,4-dioxane (70 mL), and then NaH (1.74 g, 60%, 43.6 mmol) was added in batches. Then, the mixture was stirred at 100° C. for 1 hour. After cooling, the reaction solution was diluted with EtOAc. The organic phase was washed with saturated brine, dried over anhydrous sodium sulfate, concentrated and purified by column chromatography to obtain the title compound (2-fluorophenyl)(2-(methylthio)pyrimidin-4-yl)methanone (4.3 g, 56%).

$^1$H NMR (400 MHz, CDCl$_3$): δ 8.71 (d, J=5.2 Hz, 1H), 7.68 (m, 1H), 7.51 (m, 1H), 7.44 (d, J=5.2 Hz, 1H), 7.20 (m, 1H), 7.07 (m, 1H), 2.38 (s, 3H);

MS m/z (ESI): 249.1 [M+H]$^+$.

Step 2: Preparation of 1-cyclopropyl-3-(2-(methylthio)pyrimidin-4-yl)-1H-indazole

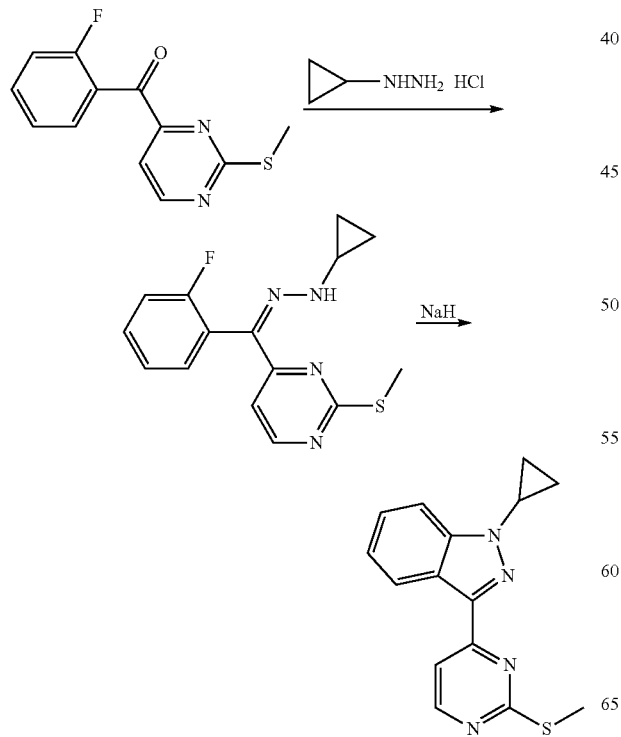

(2-fluorophenyl)(2-(methylthio)pyrimidin-4-yl)methanone (1.3 g, 5.24 mmol) and cyclopropylhydrazine hydrochloride (800 mg, 7.33 mmol) were mixed in ethanol. The mixture was heated up to reflux for 2 hours, cooled and concentrated. The resulting crude product was dissolved in 50 mL of DMF, and sodium hydride (500 mg, 12.5 mmol) was added in batches, and then the reaction solution was stifled at 80° C. for 2 hours. After cooling, water was added, then a solid was precipitated. The solid was purified by column chromatography to obtain the title compound 1-cyclopropyl-3-(2-(methylthio)pyrimidin-4-yl)-1H-indazole (140 mg, yield of two steps: 10%).

MS m/z (ESI): 283.1 [M+H]$^+$.

Step 3: Preparation of 1-cyclopropyl-3-(2-(methylsulfonyl)pyrimidin-4-yl)-1H-indazole

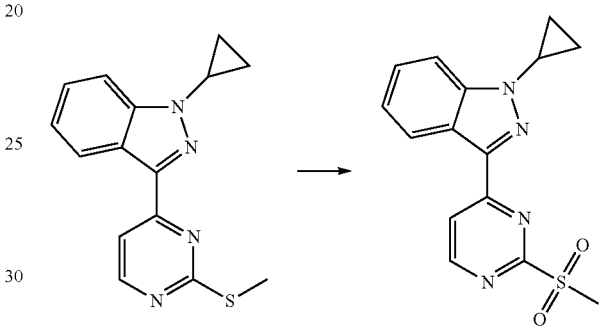

mCPBA (231 mg, 70%, 1.00 mmol) was added in one batch to a solution of 1-cyclopropyl-3-(2-(methylthio)pyrimidin-4-yl)-1H-indazole (135 mg, 0.478 mmol) in dichloromethane (3 mL) in an ice water bath. The reaction was warmed up to room temperature slowly and stirred for 2 hours. The reaction solution was washed twice with saturated sodium bicarbonate aqueous solution, washed once with saturated brine, dried over anhydrous sodium sulfate, and concentrated to obtain the title compound 1-cyclopropyl-3-(2-(methylsulfonyl)pyrimidin-4-yl)-1H-indazole (185 mg, 100%).

MS m/z (ESI): 315.1 [M+H]$^+$.

Step 4: Preparation of 4-(1-cyclopropyl-1H-indazol-3-yl)-N-(4-fluoro-2-methoxy-5-nitrophenyl)pyrimidin-2-amine

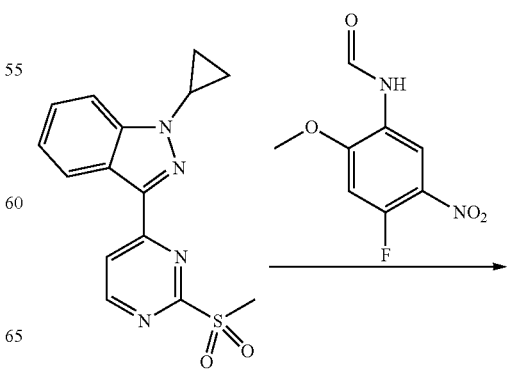

-continued

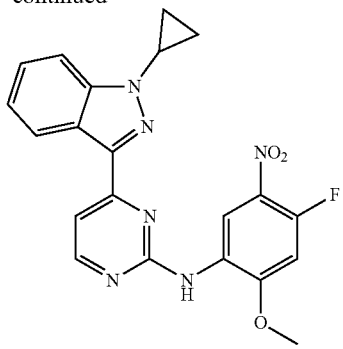

Formic acid aqueous solution (0.5 mL, 85%) was added to a solution of 4-fluoro-2-methoxy-5-nitroaniline (1.0 g, 5.4 mmol) in toluene (5 mL), and the mixture was heated to reflux overnight. The reaction solution was concentrated by rotational evaporation and used directly in the next reaction.

The aforementioned crude product (180 mg, 0.840 mmol) was dissolved in 2 mL of DMF, and NaH (41 mg, 1.68 mmol) was added in an ice-water bath. The mixture was stirred at this temperature for 30 minutes. Then, a solution of 1-cyclopropyl-3-(2-(methylsulfonyl)pyrimidin-4-yl)-1H-indazole (184 mg, 0.588 mmol) in DMF (2 mL) was added, and the mixture was stirred at room temperature overnight. The reaction solution was stirred for another 30 minutes after 0.5 mL of water was added. Then, 10 mL of water were added, and the reaction solution was filtered. The resulting solid was purified by column chromatography to obtain 4-(1-cyclopropyl-1H-indazol-3-yl)-N-(4-fluoro-2-methoxy-5-nitrophenyl)pyrimidin-2-amine (200 mg, 81%).

MS m/z (ESI): 421.1 [M+H]$^+$.

Step 5: Preparation of N1-(4-(1-cyclopropyl-1H-indazol-3-yl)pyrimidin-2-yl)-N4-(2-(dimethylamino)ethyl)-2-methoxy-N4-methyl-5-nitrobenzene-1,4-diamine

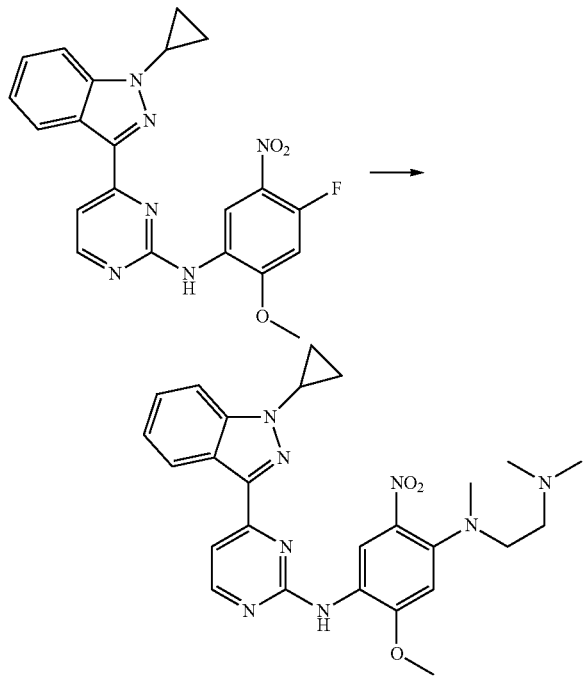

4-(1-cyclopropyl-1H-indazol-3-yl)-N-(4-fluoro-2-methoxy-5-nitrophenyl)pyrimidin-2-amine (200 mg, 0.48 mmol), trimethylethylenediamine (58.0 mg, 0.57 mmol) and DIPEA (0.24 mL, 1.43 mmol) were dissolved in 2 mL of DMA, and the mixture was stirred at 90° C. for 2 hours. After cooling, the reaction solution was diluted with EtOAc, washed several times with saturated brine, dried over anhydrous sodium sulfate, concentrated and purified by preparative thin-layer chromatography to obtain the title compound N 1-(4-(1-cyclopropyl-1H-indazol-3-yl)pyrimidin-2-yl)-N4-(2-(dimethylamino)ethyl)-2-methoxy-N4-methyl-5-nitrobenzene-1,4-diamine (40 mg, 17%).

MS m/z (ESI): 503.2 [M+H]$^+$.

Step 6: Preparation of N4-(4-(1-cyclopropyl-1H-indazol-3-yl)pyrimidin-2-yl)-N1-(2-(dimethylamino)ethyl)-5-methoxy-N1-methylbenzene-1,2,4-triamine

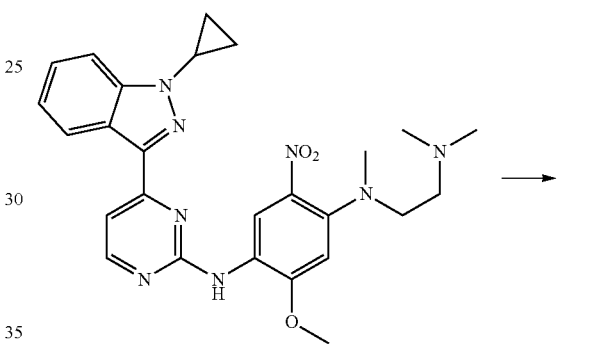

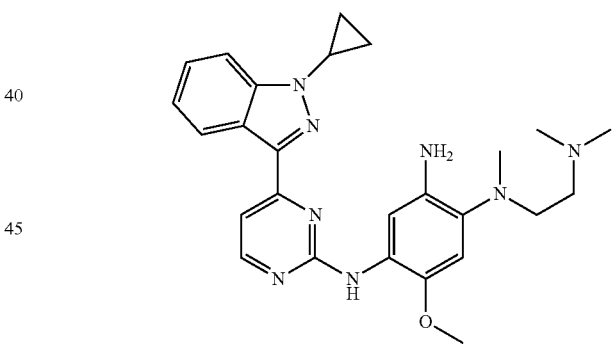

N1-(4-(1-cyclopropyl-1H-indazol-3-yl)pyrimidin-2-yl)-N4-(2-(dimethylamino)ethyl)-2-methoxy-N4-methyl-5-nitrobenzene-1,4-diamine (40 mg, 0.080 mmol), reduced iron powder (44 mg, 0.80 mmol), and ammonium chloride (3.4 mg, 0.064 mmol) were mixed in a mixture of 6 mL of ethanol and 2 mL of water, and the mixture was stirred at 70° C. overnight. After cooling, the reaction solution was filtered through celite, concentrated and purified by preparative thin-layer chromatography to obtain the title compound N4-(4-(1-cyclopropyl-1H-indazol-3-yl)pyrimidin-2-yl)-N1-(2-(dimethylamino)ethyl)-5-methoxy-N1-methylbenzene-1,2,4-triamine (19 mg, 50%).

MS m/z (ESI): 473.3 [M+H]$^+$.

Step 7: Preparation of N-(5-((4-(1-cyclopropyl-1H-indazol-3-yl)pyrimidin-2-yl)amino)-2-((2-(dimethylamino)ethyl)(methyl)amino)-4-methoxyphenyl)acrylamide

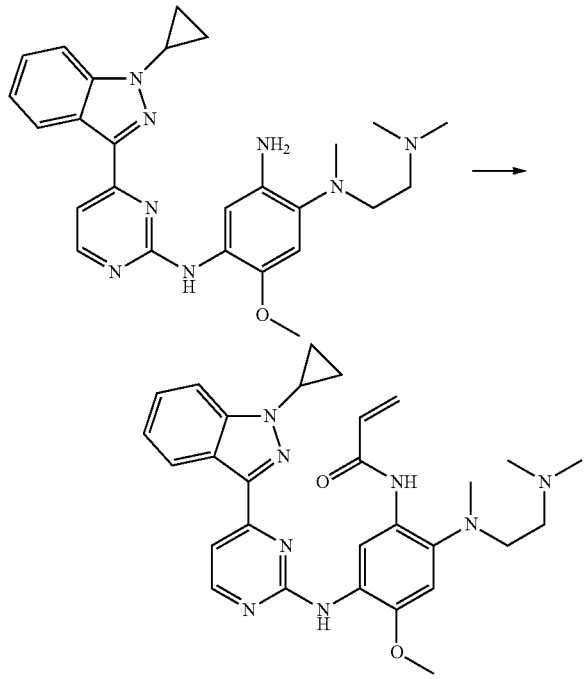

In a dry ice acetone bath, TEA (0.15 mL, 1.1 mmol) and a solution of acryloyl chloride (0.045 mL, 0.56 mmol) in THF (0.5 mL) were added dropwise successively to a solution of N4-(4-(1-cyclopropyl-1H-indazol-3-yl)pyrimidin-2-yl)-N1-(2-(dimethylamino)ethyl)-5-methoxy-N1-methylbenzene-1,2,4-triamine (19 mg, 0.040 mmol) in THF (2 mL). Then, the mixture was stirred at this temperature for 5 minutes, and the reaction was quenched with 1 mL of methanol. After the solvent was concentrated, the resulting residue was purified by preparative thin-layer chromatography to obtain the title compound N-(5-((4-(1-cyclopropyl-1H-indazol-3-yl)pyrimidin-2-yl)amino)-2-((2-(dimethylamino)ethyl)(methyl)amino)-4-methoxyphenyl)acrylamide (10 mg, 47%).

$^1$H NMR (400 MHz, CDCl$_3$): δ 10.1 (br s, 1H), 9.51 (s, 1H), 8.61 (d, J=8.0 Hz, 1H), 8.54 (d, J=5.2 Hz, 1H), 7.60 (m, 3H), 7.41 (m, 1H), 7.22 (m, 1H), 6.79 (s, 1H), 6.38 (m, 2H), 5.66 (m, 1H), 3.89 (s, 3H), 3.68 (m, 1H), 2.95 (m, 2H), 2.72 (s, 3H), 2.40 (m, 8H), 0.88 (m, 4H);
MS m/z (ESI): 527.3 [M+H]$^+$.

Example 120: Preparation of N-(5-((4-(1H-benzo[d]imidazol-1-yl)pyrimidin-2-yl)amino)-2-((2-(dimethylamino)ethyl)(methyl)amino)-4-methoxyphenyl)acrylamide

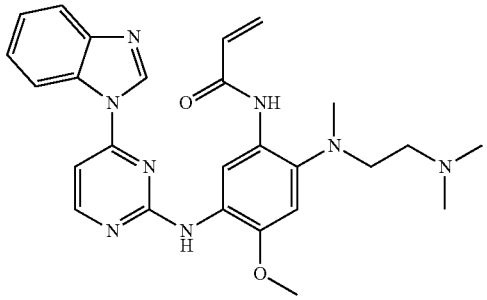 [SMILES: C=CC(=O)Nc1cc(Nc2nccc(-n3cnc4ccccc43)n2)c(OC)cc1N(C)CCN(C)C]

The preparation method of N-(5-((4-(1H-benzo[d]imidazol-1-yl)pyrimidin-2-yl)amino)-2-((2-(dimethylamino)ethyl)(methyl)amino)-4-methoxyphenyl)acrylamide was similar to Example 59.

$^1$H NMR (400 MHz, CD$_3$OD) δ 9.32 (s, 1H), 8.47 (d, J=5.8 Hz, 1H), 8.25 (s, 2H), 7.71 (dd, J=6.2, 2.8 Hz, 1H), 7.39 (dd, J=6.1, 3.2 Hz, 2H), 7.27 (d, J=5.8 Hz, 1H), 6.93 (s, 1H), 6.52 (dd, J=16.9, 10.0 Hz, 1H), 6.40 (dd, J=16.9, 1.7 Hz, 1H), 5.78 (dd, J=10.0, 1.7 Hz, 1H), 3.89 (s, 3H), 3.42 (t, J=5.5 Hz, 2H), 3.28-3.25 (m, 2H), 2.83 (s, 6H), 2.67 (s, 3H);
MS m/z (ESI): 487.3 [M+H]$^+$.

Example 121: Preparation of N-(2-((2-(dimethylamino)ethyl)(methyl)amino)-4-methoxy-5-((4-(5-(2-methoxyethoxy)-1H-indazol-1-yl)pyrimidin-2-yl)amino)phenyl)acrylamide

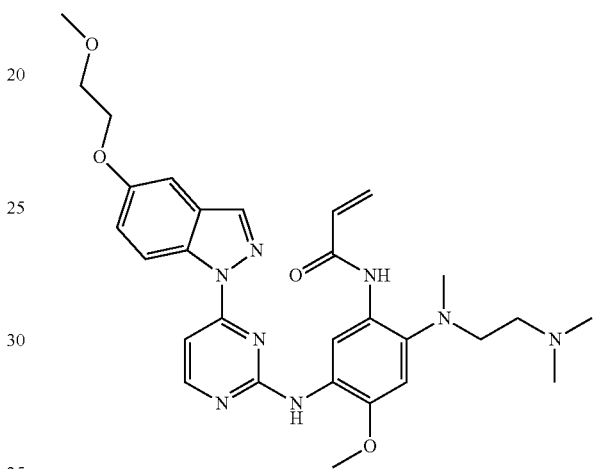

The preparation method of N-(2-((2-(dimethylamino)ethyl)(methyl)amino)-4-methoxy-5-((4-(5-(2-methoxyethoxy)-1H-indazol-1-yl)pyrimidin-2-yl)amino)phenyl)acrylamide was similar to Example 105.

$^1$H NMR (400 MHz, CD$_3$OD) δ 8.37 (s, 1H), 8.27 (s, 1H), 7.84 (s, 1H), 7.59 (s, 1H), 7.32 (s, 1H), 7.15 (s, 1H), 7.09 (s, 1H), 6.70-6.53 (m, 1H), 6.50 (s, 1H), 5.88 (s, 1H), 4.18 (s, 2H), 3.96 (s, 3H), 3.80 (s, 2H), 3.57 (s, 2H), 3.46 (s, 3H), 3.38 (s, 2H), 2.94 (s, 6H), 2.81 (s, 3H);
MS m/z (ESI): 561 [M+H]$^+$.

Example 122: Preparation of (E)-N-(5-((4-(1-cyclopropyl-1H-indol-3-yl)pyrimidin-2-yl)amino)-2-((2-(dimethylamino)ethyl)(methyl)amino)-4-methoxyphenyl)-4-(dimethylamino)but-2-enamide

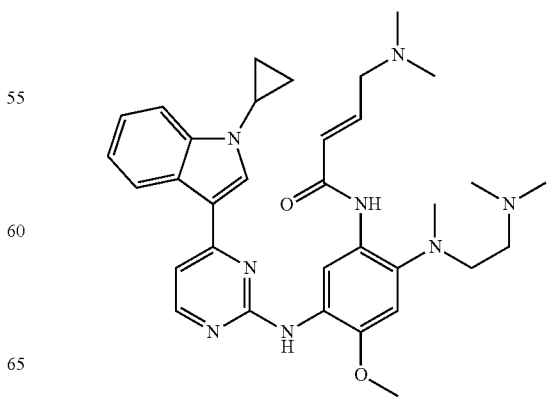

The preparation method of (E)-N-(5-((4-(1-cyclopropyl-1H-indol-3-yl)pyrimidin-2-yl)amino)-2-((2-(dimethylamino)ethyl)(methyl)amino)-4-methoxyphenyl)-4-(dimethylamino)but-2-enamide was similar to Example 22.

<sup>1</sup>H NMR (400 MHz, CDCl<sub>3</sub>) δ 9.70 (d, J=17.4 Hz, 2H), 8.49 (d, J=19.3 Hz, 1H), 8.32 (d, J=5.3 Hz, 1H), 8.05 (m, 1H), 7.59 (m, 2H), 7.09 (d, J=5.3 Hz, 1H), 6.90 (m, 1H), 6.68 (s, 1H), 6.46 (s, 1H), 3.81 (s, 3H), 3.39 (ddd, J=10.8, 7.1, 3.8 Hz, 1H), 3.16 (d, J=6.0 Hz, 2H), 2.89 (m, 2H), 2.63 (s, 3H), 2.46 (s, 2H), 2.31 (d, J=23.0 Hz, 12H), 1.16 (m, 2H), 1.01 (m, 2H);

MS m/z (ESI): 583.7 [M+H]<sup>+</sup>.

Example 123: Preparation of N-(5-((4-(1-cyclopropyl-1H-indol-3-yl)pyrimidin-2-yl)amino)-4-methoxy-2-(methyl(2-(pyrrolidin-1-yl)ethyl)amino)phenyl)acrylamide

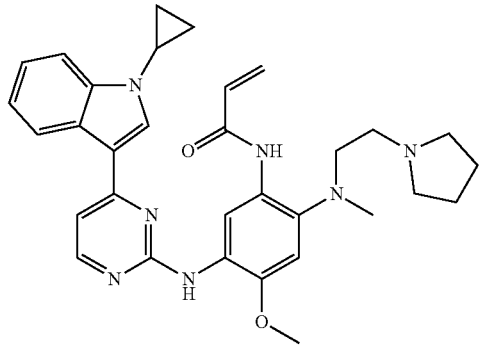 [SMILES: C=CC(=O)Nc1cc(Nc2nccc(-c3cn(C4CC4)c4ccccc34)n2)c(OC)cc1N(C)CCN1CCCC1]

The preparation method of N-(5-((4-(1-cyclopropyl-1H-indol-3-yl)pyrimidin-2-yl)amino)-4-methoxy-2-(methyl(2-(pyrrolidin-1-yl)ethyl)amino)phenyl)acrylamide was similar to Example 22.

<sup>1</sup>H NMR (400 MHz, CDCl<sub>3</sub>) δ 9.66 (s, 1H), 9.49 (s, 1H), 8.42 (s, 1H), 8.32 (d, J=5.3 Hz, 1H), 8.04 (d, J=6.9 Hz, 1H), 7.28 (m, 1H), 7.68-7.45 (m, 2H), 7.10 (d, J=5.3 Hz, 1H), 6.63 (s, 1H), 6.37 (dd, J=16.8, 1.8 Hz, 1H), 5.63 (dd, J=10.2, 1.8 Hz, 1H), 3.80 (s, 3H), 3.47-3.16 (m, 1H), 3.07 (s, 2H), 2.82 (s, 3H), 2.62 (s, 4H), 1.92 (s, 4H), 1.30 (m, 2H), 1.18 (m, 2H), 1.06-0.96 (m, 2H);

MS m/z (ESI): 552.7 [M+H]<sup>+</sup>.

Example 124: Preparation of N-(5-((4-(1-cyclopropyl-1H-indol-3-yl)pyrimidin-2-yl)amino)-4-methoxy-2-(methyl(2-morpholinoethyl)amino)phenyl)acrylamide

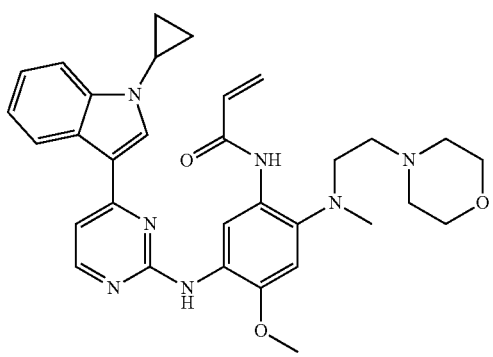 [SMILES: C=CC(=O)Nc1cc(Nc2nccc(-c3cn(C4CC4)c4ccccc34)n2)c(OC)cc1N(C)CCN1CCOCC1]

The preparation method of N-(5-((4-(1-cyclopropyl-1H-indol-3-yl)pyrimidin-2-yl)amino)-4-methoxy-2-(methyl(2-morpholinoethyl)amino)phenyl)acrylamide was similar to Example 22.

<sup>1</sup>H NMR (400 MHz, CDCl<sub>3</sub>) δ 9.72 (s, 1H), 9.21 (s, 1H), 8.49 (s, 1H), 8.33 (d, J=5.3 Hz, 1H), 8.04 (d, J=7.1 Hz, 1H), 7.65-7.42 (m, 2H), 7.34-7.13 (m, 2H), 7.11 (d, J=5.3 Hz, 1H), 6.70 (s, 1H), 6.40 (s, 2H), 5.77-5.51 (m, 1H), 3.80 (s, 3H), 3.65 (s, 4H), 3.50-3.20 (m, 1H), 3.02-2.79 (m, 2H), 2.59 (s, 3H), 2.32 (d, J=37.1 Hz, 6H), 1.20-1.08 (m, 2H), 1.08-0.95 (m, 2H);

MS m/z (ESI): 568.6 [M+H]<sup>+</sup>.

Example 125: Preparation of N-(5-((4-(5,6-dihydro-4H-pyrrolo[3,2,1-ij]quinolin-1-yl)pyrimidin-2-yl)amino)-2-((2-(dimethylamino)ethyl)(methyl)amino)-4-methoxyphenyl)acrylamide

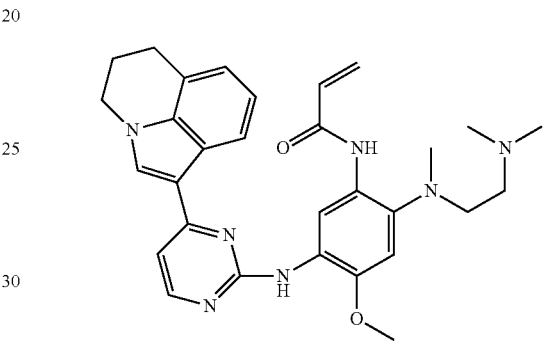

The preparation method of N-(5-((4-(5,6-dihydro-4H-pyrrolo[3,2,1-ij]quinolin-1-yl)pyrimidin-2-yl)amino)-2-((2-(dimethylamino)ethyl)(methyl)amino)-4-methoxyphenyl)acrylamide was similar to Example 22.

<sup>1</sup>H NMR (400 MHz, CD<sub>3</sub>OD): δ 8.47 (s, 1H), 7.99 (m, 3H), 7.36 (d, J=6.8 Hz, 1H), 7.12 (t, J=6.8 Hz, 1H), 7.07 (s, 1H), 7.00 (d, J=7.2 Hz, 1H), 6.58 (m, 1H), 6.45 (m, 1H), 5.85 (m, 1H), 4.30 (t, J=6.0 Hz, 2H), 3.95 (s, 3H), 3.54 (t, J=6.0 Hz, 2H), 3.36 (t, J=5.6 Hz, 2H), 3.00 (t, J=5.6 Hz, 2H), 2.90 (s, 6H), 2.80 (s, 3H), 2.25 (m, 2H);

MS m/z (ESI): 526.2 [M+H]<sup>+</sup>.

Example 126: Preparation of N-(5-((4-(1-allyl-1H-indol-3-yl)pyrimidin-2-yl)amino)-4-methoxy-2-(methyl(2-(methylamino)ethyl)amino)phenyl)acrylamide

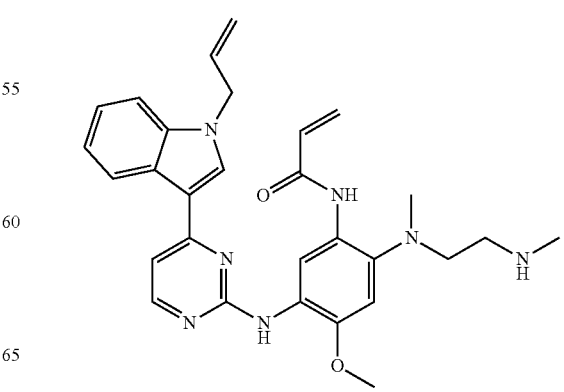

Step 1: preparation of tert-butyl {2-[(4-{[4-(1H-indol-3-yl)pyrimidin-2-yl]amino}-5-methoxy-2-nitrophenyl)(methyl) amino]ethyl}methylcarbamate

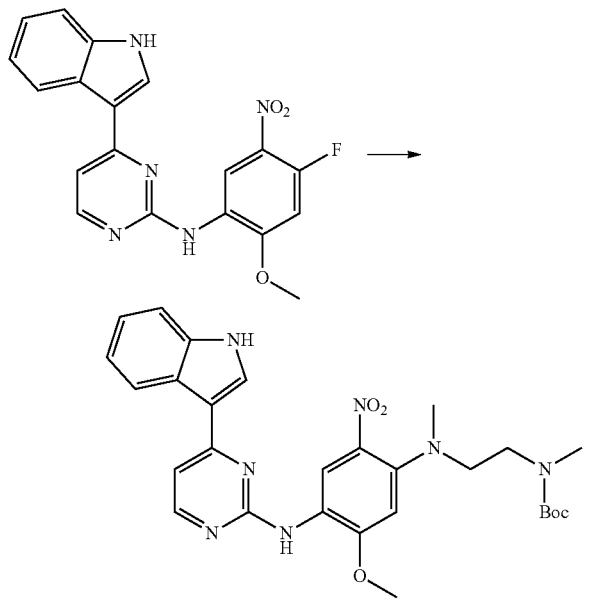

N-(4-fluoro-2-methoxy-5-nitrophenyl)-4-(1H-indol-3-yl)pyrimidin-2-amine (1.3 g, 3.43 mmol), DIPEA (2.2 gl, 7.14 mmol) and tert-butyl methyl(2-(methylamino)ethyl)carbamate (0.77 g, 4.12 mmol) were dissolved in DMA (15 mL). After heating up to 100° C. overnight, the reaction solution was concentrated and purified by column chromatography to obtain tert-butyl {2-[(4-{[4-(1H-indol-3-yl)pyrimidin-2-yl]amino}-5-methoxy-2-nitrophenyl)(methyl)amino]ethyl}methylcarbamate (1.9 g, 80%).

Step 2: Preparation of tert-butyl 3-(2-(((tert-butoxycarbonyl)(4-((2-((tert-butoxycarbonyl)(methyl)amino)ethyl)(methyl)amino)-2-methoxy-5-nitrophenyl)amino)pyrimidin-4-yl)-1H-indole-1-carboxylate

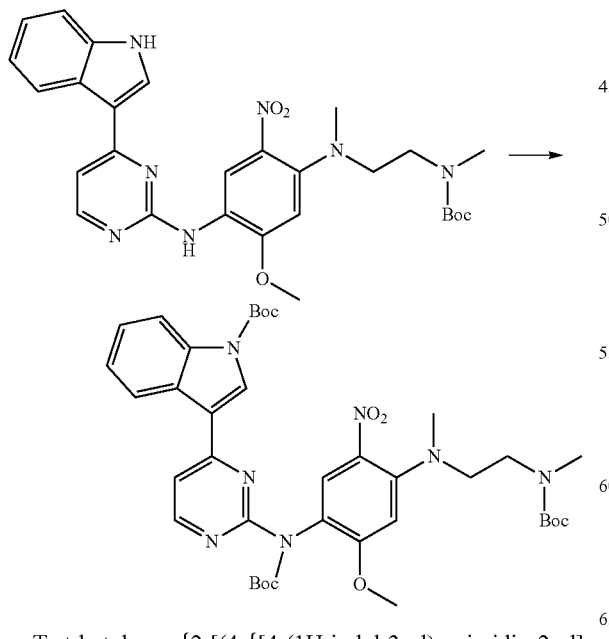

Tert-butyl {2-[(4-{[4-(1H-indol-3-yl)pyrimidin-2-yl]amino}-5-methoxy-2-nitrophenyl)(methyl)amino]

ethyl}methylcarbamate (1.9 g, 3.34 mol), Boc₂O (1.87 g, 8.58 mmol) and DMAP (84 mg, 0.69 mmol) were added to tetrahydrofuran (30 mL). The reaction solution was stirred at 50° C. overnight, and concentrated to obtain 2.0 g of a yellow solid, which was used directly in the next reaction.

Step 3: preparation of tert-butyl (2-((4-((4-(1H-indol-3-yl)pyrimidin-2-yl)(tert-butoxycarbonyl)amino)-5-methoxy-2-nitrophenyl)(methyl)amino)ethyl)(methyl)carbamate

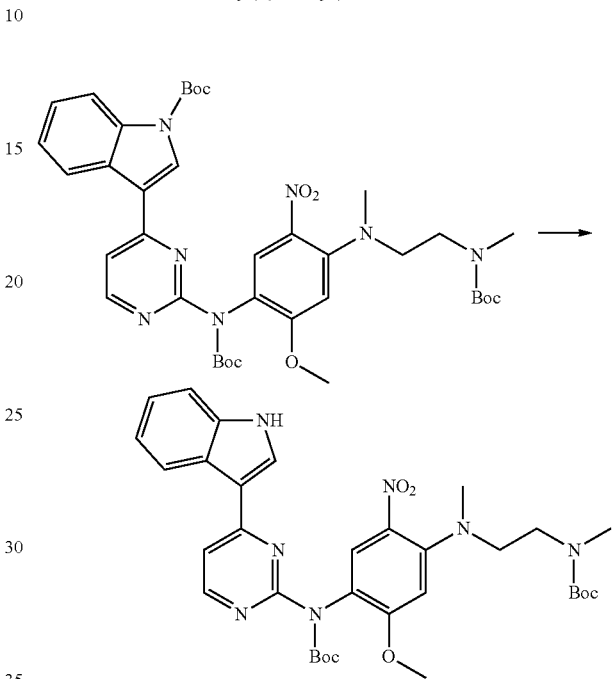

Tert-butyl 3-(2-((tert-butoxycarbonyl)(4-((2-((tert-butoxycarbonyl)(methyl)amino)ethyl)(methyl)amino)-2-methoxy-5-nitrophenyl)amino)pyrimidin-4-yl)-1H-indole-1-carboxylate (2.0 g, 2.678 mmol) was dissolved in methanol (20 mL). Then, sodium methoxide (29 mg, 0.535 mmol) was added. After the mixture was heated up to 50° C. for about 2 hours, the reaction was quenched with water. The reaction solution was concentrated, extracted with dichloromethane, concentrated and dried to obtain tert-butyl (2-((4-((4-(1H-indol-3-yl)pyrimidin-2-yl)(tert-butoxycarbonyl)amino)-5-methoxy-2-nitrophenyl)(methyl)amino)ethyl)(methyl)carbamate (2.3 g, 90%)

Step 4: Preparation of tert-butyl 2-((4-((4-(1-allyl-1H-indol-3-yl)pyrimidin-2-yl)(tert-butoxycarbonyl)amino)-5-methoxy-2-nitrophenyl)(methyl)amino)ethyl)(methyl)carbamate

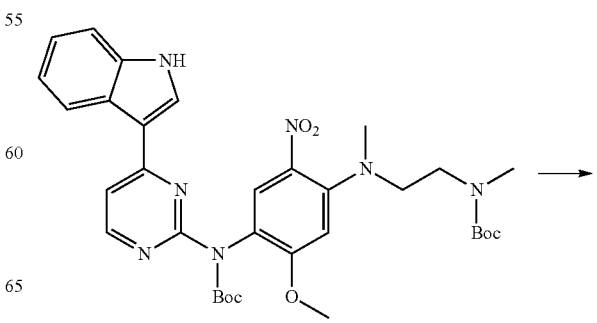

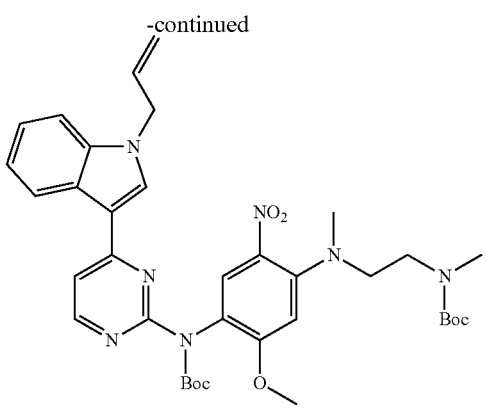

tert-butyl (2-((4-((4-(1H-indol-3-yl)pyrimidin-2-yl)(tert-butoxycarbonyl)amino)-5-methoxy-2-nitrophenyl)(methyl)amino)ethyl)(methyl)carbamate (200 mg, 0.309 mmol) and NaH (11 mg, 0.46 mmol) were added to THF (10 mL). Then, vinyl bromide (55 mg, 0.46 mmol) was added, and the mixture was stirred at room temperature for 3 hours. The reaction was quenched with water. The reaction solution was extracted with dichloromethane, concentrated, and dried to obtain 200 mg of tert-butyl 2-((4-((4-(1-allyl-1H-indol-3-yl)pyrimidin-2-yl)(tert-butoxycarbonyl)amino)-5-methoxy-2-nitrophenyl)(methyl)amino)ethyl)(methyl)carbamate as a yellow solid, which was used directly in the next step.

Step 5: Preparation of tert-butyl (2-((4-((4-(1-allyl-1H-indol-3-yl)pyrimidin-2-yl)(tert-butoxycarbonyl)amino)-2-amino-5-methoxyphenyl)(methyl)amino)ethyl)(methyl)carbamate

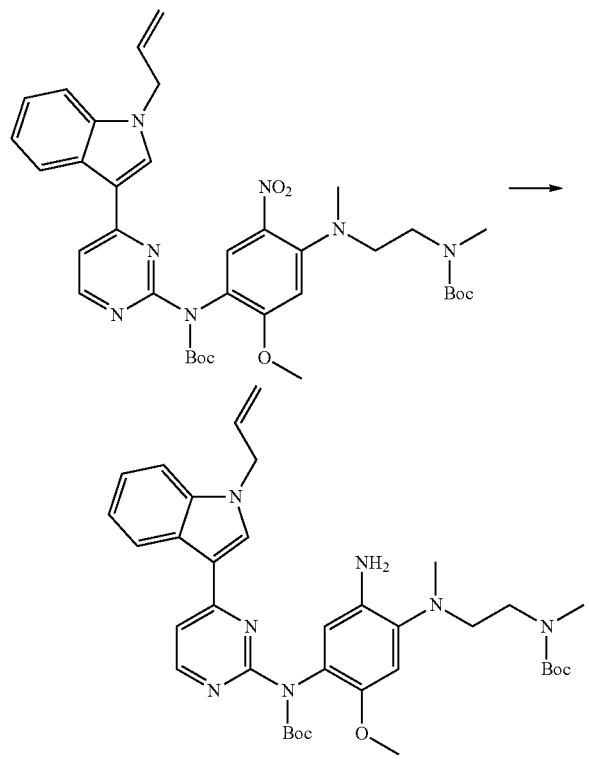

The raw material prepared in the previous step (2.4 g, 3.45 mmol), iron powder (2 g, 34.5 mmol) and ammonium chloride (3.7 g, 70 mmol) were added in a mixture of ethanol (60 mL) and water (20 mL). After heating at 60° C. overnight, the reaction solution was filtered, concentrated, extracted with dichloromethane, and purified by column chromatography to obtain tert-butyl (2-((4-((4-(1-allyl-1H-indol-3-yl)pyrimidin-2-yl)(tert-butoxycarbonyl)amino)-2-amino-5-methoxyphenyl)(methyl)amino)ethyl)(methyl)carbamate (1 g, 50%).

$^1$H NMR (400 MHz, DMSO) δ 8.45 (d, J=5.4 Hz, 1H), 8.36 (s, 1H), 8.08 (d, J=8.0 Hz, 1H), 7.48 (dd, J=9.3, 6.9 Hz, 2H), 7.17 (t, J=7.1 Hz, 1H), 7.00 (t, J=7.4 Hz, 1H), 6.79 (s, 1H), 6.47 (s, 1H), 6.09-5.97 (m, 1H), 5.19 (dd, J=10.3, 1.4 Hz, 1H), 5.06 (dd, J=17.1, 1.5 Hz, 1H), 4.90 (d, J=5.3 Hz, 2H), 4.37 (s, 2H), 3.65 (s, 3H), 3.36 (d, J=6.6 Hz, 2H), 2.96 (t, J=6.7 Hz, 2H), 2.75 (d, J=12.4 Hz, 3H), 2.66 (d, J=11.3 Hz, 3H), 1.41 (s, 18H);

MS m/z (ESI): 658 [M+H]$^+$.

Step 6: Preparation of tert-butyl (2-((2-acrylamido-4-((4-(1-allyl-1H-indol-3-yl)pyrimidin-2-yl)(tert-butoxycarbonyl) amino)-5-methoxyphenyl)(methyl)amino)ethyl)(methyl)carbamate

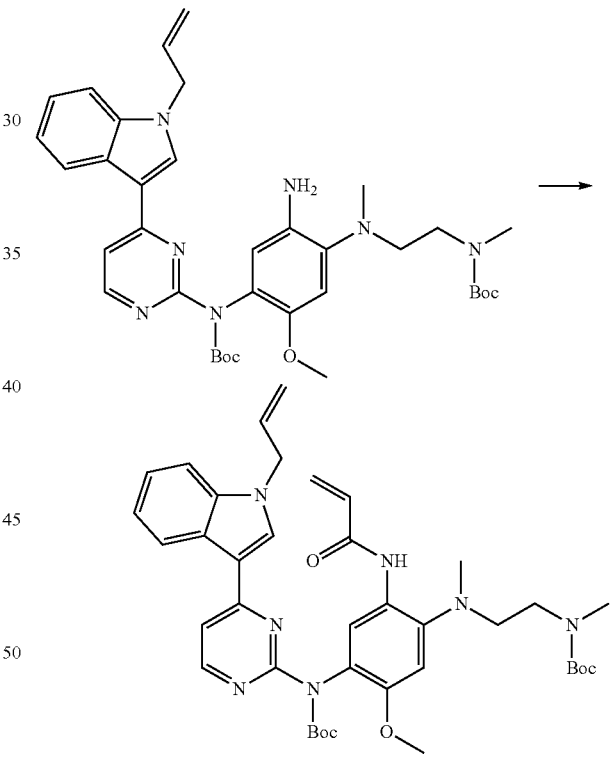

The raw material prepared in the previous step (1 g, 1.52 mmol) and DIPEA (0.56 g, 4.56 mmol) were dissolved in tetrahydrofuran (100 mL). The reaction system was cooled to −10° C., and 2.3 mL of a solution of acryloyl chloride in tetrahydrofuran (1 M) was added dropwise to the flask. The reaction was stirred for 30 minutes, and quenched with 1 mL of methanol. The reaction solution was concentrated, extracted with dichloromethane, and purified by column chromatography to obtain tert-butyl (2-((2-acrylamido-4-((4-(1-allyl-1H-indol-3-yl)pyrimidin-2-yl)(tert-butoxycarbonyl)amino)-5-methoxyphenyl)(methyl)amino)ethyl)(methyl)carbamate (0.9 g, 90%).

¹H NMR (400 MHz, CDCl₃) δ 8.73-8.39 (m, 3H), 7.91 (s, 2H), 7.29 (d, J=8.3 Hz, 2H), 7.19 (t, J=7.6 Hz, 1H), 7.01 (t, J=7.5 Hz, 1H), 6.87 (s, 1H), 6.36 (s, 2H), 6.00 (m, 1H), 5.69 (s, 1H), 5.26 (dd, J=10.3, 1.0 Hz, 1H), 5.19-5.10 (m, 1H), 4.77 (d, J=5.4 Hz, 2H), 3.80 (s, 3H), 3.44 (s, 2H), 3.00 (d, J=25.1 Hz, 2H), 2.84 (s, 3H), 2.78 (s, 3H), 1.48 (s, 9H), 1.47 (s, 9H):

MS m/z (ESI): 712 [M+H]⁺.

Step 7: Preparation of N-(5-((4-(1-allyl-1H-indol-3-yl)pyrimidin-2-yl)amino)-4-methoxy-2-(methyl(2-(methylamino)ethyl)amino)phenyl)acrylamide

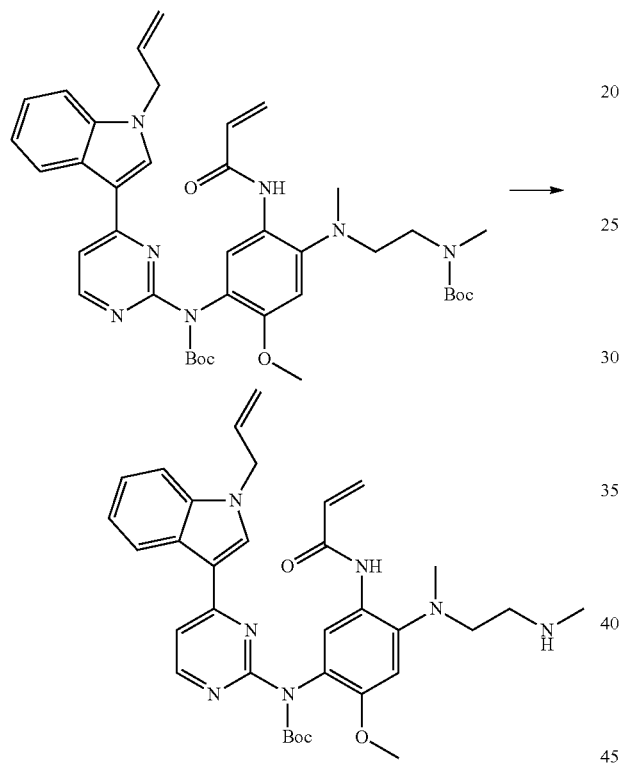

The raw material prepared in the previous step (0.9 g) was dissolved in a dichloromethane solution (50 mL) containing 20% trifluoroacetic acid by volume, and the mixture was stirred at room temperature for 6 hours. After TLC showed completion of the reaction, the pH was adjusted to alkaline with saturated sodium bicarbonate aqueous solution. Then, the reaction solution was extracted with dichloromethane and concentrated to obtain N-(5-((4-(1-allyl-1H-indol-3-yl)pyrimidin-2-yl)amino)-4-methoxy-2-(methyl(2-(methylamino)ethyl)amino)phenyl)acrylamide (535 mg, 83%).

¹H NMR (400 MHz, CDCl₃) δ 9.74 (s, 2H), 8.99-8.92 (m, 1H), 8.38 (d, J=5.3 Hz, 1H), 8.11 (s, 1H), 7.68 (s, 1H), 7.38 (s, 1H), 7.26-7.23 (m, 1H), 7.19 (d, J=5.3 Hz, 1H), 6.71 (s, 1H), 6.67-6.57 (m, 1H), 6.40 (d, J=16.9 Hz, 1H), 6.12-5.98 (m, 1H), 5.69 (d, J=11.9 Hz, 1H), 5.23-5.13 (m, 2H), 4.97 (s, 2H), 3.87 (s, 3H), 2.96 (s, 2H), 2.70 (s, 2H), 2.66 (s, 3H), 2.45 (s, 3H);

MS m/z (ESI): 512 [M+H]⁺.

Example 127: Preparation of N-(4-methoxy-5-((4-(6-methoxy-1-methyl-1H-indol-3-yl)pyrimidin-2-yl)amino)-2-(methyl(2-(methylamino)ethyl)amino)phenyl)acrylamide

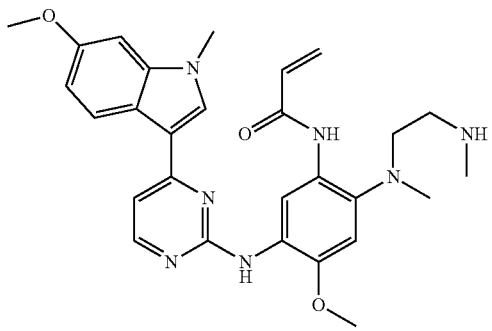

The preparation method of N-(4-methoxy-5-((4-(6-methoxy-1-methyl-1H-indol-3-yl)pyrimidin-2-yl)amino)-2-(methyl(2-(methylamino)ethyl)amino)phenyl)acrylamide was similar to Example 126.

¹H NMR (400 MHz, CD₃OD) δ 8.32 (s, 1H), 8.07 (s, 1H), 7.87 (d, J=6.9 Hz, 2H), 7.25 (d, J=7.0 Hz, 1H), 7.01-6.90 (m, 2H), 6.77 (dd, J=8.8, 2.0 Hz, 1H), 6.48 (dd, J=16.9, 10.1 Hz, 1H), 6.34 (dd, J=17.0, 1.8 Hz, 1H), 5.75 (dd, J=10.1, 1.8 Hz, 1H), 3.92-3.70 (m, 9H), 3.43-3.30 (m, 2H), 3.17-3.05 (m, 2H), 2.67 (d, J=9.0 Hz, 6H);

MS m/z (ESI): 516.2 [M+H]⁺.

Example 128: Preparation of N-(5-((4-(1-cyclopropyl-1H-indol-3-yl)pyrimidin-2-yl)amino)-4-methoxy-2-(methyl(2-(methylamino)ethyl)amino)phenyl)acrylamide

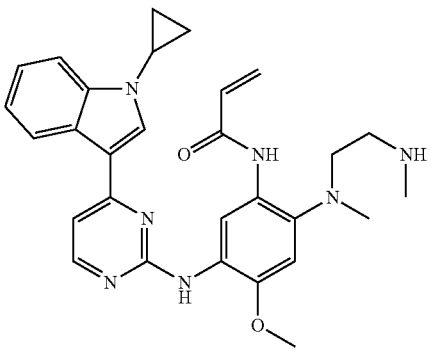 [SMILES: C=CC(=O)Nc1cc(Nc2nccc(-c3cn(C4CC4)c4ccccc34)n2)c(OC)cc1N(C)CCNC]

The preparation method of N-(5-((4-(1-cyclopropyl-1H-indol-3-yl)pyrimidin-2-yl)amino)-4-methoxy-2-(methyl(2-(methylamino)ethyl)amino)phenyl)acrylamide was similar to Example 126.

¹H NMR (400 MHz, CDCl₃) δ 9.37 (s, 1H), 9.29 (s, 1H), 8.29 (d, J=5.3 Hz, 1H), 8.18 (s, 1H), 8.07 (d, J=7.2 Hz, 1H), 7.61-7.40 (m, 2H), 7.24-7.15 (m, 2H), 7.06 (d, J=5.3 Hz, 1H), 6.94 (dd, J=15.9, 9.9 Hz, 1H), 6.45 (s, 1H), 6.17 (d, J=16.9 Hz, 1H), 5.58 (d, J=10.2 Hz, 1H), 3.79 (s, 3H), 3.39-3.15 (m, 1H), 2.93 (s, 2H), 2.65 (s, 2H), 2.44 (s, 3H), 2.26 (s, 3H), 1.01 (d, J=5.2 Hz, 4H);

MS m/z (ESI): 512.6 [M+H]⁺.

Example 129: Preparation of N-(4-methoxy-2-(methyl(2-(methylamino)ethyl)amino)-5-((4-(1-(prop-2-yn-1-yl)-1H-indol-3-yl)pyrimidin-2-yl)amino)phenyl)acrylamide

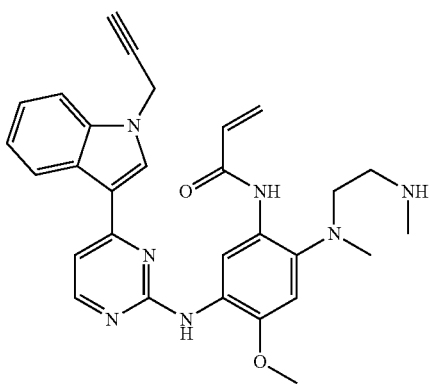 [SMILES: C#CCn1cc(-c2ccnc(Nc3cc(NC(=O)C=C)c(N(C)CCNC)cc3OC)n2)c2ccccc21]

The preparation method of N-(4-methoxy-2-(methyl(2-(methylamino)ethyl)amino)-5-((4-(1-(prop-2-yn-1-yl)-1H-indol-3-yl)pyrimidin-2-yl)amino)phenyl)acrylamide was similar to Example 126.

$^1$H NMR (400 MHz, CDCl$_3$) δ 9.90-9.83 (m, 1H), 9.81-9.73 (m, 1H), 9.25-9.12 (m, 1H), 8.39 (d, J=5.3 Hz, 1H), 8.12-8.05 (m, 1H), 7.70 (s, 1H), 7.61-7.53 (m, 1H), 7.30 (s, 2H), 7.20 (d, J=5.3 Hz, 1H), 6.75 (s, 1H), 6.62-6.44 (m, 2H), 5.81-5.63 (m, 1H), 5.30 (s, 1H), 5.18 (s, 2H), 3.88 (s, 3H), 2.97-2.87 (m, 2H), 2.69 (s, 3H), 2.68-2.63 (m, 2H), 2.47 (s, 3H), 2.38 (s, 1H);

MS m/z (ESI): 510 [M+H]$^+$.

Example 130: Preparation of N-(5-((5-chloro-4-(1-(oxetan-3-yl)-1H-indol-3-yl)pyrimidin-2-yl)amino)-2-((2-(dimethylamino)ethyl)(methyl)amino)-4-methoxyphenyl)acrylamide

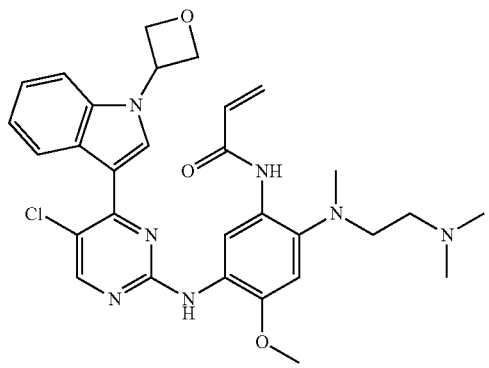 [SMILES: C=CC(=O)Nc1cc(Nc2ncc(Cl)c(-c3cn(C4COC4)c4ccccc34)n2)c(OC)cc1N(C)CCN(C)C]

The preparation method of N-(5-((5-chloro-4-(1-(oxetan-3-yl)-1H-indol-3-yl)pyrimidin-2-yl)amino)-2-((2-(dimethylamino)ethyl)(methyl)amino)-4-methoxyphenyl)acrylamide was similar to Example 126.

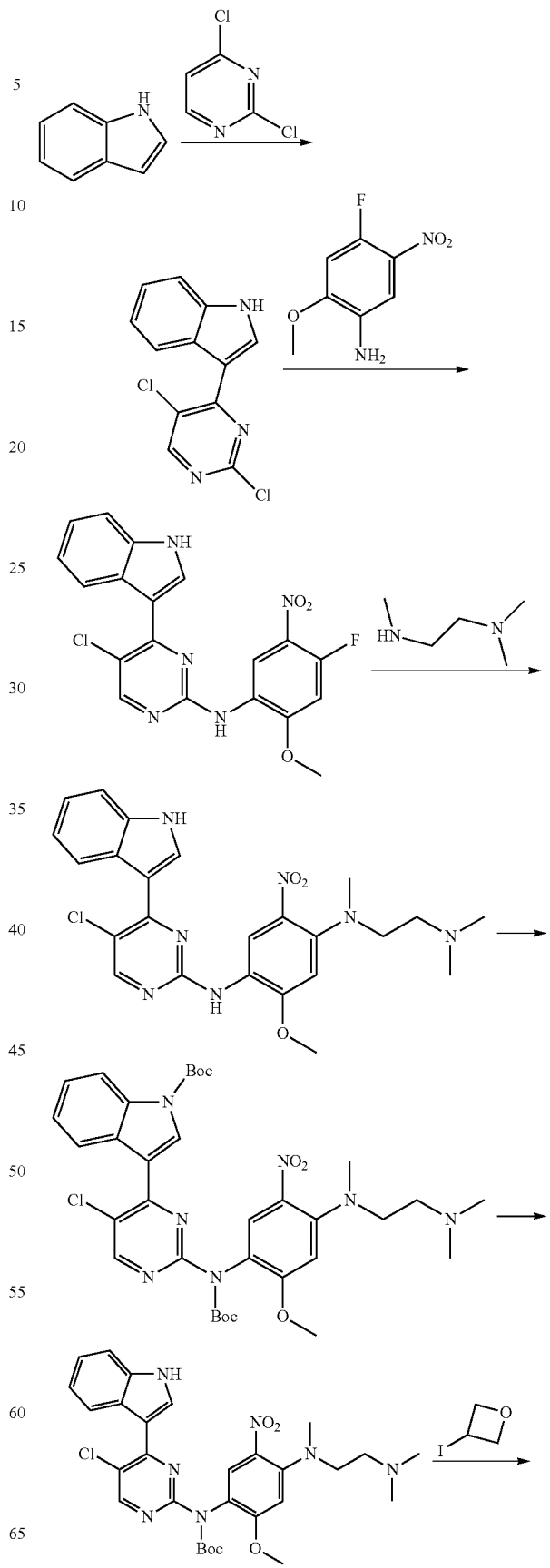

-continued

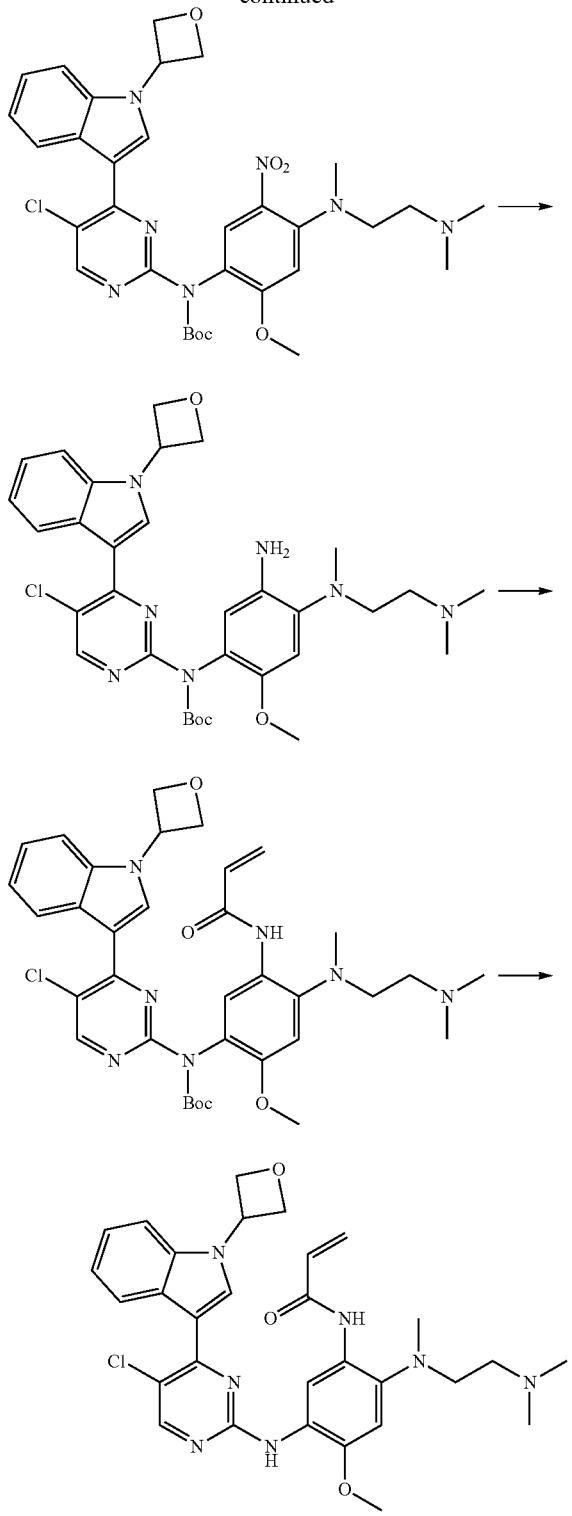

¹H NMR (400 MHz, CD₃OD) δ 8.74 (s, 1H), 8.53 (s, 1H), 8.30-8.23 (m, 2H), 7.50 (d, J=8.3 Hz, 1H), 7.17-7.10 (m, 1H), 7.03 (t, J=7.2 Hz, 1H), 6.86 (s, 1H), 6.38 (dd, J=17.0, 10.2 Hz, 1H), 6.17 (d, J=17.0 Hz, 1H), 5.69-5.59 (m, 2H), 5.10 (t, J=7.4 Hz, 2H), 4.99-4.93 (m, 2H), 3.81 (s, 3H), 3.02 (s, 2H), 2.59 (s, 3H), 2.47 (s, 2H), 2.27 (s, 6H);
MS m/z (ESI): 576.3 [M+H]⁺.

Example 131: Preparation of N-(2-((2-(dimethylamino)ethyl)(methyl)amino)-4-methoxy-5-((4-(1-(oxetan-3-yl)-1H-indol-3-yl)-5-(trifluoromethyl)pyrimidin-2-yl)amino)phenyl)acrylamide

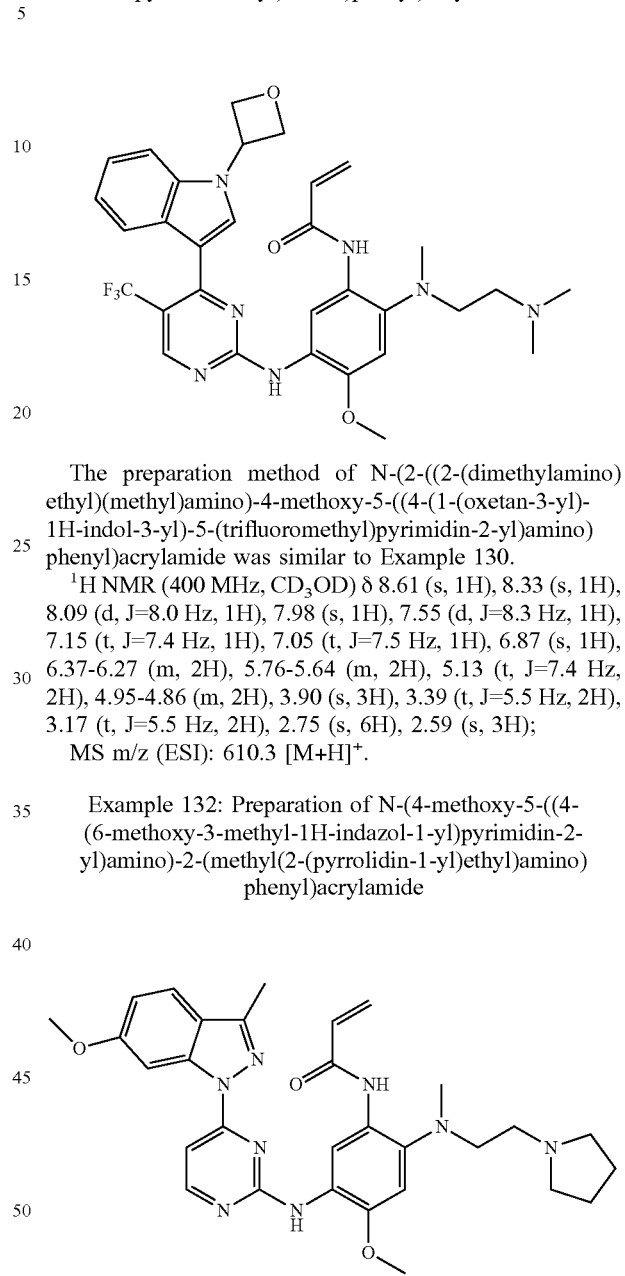

The preparation method of N-(2-((2-(dimethylamino)ethyl)(methyl)amino)-4-methoxy-5-((4-(1-(oxetan-3-yl)-1H-indol-3-yl)-5-(trifluoromethyl)pyrimidin-2-yl)amino)phenyl)acrylamide was similar to Example 130.
¹H NMR (400 MHz, CD₃OD) δ 8.61 (s, 1H), 8.33 (s, 1H), 8.09 (d, J=8.0 Hz, 1H), 7.98 (s, 1H), 7.55 (d, J=8.3 Hz, 1H), 7.15 (t, J=7.4 Hz, 1H), 7.05 (t, J=7.5 Hz, 1H), 6.87 (s, 1H), 6.37-6.27 (m, 2H), 5.76-5.64 (m, 2H), 5.13 (t, J=7.4 Hz, 2H), 4.95-4.86 (m, 2H), 3.90 (s, 3H), 3.39 (t, J=5.5 Hz, 2H), 3.17 (t, J=5.5 Hz, 2H), 2.75 (s, 6H), 2.59 (s, 3H);
MS m/z (ESI): 610.3 [M+H]⁺.

Example 132: Preparation of N-(4-methoxy-5-((4-(6-methoxy-3-methyl-1H-indazol-1-yl)pyrimidin-2-yl)amino)-2-(methyl(2-(pyrrolidin-1-yl)ethyl)amino)phenyl)acrylamide

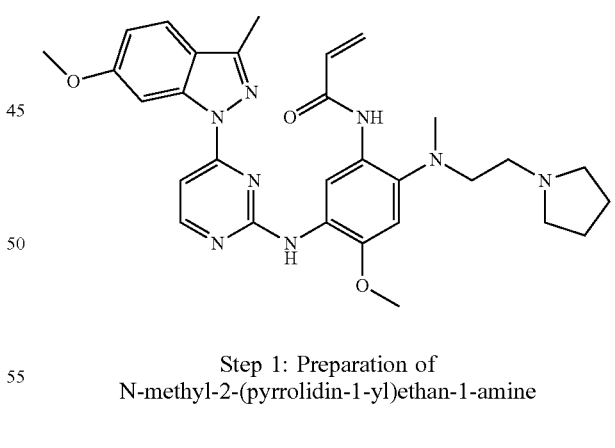

Step 1: Preparation of N-methyl-2-(pyrrolidin-1-yl)ethan-1-amine

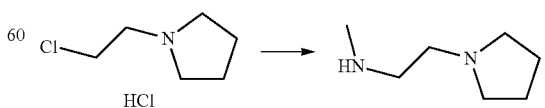

1-(2-chloroethyl) pyrrolidine hydrochloride (25 g, 0.147 mmol) aqueous solution (50 mL) was added slowly and dropwise to methylamine aqueous solution (114 mL). Upon completion of the addition, the mixture was stirred for 30 minutes, followed by addition of sodium hydroxide (46.25 g, 1.15 mmol). A yellow supernatant appeared. The reaction solution was extracted with methyl t-butyl ether, concentrated at room temperature, and dried in vacuo to obtain N-methyl-2-(pyrrolidin-1-yl)ethan-1-amine (17 g, 90%).

Steps 2 to 7: Preparation of N-(4-methoxy-5-((4-(6-methoxy-3-methyl-1H-indazol-1-yl)pyrimidin-2-yl)amino)-2-(methyl(2-(pyrrolidin-1-yl)ethyl)amino)phenyl)acrylamide

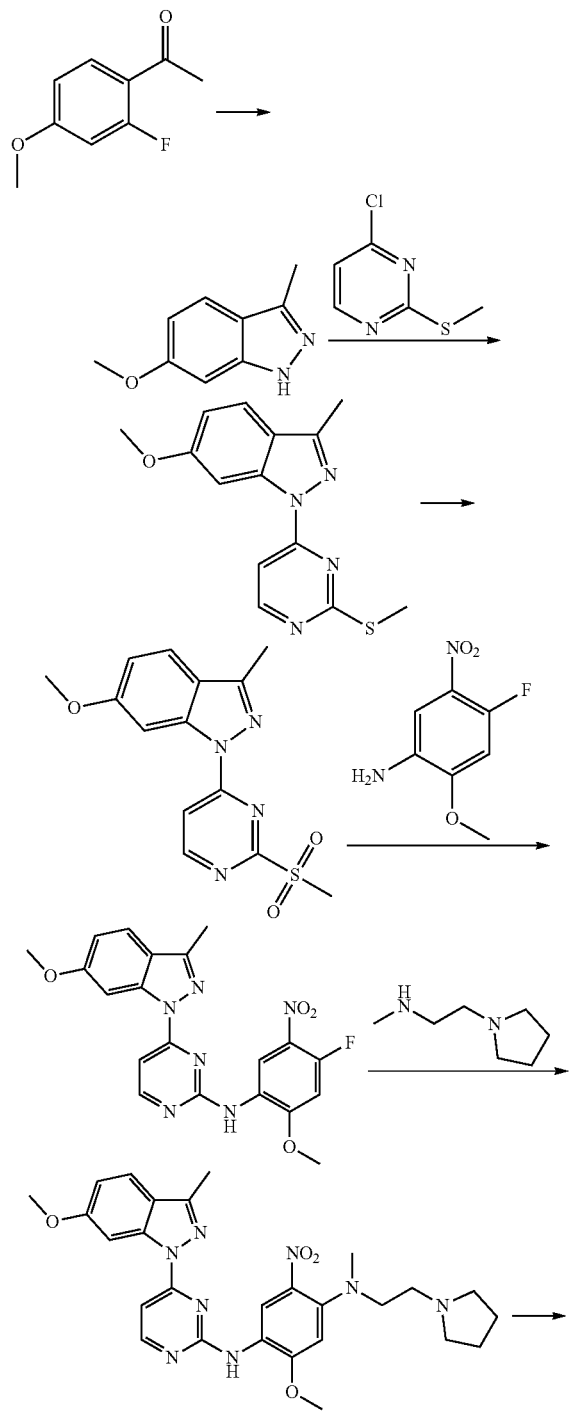

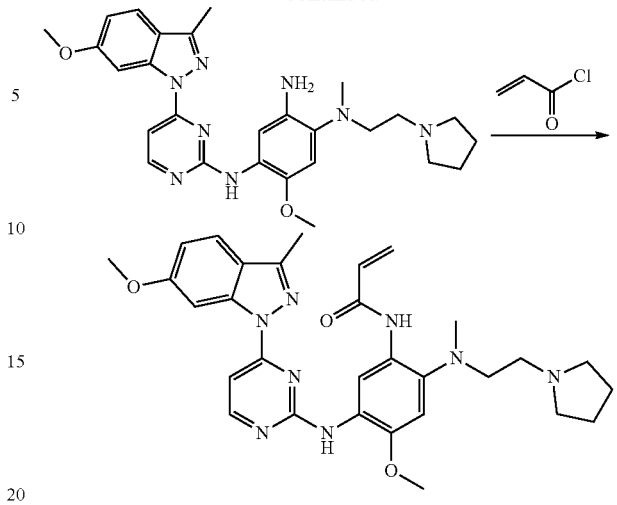

Steps 2 to 7: The preparation method of N-(4-methoxy-5-((4-(6-methoxy-3-methyl-1H-indazol-1-yl)pyrimidin-2-yl)amino)-2-(methyl(2-(pyrrolidin-1-yl)ethyl)amino)phenyl)acrylamide was similar to Example 54.

$^1$H NMR (400 MHz, CD$_3$OD) δ 8.19 (d, J=7.0 Hz, 1H), 8.05 (s, 1H), 7.78-7.66 (m, 2H), 7.58 (d, J=7.0 Hz, 1H), 7.09 (dd, J=8.5, 2.4 Hz, 2H), 6.62 (dd, J=16.9, 10.2 Hz, 1H), 6.39 (dd, J=16.9, 1.5 Hz, 1H), 5.85 (dd, J=10.2, 1.5 Hz, 1H), 3.95 (s, 3H), 3.87 (s, 3H), 3.68-3.60 (m, 2H), 3.56 (t, J=5.7 Hz, 2H), 3.43 (t, J=5.7 Hz, 2H), 3.13 (d, J=8.6 Hz, 2H), 2.82 (s, 3H), 2.58 (s, 3H), 2.17 (d, J=6.0 Hz, 4H);

MS m/z (ESI): 557 [M+H]$^+$.

Example 133: Preparation of N4-(4-(5-ethoxy-1H-indazol-1-yl)pyrimidin-2-yl)-5-methoxy-N1-methyl-N1-(2-(pyrrolidin-1-yl)ethyl)benzene-1,2,4-triamine

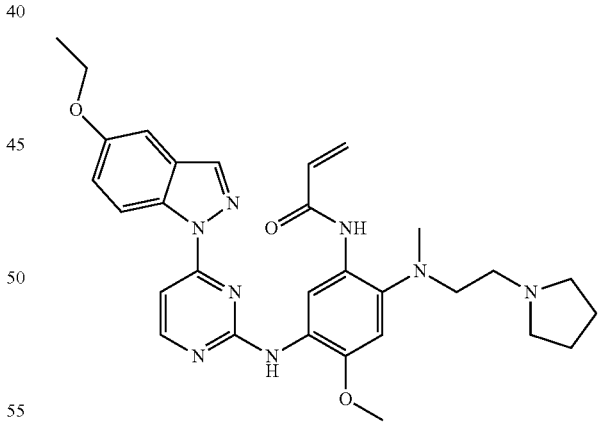

The preparation method of N4-(4-(5-ethoxy-1H-indazol-1-yl)pyrimidin-2-yl)-5-methoxy-N1-methyl-N1-(2-(pyrrolidin-1-yl)ethyl)benzene-1,2,4-triamine was similar to Example 105.

$^1$H NMR (400 MHz, CD$_3$OD) δ 8.38 (s, 1H), 8.27 (d, J=6.6 Hz, 2H), 7.76 (s, 1H), 7.60 (d, J=6.9 Hz, 1H), 7.29 (d, J=2.2 Hz, 1H), 7.12 (d, J=8.9 Hz, 1H), 7.08 (s, 1H), 6.63-6.53 (m, 1H), 6.43 (dd, J=16.9, 1.6 Hz, 1H), 5.88 (dd, J=10.1, 1.5 Hz, 1H), 4.11 (q, J=6.9 Hz, 2H), 3.96 (s, 3H), 3.65 (d, J=9.9 Hz, 2H), 3.58 (t, J=5.6 Hz, 2H), 3.43 (t, J=5.4

Hz, 2H), 3.14 (d, J=9.9 Hz, 2H), 2.83 (s, 3H), 2.21 (t, J=6.6 Hz, 4H), 1.45 (t, J=7.0 Hz, 3H);

MS m/z (ESI): 557 [M+H]⁺.

Example 134: Preparation of N-(4-methoxy-5-((4-(5-(2-methoxyethoxy)-1H-indazol-1-yl)pyrimidin-2-yl)amino)-2-(methyl(2-(pyrrolidin-1-yl)ethyl)amino)phenyl)acrylamide

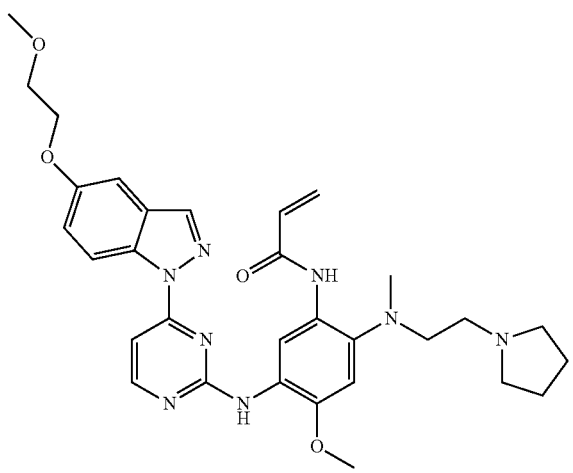 [SMILES: C=CC(=O)Nc1cc(Nc2nccc(-n3ncc4cc(OCCOC)ccc43)n2)c(OC)cc1N(C)CCN1CCCC1]

The preparation method of N-(4-methoxy-5-((4-(5-(2-methoxyethoxy)-1H-indazol-1-yl)pyrimidin-2-yl)amino)-2-(methyl(2-(pyrrolidin-1-yl)ethyl)amino)phenyl)acrylamide was similar to Example 105.

¹H NMR (400 MHz, CD₃OD) δ 8.35 (s, 1H), 8.28 (m, 2H), 7.79 (s, 1H), 7.55 (d, J=6.6 Hz, 1H), 7.30 (s, 1H), 7.13 (d, J=8.7 Hz, 1H), 7.06 (s, 1H), 6.58 (dd, J=16.8, 10.1 Hz, 1H), 6.42 (d, J=16.8 Hz, 1H), 5.86 (d, J=10.1 Hz, 1H), 4.17 (m, 2H), 3.95 (s, 3H), 3.78 (m, 2H), 3.62 (m, 2H), 3.56 (m, 2H), 3.45 (s, 3H), 3.42 (m, 2H), 3.13 (m, 2H), 2.81 (s, 3H), 2.19 (m, 4H);

MS m/z (ESI): 587 [M+H]⁺.

Example 135: Preparation of N-(4-methoxy-5-((4-(4-methoxy-1H-indazol-1-yl)pyrimidin-2-yl)amino)-2-(methyl(2-(pyrrolidin-1-yl)ethyl)amino)phenyl)acrylamide

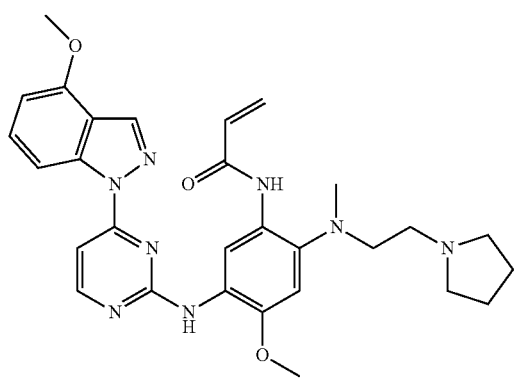 [SMILES: C=CC(=O)Nc1cc(Nc2nccc(-n3ncc4c(OC)cccc43)n2)c(OC)cc1N(C)CCN1CCCC1]

Step 1: Preparation of N-methyl-2-(pyrrolidin-1-yl)ethan-1-amine

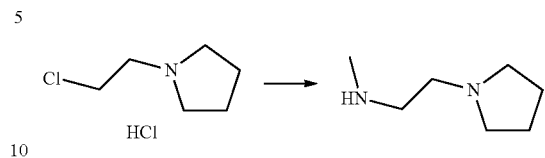

The preparation method of N-methyl-2-(pyrrolidin-1-yl)ethan-1-amine was similar to Example 132.

Steps 2 to 7: Preparation of N-(4-methoxy-5-((4-(4-methoxy-1H-indazol-1-yl)pyrimidin-2-yl)amino)-2-(methyl(2-(pyrrolidin-1-yl)ethyl)amino)phenyl)acrylamide

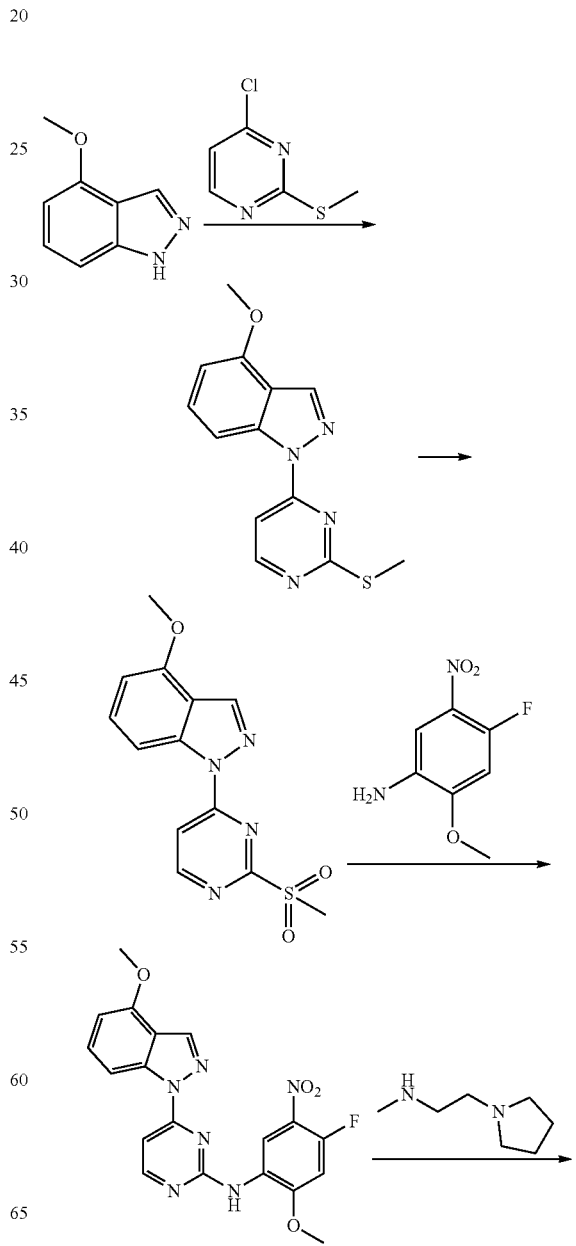

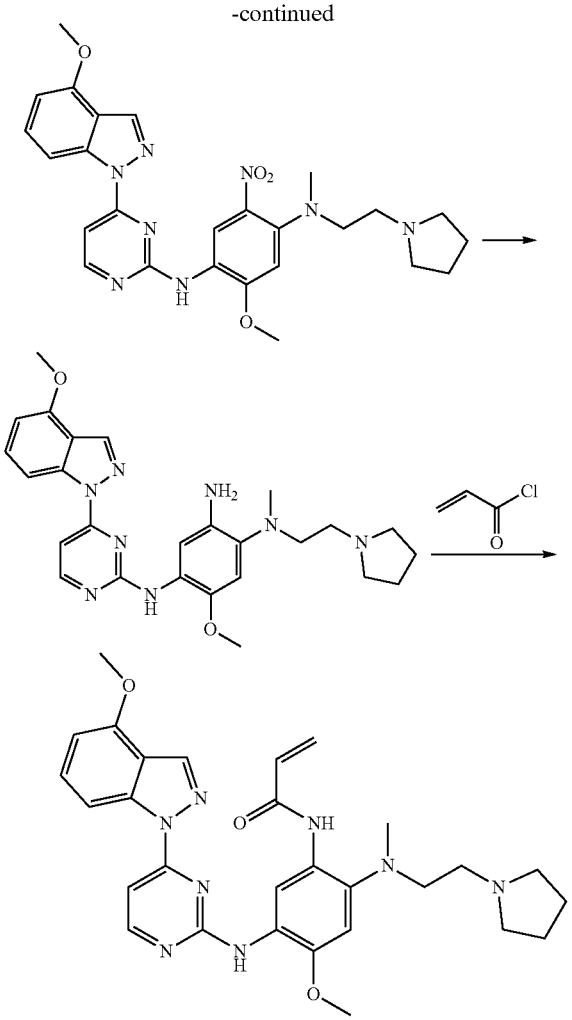

The preparation method of N-(4-methoxy-5-((4-(4-methoxy-1H-indazol-1-yl)pyrimidin-2-yl)amino)-2-(methyl(2-(pyrrolidin-1-yl)ethyl)amino)phenyl)acrylamide was similar to Example 43.

¹H NMR (400 MHz, CD₃OD) δ 8.43 (s, 1H), 8.27 (d, J=6.9 Hz, 1H), 7.99 (s, 1H), 7.82 (s, 1H), 7.59 (d, J=6.9 Hz, 1H), 7.43 (t, J=8.1 Hz, 1H), 7.07 (s, 1H), 6.85 (d, J=8.0 Hz, 1H), 6.61 (dd, J=16.9, 10.1 Hz, 1H), 6.42 (dd, J=16.9, 1.6 Hz, 1H), 5.87 (dd, J=10.2, 1.6 Hz, 1H), 3.99 (s, 3H), 3.96 (d, J=5.1 Hz, 3H), 3.64 (d, J=10.0 Hz, 2H), 3.56 (t, J=5.6 Hz, 2H), 3.43 (t, J=5.6 Hz, 2H), 3.13 (d, J=8.9 Hz, 2H), 2.82 (s, 3H), 2.19 (s, 4H);
MS m/z (ESI): 543.3 [M+H]⁺.

Example 136: Preparation of N-(4-methoxy-5-((4-(6-methoxy-1H-indazol-1-yl)pyrimidin-2-yl)amino)-2-(methyl(2-(pyrrolidin-1-yl)ethyl)amino)phenyl)acrylamide

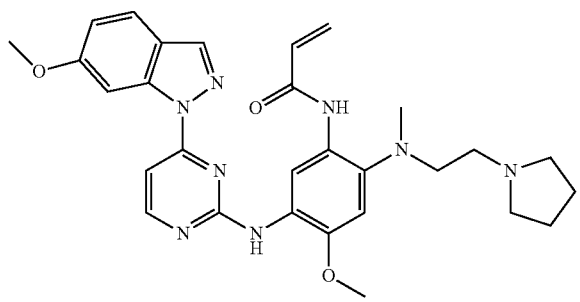 [SMILES: C=CC(=O)Nc1cc(Nc2nccc(-n3ncc4ccc(OC)cc43)n2)c(OC)cc1N(C)CCN1CCCC1]

The preparation method of N-(4-methoxy-5-((4-(6-methoxy-1H-indazol-1-yl)pyrimidin-2-yl)amino)-2-(methyl(2-(pyrrolidin-1-yl)ethyl)amino)phenyl)acrylamide was similar to Example 135.

¹H NMR (400 MHz, CD₃OD) δ 8.24 (s, 1H), 8.17 (d, J=5.5 Hz, 1H), 8.04 (s, 1H), 7.70 (s, 1H), 7.65 (d, J=8.7 Hz, 1H), 7.50 (d, J=6.5 Hz, 1H), 7.02-6.92 (m, 2H), 6.47 (dd, J=16.9, 10.2 Hz, 1H), 6.27 (d, J=16.9 Hz, 1H), 5.74 (d, J=10.1 Hz, 1H), 3.84 (s, 3H), 3.76 (s, 3H), 3.49 (s, 2H), 3.46-3.42 (m, 2H), 3.31 (d, J=5.2 Hz, 2H), 3.01 (s, 2H), 2.69 (s, 3H), 2.06 (s, 4H):
MS m/z (ESI): 543.3 [M+H]⁺.

Example 137: Preparation of N-(4-methoxy-5-((4-(5-methoxy-1H-indazol-1-yl)pyrimidin-2-yl)amino)-2-(methyl(2-(pyrrolidin-1-yl)ethyl)amino)phenyl)acrylamide

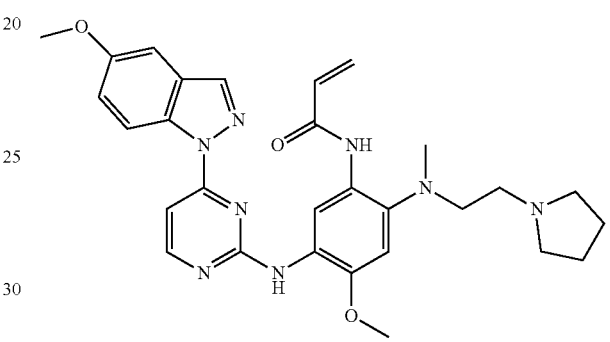

The preparation method of N-(4-methoxy-5-((4-(5-methoxy-1H-indazol-1-yl)pyrimidin-2-yl)amino)-2-(methyl(2-(pyrrolidin-1-yl)ethyl)amino)phenyl)acrylamide was similar to Example 135.

¹H NMR (400 MHz, CD₃OD) δ 8.27 (s, 1H), 8.16 (d, J=6.2 Hz, 2H), 7.66 (s, 1H), 7.48 (d, J=6.9 Hz, 1H), 7.19 (d, J=2.3 Hz, 1H), 7.01 (d, J=9.1 Hz, 1H), 6.96 (s, 1H), 6.48 (dd, J=16.9, 10.1 Hz, 1H), 6.31 (dd, J=16.9, 1.6 Hz, 1H), 5.75 (dd, J=10.1, 1.6 Hz, 1H), 3.84 (s, 3H), 3.76 (s, 3H), 3.56-3.49 (m, 2H), 3.49-3.43 (m, 2H), 3.31 (t, J=5.6 Hz, 2H), 3.01 (d, J=9.6 Hz, 2H), 2.71 (s, 3H), 2.09 (d, J=6.8 Hz, 4H);
MS m/z (ESI): 543.3 [M+H]⁺.

Example 138: Preparation of N-(4-methoxy-5-((4-(5-methoxy-1H-benzo[d]imidazol-1-yl)pyrimidin-2-yl)amino)-2-(methyl(2-(pyrrolidin-1-yl)ethyl)amino)phenyl)acrylamide

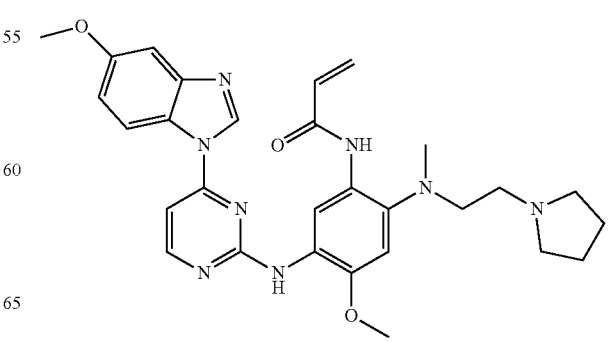

The preparation method of N-(4-methoxy-5-((4-(5-methoxy-1H-benzo[d]imidazol-1-yl)pyrimidin-2-yl)amino)-2-(methyl(2-(pyrrolidin-1-yl)ethyl)amino)phenyl)acrylamide was similar to Example 59.

¹H NMR (400 MHz, CD₃OD) δ 9.49 (s, 1H), 8.56 (d, J=5.8 Hz, 1H), 8.22 (d, J=10.4 Hz, 2H), 7.34 (d, J=5.8 Hz, 1H), 7.27 (d, J=2.1 Hz, 1H), 7.08 (dd, J=9.2, 1.9 Hz, 1H), 7.01 (s, 1H), 6.59 (dd, J=16.9, 10.1 Hz, 1H), 6.43 (dd, J=16.9, 1.6 Hz, 1H), 5.86 (dd, J=10.1, 1.6 Hz, 1H), 3.97 (s, 3H), 3.89 (s, 3H), 3.62 (s, 2H), 3.51 (t, J=5.5 Hz, 2H), 3.39 (t, J=5.5 Hz, 2H), 3.11 (d, J=8.1 Hz, 2H), 2.77 (s, 3H), 2.18 (s, 4H);

MS m/z (ESI): 543.3 [M+H]⁺.

Example 139: Preparation of N-(4-methoxy-5-((4-(6-methoxy-1H-benzo[d]imidazol-1-yl)pyrimidin-2-yl)amino)-2-(methyl(2-(pyrrolidin-1-yl)ethyl)amino)phenyl)acrylamide

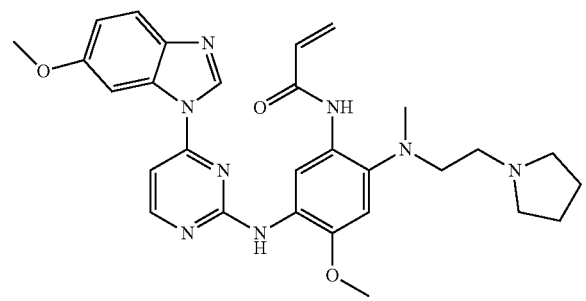 [SMILES: C=CC(=O)Nc1cc(Nc2nccc(-n3cnc4ccc(OC)cc43)n2)c(OC)cc1N(C)CCN1CCCC1]

The preparation method of N-(4-methoxy-5-((4-(6-methoxy-1H-benzo[d]imidazol-1-yl)pyrimidin-2-yl)amino)-2-(methyl(2-(pyrrolidin-1-yl)ethyl)amino)phenyl)acrylamide was similar to Example 59.

¹H NMR (400 MHz, CD₃OD) δ 9.44 (s, 1H), 8.58 (d, J=5.2 Hz, 1H), 8.29 (s, 1H), 7.88 (s, 1H), 7.72 (s, 1H), 7.33 (d, J=5.7 Hz, 1H), 7.14 (d, J=5.3 Hz, 1H), 7.00 (s, 1H), 6.60 (dd, J=16.9, 10.2 Hz, 1H), 6.39 (dd, J=16.9, 1.4 Hz, 1H), 5.84 (dd, J=10.2, 1.3 Hz, 1H), 3.97 (s, 3H), 3.85 (s, 3H), 3.62 (s, 2H), 3.49 (t, J=5.5 Hz, 2H), 3.38 (dd, J=9.6, 4.1 Hz, 2H), 3.10 (s, 2H), 2.75 (s, 3H), 2.16 (d, J=2.9 Hz, 4H);

MS m/z (ESI): 543.3 [M+H]⁺.

Example 140: Preparation of N-(2-((2-(dimethylamino)ethyl)(methyl)amino)-4-methoxy-5-((4-(1-(prop-2-yn-1-yl)-1H-indol-3-yl)pyrimidin-2-yl)amino)phenyl)acrylamide

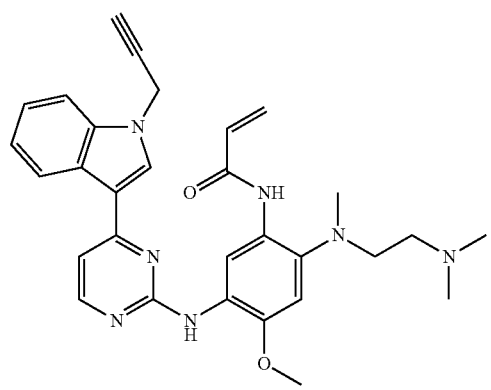 [SMILES: C#CCn1cc(-c2ccnc(Nc3cc(NC(=O)C=C)c(N(C)CCN(C)C)cc3OC)n2)c2ccccc21]

Step 1: Preparation of N1-(4-(1H-indol-3-yl)pyrimidin-2-yl)-N4-(2-(dimethylamino)ethyl)-2-methoxy-N4-methyl-5-nitrobenzene-1,4-diamine

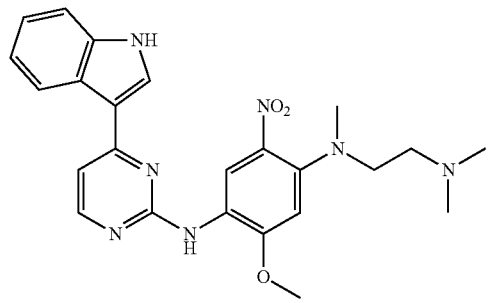 [SMILES: COc1cc(N(C)CCN(C)C)c([N+](=O)[O-])cc1Nc1nccc(-c2c[nH]c3ccccc23)n1]

The preparation method of N1-(4-(1H-Indol-3-yl)pyrimidin-2-yl)-N4-(2-(dimethylamino)ethyl)-2-methoxy-N4-methyl-5-nitrobenzene-1,4-diamine was similar to Example 102.

Step 2: Preparation of N1-(2-(dimethylamino)ethyl)-5-methoxy-N1-methyl-2-nitro-N4-(4-(1-(prop-2-yn-1-yl)-1H-indol-3-yl)pyrimidin-2-yl)benzene-1,4-diamine

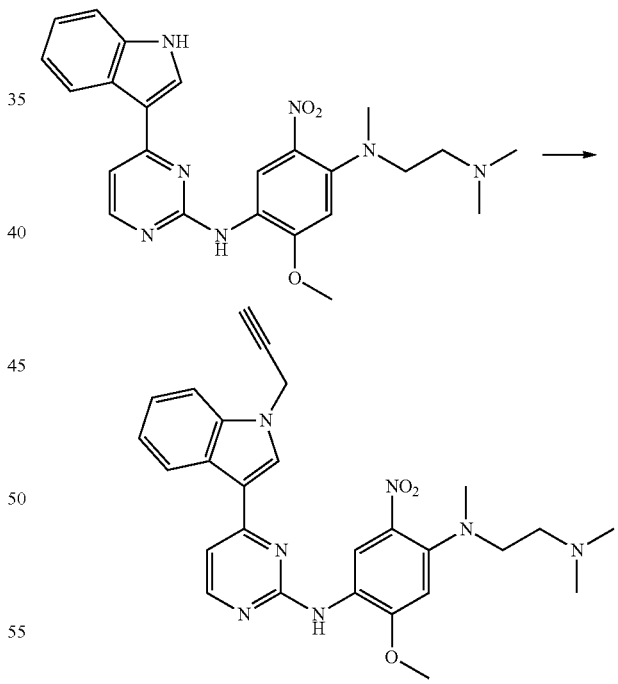

N1-(4-(1H-indol-3-yl)pyrimidin-2-yl)-N4-(2-(dimethylamino)ethyl)-2-methoxy-N4-methyl-5-nitrobenzene-1,4-diamine (0.51 g, 1.1 mmol) was dissolved in anhydrous DMF (20 mL), followed by addition of NaH (47 mg, 1.16 mmol) at room temperature under stirring. After stirring for 30 minutes, the reaction mixture was cooled to 0° C., and propargyl bromide (137 mg, 1.16 mmol) was added at 0° C. The reaction solution was stirred for 20 minutes. After the formation of product was determined by LC-MS, the reaction was quenched with saturated ammonium chloride aqueous solution. The product was purified by reversed column chromatography (eluent: 0.1% TFA aqueous solution to acetonitrile) to obtain a TFA salt of N1-(2-(dimethylamino)ethyl)-5-methoxy-N1-methyl-2-nitro-N4-(4-(1-(prop-2-yn-1-yl)-1H-indol-3-yl)pyrimidin-2-yl)benzene-1,4-diamine (0.25 g, 28%).

$^1$H NMR (400 MHz, CD$_3$OD): δ 8.62 (s, 1H), 8.57 (s, 1H), 8.28 (d, J=8.0 Hz, 1H), 8.17 (d, J=6.8 Hz, 1H), 7.64 (d, J=8.0 Hz, 1H), 7.48 (d, J=6.4 Hz, 1H), 7.37 (t, J=7.6 Hz, 1H), 7.24 (t, J=7.2 Hz, 1H), 7.09 (s, 1H), 5.19 (d, J=2.4 Hz, 2H), 4.06 (s, 3H), 3.62 (t, J=6.0 Hz, 2H), 3.52 (t, J=6.0 Hz, 2H), 3.36 (s, 1H), 3.01 (s, 6H), 2.98 (s, 3H):

MS m/z (ESI): 500.2 [M+H]$^+$.

Step 3: Preparation of N1-(2-(dimethylamino)ethyl)-5-methoxy-N1-methyl-N4-(4-(1-(prop-2-yn-1-yl)-1H-indol-3-yl)pyrimidin-2-yl)benzene-1,2,4-triamine

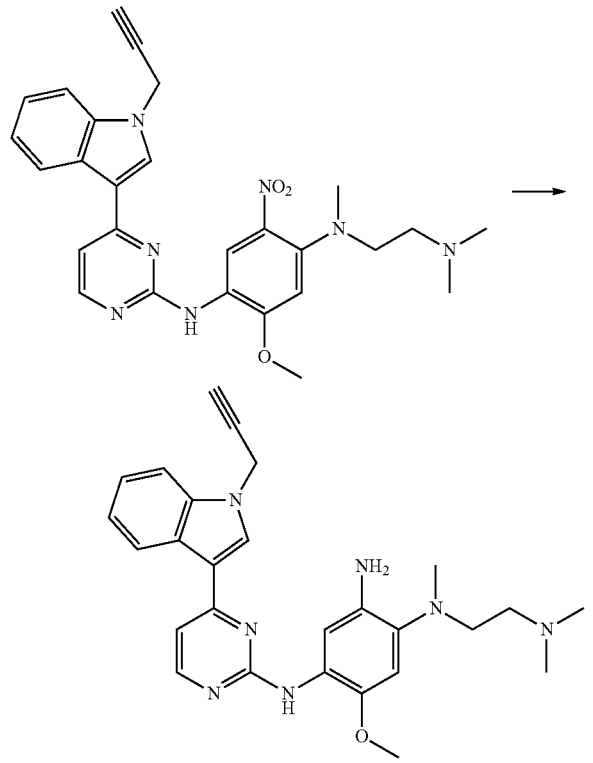

The TFA salt of N1-(2-(dimethylamino)ethyl)-5-methoxy-N1-methyl-2-nitro-N4-(4-(1-(prop-2-yn-1-yl)-1H-indol-3-yl)pyrimidin-2-yl)benzene-1,4-diamine (0.25 g, 0.30 mmol), reduced iron powder (112 mg, 2.0 mmol) and ammonium chloride (0.015 g, 0.3 mmol) were added to a mixture of ethanol (8 mL) and water (2 mL). The reaction was stirred under a nitrogen atmosphere at 75° C. overnight. After the reaction solution was cooled to room temperature the next day, ethanol (60 mL) was added. The reaction solution was filtered through celite and washed with ethanol (10 mL). The filtrate was concentrated under reduced pressure, and DCM (60 mL) was added. The layer of DCM was washed with saturated brine (30 mL), dried over anhydrous sodium sulfate and concentrated to obtain N1-(2-(dimethylamino)ethyl)-5-methoxy-N1-methyl-N4-(4-(1-(prop-2-yn-1-yl)-1H-indol-3-yl)pyrimidin-2-yl)benzene-1,2,4-triamine (130 mg, 90%), which was directly used in the next step without further purification.

MS m/z (ESI): 470.2 [M+H]$^+$.

Step 4: Preparation of N-(2-((2-(dimethylamino)ethyl)(methyl)amino)-4-methoxy-5-((4-(1-(prop-2-yn-1-yl)-1H-indol-3-yl)pyrimidin-2-yl)amino)phenyl)acrylamide

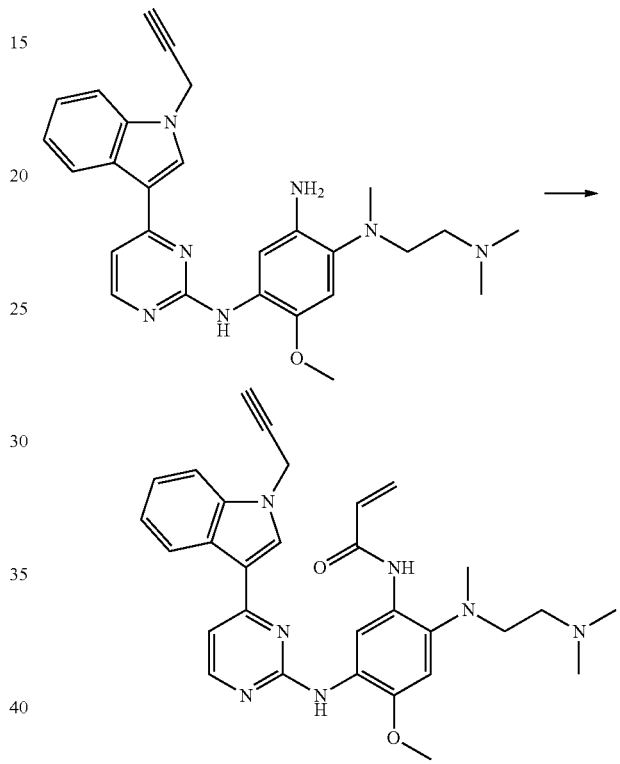

N1-(2-(dimethylamino)ethyl)-5-methoxy-N1-methyl-N4-(4-(1-(prop-2-yn-1-yl)-1H-indol-3-yl)pyrimidin-2-yl)benzene-1,2,4-triamine (130 mg, 0.28 mmol) and triethylamine (170 mg, 1.7 mmol) were dissolved in THF (20 mL). The solution was cooled to −78° C. A solution of acryloyl chloride (75 mg, 0.84 mmol) in THF (4 mL) was added dropwise to the reaction mixture. The reaction was carried out for 5 minutes at this temperature, and quenched with methanol (1 mL). After TFA (200 mg) was added, the reaction solution was concentrated under reduced pressure, and purified by reversed column chromatography (eluent: 0.1% TFA aqueous solution to acetonitrile) to obtain a TFA salt of N-(2-((2-(dimethylamino)ethyl)(methyl)amino)-4-methoxy-5-((4-(1-(prop-2-yn-1-yl)-1H-indol-3-yl)pyrimidin-2-yl)amino)phenyl)acrylamide (105 mg, 45%).

$^1$H NMR (400 MHz, CD$_3$OD): δ 8.62 (s, 1H), 8.37 (br, 1H), 8.10 (d, J=6.8 Hz, 1H), 7.96 (s, 1H), 7.64 (d, J=8.0 Hz, 1H), 7.46 (d, J=7.2 Hz, 1H), 7.36 (m, 1H), 7.27 (t, J=7.2 Hz, 1H), 7.10 (s, 1H), 6.54 (m, 2H), 5.90 (m, 1H), 5.20 (d, J=2.8 Hz, 2H), 3.99 (s, 3H), 3.57 (t, J=6.0 Hz, 2H), 3.34 (t, J=6.0 Hz, 2H), 3.03 (t, J=2.8 Hz, 1H), 2.93 (s, 6H), 2.82 (s, 3H);

MS m/z (ESI): 524.2 [M+H]$^+$.

249

Example 141: Preparation of N-(5-((4-(1-allyl-1H-indol-3-yl)pyrimidin-2-yl)amino)-2-((2-(dimethylamino)ethyl)(methyl)amino)-4-methoxyphenyl)acrylamide

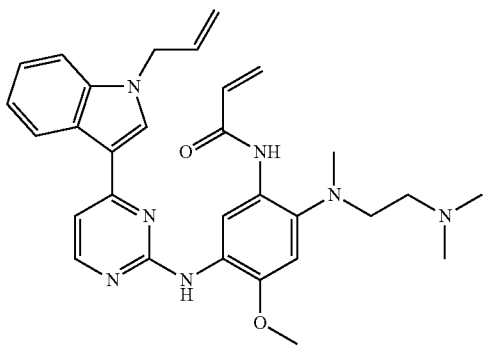 [SMILES: C=CCn1cc(-c2ccnc(Nc3cc(NC(=O)C=C)c(N(C)CCN(C)C)cc3OC)n2)c2ccccc21]

The preparation method of N-(5-((4-(1-allyl-1H-indol-3-yl)pyrimidin-2-yl)amino)-2-((2-(dimethylamino)ethyl)(methyl)amino)-4-methoxyphenyl)acrylamide was similar to Example 140.

$^1$H NMR (400 MHz, CD$_3$OD): δ 8.53 (s, 1H), 8.31 (b, 1H), 8.00 (d, J=6.8 Hz, 1H), 7.94 (s, 1H), 7.49 (d, J=8.0 Hz, 1H), 7.39 (d, J=6.8 Hz, 1H), 7.28 (t, J=7.2 Hz, 1H), 7.19 (t, J=8.0 Hz, 1H), 7.05 (s, 1H), 6.57 (m, 1H), 6.42 (m, 1H), 6.07 (m, 1H), 5.82 (m, 1H), 5.25 (m, 1H), 5.23 (m, 1H), 4.92 (d, J=5.2 Hz, 2H), 3.93 (s, 3H), 3.86 (m, 2H), 3.52 (t, J=4.4 Hz, 2H), 3.32 (t, J=5.6 Hz, 2H), 2.88 (s, 6H), 2.76 (s, 3H); MS m/z (ESI): 526.2 [M+H]$^+$.

Example 142: Preparation of N-(5-((4-(1-(N,N-dimethylsulfamoyl)-1H-indol-3-yl)pyrimidin-2-yl)amino)-4-methoxy-2-(methyl(2-(pyrrolidin-1-yl)ethyl)amino)phenyl)acrylamide

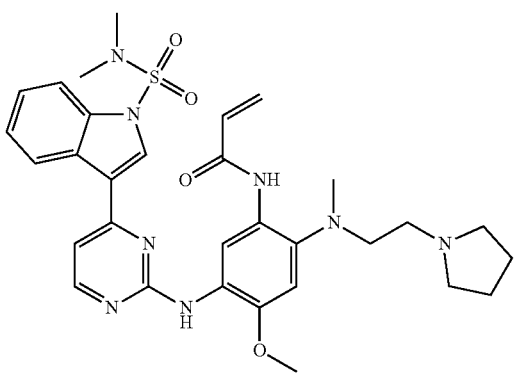 [SMILES: C=CC(=O)Nc1cc(Nc2nccc(-c3cn(S(=O)(=O)N(C)C)c4ccccc34)n2)c(OC)cc1N(C)CCN1CCCC1]

Step 1: preparation of N-(4-(1H-indol-3-yl)pyrimidin-2-yl)-2-methoxy-N4-methyl-5-nitro-N4-(2-(pyrrolidin-1-yl)ethyl)benzene-1,4-diamine

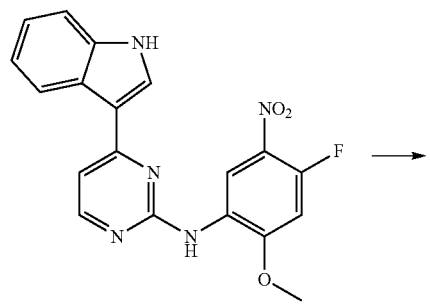

250

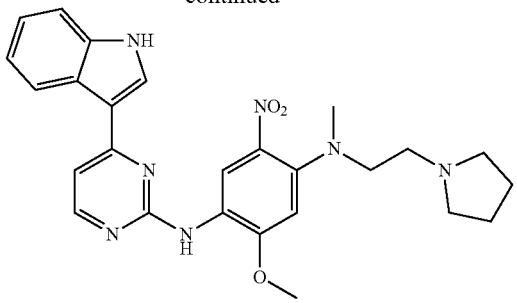

N-(4-fluoro-2-methoxy-5-nitrophenyl)-4-(1H-indol-3-yl)pyrimidin-2-amine (118 mg, 0.312 mmol) was dissolved in DMF (2 mL), and then triethylamine (95 mg, 0.936 mmol) and N-methyl-2-(pyrrolidin-1-yl)ethan-1-amine (60 mg, 0.468 mmol) were added. The reaction was heated up to 120° C. by microwave and reacted for 30 minutes. After LCMS showed completion of the reaction, the reaction solution was concentrated to dryness. The crude product was purified by preparative thin-layer chromatography to obtain N-(4-(1H-indol-3-yl)pyrimidin-2-yl)-2-methoxy-N4-methyl-5-nitro-N4-(2-(pyrrolidin-1-yl)ethyl)benzene-1,4-diamine (122 mg, 100%).

Step 2: Preparation of 3-(2-((2-methoxy-4-(methyl(2-(pyrrolidin-1-yl)ethyl)amino)-5-nitrophenyl)amino)pyrimidin-4-yl)-N,N-dimethyl-1H-indole-1-sulfonamide

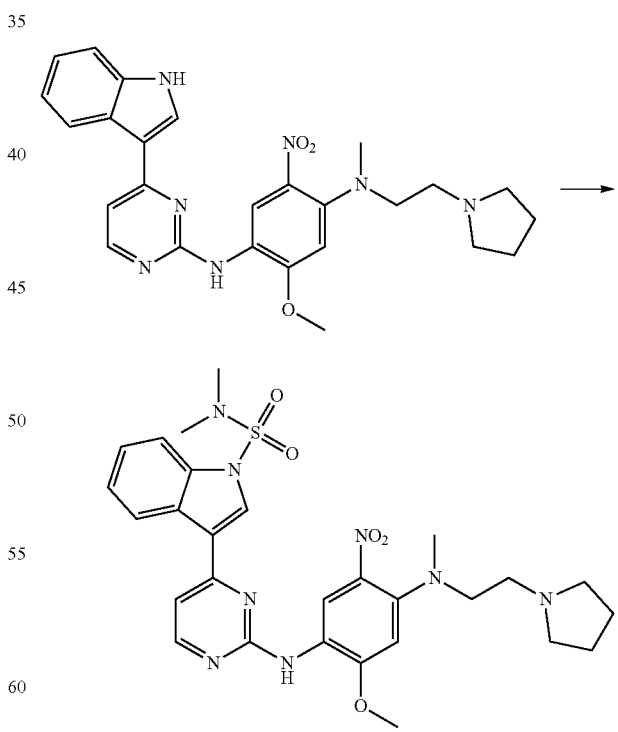

N-(4-(1H-indol-3-yl)pyrimidin-2-yl)-2-methoxy-N4-methyl-5-nitro-N4-(2-(pyrrolidin-1-yl)ethyl)benzene-1,4-diamine (122 mg, 0.25 mmol) was dissolved in DMF (10 mL), and the mixture was cooled to 0° C. in an ice bath.

Then NaH (30 mg, 0.75 mmol) was added, and the reaction was carried out at 0° C. for ten minutes, and then dimethylsulfamoyl chloride (54 mg, 0.374 mmol) was added dropwise. The reaction solution was warmed up to room temperature and stirred for 30 minutes. After the reaction was quenched, dichloromethane and water were added, and the reaction solution was extracted three times. The organic phases were combined, washed with saturated sodium bicarbonate aqueous solution, water and saturated brine, filtered, and concentrated to obtain a crude product, which was further purified by flash silica gel column chromatography to obtain 3-(2-((2-methoxy-4-(methyl(2-(pyrrolidin-1-yl)ethyl)amino)-5-nitrophenyl)amino)pyrimidin-4-yl)-N,N-dimethyl-1H-indole-1-sulfonamide (60 mg, 40%).

Step 3: Preparation of 3-(2-((5-amino-2-methoxy-4-(methyl(2-(pyrrolidin-1-yl)ethyl)amino)phenyl)amino)pyrimidin-4-yl)-N,N-dimethyl-1H-indole-1-sulfonamide

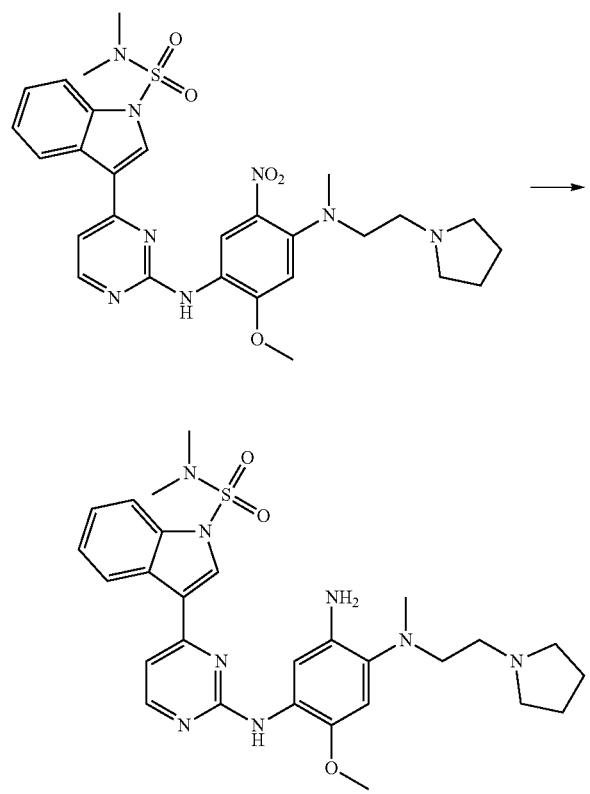 [SMILES: COc1cc(N(C)CCN2CCCC2)c(N)cc1Nc1nccc(-c2cn(S(=O)(=O)N(C)C)c3ccccc23)n1 ; C=CC(=O)Nc1cc(Nc2nccc(-c3cn(S(=O)(=O)N(C)C)c4ccccc34)n2)c(OC)cc1N(C)CCN1CCCC1]

The aforementioned compound 3-(2-((2-methoxy-4-(methyl(2-(pyrrolidin-1-yl)ethyl)amino)-5-nitrophenyl)amino)pyrimidin-4-yl)-N,N-dimethyl-1H-indole-1-sulfonamide was dissolved in methanol (5 mL), and then Pd/C (15 mg) was added. The reaction was stirred in a hydrogen atmosphere at 24° C. for 1 hour. After LC-MS showed completion of the reaction, the reaction solution was filtered, and the filtrate was concentrated. The resulting residue was purified by flash silica gel column chromatography to obtain 15 mg of the crude product 3-(2-((5-amino-2-methoxy-4-(methyl(2-(pyrrolidin-1-yl)ethyl)amino)phenyl)amino)pyrimidin-4-yl)-N,N-dimethyl-1H-indole-1-sulfonamide.

Step 4: Preparation of N-(5-((4-(1-(N,N-dimethylsulfamoyl)-1H-indol-3-yl)pyrimidin-2-yl)amino)-4-methoxy-2-(methyl(2-(pyrrolidin-1-yl)ethyl)amino)phenyl)acrylamide

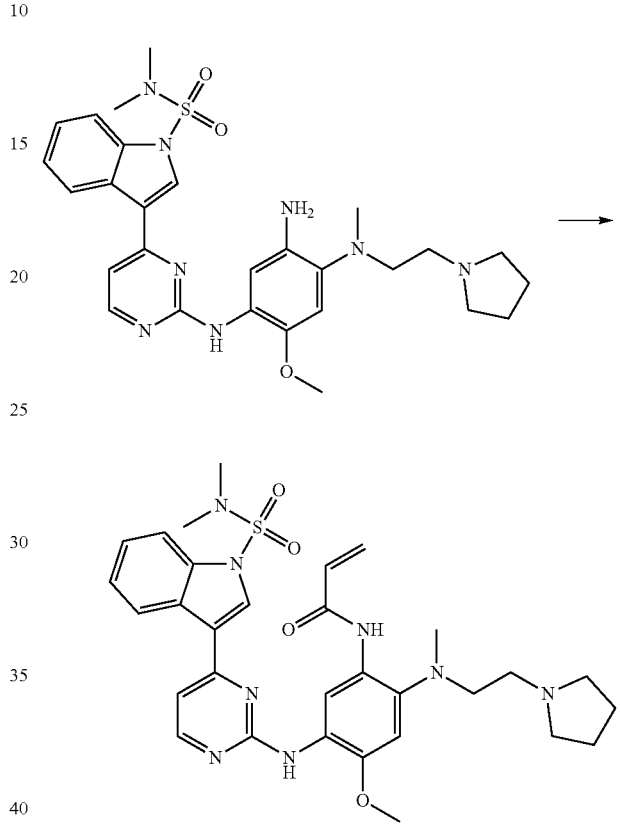

3-(2-((5-amino-2-methoxy-4-(methyl(2-(pyrrolidin-1-yl)ethyl)amino)phenyl)amino)pyrimidin-4-yl)-N,N-dimethyl-1H-indole-1-sulfonamide (15 mg, 0.027 mmol) and triethylamine (8 mg, 0.08 mmol) were dissolved in anhydrous tetrahydrofuran (20 mL). After the reaction solution was stirred at −78° C. for 10 minutes, acryloyl chloride (0.05 mL, 1 M in THF) was added slowly and dropwise. The reaction was stirred for 30 minutes in a dry ice bath. After LC-MS showed completion of the reaction, the reaction was quenched with methanol. The reaction solution was concentrated, and the resulting residue was purified by preparative thin-layer chromatography to obtain N-(5-((4-(1-(N,N-dimethylsulfamoyl)-1H-indol-3-yl)pyrimidin-2-yl)amino)-4-methoxy-2-(methyl(2-(pyrrolidin-1-yl)ethyl)amino)phenyl)acrylamide (7 mg, 44%).

$^1$H NMR (400 MHz, CD$_3$OD) δ 8.63 (s, 1H), 8.46 (d, J=7.9 Hz, 1H), 8.32 (s, 1H), 8.11-7.92 (m, 2H), 7.56 (d, J=5.9 Hz, 1H), 7.37 (dt, J=15.2, 7.3 Hz, 2H), 7.04 (s, 1H), 6.55 (dd, J=16.8, 10.1 Hz, 1H), 6.42 (dd, J=16.9, 1.7 Hz, 1H), 5.87 (dd, J=10.0, 1.7 Hz, 1H), 3.99 (s, 3H), 3.60 (s, 2H), 3.58-3.50 (m, 2H), 3.43-3.36 (m, 2H), 3.10 (s, 2H), 2.93 (s, 6H), 2.79 (s, 3H), 2.27-2.09 (m, 4H);

MS m/z (ESI): 619.6 [M+H]$^+$.

Example 143: Preparation of N-(2-((2-(dimethylamino)ethyl)(methyl)amino)-5-((4-(1-(N,N-dimethylsulfamoyl)-6-methoxy-1H-indol-3-yl)-5-(trifluoromethyl)pyrimidin-2-yl)amino)-4-methoxyphenyl) acrylamide

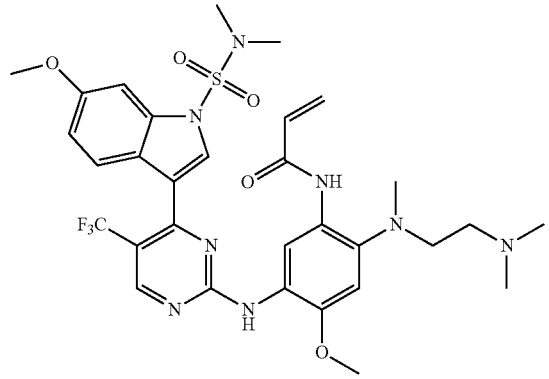

Step 1: Preparation of 3-(2-chloro-5-(trifluoromethyl)pyrimidin-4-yl)-6-methoxy-1H-indole

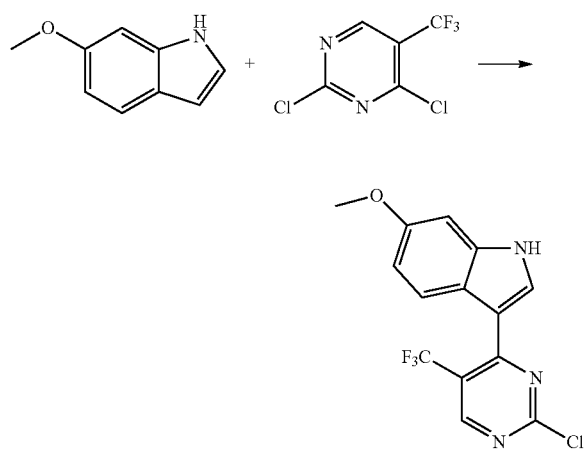

6-methoxy-1H-indole (5 g, 33.97 mmol), 2,4-dichloro-5-(trifluoromethyl)pyrimidine (8.1 g, 37.36 mmol) and aluminum trichloride (6.79 g, 50.95 mmol) were dissolved in DME (50 mL), and the reaction was stirred overnight at 70° C. After the reaction was completed, the reaction solution was poured into ice water and extracted three times with methyl tert-butyl ether. The organic phases were combined, washed with water and saturated brine, dried over anhydrous sodium sulfate, filtered and evaporated to dryness to obtain a crude product, which was further purified by flash silica gel column chromatography to obtain 3-(2-chloro-5-(trifluoromethyl)pyrimidin-4-yl)-6-methoxy-1H-indole (4.3 g, 39%).

Step 2: Preparation of N-(4-fluoro-2-methoxy-5-nitrophenyl)-4-(6-methoxy-1H-indol-3-yl)-5-(trifluoromethyl)pyrimidin-2-amine

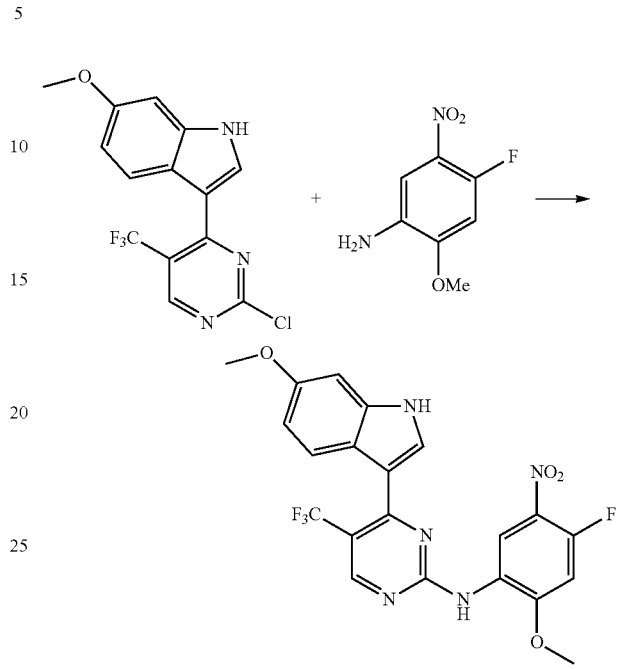

3-(2-chloro-5-(trifluoromethyl)pyrimidin-4-yl)-6-methoxy-1H-indole (165 mg, 0.504 mmol), the raw material 4-fluoro-2-methoxy-5-nitroaniline (103 mg, 0.554 mmol) and p-toluenesulfonic acid monohydrate (96 mg, 0.504 mmol) were dissolved in 2-pentanol (20 mL), and the reaction was heated up to 120° C. overnight. After LC-MS showed completion of the reaction, the reaction solution was naturally cooled to room temperature, and a dark solid was precipitated. The solid was filtered, and the filter cake was washed with methanol (1 mL) and methyl tert-butyl ether (1 mL) to obtain N-(4-fluoro-2-methoxy-5-nitrophenyl)-4-(6-methoxy-1H-indol-3-yl)-5-(trifluoromethyl)pyrimidin-2-amine (125 mg, 52%).

Step 3: Preparation of N1-(2-(dimethylamino)ethyl)-5-methoxy-N4-(4-(6-methoxy-1H-indol-3-yl)-5-(trifluoromethyl)pyrimidin-2-yl)-N1-methyl-2-nitrobenzene-1,4-diamine

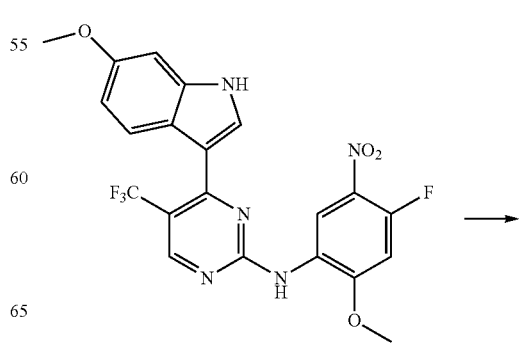

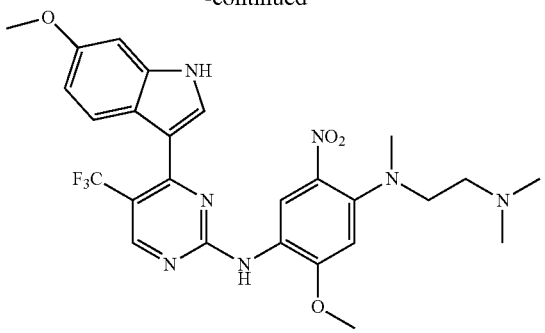

N-(4-fluoro-2-methoxy-5-nitrophenyl)-4-(6-methoxy-1H-indol-3-yl)-5-(trifluoromethyl)pyrimidin-2-amine (125 mg, 0.262 mmol) was dissolved in 2 mL of DMF, and then triethylamine (80 mg, 0.786 mmol) and trimethylethylenediamine (80 mg, 0.786 mmol) were added. The reaction was heated up to 120° C. by microwave and reacted for 30 minutes. After LC-MS showed completion of the reaction, the reaction solution was concentrated to dryness. The crude product was purified by preparative thin-layer chromatography to obtain N1-(2-(dimethylamino)ethyl)-5-methoxy-N4-(4-(6-methoxy-1H-indol-3-yl)-5-(trifluoromethyl)pyrimidin-2-yl)-N1-methyl-2-nitrobenzene-1,4-diamine (146 mg, 99%).

Step 4: Preparation of 3-(2-((4-((2-(dimethylamino)ethyl)(methyl)amino)-2-methoxy-5-nitrophenyl)amino)-5-(trifluoromethyl)pyrimidin-4-yl)-6-methoxy-N,N-dimethyl-1H-indole-1-sulfonamide

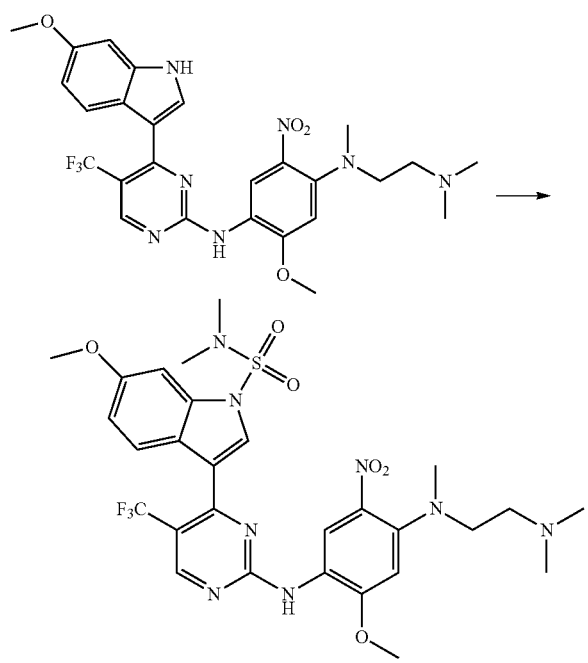

N1-(2-(dimethylamino)ethyl)-5-methoxy-N4-(4-(6-methoxy-1H-indol-3-yl)-5-(trifluoromethyl)pyrimidin-2-yl)-N1-methyl-2-nitrobenzene-1,4-diamine (146 mg, 0.262 mmol) was dissolved in DMF (10 mL), and the mixture was cooled to 0° C. in an ice bath before NaH (31 mg, 0.786 mmol) was added. The reaction was carried out at 0° C. for ten minutes, and then dimethylsulfamoyl chloride (41 mg, 0.288 mmol) was added dropwise. The reaction solution was warmed up to room temperature and stirred for 30 minutes. After the reaction was quenched, dichloromethane and water were added, and the reaction solution was extracted three times. The organic phases were combined, washed with saturated sodium bicarbonate aqueous solution, water and saturated brine, successively, filtered and evaporated to dryness to obtain a crude product, which was further purified by flash silica gel column chromatography to obtain 3-(2-((4-((2-(dimethylamino)ethyl)(methyl)amino)-2-methoxy-5-nitrophenyl)amino)-5-(trifluoromethyl)pyrimidin-4-yl)-6-methoxy-N,N-dimethyl-1H-indole-1-sulfonamide (80 mg, 46%).

Step 5: Preparation of 3-(2-((5-amino-4-((2-(dimethylamino)ethyl)(methyl)amino)-2-methoxyphenyl)amino)-5-(trifluoromethyl)pyrimidin-4-yl)-6-methoxy-N,N-dimethyl-1H-indole-1-sulfonamide

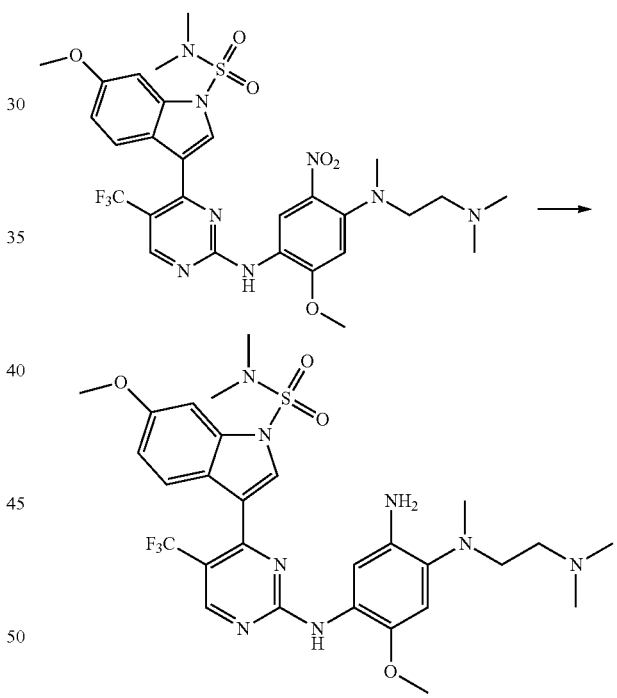

The aforementioned compound N1-(2-(dimethylamino)ethyl)-5-methoxy-N4-(4-(6-methoxy-1H-indol-3-yl)-5-(trifluoromethyl)pyrimidin-2-yl)-N1-methyl-2-nitrobenzene-1,4-diamine was dissolved in methanol (10 mL), and Pd/C (20 mg) was added. The reaction was stirred in a hydrogen atmosphere at 24° C. for 1 hour. After LC-MS showed completion of the reaction, the reaction solution was filtered, and the filtrate was concentrated to obtain a crude product, which was further purified by flash silica gel column chromatography to obtain 44 mg of 3-(2-((5-amino-4-((2-(dimethylamino)ethyl)(methyl)amino)-2-methoxyphenyl)amino)-5-(trifluoromethyl)pyrimidin-4-yl)-6-methoxy-N,N-dimethyl-1H-indole-1-sulfonamide.

Step 6: Preparation of N-(2-((2-(dimethylamino) ethyl)(methyl)amino)-5-((4-(1-(N,N-dimethylsulfamoyl)-6-methoxy-1H-indol-3-yl)-5-(trifluoromethyl)pyrimidin-2-yl)amino)-4-methoxyphenyl)acrylamide

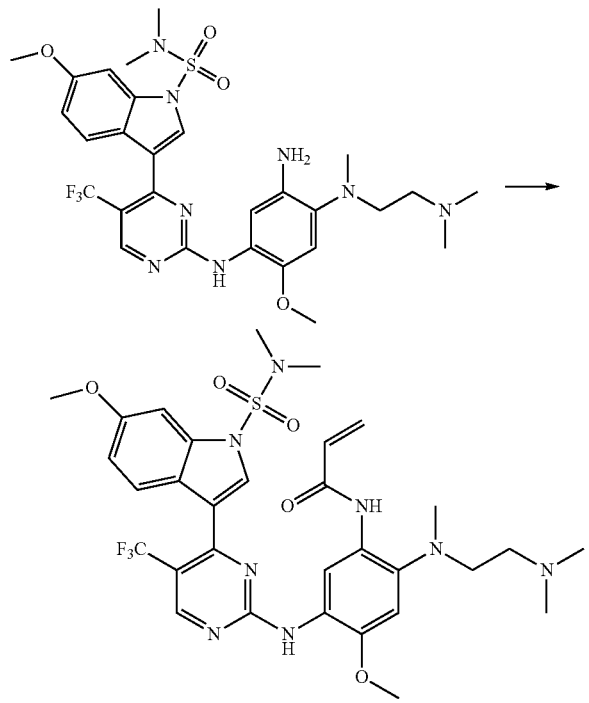

3-(2-((5-amino-4-((2-(dimethylamino)ethyl)(methyl)amino)-2-methoxyphenyl)amino)-5-(trifluoromethyl)pyrimidin-4-yl)-6-methoxy-N,N-dimethyl-1H-indole-1-sulfonamide (44 mg, 0.069 mmol) and triethylamine (21 mg, 0.207 mmol) were dissolved in anhydrous tetrahydrofuran (20 mL). The reaction was stirred at −78° C. for 10 minutes before acryloyl chloride (0.2 mL, 1 M in THF) was added slowly and dropwise. Then the reaction was stirred for 30 minutes in a dry ice bath. After LC-MS showed completion of the reaction, the reaction was quenched with methanol. The reaction solution was concentrated, and the resulting residue was purified by preparative thin-layer chromatography to obtain N-(2-((2-(dimethylamino)ethyl)(methyl)amino)-5-((4-(1-(N,N-dimethylsulfamoyl)-6-m ethoxy-1H-indol-3-yl)-5-(tri fluoromethyl)pyrimidin-2-yl)amino)-4-methoxyphenyl)acrylamide (16 mg, 33%).

$^1$H NMR (400 MHz, CD$_3$OD) δ 8.78 (s, 1H), 8.39 (s, 1H), 7.91 (d, J=8.8 Hz, 1H), 7.82 (s, 1H), 7.50 (d, J=2.1 Hz, 1H), 6.97 (s, 1H), 6.90 (d, J=8.2 Hz, 1H), 6.41 (d, J=5.3 Hz, 2H), 5.83 (t, J=5.9 Hz, 1H), 4.00 (s, 3H), 3.88 (s, 3H), 3.49 (t, J=5.5 Hz, 2H), 3.28 (t, J=5.5 Hz, 2H), 2.89 (s, 6H), 2.86 (s, 6H), 2.70 (s, 3H);

MS m/z (ESI): 691.5 [M+H]$^+$.

Biological Test and Evaluation

1. Enzymologic Experiment of T790M Mutant-Type EGFR

In this experiment, the inhibitory effect of the compounds on exon 20 T790M mutant-type EGFR enzyme was tested by a fluorescence resonance energy transfer (TR-FRET) method, and the half maximal inhibitory concentration (IC$_{50}$) of the compounds on enzymatic activity was determined.

1) 1 to 5 μL of T790M EGFR enzyme solution was added to a 384-well plate, and the final concentration of the enzyme was 0.1 to 1 nM.
2) 1 to 5 μL of diluted solution in gradient of the compound was added.
3) The mixture was incubated for 10 minutes at room temperature.
4) 1 to 5 μL of a substrate mixture containing substrate polypeptide to a final concentration of 5 to 50 nM and ATP to a final concentration of 1 to 10 uM was added.
5) The mixture was incubated at room temperature for 0.5 to 2 hours.
6) 5 μL of EDTA stop solution was added to terminate the reaction for 5 minutes.
7) 5 tit of a test solution containing the labeled antibody was added, and the mixture was incubated at room temperature for 1 hour.
8) The fluorescence signal values of each plate were determined by a microplate reader at 665 nm.
9) The inhibition rates were calculated according to the fluorescence signal values.
10) The IC$_{50}$ of the compound was obtained by curve fitting according to the inhibition rates at different concentrations.

2. Enzymologic Experiment of Wild-Type (WT) EGFR

In this experiment, the inhibitory effect of compounds on wild-type EGFR enzyme was tested by a fluorescence resonance energy transfer (TR-FRET) method, and the half maximal inhibitory concentration IC$_{50}$ of the compounds on enzymatic activity was determined.

1) 1 to 5 μL of wild-type EGFR enzyme solution was added to a 384-well plate, and the final concentration of the enzyme was 0.1 to 1 nM.
2) 1 to 5 μL of diluted solution in gradient of the compound was added.
3) The mixture was incubated for 10 minutes at room temperature.
4) 1 to 5 μL of a substrate mixture containing substrate polypeptide to a final concentration of 5 to 50 nM and ATP to a final concentration of 0.1 to 5 uM was added.
5) The mixture was incubated at room temperature for 0.5 to 2 hours.
6) 5 μL of EDTA stop solution was added to terminate the reaction for 5 minutes.
7) 5 μL of a test solution containing the labeled antibody was added, and the mixture was incubated at room temperature for 1 hour.
8) The fluorescence signal values of each plate were determined by a microplate reader at 665 nm.
9) The inhibition rates were calculated from the fluorescence signal values.
10) The IC$_{50}$ of the compound was obtained by curve fitting according to the inhibition rates at different concentrations.

The biochemical activity of the compounds of the present invention was determined by the aforesaid experiment, and the IC$_{50}$ values are shown in the table below.

| Example | EGFR IC$_{50}$ (nM) | | Selectivity of wild-type/mutant-type |
|---|---|---|---|
| | T790M | WT | |
| Example 1 | 0.15 | 2 | 13 |
| Example 2 | 9.26 | 142.9 | 15 |

| Example | EGFR IC$_{50}$ (nM) T790M | WT | Selectivity of wild-type/mutant-type |
|---|---|---|---|
| Example 3 | 143.8 | NT | NT |
| Example 4 | 0.39 | 6.41 | 16.3 |
| Example 5 | 0.32 | 0.80 | 2.5 |
| Example 6 | 0.86 | 1.54 | 1.8 |
| Example 7 | 2.09 | 15.49 | 7.4 |
| Example 8 | 0.42 | 3.64 | 8.8 |
| Example 9 | 0.39 | 2.12 | 5.44 |
| Example 11 | 2.74 | 64.1 | 23.39 |
| Example 12 | 0.32 | 6.01 | 18.7 |
| Example 21 | 0.30 | 0.40 | 1.33 |
| Example 22 | 0.71 | 7.44 | 10.4 |
| Example 23 | 2.75 | NT | NT |
| Example 24 | 3.53 | 4.02 | 1.1 |
| Example 25 | 0.36 | 7.11 | 19.9 |
| Example 26 | 0.49 | 1.89 | 3.9 |
| Example 27 | 50.24 | NT | NT |
| Example 28 | 1.83 | 1.89 | 1.0 |
| Example 29 | 16.46 | NT | NT |
| Example 40 | 0.39 | 3.36 | 8.62 |
| Example 41 | 0.51 | 2.50 | 4.90 |
| Example 42 | 0.48 | 0.82 | 1.71 |
| Example 43 | 0.38 | 3.77 | 9.8 |
| Example 44 | 0.38 | 2.50 | 6.58 |
| Example 47 | 41.38 | NT | NT |
| Example 48 | 0.24 | 2.52 | 10.5 |
| Example 49 | 0.17 | 6.30 | 37.06 |
| Example 50 | 0.66 | 6.39 | 9.68 |
| Example 51 | 0.53 | 14.50 | 27.56 |
| Example 52 | 1.08 | 115.70 | 107.1 |
| Example 53 | 2.53 | 34.15 | 13.50 |
| Example 54 | 0.36 | 2.21 | 6.14 |
| Example 56 | 1.54 | 16.26 | 10.56 |
| Example 59 | 0.35 | 4.44 | 12.7 |
| Example 60 | 0.33 | 2.03 | 6.16 |
| Example 62 | 8.32 | 26.43 | 3.18 |
| Example 63 | 0.36 | 14.95 | 41.53 |
| Example 67 | 1.63 | 378.00 | 231.9 |
| Example 68 | 0.99 | 191.10 | 193.03 |
| Example 71 | 28.14 | NT | NT |
| Example 74 | 25.99 | NT | NT |
| Example 89 | 8.57 | 34.62 | 4.04 |
| Example 90 | 1.14 | 4.91 | 4.31 |
| Example 91 | 2.25 | 14.72 | 6.54 |
| Example 92 | 0.16 | 0.40 | 2.5 |
| Example 94 | 0.71 | 1.26 | 1.771 |
| Example 95 | 0.51 | 5.35 | 0.49 |
| Example 96 | 1.57 | 8.90 | 5.67 |
| Example 97 | 0.18 | 0.50 | 2.78 |
| Example 98 | 0.20 | 1.00 | 5.00 |
| Example 99 | 0.21 | 5.01 | 23.86 |
| Example 100 | 0.33 | 1.81 | 5.48 |
| Example 101 | 12.08 | 50.58 | 4.19 |
| Example 102 | 0.20 | 1.4 | 7.00 |
| Example 103 | 0.24 | 1.61 | 6.71 |
| Example 104 | 0.98 | 7.43 | 7.6 |
| Example 105 | 0.26 | 0.62 | 2.38 |
| Example 106 | 0.88 | 190.2 | 216.14 |
| Example 107 | 0.76 | 28.00 | 36.84 |
| Example 108 | 1.33 | 119.00 | 89.47 |
| Example 109 | 5.18 | 387.40 | 74.79 |
| Example 110 | 1.06 | 9.65 | 9.10 |
| Example 111 | 0.42 | 2.77 | 6.60 |
| Example 112 | 3.45 | 46.94 | 13.61 |
| Example 113 | 0.36 | 1.62 | 4.50 |
| Example 114 | 2.28 | 41.96 | 18.40 |
| Example 115 | 0.37 | 3.94 | 10.65 |
| Example 116 | 0.80 | 19.56 | 24.45 |
| Example 117 | 0.61 | 43.34 | 71.05 |
| Example 118 | 0.71 | 27.90 | 39.30 |
| Example 119 | 0.47 | 4.34 | 9.23 |
| Example 120 | 1.05 | 3.66 | 3.49 |
| Example 121 | 0.40 | 3.50 | 8.75 |
| Example 122 | 0.49 | 8.40 | 17.14 |
| Example 123 | 1.28 | 27.17 | 21.23 |
| Example 124 | 4.18 | 189.90 | 45.43 |
| Example 125 | 1.42 | 12.99 | 9.15 |
| Example 126 | 1.51 | 15.36 | 10.17 |
| Example 127 | 0.44 | 2.30 | 5.23 |
| Example 129 | 1.01 | 13.72 | 13.58 |
| Example 130 | 0.20 | 0.77 | 3.85 |
| Example 131 | 0.17 | 2.69 | 15.82 |
| Example 132 | 1.29 | 12.05 | 9.34 |
| Example 133 | 0.69 | 7.49 | 10.86 |
| Example 134 | 1.85 | 19.89 | 10.75 |
| Example 135 | 0.46 | 4.62 | 10.04 |
| Example 136 | 0.78 | 4.33 | 5.55 |
| Example 137 | 1.03 | 6.31 | 6.13 |
| Example 138 | 0.50 | 4.92 | 9.84 |
| Example 139 | 1.44 | 9.16 | 6.36 |
| Example 140 | 0.58 | 8.56 | 14.76 |
| Example 141 | 0.60 | 6.62 | 11.1 |
| Example 142 | 0.23 | 1.8 | 7.83 |
| Example 143 | 0.44 | 4.18 | 9.50 |

Wherein, NT means no activity determined.

The IC$_{50}$ values of EGFR of other example compounds of the present invention were similar to the effect of the aforesaid examples, and these compounds exhibited similar inhibitory activity and regularity.

Conclusion: the example compounds of the present invention had strong inhibitory activity against the mutant-type EGFR kinase, but had weak inhibitory activity against the wild-type kinase. Therefore, the compounds of the present invention had very good selectivity.

3. Experiment on the Inhibition of NCI-H1975 Cell Proliferation

In this experiment, the inhibitory effect of the compounds on NCI-H1975 cell proliferation was tested by a CellTiter-Glo method, and the half maximal inhibitory concentration (IC$_{50}$) of the compounds on the activity of cell proliferation was determined.

1) A 96-well cell culture plate was seeded with 90 µL of H1975 cell suspension at a density of 1 to 5×10$^3$ cells/ml. The culture plate was incubated in an incubator for 16 to 24 hours (37° C., 5% CO$_2$).

2) Different concentrations of the test compound in a gradient dilution were added to the cells in the culture plate. The culture plate was incubated in an incubator for 72 hours (37° C., 5% CO$_2$).

3) 50 to 100 µL of CellTiter-Glo reagent was added to each well. Then, the culture plate was shaken for 10 minutes, and left to stand at room temperature for 10 minutes.

4) The chemiluminescence signal values of each plate were determined by a microplate reader.

5) The inhibition rates were calculated according to the chemiluminescence signal values.

6) The IC$_{50}$ of the compound was obtained by curve fitting according to the inhibition rates at different concentrations.

4. Experiment on the Inhibition of A431 Cell Proliferation

In this experiment, the inhibitory effect of the compounds on A431 cell proliferation was tested by a CellTiter-Glo method, and the half maximal inhibitory concentration (IC$_{50}$) of the compounds on the activity of cell proliferation was determined.

1) A 96-well cell culture plate was seeded with 90 µL of A431 cell suspension at a density of 1 to 5×10$^3$ cells/ml. The culture plate was incubated in the incubator for 16 to 24 hours (37° C., 5% CO$_2$).

2) Different concentrations of the test compound in a gradient dilution were added to the cells in the culture plate. The culture plate was incubated in an incubator for 72 hours (37° C., 5% $CO_2$).

3) 50 to 100 μL of CellTiter-Glo reagent was added to each well. Then the culture plate was shaken for 10 minutes, and left to stand at room temperature for 10 minutes.

4) The chemiluminescence signal values of each plate were determined by a microplate reader.

5) The inhibition rates were calculated according to the chemiluminescence signal values. 6) The $IC_{50}$ of the compound was obtained by curve fitting according to the inhibition rates at different concentrations.

The biochemical activity of the compounds of the present invention was determined by the aforesaid experiment, and the $IC_{50}$ values are shown in the table below.

| Example | EGFR $IC_{50}$ (nM) H1975 | A431 | Selectivity of wild-type/ mutant-type |
|---|---|---|---|
| Example 2 | 1.36 | 223.70 | 164 |
| Example 4 | 10 | 157.80 | 15.78 |
| Example 5 | 5.90 | 211.6 | 36 |
| Example 6 | 2.20 | 208.40 | 95 |
| Example 7 | 15.80 | 191.60 | 12.1 |
| Example 8 | 5.21 | 56.19 | 10.8 |
| Example 9 | 4.58 | 215.60 | 47.07 |
| Example 11 | 24.55 | NT | NT |
| Example 21 | 3.23 | 70.84 | 21.93 |
| Example 22 | 13.19 | 799.5 | 60.6 |
| Example 23 | 46.75 | NT | NT |
| Example 24 | 8.62 | 453.30 | 52.59 |
| Example 25 | 4.56 | 93.25 | 20.45 |
| Example 26 | 2.44 | 508.8 | 208.7 |
| Example 28 | 6.40 | 272.10 | 42.52 |
| Example 40 | 1.95 | 339.40 | 174.05 |
| Example 41 | 5.93 | 138.50 | 23.36 |
| Example 42 | 5.00 | 76.27 | 15.25 |
| Example 44 | 7.13 | 405.90 | 56.93 |
| Example 48 | 1.75 | 101.60 | 58.06 |
| Example 49 | 1.93 | 128.30 | 66.48 |
| Example 50 | 6.14 | 502.70 | 81.87 |
| Example 51 | 5.06 | 394.40 | 77.94 |
| Example 52 | 4.52 | NT | NT |
| Example 53 | 20.02 | 628.20 | 31.38 |
| Example 54 | 2.75 | 71.22 | 25.90 |
| Example 56 | 7.08 | 688.50 | 97.25 |
| Example 60 | 2.94 | 149.40 | 50.82 |
| Example 62 | 26.33 | NT | NT |
| Example 63 | 1.87 | 71.00 | 37.97 |
| Example 67 | 3.73 | 320.60 | 85.95 |
| Example 89 | 112.10 | NT | NT |
| Example 90 | 6.32 | 105.70 | 16.72 |
| Example 91 | 25.95 | 557.70 | 21.49 |
| Example 92 | 1.95 | 9.22 | 4.73 |
| Example 94 | 3.91 | 38.81 | 9.93 |
| Example 95 | 10.87 | NT | NT |
| Example 96 | 17.48 | 323.60 | 18.51 |
| Example 97 | 1.28 | 140.7 | 109.92 |
| Example 98 | 2.92 | 153.90 | 52.71 |
| Example 99 | 2.08 | 36.54 | 17.57 |
| Example 100 | 8.72 | 350.00 | 40.14 |
| Example 102 | 1.71 | 26.03 | 15.22 |
| Example 103 | 1.95 | 98.58 | 50.55 |
| Example 104 | 3.61 | 148.20 | 41.05 |
| Example 105 | 3.12 | 887.00 | 284.29 |
| Example 106 | 14.33 | 353.90 | 24.70 |
| Example 107 | 2.76 | 98.29 | 35.61 |
| Example 111 | 5.65 | 313.70 | 55.52 |
| Example 112 | 15.57 | 257.10 | 16.51 |
| Example 113 | 3.172 | 232.9 | 73.42 |
| Example 114 | 11.61 | 121.50 | 10.47 |
| Example 115 | 4.98 | 101.30 | 20.34 |
| Example 117 | 29.95 | 199.10 | 6.65 |
| Example 118 | 93.69 | 373.90 | 3.99 |
| Example 119 | 2.32 | NT | NT |
| Example 120 | 4.91 | 115.10 | 23.44 |
| Example 121 | 2.09 | 347.80 | 166.41 |
| Example 122 | 113.5 | 890 | 7.84 |
| Example 123 | 14.89 | 526.70 | 35.37 |
| Example 124 | 30.80 | NT | NT |
| Example 125 | 9.58 | 384.90 | 40.18 |
| Example 126 | 33.99 | NT | NT |
| Example 127 | 2.98 | 88.15 | 29.58 |
| Example 129 | 6.22 | 690.00 | 110.93 |
| Example 130 | 1.45 | 97.03 | 66.92 |
| Example 131 | 1.45 | 64.83 | 44.71 |
| Example 132 | 10.12 | NT | NT |
| Example 133 | 6.47 | NT | NT |
| Example 134 | 12.28 | 324.80 | 26.45 |
| Example 135 | 7.50 | 443.90 | 59.19 |
| Example 136 | 11.18 | 335.80 | 30.04 |
| Example 137 | 9.52 | 406.50 | 42.70 |
| Example 138 | 3.37 | 408.50 | 121.22 |
| Example 139 | 6.28 | NT | NT |
| Example 140 | 2.66 | 576.40 | 216.69 |
| Example 141 | 7.51 | NT | NT |
| Example 142 | 3.16 | 118.60 | 37.53 |
| Example 143 | 8.29 | 376.70 | 45.44 |

The $IC_{50}$ values of other example compounds of the present invention for EGFR were similar to the effect of the aforesaid examples, and these compounds exhibited similar inhibitory activity and regularity.

Conclusion: The example compounds of the present invention had strong inhibitory activity on the proliferation of mutant-type H1975 cells with mutant-type EGFR, but had weak inhibitory effect on the proliferation of wild-type A431 cells, such that the example compounds had very good selectivity for wild-type/mutant-type cells.

Pharmacokinetic (PK) Test of the Example Compounds

I. PK Analysis in Rats

The pharmacokinetic test in rats of the preferred compound of Example 26 of the present invention and of the positive control compound AZD-9291 was performed with Sprague Dawley (SD) rats (Shanghai Slac Laboratory Animal Co., LTD).

Mode of administration: a single intragastric administration.

Dosage: 5 mg/10 ml/kg.

Formulation: 0.5% methyl cellulose, ultrasonic dissolution.

Sampling points: 0.5, 1, 2, 4, 6, 8 and 24 hours after administration.

Sample treatment:

1. 1.0 ml of intravenous blood was collected and placed in a K2EDTA test tube. The blood was centrifuged at RT 6000 rpm for 5 minutes to isolate the plasma, which was stored at −80° C.

2. 160 μL of acetonitrile were added to 40 μL of plasma sample for precipitation, and then the mixture was centrifuged at 3500 rpm for 5 minutes.

3. 100 μL of treated solution was taken, and the concentration of the test compound was analyzed by LC/MS/MS. The LC/MS/MS analytical instrument was AB Sciex API 4000.

Liquid Chromatography:
Condition of Liquid chromatography Shimadzu LC-20AD pump
Chromatographic column: phenomenex Gemiu 5 μm C18 50×4.6 mm
Mobile phase: Solution A is 0.1% formic acid aqueous solution, and Solution B is acetonitrile
Flow rate: 0.8 mL/min
Elution time: 0-3.5 minutes, the eluent used was as follows:

| Time/Minute | Solution A | Solution B |
|---|---|---|
| 0.01 | 90% | 10% |
| 0.5 | 90% | 10% |
| 1.2 | 5% | 95% |
| 2.2 | 5% | 95% |
| 2.21 | 100% | 0 |
| 3.5 | 100% | 0 |

Mass Spectrometry:
Condition of mass spectrometer: positive ion electrospray ionization (ESI) mode.
Analysis results of liquid chromatography and mass spectrometry:
1. Compound of Example 26:
$^1$H NMR (400 MHz, CDCl$_3$): δ 9.78 (s, 1H), 9.74 (s, 1H), 8.55 (s, 1H), 8.39 (d, J=5.3 Hz, 1H), 8.11 (d, J=7.0 Hz, 1H), 7.74-7.55 (m, 2H), 7.18 (d, J=5.3 Hz, 1H), 6.76 (s, 1H), 6.62 (dd, J=16.8, 10.1 Hz, 1H), 6.46 (dd, J=16.9, 1.9 Hz, 1H), 6.24 (m, 1H), 5.80-5.59 (m, 1H), 3.88 (s, 3H), 3.55-3.34 (m, 1H), 3.02 (t, J=5.8 Hz, 2H), 2.68 (s, 3H), 2.57 (t, J=5.7 Hz, 2H), 2.42 (s, 6H), 1.24-1.17 (m, 2H), 1.14-1.04 (m, 2H):
MS m/z (ESI): 526.3 [M+H]$^+$.
Metabolite:
1H NMR (400 MHz, CDCl3) δ 9.37 (s, 1H), 9.29 (s, 1H), 8.29 (d, J=5.3 Hz, 1H), 8.18 (s, 1H), 8.07 (d, J=7.2 Hz, 1H), 7.61-7.40 (m, 2H), 7.24-7.15 (m, 2H), 7.06 (d, J=5.3 Hz, 1H), 6.94 (dd, J=15.9, 9.9 Hz, 1H), 6.45 (s, 1H), 6.17 (d, J=16.9 Hz, 1H), 5.58 (d, J=10.2 Hz, 1H), 3.79 (s, 3H), 3.39-3.15 (m, 1H), 2.93 (s, 2H), 2.65 (s, 2H), 2.44 (s, 3H), 2.26 (s, 3H), 1.01 (d, J=5.2 Hz, 4H);
MS m/z (ESI): 512.6 [M+H]$^+$.
The Structure was Identified as Follows:

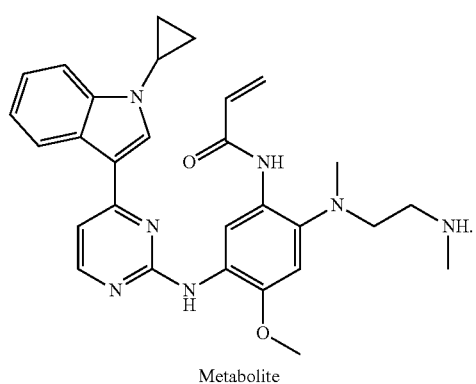 [SMILES: C=CC(=O)Nc1cc(Nc2nccc(-c3cn(C4CC4)c4ccccc34)n2)c(OC)cc1N(C)CCNC]

Metabolite

2. The Structure of the Metabolite of the Positive Control compound AZD-9291 was Identified as Follows:

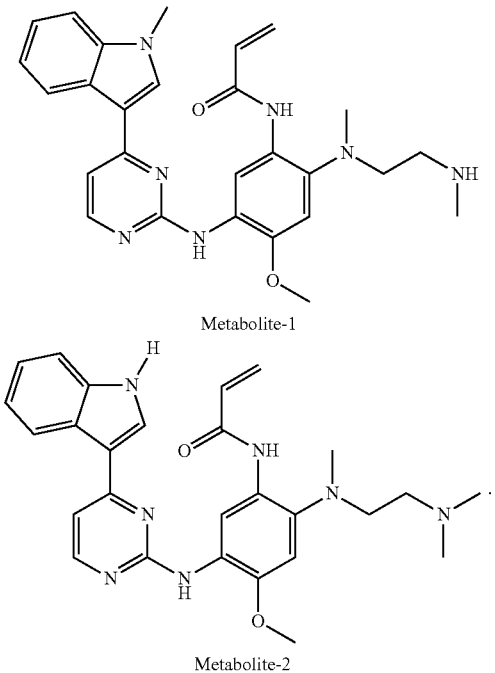

Metabolite-1

Metabolite-2

The data were substantially consistent with the data disclosed in the *Journal of Medicinal Chemistry* (2014), 57 (20), 8249-8267).

Pharmacokinetics:
The main parameters were calculated with WinNonlin 6.1, and the experimental results of the pharmacokinetic test in rats are shown in Table 11 below:

| Main parameters | Positive control compound AZD-9291 | | | Compound of Example 26 | |
|---|---|---|---|---|---|
| | AZD-9291 | Metab-olite-1 | Metab-olite-2 | Compound of Example 26 | Metab-olite |
| $t_{max}$ (h) | 2 | 6 | 2 | 0.5 | 0.5 |
| $C_{max}$ (ng/mL) | 58.3 | 8.4 | 6.9 | 58.4 | 16.4 |
| $AUC_{0-8}$ (ng/mL*h) | 278 | 40.8 | 45.6 | 235 | 77.4 |
| $AUC_{0-\infty}$ (ng/mL*h) | 283 | NA | NA | 268 | NA |
| $t_{1/2}$ (h) | 3.8 | NA | NA | 2.3 | NA |
| $MRT_{0-\infty}$ (h) | 3.9 | NA | NA | 3.9 | NA | note
NA means "not up to the detection limit" or "not determined"

It can be seen from the results of the pharmacokinetic test in rats shown in Table 11 that:

1. The positive control compound AZD-9291 had two metabolites in the plasma of rat, whereas the compound of Example 26 of the present invention had only one metabolite in rat.

2. The compound of Example 26 of the present invention did not produce Metabolite-2 of the positive control compound AZD-9291, thereby avoiding the problem resulting from the poor selectivity of Metabolite-2 of AZD-9291 to T790M mutant-type/wild-type target protein, thus overcoming the defects of the prior art.

II. PK Analysis in Dogs

The pharmacokinetic test in dogs of the preferred compound of Example 26 of the present invention and of the positive control compound AZD-9291 was performed with beagle dogs.

Mode of administration: a single intragastric administration.

Dosage: 2 mg/2.5 ml/kg.

Formulation: 0.5% methyl cellulose, ultrasonic dissolution.

Sampling points: 0.5, 1, 2, 4, 6, 8 and 24 hours after administration.

Sample treatment:

1. 1.0 ml of intravenous blood was collected and placed in a Heparin test tube. The blood was centrifuged at RT 6000 rpm for 5 minutes to isolate the plasma, which was stored at −80° C.

2. 160 μL of acetonitrile were added to 40 μL of plasma sample for precipitation, and then the mixture was centrifuged at 3500 rpm for 5 minutes.

3. 100 μL of treated solution was taken, and the concentration of the test compound was analyzed by LC/MS/MS. The LC/MS/MS analytical instrument was AB Sciex API 4000.

Liquid Chromatography:

Condition of Liquid chromatography: Shimadzu LC-20AD pump

Chromatographic column: phenomenex Gemiu 5 μm C18 50×4.6 mm

Mobile phase: Solution A is 0.1% formic acid aqueous solution, and Solution B is acetonitrile Flow rate: 0.8 mL/min Elution time: 0-3.5 minutes, the eluent used was as follows:

| Time/Minute | Solution A | Solution B |
| --- | --- | --- |
| 0.01 | 90% | 10% |
| 0.5 | 90% | 10% |
| 1.2 | 5% | 95% |
| 2.2 | 5% | 95% |
| 2.21 | 100% | 0 |
| 3.5 | 100% | 0 |

Mass Spectrometry:

Condition of mass spectrometer: positive ion electrospray ionization (ESI) mode.

Analysis results of liquid chromatography and mass spectrometry are in accordance with the analysis results of PK analysis in rats Pharmacokinetics:

The main parameters were calculated with WinNonlin 6.1, and the experimental results of the pharmacokinetic test in dogs are shown in Table 12 below:

| Main parameters | Positive control compound AZD-9291 | | | Compound of Example 26 | |
| --- | --- | --- | --- | --- | --- |
| | AZD-9291 | Metabolite-1 | Metabolite-2 | Compound of Example 26 | Metabolite |
| $t_{max}$ (h) | 1 | 6 | NA | 1 | 6 |
| $C_{max}$ (ng/mL) | 81.4 | 48.3 | NA | 528 | 126 |
| $AUC_{0-8}$ (ng/mL*h) | 883 | 796 | NA | 4584 | 2062 |
| $AUC_{0-\infty}$ (ng/mL*h) | 929 | 974 | NA | 5151 | NA |
| $t_{1/2}$ (h) | 5.4 | 9.9 | NA | 7 | NA |
| $MRT_{0-\infty}$ (h) | 9 | 14.1 | NA | 9.2 | NA | note
The plasma concentration of Metabolite-2 of AZD-9291 in dogs was lower than the detection limit of 1 ng/mL, and NA means "not calculated".

It can be seen from the results of the pharmacokinetic test in dogs shown in Table 12 that: The pharmacokinetic parameters in dogs of the preferred compound of Example 26 of the present invention are superior to those of the positive control compound AZD-9291. The exposure amount of the compound of Example 26 can reach more than 6 times as much as that of the positive control compound AZD-9291. Meanwhile, the half-life of the compound of Example 26 is also greatly extended. Therefore, it is more in line with the medical requirements of administration.

What is claimed is:

1. A compound selected from the group consisting of a compound of formula (IIIA1-7), a compound of formula (IIIA1-8), a compound of formula (IIIA1-9), a compound of formula (IVA1-4), a compound of formula (IVA-5), a compound of formula (IVA1-6), and a compound of formula (IVA1-7), or a stereoisomer or a pharmaceutically acceptable salt thereof:

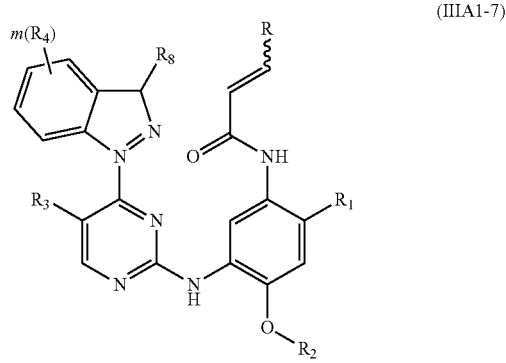

(IIIA1-7)

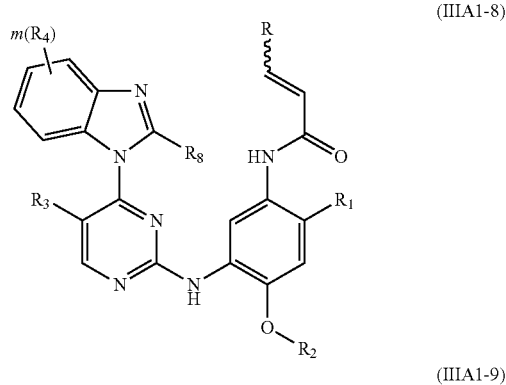

(IIIA1-8)

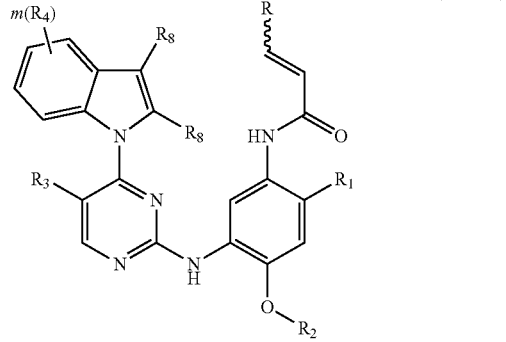

(IIIA1-9)

-continued

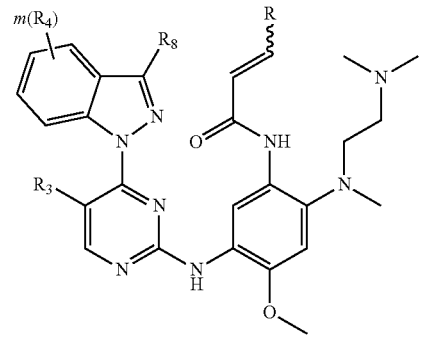
(IVA1-4)

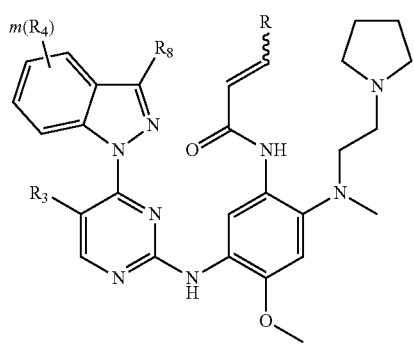
(IVA1-5)

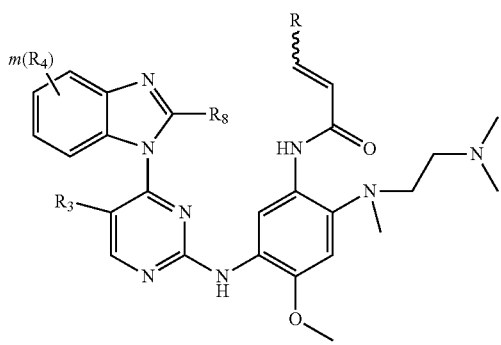
(IVA1-6)

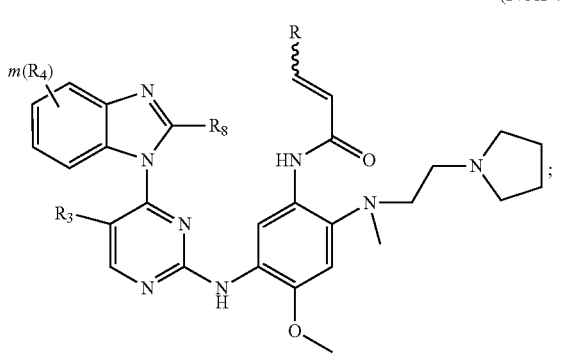
(IVA1-7)

wherein
R is selected from the group consisting of hydrogen and bis-$C_{1-8}$ alkylaminomethyl;
$R_1$ is selected from the group consisting of:

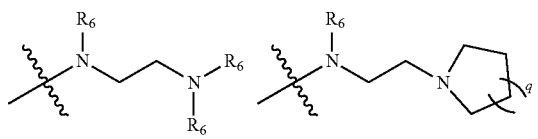

-continued

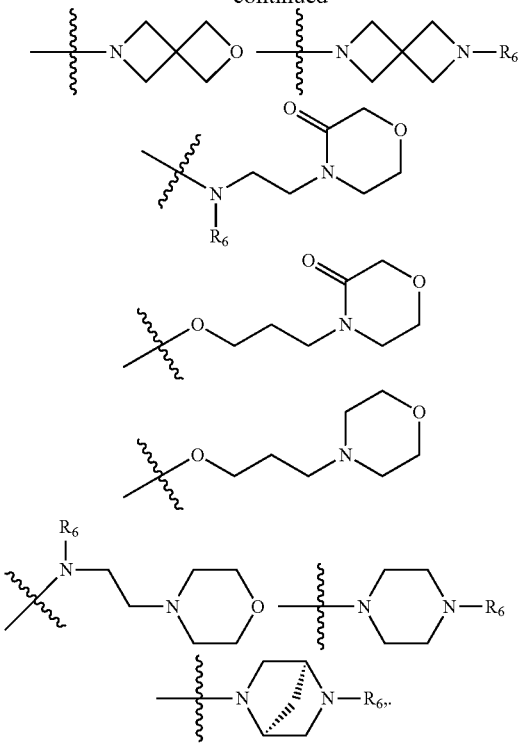

wherein the three $R_6$ in

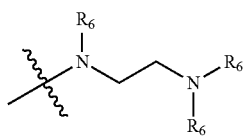

are optionally the same or different substituents;

$R_2$ is selected from the group consisting of $C_{1-8}$ alkyl and $C_{3-8}$ cycloalkyl, wherein the $C_{1-8}$ alkyl and $C_{3-8}$ cycloalkyl are each optionally substituted by one or more groups selected from the group consisting of halogen, hydroxy, $C_{1-8}$ alkyl, $C_{1-8}$ alkoxy, halo$C_{1-8}$ alkoxy, $C_{3-8}$ cycloalkyl and $C_{3-8}$ cycloalkoxy;

$R_3$ is selected from the group consisting of hydrogen, deuterium, halogen, cyano, nitro, $C_{1-8}$ alkyl, $C_{1-8}$ alkoxy, $C_{3-8}$ cycloalkyl, trifluoromethyl, trifluoromethoxy, $SO_2R_9$, $C(O)R_{10}$, $C(O)OR_{10}$ and $P(O)R_{11}R_{12}$;

each $R_4$ is independently selected from the group consisting of hydrogen, deuterium, halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, —$C_{0-8}$—$P(O)R_{11}R_{12}$, —$C_{0-8}$—$S(O)rR_9$, —$C_{0-8}$—O—$R_{10}$, —$C_{0-8}$—$C(O)R_{10}$, —$C_{0-8}$—$C(O)OR_{10}$, —$C_{0-8}$—O—$C(O)R_{10}$, —$C_{0-8}$—$NR_7R_8$, —$C_{0-8}$—$C(O)NR_7R_8$, —$N(R_7)$—$C(O)R_{10}$ and —$N(R_7)$—$C(O)OR_{10}$;

wherein the $C_{1-8}$ alkyl, $C_{3-8}$ cycloalkyl, 3- to 8-membered heterocyclyl, $C_{5-10}$ aryl, 5- to 10-membered heteroaryl, 5- to 7-membered carbocycle, 5- to 7-membered heterocycle, $C_{5-7}$ aryl and 5- to 7-membered heteroaryl are each optionally substituted by one or more groups selected from the group consisting of halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, $-C_{0-8}-S(O)rR_9$, $-C_{0-8}-O-R_{10}$, $-C_{0-8}-C(O)R_{10}$, $-C_{0-8}-C(O)OR_{10}$, $-C_{0-8}-O-C(O)R_{10}$, $-C_{0-8}-NR_7R_8$, $-C_{0-8}-C(O)NR_7R_8$, $-N(R_7)-C(O)R_{10}$ and $-N(R_7)-C(O)OR_{10}$;

$R_6$ is selected from the group consisting of hydrogen, deuterium, $C_{1-8}$ alkyl, halo$C_{1-8}$ alkyl and $C(O)R_{10}$;

$R_7$ is selected from the group consisting of hydrogen, deuterium, $C_{1-8}$ alkyl, $C_{2-8}$ alkenyl, $C_{2-8}$ alkynyl, $C_{3-8}$ cycloalkyl, 3- to 8-membered heterocyclyl, $C_{5-10}$ aryl, 5- to 10-membered heteroaryl, $-C_{0-8}-S(O)rR_9$, $-C_{0-8}-O-R_{10}$, $-C_{0-8}-C(O)R_{10}$, $-C_{0-8}-C(O)OR_{10}$, $-C_{0-8}-O-C(O)R_{10}$, $-C_{0-8}-NR_7R_8$ and $-C_{0-8}-C(O)NR_7R_8$, wherein the $C_{1-8}$ alkyl, $C_{3-8}$ cycloalkyl, 3- to 8-membered heterocyclyl, $C_{5-10}$ aryl and 5- to 10-membered heteroaryl are each optionally substituted by one or more groups selected from the group consisting of halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, $-C_{0-8}-S(O)rR_9$, $-C_{0-8}-O-R_{10}$, $-C_{0-8}-C(O)R_{10}$, $-C_{0-8}-C(O)OR_{10}$, $-C_{0-8}-O-C(O)R_{10}$, $-C_{0-8}-NR_7R_8$, $-C_{0-8}-C(O)NR_7R_8$, $-N(R_7)-C(O)R_{10}$ and $-N(R_7)-C(O)OR_{10}$;

$R_8$ is selected from the group consisting of hydrogen, deuterium, halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, $-C_{0-8}-S(O)rR_9$, $-C_{0-8}-O-R_{10}$, $-C_{0-8}-C(O)R_{10}$, $-C_{0-8}-C(O)OR_{10}$, $-C_{0-8}-O-C(O)R_{10}$, $-C_{0-8}-NR_7R_8$, $-C_{0-8}-C(O)NR_7R_8$, $-N(R_7)-C(O)R_{10}$ and $-N(R_7)-C(O)OR_{10}$, wherein the $C_{1-8}$ alkyl, $C_{3-8}$ cycloalkyl, 3- to 8-membered heterocyclyl, $C_{5-10}$ aryl and 5- to 10-membered heteroaryl are each optionally substituted by one or more groups selected from the group consisting of halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, $-C_{0-8}-S(O)rR_9$, $-C_{0-8}-O-R_{10}$, $-C_{0-8}-C(O)R_{10}$, $-C_{0-8}-C(O)OR_{10}$, $-C_{0-8}-O-C(O)R_{10}$, $-C_{0-8}-NR_7R_8$, $-C_{0-8}-C(O)NR_7R_8$, $-N(R_7)-C(O)R_{10}$ and $-N(R_7)-C(O)OR_{10}$;

$R_9$ is selected from the group consisting of hydrogen, deuterium, $C_{1-8}$ alkyl, $C_{3-8}$ cycloalkyl, halo$C_{1-8}$ alkyl, bis-$C_{1-8}$ alkylamino, phenyl and p-methylphenyl;

$R_{10}$, $R_{11}$ and $R_{12}$ are each independently selected from the group consisting of hydrogen, deuterium, $C_{1-8}$ alkyl, $C_{3-8}$ cycloalkyl, halo$C_{1-8}$ alkyl and hydroxy$C_{1-8}$ alkyl, provided that when the compound is a compound of formula (IIIA1-9), each $R_{10}$ is independently selected from the group consisting of hydrogen, deuterium, $C_{3-8}$ cycloalkyl, halo$C_{1-8}$ alkyl and hydroxy $C_{1-8}$ alkyl;

m is 0, 1, 2, 3 or 4;

r is 0, 1 or 2;

q is 0, 1, 2, 3 or 4; and

" " means that substituent R can have a Z or E configuration.

2. The compound according to claim 1, wherein $R_2$ is selected from the group consisting of methyl, difluoromethyl and trifluoromethyl; $R_3$ is selected from the group consisting of hydrogen, fluorine, chlorine and trifluoromethyl; and $R_4$ is selected from the group consisting of hydrogen and $-C_{0-8}-O-R_{10}$.

3. The compound according to claim 2, wherein $R_1$ is selected from the group consisting of

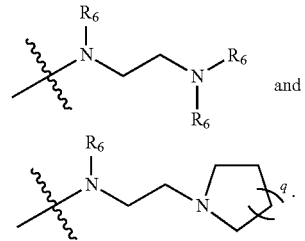

and

4. The compound according to claim 3, wherein the compound is selected from the group consisting of a compound of formula (IVA1-4) and a compound of formula (IVA1-5), or a stereoisomer or pharmaceutically acceptable salt thereof:

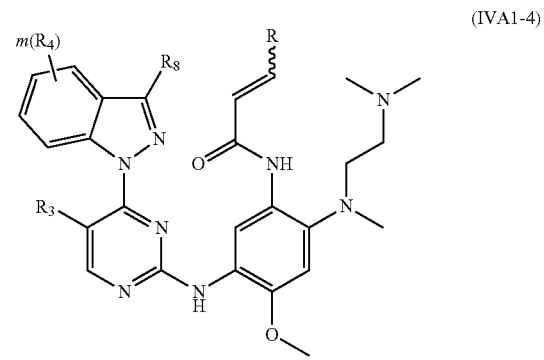

(IVA1-4)

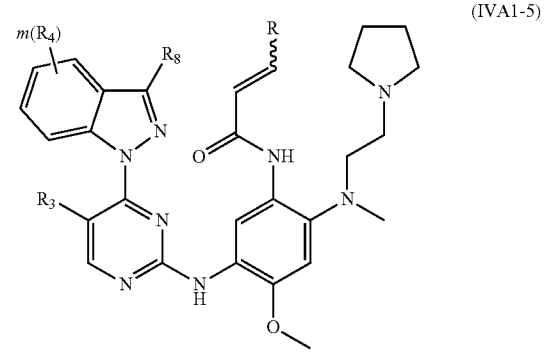

(IVA1-5)

wherein $R_3$ is selected from the group consisting of hydrogen, fluorine, chlorine and trifluoromethyl; and R, $R_4$, $R_6$, $R_7$, $R_8$, $R_9$, $R_{10}$, $R_{11}$, $R_{12}$, m and r are as defined in claim 1.

5. A compound selected from the group consisting of:
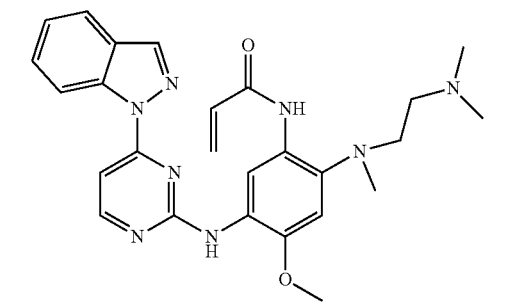
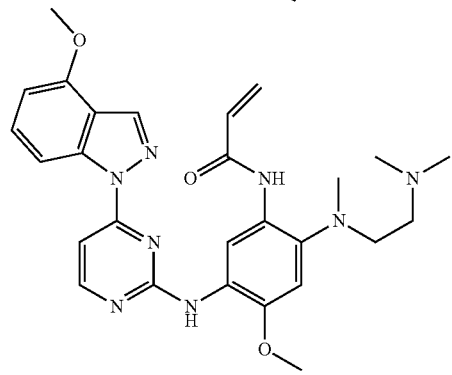
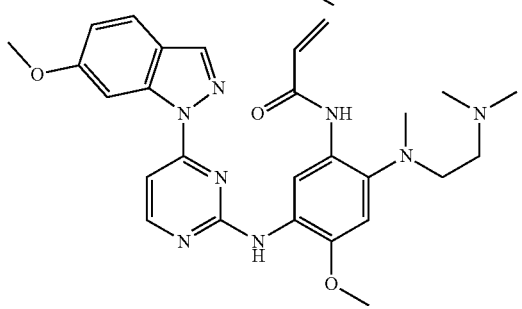
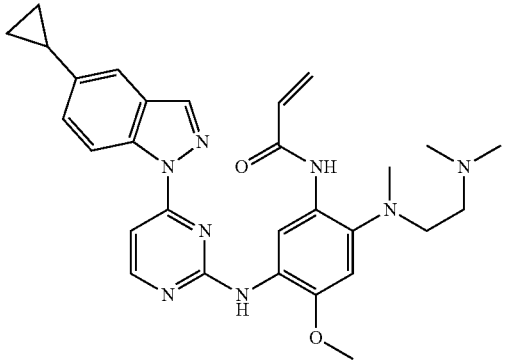
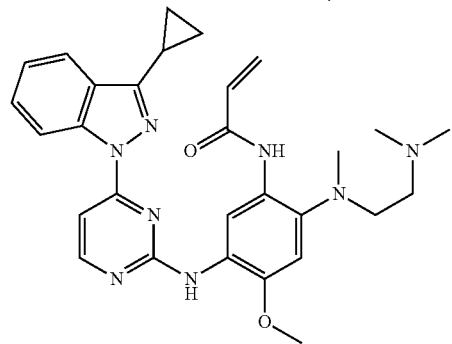
-continued
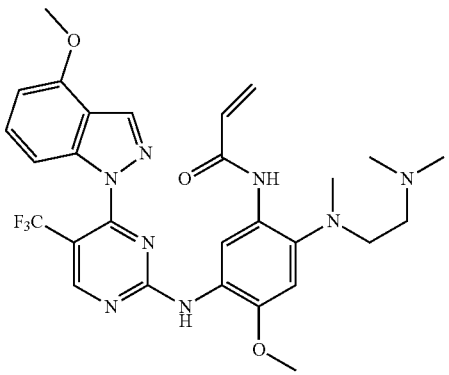
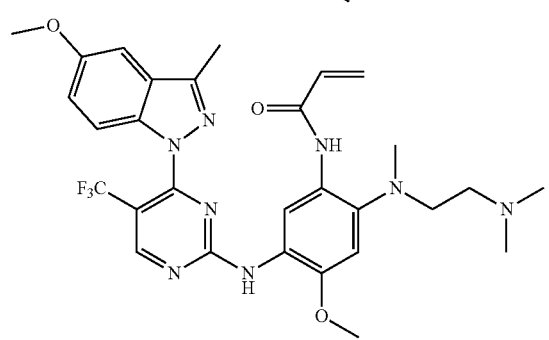
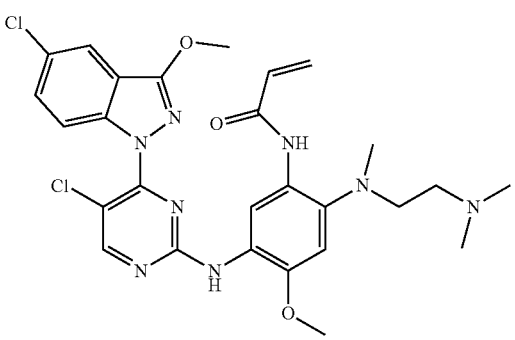
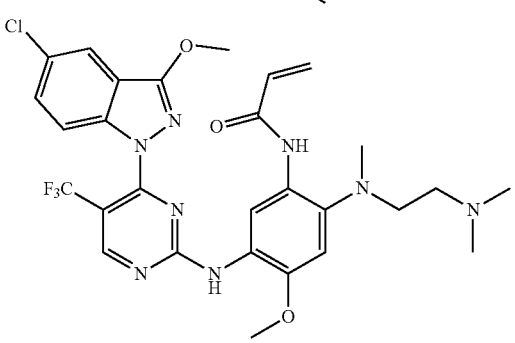
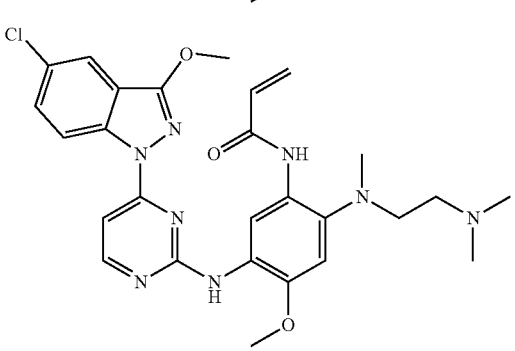

273
-continued
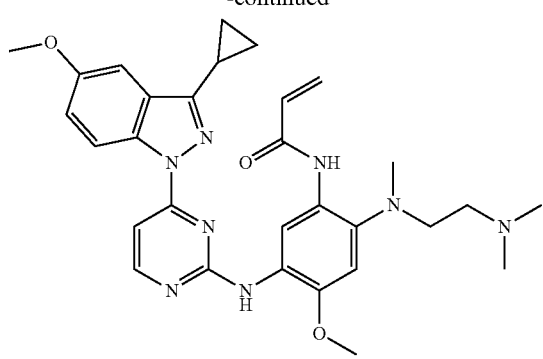
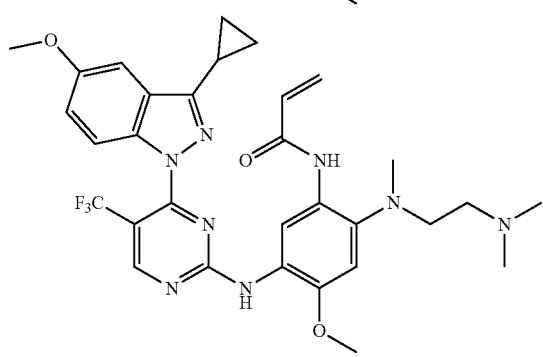
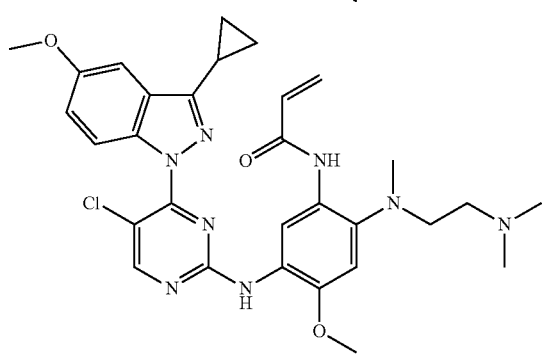
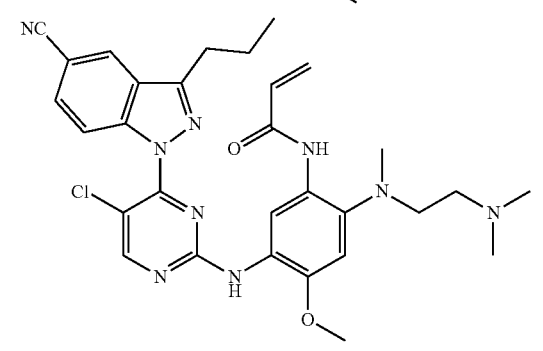
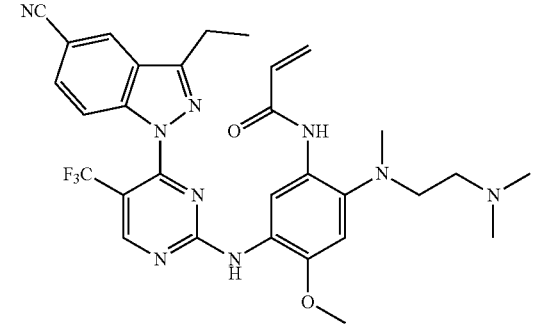
274
-continued
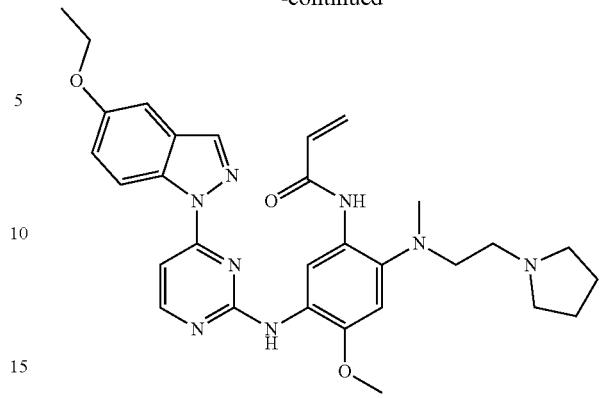
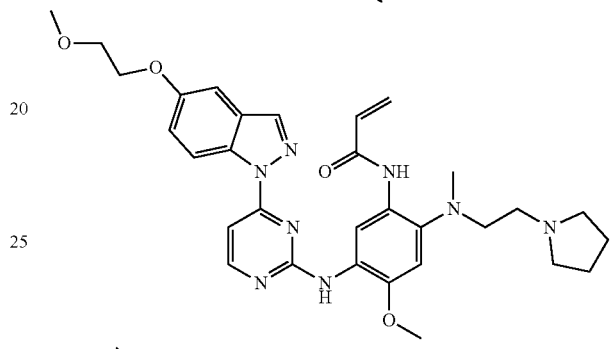
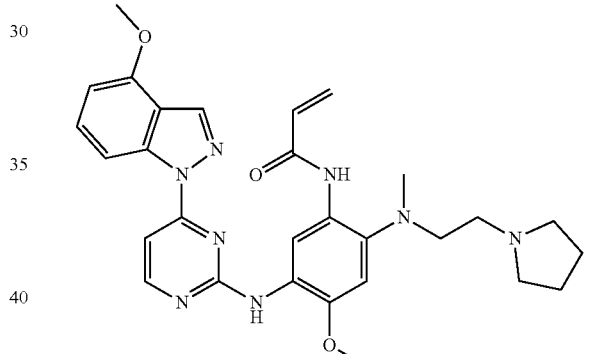
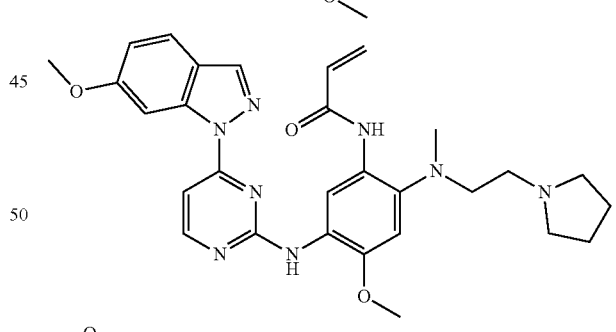
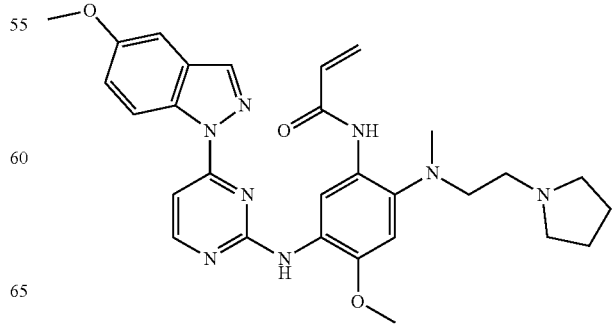

275
-continued
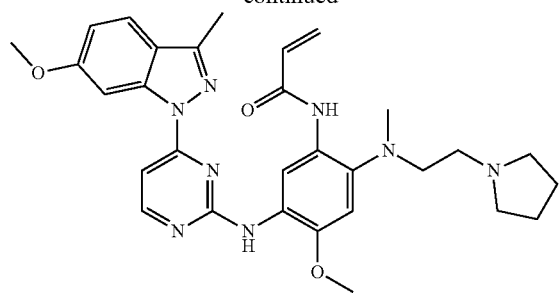
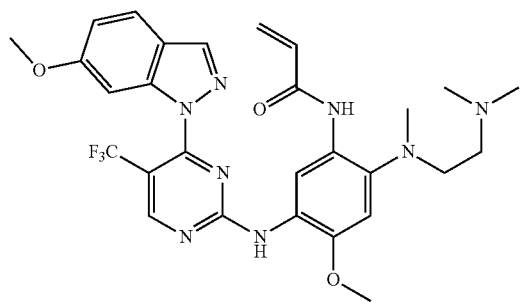
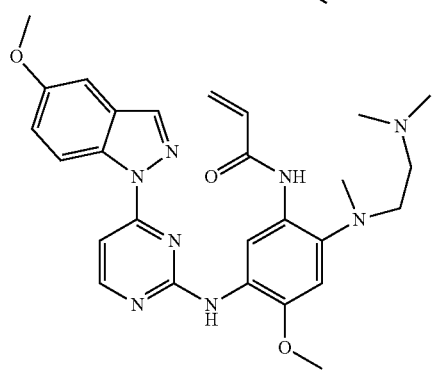
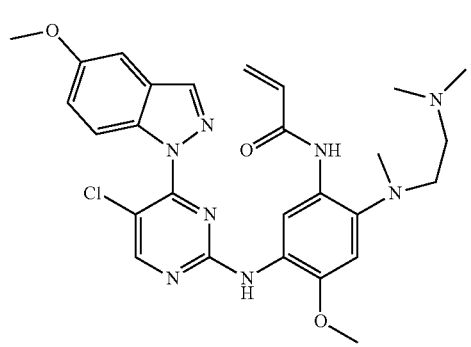
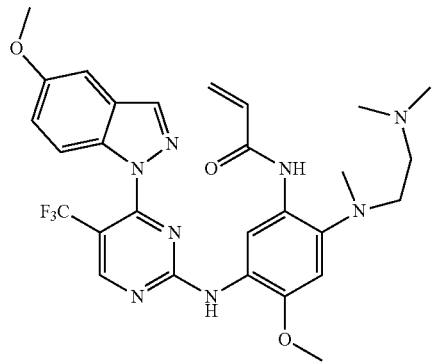
276
-continued
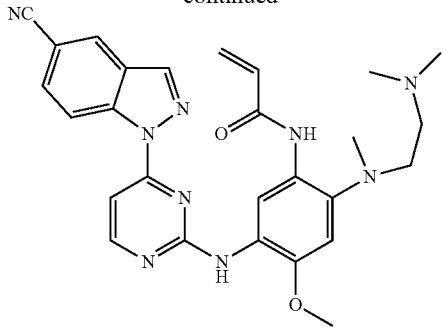
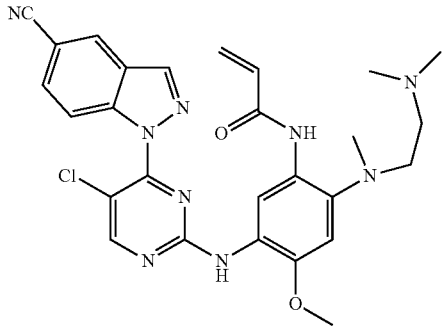
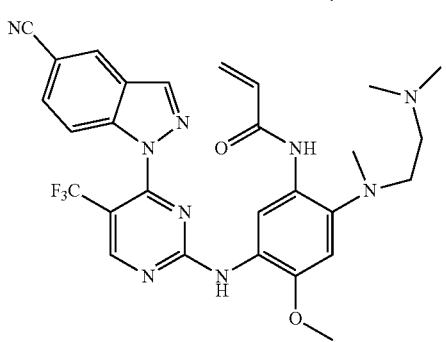
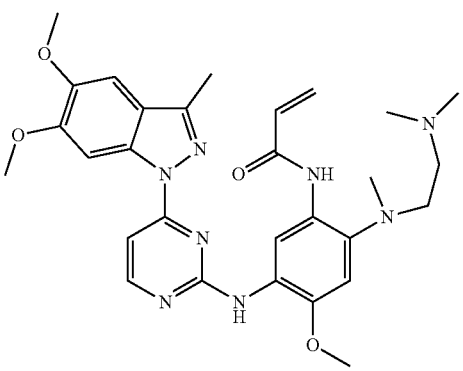
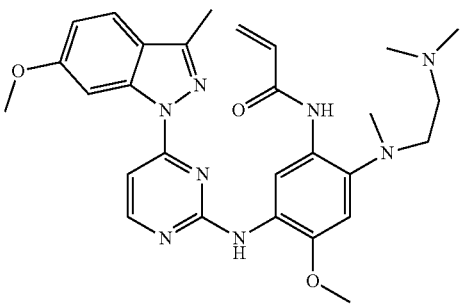

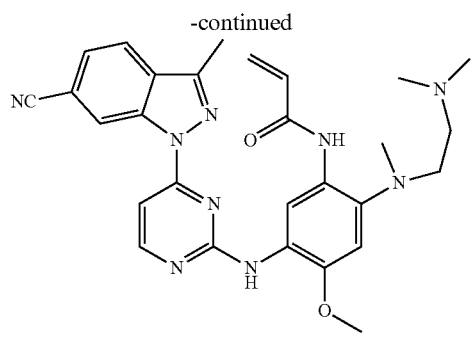

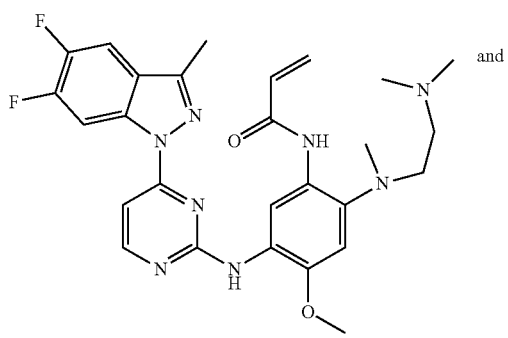

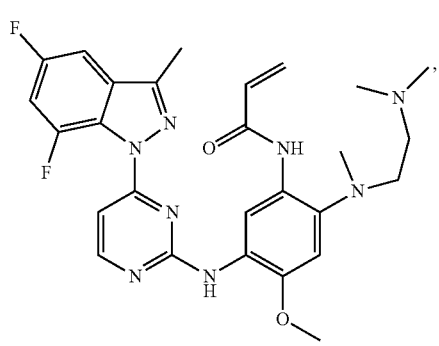

or a stereoisomer or a pharmaceutically acceptable salt thereof.

6. The compound according to claim 1, wherein the compound is selected from the group consisting of a compound of formula (IVA1-6) and a compound of formula (IVA1-7), or a stereoisomer or a pharmaceutically acceptable salt thereof:

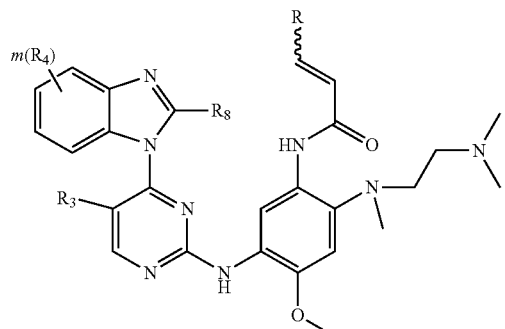

(IVA1-6)

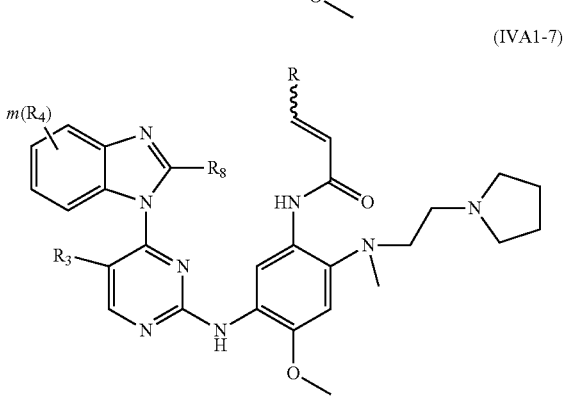

(IVA1-7)

wherein $R_3$ is selected from the group consisting of hydrogen, fluorine, chlorine and trifluoromethyl; and R, $R_4$, $R_6$, $R_7$, $R_8$, $R_9$, $R_{10}$, $R_{11}$, $R_{12}$, m and r are as defined in claim 1.

7. A compound selected from the group consisting of

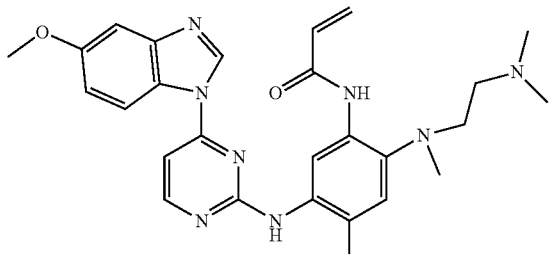

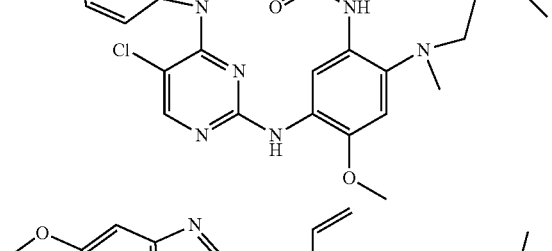

279
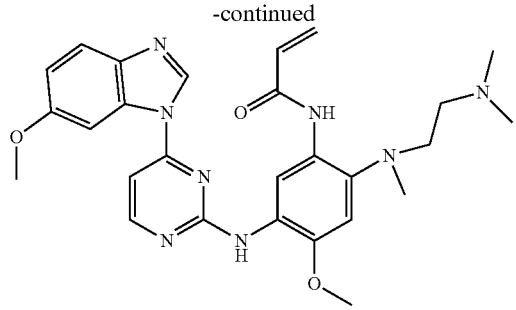
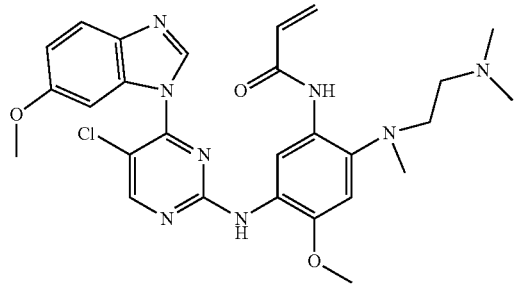
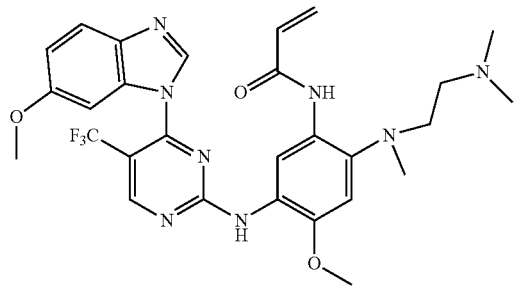
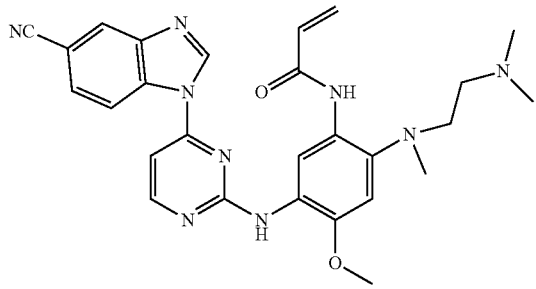
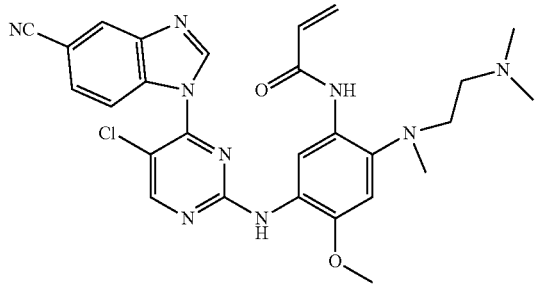
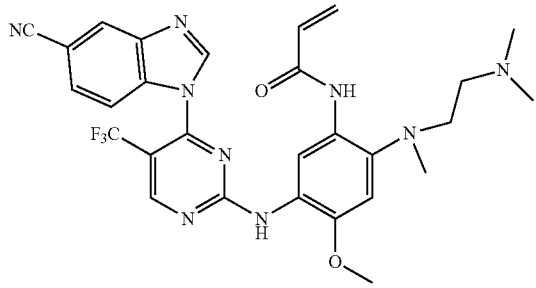
280
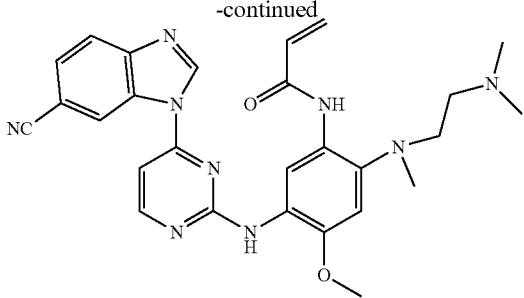
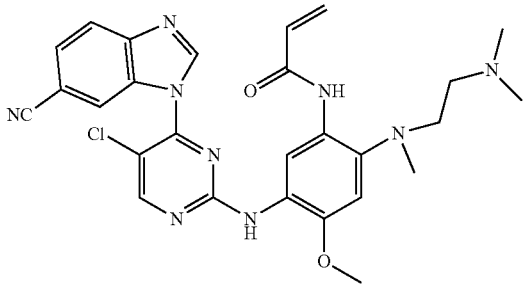
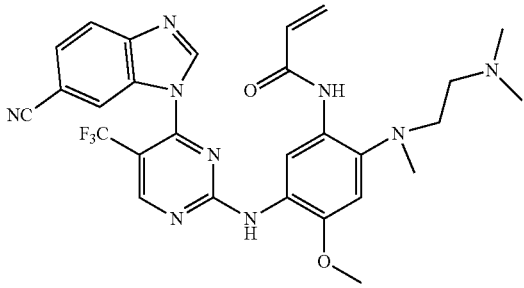
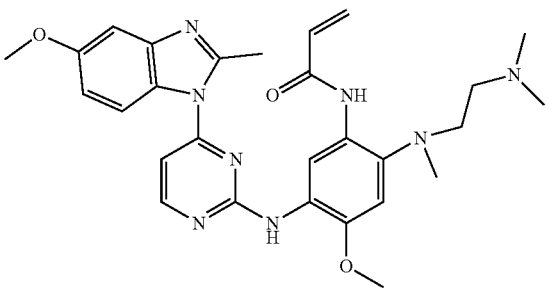
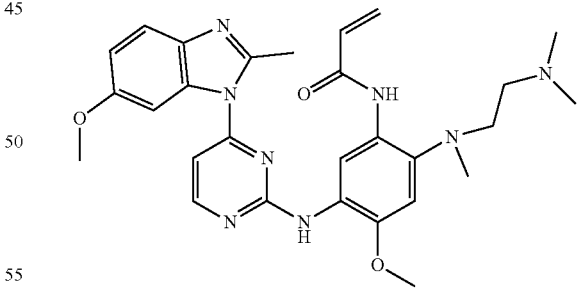
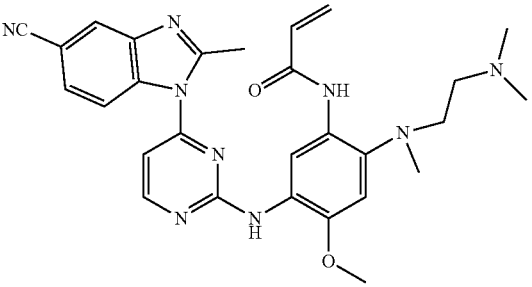

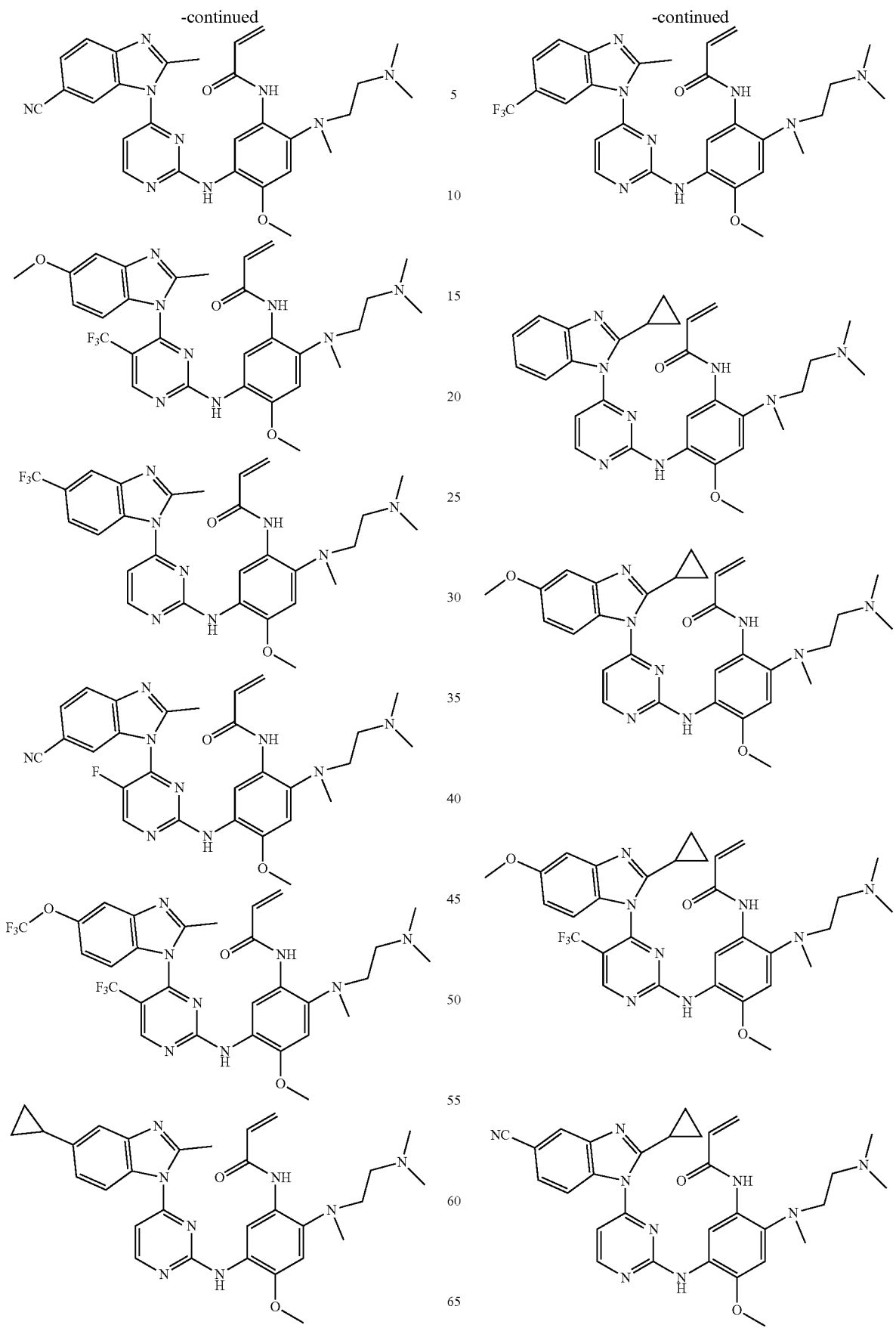

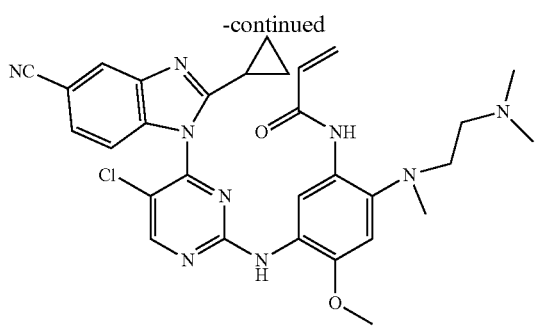

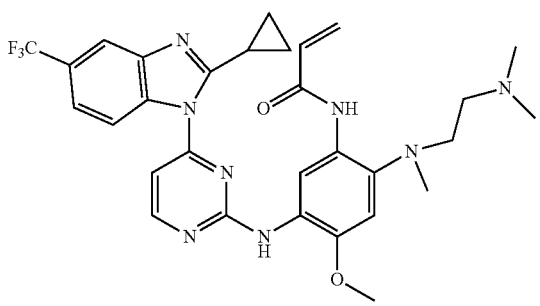

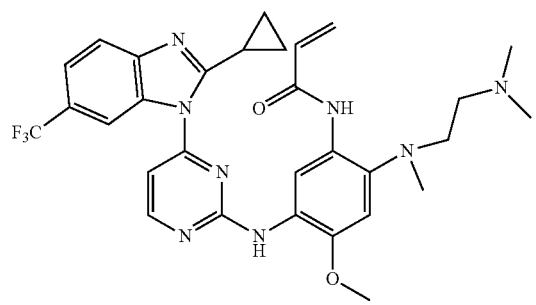

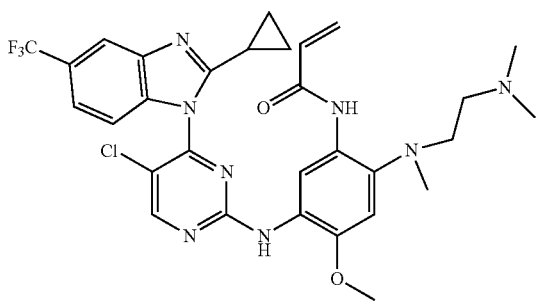

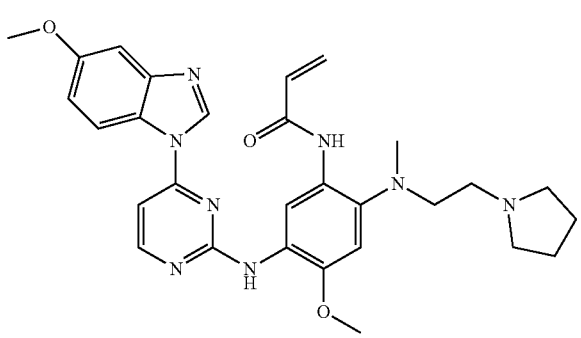

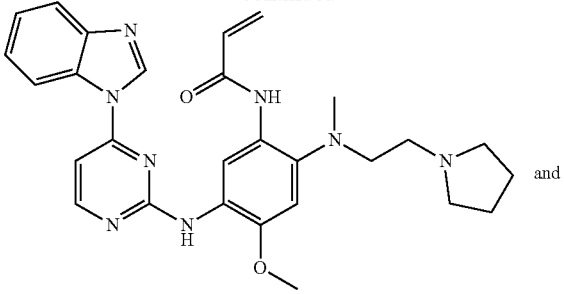

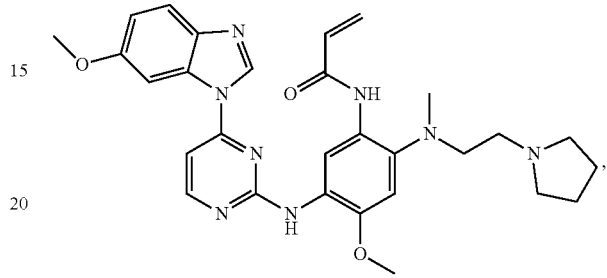

or a stereoisomer or a pharmaceutically acceptable salt thereof.

8. The compound according to claim 3, wherein $R_1$ is

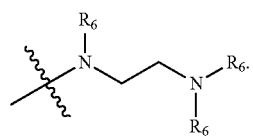

9. A pharmaceutical composition comprising a therapeutically effective amount of the compound according to claim 1, and a pharmaceutically acceptable carrier.

10. The compound according to claim 1, wherein:

R is hydrogen;

$R_1$ is selected from the group consisting of:

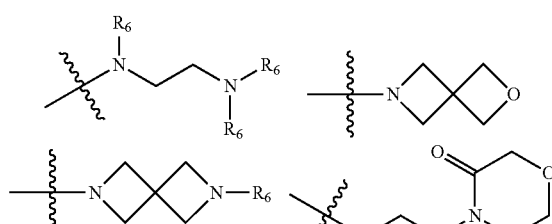

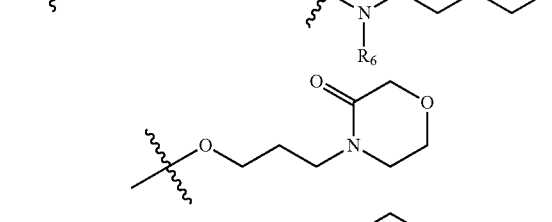

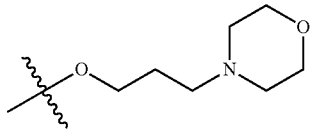

-continued

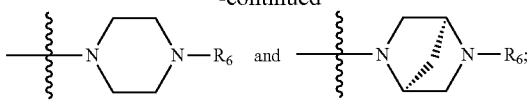

each $R_4$ is independently selected from the group consisting of hydrogen, deuterium, halogen, hydroxy, sulfhydryl, cyano, nitro, azido, $C_{1-8}$ alkyl, $C_{2-8}$ alkenyl, $C_{2-8}$ alkynyl, $C_{3-8}$ cycloalkyl, 3- to 8-membered heterocyclyl, 3- to 8-membered heterocyclyloxy, 3- to 8-membered heterocyclylthio, $C_{5-10}$ aryl, $C_{5-10}$ aryloxy, $C_{5-10}$ arylthio, 5- to 10-membered heteroaryl, 5- to 10-membered heteroaryloxy, 5- to 10-membered heteroarylthio, —P(O)—(CH$_3$)$_2$, —C$_{0-8}$—S(O)rR$_9$, —C$_{0-8}$—O—R$_{10}$, —C$_{0-8}$—C(O)R$_{10}$, —C$_{0-8}$—C(O)OR$_{10}$, —C$_{0-8}$—O—C(O)R$_{10}$, —C$_{0-8}$—NR$_7$R$_8$, —C$_{0-8}$—C(O)NR$_7$R$_8$, —N(R$_7$)—C(O)R$_{10}$ and —N(R$_7$)—C(O)OR$_{10}$;

$R_7$ is selected from the group consisting of hydrogen, deuterium, $C_{1-8}$ alkyl, $C_{2-8}$ alkenyl, $C_{2-8}$ alkynyl, $C_{3-8}$ cycloalkyl, 3- to 8-membered heterocyclyl, $C_{5-10}$ aryl, and 5- to 10-membered heteroaryl; and $R_9$ is selected from the group consisting of hydrogen, deuterium, $C_{1-8}$ alkyl, $C_{3-8}$ cycloalkyl, haloC$_{1-8}$ alkyl, and phenyl.

11. A method of inhibiting an epidermal growth factor receptor (EGFR) having a point mutation or exon 19 deletion in a subject in need of treatment of cancer, the method comprising administering to the subject the pharmaceutical composition of claim 9, wherein the EGFR point mutation is selected from the group consisting of EGFR-L858R and EGFR-T790M.

12. A method of treating cancer, the method comprising administering to a subject in need thereof the pharmaceutical composition according to claim 9.

13. The method according to claim 12, wherein the cancer is selected from the group consisting of ovarian cancer, cervical cancer, colorectal cancer, breast cancer, pancreatic cancer, glioma, glioblastoma, melanoma, prostate cancer, leukemia, lymphoma, non-Hodgkin lymphoma, gastric cancer, lung cancer, hepatocellular carcinoma, gastric cancer, gastrointestinal stromal tumor (GIST), thyroid cancer, cholangiocarcinoma, endometrial cancer, renal cancer, anaplastic large cell lymphoma, acute myeloid leukemia (AML), multiple myeloma, melanoma and mesothelioma.

14. The method according to claim 13, wherein the cancer is non-small cell lung cancer.

15. A pharmaceutical composition comprising the compound according to claim 5, and a pharmaceutically acceptable carrier.

16. A method of treating cancer, the method comprising administering to a subject in need thereof the pharmaceutical composition according to claim 15.

17. The method according to claim 16, wherein the cancer is non-small cell lung cancer.

18. A pharmaceutical composition comprising the compound according to claim 7, and a pharmaceutically acceptable carrier.

19. A method of treating cancer, the method comprising administering to a subject in need thereof the pharmaceutical composition according to claim 18.

20. The method according to claim 19, wherein the cancer is non-small cell lung cancer.

\* \* \* \* \*